United States Patent
May et al.

(10) Patent No.: US 10,125,361 B2
(45) Date of Patent: Nov. 13, 2018

(54) COMPOSITIONS AND METHODS OF NUCLEIC ACID-TARGETING NUCLEIC ACIDS

(71) Applicant: Caribou Biosciences, Inc., Berkeley, CA (US)

(72) Inventors: Andrew Paul May, San Francisco, CA (US); Rachel E. Haurwitz, Kensington, CA (US); Jennifer A. Doudna, Berkeley, CA (US); James M. Berger, Baltimore, MD (US); Matthew Merrill Carter, Berkeley, CA (US); Paul Daniel Donohoue, Berkeley, CA (US)

(73) Assignee: Caribou Biosciences, Inc., Berkeley, CA (US)

( * ) Notice: Subject to any disclaimer, the term of this patent is extended or adjusted under 35 U.S.C. 154(b) by 95 days.

(21) Appl. No.: 15/159,776

(22) Filed: May 19, 2016

(65) Prior Publication Data
US 2016/0251640 A1 Sep. 1, 2016

Related U.S. Application Data

(63) Continuation of application No. 14/977,514, filed on Dec. 21, 2015, now Pat. No. 9,909,122, which is a continuation of application No. 14/416,338, filed as application No. PCT/US2014/023828 on Mar. 12, 2014, now Pat. No. 9,260,752.

(60) Provisional application No. 61/907,777, filed on Nov. 22, 2013, provisional application No. 61/907,216, filed on Nov. 21, 2013, provisional application No. 61/906,335, filed on Nov. 19, 2013, provisional application No. 61/906,211, filed on Nov. 19, 2013, provisional application No. 61/903,232, filed on Nov. 12, 2013, provisional application No. 61/902,723, filed on Nov. 11, 2013, provisional application No. 61/900,311, filed on Nov. 5, 2013, provisional application No. 61/899,712, filed on Nov. 4, 2013, provisional application No. 61/883,804, filed on Sep. 27, 2013, provisional application No. 61/865,743, filed on Aug. 14, 2013, provisional application No. 61/859,661, filed on Jul. 29, 2013, provisional application No. 61/858,767, filed on Jul. 26, 2013, provisional application No. 61/845,714, filed on Jul. 12, 2013, provisional application No. 61/832,690, filed on Jun. 7, 2013, provisional application No. 61/822,002, filed on May 10, 2013, provisional application No. 61/818,382, filed on May 1, 2013, provisional application No. 61/818,386, filed on May 1, 2013, provisional application No. 61/781,598, filed on Mar. 14, 2013.

(51) Int. Cl.
| | |
|---|---|
| C12P 21/02 | (2006.01) |
| C12N 15/11 | (2006.01) |
| C12Q 1/68 | (2018.01) |
| C12N 15/85 | (2006.01) |
| C12Q 1/6818 | (2018.01) |
| C12N 15/10 | (2006.01) |
| A61K 38/46 | (2006.01) |
| C12Q 1/6869 | (2018.01) |
| C12N 9/22 | (2006.01) |
| C12N 15/52 | (2006.01) |
| C12N 15/90 | (2006.01) |
| C12Q 1/6806 | (2018.01) |
| C12Q 1/686 | (2018.01) |
| C12Q 1/6874 | (2018.01) |
| A61K 47/64 | (2017.01) |
| A61K 47/54 | (2017.01) |
| C12N 15/113 | (2010.01) |

(52) U.S. Cl.
CPC ............ *C12N 15/11* (2013.01); *A61K 38/465* (2013.01); *A61K 47/549* (2017.08); *A61K 47/6455* (2017.08); *C12N 9/22* (2013.01); *C12N 15/102* (2013.01); *C12N 15/52* (2013.01); *C12N 15/85* (2013.01); *C12N 15/90* (2013.01); *C12N 15/902* (2013.01); *C12N 15/907* (2013.01); *C12Q 1/68* (2013.01); *C12Q 1/686* (2013.01); *C12Q 1/6806* (2013.01); *C12Q 1/6818* (2013.01); *C12Q 1/6869* (2013.01); *C12Q 1/6874* (2013.01); *C12N 15/113* (2013.01); *C12N 2310/20* (2017.05); *C12N 2310/531* (2013.01); *C12N 2310/533* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 5,034,506 A | 7/1991 | Summerton et al. |
| 5,489,677 A | 2/1996 | Sanghvi et al. |
| 5,602,240 A | 2/1997 | De Mesmaeker et al. |

(Continued)

FOREIGN PATENT DOCUMENTS

| | | |
|---|---|---|
| CN | 103224947 A | 7/2013 |
| CN | 103233028 A | 8/2013 |

(Continued)

OTHER PUBLICATIONS

Marraffini, et al. CRISPR interference: RNA-directed adaptive immunity in bacteria and archaea. Nat Rev Genet. Mar. 2010;11(3):181-90. doi: 10.1038/nrg2749.

(Continued)

*Primary Examiner* — James S Ketter
(74) *Attorney, Agent, or Firm* — Gary R. Fabian; Barbara G. McClung

(57) ABSTRACT

This disclosure provides for compositions and methods for the use of nucleic acid-targeting nucleic acids and complexes thereof.

20 Claims, 73 Drawing Sheets
Specification includes a Sequence Listing.

(56) References Cited

U.S. PATENT DOCUMENTS

| | | |
|---|---|---|
| 5,766,900 A | 6/1998 | Shillito et al. |
| 5,767,367 A | 6/1998 | Dudits et al. |
| 5,968,738 A | 10/1999 | Anderson et al. |
| 6,066,476 A | 5/2000 | Tsien et al. |
| 6,306,610 B1 | 10/2001 | Bawendi et al. |
| 7,919,277 B2 | 4/2011 | Russell et al. |
| 8,361,725 B2 | 1/2013 | Russell et al. |
| 8,546,553 B2 | 10/2013 | Terns et al. |
| 8,685,737 B2 | 4/2014 | Serber et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang et al. |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,921,332 B2 | 12/2014 | Choulika et al. |
| 8,932,814 B2 | 1/2015 | Cong et al. |
| 8,945,839 B2 | 2/2015 | Zhang et al. |
| 8,993,233 B2 | 3/2015 | Zhang et al. |
| 8,999,641 B2 | 4/2015 | Zhang et al. |
| 9,023,649 B2 | 5/2015 | Mali et al. |
| 2002/0119570 A1 | 8/2002 | Yoon et al. |
| 2002/0182673 A1 | 12/2002 | Chen et al. |
| 2003/0003547 A1 | 1/2003 | Dutreix et al. |
| 2003/0232410 A1 | 12/2003 | Lilhedahl et al. |
| 2004/0111221 A1 | 6/2004 | Beattie et al. |
| 2005/0026157 A1 | 2/2005 | Baltimore et al. |
| 2005/0208489 A1 | 9/2005 | Carroll et al. |
| 2006/0147980 A1 | 7/2006 | Keene et al. |
| 2006/0199190 A1 | 9/2006 | Russell et al. |
| 2006/0253913 A1 | 11/2006 | Huang et al. |
| 2007/0016012 A1 | 1/2007 | Hartlep et al. |
| 2007/0134796 A1 | 6/2007 | Holmes et al. |
| 2007/0218528 A1 | 9/2007 | Miller et al. |
| 2008/0124725 A1 | 5/2008 | Barrangou et al. |
| 2008/0159996 A1 | 7/2008 | Ando et al. |
| 2009/0227029 A1 | 9/2009 | Radman et al. |
| 2010/0034924 A1 | 2/2010 | Fremaux et al. |
| 2010/0047805 A1 | 2/2010 | Wang et al. |
| 2010/0055728 A1 | 3/2010 | Yang et al. |
| 2010/0076057 A1 | 3/2010 | Sontheimer et al. |
| 2010/0093617 A1 | 4/2010 | Barrangou et al. |
| 2010/0104690 A1 | 4/2010 | Barrangou et al. |
| 2011/0002889 A1 | 1/2011 | Barrangou et al. |
| 2011/0041195 A1 | 2/2011 | Doyon |
| 2011/0082093 A1 | 4/2011 | Gregory et al. |
| 2011/0105364 A1 | 5/2011 | Kurn |
| 2011/0145940 A1 | 6/2011 | Voytas et al. |
| 2011/0182867 A1 | 7/2011 | Orkin et al. |
| 2011/0189776 A1 | 8/2011 | Terns et al. |
| 2011/0203012 A1 | 8/2011 | Dotson et al. |
| 2011/0207221 A1 | 8/2011 | Cost et al. |
| 2011/0217739 A1 | 9/2011 | Terns et al. |
| 2011/0223638 A1 | 9/2011 | Wiedenheft et al. |
| 2011/0236530 A1 | 9/2011 | Manoury et al. |
| 2011/0287545 A1 | 11/2011 | Cost et al. |
| 2011/0294114 A1 | 12/2011 | Van Der Loo et al. |
| 2011/0300538 A1 | 12/2011 | Barrangou et al. |
| 2011/0301073 A1 | 12/2011 | Gregory et al. |
| 2012/0029891 A1 | 2/2012 | Behlke et al. |
| 2012/0149115 A1 | 6/2012 | Kim et al. |
| 2012/0192298 A1 | 7/2012 | Weinstein et al. |
| 2012/0196370 A1 | 8/2012 | Urnov et al. |
| 2012/0230971 A1 | 9/2012 | Choulika et al. |
| 2012/0324603 A1 | 12/2012 | Hlubek et al. |
| 2013/0011828 A1 | 1/2013 | Barrangou et al. |
| 2013/0017541 A1 | 1/2013 | Forsyth |
| 2013/0065310 A1 | 3/2013 | Davis et al. |
| 2013/0130248 A1 | 5/2013 | Haurwitz et al. |
| 2013/0145497 A1 | 6/2013 | Choi et al. |
| 2013/0158245 A1 | 6/2013 | Russell et al. |
| 2013/0253040 A1 | 9/2013 | Miller et al. |
| 2013/0288251 A1 | 10/2013 | Horvath et al. |
| 2013/0326645 A1 | 12/2013 | Cost et al. |
| 2013/0326725 A1 | 12/2013 | Shukla et al. |
| 2013/0330778 A1 | 12/2013 | Gusti et al. |
| 2014/0017212 A1 | 1/2014 | Rebar et al. |
| 2014/0017214 A1 | 1/2014 | Cost |
| 2014/0045176 A1 | 2/2014 | Kim et al. |
| 2014/0068797 A1 | 3/2014 | Doudna et al. |
| 2014/0080216 A1 | 3/2014 | Cost et al. |
| 2014/0090112 A1 | 3/2014 | Cogan et al. |
| 2014/0090113 A1 | 3/2014 | Cogan et al. |
| 2014/0090116 A1 | 3/2014 | Ainley et al. |
| 2014/0112896 A1 | 4/2014 | Rebar et al. |
| 2014/0123330 A1 | 5/2014 | Carlson et al. |
| 2014/0127752 A1 | 5/2014 | Zhou et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0242664 A1 | 8/2014 | Zhang et al. |
| 2014/0242699 A1 | 8/2014 | Zhang et al. |
| 2014/0287938 A1 | 9/2014 | Zhang et al. |
| 2014/0294773 A1 | 10/2014 | Brouns et al. |
| 2014/0302563 A1 | 10/2014 | Doudna et al. |
| 2014/0310830 A1 | 10/2014 | Zhang et al. |
| 2014/0315985 A1 | 10/2014 | May et al. |
| 2014/0342458 A1 | 11/2014 | Mali et al. |
| 2014/0357530 A1 | 12/2014 | Zhang et al. |
| 2015/0020223 A1 | 1/2015 | Zhang et al. |
| 2015/0024499 A1 | 1/2015 | Brauns et al. |
| 2015/0031134 A1 | 1/2015 | Zhang et al. |
| 2015/0079681 A1 | 3/2015 | Zhang et al. |
| 2015/0152398 A1 | 6/2015 | Doudna et al. |
| 2015/0184139 A1 | 7/2015 | Zhang et al. |
| 2015/0203872 A1 | 7/2015 | Zhang et al. |
| 2015/0232882 A1 | 8/2015 | Zhang et al. |
| 2015/0232883 A1 | 8/2015 | Dahlman et al. |
| 2015/0247150 A1 | 9/2015 | Zhang et al. |
| 2015/0284697 A1 | 10/2015 | Haurwitz et al. |

FOREIGN PATENT DOCUMENTS

| | | |
|---|---|---|
| CN | 103343120 A | 10/2013 |
| EP | 2292731 A1 | 3/2011 |
| EP | 2341149 A1 | 7/2011 |
| EP | 2489275 A1 | 8/2012 |
| EP | 2674501 A1 | 12/2013 |
| WO | WO 88/08450 A1 | 11/1988 |
| WO | WO 93/19191 A1 | 9/1993 |
| WO | WO 02/34771 A3 | 5/2002 |
| WO | WO 2006/073445 A2 | 7/2006 |
| WO | WO 2007/025097 A2 | 3/2007 |
| WO | WO 2007/136815 A2 | 11/2007 |
| WO | WO 2007/144770 A2 | 12/2007 |
| WO | WO 2008/108989 A2 | 9/2008 |
| WO | WO 2009/115861 A2 | 9/2009 |
| WO | WO 2010/011961 A2 | 1/2010 |
| WO | WO 2010/054108 A2 | 5/2010 |
| WO | WO 2010/054154 A2 | 5/2010 |
| WO | WO 2010/066907 A1 | 6/2010 |
| WO | WO 2010/075424 A2 | 7/2010 |
| WO | WO 2010/117464 A1 | 10/2010 |
| WO | WO 2010/125471 A2 | 11/2010 |
| WO | WO 2011/011767 A1 | 1/2011 |
| WO | WO 2011/143124 A2 | 11/2011 |
| WO | WO 2011/156430 A2 | 12/2011 |
| WO | WO 2012/012738 A1 | 1/2012 |
| WO | WO 2012/054726 A1 | 4/2012 |
| WO | WO 2012/164565 A1 | 12/2012 |
| WO | WO 2013/044008 A2 | 3/2013 |
| WO | WO 2013/082519 A2 | 6/2013 |
| WO | WO 2013/088446 A1 | 6/2013 |
| WO | WO 2013/098244 A1 | 7/2013 |
| WO | WO 2013/126794 A1 | 8/2013 |
| WO | WO 2013/130824 A1 | 9/2013 |
| WO | WO 2013/141680 A1 | 9/2013 |

(56) References Cited

FOREIGN PATENT DOCUMENTS

| | | |
|---|---|---|
| WO | WO 2013/142578 A1 | 9/2013 |
| WO | WO 2013/155572 A1 | 10/2013 |
| WO | WO 2013/160230 A1 | 10/2013 |
| WO | WO 2013/169398 A2 | 11/2013 |
| WO | WO 2013/169802 A1 | 11/2013 |
| WO | WO 2013/176772 A1 | 11/2013 |
| WO | WO 2013/181440 A1 | 12/2013 |
| WO | WO 2013/188522 A2 | 12/2013 |
| WO | WO 2013/188638 A2 | 12/2013 |
| WO | WO 2013/192278 A1 | 12/2013 |
| WO | WO 2014/011237 A1 | 1/2014 |
| WO | WO 2014/011901 A2 | 1/2014 |
| WO | WO 2014/018423 A2 | 1/2014 |
| WO | WO 2013/186754 A3 | 2/2014 |
| WO | WO 2014/039684 A1 | 3/2014 |
| WO | WO 2014/039692 A2 | 3/2014 |
| WO | WO 2014/039702 A2 | 3/2014 |
| WO | WO 2014/039872 A1 | 3/2014 |
| WO | WO 2014/059255 A1 | 4/2014 |
| WO | WO 2014/065596 A1 | 5/2014 |
| WO | WO 2014/071006 A1 | 5/2014 |
| WO | WO 2014/089290 A1 | 6/2014 |
| WO | WO 2014/093595 A1 | 6/2014 |
| WO | WO 2014/093622 A2 | 6/2014 |
| WO | WO 2014/093635 A1 | 6/2014 |
| WO | WO 2014/093655 A2 | 6/2014 |
| WO | WO 2014/093661 A2 | 6/2014 |
| WO | WO 2014/093694 A1 | 6/2014 |
| WO | WO 2014/093701 A1 | 6/2014 |
| WO | WO 2014/093709 A1 | 6/2014 |
| WO | WO 2014/093712 A1 | 6/2014 |
| WO | WO 2014/093718 A1 | 6/2014 |
| WO | WO 2014/099744 A1 | 6/2014 |
| WO | WO 2014/099750 A2 | 6/2014 |
| WO | WO 2014/104878 A1 | 7/2014 |
| WO | WO 2014/113493 A1 | 7/2014 |

OTHER PUBLICATIONS

Third-Party Submission Under 37 CFR 1.290 Application No. 14206319; includes U.S. Appl. No. 61/779,169, filed Mar. 13, 2013, Mali, P. et al.
Supplementary European Search Report for EP Application No. 14771135.2, dated Feb. 15, 2016, which corresponds to PCT/US2014/023828, which is related to the present application.
Cong, L., et al., "Multiplex genome engineering using CRISPR/Cas systems," Science. Feb. 15, 2013;339(6121):819-23. doi: 10.1126/science.1231143. Epub Jan. 3, 2013. Supplemental Materials.
Jinek, M., "A programmable dual-RNA-guided DNA endonuclease in adaptive bacterial immunity," Science. Aug. 17, 2012;337(6096):816-21. doi: 10.1126/science.1225829. Epub Jun. 28, 2012. Supplemental Materials.
Third Party Observation, filed Jul. 13, 2015, in PCT/US2014/023828 (Publication No. WO/2014/150624), filed Mar. 14, 2014.
The PCT Application corresponds to U.S. Appl. No. 14/416,338. The present application is a continuation of U.S. Appl. No. 14/416,338. "Third Party Submission filed on Apr. 21, 2015 with the US Patent and Trademark Office against U.S. Appl. No. 14/206,319.".
U.S. Appl. No. 14/610,840, filed Jan. 30, 2015, May et al.
U.S. Appl. No. 14/610,856, filed Jan. 30, 2015, May et al.
U.S. Appl. No. 14/610,880, filed Jan. 30, 2015, May et al.
U.S. Appl. No. 14/610,889, filed Jan. 30, 2015, May et al.
U.S. Appl. No. 14/610,907, filed Jan. 30, 2015, May et al.
U.S. Appl. No. 14/610,917, filed Jan. 30, 2015, May et al.
U.S. Appl. No. 14/610,927, filed Jan. 30, 2015, May et al.
U.S. Appl. No. 14/610,936, filed Jan. 30, 2015, May et al.
U.S. Appl. No. 14/240,735, filed Feb. 24, 2014, Brouns et al.
U.S. Appl. No. 14/326,099, filed Jul. 8, 2014, Brouns et al.
U.S. Appl. No. 14/603,864, filed Jan. 23, 2015, May et al.
Aguilera, et al. Systemic in vivo distribution of activatable cell penetrating peptides is superior to that of cell penetrating peptides. Integr Biol (Camb). Jun. 2009;1(5-6):371-81. doi: 10.1039/b904878b. Epub May 11, 2009.
Al-Attar, et al. Clustered regularly interspaced short palindromic repeats (CRISPRs): the hallmark of an ingenious antiviral defense mechanism in prokaryotes. Biol Chem. Apr. 2011;392(4):277-89. doi: 10.1515/BC.2011.042. Epub Feb. 7, 2011.
Amantana, et al. Pharmacokinetics, biodistribution, stability and toxicity of a cell-penetrating peptide-morpholino oligomer conjugate. Bioconjug Chem. Jul.-Aug. 2007;18(4):1325-31. Epub Jun. 21, 2007.
Anguela, et al. In Vivo Genome Editing of Liver Albumin for Therapeutic Gene Expression: Rescue of Hemophilic Mice Via Integration of Factor 9. 54th ASH Annual Meeting and Exposition, Dec. 10, 2012, Atlanta, Georgia.
Barranger, et al. Gene transfer approaches to the lysosomal storage disorders. Neurochem Res. Apr. 1999;24(4):601-15.
Barrangou, et al. CRISPR Provides Acquired Resistance Against Viruses in Prokaryotes. Science, 2007, vol. 313, pp. 1709-1712.
Barrangou, R. RNA-mediated programmable DNA cleavage. Nat Biotechnol. Sep. 2012;30(9):836-8. doi: 10.1038/nbt.2357.
Barras. Right on Target: New Era of Fast Genetic Engineering. New Scientist, Jan. 2014, vol. 2953.
Bassett, et al. Highly Efficient Targeted Mutagenesis of *Drosophila* with the CRISPR/Cas9 System. Cell Rep. Jul. 11, 2013;4(1):220-8. doi: 10.1016/j.celrep.2013.06.020. Epub Jul. 1, 2013.
Beloglazova, et al. A novel family of sequence-specific endoribonucleases associated with the clustered regularly interspaced short palindromic repeats. J Biol Chem. Jul. 18, 2008;283(29):20361-71. doi: 10.1074/jbc.M803225200. Epub May 15, 2008.
Beres et al. Genome sequence of a serotype M3 strain of group A *Streptococcus*: phage-encoded toxins, the high-virulence phenotype, and clone emergence. Proc Natl Acad Sci U S A. Jul. 23, 2002;99(15):10078-83. Epub Jul. 16, 2002.
Bhaya, et al. CRISPR-Cas systems in bacteria and archaea: versatile small RNAs for adaptive defense and regulation. Annu Rev Genet. 2011;45:273-97. doi: 10.1146/annurev-genet-110410-132430.
Biffi, et al. Genetically-modified hematopoietic stem cells and their progeny for widespread and efficient protein delivery to diseased sites: the case of lysosomal storage disorders. Curr Gene Ther. Oct. 2012;12(5):381-8.
Biffi, et al. Metachromatic Leukodystrophy: an Overview of Current and Prospective Treatments. Bone Marrow Transplantation, 2008, vol. 42, pp. S2-S6.
Bolotin, et al. Clustered regularly interspaced short palindrome repeats (CRISPRs) have spacers of extrachromosomal origin. Microbiology. Aug. 2005;151(Pt 8):2551-61.
Bolotin, et al. Complete sequence and comparative genome analysis of the dairy bacterium *Streptococcus thermophilus*. Nat Biotechnol. Dec. 2004;22(12):1554-8. Epub Nov. 14, 2004.
Brouns, et al. Small CRISPR RNAs guide antiviral defense in prokaryotes. Science. Aug. 15, 2008;321(5891):960-4. doi: 10.1126/science.1159689.
Carr, et al. Genome engineering. Nat Biotechnol. Dec. 2009;27(12):1151-62. doi: 10.1038/nbt.1590.
Carroll. A CRISPR approach to gene targeting. Mol Ther. Sep. 2012;20(9):1658-60. doi: 10.1038/mt.2012.171.
Carte, et al. Binding and cleavage of CRISPR RNA by Cas6. RNA 2010, 16(11): 2181-2188.
Carte, et al. Cas6 is an endoribonuclease that generates guide RNAs for invader defense in prokaryotes. Genes Dev. Dec. 15, 2008;22(24):3489-96. doi: 10.1101/gad.1742908.
Cermak, et al. Efficient design and assembly of custom TALEN and other TAL effector-based constructs for DNA targeting. Nucleic Acids Res. Jul. 2011;39(12):e82. doi: 10.1093/nar/gkr218. Epub Apr. 14, 2011.
Charpentier, Abstracts of the Interscience Conference on Antimicrobial Agents and Chemotherapy, 2012, 52, 1785.
Cho, et al. Targeted genome engineering in human cells with the Cas9 RNA-guided endonuclease. Nat Biotechnol. Mar. 2013;31(3):230-2. doi: 10.1038/nbt.2507. Epub Jan. 29, 2013.
Chylinski, et al. The tracrRNA and Cas9 families of type II CRISPR-Cas immunity systems. RNA Biol. May 2013;10(5):726-737. doi: 10.4161/rna.24321. Epub Apr. 5, 2013.

(56) References Cited

OTHER PUBLICATIONS

Cong et al. Comprehensive interrogation of natural TALE DNA-binding modules and transcriptional repressor domains. Nat Commun. Jul. 24, 2012;3:968. doi: 10.1038/ncomms1962.
Cong, et al. Multiplex genome engineering using CRISPR/Cas systems. Science. Feb. 15, 2013;339(6121):819-23. doi: 10.1126/science.1231143. Epub Jan. 3, 2013.
Courtin, et al., "Interactions Between Microorganisms in a Simple Ecosystem: Yogurt Bacteria as a Study Model", LAIT, 2004, vol. 84, pp. 125-134.
Cradick, et al. ZFN-site searches genomes for zinc finger nuclease target sites and off-target sites. BMC Bioinformatics. May 13, 2011;12:152. doi: 10.1186/1471-2105-12-152.
Dagnino, et al. Molecular diagnosis of analbuminemia: a new case caused by a nonsense mutation in the albumin gene. Int J Mol Sci. 2011;12(11):7314-22. doi: 10.3390/ijms12117314. Epub Oct. 25, 2011.
Dame, et al. H-NS mediated compaction of DNA visualised by atomic force microscopy. Nucleic Acids Res. Sep. 15, 2000;28(18):3504-10.
Dekelver, et al. Functional genomics, proteomics, and regulatory DNA analysis in isogenic settings using zinc finger nuclease-driven transgenesis into a safe harbor locus in the human genome. Genome Res. Aug. 2010;20(8):1133-42. doi: 10.1101/gr.106773.110. Epub May 27, 2010.
Deltcheva, et al. CRISPR RNA maturation by trans-encoded small RNA and host factor RNase III. Nature. Mar. 31, 2011;471(7340):602-7. doi: 10.1038/nature09886.
Dicarlo, et al. Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.
Donnelly, et al. The 'cleavage' activities of foot-and-mouth disease virus 2A site-directed mutants and naturally occurring '2A-like' sequences. J Gen Virol. May 2001;82(Pt 5):1027-41.
Doyon, et al. Enhancing zinc-finger-nuclease activity with improved obligate heterodimeric architectures. Nat Methods. Jan. 2011;8(1):74-9. doi: 10.1038/nmeth.1539. Epub Dec. 5, 2010.
Drag, et al. DeSUMOylating enzymes—SENPs. IUBMB Life. Nov. 2008;60(11):734-42. doi: 10.1002/iub.113.
Editas Press Release, "Editas Medicine Created to Discover and Develop Novel Class of Genome Editing Therapeutics", Nov. 25, 2013.
Ferretti, et al. Complete genome sequence of an M1 strain of *Streptococcus pyogenes*. Proc Natl Acad Sci U S A. Apr. 10, 2001;98(8):4658-63.
Fineran, et al. Degenerate target sites mediate rapid primed CRISPR adaptation. Proc Natl Acad Sci U S A. Apr. 22, 2014;111(16):E1629-38. doi: 10.1073/pnas.1400071111. Epub Apr. 7, 2014.
Friedland, et al. Heritable genome editing in C. elegans via a CRISPR-Cas9 system. Nat Methods. Aug. 2013;10(8):741-3. doi: 10.1038/nmeth.2532. Epub Jun. 30, 2013.
Fu, et al. High-frequency off-target mutagenesis induced by CRISPR-Cas nucleases in human cells. Nat Biotechnol. Jun. 23, 2013. doi: 10.1038/nbt.2623. [Epub ahead of print].
Fu, et al. Improving CRISPR-Cas nuclease specificity using truncated guide RNAs. Nat Biotechnol. Mar. 2014;32(3):279-84. doi: 10.1038/nbt.2808. Epub Jan. 26, 2014.
Gaj, et al. ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
Galkin, et al. BRCA2 BRC motifs bind RAD51-DNA filaments. Proc Natl Acad Sci U S A. Jun. 14, 2005;102(24):8537-42. Epub Jun. 3, 2005.
Garneau, et al. The CRISPR/Cas bacterial immune system cleaves bacteriophage and plasmid DNA. Nature. Nov. 4, 2010;468(7320):67-71. doi: 10.1038/nature09523.
Gasiunas, et al. Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012.

GenBank Accession No. AAL81255, Feb. 25, 2002, "hypothetical protein PF1131 [Pyrococcus furiosus DSM 3638]".
GenBank Direct Submission M33159.1. T. thermophilus insertion sequences 1s1000A and 1s1000B. May 5, 1993. [Retrieved from the Internet Oct. 24, 2013:<http://www.ncbi.nlm.nih.gov/nuccore/M33159>] (nucleotides 6325-6290).
Gentner et al., Identification of hematopoietic stem cell-specific miRNAs enables gene therapy of globoid cell leukodystrophy. Sci Transl Med. Nov. 17, 2010;2(58):58ra84. doi: 10.1126/scitranslmed.3001522.
Geoghegan, et al. Gene Silencing Mediated by siRNA-binding Fusion Proteins Is Attenuated by Double-stranded RNA-binding Domain Structure. Mol Ther Nucleic Acids. Nov. 13, 2012;1:e53. doi: 10.1038/mtna.2012.43.
Gerrits, et al. Cellular barcoding tool for clonal analysis in the hematopoietic system. Blood. Apr. 1, 2010;115(13):2610-8. doi: 10.1182/blood-2009-06-229757. Epub Jan. 21, 2010.
Giacomini, et al. Breakpoint analysis of transcriptional and genomic profiles uncovers novel gene fusions spanning multiple human cancer types. PLoS Genet. Apr. 2013;9(4):e1003464. doi: 10.1371/journal.pgen.1003464. Epub Apr. 25, 2013.
Gilbert, et al. CRISPR-mediated modular RNA-guided regulation of transcription in eukaryotes. Cell. Jul. 18, 2013;154(2):442-51. doi: 10.1016/j.cell.2013.06.044. Epub Jul. 11, 2013.
Grabowski. Phenotype, diagnosis, and treatment of Gaucher's disease. Lancet. Oct. 4, 2008;372(9645):1263-71. doi: 10.1016/S0140-6736(08)61522-6.
Gray, et al., Maturase [Neosartorya fischeri] GenBank Accession No. AAX39426, May 19, 2005.
Grissa, et al. The CRISPRdb database and tools to display CRISPRs and to generate dictionaries of spacers and repeats. BMC Bioinformatics. May 23, 2007;8:172.
Gritti. Gene therapy for lysosomal storage disorders. Expert Opin Biol Ther. Sep. 2011;11(9):1153-67. doi: 10.1517/14712598.2011.582036. Epub May 9, 2011.
Guo, et al. Directed evolution of an enhanced and highly efficient FokI cleavage domain for zinc finger nucleases. J Mol Biol. Jul. 2, 2010;400(1):96-107. doi: 10.1016/j.jmb.2010.04.060. Epub May 4, 2010.
Gupta, et al. Zinc finger protein-dependent and -independent contributions to the in vivo off-target activity of zinc finger nucleases. Nucleic Acids Res. Jan. 2011;39(1):381-92. doi: 10.1093/nar/gkq787. Epub Sep. 14, 2010.
Guschin, et al. A rapid and general assay for monitoring endogenous gene modification. Methods Mol Biol. 2010;649:247-56. doi: 10.1007/978-1-60761-753-2_15.
Haft, et al. A guild of 45 CRISPR-associated (Cas) protein families and multiple CRISPR/Cas subtypes exist in prokaryotic genomes. PLoS Comput Biol. Nov. 2005;1(6):e60. Epub Nov. 11, 2005.
Hale, et al. Essential features and rational design of CRISPR RNAs that function with the Cas RAMP module complex to cleave RNAs. Mol Cell. Feb. 10, 2012;45(3):292-302. doi: 10.1016/j.molcel.2011.10.023. Epub Jan. 5, 2012.
Hale, et al. Prokaryotic silencing (psi)RNAs in Pyrococcus furiosus. RNA. Dec. 2008;14(12):2572-9. doi: 10.1261/rna.1246808. Epub Oct. 29, 2008.
Hale, et al. RNA-guided RNA cleavage by a CRISPR RNA-Cas protein complex. Cell. Nov. 25, 2009;139(5):945-56. doi: 10.1016/j.cell.2009.07.040.
Hatoum-Aslan, et al. Mature clustered, regularly interspaced, short palindromic repeats RNA (crRNA) length is measured by a ruler mechanism anchored at the precursor processing site. Proc Natl Acad Sci U S A. Dec. 27, 2011;108(52):21218-22. doi: 10.1073/pnas.1112832108. Epub Dec. 12, 2011.
Haurwitz, et al. Csy4 relies on an unusual catalytic dyad to position and cleave CRISPR RNA. EMBO J Epub Apr. 20, 2012, 31(12):2824-32.
Haurwitz, et al. Sequence- and structure-specific RNA processing by a CRISPR endonuclease. Science. Sep. 10, 2010;329(5997):1355-8. doi: 10.1126/science.1192272.
Haurwitz, et al. The CRISPR endoribonuclease Csy4 utilizes unusual sequence and 17 structure-specific mechanisms to recognize and

(56) References Cited

OTHER PUBLICATIONS process crRNAs. Electronic Thesis and Dissertations UC Berkley, pp. 1-108. Spring 2012. entire document URL: <http://escholarship.org/uc/item/0rh5940p>.

Heasman. Morpholino oligos: making sense of antisense? Dev Biol. Mar. 15, 2002;243(2):209-14.

Hockmeyer, et al. Efficient targeting of expressed and silent genes in human ESCs and iPSCs using zinc-finger nucleases. Nat Biotechnol. Sep. 2009;27(9):851-7. doi: 10.1038/nbt.1562. Epub Aug. 13, 2009.

Hockmeyer, et al. Genetic engineering of human pluripotent cells using TALE nucleases. Nat Biotechnol. Jul. 7, 2011;29(8):731-4. doi: 10.1038/nbt.1927.

Hofling, et al. Human CD34+ hematopoietic progenitor cell-directed lentiviral-mediated gene therapy in a xenotransplantation model of lysosomal storage disease.Mol Ther. Jun. 2004;9(6):856-65.

Horvath, et al. CRISPR/Cas, the immune system of bacteria and archaea. Science. Jan. 8, 2010;327(5962):167-70. doi: 10.1126/science.1179555.

Hou, et al. Efficient genome engineering in human pluripotent stem cells using Cas9 from Neisseria meningitidis. oc Natl Acad Sci U S A. Sep. 24, 2013;110(39):15644-9. doi: 10.1073/pnas.1313587110. Epub Aug 12, 2013.

Hsu, et al. DNA targeting specificity of RNA-guided Cas9 nucleases. Nat Biotechnol. Jul. 21, 2013. doi: 10.1038/nbt.2647. [Epub ahead of print].

Huang, et al. A simple, high sensitivity mutation screening using Ampligase mediated T7 endonuclease I and Surveyor nuclease with microfluidic capillary electrophoresis. Electrophoresis. Mar. 2012;33(5):788-96. doi: 10.1002/elps.201100460. Epub Mar. 21, 2012.

Hudziak, et al. Resistance of morpholino phosphorodiamidate oligomers to enzymatic degradation. Antisense Nucleic Acid Drug Dev. 1996 Winter;6(4):267-72.

Hwang, et al. Efficient genome editing in zebrafish using a CRISPR-Cas system. Nat Biotechnol. Mar. 2013;31(3):227-9. doi: 10.1038/nbt.2501. Epub Jan. 29, 2013.

International search report and written opinion dated Jan. 18, 2014 for PCT/US2013/045602.

International search report and written opinion dated Feb. 17, 2012 for PCt/US2011/035775.

International search report and written opinion dated Mar. 7, 2013 for PCT Application No. EP2012/076674.

International search report and written opinion dated Jun. 16, 2014 for PCT/US2014/023828.

International search report and written opinion dated Jul. 26, 2013 for PCT/US2013/032589.

International search report dated Mar. 7, 2013 for PCT Application No. EP2012/07664.

Ishino, et al. Nucleotide sequence of the iap gene, responsible for alkaline phosphatase isozyme conversion in *Escherichia coli*, and identification of the gene product. J Bacteriol. Dec. 1987;169(12):5429-33.

Jacoby, et al. Expanding LAGLIDADG endonuclease scaffold diversity by rapidly surveying evolutionary sequence space. Nucleic Acids Res. Jun. 2012;40(11):4954-64. doi: 10.1093/nar/gkr1303. Epub Feb. 14, 2012.

Jacoby, et al., "Chain A, Expanding LAGLIDADG Endonuclease Scaffold Diversity by Rapidly Surveying Evolutionary Sequence Space", GenBank Record Accession No. 3UVF_A, Oct. 10, 2012.

Jacoby, et al., TPA_exp: LAGLIDADG Endonuclease, partial (mitochondrion) [Trichoderma reesei], GenBank Accession No. DAA35182, Jun. 30, 2012.

Jansen, et al. Identification of genes that are associated with DNA repeats in prokaryotes. Mol Microbiol. Mar. 2002;43(6):1565-75.

Jiang, et al. RNA-guided editing of bacterial genomes using CRISPR-Cas systems. Nat Biotechnol. Mar. 2013;31(3):233-9. doi: 10.1038/nbt.2508. Epub Jan. 29, 2013.

Jinek, et al. A programmable dual-RNA-guided DNA endonuclease in adaptive bacterial immunity Science. Aug. 17, 2012;337(6096):816-21. doi: 10.1126/science.1225829. Epub Jun. 28, 2012.

Jinek, et al. Bacterial Immunity a Programmable Dual-RNA-Guided DNA Endonuclease in Adaptive. Science, vol. 337, pp. 816-820. Aug. 12, 2012.

Jinek, et al. RNA-programmed genome editing in human cells. Elife. 2013;2:e00471. doi: 10.7554/eLife.00471. Epub Jan. 29, 2013.

Jore, et al. Structural basis for CRISPR RNA-guided DNA recognition by Cascade. Nat Struct Mol Biol. May 2011;18(5):529-36. doi: 10.1038/nsmb.2019. Epub Apr. 3, 2011.

Kennedy, et al. Rapid blue-light-mediated induction of protein interactions in living cells. Nat Methods. Dec. 2010;7(12):973-5. doi: 10.1038/nmeth.1524. Epub Oct. 31, 2010.

Kim, et al. A library of TAL effector nucleases spanning the human genome. Nat Biotechnol. Mar. 2013;31(3):251-8. doi: 10.1038/nbt.2517. Epub Feb. 17, 2013.

Kim, et al. Long-term expression of the human glucocerebrosidase gene in vivo after transplantation of bone-marrow-derived cells transformed with a lentivirus vector. J Gene Med. Jul. 2005;7(7):878-87.

Kim, et al. TALEN-based knockout library for human microRNAs. Nat Struct Mol Biol. Dec. 2013;20(12):1458-64. doi: 10.1038/nsmb.2701. Epub Nov. 10, 2013.

Kunin, et al. Evolutionary conservation of sequence and secondary structures in CRISPR repeats. Genome Biol. 2007;8(4):R61.

Larson, et al. CRISPR interference (CRISPRi) for sequence-specific control of gene expression. Nature Protocols. 2013; 8:2180-2196.

Lee, et al. RNA-protein analysis using a conditional CRISPR nuclease. Proc Nat! Acad Sci USA. Apr. 2, 2013, 110(14):5416-21.

Leimig, et al. Functional amelioration of murine galactosialidosis by genetically modified bone marrow hematopoietic progenitor cells. Blood. May 1, 2002;99(9):3169-78.

Li, et al. High-efficiency TALEN-based gene editing produces disease-resistant rice. Nat Biotechnol. May 7, 2012;30(5):390-2. doi: 10.1038/nbt.2199.

Lillestol, et al. A putative viral defence mechanism in archaeal cells. Archaea. Aug. 2006;2(1):59-72.

Lillestol, et al. CRISPR families of the crenarchaeal genus *Sulfolobus*: bidirectional transcription and dynamic properties. Mol Microbiol. Apr. 2009;72(1):259-72. doi: 10.1111/j.1365-2958.2009.06641.x. Epub Feb. 23, 2009.

Lintner, et al. Structural and functional characterization of an archaeal clustered regularly interspaced short palindromic repeat (CRISPR)-associated complex for antiviral defense (CASCADE). J Biol Chem. Jun. 17, 2011;286(24):21643-56. doi: 10.1074/jbc.M111.238485. Epub Apr. 20, 2011.

Lu, et al. Tracking single hematopoietic stem cells in vivo using high-throughput sequencing in conjunction with viral genetic barcoding Nat Biotechnol. Oct. 2, 2011;29(10):928-33. doi: 10.1038/nbt.1977.

Luo, et al. Highly parallel identification of essential genes in cancer cells. Proc Natl Acad Sci U S A. Dec. 23, 2008;105(51):20380-5. doi: 10.1073/pnas.0810485105. Epub Dec. 17, 2008.

Ma, et al. A guide RNA sequence design platform for the CRISPR/Cas9 system for model organism genomes. Biomed Res Int. 2013;2013:270805. doi: 10.1155/2013/270805. Epub Oct. 3, 2013.

Makarova, et al. A putative RNA-interference-based immune system in prokaryotes: computational analysis of the predicted enzymatic machinery, functional analogies with eukaryotic RNAi, and hypothetical mechanisms of action. Biology Direct 2006, 1:7.

Makarova, et al. Evolution and classification of the CRISPR-Cas systems. Nat Rev Microbiol. Jun. 2011;9(6):467-77. doi: 10.1038/nrmicro2577. Epub May 9, 2011.

Makarova, et al. Unification of Cas protein families and a simple scenario for the origin and evolution of CRISPR-Cas systems. Biol Direct. Jul. 14, 2011;6:38. doi: 10.1186/1745-6150-6-38.

Makinen, et al. Stable RNA interference: comparison of U6 and H1 promoters in endothelial cells and in mouse brain. J Gene Med. Apr. 2006;8(4):433-41.

(56) References Cited

OTHER PUBLICATIONS

Malanowska, et al. CTnDOT integrase performs ordered homology-dependent and homology-independent strand exchanges. Nucleic Acids Res. 2007;35(17):5861-73. Epub Aug. 24, 2007.
Mali, et al. CAS9 transcriptional activators for target specificity screening and paired nickases for cooperative genome engineering. Nat Biotechnol. Sep. 2013; 31(9): 10.1038/nbt.2675.
Mali, et al. RNA-guided human genome engineering via Cas9. Science. Feb. 15, 2013;339(6121):823-6. doi: 10.1126/science.1232033. Epub Jan. 3, 2013.
Marraffini, et al. CRISPR interference limits horizontal gene transfer in staphylococci by targeting DNA. Science. Dec. 19, 2008;322(5909):1843-5. doi: 10.1126/science.1165771.
Marrafini, et al. Self versus non-self discrimination during CRISPR RNA-directed immunity Nature. Jan. 28, 2010;463(7280):568-71. doi: 10.1038/nature08703. Epub Jan. 13, 2010.
Melton, et al. Efficient in vitro synthesis of biologically active RNA and RNA hybridization probes from plasmids containing a bacteriophage SP6 promoter. Nucleic Acids Res. Sep. 25, 1984;12(18):7035-56.
Mittelman, et al. Zinc-finger directed double-strand breaks within CAG repeat tracts promote repeat instability in human cells. Proc Natl Acad Sci U S A. Jun. 16, 2009;106(24):9607-12. doi: 10.1073/pnas.0902420106. Epub May 29, 2009.
Mojica, et al. Intervening sequences of regularly spaced prokaryotic repeats derive from foreign genetic elements. J Mol Evol. Feb. 2005;60(2):174-82.
Mojica, et al. Long stretches of short tandem repeats are present in the largest replicons of the Archaea Haloferax mediterranei and Haloferax volcanii and could be involved in replicon partitioning. Mol Microbiol. Jul. 1995;17(1):85-93.
Mojica, et al. Short motif sequences determine the targets of the prokaryotic CRISPR defence system. Microbiology. Mar. 2009;155(Pt 3):733-40. doi: 10.1099/mic.0.023960-0.
Moore, et al. Improved somatic mutagenesis in zebrafish using transcription activator-like effector nucleases (TALENs). S One. 2012;7(5):e37877. doi: 10.1371/journal.pone.0037877. Epub May 24, 2012.
Morcos, et al. Vivo-Morpholinos: A non-peptide transported delivers morpholinos into a wide array of mouse tissues. BioTechniques. [2008]1 45:616-626.
Moscou, et al. A simple cipher governs DNA recognition by TAL effectors. Science. Dec. 11, 2009;326(5959):1501. doi: 10.1126/science.1178817.
Mussolino, et al. TALE nucleases: tailored genome engineering made easy. Curr Opin Biotechnol. Oct. 2012;23(5):644-50. doi: 10.1016/j.copbio.2012.01.013. Epub Feb. 17, 2012.
Muzykantov. Drug delivery by red blood cells: vascular carriers designed by mother nature. Expert Opin Drug Deliv. Apr. 2010;7(4):403-27. doi: 10.1517/17425241003610633.
Nagai, et al. A variant of yellow fluorescent protein with fast and efficient maturation for cell-biological applications. Nat Biotechnol. Jan. 2002;20(1):87-90.
Nishimasu, et al. Crystal Structure of Cas9 in Complex with Guide RNA and Target DNA. Cell. 2014;156(5):935-949.
Niu, et al. Generation of Gene-Modified Cynomolgus Monkey via Cas9/RNA-Mediated Gene Targeting in One-Cell Embryos. Cell. Feb. 13, 2014;156(4):836-43. doi: 10.1016/j.cell.2014.01.027. Epub Jan. 30, 2014.
Notice of allowance dated Feb. 20, 2014 for U.S. Appl. No. 14/054,414.
Office action dated Jan. 17, 2014 for U.S. Appl. No. 14/054,414.
Office action dated Dec. 5, 2013 for U.S. Appl. No. 14/054,414.
Olson, et al. In vivo characterization of activatable cell penetrating peptides for targeting protease activity in cancer. Integr Biol (Camb). Jun. 2009;1(5-6):382-93. doi: 10.1039/b904890a. Epub May 11, 2009.
Orlando, et al. Zinc-finger nuclease-driven targeted integration into mammalian genomes using donors with limited chromosomal homology. Nucleic Acids Res. Aug. 2010;38(15):e152. doi: 10.1093/nar/gkq512. Epub Jun. 8, 2010.
Papapetrou, et al. Genomic safe harbors permit high β-globin transgene expression in thalassemia induced pluripotent stem cells. Nat Biotechnol. Jan. 2011;29(1):73-8. doi: 10.1038/nbt.1717. Epub Dec. 12, 2010.
Partridge, et al. A simple method for delivering morpholino antisense oligos into the cytoplasm of cells. Antisense Nucleic Acid Drug Dev. 1996 Fall;6(3):169-75.
Pattanayak, et al. Revealing off-target cleavage specificities of zinc-finger nucleases by in vitro selection. Nat Methods. Aug. 7, 2011;8(9):765-70. doi: 10.1038/nmeth.1670.
Pennisi. The CRISPR craze. Science. Aug. 23, 2013;341(6148):833-6. doi: 10.1126/science.341.6148.833.
Perez-Rodriguez, et al. Envelope stress is a trigger of CRISPR RNA-mediated DNA silencing in *Escherichia coli*. Mol Microbiol. Feb. 2011;79(3):584-99. doi: 10.1111/j.1365-2958.2010.07482.x. Epub Dec. 13, 2010.
Povirk, et al., "Role of Braca 1 in Nonhomologous DNA End Joining", U.S. Army Medical Research and Material Command, Award No. DAMD 17-03-01-0620, Sep. 2004, pp. 1-11.
Qi, et al. Repurposing CRISPR as an RNA-guided platform for sequence-specific control of gene expression. Cell. Feb. 28, 2013;152(5):1173-83. doi: 10.1016/j.cell.2013.02.022.
Ramsubir, et al. In vivo delivery of human acid ceramidase via cord blood transplantation and direct injection of lentivirus as novel treatment approaches for Farber disease. Mol Genet Metab. Nov. 2008;95(3):133-41. doi: 10.1016/j.ymgme.2008.08.003. Epub Sep. 20, 2008.
Ran, et al. Double Nicking by RNA-Guided CRISPR Cas9 for Enhanced Genome Editing Specificity. Cell. Aug. 28, 2013. pii: S0092-8674(13)01015-5. doi: 10.1016/j.cell.2013.08.021. [Epub ahead of print].
Rho, et al. Diverse CRISPRs evolving in human microbiomes. PLoS Genet. 2012;8(6):e1002441. doi: 10.1371/journal.pgen.1002441. Epub Jun. 13, 2012.
Ryan, et al. Cleavage of foot-and-mouth disease virus polyprotein is mediated by residues located within a 19 amino acid sequence. J Gen Virol. Nov. 1991;72 ( Pt 11):2727-32.
Sampson, et al. A CRISPR/Cas system mediates bacterial innate immune evasion and virulence. Nature. May 9, 2013;497(7448):254-7. doi: 10.1038/nature12048. Epub Apr. 14, 2013.
Sanjana, et al. A transcription activator-like effector toolbox for genome engineering. Nat Protoc. Jan. 5, 2012;7(1):171-92. doi: 10.1038/nprot.2011.431.
Sapranauskas, et al. The *Streptococcus thermophilus* CRISPR/Cas system provides immunity in *Escherichia coli*. Nucleic Acids Res. Nov. 2011;39(21):9275-82. doi: 10.1093/nar/gkr606. Epub Aug. 3, 2011.
Sashital, et al. Mechanism of foreign DNA selection in a bacterial adaptive immune system. Mol Cell. Jun. 8, 2012;46(5):606-15. doi: 10.1016/j.molcel.2012.03.020. Epub Apr. 19, 2012.
SBI. PrecisionX Cas9 SmartNuclease vector system user manual. System Biosciences. 2013.
Semenova, et al. Interference by clustered regularly interspaced short palindromic repeat (CRISPR) RNA is governed by a seed sequence. Proc Natl Acad Sci U S A. Jun. 21, 2011;108(25):10098-103. doi: 10.1073/pnas.1104144108. Epub Jun. 6, 2011.
Shalem, et al. Genome-scale CRISPR-Cas9 knockout screening in human cells. Science. Jan. 3, 2014;343(6166):84-7. doi: 10.1126/science.1247005. Epub Dec. 12, 2013.
Shekhawat, et al. Split-Protein Systems: Beyond Binary Protein-Protein Interactions. Curr Opin Chem Biol. Dec. 2011;15(6):789-97. doi: 10.1016/j.cbpa.2011.10.014. Epub Nov. 7, 2011.
Sigma Aldrich Product Information Cas9 GFP Expression Plasmids. Aug. 2013.
Sigma-Aldrich. Cas9-GFP Expression Plasmids. Product information. 2013.
Sims, et al. High-throughput RNA interference screening using pooled shRNA libraries and next generation sequencing. Genome Biol. Oct. 21, 2011;12(10):R104. doi: 10.1186/gb-2011-12-10-r104.

(56) References Cited

OTHER PUBLICATIONS

Sontheimer et al., "Project 7: Establishing RNA-Directed DNA Targeting in Eukaryotic Cells; Project dates: Nov. 16, 2011 to Dec. 31, 2012" (Feb. 4, 2012).
Sorek et al. CRISPR-mediated adaptive immune systems in bacteria and archaea. Annu Rev Biochem. 2013;82:237-66. doi: 10.1146/annurev-biochem-072911-172315. Epub Mar. 11, 2013.
Sorek, et al. CRISPR—a widespread system that provides acquired resistance against phages in bacteria and archaea. Nat Rev Microbiol. Mar. 2008;6(3):181-6.
Stern, et al. Self-targeting by CRISPR: gene regulation or autoimmunity? Trends Genet. Aug. 2010;26(8):335-40. doi: 10.1016/j.tig.2010.05.008. Epub Jul. 1, 2010.
Sternberg, et al. Mechanism of substrate selection by a highly specific CRISPR endoribonuclease. RNA. Apr. 2012;18(4):661-72. doi: 10.1261/rna.030882.111. Epub Feb. 16, 2012.
Subach, et al. Conversion of red fluorescent protein into a bright blue probe. Chem Biol. Oct. 20, 2008;15(10):1116-24. doi: 10.1016/j.chembiol.2008.08.006.
Summerton, et al. Morpholino antisense oligomers: design, preparation, and properties.Antisense Nucleic Acid Drug Dev. Jun. 1997;7(3):187-95.
Summerton. Morpholino antisense oligomers: the case for an RNase H-independent structural type. Biochim Biophys Acta. Dec. 10, 1999;1489(1):141-58.
Sun, et al. Optimized TAL effector nucleases (TALENs) for use in treatment of sickle cell disease. Mol Biosyst. Apr. 2012;8(4):1255-63. doi: 10.1039/c2mb05461b. Epub Feb. 3, 2012.
Tahallah, et al. The effect of the source pressure on the abundance of ions of noncovalent protein assemblies in an electrospray ionization orthogonal time-of-flight instrument. Rapid Commun Mass Spectrom. 2001;15(8):596-601.
Tan, et al. Precision editing of large animal genomes. Adv Genet. 2012;80:37-97. doi: 10.1016/B978-0-12-404742-6.00002-8.
Tanaka, et al. Conformational variations in an infectious protein determine prion strain differences. Nature. Mar. 18, 2004;428(6980):323-8.
Tang, et al. Identification of 86 candidates for small non-messenger RNAs from the archaeon Archaeoglobus fulgidus. Proc Natl Acad Sci U S A. May 28, 2002;99(11):7536-41.
Tang, et al. Identification of novel non-coding RNAs as potential antisense regulators in the archaeon Sulfolobus solfataricus. Mol Microbiol. Jan. 2005;55(2):469-81.
Terns, et al. CRISPR-based adaptive immune systems. Curr Opin Microbiol. Jun. 2011;14(3):321-7. doi: 10.1016/j.mib.2011.03.005. Epub Apr. 29, 2011.
Terns, et al. The CRISPR-Cas system: small RNA-guided invader small RNA-guided invader silencing in prokaryotes. The FASEB J. 2012, vol. 26, Abstract 353.3.
UniProt Direct Submission D7BB61_MEISD. CRISPR-associated protein Cas6. May 16, 2012. [Retrieved from the Internet Oct. 24, 2013:<http://www.uniprot.org/uniproUD7BB61.txt?version=9> ]; in entirety.
Urnov, et al. Genome editing with engineered zinc finger nucleases. Nat Rev Genet. Sep. 2010;11(9):636-46. doi: 10.1038/nrg2842.
Urnov, et al. Highly efficient endogenous human gene correction using designed zinc-finger nucleases. Nature. Jun. 2, 2005;435(7042):646-51. Epub Apr. 3, 2005.
Van Den Heuvel, et al. Improving the performance of a quadrupole time-of-flight instrument for macromolecular mass spectrometry. Anal Chem. Nov. 1, 2006;78(21):7473-83.
Van Der Oost, et al. CRISPR-based adaptive and heritable immunity in prokaryotes. Trends Biochem Sci. Aug. 2009;34(8):401-7. doi: 10.1016/j.tibs.2009.05.002. Epub Jul. 29, 2009.
Van Til, et al. Lentiviral gene therapy of murine hematopoietic stem cells ameliorates the Pompe disease phenotype. Blood. Jul. 1, 2010;115(26):5329-37. doi: 10.1182/blood-2009-11-252874. Epub Apr. 12, 2010.
Vercoe, et al. Cytotoxic chromosomal targeting by CRISPR/Cas systems can reshape bacterial genomes and expel or remodel pathogenicity islands. PLoS Genet. Apr. 2013;9(4):e1003454. doi: 10.1371/journal.pgen.1003454. Epub Apr. 18, 2013.
Wang, et al. Genetic correction of β-thalassemia patient-specific iPS cells and its use in improving hemoglobin production in irradiated SCID mice. Cell Res. Apr. 2012;22(4):637-48. doi: 10.1038/cr.2012.23. Epub Feb. 7, 2012.
Wang, et al. One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.
Wang, et al. Reprogramming erythroid cells for lysosomal enzyme production leads to visceral and CNS cross-correction in mice with Hurler syndrome. Proc Natl Acad Sci U S A. Nov. 24, 2009;106(47):19958-63. doi: 10.1073/pnas.0908528106. Epub Nov. 10, 2009.
Wang, et al. Spatiotemporal control of gene expression by a light-switchable transgene system. Nat Methods. Feb. 12, 2012;9(3):266-9. doi: 10.1038/nmeth.1892.
Wang, et al. TALEN-mediated editing of the mouse Y chromosome. Nat Biotechnol. Jun. 2013;31(6):530-2. doi: 10.1038/nbt.2595. Epub May 12, 2013.
Westra, et al. Cascade-mediated binding and bending of negatively supercoiled DNA. RNA Biol. Sep. 2012;9(9):1134-8. doi: 10.4161/rna.21410. Epub Sep. 1, 2012.
Westra, et al. H-NS-mediated repression of CRISPR-based immunity in Escherichia coli K12 can be relieved by the transcription activator LeuO. Mol Microbiol. Sep. 2010;77(6):1380-93. doi: 10.1111/j.1365-2958.2010.07315.x. Epub Aug. 18, 2010.
Wiedenheft, et al. RNA-guided complex from a bacterial immune system enhances target recognition through seed sequence interactions. Proc Natl Acad Sci U S A. Jun. 21, 2011;108(25):10092-7. doi: 10.1073/pnas.1102716108. Epub May 2, 2011.
Wiedenheft, et al. RNA-guided genetic silencing systems in bacteria and archaea. Nature. Feb. 15, 2012;482(7385):331-8. doi: 10.1038/nature10886.
Wiedenheft, et al. Structural basis for DNase activity of a conserved protein implicated in CRISPR-mediated genome defense. Structure. Jun. 10, 2009;17(6):904-12. doi: 10.1016/j.str.2009.03.019.
Wiedenheft, et al. Structures of the RNA-guided surveillance complex from a bacterial immune system. Nature. Sep. 21, 2011;477(7365):486-9. doi: 10.1038/nature10402.
Xia, et al. Bioluminescence of Aequorea macrodactyla, a common jellyfish species in the East China Sea. Mar Biotechnol (NY). Mar. 2002;4(2):155-62.
Yahata, et al. Clonal analysis of thymus-repopulating cells presents direct evidence for self-renewal division of human hematopoietic stem cells. Blood. Oct. 1, 2006;108(7):2446-54. Epub Jun. 6, 2006.
Zhang, et al. cSSMD: assessing collective activity for addressing off-target effects in genome-scale RNA interference screens. Bioinformatics. Oct. 15, 2011;27(20):2775-81. doi: 10.1093/bioinformatics/btr474. Epub Aug. 16, 2011.
Zhou, et al. Mouse model for the lysosomal disorder galactosialidosis and correction of the phenotype with overexpressing erythroid precursor cells. Genes Dev. Nov. 1, 1995;9(21):2623-34.

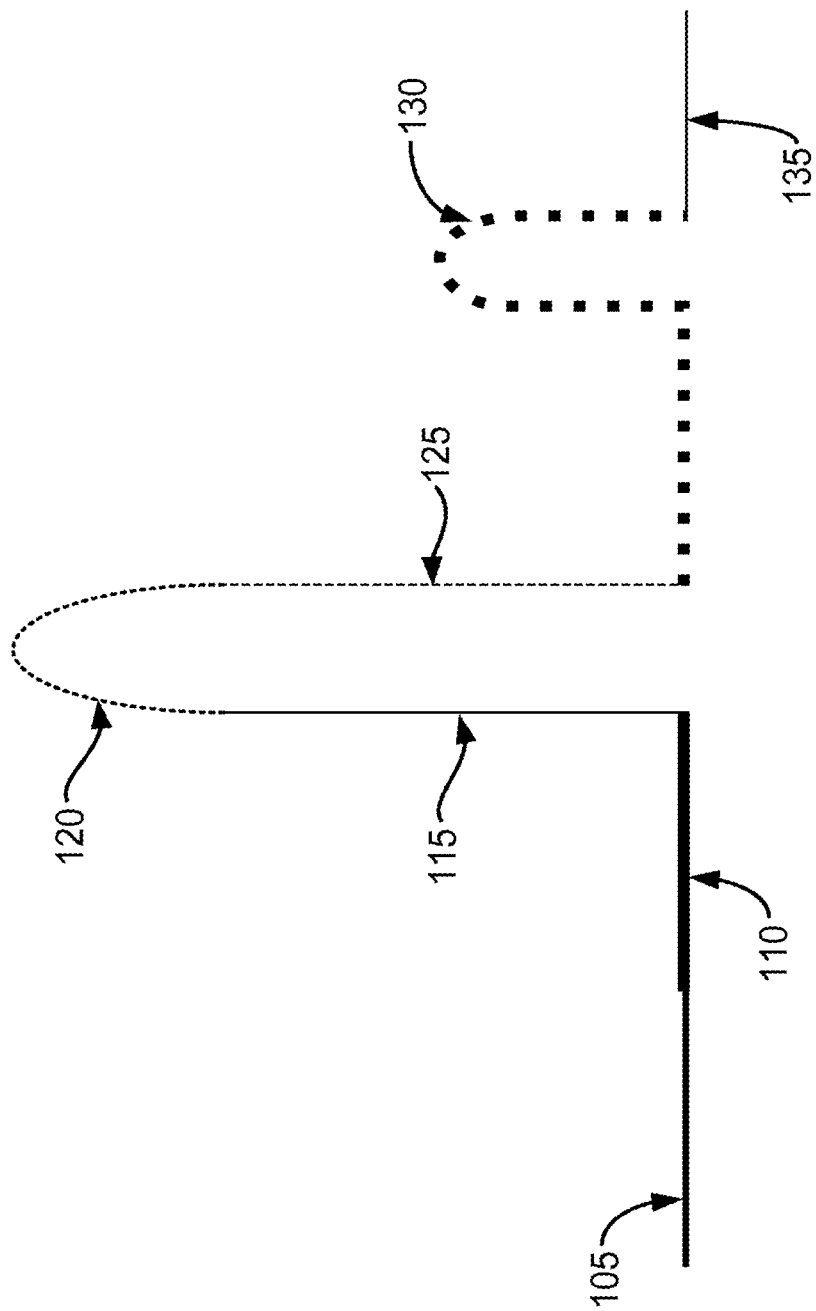

5'-GUUUAG-AGCUAUGCUGUUUUGAAUGGUCCCAAAAC-3' – crRNA repeat sequence

3'-UAAAAUUGAACGAUACGACAAAACUUACCAAGGUUGUU-5' – tracrRNA sequence

FL- TRACR-CRRNA
Sequence

```
        G U U U U A G   A   G C U A U G C U G U U U G G   A
        | | | | | |     |   | | | | | | | | | | | | | |   A
       A U A A A A U U       C G A U A C G A C A A A A C
      A             G A A                               A
       A
        G G C U A G U C C G U U A U C A A C U U G   A
                                        | | | |     A
                                        G A A A
                                        U G G C A C C G A
                                        | | | | | | | | G
                                        A C C G U G G C U

G U U U U A G   A   G C U A G   A
        | | | | | |     |   | | | |     A
       A U A A A A U U       C G A U A
      A             G A A              A
       A
        G G C U A G U C C G
```

Duplex Variants Group 1

FL- TRACR-CRRNA Sequence

```
          G U U U U A G  A   G C U A U G C U G U U U U G G A
          | | | | | |        | | | | | | | | | | | | | |   A
        A U A A A A U U G A A C G A U A C G A C A A A A C A A
        A
          G G C U A G U C C G U U A U C A A C U U G A
                                            | | |     A
                                            G A A A
                                                U G G C A C C G A
                                                | | | | | | | | | G
                                                A C C G U G G C U
```

Duplex Variants Group 2

FL- TRACR-CRRNA Sequence

```
           G U U U U A G  A  G C U A U G C U G U U U G G G
           | | | | | |       | | | | | | | | | | | | |   A
         A U A A A A U U G A A C G A U A C G A C A A A A C A
         A                                                A
          G G C U A G U C C G U U A U C A A C U U G
                                              | | |   A
                                              G A A A
                                                    A
                                              U G G C A C C G A
                                              | | | | | | | | |
                                              A C C G U G G C U  G
```

Tracr Variants – Group 1

TIGR01865: cas_Csn1
CRISPR-associated protein Cas9/Csn1, subtype II/NMEMI
CRISPR loci appear to be mobile elements with a wide host range. This model represents a protein found only in CRISPR-containing species, near other CRISPR-associated proteins(cas), as part of the NMENI subtype of CRISPR/Cas locus. The species range so far for this protein is animal pathogens and commensals only [Mobile and extrachromosomal element functions, Other].

⊞ Links
⊞ Statistics
⊞ Structure

PubMed References

A DNA repair system specific for thermophilic Archaea and bacteria predicted by genomic context analysis. *Nucleic Acids Res.* 2002 Jan 15;30(2):482-496

TIGR01865 is classified as a model that may span more than one domain.
TIGR01865 is not assigned to any domain superfamily.

Sequence Alignment

Reformat  Format: Hypertext  Row Display: All 12 rows  Color Bits: 3.0 bit  Type Selection: top listed sequences  ☑ Include consensus sequence

```
                     10        20        30        40        50        60        70        80
                      *         *         *         *         *         *         *         *
consensus     1  EYILGLDIGIASVGWAIVEDDYKVPAAKRLIDGG------VRNFTGAELPKTGETAAIDRRLARGARRIRRKHRLLRL   74
gi 22533915   4  PYSIGLDIGTNSVGWSIITDDYKVPAKKMRVLGNtdkeyiKKNLIGALLFDGGNTAA--DRRLKRTARRYTRRNRILYL   82
gi 34483507   3  ERILGVDLGISSLGWAIVEYDKDDEAANRIIDCG------VRLFTAAETPKKKESPNKARREARGIRRVLNRRVRMNMI   76
gi 12721472   7  SYILGLDLGIASVGMAVVEINEN-EDPIGLIVG-------VRIFERAEVPKTGESLAISRRLARSTRRLIRRAHRLLLA   79
gi 24377777   4  PYSIGLDIGTNSVGMAVVTDDYKVPAKKMKVLGNtdkshiEKNLLGALLFDSGNTAE--DRRLKRTARRYTRRNRILYL   82
gi 13622193   4  KYSIGLDIGTNSVGMAVITDEYKVPSKKFFKVLGNtdrhsiKKNLIGALLFDSGETAE--ATRLKRTARRYTRRNRICYL   82
gi 41815893   7  DYFLGLDVGTGSVGMAVTDTDYKLLKANR---------KDLWGMRCFETAETAE--VRRLHRGARRIERRKKRKLL    73
gi 218767588 10  NYILGLDIGIASVGMAVEIDEDEN-PICLIDIG------VRVFERAEVPKTGDSLAmARRLARSVRRLTRRRAHRLLRA   82
gi 157150687  3  GIVLGLDIGIASVGVGILEKDT-----------GK----IIHASSRLFPAATADNNvERRSNRQGRRLNRKKHHRSVRL   66
gi 294660600 10  EVTIGLDLGVGSVGMAIVDNETN---------------IIHHLGSRLFSQAKTAE--DRRSFRGVRRLIRRRKYKLKRF   71
gi 218563121  2  ARILAFDIGISSIGWAFSENDE--------LKDCG----VRIFTKVENPKTGESLAIPRRLARSARKLARKARLNHL    68
gi 370792169  7  PYTIGLDIGTNSVGWAVLTDQYDLVKRKMKIAGDsekkqiKKNFWGVRLFDEGQTAA--DRRMARTARRIERRNRISYL   85
                  xxxxxxxxxxxxxxxxxxxx                                   xxxxxxxxxxxxxxxxxxxxxxx
```

*FIG. 35*

```
                         90         100        110        120        130        140        150        160
                          *          *          *          *          *          *          *          *
consensus         75 QELFSREGSLITDEFFsrlENSPlVEEDKRN------------------------------------TIYHLRKAALENKLKPDE--LYLALLH 130
gi 225339915      83 QEIFAEEMSKVDDSFFhrLEDSFlVEEDKRGskypifatlq--eekdyhekfSTIYHLRKELADKKEKADLrlIYIALAH 160
gi 34483507       77 KKLFLRAGLIQDVDLD--GEGGMFYSKANRA-----------------------------------DVWELRHDGLYRLLKGDE--LARVLLH 130
gi 12721472       80 KRFLKREGILSTIDLEk----gLPNQA-------------------------------------------WELRVAGLERRLSAIE--WGAVLLH 125
gi 24377777       83 QEIFSEEMGKVDDSFFhrLEDSFlVTEDKRGerhpifgnle--eevkyhenfpTIYHLRQYLADNPEKVDLrlVYLALAH 160
gi 13622193       83 QEIFSNEMAKVDDSFFhrLEESFlVEEDKKHerhpifgniv--devayhekypTIYHLRKKLVDSTDKADLrlIYLALAH 160
gi 41815893       74 QELFSQEIAKTDEGFFqrMKESPFYAEDKTIlqentlindkdfadktyhkaypTINHLIKAWIENKVKPDPrilYLACHN 153
gi 218767588      83 RRLLKREGVLQAADFDenGLIKSLP------N----------------------------------TPWQLRAAALDRKLTPLE--WSAVLLH 133
gi 157150687      67 QDLFEGYGLLTDFSKVsmNLN-------------------------------------------PYQLRVQGMENQLTNEE--LFVALKN 111
gi 294660600      72 VNLIWKYNSYFGFKNKedILNNYQBQQKLHN---------------------------------TVLNLKLEALNAKIDPKA--LSWILHD 127
gi 218563121      69 KHLIANEFKLNYEDYQsfDESLAKAYKGSLI--------------------------------SPYELRFRALNELLSKQD--FARVILH 124
gi 370792169      86 QGIFAEEMSKTDANFFcrLSDSFYVDNEKRNsrhpfifatie--eeveyhknypTIYHLREELVNSSEKADLrlVYLALAH 163
                     XXXXXYXXXXXXXXXX                                                  YYYXXXXXXXXXXXX XXXXXXY 170        180        190        200        210        220        230        240
                          *          *          *          *          *          *          *          *
consensus        131 IIKHRGHFLIEGNDfdtAN------------------------------------------------------------ 149
gi 225339915     161 IIKHRGFLIEDDSfdvRNtdiskqvqdfleifnttfenndilsqnvdveailtdkisksakkdrilaqypnqkstgifa 240
gi 34483507      131 IAKHRGYKFIGDDE---AD---------------------------------------------------------- 146
gi 12721472      126 LIKHRGYLSKRKNEsqtNN---------------------------------------------------------- 144
gi 24377777      161 IIKFRGHFLIEG-KfdtRNndvqrlfqeflavydntfensslgeqnvqveeiltdkisksakkdrvlklifpneksngrifa 239
gi 13622193      161 MIKFRGHFLIEG-DlnpDNsdvdklfiqivqtynqlfeenpinasgvdakailsarlsksrrlenliaqipgeknglifg 239
gi 41815893      154 IIKKRGHFLFEG-DfdsENqfdtsiqalfeylredmevdidadsqkvkeilkdssiknsekqsrinkilgikpsdkgkka 232
gi 218767588     134 LIKHRGYLSQRKNEgetAD---------------------------------------------------------- 152
gi 157150687     112 IVKRRGISYLDDASedgGT---------------------------------------------------------- 130
gi 294660600     128 YLKNRGYFYEDNRDfnvYP---------D------------------------------------------------- 146
gi 218563121     125 IAKRRGYDDIKNSD-----D----------------------------------------------------------- 139
gi 370792169     164 IIKYRGNFLIEG-AldtQNtsvdgiykqfiqtynqvfasgiedgelkkledkdvakilvekvtrkeklerilklypgek 242
                     XXXYYYXXXXXX X       X
```

FIG. 35
*(Continued)*

```
                    250        260        270        280        290        300        310        320
                     *          *          *          *          *          *          *          *
consensus       150  ------------------------------------------------------------------------------KET  152
gi 22533915     241  efiki------ivgnqadfkkyfniedktplqfakdsyededlenliggigdefadifsaakklydsvllsgiltvidLST  314
gi 34483507     147  ----------------------------------------------------------------------------EES  149
gi 12721472     145  --------------------------------------------------------------------------KEL  147
gi 24377777     240  efiki------ivgnqadfkhfeieekaplqfskdtyeeelevliagiqgnyaelfisaakklydsillsgiltvtdVGT  313
gi 13622193     240  nliai------siglfpnfksnfdiaedakiqlskdtyddldnliaqigdqyadiflaaknisdailsdilrvntEIT  313
gi 41815893     233  itnl------isgnkinfadlydnpdikdaeknsifskddfdalsdlasilgdsfellikakavyncsvlskvIGD  304
gi 218767588    153  --------------------------------------------------------------------------KEL  155
gi 157150687    131  ---------------------------------------------------------------------------VS  132
gi 294660600    147  ----------------------------------------------------------------------------T-  147
gi 218563121    140  -------------------------------------------------------------------------KEK  142
gi 370792169    243  sagmfaqfislivgskgnfqkpfdlieksdiecakdsyeedleslialigdeyaelfvaaknaysavvlssiitvaeTET  322

330        340        350        360        370        380        390        400
                     *          *          *          *          *          *          *          *
consensus       153  GALLSAVMINRYLEHEADLRTLKELILKKFPKKYKElfse-------------------------------------  192
gi 22533915     315  KAPLSASMIQRYDEHREDLKQLKQFVKASLPEKYQEifadsskdgyagyleqktnqeafyk----------------  375
gi 34483507     150  GKVKKAGVVLRQNFEAAGCRFVGEWLWRERGANGKK----------------------------------------  185
gi 12721472     148  GALLSGVAQNHQLLQSDDYRTPAELALKKFAKEEGHi---------------------------------------  184
gi 24377777     314  KAPLSASMIQRYNEHQMDLAQLKQFIRQKLSDKYNEvfsdvskdgyagyidgktnqeafyk---------------  374
gi 13622193     314  KAPLSASMIKRYDEHHQDLTLLKAVFRQQLPEKYKEifdqskngyagyidggasqeefyk----------------  374
gi 41815893     305  EQYLSFAKVKIYEKHKTDLTKLKNVIKKHHFPKDYKKvfgynkneknnnysgyvgvcktkskkliinnsvnqedfykflk  384
gi 218767588    156  GALLKGVADNAHALQTGDFRTPAELALNKFEKESGHi---------------------------------------  192
gi 157150687    133  SDYGKAVEENRKLLAEKTPGQIQLERFEKYGOLRGDftv-------------------------------------  171
gi 294660600    148  EELANYFDEFGYYKGIIDSKNDDDDKLEEGLTKYKFsngh------------------------------------  187
gi 218563121    143  GAILKA--IKQNEEKLANYQSVGEYLYKEYFQKFKEnske------------------------------------  180
gi 370792169    323  KANLSASMIERFDTHEEDLGELKAFIKILHLPKHYEEifsntehgyagyidgktkqadfyk---------------  383
                     XXXXXXXX XXXXXXXXXXXXXXXXXXXXXXXXXXXXXXXX
```

```
consensus      292                                                                                                                      353
gi 225333915   522 LNELNNVR----IIILeQGETKILSKEEKQELLDLLFKKKIITYKKLRKLLGLSEDAIFKGLRYEG----------------------------                         582
gi 344834507   270 YNELFKVR----YKNE-QGETYFFDSNIKQEIFDGVFKEHRKVSKKKLLDFLAKEYEEFRIVDVIG---------------------------                         346
gi 127214472   272 ISKFFSTV----IIDNeGWEQKIIERKTLEELLDFAVSREKVEFRHLRKFLDLSDNEIFKGLHYKGkpktakkreatlfdp                                       330
gi 243777777   521 LTKLNN------LRILeDGAERALNEEERQLLINHPYEKSKLTYAQVRKLLGLSEQAIFKNLRYS---------------------------                          581
gi 136222193   521 YNELTKVK----YKTE-QGKTAFFDANMKQEIFDGVFKVYRKVTKDKLMDFLEKEFDEFRIVDLTG----------------------------                        582
gi 418158893   545 YVTEgMRKPAFLSGEQRKAIVDLLFKTNRKVTVKQLKEDYFKKIECFDSVEISG------------------------                                        603
gi 218767588   280 LNEINNLQ----IIID---GKNICDIKLKQKIYEDLFKKYKKITQKQISTFIKHEGICNKTDEVII--------------------------                          338
gi 157150687   281 LTKLNN------LRILeQGSERPLTDTERATLMDEPYRKSKLTYAQARKLLGLEDTAFFKGLRY-G---------------------------                         338
gi 294660600   282 -----LNDL---NNLTvPTETKKLSEEQKKLIIEYAKSAKTLGASTLLKYIAKMIDASVDQIRGYR---------------------------                         360
gi 218563121   268 INELSTIRsysIYLTgWFINQEFKKAYLNKLLDLLIKTNSEKPIDARQFKKLREETIAESIGKETikdveseeklek-dd                                       323
gi 370792169   530 LTRIINL-----LNNLKNTEGILYTKDDINALLNEVLKNGTLTFYKQTKKLLGLSDDYEFKG------------------------                                589
                    YNELTKVR----YIND-QGKTSYFSGQEKEQIFNDLFQKRKVK--KKDLELFLRNMSHVESPTIEG--------------------------

650          660          670          680          690          700          710          720
                    *            |            *            |            *            |            *            |            * consensus      354                            XXXXXXXXXXXXXXXXXXXXXX       XXX                  XXX                                    407
gi 225333915   583 -------------LDNAEKAFNISLKTYHLKRKAlgDKDLLDn------PKNPKDLDELVKILTLYKDREm---------------iK        635
gi 344834507   347 -------------LDKENKAFNASLGTYHDLEKIL-DKDFLDn------PDNESILEDIVQLTLFEDREm---------------iK        407
gi 127214472   331 neptelefdKVEAEKKAWISLRGAAKLREAlgNEFYGRf--------VALGKHADEATKILTYYKDEG----------------Q          386
gi 243777777   582 -------------KENAESATFMELKAWHAIRKAleNQGLKDtwqdiAKKPDLLDEIGTAFSLYKTDE----------------D          634
gi 136222193   583 -------------LDKENKVFNASYGTYHDLCKIL-DKDFLDn------SKNEKILEDIVLTLTLFEDREm---------------iR        633
gi 418158893   604 -------------VEDR---FNASLGTYHDLLKIINEL--KNIF-GKQVDe------EENEDILEDIVLTLTLFEDREm--------iE        658
gi 218767588   339 -------------LGID-KECT3SLKSYIELKNIF-GKQVDe------ISTKNMLEEIIRWATIYDEGEgkt---------------ilkT    394
gi 157150687   339 -------------KDNAEASTLMEMKAYHAISRALeKEGLKDkkspINLSPELQDEIGTAFSLFKTDE-----------D               390
gi 294660600   361 hkwklkgikLNTNGKIQYNDLSSLAKFVHKLKQHLKLDflieDQYTPLDKINFLQSLYVYLGKHlrysnrvdsanlkefS               440
gi 218563121   324 -------------EKGTYFIEFKKYKEFIKAlgEHNL-------------SQDDLNEIAKDITLIKDEi--------------K         367
gi 370792169   590 LEDS---------FNSSYSTYHDLLIKVGiKQEIlDn------PVNTEMLENIVKILTVFEDKRm---------------iK           640
                                 X                 XXXXXXXYYYYXXXX      XXX       XXXXXXXXXXXXXYYXXXX                         X
```

```
                  890        900        910        920        930        940        950        960
                   *          *          *          *          *          *          *          *
consensus    531  FGKRNSKERYKKNEDKIKEFASALGKEILKEEPtensSKNILKLRLYYQQNGKCMYTGKEIDIDdl-fDLSYYEIDHILP  609
gi 22533915  773  QGRRNSRQRYKLLDDGVKNLASDLNGNILKEYPTdnqALQNERLFLYYLQNGRDMYTGEALDID----NLSQYDIDHIIP  848
gi 34483507  523  GEIEDIKESQRKNEKERKEAADWIAETSFQVPLT---RKNILKKRLYIQQDGRCAYTGDVIELErl-fDEGYCEIDHILP  598
gi 12721472  505  FKERREIQKQQEDNRTKRESAVQKFKELFSDFSSepkSKDILKFRLYEQQHGKCLYSGKEINIHrl-nEKGYVEIDHALP  583
gi 24377777  772  QGRRNSQQRFLKGLTDSIKEFGS-----QILKEHPVensQLQNDRLFLYLQNGRDMYTGEELDID----YLSQYDIDHIIP  843
gi 13622193  772  KGQKNSRERMKRIEEGIKELGS-----QILKEHPVentQLQNEKLYLYLYLQNGRDMYTGEELDID----YLSQYDIDHIIP  843
gi 41815893  804  TRLKILQDLYNNCKNDADAFSSEIKDLSGKIENEdnlRLRSDKLYLYLYTQLGKCMYCGKPIEIGhv-fDTSNYDIDHIYP  882
gi 218767588 513  FKDRKEIEKRQEENRKDREKAAAKFREYFPNFVGepkSKDILKLRTKIRLMHQQGEKCLYSGKEINLGrl-nEKGYVEIDHALP  591
gi 157150687 522  YIKRQKANQDEKNAAMEKAAFQYNGKKELPDNIFhghKELTTKIRLMHQQGEKCLYTGKNIPISdlihNQKYEIDHILP  601
gi 294660600 594  ENTKNYKLIKKNGDKISEGLKALGIAEDKIEEIlkePTKSYKVLLMLQQDHIDPYSQKEIAFDdiltKTEKTEIDHIIP  673
gi 218563121 488  -HSQRAKIEKEQNENYKAKKDAELECEKLGLKIN---SKNILKLRLFKEQKEFCAYSGEKIKISdl-qDEKMLEIDHIYP  562
gi 370792169 778  KGKNNSRPRYKSLEKAIKEFGS----------QILKEHPTdnqELRNNRLYLYLQNGKDMYTGQDLDIH----NLSNYDIDHIVP  849
                  XXXXXXXX                  XXXXXXX                                  XXXXXYYYYXY 970        980        990       1000       1010       1020       1030       1040
                   *          *          *          *          *          *          *          *
consensus    610  QSRSFDDSISNKVLVLASENQEKGDQTPYEaEIvkkDSAFWNKFEAYVLISKR-----------KSDKLT----RAERGGL  675
gi 22533915  848  QAFIKDDSIDNRVLVSSAKNRGKSDDVPSL-EIVkdCKVFWKKLLDAKLMSQR-----------KYDNLT----KAERGGL  913
gi 34483507  599  RSRSADDSFANKVLCLARANQQKTDRTPYEwFGH--DAARWNAFETRTSAPSN-----------RVRTCKgkidRLLKKNF  666
gi 12721472  584  FSRTWDDSFNNKVLVLASENQEKGNQTPYEwLQGkinSERWKNFVALVLGSQC-----------SAAKKQ----RLLTQVI  649
gi 24377777  844  QAFIKDNAIDNRVLTSSKENRGKSDDVPSK-DVVrkMKSYWSKLLSAKLITQR-----------KFDNLT----KAERGGL  908
gi 13622193  844  QSFLKDDSIDNKVLTRSDKNRGKSDNVPSE-EVVkkMKNYWRQLLNAKLITQR-----------KFDNLT----KAERGGL  908
gi 41815893  883  QSKIKDDSISNRVLVCSSCNKNKEDKYPLKsEIQskQRGFWNFLQRNNFISLE-----------KLNRLT----RATP--I  946
gi 218767588 592  FSRTWDDSFNNKVLVLGSENQNKGNQTPYEyFNGkdNSREWQEFFKARVETSRF----------PRSKKQ----RILLQKF  657
gi 157150687 602  LSLSFDDSLSNKVLVLATANQEKGQRTPFQaLDSmdDAWSYREFKSYVKDSKL-----------LSNKKKdy-lLTBEDIS  670
gi 294660600 674  YSISFDDSSNKLLVLAESNQAKSNQTPYEFINSgkAEITWEVYEAYCHKFKNgdssl1dstgRSKKFA-----KMMKTDT  749
gi 218563121 563  YSRSFDDSYMNKVLVFTKQNQEKLNQTPFEaFGN--DSAKWQKIEVLAKNLPT-----------KKQK-----RILEKNY  624
gi 370792169 850  QSFITDNSIDNLVLTSSAGNREKGDDVPPL-EIVrkRKVFWEKLYQGNLMSKR-----------KFDYLT----KAERGGL  914
                  XYXXXXYYYYYXYYYYYXYXYXXYX  XXX   XXXXXXXXXXXXXXXXXX              XXXX       X
```

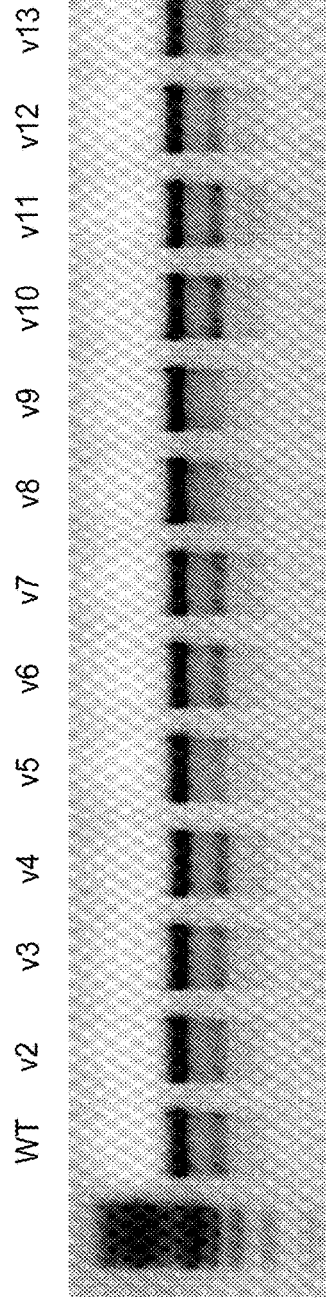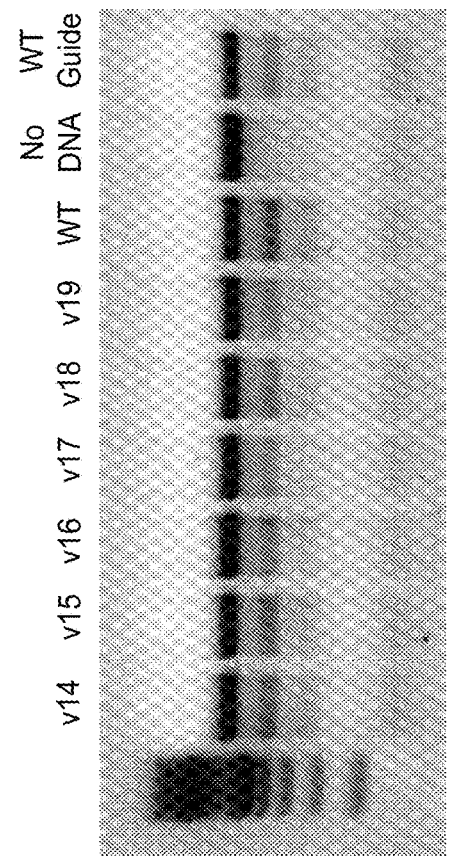
FIG. 36

Csy4 sequence

>gi|107101871|ref|ZP_01365789.1| hypothetical protein PaerPA_01002916 [Pseudomonas aeruginosa PACS2]
MDHYLDIRLRPDPEFPPAQLMSVLFGKLHQALVAQGGDRIGVSFPDLDESRSRLGERLRIHASADDIRALLARPWLEGLRDHLQFGEPAVVPHPTPYRQVS
RVQVKSNPERLRRRLMRRHELSEEEARKRIPDTVARALDLPFVTLRSQSTGQHFRLFIRHGPLQVTAEEGGFTCYGLSKGGFVPWF >gi|254235433|ref|ZP_04928756.1| hypothetical protein PACG_01340 [Pseudomonas aeruginosa C3719]
MDHYLDIRLRPDPEFPPAQLMSVLFGKLHQALVAQGGDRIGVSFPDLDESRSRLGERLRIHASADDLRAL
LARPWLEGLRDHLQFGEPAVVPHPTPYRQVSRVQAKSNPERLRRRLMRRHDLSEEEARKRIPDTVARTLD
LPFVTLRSQSTGQHFRLFIRHGPLQATAEEGGFTCYGLSKGGFVPWF >gi|254240857|ref|ZP_04934179.1| hypothetical protein PA2G_01531 [Pseudomonas aeruginosa 2192]
MDHYLDIRLRPDPEFPPAQLMSVLFGKLHQALVAQGGDRIGVSFPDLDESRSRLGERLRIHASADDLHAL
LARPWLEGLRDHLQFGEAAVVPHPTPYRQVSRVQAKSNPERLRRRLMRRHDLSEEEARKRIPDTVARTLD
LPFVTLRSQSTGQHFRLFIRHGPLQATAEEGGFTCYGLSKGGFVPWF

*FIG. 38*

His29Ala

```
  1 mdhyldirlr pdpefppaql msvlfgklaq alvagggdri gvsfpdldes rsrlgerlri
 61 hasaddlral larpwleglr dhlqfgepav vphptpyrqv srvqvksnpe rlrrrlmrrh
121 dlseeearkr ipdtvarald lpfvtlrsqs tgqhfrlfir hgplqataee ggftcyglsk
181 ggfvpwf
```

His29Ala/Ser50Cys

```
  1 mdhyldirlr pdpefppaql msvlfgklaq alvagggdri gvsfpdldec rsrlgerlri
 61 hasaddlral larpwleglr dhlqfgepav vphptpyrqv srvqvksnpe rlrrrlmrrh
121 dlseeearkr ipdtvarald lpfvtlrsqs tgqhfrlfir hgplqataee ggftcyglsk
181 ggfvpwf
```

FIG. 39

Csy4 sequences
<213>     Pseudomonas aeruginosa
Met Asp His Tyr Leu Asp Ile Arg Leu Arg Pro Asp Pro Glu Phe Pro
Pro Ala Gln Leu Met Ser Val Leu Phe Gly Lys Leu His Gln Ala Leu
Val Ala Gln Gly Gly Asp Arg Ile Gly val Ser Phe Pro Asp Leu Asp
Glu Ser Arg Ser Arg Leu Gly Glu Arg Leu Arg Ile His Ala Ser Ala
Asp Asp Leu Arg Ala Leu Leu Ala Arg Pro Trp Leu Glu Gly Leu Arg
Asp His Leu Gln Phe Gly Glu Pro Ala Val Val Pro His Pro Thr Pro
Tyr Arg Gln Val Ser Arg Val Gln Val Lys Ser Asn Pro Glu Arg Leu
Arg Arg Arg Leu Met Arg Arg His Asp Leu Ser Glu Glu Glu Ala Arg
Lys Arg Ile Pro Asp Thr val Ala Arg Ala Leu Asp Leu Pro Phe Val
Thr Leu Arg Ser Gln Ser Thr Gly Gln His Phe Arg Leu Phe Ile Arg
His Gly Pro Leu Gln val Thr Ala Glu Glu Gly Gly Phe Thr Cys Tyr
Gly Leu Ser Lys Gly Gly Phe Val Pro Trp Phe <213>     Pseudomonas aeruginosa
Met Asp His Tyr Leu Asp Ile Arg Leu Arg Pro Asp Pro Glu Phe Pro
Pro Ala Gln Leu Met Ser Val Leu Phe Gly Lys Leu His Gln Ala Leu
Val Ala Gln Gly Gly Asp Arg Ile Gly val Ser Phe Pro Asp Leu Asp
Glu Ser Arg Ser Arg Leu Gly Glu Arg Leu Arg Ile His Ala Ser Ala
Asp Asp Leu Arg Ala Leu Leu Ala Arg Pro Trp Leu Glu Gly Leu Arg
Asp His Leu Gln Phe Gly Glu Pro Ala Val Val Pro His Pro Thr Pro
Tyr Arg Gln Val Ser Arg Val Gln Ala Lys Ser Asn Pro Glu Arg Leu
Arg Arg Arg Leu Met Arg Arg His Asp Leu Ser Glu Glu Glu Ala Arg
Lys Arg Ile Pro Asp Thr Val Ala Arg Thr Leu Asp Leu Pro Phe Val
Thr Leu Arg Ser Gln Ser Thr Gly Gln His Phe Arg Leu Phe Ile Arg
His Gly Pro Leu Gln Ala Thr Ala Glu Glu Gly Gly Phe Thr Cys Tyr
Gly Leu Ser Lys Gly Gly Phe Val Pro Trp Phe <213>     Pseudomonas aeruginosa
Met Asp His Tyr Leu Asp Ile Arg Leu Arg Pro Asp Pro Glu Phe Pro
Pro Ala Gln Leu Met Ser Val Leu Phe Gly Lys Leu His Gln Ala Leu
Val Ala Gln Gly Gly Asp Arg Ile Gly Val Ser Phe Pro Asp Leu Asp
Glu Ser Arg Ser Arg Leu Gly Glu Arg Leu Arg Ile His Ala Ser Ala
Asp Asp Leu His Ala Leu Leu Ala Arg Pro Trp Leu Glu Gly Leu Arg
Asp His Leu Gln Phe Gly Glu Ala Ala Val Val Pro His Pro Thr Pro
Tyr Arg Gln Val Ser Arg Val Gln Ala Lys Ser Asn Pro Glu Arg Leu
Arg Arg Arg Leu Met Arg Arg His Asp Leu Ser Glu Glu Glu Ala Arg
Lys Arg Ile Pro Asp Thr Val Ala Arg Thr Leu Asp Leu Pro Phe Val
Thr Leu Arg Ser Gln Ser Thr Gly Gln His Phe Arg Leu Phe Ile Arg
His Gly Pro Leu Gln Ala Thr Ala Glu Glu Gly Gly Phe Thr Cys Tyr
Gly Leu Ser Lys Gly Gly Phe val Pro Trp Phe

*FIG. 40*

Cas6 sequences

Thermus thermophilus HB8
Met Val Leu Ala Ala Leu Val Leu Val Leu Glu Gly Glu Gly Leu Pro
Glu Pro Leu Gly Leu Arg Gly Phe Phe Tyr Gly Leu Leu Arg Glu Val
Ala Pro Glu Val His Asp Gln Gly Glu Asn Pro Phe Ala Leu Gly Phe
Gly Gly Arg Glu Gly Ala Ala Trp Ala Arg Val Ser Leu Leu Val Glu
Gly Leu Tyr Ala Arg Leu Ala Pro Arg Leu Tyr Ala Leu Glu Gly Glu
Glu Val Arg Leu Gly Pro Pro Phe Arg Val Arg Ala Val Leu Gln Glu
Gly His Pro Trp Ala Gly Val Ser Thr Tyr Pro Arg Leu Phe Gln Gly
Pro Pro Ser Arg Asp Leu Ala Leu Arg Phe Ala Ser Pro Thr Phe Phe
Arg Arg Lys Gly Val His Tyr Pro Val Pro Glu Pro Arg Leu Val Leu
Glu Ser Leu Leu Arg Arg Leu Glu Ala Phe Gly Pro Leu Lys Ala Pro
Glu Gly Val Arg Glu Ala Leu Leu Glu Arg Thr Thr Val Arg Ser Leu
Glu Gly Arg Thr Leu Pro Ala Arg Thr Glu Val Asp Thr Ala Gly Phe
Val Gly Arg Val Val Tyr His Leu Pro Arg Ala Thr Glu Glu Glu Ala
Leu Trp Leu Ser Ala Leu Gly Arg Phe Ala Phe Tyr Ser Gly Val Gly
Ala Lys Thr Ser Leu Gly Tyr Gly Arg Ala Arg Ala Glu Ser Ala Thermus thermophilus HB8
Met Pro Gln Ala Val Val Leu Glu Leu Val Gly Glu Lys Pro Pro Leu
Tyr Pro Ala Arg Tyr Ala His Gly Leu Phe Phe Ala Leu Leu Ser Arg
Val Ser Pro Glu Leu Ala Gln Lys Leu His Glu Ala Pro Arg Lys Pro
Phe Thr Leu Ala Pro Leu Pro Arg Ala Gly Pro Glu Gly Ala Thr Leu
Lys Gly Thr Leu Arg Leu Arg Leu Thr Thr Leu Asp Asp Gly Leu Phe
Ala Pro Phe Leu Arg Ala Leu Leu Glu Ala Ala Pro Asp Gly Leu Pro
Leu Gly Asp Ser Ser Tyr Arg Leu Ala Arg Val Leu Ala Thr Arg Glu
Gly His Pro Leu Ala Gly Ala Thr Ser Trp Glu Glu Leu Lys Glu Ala
Pro Lys Arg Glu Lys Ala Thr Phe Arg Phe Leu Thr Pro Thr Val Phe
Ala Thr Ser Lys Pro Gly Gly Arg Thr Arg Tyr Thr Pro Leu Pro Asp
Pro Arg Leu Ile Ala Gly Ser Leu Leu Asp Lys Trp Gln Ala His Ser
Pro Phe Pro Tyr Asn Pro Lys Glu Glu Ala Ala Leu Arg Glu Leu Phe
Glu Leu Asp Leu Glu Val Ala Gly Phe Arg Asn Leu Arg Phe His Arg
Val Gln Ala Gly Lys Gly Phe Phe Pro Gly Phe Thr Gly Glu Ala Thr
Leu Arg Leu Trp Ser Gln Ser Leu Glu Ala Gln Glu Ala Leu Gly Arg
Leu His Ala Leu Ala Phe Phe Ser Gly Val Gly Ala Lys Thr Pro Tyr
Gly Met Gly Leu Ala Val Pro Leu

*FIG. 41A*

Cas6 sequences

Staphylococcus epidermidis RP62A
Met Ile Asn Lys Ile Thr Val Glu Leu Asp Leu Pro Glu Ser Ile Arg
Phe Gln Tyr Leu Gly Ser Val Leu His Gly Val Leu Met Asp Tyr Leu
Ser Asp Asp Ile Ala Asp Gln Leu His His Glu Phe Ala Tyr Ser Pro
Leu Lys Gln Arg Ile Tyr His Lys Asn Lys Lys Ile Ile Trp Glu Ile
Val Cys Met Ser Asp Asn Leu Phe Lys Glu Val Val Lys Leu Phe Ser
Ser Lys Asn Ser Leu Leu Leu Lys Tyr Tyr Gln Thr Asn Ile Asp Ile
Gln Ser Phe Gln Ile Glu Lys Ile Asn Val Gln Asn Met Met Asn Gln
Leu Leu Gln Val Glu Asp Leu Ser Arg Tyr Val Arg Leu Asn Ile Gln
Thr Pro Met Ser Phe Lys Tyr Gln Asn Ser Tyr Met Ile Phe Pro Asp
Val Lys Arg Phe Phe Arg Ser Ile Met Ile Gln Phe Asp Ala Phe Phe
Glu Glu Tyr Arg Met Tyr Asp Lys Glu Thr Leu Asn Phe Leu Glu Lys
Asn Val Asn Ile Val Asp Tyr Lys Leu Lys Ser Thr Arg Phe Asn Leu
Glu Lys Val Lys Ile Pro Ser Phe Thr Gly Glu Ile Val Phe Lys Ile
Lys Gly Pro Leu Pro Phe Leu Gln Leu Thr His Phe Leu Leu Lys Phe
Gly Glu Phe Ser Gly Ser Gly Ile Lys Thr Ser Leu Gly Met Gly Lys
Tyr Ser Ile Ile Mycobacterium tuberculosis H37Rv
Met Ala Ala Arg Arg Gly Gly Ile Arg Arg Thr Asp Leu Leu Arg Arg
Ser Gly Gln Pro Arg Gly Arg His Arg Ala Ser Ala Ala Glu Ser Gly
Leu Thr Trp Ile Ser Pro Thr Leu Ile Leu Val Gly Phe Ser His Arg
Gly Asp Arg Arg Met Thr Glu His Leu Ser Arg Leu Thr Leu Thr Leu
Glu Val Asp Ala Pro Leu Glu Arg Ala Arg Val Ala Thr Leu Gly Pro
His Leu His Gly Val Leu Met Glu Ser Ile Pro Ala Asp Tyr Val Gln
Thr Leu His Thr Val Pro Val Asn Pro Tyr Ser Gln Tyr Ala Leu Ala
Arg Ser Thr Thr Ser Leu Glu Trp Lys Ile Ser Thr Leu Thr Asn Glu
Ala Arg Gln Gln Ile Val Gly Pro Ile Asn Asp Ala Ala Phe Ala Gly
Phe Arg Leu Arg Ala Ser Gly Ile Ala Thr Gln Val Thr Ser Arg Ser
Leu Glu Gln Asn Pro Leu Ser Gln Phe Ala Arg Ile Phe Tyr Ala Arg
Pro Glu Thr Arg Lys Phe Arg Val Glu Phe Leu Thr Pro Thr Ala Phe
Lys Gln Ser Gly Glu Tyr Val Phe Trp Pro Asp Pro Arg Leu Val Phe
Gln Ser Leu Ala Gln Lys Tyr Gly Ala Ile Val Asp Gly Glu Glu Pro
Asp Pro Gly Leu Ile Ala Glu Phe Gly Gln Ser Val Arg Leu Ser Ala
Phe Arg Val Ala Ser Ala Pro Phe Ala Val Gly Ala Ala Arg Val Pro
Gly Phe Thr Gly Ser Ala Thr Phe Thr Val Arg Gly Val Asp Thr Phe
Ala Ser Tyr Ile Ala Ala Leu Leu Trp Phe Gly Glu Phe Ser Gly Cys
Gly Ile Lys Ala Ser Met Gly Met Gly Ala Ile Arg Val Gln Pro Leu
Ala Pro Arg Glu Lys Cys Val Pro Lys Pro

*FIG. 41B*

Cas6 sequences

Streptococcus thermophilus LMG 18311
```
Met Lys Lys Leu Val Phe Thr Phe Lys Arg Ile Asp His Pro Ala Gln
Asp Leu Ala Val Lys Phe His Gly Phe Leu Met Glu Gln Leu Asp Ser
Asp Tyr Val Asp Tyr Leu His Gln Gln Gln Thr Asn Pro Tyr Ala Thr
Lys Val Ile Gln Gly Lys Glu Asn Thr Gln Trp Val Val His Leu Leu
Thr Asp Asp Ile Glu Asp Lys Val Phe Met Thr Leu Leu Gln Ile Lys
Glu Val Ser Leu Asn Asp Leu Pro Lys Leu Ser Val Glu Lys Val Glu
Ile Gln Glu Leu Gly Ala Asp Lys Leu Leu Glu Ile Phe Asn Ser Glu
Glu Asn Gln Thr Tyr Phe Ser Ile Ile Phe Glu Thr Pro Thr Gly Phe
Lys Ser Gln Gly Ser Tyr Val Ile Phe Pro Ser Met Arg Leu Ile Phe
Gln Ser Leu Met Gln Lys Tyr Gly Arg Leu Val Glu Asn Gln Pro Glu
Ile Glu Glu Asp Thr Leu Asp Tyr Leu Ser Glu His Ser Thr Ile Thr
Asn Tyr Arg Leu Glu Thr Ser Tyr Phe Arg Val His Arg Gln Arg Ile
Pro Ala Phe Arg Gly Lys Leu Thr Phe Lys Val Gln Gly Ala Gln Thr
Leu Lys Ala Tyr Val Lys Met Leu Leu Thr Phe Gly Glu Tyr Ser Gly
Leu Gly Met Lys Thr Ser Leu Gly Met Gly Gly Ile Lys Leu Glu Glu
Arg Lys Asp
```

Streptococcus sanguinis SK36
```
Met Lys Lys Ile Arg Leu His Leu Ser Lys Val Ser Leu Lys Asp Asp
Asp Leu Val Cys Lys Leu Gln Gly Phe Leu Met Glu Lys Leu Ser Asp
Asp Phe Ala Ser Phe Leu His Gln Gln Glu Thr Asn Pro Tyr Ser Met
Asn Leu Arg Ser Glu Arg Glu Glu Ser Ile Trp Thr Val Asn Leu Leu
Ser Glu Glu Ala Glu Gln Gln Ile Leu Pro Gln Leu Leu Ser Leu Glu
Met Ile Lys Leu Glu Thr Tyr Ser Glu Glu Ile Leu Val Lys Asn Ile
Glu Ile Gln Ser Leu Ser Ser Gln Ser Leu Leu Glu Val Phe Gln Gly
Asp Glu Ala Ser His Leu Ile Ser Leu Asn Phe Tyr Thr Pro Thr Thr
Phe Lys Arg Gln Gly Gln Phe Val Leu Phe Pro Asp Thr Arg Leu Ile
Phe Gln Ser Leu Met Gln Lys Tyr Ser Arg Leu Val Glu Gly Lys Ala
Glu Ile Glu Glu Glu Thr Leu Glu Phe Leu Ala Glu His Ser Gln Ile
Ser Ser Tyr Arg Leu Lys Ser His Tyr Phe Pro Ile His Gly Arg Lys
Tyr Pro Ala Phe Glu Gly Arg Val Thr Ile Arg Ile Gln Gly Ala Ser
Thr Leu Lys Ala Tyr Ala Gln Met Leu Leu Arg Phe Gly Glu Tyr Ser
Gly Val Gly Ala Lys Cys Ser Leu Gly Met Gly Gly Met Arg Ile Glu
Glu Arg Lys Thr
```

*FIG. 41C*

Cas6 sequences

Microcystis aeruginosa NIES-843
Met Pro Tyr Ser Leu Val Leu Asn Leu Thr Pro Arg Ser Pro Ile Tyr
Pro Asn Phe Leu Thr Gly Arg His Leu His Ala Leu Phe Leu Thr Leu
Val Ser Ser Val Asp Gln Glu Leu Gly Lys Ile Leu His Thr Ala Glu
Ala Asp Lys Ala Phe Thr Leu Ser Pro Leu Gln Met Gln Ser Gly Gly
Lys Thr Ile Asn Ser Pro Gln Trp Arg Tyr Glu Arg Pro Ile Ala Pro
Glu Thr Pro Cys Trp Trp Arg Ile Ser Leu Leu Asp Asp Arg Leu Phe
Gly Lys Leu Thr Pro Leu Trp Leu Asn Leu Asn Pro Lys His Pro Trp
His Leu Gly Ser Ala Asp Leu Val Ile Thr Ser Val Leu Ala Thr Pro
Gln Ser Val Gln Pro Trp Ala Asn Ser Cys Thr Tyr Gln Tyr Leu Tyr
Glu Asn Ala Ser Glu Thr Asn Arg Glu Phe Asp Phe Leu Phe Ala Thr
Pro Val Thr Phe Arg Gln Gly Lys Phe Asp Ser Ala Leu Pro Thr Arg
Glu Leu Val Phe Asn Ser Leu Leu Asn Arg Trp Asn Arg Tyr Ser Ala
Ile Pro Phe Asp Ser Ile Val Leu Glu Ser Ile Phe Pro Ser Phe Phe
Asp Ile Gln Thr Lys Leu Ala Asp Glu Ala Tyr Lys Asn Gln Ser Phe
Gly Cys Val Gly Glu Ile His Tyr Arg Leu Leu Gly Glu Val Glu Pro
Ala Lys Ile Lys Ala Ile Asn Val Leu Ala Asp Phe Ala Leu Tyr Ala
Gly Val Gly Arg Lys Thr Thr Met Gly Met Gly Met Thr Arg Arg Ile
Ala Lys Glu Lys Arg Meiothermus silvanus DSM 9946
Met Met Leu Ala Ala Leu Val Leu Pro Leu Glu Gly Gln Ala Arg Pro
Asp Pro Asp Gly Trp Arg Gly Leu Val Tyr Gly Leu Leu Lys Glu Ile
Asp Pro Glu Leu His Thr Ala Gln His Asn Pro Phe Ser Leu Gly Leu
Gly Gly Ala Glu Gly Gln Trp Trp Val Arg Ile Ala Leu Leu Glu Glu
Gly Leu Tyr Ala Arg Leu Ser Pro His Leu Phe Gly Leu Val Gly Gln
Ser Val Lys Leu Lys Glu Pro Phe Arg Val Arg Ala Val Leu Gln Glu
Glu His Pro Trp Ala Ser Leu Ser Thr Tyr Pro Arg Leu Phe Gln Gly
Gln Ala Ser Pro Ser Leu Gly Leu Gln Phe Ala Ser Pro Thr Phe Phe
Arg Arg Lys Gly Asn Ser Tyr Pro Leu Pro Glu Pro Lys Leu Val Phe
Asp Ser Leu Thr Gln Arg Trp Asn Ala Phe Ala Pro Val Lys Val Pro
Pro Glu Met Ala Glu Thr Trp Glu Arg Val Thr Ile Thr Arg Leu Gln
Gly His Thr Gln Ala Ile Arg Pro Asn Pro Asp Glu Arg Gly Val Gly
Phe Val Gly Arg Val Val Tyr His Leu Pro Ala Ala Lys Pro Thr Glu
Ala Gln Trp Met Gln Ala Leu Gly Arg Phe Ala Phe Tyr Ala Gly Val
Gly Ala Lys Thr Ser Leu Gly Phe Gly Arg Val Arg Gly Phe Asp Pro
Ile Leu Lys Glu Glu Ser Ala Asn Gly Arg Leu Asp Ala Glu Asp Ser
Ser Ser Leu Ala Thr Pro Gln Asp Pro Gly Ala

*FIG. 41D*

Cas6 sequences

Meiothermus silvanus DSM 9946
Met Met Leu Ala Ala Leu Val Leu Pro Leu Glu Gly Gln Ala Arg Pro
Asp Pro Asp Gly Trp Arg Gly Leu Val Tyr Gly Leu Leu Lys Glu Ile
Asp Pro Glu Leu His Thr Ala Gln His Asn Pro Phe Ser Leu Gly Leu
Gly Gly Ala Glu Gly Gln Trp Trp Val Arg Ile Ala Leu Leu Glu Glu
Gly Leu Tyr Ala Arg Leu Ser Pro His Leu Phe Gly Leu Val Gly Gln
Ser Val Lys Leu Lys Glu Pro Phe Arg Val Arg Ala Val Leu Gln Glu
Glu His Pro Trp Ala Ser Leu Ser Thr Tyr Pro Arg Leu Phe Gln Gly
Gln Ala Ser Pro Ser Leu Gly Leu Gln Phe Ala Ser Pro Thr Phe Phe
Arg Arg Lys Gly Asn Ser Tyr Pro Leu Pro Glu Pro Lys Leu Val Phe
Asp Ser Leu Thr Gln Arg Trp Asn Ala Phe Ala Pro Val Lys Val Pro
Pro Glu Met Ala Glu Thr Trp Glu Arg Val Thr Ile Thr Arg Leu Gln
Gly His Thr Gln Ala Ile Arg Pro Asn Pro Asp Glu Arg Gly Val Gly
Phe Val Gly Arg Val Val Tyr His Leu Pro Ala Ala Lys Pro Thr Glu
Ala Gln Trp Met Gln Ala Leu Gly Arg Phe Ala Phe Tyr Ala Gly Val
Gly Ala Lys Thr Ser Leu Gly Phe Gly Arg Val Arg Gly Phe Asp Pro
Ile Leu Lys Glu Glu Ser Ala Asn Gly Arg Leu Asp Ala Glu Asp Ser
Ser Ser Leu Ala Thr Pro Gln Asp Pro Gly Ala Meiothermus ruber DSM 1279
Met Ile Leu Ala Ala Leu Ile Leu Pro Leu Glu Gly Pro Thr Arg Pro
Asp Pro Asp Gly Trp Arg Gly Leu Val Tyr Gly Leu Leu Lys Glu Ile
Asp Pro Glu Leu His Ala Ala Gln His Asn Pro Phe Ser Leu Gly Leu
Gly Gly Ala Leu Gly Gln Trp Trp Val Arg Ile Ala Phe Leu Glu Glu
Gly Leu Tyr Ala Arg Leu Ser Pro His Leu Phe Gly Leu Ala Gly Gln
Thr Val Arg Leu Lys Glu Ala Phe Gln Val Arg Ala Val Leu Gln Glu
Ala His Pro Trp Ala Gly Val Ser Thr Tyr Pro Lys Leu Phe Gln Gly
Gln Ala Thr Ala Ser Leu Gly Leu Gln Phe Ala Ser Pro Thr Phe Phe
Arg Arg Lys Gly His Ser Tyr Pro Leu Pro Glu Pro Arg Leu Val Phe
Glu Ser Leu Thr Gln Arg Trp Asn Ala Phe Ala Pro Val Lys Val Pro
Gln Glu Val Gln Glu Ala Trp Glu Arg Leu Leu Val Gly Gln Phe Gln
Gly Arg Thr His His Ile Ala Pro Asn Gln Asp Glu Arg Gly Val Gly
Phe Val Gly Arg Val Val Tyr Tyr Leu Pro Lys Ala Ser Pro Thr Glu
Ala Gln Trp Leu Gln Ala Leu Gly Arg Phe Ala Phe Tyr Ala Gly Val
Gly Ala Lys Thr Ser Leu Gly Phe Gly Arg Val Arg Met Phe Asp Pro
Leu Gln Gln Glu Arg Arg Pro Asp Glu Ser Glu Gln Gly Ala Leu Thr
Gly Thr Val Gly Gly Val

*FIG. 41E*

Cas6 sequences

Thermus thermophilus HB8
Met Val Leu Ala Ala Leu Val Leu Val Leu Glu Gly Glu Gly Leu Pro
Glu Pro Leu Gly Leu Arg Gly Phe Phe Tyr Gly Leu Leu Arg Glu Val
Ala Pro Glu Val His Asp Gln Gly Glu Asn Pro Phe Ala Leu Gly Phe
Gly Gly Arg Glu Gly Ala Ala Trp Ala Arg Val Ser Leu Leu Val Glu
Gly Leu Tyr Ala Arg Leu Ala Pro Arg Leu Tyr Ala Leu Glu Gly Glu
Glu Val Arg Leu Gly Pro Pro Phe Arg Val Arg Ala Val Leu Gln Glu
Gly His Pro Trp Ala Gly Val Ser Thr Tyr Pro Arg Leu Phe Gln Gly
Pro Pro Ser Arg Asp Leu Ala Leu Arg Phe Ala Ser Pro Thr Phe Phe
Arg Arg Lys Gly Val His Tyr Pro Val Pro Glu Pro Arg Leu Val Leu
Glu Ser Leu Leu Arg Arg Leu Glu Ala Phe Gly Pro Leu Lys Ala Pro
Glu Gly Val Arg Glu Ala Leu Leu Glu Arg Thr Thr Val Arg Ser Leu
Glu Gly Arg Thr Leu Pro Ala Arg Thr Glu Val Asp Thr Ala Gly Phe
Val Gly Arg Val Val Tyr His Leu Pro Arg Ala Thr Glu Glu Glu Ala
Leu Trp Leu Ser Ala Leu Gly Arg Phe Ala Phe Tyr Ser Gly Val Gly
Ala Lys Thr Ser Leu Gly Tyr Gly Arg Ala Arg Ala Glu Ser Ala Thermus thermophilus JL-18
Met Val Leu Ala Ala Leu Val Leu Val Leu Glu Gly Glu Gly Leu Pro
Glu Pro Leu Gly Leu Arg Gly Phe Phe Tyr Gly Leu Leu Arg Glu Val
Ala Pro Glu Val His Asp Gln Gly Glu Asn Pro Phe Ala Leu Gly Phe
Gly Gly Arg Glu Gly Ala Ser Trp Ala Arg Val Ser Leu Leu Arg Glu
Glu Leu Tyr Ala Arg Leu Ala Pro Arg Leu Tyr Ala Leu Glu Gly Glu
Glu Val Arg Leu Gly Pro Pro Phe Arg Val Arg Ala Val Leu Gln Glu
Gly His Pro Trp Ala Gly Val Ser Thr Tyr Pro Arg Leu Phe Gln Gly
Pro Pro Ser Arg Asp Leu Ala Leu Arg Phe Ala Ser Pro Thr Phe Phe
Arg Arg Lys Gly Val His Tyr Pro Val Pro Glu Pro Arg Leu Val Leu
Glu Ser Leu Leu Arg Arg Leu Glu Ala Phe Gly Pro Leu Lys Ala Pro
Glu Gly Val Arg Glu Ala Leu Leu Glu Arg Thr Thr Val Arg Ser Leu
Glu Gly Arg Thr Leu Pro Ala Arg Thr Glu Val Asp Thr Ala Gly Phe
Val Gly Arg Val Val Tyr His Leu Pro Arg Ala Thr Glu Glu Glu Ala
Leu Trp Leu Ser Ala Leu Gly Arg Phe Ala Phe Tyr Ser Gly Val Gly
Ala Lys Thr Ser Leu Gly Tyr Gly Arg Ala Arg Ala Glu Ser Pro

*FIG. 41F*

Cas6 sequences

Thermus sp. CCB US3 UF1
Met Leu Ala Ala Leu Val Leu Thr Leu Glu Gly Glu Ala Pro Pro Glu
Pro Arg Gly Leu Arg Gly Phe Phe Tyr Gly Leu Leu Gln Glu Val Ala
Pro Glu Val His Asp Gln Gly Glu Asn Pro Phe Ala Leu Gly Phe Gly
Gly Lys Glu Gly Ala Tyr Trp Ala Arg Phe Ser Leu Leu Gln Glu Gly
Leu Tyr Ala Arg Leu Ala Pro Arg Leu Phe Ala Leu Glu Gly Lys Glu
Val Arg Leu Gly Lys Pro Phe Arg Val Arg Gly Val Leu Gln Glu Gly
His Pro Trp Ala Gly Val Ser Thr Tyr Ala Arg Leu Phe Gln Gly Glu
Ala Leu Pro Asp Leu Pro Leu Arg Phe Ala Ser Pro Thr Phe Phe Arg
Arg Lys Gly Val His Tyr Pro Leu Pro Glu Pro Arg Leu Val Val Glu
Ser Leu Leu Arg Arg Leu Glu Ala Phe Gly Pro Leu Lys Ala Pro Glu
Gly Val Arg Glu Ala Leu Leu Glu Arg Thr Thr Val Arg Trp Phe Glu
Gly Lys Thr Leu Lys Ala Glu Thr Glu Val Glu Ala Val Gly Phe Val
Gly Lys Val Val Tyr His Leu Pro Arg Ala Thr Glu Glu Glu Ala Arg
Trp Leu Gln Ala Leu Gly Arg Phe Ala Phe Tyr Ser Gly Val Gly Ala
Lys Thr Gly Leu Gly Tyr Gly Arg Ala Arg Val Gly Thermus aquaticus Y51MC23
Met Val Leu Val Ala Leu Val Leu Val Leu Glu Gly Glu Gly Pro Pro
Glu Pro Leu Gly Leu Arg Gly Phe Phe Tyr Thr Leu Leu Lys Glu Ala
Phe Pro Glu Leu His Asp Gln Gly Glu Asn Pro Phe Ala Leu Gly Phe
Gly Leu Arg Gly Gly Glu Pro Trp Ala Arg Val Ser Leu Leu Arg Glu
Asp Leu Tyr Gly Arg Leu Ser Pro Ala Leu Phe Gly Leu Glu Gly Arg
Glu Val Arg Leu Gly Arg Leu Phe Arg Val Arg Ala Val Leu Gln Glu
Gly His Pro Trp Ala Gly Leu Thr Thr Tyr Ala Arg Leu Phe Gln Gly
Pro His Ser Pro Asn Leu Pro Leu Arg Phe Tyr Ser Pro Thr Phe Phe
Arg Arg Lys Gly Val Gln Tyr Pro Leu Pro Glu Pro Arg Leu Val Leu
Glu Ser Leu Leu Arg Arg Leu Glu Ala Phe Gly Pro Leu Lys Ala Pro
Gln Glu Val Arg Glu Ala Leu Leu Glu Arg Thr Thr Val Arg Phe Leu
Glu Gly Arg Thr Gln Met Ala Arg Thr Glu Val Asp Thr Val Gly Phe
Val Gly Lys Val Val Tyr His Leu Pro Lys Ala Thr Glu Glu Glu Ala
Leu Trp Leu Ser Ala Leu Gly Arg Tyr Ala Phe Phe Ser Gly Val Gly
Ala Lys Thr Ser Leu Gly Tyr Gly Leu Ala Arg Ala Phe Thr Gln Val
Gly Pro Gln Asp Ala Glu Thr

FIG. 41G

Cas6 sequences

Marinithermus hydrothermalis DSM 14884
Met Leu Leu Ala Ala Leu Val Leu Pro Leu Glu Gly Pro Asp Arg Pro
Gln Pro Leu His Ala Arg Gly Trp Val Tyr Arg Leu Leu Arg Glu Ala
Ala Pro Glu Ile His Asp Ala Glu Gly Pro Lys Pro Phe Thr Val Gly
Val Gly Gly Arg Pro Asn Ala Val Trp Val Arg Leu Thr Cys Leu Ala
Glu Glu Val Tyr Ala Ala Leu Ser Pro Arg Leu Trp Ser Gln Val Gly
Leu Glu Val Arg Leu Gly Glu Asp Thr Tyr Arg Ile Lys Ala Val Leu
Glu Ala Glu His Pro Trp Ala Gly Leu Ala Thr Trp Pro Arg Leu Phe
Gln Gly Glu Ala Gly Pro Asp Leu Gly Leu Glu Phe Ala Ser Pro Thr
Phe Phe Arg Arg Gln Gly Ala Asn Tyr Pro Leu Pro Glu Pro Arg Leu
Val Leu Gly Ser Leu Ile Glu Arg Trp Asn Ala His Ala Pro Thr Pro
Val Pro Pro Glu Val Ala Glu Arg Leu Val Glu Ala Thr Thr Leu Arg
Tyr Leu Lys Gly His Thr Val Ser Ala Val Gly His Asp Arg Thr Val
Gly Phe Arg Gly Arg Val Thr Tyr His Leu Pro Arg Ala Ser Thr Glu
Glu Ala Arg Trp Leu Ala Ala Leu Gly Arg Phe Ala Phe Phe Ser Gly
Val Gly Ala Lys Thr Thr Leu Gly Phe Gly Gln Val Arg Pro Tyr Pro
Leu Leu Ala Pro Ser Ala Ala Pro Pro Gly Pro Thermus thermophilus HB8
Met Pro Gln Ala Val Val Leu Glu Leu Val Gly Glu Lys Pro Pro Leu
Tyr Pro Ala Arg Tyr Ala His Gly Leu Phe Phe Ala Leu Leu Ser Arg
Val Ser Pro Glu Leu Ala Gln Lys Leu His Glu Ala Pro Arg Lys Pro
Phe Thr Leu Ala Pro Leu Pro Arg Ala Gly Pro Glu Gly Ala Thr Leu
Lys Gly Thr Leu Arg Leu Arg Leu Thr Thr Leu Asp Asp Gly Leu Phe
Ala Pro Phe Leu Arg Ala Leu Leu Glu Ala Ala Pro Asp Gly Leu Pro
Leu Gly Asp Ser Ser Tyr Arg Leu Ala Arg Val Leu Ala Thr Arg Glu
Gly His Pro Leu Ala Gly Ala Thr Ser Trp Glu Glu Leu Lys Glu Ala
Pro Lys Arg Glu Lys Ala Thr Phe Arg Phe Leu Thr Pro Thr Val Phe
Ala Thr Ser Lys Pro Gly Gly Arg Thr Arg Tyr Thr Pro Leu Pro Asp
Pro Arg Leu Ile Ala Gly Ser Leu Leu Asp Lys Trp Gln Ala His Ser
Pro Phe Pro Tyr Asn Pro Lys Glu Glu Ala Ala Leu Arg Glu Leu Phe
Glu Leu Asp Leu Glu Val Ala Gly Phe Arg Asn Leu Arg Phe His Arg
Val Gln Ala Gly Lys Gly Phe Phe Pro Gly Phe Thr Gly Glu Ala Thr
Leu Arg Leu Trp Ser Gln Ser Leu Glu Ala Gln Glu Ala Leu Gly Arg
Leu His Ala Leu Ala Phe Phe Ser Gly Val Gly Ala Lys Thr Pro Tyr
Gly Met Gly Leu Ala Val Pro Leu

*FIG. 41H*

Cas6 sequences

Thermus thermophilus HB27
```
Met Pro Gln Ala Val Val Leu Glu Leu Val Gly Glu Lys Pro Pro Leu
Tyr Pro Ala Arg Tyr Ala His Gly Leu Phe Phe Ala Leu Leu Ser Arg
Val Ser Pro Glu Leu Ala Gln Lys Leu His Glu Ala Pro Arg Lys Pro
Phe Thr Leu Ala Pro Leu Pro Arg Ala Gly Pro Glu Gly Ala Thr Leu
Lys Gly Thr Leu Arg Leu Arg Leu Thr Thr Leu Asp Asp Gly Leu Phe
Ala Pro Phe Leu Arg Ala Leu Leu Glu Ala Ala Pro Asp Gly Leu Pro
Leu Gly Asp Ser Ser Tyr Arg Leu Ala Arg Val Leu Ala Thr Arg Glu
Gly His Pro Leu Ala Gly Ala Thr Ser Trp Glu Glu Leu Lys Glu Ala
Pro Lys Arg Glu Lys Val Thr Phe Arg Phe Leu Thr Pro Thr Val Phe
Ala Thr Ser Lys Pro Gly Gly Arg Thr Arg Tyr Thr Pro Leu Pro Asp
Pro Arg Leu Ile Ala Gly Ser Leu Leu Asp Lys Trp Gln Ala His Ser
Pro Phe Pro Tyr Asn Pro Lys Glu Glu Ala Ala Leu Arg Gly Leu Phe
Glu Leu Asp Leu Glu Val Ala Gly Phe Arg Asn Leu Arg Phe His Arg
Val Gln Ala Gly Lys Gly Phe Phe Pro Gly Phe Thr Gly Glu Met Thr
Leu Arg Leu Trp Ser Gln Ser Leu Glu Ala Arg Glu Ala Leu Gly Arg
Leu His Ala Leu Ala Phe Phe Ser Gly Val Gly Ala Lys Thr Pro Tyr
Gly Met Gly Leu Ala Val Pro Leu
```

Thermus thermophilus SG0.5JP17-16
```
Met Pro Gln Ala Val Val Leu Glu Leu Val Gly Glu Lys Pro Pro Leu
Tyr Pro Gly Arg Tyr Ala His Gly Leu Phe Phe Ala Leu Leu Ser Arg
Val Ser Pro Glu Leu Ala Gln Lys Leu His Glu Ala Pro Arg Lys Pro
Phe Thr Leu Ala Pro Leu Pro Arg Val Gly Pro Glu Gly Ala Thr Leu
Lys Gly Ile Leu Arg Leu Arg Leu Thr Ala Leu Asp Asp Gly Leu Phe
Ala Pro Phe Leu Arg Ala Leu Leu Glu Ala Ala Pro Asp Gly Leu Pro
Leu Gly Asp Ser Ser Tyr Arg Leu Ala Arg Val Leu Ala Thr Arg Glu
Gly His Pro Leu Ala Gly Ala Thr Ser Trp Glu Glu Leu Lys Glu Ala
Pro Lys Arg Glu Lys Ala Thr Phe Arg Phe Leu Thr Pro Thr Val Phe
Ala Thr Ser Lys Pro Gly Gly Arg Thr Arg Tyr Thr Pro Leu Pro Asp
Pro Arg Leu Ile Ala Gly Ser Leu Leu Asp Lys Trp Gln Ala His Ser
Pro Phe Pro Tyr Asn Pro Lys Glu Glu Ala Ala Leu Arg Glu Leu Phe
Glu Leu Asp Leu Glu Val Ala Gly Phe Arg Asn Leu Arg Phe His Arg
Val Gln Ala Gly Lys Gly Phe Phe Pro Gly Phe Thr Gly Glu Ala Thr
Leu Arg Leu Trp Ser Gln Ser Leu Glu Ala Gln Glu Ala Leu Gly Arg
Leu His Ala Leu Ala Phe Phe Ser Gly Val Gly Ala Lys Thr Pro Tyr
Gly Met Gly Leu Ala Val Pro Leu
```

*FIG. 41I*

Cas6 sequences

Thermus thermophilus JL-18

```
Met Pro Gln Ala Val Val Leu Glu Leu Val Gly Glu Glu Ser Pro Leu
Tyr Pro Ala Arg Tyr Ala His Gly Leu Phe Phe Ala Leu Leu Ser Arg
Val Ser Pro Glu Leu Ala Gln Lys Leu His Glu Ala Pro Arg Lys Pro
Phe Thr Leu Ala Pro Leu Pro Arg Val Gly Ser Glu Gly Ala Thr Leu
Lys Gly Ile Leu Arg Leu Arg Leu Thr Ile Leu Asp Asp Gly Leu Phe
Ala Pro Phe Leu Arg Ala Leu Leu Glu Ala Ala Pro Asp Gly Leu Pro
Leu Gly Asp Ser Ser Tyr Arg Leu Ala Arg Val Leu Ala Thr Arg Glu
Gly His Pro Leu Ala Gly Ala Thr Ser Trp Glu Glu Leu Lys Glu Ala
Pro Lys Arg Glu Lys Ala Thr Phe Arg Phe Leu Thr Pro Thr Val Phe
Ala Thr Ser Lys Pro Gly Gly Arg Thr Arg Tyr Thr Pro Leu Pro Asp
Pro Arg Leu Ile Ala Gly Ser Leu Leu Asp Lys Trp Gln Ala His Ser
Pro Phe Pro Tyr Asn Pro Lys Glu Glu Ala Ala Leu Arg Glu Leu Phe
Glu Leu Asp Leu Glu Val Ala Gly Phe Arg Asn Leu Arg Phe His Arg
Val Gln Ala Gly Lys Ser Phe Phe Pro Gly Phe Thr Gly Glu Met Thr
Leu Arg Leu Trp Ser Gln Ser Leu Glu Ala Gln Gly Ala Leu Gly Arg
Leu His Ala Leu Ala Phe Phe Ser Gly Val Gly Ala Lys Thr Pro Tyr
Gly Met Gly Leu Ala Val Pro Leu
```

*FIG. 41J*

Cas5 sequences

Desulfovibrio vulgaris str. Hildenborough
```
Met Thr His Gly Ala Val Lys Thr Tyr Gly Ile Arg Leu Arg Val Trp
Gly Asp Tyr Ala Cys Phe Thr Arg Pro Glu Met Lys Val Glu Arg Val
Ser Tyr Asp Val Met Pro Pro Ser Ala Ala Arg Gly Ile Leu Glu Ala
Ile His Trp Lys Pro Ala Ile Arg Trp Ile Val Asp Arg Ile His Val
Leu Arg Pro Ile Val Phe Asp Asn Val Arg Arg Asn Glu Val Ser Ser
Lys Ile Pro Lys Pro Asn Pro Ala Thr Ala Met Arg Asp Arg Lys Pro
Leu Tyr Phe Leu Val Asp Asp Gly Ser Asn Arg Gln Gln Arg Ala Ala
Thr Leu Leu Arg Asn Val Asp Tyr Val Ile Glu Ala His Phe Glu Leu
Thr Asp Lys Ala Gly Ala Glu Asp Asn Ala Gly Lys His Leu Asp Ile
Phe Arg Arg Arg Ala Arg Ala Gly Gln Ser Phe Gln Gln Pro Cys Leu
Gly Cys Arg Glu Phe Pro Ala Ser Phe Glu Leu Leu Glu Gly Asp Val
Pro Leu Ser Cys Tyr Ala Gly Glu Lys Arg Asp Leu Gly Tyr Met Leu
Leu Asp Ile Asp Phe Glu Arg Asp Met Thr Pro Leu Phe Phe Lys Ala
Val Met Glu Asp Gly Val Ile Thr Pro Pro Ser Arg Thr Ser Pro Glu
Val Arg Ala
```

Neisseria mucosa ATCC 25996
```
Met Asn Gln Ile Arg Leu His Val Trp Gly Asp Tyr Ala Cys Phe Thr
Arg Pro Glu Met Lys Val Glu Arg Val Ser Tyr Asp Val Ile Thr Pro
Ser Ala Ala Arg Gly Ile Leu Ala Ala Val His Trp Lys Pro Ala Ile
Arg Trp Val Ile Asp Arg Ile Tyr Val Leu Lys Pro Ile Arg Phe Glu
Ser Val Arg Arg Asn Glu Leu Gly Gly Lys Ile Ser Ala Gly Lys Val
Ser Gly Ala Met Lys Arg Lys Ser Val Ala Asp Leu Tyr Thr Leu Ile
Glu Asp Asp Arg Gln Gln Arg Ala Ala Thr Val Leu Lys Asp Val Ala
Tyr Val Ile Glu Ala His Ala Val Leu Thr Ala Lys Ala Gly Ala Asp
Glu Thr Val Thr Lys His Ile Glu Met Phe Lys Arg Arg Ala Lys Lys
Gly Gln Cys Phe Gln Gln Pro Cys Leu Gly Val Arg Glu Phe Pro Ala
Asp Phe Ala Leu Ile Asp Glu Gly Glu Pro Leu Pro Pro Ser Ala Leu
Ser Glu Ser Glu Ala Asn Arg Asp Leu Gly Trp Met Leu His Asp Ile
Asp Phe Asp His Gly Asn Thr Pro His Phe Phe Arg Ala Gln Met Lys
Asp Gly Val Ile Asp Val Pro Pro Phe Tyr Ala Glu Glu Val Lys Ala
```

*FIG. 42A*

Cas5 sequences

Bacillus halodurans C-125
Met Arg Asn Glu Val Gln Phe Glu Leu Phe Gly Asp Tyr Ala Leu Phe
Thr Asp Pro Leu Thr Lys Ile Gly Gly Glu Lys Leu Ser Tyr Ser Val
Pro Thr Tyr Gln Ala Leu Lys Gly Ile Ala Glu Ser Ile Tyr Trp Lys
Pro Thr Ile Val Phe Val Ile Asp Glu Leu Arg Val Met Lys Pro Ile
Gln Met Glu Ser Lys Gly Val Arg Pro Ile Glu Tyr Gly Gly Gly Asn
Thr Leu Ala His Tyr Thr Tyr Leu Lys Asp Val His Tyr Gln Val Lys
Ala His Phe Glu Phe Asn Leu His Arg Pro Asp Leu Ala Phe Asp Arg
Asn Glu Gly Lys His Tyr Ser Ile Leu Gln Arg Ser Leu Lys Ala Gly
Gly Arg Arg Asp Ile Phe Leu Gly Ala Arg Glu Cys Gln Gly Tyr Val
Ala Pro Cys Glu Phe Gly Ser Gly Asp Gly Phe Tyr Asp Gly Gln Gly
Lys Tyr His Leu Gly Thr Met Val His Gly Phe Asn Tyr Pro Asp Glu
Thr Gly Gln His Gln Leu Asp Val Arg Leu Trp Ser Ala Val Met Glu
Asn Gly Tyr Ile Gln Phe Pro Arg Pro Glu Asp Cys Pro Ile Val Arg
Pro Val Lys Glu Met Glu Pro Lys Ile Phe Asn Pro Asp Asn Val Gln
Ser Ala Glu Gln Leu Leu His Asp Leu Gly Gly Glu Bacillus cereus F65185
Met Lys Lys Glu Glu Glu Ser Leu Arg Asn Ser Ile Glu Phe Glu Val
Phe Gly Asp Tyr Ala Leu Phe Thr Asp Pro Leu Met Lys Met Gly Gly
Glu Lys Leu Thr Tyr Gln Val Pro Thr Tyr Gln Ala Ile Lys Gly Ile
Val Glu Ser Ile Tyr Trp Lys Pro Thr Leu Leu Met Ile Val Asp Lys
Ile Arg Ile Met Asn Ala Ile Lys Met Glu Ser Lys Gly Ile Arg Pro
Ile Glu Tyr Gly Gly Gly Asn Thr Leu Ala Asn Tyr Thr Tyr Leu Lys
Asn Val Arg Tyr Gln Val Gln Ala His Phe Ile Phe Asn Pro His Arg
Pro Asp Leu Ala Phe Asp Arg Asn Glu Tyr Lys His His Asn Ile Leu
Lys Arg Ser Leu Lys Val Gly Gly Arg Arg Asp Ile Phe Leu Gly Thr
Arg Glu Cys Gln Gly Tyr Val Glu Pro Cys Val Phe Gly Glu Gly Glu
Gly Phe Tyr Asp Asn Tyr Gly Gly Asp Ile His Leu Gly Thr Met Val
His Gly Leu Asn Tyr Pro Asp Glu Thr Gly Arg Asn Glu Leu Glu Val
Arg Leu Trp Asn Pro Val Met Arg Asp Gly Ile Ile Gln Phe Ile Arg
Pro Glu Glu Cys Thr Lys Ile Arg Lys Ile Ser Lys Met Glu Pro Lys
Ile Phe Asp Ser Ser Asn Val Glu Ser Val Asp Glu Leu Ile Lys Gln
Leu Glu Glu Gly Gly Glu

*FIG. 42B*

Cas5 sequences

Selenomonas noxia ATCC 43541

```
Met Arg Asn Ser Ile Glu Phe Gln Val Tyr Gly Arg Met Ala Leu Phe
Thr Asp Pro Ile Thr Lys Ile Gly Gly Glu Lys Ala Ser Tyr Ser Val
Pro Thr Tyr Gln Ala Leu Lys Gly Ile Thr Glu Ser Ile Tyr Trp Lys
Pro Thr Ile Ile Trp Phe Ile Asp Glu Val Arg Val Met Lys Arg Ile
Thr Thr Gln Val Arg Gly Val Lys Pro Leu Lys Tyr Gly Asp Ser Gly
Asn Asp Leu Ser Tyr Tyr Lys Tyr Leu Ser Asp Val Cys Tyr Gln Val
Arg Ala His Phe Glu Phe Asn Met His Arg Glu Glu Leu Lys Glu Asp
Arg Asp Glu His Lys His His Asn Ile Ala Lys Arg Met Val Glu Arg
Gly Gly Arg Arg Asp Ile Phe Leu Gly Thr Arg Glu Cys Gln Gly Tyr
Val Glu Pro Val Lys Tyr Gly Val Gly Lys Gly Tyr Tyr Asp Asn Val
Asp Glu Leu Pro Leu Gly Ile Met Leu His Gly Phe Asn Tyr Pro Asp
Glu Thr Gly Glu Asp Lys Leu Gln Val Arg Phe Trp Lys Pro Thr Met
Lys Lys Gly Ile Ile His Phe Arg Arg Pro Glu Lys Cys Glu Met Val
Arg Asp Ile Arg Glu Val Arg Thr Lys Gln Phe Asp Ala Asp Asn Val
Phe Phe Ala Glu Glu Glu Glu Lys Gln Leu Glu Gly Gly His Leu
```

*FIG. 42C*

COMPOSITIONS AND METHODS OF NUCLEIC ACID-TARGETING NUCLEIC ACIDS

CROSS-REFERENCE

This application is a continuation of U.S. patent application Ser. No. 14/977,514, filed Dec. 21, 2015, now pending, which is a continuation of U.S. patent application Ser. No. 14/416,338, filed Jan. 22, 2015, now U.S. Pat. No. 9,260,752, issued Feb. 16, 2016, which is a National Stage Entry of International Application No. PCT/US2014/023828, filed on Mar. 12, 2014, now expired, which claims the benefit of U.S. Provisional Application No. 61/818,386, filed May 1, 2013, U.S. Provisional Application No. 61/902,723, filed Nov. 11, 2013, U.S. Provisional Application No. 61/818,382, filed May 1, 2013, U.S. Provisional Application No. 61/859,661, filed Jul. 29, 2013, U.S. Provisional Application No. 61/858,767, filed Jul. 26, 2013, U.S. Provisional Application No. 61/822,002, filed May 10, 2013, U.S. Provisional Application No. 61/832,690, filed Jun. 7, 2013, U.S. Provisional Application No. 61/906,211, filed Nov. 19, 2013, U.S. Provisional Application No. 61/900,311, filed Nov. 5, 2013, U.S. Provisional Application No. 61/845,714, filed Jul. 12, 2013, U.S. Provisional Application No. 61/883,804, filed Sep. 27, 2013, U.S. Provisional Application No. 61/781,598, filed Mar. 14, 2013, U.S. Provisional Application No. 61/899,712, filed Nov. 4, 2013, U.S. Provisional Application No. 61/865,743, filed Aug. 14, 2013, U.S. Provisional Application No. 61/907,777, filed Nov. 22, 2013, U.S. Provisional Application No. 61/903,232, filed Nov. 12, 2013, U.S. Provisional Application No. 61/906,335, filed Nov. 19, 2013, and U.S. Provisional Application No. 61/907,216, filed Nov. 21, 2013, each of which applications is incorporated herein by reference in its entirety.

SEQUENCE LISTING

The present application contains a Sequence Listing that has been submitted electronically in ASCII format and is hereby incorporated by reference in its entirety. The ASCII copy, created on 1 Feb. 2017, is named CBI011-203_ST25.txt and is 8.1 MB in size.

BACKGROUND OF THE INVENTION

Genome engineering can refer to altering the genome by deleting, inserting, mutating, or substituting specific nucleic acid sequences. The altering can be gene or location specific. Genome engineering can use nucleases to cut a nucleic acid thereby generating a site for the alteration. Engineering of non-genomic nucleic acid is also contemplated. A protein containing a nuclease domain can bind and cleave a target nucleic acid by forming a complex with a nucleic acid-targeting nucleic acid. In one example, the cleavage can introduce doublestranded breaks in the target nucleic acid. A nucleic acid can be repaired e.g. by endogenous non-homologous end joining (NHEJ) machinery. In a further example, a piece of nucleic acid can be inserted. Modifications of nucleic acid-targeting nucleic acids and site-directed polypeptides can introduce new functions to be used for genome engineering.

SUMMARY OF THE INVENTION

In one aspect, the disclosure provides for an engineered nucleic acid-targeting nucleic acid comprising: a mutation in a P-domain of the nucleic acid-targeting nucleic acid. In some embodiments, the P-domain starts downstream of a last paired nucleotide of a duplex between a CRISPR repeat and a tracrRNA sequence of the nucleic acid-targeting nucleic acid. In some embodiments, the engineered nucleic acid-targeting nucleic acid further comprises a linker sequence. In some embodiments, the linker sequence links the CRISPR repeat and the tracrRNA sequence. In some embodiments, the engineered nucleic acid-targeting nucleic acid is an isolated engineered nucleic acid-targeting nucleic acid. In some embodiments, the engineered nucleic acid-targeting nucleic acid is a recombinant engineered nucleic acid-targeting nucleic acid. In some embodiments, the engineered nucleic acid-targeting nucleic acid is adapted to hybridize to a target nucleic acid. In some embodiments, the P-domain comprises 2 adjacent nucleotides. In some embodiments, the P-domain comprises 3 adjacent nucleotides. In some embodiments, the P-domain comprises 4 adjacent nucleotides. In some embodiments, the P-domain comprises 5 adjacent nucleotides. In some embodiments, the P-domain comprises 6 or more adjacent nucleotides. In some embodiments, the P-domain starts 1 nucleotide downstream of the last paired nucleotide of the duplex. In some embodiments, the P-domain starts 2 nucleotides downstream of the last paired nucleotide of the duplex. In some embodiments, the P-domain starts 3 nucleotides downstream of the last paired nucleotide of the duplex. In some embodiments, the P-domain starts 4 nucleotides downstream of the last paired nucleotide of the duplex. In some embodiments, the P-domain starts 5 nucleotides downstream of the last paired nucleotide of the duplex. In some embodiments, the P-domain starts 6 or more nucleotides downstream of the last paired nucleotide of the duplex. In some embodiments, the mutation comprises one or more mutations. In some embodiments, the one or more mutations are adjacent to each other. In some embodiments, the one or more mutations are separated from each other. In some embodiments, the mutation is adapted to allow the engineered nucleic acid-targeting nucleic acid to hybridize to a different protospacer adjacent motif. In some embodiments, the different protospacer adjacent motif comprises at least 4 nucleotides. In some embodiments, the different protospacer adjacent motif comprises at least 5 nucleotides. In some embodiments, the different protospacer adjacent motif comprises at least 6 nucleotides. In some embodiments, the different protospacer adjacent motif comprises at least 7 or more nucleotides. In some embodiments, the different protospacer adjacent motif comprises two non-adjacent regions. In some embodiments, the different protospacer adjacent motif comprises three non-adjacent regions. In some embodiments, the mutation is adapted to allow the engineered nucleic acid-targeting nucleic acid to bind to a target nucleic acid with a lower dissociation constant than an un-engineered nucleic acid-targeting nucleic acid. In some embodiments, the mutation is adapted to allow the engineered nucleic acid-targeting nucleic acid to bind to a target nucleic acid with greater specificity than an un-engineered nucleic acid-targeting nucleic acid. In some embodiments, the mutation is adapted to reduce binding of the engineered nucleic acid-targeting nucleic acid to a non-specific sequence in a target nucleic acid than an un-engineered nucleic acid-targeting nucleic acid. In some embodiments, the engineered nucleic acid-targeting nucleic acid further comprises two hairpins, wherein one of the two hairpins comprises a duplex between a polynucleotide comprising at least 50% identity to a CRISPR RNA over 6 contiguous nucleotides, and a polynucleotide comprising at least 50% identity to a tracrRNA over 6 contiguous nucleotides; and, wherein one of the two hairpins is 3' of the first hairpin, wherein the second hairpin comprises an engineered P-domain. In some embodiments, the second hairpin is adapted to de-duplex when the nucleic acid is in contact with a target nucleic acid. In some embodiments, the P-domain is adapted to: hybridize with a first polynucleotide, wherein the first polynucleotide comprises a region of the engineered nucleic acid-targeting nucleic acid, hybridize to a second polynucleotide, wherein the second polynucleotide comprises a target nucleic acid, and hybridize specifically to the first or second polynucleotide. In some embodiments, the first polynucleotide comprises at least 50% identity to a tracrRNA over 6 contiguous nucleotides. In some embodiments, the first polynucleotide is located downstream of a duplex between a polynucleotide comprising at least 50% identity to a CRISPR repeat over 6 contiguous nucleotides, and a polynucleotide comprising at least 50% identity to a tracrRNA sequence over 6 contiguous nucleotides. In some embodiments, the second polynucleotide comprises a protospacer adjacent motif. In some embodiments, the engineered nucleic acid-targeting nucleic acid is adapted to bind to a site-directed polypeptide. In some embodiments, the mutation comprises an insertion of one or more nucleotides into the P-domain. In some embodiments, the mutation comprises deletion one or more nucleotides from the P-domain. In some embodiments, the mutation comprises mutation of one or more nucleotides. In some embodiments, the mutation is configured to allow the nucleic acid-targeting nucleic acid to hybridize to a different protospacer adjacent motif. In some embodiments, the different protospacer adjacent motif comprises a protospacer adjacent motif selected from the group consisting of: 5'-NGGNG-3', 5'-NNAAAAW-3', 5'-NNNNGATT-3', 5'-GNNNCNNA-3', and 5'-NNNACA-3', or any combination thereof. In some embodiments, the mutation is configured to allow the engineered nucleic acid-targeting nucleic acid to bind with a lower dissociation constant than an un-engineered nucleic acid-targeting nucleic acid. In some embodiments, the mutation is configured to allow the engineered nucleic acid-targeting nucleic acid to bind with greater specificity than an un-engineered nucleic acid-targeting nucleic acid. In some embodiments, the mutation is configured to reduce binding of the engineered nucleic acid-targeting nucleic acid to a non-specific sequence in a target nucleic acid than an un-engineered nucleic acid-targeting nucleic acid.

In one aspect, the disclosure provides for a method for modifying a target nucleic acid comprising contacting a target nucleic acid with an engineered nucleic acid-targeting nucleic acid comprising: a mutation in a P-domain of the nucleic acid-targeting nucleic acid, and modifying the target nucleic acid. In some embodiments, the method further comprises inserting a donor polynucleotide into the target nucleic acid. In some embodiments, the modifying comprises cleaving the target nucleic acid. In some embodiments, the modifying comprises modifying transcription of the target nucleic acid.

In one aspect the disclosure provides for a vector comprising a polynucleotide sequence encoding an engineered nucleic acid-targeting nucleic acid comprising: a mutation in a P-domain of the nucleic acid-targeting nucleic acid.

In one aspect the disclosure provides for a kit comprising: an engineered nucleic acid-targeting nucleic acid comprising: a mutation in a P-domain of the nucleic acid-targeting nucleic acid; and a buffer. In some embodiments, the kit further comprises a site-directed polypeptide. In some embodiments, the kit further comprises a donor polynucleotide. In some embodiments, the kit further comprises instructions for use.

In one aspect, the disclosure provides for an engineered nucleic acid-targeting nucleic acid comprising: a mutation in a bulge region of a nucleic acid-targeting nucleic acid. In some embodiments, the bulge is located within a duplex between a CRISPR repeat and a tracrRNA sequence of the nucleic acid-targeting nucleic acid. In some embodiments, the engineered nucleic acid-targeting nucleic acid further comprises a linker sequence. In some embodiments, the linker sequence links the CRISPR repeat and the tracrRNA sequence. In some embodiments, the engineered nucleic acid-targeting nucleic acid is an isolated engineered nucleic acid-targeting nucleic acid. In some embodiments, the engineered nucleic acid-targeting nucleic acid is a recombinant engineered nucleic acid-targeting nucleic acid. In some embodiments, the bulge comprises at least 1 unpaired nucleotide on the CRISPR repeat, and 1 unpaired nucleotide on a the tracrRNA sequence. In some embodiments, the bulge comprises at least 1 unpaired nucleotide on the CRISPR repeat, and at least 2 unpaired nucleotides on a the tracrRNA sequence. In some embodiments, the bulge comprises at least 1 unpaired nucleotide on the CRISPR repeat, and at least 3 unpaired nucleotides on a the tracrRNA sequence. In some embodiments, the bulge comprises at least 1 unpaired nucleotide on the CRISPR repeat, and at least 4 unpaired nucleotides on a the tracrRNA sequence. In some embodiments, the bulge comprises at least one 1 unpaired nucleotide on the CRISPR repeat, and at least 5 unpaired nucleotides on a the tracrRNA sequence. In some embodiments, the bulge comprises at least 2 unpaired nucleotide on the CRISPR repeat, and 1 unpaired nucleotide on a the tracrRNA sequence. In some embodiments, the bulge comprises at least 3 unpaired nucleotide on the CRISPR repeat, and at least 2 unpaired nucleotides on a the tracrRNA sequence. In some embodiments, the bulge comprises at least 4 unpaired nucleotide on the CRISPR repeat, and at least 3 unpaired nucleotides on a the tracrRNA sequence. In some embodiments, the bulge comprises at least 5 unpaired nucleotide on the CRISPR repeat, and at least 4 unpaired nucleotides on the tracrRNA sequence. In some embodiments, the bulge comprises at least one nucleotide on the CRISPR repeat adapted to form a wobble pair with at least one nucleotide on the tracrRNA sequence. In some embodiments, the mutation comprises one or more mutations. In some embodiments, the one or more mutations are adjacent to each other. In some embodiments, the one or more mutations are separated from each other. In some embodiments, the mutation is adapted to allow the engineered nucleic acid-targeting nucleic acid to bind to a different site-directed polypeptide. In some embodiments, the different site-directed polypeptide is a homologue of Cas9. In some embodiments, the different site-directed polypeptide is a mutated version of Cas9. In some embodiments, the different site-directed polypeptide comprises 10% amino acid sequence identity to Cas9 in a nuclease domain selected from the group consisting of: a RuvC nuclease domain, and a HNH nuclease domain, or any combination thereof. In some embodiments, the mutation is adapted to allow the engineered nucleic acid-targeting nucleic acid to hybridize to a different protospacer adjacent motif. In some embodiments, the mutation is adapted to allow the engineered nucleic acid-targeting nucleic acid to bind to a site-directed polypeptide with a lower dissociation constant than an un-engineered nucleic acid-targeting nucleic acid. In some embodiments, the mutation is adapted to allow the engineered nucleic acid-targeting nucleic acid to bind to a site-directed polypeptide with greater specificity than an un-engineered nucleic acid-targeting nucleic acid. In some embodiments, the mutation is adapted to allow the engineered nucleic acid-targeting nucleic acid to direct a site-directed polypeptide to cleave a target nucleic acid with greater specificity than an un-engineered nucleic acid-targeting nucleic acid. In some embodiments, the mutation is adapted to reduce binding of the engineered nucleic acid-targeting nucleic acid to a non-specific sequence in a target nucleic acid than an un-engineered nucleic acid-targeting nucleic acid. In some embodiments, the engineered nucleic acid-targeting nucleic acid is adapted to hybridize to a target nucleic acid. In some embodiments, the mutation comprises insertion one or more nucleotides into the bulge. In some embodiments, the mutation comprises deletion of one or more nucleotides from the bulge. In some embodiments, the mutation comprises mutation of one or more nucleotides. In some embodiments, the mutation is configured to allow the engineered nucleic acid-targeting nucleic acid to hybridize to a different protospacer adjacent motif compared to an un-engineered nucleic acid-targeting nucleic acid. In some embodiments, the mutation is configured to allow the engineered nucleic acid-targeting nucleic acid to bind to a site-directed polypeptide with a lower dissociation constant than an un-engineered nucleic acid-targeting nucleic acid. In some embodiments, the mutation is configured to allow the engineered nucleic acid-targeting nucleic acid to bind to a site-directed polypeptide with greater specificity than an un-engineered nucleic acid-targeting nucleic acid. In some embodiments, the mutation is configured to reduce binding of the engineered nucleic acid-targeting nucleic acid to a non-specific sequence in a target nucleic acid than an un-engineered nucleic acid-targeting nucleic acid.

In one aspect the disclosure provides for a method for modifying a target nucleic acid comprising: contacting the target nucleic acid with an engineered nucleic acid-targeting nucleic acid comprising: a mutation in a bulge region of a nucleic acid-targeting nucleic acid; and modifying the target nucleic acid. In some embodiments, the method further comprises inserting a donor polynucleotide into the target nucleic acid. In some embodiments, the modifying comprises cleaving the target nucleic acid. In some embodiments, the modifying comprises modifying transcription of the target nucleic acid.

In one aspect the disclosure provides for a vector comprising a polynucleotide sequence encoding an engineered nucleic acid-targeting nucleic acid comprising: a mutation in a bulge region of a nucleic acid-targeting nucleic acid; and modifying the target nucleic acid.

In one aspect the disclosure provides for a kit comprising: an engineered nucleic acid-targeting nucleic acid comprising: a mutation in a bulge region of a nucleic acid-targeting nucleic acid; and modifying the target nucleic acid; and a buffer. In some embodiments, the kit further comprises a site-directed polypeptide. In some embodiments, the kit further comprises a donor polynucleotide. In some embodiments, the kit further comprises instructions for use.

In one aspect the disclosure provides for a method for producing a donor polynucleotide-tagged cell comprising: cleaving a target nucleic acid in a cell using a complex comprising a site-directed polypeptide and a nucleic acid-targeting nucleic acid, inserting a donor polynucleotide into a cleaved target nucleic acid, propagating the cell carrying the donor polynucleotide, and determining an origin of the donor-polynucleotide tagged cell. In some embodiments, the method is performed in vivo. In some embodiments, the method is performed in vitro. In some embodiments, the method is performed in situ. In some embodiments, the propagating produces a population of cells. In some embodiments, the propagating produces a cell line. In some embodiments, the method further comprises determining a nucleic acid sequence of a nucleic acid in the cell. In some embodiments, the nucleic acid sequence determines an origin of the cell. In some embodiments, the determining comprises determining a genotype of the cell. In some embodiments, the propagating comprises differentiating the cell. In some embodiments, the propagating comprises de-differentiating the cell. In some embodiments, the propagating comprises differentiating the cell and then dedifferentiating the cell. In some embodiments, the propagating comprises passaging the cell. In some embodiments, the propagating comprises inducing the cell to divide. In some embodiments, the propagating comprises inducing the cell to enter the cell cycle. In some embodiments, the propagating comprises the cell forming a metastasis. In some embodiments, the propagating comprises differentiating a pluripotent cell into a differentiated cell. In some embodiments, the cell is a differentiated cell. In some embodiments, the cell is a de-differentiated cell. In some embodiments, the cell is a stem cell. In some embodiments, the cell is a pluripotent stem cell. In some embodiments, the cell is a eukaryotic cell line. In some embodiments, the cell is a primary cell line. In some embodiments, the cell is a patient-derived cell line. In some embodiments, the method further comprises transplanting the cell into an organism. In some embodiments, the organism is a human. In some embodiments, the organism is a mammal. In some embodiments, the organism is selected from the group consisting of: a human, a dog, a rat, a mouse, a chicken, a fish, a cat, a plant, and a primate. In some embodiments, the method further comprises selecting the cell. In some embodiments, the donor polynucleotide is inserted into a target nucleic acid that is expressed in one cell state. In some embodiments, the donor polynucleotide is inserted into a target nucleic acid that is expressed in a plurality of cell types. In some embodiments, the donor polynucleotide is inserted into a target nucleic acid that is expressed in a pluripotent state. In some embodiments, the donor polynucleotide is inserted into a target nucleic acid that is expressed in a differentiated state.

In one aspect the disclosure provides for a method for making a clonally expanded cell line comprising: introducing into a cell a complex comprising: a site-directed polypeptide and a nucleic acid-targeting nucleic acid, contacting the complex to a target nucleic acid, cleaving the target nucleic acid, wherein the cleaving is performed by the complex, thereby producing a cleaved target nucleic acid, inserting a donor polynucleotide into the cleaved target nucleic acid, propagating the cell, wherein the propagating produces the clonally expanded cell line. In some embodiments, the cell is selected from the group consisting of: HeLa cell, Chinese Hamster Ovary cell, 293-T cell, a pheochromocytoma, a neuroblastomas fibroblast, a rhabdomyosarcoma, a dorsal root ganglion cell, a NSO cell, CV-I (ATCC CCL 70), COS-I (ATCC CRL 1650), COS-7 (ATCC CRL 1651), CHO-K1 (ATCC CCL 61), 3T3 (ATCC CCL 92). NIH/3T3 (ATCC CRL 1658), HeLa (ATCC CCL 2), C 1271 (ATCC CRL 1616), BS-C-I (ATCC CCL 26), MRC-5 (ATCC CCL 171), L-cells, HEK-293 (ATCC CRL1573) and PC 12 (ATCC CRL-1721), HEK293T (ATCC CRL-11268), RBL (ATCC CRL-1378), SH-SY5Y (ATCC CRL-2266), MDCK (ATCC CCL-34), SJ-RH30 (ATCC CRL-2061), HepG2 (ATCC HB-8065), ND7/23 (ECACC 92090903), CHO (ECACC 85050302), Vera (ATCC CCL 81), Caco-2

(ATCC HTB 37), K562 (ATCC CCL 243), Jurkat (ATCC TIB-152), Per.C6, Huvec (ATCC Human Primary PCS 100-010, Mouse CRL 2514, CRL 2515, CRL 2516), HuH-7D12 (ECACC 01042712), 293 (ATCC CRL 10852), A549 (ATCC CCL 185), IMR-90 (ATCC CCL 186), MCF-7 (ATC HTB-22), U-2 OS (ATCC HTB-96), and T84 (ATCC CCL 248), or any combination thereof. In some embodiments, the cell is stem cell. In some embodiments, the cell is a differentiated cell. In some embodiments, the cell is a pluripotent cell.

In one aspect the disclosure provides for a method for multiplex cell type analysis comprising: cleaving at least one target nucleic acid in two or more cells using a complex comprising a site-directed polypeptide and a nucleic acid-targeting nucleic acid, to create two cleaved target nucleic acids, inserting a different a donor polynucleotide into each of the cleaved target nucleic acids, and analyzing the two or more cells. In some embodiments, the analyzing comprises simultaneously analyzing the two or more cells. In some embodiments, the analyzing comprises determining a sequence of the target nucleic acid. In some embodiments, the analyzing comprises comparing the two or more cells. In some embodiments, the analyzing comprises determining a genotype of the two or more cells. In some embodiments, the cell is a differentiated cell. In some embodiments, the cell is a de-differentiated cell. In some embodiments, the cell is a stem cell. In some embodiments, the cell is a pluripotent stem cell. In some embodiments, the cell is a eukaryotic cell line. In some embodiments, the cell is a primary cell line. In some embodiments, the cell is a patient-derived cell line. In some embodiments, a plurality of donor polynucleotides are inserted into a plurality of cleaved target nucleic acids in the cell.

In one aspect, the disclosure provides for a composition comprising: an engineered nucleic acid-targeting nucleic acid comprising a 3' hybridizing extension, and a donor polynucleotide, wherein the donor polynucleotide is hybridized to the 3' hybridizing extension. In some embodiments, the 3' hybridizing extension is adapted to hybridize to at least 5 nucleotides from the 3' of the donor polynucleotide. In some embodiments, the 3' hybridizing extension is adapted to hybridize to at least 5 nucleotides from the 5' of the donor polynucleotide. In some embodiments, the 3' hybridizing extension is adapted to hybridize to at least 5 adjacent nucleotides in the donor polynucleotide. In some embodiments, the 3' hybridizing extension is adapted to hybridize to all of the donor polynucleotide. In some embodiments, the 3' hybridizing extension comprises a reverse transcription template. In some embodiments, the reverse transcription template is adapted to be reverse transcribed by a reverse transcriptase. In some embodiments, the composition further comprises a reverse transcribed DNA polynucleotide. In some embodiments, the reverse transcribed DNA polynucleotide is adapted to hybridize to the reverse transcription template. In some embodiments, the donor polynucleotide is DNA. In some embodiments, the 3' hybridizing extension is RNA. In some embodiments, the engineered nucleic acid-targeting nucleic acid is an isolated engineered nucleic acid-targeting nucleic acid. In some embodiments, the engineered nucleic acid-targeting nucleic acid is a recombinant engineered nucleic acid-targeting nucleic acid.

In one aspect the disclosure provides for a method for introducing a donor polynucleotide into a target nucleic acid comprising: contacting the target nucleic acid with a composition comprising: an engineered nucleic acid-targeting nucleic acid comprising a 3' hybridizing extension, and a donor polynucleotide, wherein the donor polynucleotide is hybridized to the 3' hybridizing extension. In some embodiments, the method further comprises cleaving the target nucleic acid to produce a cleaved target nucleic acid. In some embodiments, the cleaving is performed by a site-directed polypeptide. In some embodiments, the method further comprises inserting the donor polynucleotide into the cleaved target nucleic acid.

In one aspect, the disclosure provides for a composition comprising: an effector protein, and a nucleic acid, wherein the nucleic acid comprises at least 50% sequence identity to a crRNA over 6 contiguous nucleotides, at least 50% sequence identity to a tracrRNA over 6 contiguous nucleotides; and a non-native sequence, wherein the nucleic acid is adapted to bind to the effector protein. In some embodiments, the composition further comprises a polypeptide comprising at least 10% amino acid sequence identity to a nuclease domain of Cas9, wherein the nucleic acid binds to the polypeptide. In some embodiments, the polypeptide comprises at least 60% amino acid sequence identity in a nuclease domain to a nuclease domain of Cas9. In some embodiments, the polypeptide is Cas9. In some embodiments, the nucleic acid further comprises a linker sequence, wherein the linker sequence links the sequence comprising at least 50% sequence identity to a crRNA over 6 contiguous nucleotides and the sequence comprising at least 50% sequence identity to a tracrRNA over 6 contiguous nucleotides. In some embodiments, the non-native sequence is located at a position of the nucleic acid selected from the group consisting of: a 5' end and a 3' end, or any combination thereof. In some embodiments, the nucleic acid comprises two nucleic acid molecules. In some embodiments, the nucleic acid comprises a single continuous nucleic acid molecule. In some embodiments, the non-native sequence comprises a CRISPR RNA-binding protein binding sequence. In some embodiments, the non-native sequence comprises a binding sequence selected from the group consisting of: a Cas5 RNA-binding sequence, a Cas6 RNA-binding sequence, and a Csy4 RNA-binding sequence, or any combination thereof. In some embodiments, the effector protein comprises a CRISPR RNA-binding protein. In some embodiments, the effector protein comprises at least 15% amino acid sequence identity to a protein selected from the group consisting of: Cas5, Cas6, and Csy4, or any combination thereof. In some embodiments, an RNA-binding domain of the effector protein comprises at least 15% amino acid sequence identity to an RNA-binding domain of a protein selected from the group consisting of: Cas5, Cas6, and Csy4, or any combination thereof. In some embodiments, the effector protein is selected from the group consisting of: Cas5, Cas6, and Csy4, or any combination thereof. In some embodiments, the effector protein further comprises one or more non-native sequences. In some embodiments, the non-native sequence confers an enzymatic activity to the effector protein. In some embodiments, the enzymatic activity is selected from the group consisting of: methyltransferase activity, demethylase activity, acetylation activity, deacetylation activity, ubiquitination activity, deubiquitination activity, deamination activity, dismutase activity, alkylation activity, depurination activity, oxidation activity, pyrimidine dimer forming activity, transposase activity, recombinase activity, polymerase activity, ligase activity, helicase activity, photolyase activity or glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, remodelling activity, protease activity, oxidoreductase activity, transferase activity, hydrolase activity, lyase activity, isomerase activity, synthase activity, synthetase activity, and demyristoylation activity, or any combination thereof. In some embodiments, the nucleic acid is RNA. In some embodiments, the effector protein comprises a fusion protein comprising an RNA-binding protein and a DNA-binding protein. In some embodiments, the composition further comprises a donor polynucleotide. In some embodiments, the donor polynucleotide is bound directly to the DNA binding protein, and wherein the RNA binding protein is bound to the nucleic acid-targeting nucleic acid. In some embodiments, the 5' end of the donor polynucleotide is bound to the DNA-binding protein. In some embodiments, the 3' end of the donor polynucleotide is bound to the DNA-binding protein. In some embodiments, at least 5 nucleotides of the donor polynucleotide bind to the DNA-binding protein. In some embodiments, the nucleic acid is an isolated nucleic acid. In some embodiments, the nucleic acid is a recombinant nucleic acid.

In one aspect, the disclosure provides for a method for introducing a donor polynucleotide into a target nucleic acid comprising: contacting a target nucleic acid with a complex comprising a site-directed polypeptide and a composition comprising: an effector protein, and a nucleic acid, wherein the nucleic acid comprises at least 50% sequence identity to a crRNA over 6 contiguous nucleotides, at least 50% sequence identity to a tracrRNA over 6 contiguous nucleotides; and a non-native sequence, wherein the nucleic acid is adapted to bind to the effector protein. In some embodiments, the method further comprises cleaving the target nucleic acid. In some embodiments, the cleaving is performed by the site-directed polypeptide. In some embodiments, the method further comprises inserting the donor polynucleotide into the target nucleic acid.

In one aspect the disclosure provides for a method for modulating a target nucleic acid comprising: contacting a target nucleic acid with one or more complexes, each complex comprising a site-directed polypeptide and a composition comprising: an effector protein, and a nucleic acid, wherein the nucleic acid comprises at least 50% sequence identity to a crRNA over 6 contiguous nucleotides, at least 50% sequence identity to a tracrRNA over 6 contiguous nucleotides; and a non-native sequence, wherein the nucleic acid is adapted to bind to the effector protein, and modulating the target nucleic acid. In some embodiments, the site-directed polypeptide comprises at least 10% amino acid sequence identity to a nuclease domain of Cas9. In some embodiments, the modulating is performed by the effector protein. In some embodiments, the modulating comprises an activity selected from the group consisting of: methyltransferase activity, demethylase activity, acetylation activity, deacetylation activity, ubiquitination activity, deubiquitination activity, deamination activity, dismutase activity, alkylation activity, depurination activity, oxidation activity, pyrimidine dimer forming activity, transposase activity, recombinase activity, polymerase activity, ligase activity, helicase activity, photolyase activity or glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, remodelling activity, protease activity, oxidoreductase activity, transferase activity, hydrolase activity, lyase activity, isomerase activity, synthase activity, synthetase activity, and demyristoylation activity, or any combination thereof. In some embodiments, the effector protein comprises one or more effector proteins.

In one aspect the disclosure provides for a method for detecting if two complexes are in proximity to one another comprising: contacting a first target nucleic acid with a first complex, wherein the first complex comprises a first site-directed polypeptide, a first modified nucleic acid-targeting nucleic acid, and a first effector protein, wherein the effector protein is adapted to bind to the modified nucleic acid-targeting nucleic acid, and wherein the first effector protein comprises a non-native sequence that comprises a first portion of a split system, and contacting a second target nucleic acid with a second complex, wherein the second complex comprises a second site-directed polypeptide, a second modified nucleic acid-targeting nucleic acid, and a second effector protein, wherein the effector protein is adapted to bind to the modified nucleic acid-targeting nucleic acid, and wherein the second effector protein comprises a non-native sequence that comprises a second portion of a split system. In some embodiments, the first target nucleic acid and the second target nucleic acid are on the same polynucleotide polymer. In some embodiments, the split system comprises two or more protein fragments that individually are not active, but, when formed into a complex, result in an active protein complex. In some embodiments, the method further comprises detecting an interaction between the first portion and the second portion. In some embodiments, the detecting indicates the first and second complex are in proximity to one another. In some embodiments, the site-directed polypeptide is adapted to be unable to cleave the target nucleic acid. In some embodiments, the detecting comprises determining the occurrence of a genetic mobility event. In some embodiments, the genetic mobility event comprises a translocation. In some embodiments, prior to the genetic mobility event the two portions of the split system do not interact. In some embodiments, after the genetic mobility event the two portions of the split system do interact. In some embodiments, the genetic mobility event is a translocation between a BCR and an Abl gene. In some embodiments, the interaction activates the split system. In some embodiments, the interaction indicates the target nucleic acids bound by the complexes are close together. In some embodiments, the split system is selected from the group consisting of: split GFP system, a split ubiquitin system, a split transcription factor system, and a split affinity tag system, or any combination thereof. In some embodiments, the split system comprises a split GFP system. In some embodiments, the detecting indicates a genotype. In some embodiments, the method further comprises: determining a course of treatment for a disease based on the genotype. In some embodiments, the method further comprises treating the disease. In some embodiments, the treating comprises administering a drug. In some embodiments, the treating comprises administering a complex comprising a nucleic acid-targeting nucleic acid and a site-directed polypeptide, wherein the complex can modify a genetic element involved in the disease. In some embodiments, the modifying is selected from the group consisting of: adding a nucleic acid sequence to the genetic element, substituting a nucleic acid sequence in the genetic element, and deleting a nucleic acid sequence from the genetic element, or any combination thereof. In some embodiments, the method further comprises: communicating the genotype from a caregiver to a patient. In some embodiments, the communicating comprises communicating from a storage memory system to a remote computer. In some embodiments, the detecting diagnoses a disease. In some embodiments, the method further comprises: communicating the diagnosis from a caregiver to a patient. In some embodiments, the detecting indicates the presence of a single nucleotide polymorphism (SNP). In some embodiments, the method further comprises: communicating the occurrence of a genetic mobility event from a caregiver to a patient. In some embodiments, the communicating comprises communicating from a storage memory system to a remote computer. In some embodiments, the site-directed polypeptide comprises at least 20% amino acid sequence identity to Cas9. In some embodiments, the site-directed polypeptide comprises at least 60% amino acid sequence identity to Cas9. In some embodiments, the site-directed polypeptide comprises at least 60% amino acid sequence identity in a nuclease domain to a nuclease domain of Cas9. In some embodiments, the site-directed polypeptide is Cas9. In some embodiments, the modified nucleic acid-targeting nucleic acid comprises a non-native sequence. In some embodiments, the non-native sequence is located at a position of the modified nucleic acid-targeting nucleic acid selected from the group consisting of: a 5' end, and a 3' end, or any combination thereof. In some embodiments, the modified nucleic acid-targeting nucleic acid comprises two nucleic acid molecules. In some embodiments, the nucleic acid comprises a single continuous nucleic acid molecule comprising a first portion comprising at least 50% identity to a CRISPR repeat over 6 contiguous nucleotides and a second portion comprising at least 50% identity to a tracrRNA sequence over 6 contiguous nucleotides. In some embodiments, the first portion and the second portion are linked by a linker. In some embodiments, the non-native sequence comprises a CRISPR RNA-binding protein binding sequence. In some embodiments, the non-native sequence comprises a binding sequence selected from the group consisting of: a Cas5 RNA-binding sequence, a Cas6 RNA-binding sequence, and a Csy4 RNA-binding sequence, or any combination thereof. In some embodiments, the modified nucleic acid-targeting nucleic acid is adapted to bind to an effector protein. In some embodiments, the effector protein is a CRISPR RNA-binding protein. In some embodiments, the effector protein comprises at least 15% amino acid sequence identity to a protein selected from the group consisting of: Cas5, Cas6, and Csy4, or any combination thereof. In some embodiments, a RNA-binding domain of the effector protein comprises at least 15% amino acid sequence identity to an RNA-binding domain of a protein selected from the group consisting of: Cas5, Cas6, and Csy4, or any combination thereof. In some embodiments, the effector protein is selected from the group consisting of: Cas5, Cash, and Csy4, or any combination thereof. In some embodiments, the nucleic acid-targeting nucleic acid is RNA. In some embodiments, the target nucleic acid is DNA. In some embodiments, the interaction comprises forming an affinity tag. In some embodiments, the detecting comprises capturing the affinity tag. In some embodiments, the method further comprises sequencing nucleic acid bound to the first and second complexes. In some embodiments, the method further comprises fragmenting the nucleic acid prior to the capturing. In some embodiments, the interaction forms an activated system. In some embodiments, the method further comprises altering transcription of a first target nucleic acid or a second target nucleic acid, wherein the altering is performed by the activated system. In some embodiments, the second target nucleic acid is unattached to the first target nucleic acid. In some embodiments, the altering transcription of the second target nucleic acid is performed in trans. In some embodiments, the altering transcription of the first target nucleic acid is performed in cis. In some embodiments, the first or second target nucleic acid is selected from the group consisting of: an endogenous nucleic acid, and an exogenous nucleic acid, or any combination thereof. In some embodiments, the altering comprises increasing transcription of the first or second target nucleic acids. In some embodiments, the first or second target nucleic acid comprises a polynucleotide encoding one or more genes that cause cell death. In some embodiments, the first or second target nucleic acid comprises a polynucleotide encoding a cell-lysis inducing peptide. In some embodiments, the first or second target nucleic acid comprises a polynucleotide encoding an immune-cell recruiting antigen. In some embodiments, the first or second target nucleic acid comprises a polynucleotide encoding one or more genes involved in apoptosis. In some embodiments, the one or more genes involved in apoptosis comprises caspases. In some embodiments, the one or more genes involved in apoptosis comprises cytokines. In some embodiments, the one or more genes involved in apoptosis are selected from the group consisting of: tumor necrosis factor (TNF), TNF receptor 1 (TNFR1), TNF receptor 2 (TNFR2), Fas receptor, FasL, caspase-8, caspase-10, caspase-3, caspase-9, caspase-3, caspase-6, caspase-7, Bcl-2, and apoptosis inducing factor (AIF), or any combination thereof. In some embodiments, the first or second target nucleic acid comprises a polynucleotide encoding one or more nucleic acid-targeting nucleic acids. In some embodiments, the one or more nucleic acid-targeting nucleic acids target a plurality of target nucleic acids. In some embodiments, the detecting comprises generating genetic data. In some embodiments, the method further comprises communicating the genetic data from a storage memory system to a remote computer. In some embodiments, the genetic data indicates a genotype. In some embodiments, the genetic data indicates the occurrence of a genetic mobility event. In some embodiments, the genetic data indicates a spatial location of genes.

In one aspect, the disclosure provides for a kit comprising: a site-directed polypeptide, a modified nucleic acid-targeting nucleic acid, wherein the modified nucleic acid-targeting nucleic acid comprises a non-native sequence, an effector protein that is adapted to bind to the non-native sequence, and a buffer. In some embodiments, the kit further comprises instructions for use.

In one aspect the disclosure provides for a vector comprising a polynucleotide sequence encoding a modified nucleic acid-targeting nucleic acid, wherein the modified nucleic acid-targeting nucleic acid comprises a non-native sequence. In some embodiments, the polynucleotide sequence is operably linked to a promoter. In some embodiments, the promoter is an inducible promoter.

In one aspect the disclosure provides for a vector comprising: a polynucleotide sequence encoding: a modified nucleic acid-targeting nucleic acid, wherein the modified nucleic acid-targeting nucleic acid comprises a sequence configured to bind to an effector protein, and a site-directed polypeptide. In some embodiments, the polynucleotide sequence is operably linked to a promoter. In some embodiments, the promoter is an inducible promoter.

In one aspect, the disclosure provides for a vector comprising: a polynucleotide sequence encoding: a modified nucleic acid-targeting nucleic acid, wherein the modified nucleic acid-targeting nucleic acid comprises a non-native sequence, a site-directed polypeptide, and an effector protein. In some embodiments, the polynucleotide sequence is operably linked to a promoter. In some embodiments, the promoter is an inducible promoter.

In one aspect the disclosure provides for a genetically modified cell comprising a composition comprising: an effector protein, and a nucleic acid, wherein the nucleic acid comprises at least 50% sequence identity to a crRNA over 6 contiguous nucleotides, at least 50% sequence identity to a tracrRNA over 6 contiguous nucleotides; and a non-native sequence, wherein the nucleic acid is adapted to bind to the effector protein.

In one aspect the disclosure provides for a genetically modified cell comprising a vector comprising a polynucleotide sequence encoding a modified nucleic acid-targeting nucleic acid, wherein the modified nucleic acid-targeting nucleic acid comprises a non-native sequence.

In one aspect the disclosure provides for a genetically modified cell comprising a vector comprising: a polynucleotide sequence encoding: a modified nucleic acid-targeting nucleic acid, wherein the modified nucleic acid-targeting nucleic acid comprises a sequence configured to bind to an effector protein, and a site-directed polypeptide.

In one aspect the disclosure provides for a genetically modified cell comprising a vector comprising: a polynucleotide sequence encoding: a modified nucleic acid-targeting nucleic acid, wherein the modified nucleic acid-targeting nucleic acid comprises a non-native sequence, a site-directed polypeptide, and an effector protein.

In one aspect the disclosure provides for a kit comprising: a vector comprising a polynucleotide sequence encoding a modified nucleic acid-targeting nucleic acid, wherein the modified nucleic acid-targeting nucleic acid comprises a non-native sequence, and a buffer. In some embodiments, the kit further comprises instructions for use.

In one aspect the disclosure provides for a kit comprising: a vector comprising: a polynucleotide sequence encoding: a modified nucleic acid-targeting nucleic acid, wherein the modified nucleic acid-targeting nucleic acid comprises a sequence configured to bind to an effector protein, and a site-directed polypeptide, and a buffer. In some embodiments, the kit further comprises instructions for use.

In one aspect the disclosure provides for a kit comprising: a vector comprising: a polynucleotide sequence encoding: a modified nucleic acid-targeting nucleic acid, wherein the modified nucleic acid-targeting nucleic acid comprises a non-native sequence, a site-directed polypeptide, and an effector protein, and a buffer. In some embodiments, the kit further comprises instructions for use.

In one aspect, the disclosure provides for a composition comprising: a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 10% amino acid sequence identity to a nuclease domain of Cas9 and wherein the nucleic acid module is configured to hybridize to a target nucleic acid. In some embodiments, the nucleic acid module comprises a first sequence comprising at least 50% sequence identity to a crRNA over 6 contiguous nucleotides, and a second sequence comprising at least 50% sequence identity to a tracrRNA over 6 contiguous nucleotides. In some embodiments, the composition further comprises a linker sequence that links the first and second sequences. In some embodiments, the one or more nucleic acid modules hybridize to one or more target nucleic acids. In some embodiments, the one or more nucleic acid modules differ by at least one nucleotide in a spacer region of the one or more nucleic acid modules. In some embodiments, the one or more nucleic acid modules is RNA. In some embodiments, the multiplexed genetic targeting agent is RNA. In some embodiments, the non-native sequence comprises a ribozyme. In some embodiments, the non-native sequence comprises an endoribonuclease binding sequence. In some embodiments, the endoribonuclease binding sequence is located at a 5' end of the nucleic acid module. In some embodiments, the endoribonuclease binding sequence is located at a 3' end of the nucleic acid module. In some embodiments, the endoribonuclease binding sequence is adapted to be bound by a CRISPR endoribonuclease. In some embodiments, the endoribonuclease binding sequence is adapted to be bound by an endoribonuclease comprising a RAMP domain. In some embodiments, the endoribonuclease binding sequence is adapted to be bound by an endoribonuclease selected from the group consisting of: a Cas5 superfamily member endoribonuclease, and a Cas6 superfamily member endoribonuclease, or any combination thereof. In some embodiments, the endoribonuclease binding sequence is adapted to be bound by an endoribonuclease comprising at least 15% amino acid sequence identity to a protein selected from the group consisting of: Csy4, Cas5, and Cas6. In some embodiments, the endoribonuclease binding sequence is adapted to be bound by an endoribonuclease comprising at least 15% amino acid sequence identity to a nuclease domain of a protein selected from the group consisting of: Csy4, Cas5, and Cas6. In some embodiments, the endoribonuclease binding sequence comprises a hairpin. In some embodiments, the hairpin comprises at least 4 consecutive nucleotides in a stem loop structure. In some embodiments, the endoribonuclease binding sequence comprises at least 60% identity to a sequence selected from the group consisting of:

(SEQ ID NO: 1347)
5'-GUUCACUGCCGUAUAGGCAGCUAAGAAA-3';

(SEQ ID NO: 1348)
5'-GUUGCAAGGGAUUGAGCCCCGUAAGGGGAUUGCGAC-3';

(SEQ ID NO: 1349)
5'-GUUGCAAACCUCGUUAGCCUGUAGAGGAUUGAAAC-3';

(SEQ ID NO: 1350)
5'-GGAUCGAUACCCACCCCGAAGAAAAGGGGACGAGAAC-3';

(SEQ ID NO: 1351)
5'-GUCGUCAGACCCAAAACCCCGAGAGGGGACGGAAAC-3';

(SEQ ID NO: 1352)
5'-GAUAUAAACCUAAUUACCUCGAGAGGGGACGGAAAC-3';

(SEQ ID NO: 1353)
5'-CCCCAGUCACCUCGGGAGGGGACGGAAAC-3';

(SEQ ID NO: 1354)
5'-GUUCCAAUUAAUCUUAAACCCUAUUAGGGAUUGAAAC-3';

(SEQ ID NO: 1348)
5'-GUUGCAAGGGAUUGAGCCCCGUAAGGGGAUUGCGAC-3';

(SEQ ID NO: 1349)
5'-GUUGCAAACCUCGUUAGCCUCGUAGAGGAUUGAAAC-3';

(SEQ ID NO: 1350)
5'-GGAUCGAUACCCACCCCGAAGAAAAGGGGACGAGAAC-3';

(SEQ ID NO: 1351)
5'-GUCGUCAGACCCAAAACCCCGAGAGGGGACGGAAAC-3';

(SEQ ID NO: 1352)
5'-GAUAUAAACCUAAUUACCUCGAGAGGGGACGGAAAC-3';

(SEQ ID NO: 1353)
5'-CCCCAGUCACCUCGGGAGGGGACGGAAAC-3';

-continued

```
                                        (SEQ ID NO: 1354)
5'-GUUCCAAUUAAUCUUAAACCCUAUUAGGGAUUGAAAC-3';

(SEQ ID NO: 1355)
5'-GUCGCCCCCACGCGGGGGCGUGGAUUGAAAC-3';

(SEQ ID NO: 1356)
5'-CCAGCCGCCUUCGGGCGGCUGUGUGUUGAAAC-3';

(SEQ ID NO: 1357)
5'-GUCGCACUCUACAUGAGUGCGUGGAUUGAAAU-3';

(SEQ ID NO: 1358)
5'-UGUCGCACCUUAUAUAGGUGCGUGGAUUGAAAU-3';
and (SEQ ID NO: 1359)
5'-GUCGCGCCCCGCAUGGGGCGCGUGGAUUGAAA-3';
``` or any combination thereof. In some embodiments, the one or more nucleic acid modules are adapted to be bound by different endoribonucleases. In some embodiments, the multiplexed genetic target agent is an isolated multiplexed genetic targeting agent. In some embodiments, the multiplexed genetic target agent is a recombinant multiplexed genetic target agent.

In one aspect the disclosure provides for a vector comprising a polynucleotide sequence encoding a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 10% amino acid sequence identity to a nuclease domain of Cas9 and wherein the nucleic acid module is configured to hybridize to a target nucleic acid. In some embodiments, the polynucleotide sequence is operably linked to a promoter. In some embodiments, the promoter is an inducible promoter.

In one aspect, the disclosure provides for a genetically modified cell comprising a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 10% amino acid sequence identity to a nuclease domain of Cas9 and wherein the nucleic acid module is configured to hybridize to a target nucleic acid.

In one aspect the disclosure provides for a genetically modified cell comprising a vector comprising a polynucleotide sequence encoding a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 10% amino acid sequence identity to a nuclease domain of Cas9 and wherein the nucleic acid module is configured to hybridize to a target nucleic acid.

In one aspect the disclosure provides for a kit comprising a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 10% amino acid sequence identity to a nuclease domain of Cas9 and wherein the nucleic acid module is configured to hybridize to a target nucleic acid, and a buffer. In some embodiments, the kit further comprises instructions for use.

In one aspect the disclosure provides for a kit comprising: a vector comprising a polynucleotide sequence encoding a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 10% amino acid sequence identity to a nuclease domain of Cas9 and wherein the nucleic acid module is configured to hybridize to a target nucleic acid, and a buffer. In some embodiments, the kit further comprises instructions for use.

In one aspect the disclosure provides for a method for generating a nucleic acid, wherein the nucleic acid binds to a polypeptide comprising at least 10% amino acid sequence identity to a nuclease domain of Cas9 and hybridizes to a target nucleic acid comprising: introducing the a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 10% amino acid sequence identity to a nuclease domain of Cas9 and wherein the nucleic acid module is configured to hybridize to a target nucleic acid into a host cell, processing the multiplexed genetic targeting agent into the one or more nucleic acid modules, and contacting the processed one or more nucleic acid modules to one or more target nucleic acids in the cell. In some embodiments, the method further comprises cleaving the target nucleic acid. In some embodiments, the method further comprises modifying the target nucleic acid. In some embodiments, the modifying comprises altering transcription of the target nucleic acid. In some embodiments, the modifying comprises inserting a donor polynucleotide into the target nucleic acid.

In one aspect the disclosure provides for a modified site-directed polypeptide comprising: a first nuclease domain, a second nuclease domain, and an inserted nuclease domain. In some embodiments, the site-directed polypeptide comprises at least 15% identity to a nuclease domain of Cas9. In some embodiments, the first nuclease domain comprises a nuclease domain selected from the group consisting of: a HNH domain, and a RuvC domain, or any combination thereof. In some embodiments, the second nuclease domain comprises a nuclease domain selected from the group consisting of: a HNH domain, and a RuvC domain, or any combination thereof. In some embodiments, the inserted nuclease domain comprises a HNH domain. In some embodiments, the inserted nuclease domain comprises a RuvC domain. In some embodiments, the inserted nuclease domain is N-terminal to the first nuclease domain. In some embodiments, the inserted nuclease domain is N-terminal to the second nuclease domain. In some embodiments, the inserted nuclease domain is C-terminal to the first nuclease domain. In some embodiments, the inserted nuclease domain is C-terminal to the second nuclease domain. In some embodiments, the inserted nuclease domain is in tandem to the first nuclease domain. In some embodiments, the inserted nuclease domain is in tandem to the second nuclease domain. In some embodiments, the inserted nuclease domain is adapted to cleave a target nucleic acid at a site different than the first or second nuclease domains. In some embodiments, the inserted nuclease domain is adapted to cleave an RNA in a DNA-RNA hybrid. In some embodiments, the inserted nuclease domain is adapted to cleave a DNA in a DNA-RNA hybrid. In some embodiments, the inserted nuclease domain is adapted to increase specificity of binding of the modified site-directed polypeptide to a target nucleic acid. In some embodiments, the inserted nuclease domain is adapted to increase strength of binding of the modified site-directed polypeptide to a target nucleic acid.

In one aspect the disclosure provides for a vector comprising a polynucleotide sequence encoding a modified site-directed polypeptide comprising: a first nuclease domain, a second nuclease domain, and an inserted nuclease domain.

In one aspect the disclosure provides for a kit comprising: a modified site-directed polypeptide comprising: a first nuclease domain, a second nuclease domain, and an inserted nuclease domain, and a buffer. In some embodiments, the kit further comprises instructions for use.

In one aspect the disclosure provides for a composition comprising: a modified site-directed polypeptide, wherein the polypeptide is modified such that it is adapted to target a second protospacer adjacent motif compared to a wild-type site-directed polypeptide. In some embodiments, the site-directed polypeptide is modified by a modification selected from the group consisting of: an amino acid addition, an amino acid substitution, an amino acid replacement, and an amino acid deletion, or any combination thereof. In some embodiments, the modified site-directed polypeptide comprises a non-native sequence. In some embodiments, the modified site-directed polypeptide is adapted to target the second protospacer adjacent motif with greater specificity than the wild-type site-directed polypeptide. In some embodiments, the modified site-directed polypeptide is adapted to target the second protospacer adjacent motif with a lower dissociation constant compared to the wild-type site-directed polypeptide. In some embodiments, the modified site-directed polypeptide is adapted to target the second protospacer adjacent motif with a higher dissociation constant compared to the wild-type site-directed polypeptide. In some embodiments, the second protospacer adjacent motif comprises a protospacer adjacent motif selected from the group consisting of: 5'-NGGNG-3', 5'-NNAAAAW-3', 5'-NNNNGATT-3', 5'-GNNNCNNA-3', and 5'-NNNACA-3', or any combination thereof.

In one aspect the disclosure provides for a vector comprising a polynucleotide sequence encoding a modified site-directed polypeptide, wherein the polypeptide is modified such that it is adapted to target a second protospacer adjacent motif compared to a wild-type site-directed polypeptide.

In one aspect the disclosure provides for a kit comprising: a modified site-directed polypeptide, wherein the polypeptide is modified such that it is adapted to target a second protospacer adjacent motif compared to a wild-type site-directed polypeptide, and a buffer. In some embodiments, the kit further comprises instructions for use.

In one aspect the disclosure provides for a composition comprising: a modified site-directed polypeptide, wherein the polypeptide is modified such that it is adapted to target a second nucleic acid-targeting nucleic acid compared to a wild-type site-directed polypeptide. In some embodiments, the site-directed polypeptide is modified by a modification selected from the group consisting of: an amino acid addition, an amino acid substitution, an amino acid replacement, and an amino acid deletion, or any combination thereof. In some embodiments, the modified site-directed polypeptide comprises a non-native sequence. In some embodiments, the modified site-directed polypeptide is adapted to target the second nucleic acid-targeting nucleic acid with greater specificity than the wild-type site-directed polypeptide. In some embodiments, the modified site-directed polypeptide is adapted to target the second nucleic acid-targeting nucleic acid with a lower dissociation constant compared to the wild-type site-directed polypeptide. In some embodiments, the modified site-directed polypeptide is adapted to target the second nucleic acid-targeting nucleic acid with a higher dissociation constant compared to the wild-type site-directed polypeptide. In some embodiments, the site-directed polypeptide targets a tracrRNA portion of the second nucleic acid target nucleic acid.

In one aspect the disclosure provides for a vector comprising a polynucleotide sequence encoding a modified site-directed polypeptide, wherein the polypeptide is modified such that it is adapted to target a second nucleic acid-targeting nucleic acid compared to a wild-type site-directed polypeptide.

In one aspect the disclosure provides for a kit comprising: a modified site-directed polypeptide, wherein the polypeptide is modified such that it is adapted to target a second nucleic acid-targeting nucleic acid compared to a wild-type site-directed polypeptide, and a buffer. In some embodiments, the kit further comprises instructions for use.

In one aspect the disclosure provides for a composition comprising: a modified site-directed polypeptide comprising a modification in a bridge helix as compared to SEQ ID: 8. In some embodiments, the composition is configured to cleave a target nucleic acid.

In one aspect the disclosure provides for a composition comprising: a modified site-directed polypeptide comprising a modification in a highly basic patch as compared to SEQ ID: 8. In some embodiments, the composition is configured to cleave a target nucleic acid.

In one aspect the disclosure provides for a composition comprising: a modified site-directed polypeptide comprising a modification in a polymerase-like domain as compared to SEQ ID: 8. In some embodiments, the composition is configured to cleave a target nucleic acid.

In one aspect the disclosure provides for a composition comprising: a modified site-directed polypeptide comprising a modification in a bridge helix, highly basic patch, nuclease domain, and polymerase domain as compared to SEQ ID: 8, or any combination thereof.

In one aspect the disclosure provides for a vector comprising a polynucleotide sequence encoding a modified site-directed polypeptide comprising a modification in a bridge helix, highly basic patch, nuclease domain, and polymerase domain as compared to SEQ ID: 8, or any combination thereof.

In one aspect the disclosure provides for a kit comprising: a modified site-directed polypeptide comprising a modification in a bridge helix, highly basic patch, nuclease domain, and polymerase domain as compared to SEQ ID: 8, or any combination thereof, and a buffer. In some embodiments, the kit further comprises instructions for use. In some embodiments, the kit further comprises a nucleic acid-targeting nucleic acid.

In one aspect the disclosure provides for a genetically modified cell a modified site-directed polypeptide comprising a modification in a bridge helix, highly basic patch, nuclease domain, and polymerase domain as compared to SEQ ID: 8, or any combination thereof.

In one aspect the disclosure provides for a method for genome engineering comprising: contacting a target nucleic acid with a complex, wherein the complex comprises a modified site-directed polypeptide comprising a modification in a bridge helix, highly basic patch, nuclease domain, and polymerase domain as compared to SEQ ID: 8, or any combination thereof and a nucleic acid-targeting nucleic acid, and modifying the target nucleic acid. In some embodiments, the contacting comprises contacting the complex to a protospacer adjacent motif in the target nucleic acid. In some embodiments, the contacting comprises contacting the complex to a longer target nucleic acid sequence compared to an unmodified site-directed polypeptide. In some embodiments, the modifying comprises cleaving the target nucleic acid. In some embodiments, the target nucleic acid comprises RNA. In some embodiments, the target nucleic acid comprises DNA. In some embodiments, the modifying comprises cleaving the RNA strand of a hybridized RNA and DNA. In some embodiments, the modifying comprises cleaving the DNA strand of a hybridized RNA and DNA. In some embodiments, the modifying comprises inserting into the target nucleic acid a donor polynucleotide, a portion of a donor polynucleotide, a copy of a donor polynucleotide, or a portion of a copy of a donor polynucleotide, or any combination thereof. In some embodiments, the modifying comprises modifying transcriptional activity of the target nucleic acid. In some embodiments, the modifying comprises a deleting of one or more nucleotides of the target nucleic acid.

In one aspect the disclosure provides for a composition comprising: a modified site-directed polypeptide comprising a modified nuclease domain as compared to SEQ ID: 8. In some embodiments, the composition is configured to cleave a target nucleic acid. In some embodiments, the modified nuclease domain comprises a RuvC domain nuclease domain. In some embodiments, the modified nuclease domain comprises an HNH nuclease domain. In some embodiments, the modified nuclease domain comprises duplication of an HNH nuclease domain. In some embodiments, the modified nuclease domain is adapted to increase specificity of the amino acid sequence for a target nucleic acid compared to an unmodified site-directed polypeptide. In some embodiments, the modified nuclease domain is adapted to increase specificity of the amino acid sequence for a nucleic acid-targeting nucleic acid compared to an unmodified site-directed polypeptide. In some embodiments, the modified nuclease domain comprises a modification selected from the group consisting of: an amino acid addition, an amino acid substitution, an amino acid replacement, and an amino acid deletion, or any combination thereof. In some embodiments, the modified nuclease domain comprises an inserted non-native sequence. In some embodiments, the non-native sequence confers an enzymatic activity to the modified site-directed polypeptide. In some embodiments, the enzymatic activity is selected from the group consisting of: nuclease activity, methylase activity, acetylase activity, demethylase activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, remodelling activity, protease activity, oxidoreductase activity, transferase activity, hydrolase activity, lyase activity, isomerase activity, synthase activity, synthetase activity, and demyristoylation activity, or any combination thereof. In some embodiments, the enzymatic activity is adapted to modulate transcription of a target nucleic acid. In some embodiments, the modified nuclease domain is adapted to allow binding of the amino acid sequence to a protospacer adjacent motif sequence that is different from a protospacer adjacent motif sequence to which an unmodified site-directed polypeptide is adapted to bind. In some embodiments, the modified nuclease domain is adapted to allow binding of the amino acid sequence to a nucleic acid-targeting nucleic acid that is different from a nucleic acid-targeting nucleic acid to which an unmodified site-directed polypeptide is adapted to bind. In some embodiments, the modified site-directed polypeptide is adapted to bind to a longer target nucleic acid sequence than an unmodified site-directed polypeptide. In some embodiments, the modified site-directed polypeptide is adapted to cleave double-stranded DNA. In some embodiments, the modified site-directed polypeptide is adapted to cleave the RNA strand of a hybridized RNA and DNA. In some embodiments, the modified site-directed polypeptide is adapted to cleave the DNA strand of a hybridized RNA and DNA. In some embodiments, the composition further comprises a modified nucleic acid-targeting nucleic acid, wherein the modification of the site-directed polypeptide is adapted to enable the site-directed polypeptide to bind to the modified nucleic acid-targeting nucleic acid. In some embodiments, the modified nucleic acid-targeting nucleic acid and the modified site-directed polypeptide comprise compensatory mutations.

In one aspect the disclosure provides for a method for enriching a target nucleic acid for sequencing comprising: contacting a target nucleic acid with a complex comprising a nucleic acid-targeting nucleic acid and a site-directed polypeptide, enriching the target nucleic acid using the complex, and determining a sequence of the target nucleic acid. In some embodiments, the method does not comprise an amplification step. In some embodiments, the method further comprises analyzing the sequence of the target nucleic acid. In some embodiments, the method further comprises fragmenting the target nucleic acid prior to the enriching. In some embodiments, the nucleic acid-targeting nucleic acid comprises RNA. In some embodiments, the method the nucleic acid-targeting nucleic acid comprises two RNA molecules. In some embodiments, the method a portion of each of the two RNA molecules hybridize together. In some embodiments, the method one of the two RNA molecules comprises a CRISPR repeat sequence. In some embodiments, the CRISPR repeat sequence is homologous to a crRNA over 6 contiguous nucleotides. In some embodiments, the CRISPR repeat sequence comprises at least 60% identity to a crRNA over 6 contiguous nucleotides. In some embodiments, the one of the two RNA molecules comprises a tracrRNA sequence. In some embodiments, the tracRNA sequence is homologous to a tracrRNA over 6 contiguous nucleotides. In some embodiments, the tracRNA sequence comprises at least 60% identity to a tracrRNA over 6 contiguous nucleotides. In some embodiments, the nucleic acid-targeting nucleic acid is a double guide nucleic acid. In some embodiments, the nucleic acid-targeting nucleic acid comprises one continuous RNA molecule wherein the continuous RNA molecule further comprises two domains and a linker. In some embodiments, a portion of each of the two domains of the continuous RNA molecule hybridize together. In some embodiments, the continuous RNA molecule comprises a CRISPR repeat sequence. In some embodiments, the CRISPR repeat sequence is homologous to a crRNA over 6 contiguous nucleotides. In some embodiments, the CRISPR repeat sequence comprises at least 60% identity to a crRNA over 6 contiguous nucleotides. In some embodiments, the continuous RNA molecule comprises a tracrRNA sequence.

In some embodiments, the tracRNA sequence is homologous to a tracrRNA over 6 contiguous nucleotides. In some embodiments, the tracRNA sequence comprises at least 60% identity to a tracrRNA over 6 contiguous nucleotides. In some embodiments, the nucleic acid-targeting nucleic acid is a single guide nucleic acid. In some embodiments, the contacting comprises hybridizing a portion of the nucleic acid-targeting nucleic acid with a portion of the target nucleic acid. In some embodiments, the nucleic acid-targeting nucleic acid hybridizes with the target nucleic acid over a region comprising 6-20 nucleotides. In some embodiments, the site-directed polypeptide comprises Cas9. In some embodiments, the site-directed polypeptide comprises at least 20% homology to a nuclease domain of Cas9. In some embodiments, the site-directed polypeptide comprises at least 60% homology to Cas9. In some embodiments, the site-directed polypeptide comprises an engineered nuclease domain wherein the nuclease domain comprises reduced nuclease activity compared to a site-directed polypeptide that comprises an unengineered nuclease domain. In some embodiments, the site-directed polypeptide introduces a single-strand break in the target nucleic acid. In some embodiments, the engineered nuclease domain comprises mutation of a conserved aspartic acid. In some embodiments, the engineered nuclease domain comprises a D10A mutation. In some embodiments, the engineered nuclease domain comprises mutation of a conserved histidine. In some embodiments, the engineered nuclease domain comprises a H840A mutation. In some embodiments, the site-directed polypeptide comprises an affinity tag. In some embodiments, the affinity tag is located at the N-terminus of the site-directed polypeptide, the C-terminus of the site-directed polypeptide, a surface-accessible region, or any combination thereof. In some embodiments, the affinity tag is selected from a group comprising: biotin, FLAG, His6× (SEQ ID NO: 1360), His9× (SEQ ID NO: 1361), and a fluorescent protein, or any combination thereof. In some embodiments, the nucleic acid-targeting nucleic acid comprises a nucleic acid affinity tag. In some embodiments, the nucleic acid affinity tag is located at the 5' end of the nucleic acid-targeting nucleic acid, the 3' end of the nucleic acid-targeting nucleic acid, a surface-accessible region, or any combination thereof. In some embodiments, the nucleic acid affinity tag is selected from the group comprising a small molecule, fluorescent label, a radioactive label, or any combination thereof. In some embodiments, the nucleic acid affinity tag comprises a sequence that is configured to bind to Csy4, Cas5, Cas6, or any combination thereof. In some embodiments, the nucleic acid affinity tag comprises 50% identity to 5'-GUUCACUGCCGUAUAGGCAGC-UAAGAAA-3' (SEQ ID NO: 1347). In some embodiments, the method further comprises diagnosing a disease and making a patient-specific treatment decision, or any combination thereof. In some embodiments, the determining comprises determining a genotype. In some embodiments, the method further comprises communicating the sequence from a storage memory system to a remote computer. In some embodiments, the enriching comprises contacting an affinity tag of the complex with a capture agent. In some embodiments, the capture agent comprises an antibody. In some embodiments, the capture agent comprises a solid support. In some embodiments, the capture agent is selected from the group comprising: Csy4, Cas5, and Cas6. In some embodiments, the capture agent comprises reduced enzymatic activity in the absence of imidazole. In some embodiments, the capture agent comprises an activatable enzymatic domain, wherein the activatable enzymatic domain is activated by coming in contact with imidazole. In some embodiments, the capture agent is a Cas6 family member. In some embodiments, the capture agent comprises an affinity tag. In some embodiments, the capture agent comprises a conditionally enzymatically inactive endoribonuclease comprising a mutation in a nuclease domain. In some embodiments, the mutation is a conserved histidine. In some embodiments, the mutation comprises a H29A mutation. In some embodiments, the target nucleic acid is bound to the complex. In some embodiments, the target nucleic acid is an excised nucleic acid that is not bound to the complex. In some embodiments, a plurality of complexes are contacted to a plurality of target nucleic acids. In some embodiments, the plurality of target nucleic acids differ by at least one nucleotide. In some embodiments, the plurality of complexes comprise a plurality of nucleic acid-targeting nucleic acids that differ by at least one nucleotide.

In one aspect the disclosure provides for a method for excising a nucleic acid comprising: contacting a target nucleic acid with two or more complexes, wherein each complex comprises a site-directed polypeptide and a nucleic acid-targeting nucleic acid, and cleaving the target nucleic acid, wherein the cleaving produces an excised target nucleic acid. In some embodiments, the cleaving is performed by a nuclease domain of the site-directed polypeptide. In some embodiments, the method does not comprise amplification. In some embodiments, the method further comprises enriching the excised target nucleic acid. In some embodiments, the method further comprises sequencing the excised target nucleic acid. In some embodiments, the nucleic acid-targeting nucleic acid is RNA. In some embodiments, the nucleic acid-targeting nucleic acid comprises two RNA molecules. In some embodiments, a portion of each of the two RNA molecules hybridize together. In some embodiments, one of the two RNA molecules comprises a CRISPR repeat sequence. In some embodiments, the CRISPR repeat sequence comprises a sequence that is homologous to a crRNA over 6 contiguous nucleotides. In some embodiments, the CRISPR repeat sequence comprises a sequence that has at least 60% identity to a crRNA over 6 contiguous nucleotides. In some embodiments, one of the two RNA molecules comprises a tracrRNA sequence. In some embodiments, the tracRNA sequence is homologous to a crRNA over 6 contiguous nucleotides. In some embodiments, the tracRNA sequence comprises at least 60% identity to a crRNA over 6 contiguous nucleotides. In some embodiments, the nucleic acid-targeting nucleic acid is a double guide nucleic acid. In some embodiments, the nucleic acid-targeting nucleic acid comprises one continuous RNA molecule wherein the continuous RNA molecule further comprises two domains and a linker. In some embodiments, a portion of each of the two domains of the continuous RNA molecule hybridize together. In some embodiments, the continuous RNA molecule comprises a CRISPR repeat sequence. In some embodiments, the CRISPR repeat sequence is homologous to a crRNA over 6 contiguous nucleotides. In some embodiments, the CRISPR repeat sequence comprises at least 60% identity to a crRNA over 6 contiguous nucleotides. In some embodiments, the continuous RNA molecule comprises a tracrRNA sequence. In some embodiments, the tracRNA sequence is homologous to a crRNA over 6 contiguous nucleotides. In some embodiments, the tracRNA sequence comprises at least 60% identity to a crRNA over 6 contiguous nucleotides. In some embodiments, the nucleic acid-targeting nucleic acid is a single guide nucleic acid. In some embodiments, the nucleic acid-targeting nucleic acid hybridizes with a target nucleic acid. In some embodiments, the nucleic acid-targeting nucleic acid hybridizes with a target nucleic acid over a region, wherein the region comprises at least 6 nucleotides and at most 20 nucleotides. In some embodiments, the site-directed polypeptide is Cas9. In some embodiments, the site-directed polypeptide comprises a polypeptide comprising at least 20% homology to a nuclease domain of Cas9. In some embodiments, the site-directed polypeptide comprises a polypeptide comprising at least 60% homology to Cas9. In some embodiments, the site-directed polypeptide comprises an affinity tag. In some embodiments, the affinity tag is located at the N-terminus of the site-directed polypeptide, the C-terminus of the site-directed polypeptide, a surface-accessible region, or any combination thereof. In some embodiments, the affinity tag is selected from a group comprising: biotin, FLAG, His6x (SEQ ID NO: 1360), His9x (SEQ ID NO: 1361), and a fluorescent protein, or any combination thereof. In some embodiments, the nucleic acid-targeting nucleic acid comprises a nucleic acid affinity tag. In some embodiments, the nucleic acid affinity tag is located at the 5' end of the nucleic acid-targeting nucleic acid, the 3' end of the nucleic acid-targeting nucleic acid, a surface-accessible region, or any combination thereof. In some embodiments, the nucleic acid affinity tag is selected from the group comprising a small molecule, fluorescent label, a radioactive label, or any combination thereof. In some embodiments, the nucleic acid affinity tag is a sequence that can bind to Csy4, Cas5, Cash, or any combination thereof. In some embodiments, the nucleic acid affinity tag comprises 50% identity to GUUCACUGC-CGUAUAGGCAGCUAAGAAA (SEQ ID NO: 1347). In some embodiments, the target nucleic acid is an excised nucleic acid that is not bound to the two or more complexes. In some embodiments, the two or more complexes are contacted to a plurality of target nucleic acids. In some embodiments, the plurality of target nucleic acids differ by at least one nucleotide. In some embodiments, the two or more complexes comprise nucleic acid-targeting nucleic acids that differ by at least one nucleotide.

In one aspect the disclosure provides for a method for generating a library of target nucleic acids comprising: contacting a plurality of target nucleic acids with a complex comprising a site-directed polypeptide and a nucleic acid-targeting nucleic acid, cleaving the plurality of target nucleic acids, and purifying the plurality of target nucleic acids to create the library of target nucleic acids. In some embodiments, the method further comprises screening the library of target nucleic acids.

In one aspect the disclosure provides for a composition comprising: a first complex comprising: a first site-directed polypeptide and a first nucleic acid-targeting nucleic acid, a second complex comprising: a second site-directed polypeptide and a second nucleic acid-targeting nucleic acid, wherein, the first and second nucleic acid-targeting nucleic acids are different. In some embodiments, the composition further comprises a target nucleic acid, which is bound by the first or the second complex. In some embodiments, the first site-directed polypeptide and the second site-directed polypeptide are the same. In some embodiments, the first site-directed polypeptide and the second site-directed polypeptide are different.

In one aspect the disclosure provides for a vector comprising a polynucleotide sequence encoding: two or more nucleic acid-targeting nucleic acids that differ by at least one nucleotide, and a site-directed polypeptide.

In one aspect the disclosure provides a genetically modified host cell comprising: a vector comprising a polynucleotide sequence encoding: two or more nucleic acid-targeting nucleic acids that differ by at least one nucleotide, and a site-directed polypeptide.

In one aspect the disclosure provides a kit comprising: a vector comprising a polynucleotide sequence encoding: two or more nucleic acid-targeting nucleic acids that differ by at least one nucleotide, a site-directed polypeptide, and a suitable buffer. In some embodiments, the kit further comprises: a capture agent, a solid support, sequencing adaptors, and a positive control, or any combination thereof. In some embodiments, the kit further comprises instructions for use.

In one aspect the disclosure provides for a kit comprising: a site-directed polypeptide comprising reduced enzymatic activity compared to a wild-type site-directed polypeptide, a nucleic acid-targeting nucleic acid, and a capture agent. In some embodiments, the kit further comprises: instructions for use. In some embodiments, the kit further comprises a buffer selected from the group comprising: a wash buffer, a stabilization buffer, a reconstituting buffer, or a diluting buffer.

In one aspect the disclosure provides for a method for cleaving a target nucleic acid using two or more nickases comprising: contacting a target nucleic acid with a first complex and a second complex, wherein the first complex comprises a first nickase and a first nucleic acid-targeting nucleic acid, and wherein the second complex comprises a second nickase and a second nucleic acid-targeting nucleic acid, wherein the target nucleic acid comprises a first protospacer adjacent motif on a first strand and a second protospacer adjacent motif on a second strand, wherein the first nucleic acid-targeting nucleic acids is adapted to hybridize to the first protospacer adjacent motif, and wherein the second nucleic acid-targeting nucleic acid is adapted to hybridize to the second protospacer adjacent motif, and nicking the first and second strands of the target nucleic acid, wherein the nicking generates a cleaved target nucleic acid. In some embodiments, the first and second nickase are the same. In some embodiments, the first and second nickase are different. In some embodiments, the first and second nucleic acid-targeting nucleic acid are different. In some embodiments, there are less than 125 nucleotides between the first protospacer adjacent motif and the second protospacer adjacent motif. In some embodiments, the first and second protospacer adjacent motifs comprise of the sequence NGG, where N is any nucleotide. In some embodiments, the first or second nickase comprises at least one substantially inactive nuclease domain. In some embodiments, the first or second nickase comprises a mutation of a conserved aspartic acid. In some embodiments, the mutation is a D10A mutation. In some embodiments, the first or second nickase comprises a mutation of a conserved histidine. In some embodiments, the mutation is a H840A mutation. In some embodiments, there are less than 15 nucleotides between the first and second protospacer adjacent motifs. In some embodiments, there are less than 10 nucleotides between the first and second protospacer adjacent motifs. In some embodiments, there are less than 5 nucleotides between the first and second protospacer adjacent motifs. In some embodiments, the first and second protospacer adjacent motifs are adjacent to one another. In some embodiments, the nicking comprises the first nickase nicking the first strand and the second nickase nicking the second strand. In some embodiments, the nicking generates a sticky end cut. In some embodiments, the nicking generates a blunt end cut. In some embodiments, the method further comprises inserting a donor polynucleotide into the cleaved target nucleic acid.

In one aspect the disclosure provides for a composition comprising: a plurality of nucleic acid molecules, wherein each nucleic acid molecule comprises a nucleic acid-binding protein binding site, wherein at least one of the plurality of nucleic acid molecules encodes for a nucleic acid-targeting nucleic acid and one of the plurality of nucleic acid molecules encodes for a site-directed polypeptide, and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site. In some embodiments, one or more of the plurality of nucleic acid-binding proteins comprise a non-native sequence. In some embodiments, the non-native sequence is located at a position selected from the group consisting of: the N-terminus, the C-terminus, a surface accessible region, or any combination thereof. In some embodiments, the non-native sequence encodes for a nuclear localization signal. In some embodiments, the plurality of nucleic acid-binding proteins are separated by a linker. In some embodiments, some of the plurality of nucleic acid-binding proteins are the same nucleic acid-binding protein. In some embodiments, all of the plurality of nucleic acid-binding proteins are the same nucleic acid-binding protein. In some embodiments, the plurality of nucleic acid-binding proteins are different nucleic acid-binding proteins. In some embodiments, the plurality of nucleic acid-binding proteins comprise RNA-binding proteins. In some embodiments, the RNA-binding proteins are selected from the group consisting of: a Type I Clustered Regularly Interspaced Short Palindromic Repeat system endoribonuclease, a Type II Clustered Regularly Interspaced Short Palindromic Repeat system endoribonuclease, or a Type III Clustered Regularly Interspaced Short Palindromic Repeat system endoribonuclease, or any combination thereof. In some embodiments, the RNA-binding proteins are selected from the group consisting of: Cas5, Cas6, and Csy4, or any combination thereof. In some embodiments, the plurality of nucleic acid-binding proteins comprise DNA-binding proteins. In some embodiments, the nucleic acid-binding protein binding site is configured to bind a nucleic acid-binding protein selected from the group consisting of: Type I, Type II, and Type III Clustered Regularly Interspaced Short Palindromic Repeat system nucleic acid-binding protein, or any combination thereof. In some embodiments, the nucleic acid-binding protein binding site is configured to bind a nucleic acid-binding protein selected from the group consisting of: Cas6, Cas5, and Csy4, or any combination thereof. In some embodiments, some of the plurality of nucleic acid molecules comprise the same nucleic acid-binding protein binding site. In some embodiments, the plurality of nucleic acid molecules comprise the same nucleic acid-binding protein binding site. In some embodiments, the none of the plurality of nucleic acid molecules comprise the same nucleic acid-binding protein binding site. In some embodiments, the site-directed polypeptide comprises at least 20% sequence identity to a nuclease domain of Cas9. In some embodiments, the site-directed polypeptide is Cas9. In some embodiments, at least one of the nucleic acid molecules encodes for a Clustered Regularly Interspaced Short Palindromic Repeat endoribonuclease. In some embodiments, the Clustered Regularly Interspaced Short Palindromic Repeat endoribonuclease comprises at least 20% sequence similarity to Csy4. In some embodiments, the Clustered Regularly Interspaced Short Palindromic Repeat endoribonuclease comprises at least 60% sequence similarity to Csy4. In some embodiments, the Clustered Regularly Interspaced Short Palindromic Repeat endoribonuclease is Csy4. In some embodiments, the plurality of nucleic acid-binding proteins comprise reduced enzymatic activity. In some embodiments, the plurality of nucleic acid-binding proteins are adapted to bind to the nucleic acid-binding protein binding site but cannot cleave the nucleic acid-binding protein binding site. In some embodiments, the nucleic acid-targeting nucleic acid comprises two RNA molecules. In some embodiments, a portion of each of the two RNA molecules hybridize together. In some embodiments, a first molecule of the two RNA molecules comprises a sequence comprising at least 60% identity to a Clustered Regularly Interspaced Short Palindromic Repeat RNA sequence over 8 contiguous nucleotides, and wherein a second molecule of the two RNA molecules comprises a sequence comprising at least 60% identity to a trans-activating-Clustered Regularly Interspaced Short Palindromic Repeat RNA sequence over 6 contiguous nucleotides. In some embodiments, the nucleic acid-targeting nucleic acid comprises one continuous RNA molecule wherein the continuous RNA molecule further comprises two domains and a linker. In some embodiments, a portion of the two domains of the continuous RNA molecule hybridize together. In some embodiments, a first portion of the continuous RNA molecule comprises a sequence comprising at least 60% identity to a Clustered Regularly Interspaced Short Palindromic Repeat RNA sequence over 8 contiguous nucleotides, and wherein a second portion of the continuous RNA molecule comprises a sequence comprising at least 60% identity to a trans-activating-Clustered Regularly Interspaced Short Palindromic Repeat RNA sequence over 6 contiguous nucleotides. In some embodiments, the nucleic acid targeting nucleic acid is adapted to hybridize with a target nucleic acid over 6-20 nucleotides. In some embodiments, the composition is configured to be delivered to a cell. In some embodiments, the composition is configured to deliver equal amounts of the plurality of nucleic acid molecules to a cell. In some embodiments, the composition further comprises a donor polynucleotide molecule, wherein the donor polynucleotide molecule comprises a nucleic acid-binding protein binding site, wherein the binding site is bound by a nucleic acid-binding protein of the fusion polypeptide.

In one aspect the disclosure provides for a method for delivery of nucleic acids to a subcellular location in a cell comprising: introducing into a cell a composition comprising: a plurality of nucleic acid molecules, wherein each nucleic acid molecule comprises a nucleic acid-binding protein binding site, wherein at least one of the plurality of nucleic acid molecules encodes for a nucleic acid-targeting nucleic acid and one of the plurality of nucleic acid molecules encodes for a site-directed polypeptide, and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site stoichiometrically delivering the composition to the subcellular location, forming a unit comprising a site-directed polypeptide translated from the nucleic acid molecule encoding for a site-directed polypeptide and the nucleic acid-targeting nucleic acid, and cleaving a target nucleic acid, wherein the site-directed polypeptide of the unit cleaves the target nucleic acid. In some embodiments, the plurality of nucleic acid-binding proteins bind to their cognate nucleic acid-binding protein binding site. In some embodiments, an endoribonuclease cleaves one of the one or more nucleic acid-binding protein binding sites. In some embodiments, an endoribonuclease cleaves the nucleic acid-binding protein binding sites of the nucleic acid encoding the nucleic acid-targeting nucleic acid, thereby liberating the nucleic acid-targeting nucleic acid. In some embodiments, the subcellular location is selected from the group consisting of: the nuclease, the ER, the golgi, the mitochondria, the cell wall, the lysosome, and the nucleus. In some embodiments, the subcellular location is the nucleus.

In one aspect the disclosure provides for a vector comprising: a polynucleotide sequence encoding a composition comprising: a plurality of nucleic acid molecules, wherein each nucleic acid molecule comprises a nucleic acid-binding protein binding site, wherein at least one of the plurality of nucleic acid molecules encodes for a nucleic acid-targeting nucleic acid and one of the plurality of nucleic acid molecules encodes for a site-directed polypeptide; and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site stoichiometrically delivering the composition to the subcellular location. In some embodiments, the vector further comprises a polynucleotide encoding a promoter. In some embodiments, the promoter is operably linked to the polynucleotide. In some embodiments, the promoter is an inducible promoter.

In one aspect the disclosure provides for a genetically modified organism comprising a vector comprising: a polynucleotide sequence encoding for a plurality of nucleic acid molecules, wherein each nucleic acid molecule comprises a nucleic acid-binding protein binding site, wherein at least one of the plurality of nucleic acid molecules encodes for a nucleic acid-targeting nucleic acid and one of the plurality of nucleic acid molecules encodes for a site-directed polypeptide, and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site stoichiometrically delivering the composition to the subcellular location.

In one aspect the disclosure provides for a genetically modified organism comprising: a composition comprising: a plurality of nucleic acid molecules, wherein each nucleic acid molecule comprises a nucleic acid-binding protein binding site, wherein at least one of the plurality of nucleic acid molecules encodes for a nucleic acid-targeting nucleic acid and one of the plurality of nucleic acid molecules encodes for a site-directed polypeptide; and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site.

In one aspect the disclosure provides for a kit comprising: a composition comprising: a plurality of nucleic acid molecules, wherein each nucleic acid molecule comprises a nucleic acid-binding protein binding site, wherein at least one of the plurality of nucleic acid molecules encodes for a nucleic acid-targeting nucleic acid and one of the plurality of nucleic acid molecules encodes for a site-directed polypeptide, and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site, and a buffer.

In one aspect the disclosure provides for a kit comprising: a vector comprising: a polynucleotide sequence encoding for a plurality of nucleic acid molecules, wherein each nucleic acid molecule comprises a nucleic acid-binding protein binding site, wherein at least one of the plurality of nucleic acid molecules encodes for a nucleic acid-targeting nucleic acid and one of the plurality of nucleic acid molecules encodes for a site-directed polypeptide; and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site stoichiometrically delivering the composition to the subcellular location, and a buffer. In some embodiments, the kit further comprises instructions for use. In some embodiments, the buffer is selected from the group comprising: a dilution buffer, a reconstitution buffer, and a stabilization buffer, or any combination thereof.

In one aspect the disclosure provides for a donor polynucleotide comprising: a genetic element of interest, and a reporter element, wherein the reporter element comprises a polynucleotide sequence encoding a site-directed polypeptide, and one or more a nucleic acids, wherein the one or more nucleic acids comprises a sequence comprising at least 50% sequence identity to a crRNA over 6 contiguous nucleotides and a sequence comprising at least 50% sequence identity to a tracrRNA over 6 contiguous nucleotides. In some embodiments, the genetic element of interest comprises a gene. In some embodiments, the genetic element of interest comprises a non-coding nucleic acid selected from the group consisting of: a microRNA, a siRNA, and a long non-coding RNA, or any combination thereof. In some embodiments, the genetic element of interest comprises a non-coding gene. In some embodiments, the genetic element of interest comprises a non-coding nucleic acid selected from the group consisting of: a microRNA, a siRNA, and a long non-coding RNA, or any combination thereof. In some embodiments, the reporter element comprises a gene selected from the group consisting of: a gene encoding a fluorescent protein, a gene encoding a chemiluminescent protein, and an antibiotic resistance gene, or any combination thereof. In some embodiments, the reporter element comprises a gene encoding a fluorescent protein. In some embodiments, the fluorescent protein comprises green fluorescent protein. In some embodiments, the reporter element is operably linked to a promoter. In some embodiments, the promoter comprises an inducible promoter. In some embodiments, the promoter comprises a tissue-specific promoter. In some embodiments, the site-directed polypeptide comprises at least 15% amino acid sequence identity to a nuclease domain of Cas9. In some embodiments, the site-directed polypeptide comprises at least 95% amino acid sequence identity over 10 amino acids to Cas9. In some embodiments, the nuclease domain is selected from the group consisting of: an HNH domain, an HNH-like domain, a RuvC domain, and a RuvC-like domain, or any combination thereof.

In one aspect the disclosure provides for an expression vector comprising a polynucleotide sequence encoding for a genetic element of interest; and a reporter element, wherein the reporter element comprises a polynucleotide sequence encoding a site-directed polypeptide, and one or more a nucleic acids, wherein the one or more nucleic acids comprises a sequence comprising at least 50% sequence identity to a crRNA over 6 contiguous nucleotides and a sequence comprising at least 50% sequence identity to a tracrRNA over 6 contiguous nucleotides.

In one aspect the disclosure provides for a genetically modified cell comprising a donor polynucleotide comprising: a genetic element of interest; and a reporter element, wherein the reporter element comprises a polynucleotide sequence encoding a site-directed polypeptide, and one or more a nucleic acids, wherein the one or more nucleic acids comprises a sequence comprising at least 50% sequence identity to a crRNA over 6 contiguous nucleotides and a sequence comprising at least 50% sequence identity to a tracrRNA over 6 contiguous nucleotides.

In one aspect the disclosure provides for a kit comprising: a donor polynucleotide comprising: a genetic element of interest; and a reporter element, wherein the reporter element comprises a polynucleotide sequence encoding a site-directed polypeptide, and one or more a nucleic acids, wherein the one or more nucleic acids comprises a sequence comprising at least 50% sequence identity to a crRNA over 6 contiguous nucleotides and a sequence comprising at least 50% sequence identity to a tracrRNA over 6 contiguous nucleotides; and a buffer. In some embodiments, the kit further comprises: a polypeptide comprising at least 10% amino acid sequence identity to Cas9; and a nucleic acid, wherein the nucleic acid binds to the polypeptide and hybridizes to a target nucleic acid. In some embodiments, the kit further comprises instructions for use. In some embodiments, the kit further comprises a polynucleotide encoding a polypeptide, wherein the polypeptide comprises at last 15% amino acid sequence identity to Cas9. In some embodiments, the kit further comprises a polynucleotide encoding a nucleic acid, wherein the nucleic acid comprises a sequence comprising at least 50% sequence identity to a crRNA over 6 contiguous nucleotides and a sequence comprising at least 50% sequence identity to a tracrRNA over 6 contiguous nucleotides.

In one aspect the disclosure provides for a method for selecting a cell using a reporter element and excising the reporter element from the cell comprising: contacting a target nucleic acid with a complex comprising a site-directed polypeptide and a nucleic acid-targeting nucleic acid; cleaving the target nucleic acid with the site-directed polypeptide, to generate a cleaved target nucleic acid; inserting the donor polynucleotide comprising a genetic element of interest; and a reporter element, wherein the reporter element comprises a polynucleotide sequence encoding a site-directed polypeptide, and one or more a nucleic acids, wherein the one or more nucleic acids comprises a sequence comprising at least 50% sequence identity to a crRNA over 6 contiguous nucleotides and a sequence comprising at least 50% sequence identity to a tracrRNA over 6 contiguous nucleotides into the cleaved target nucleic acid; and selecting the cell based on the donor polynucleotide to generate a selected cell. In some embodiments, selecting comprises selecting the cell from a subject being treated for a disease. In some embodiments, selecting comprises selecting the cell from a subject being diagnosed for a disease. In some embodiments, after the selecting, the cell comprises the donor polynucleotide. In some embodiments, the method further comprises excising all, some or none of the reporter element, thereby generating a second selected cell. In some embodiments, excising comprises contacting the 5' end of the reporter element with a complex comprising a site-directed polypeptide and a nucleic acid-targeting nucleic acid, wherein the complex cleaves the 5' end. In some embodiments, excising comprises contacting the 3' end of the reporter element with a complex comprising a site-directed polypeptide and a nucleic acid-targeting nucleic acid, wherein the complex cleaves the 3' end. In some embodiments, excising comprises contacting the 5' and 3' end of the reporter element with one or more complexes comprising a site-directed polypeptide and a nucleic acid-targeting nucleic acid, wherein the complex cleaves the 5' and 3' end.

In some embodiments, the method further comprises screening the second selected cell. In some embodiments, screening comprises observing an absence of all or some of the reporter element.

In one aspect the disclosure provides for a composition comprising: a nucleic acid comprising: a spacer, wherein the spacer is between 12-30 nucleotides, inclusive, and wherein the spacer is adapted to hybridize to a sequence that is 5' to a PAM; a first duplex, wherein the first duplex is 3' to the spacer; a bulge, wherein the bulge comprises at least 3 unpaired nucleotides on a first strand of the first duplex and at least 1 unpaired nucleotide on a second strand of the first duplex; a linker, wherein the linker links the first strand and the second strand of the duplex and is at least 3 nucleotides in length; a P-domain; and a second duplex, wherein the second duplex is 3' of the P-domain and is adapted to bind to a site directed polypeptide. In some embodiments, the sequence that is 5' to a PAM is at least 18 nucleotides in length. In some embodiments, the sequence that is 5' to a PAM is adjacent to the PAM. In some embodiments, the PAM comprises 5'-NGG-3'. In some embodiments, the first duplex is adjacent to the spacer. In some embodiments, the P-domain starts from 1-5 nucleotides downstream of the duplex, comprises at least 4 nucleotides, and is adapted to hybridize to sequence selected from the group consisting of: a 5'-NGG-3' protospacer adjacent motif sequence, a sequence comprising at least 50% identity to amino acids 1096-1225 of Cas9 from *S. pyogenes*, or any combination thereof. In some embodiments, the site-directed polypeptide comprises at least 15% identity to a nuclease domain of Cas9 from *S. pyogenes*. In some embodiments, the nucleic acid is RNA. In some embodiments, the nucleic acid is an A-form RNA. In some embodiments, the first duplex is at least 6 nucleotides in length. In some embodiments, the 3 unpaired nucleotides of the bulge comprise 5'-AAG-3'. In some embodiments, adjacent to the 3 unpaired nucleotides is a nucleotide that forms a wobble pair with a nucleotide on the second strand of the first duplex. In some embodiments, the polypeptide binds to a region of the nucleic acid selected from the group consisting of: the first duplex, the second duplex, and the P-domain, or any combination thereof.

In one aspect the disclosure provides for a method of modifying a target nucleic acid comprising: contacting a target nucleic acid with a composition comprising: a nucleic acid comprising: a spacer, wherein the spacer is between 12-30 nucleotides, inclusive, and wherein the spacer is adapted to hybridize to a sequence that is 5' to a PAM; a first duplex, wherein the first duplex is 3' to the spacer; a bulge, wherein the bulge comprises at least 3 unpaired nucleotides on a first strand of the first duplex and at least 1 unpaired nucleotide on a second strand of the first duplex; a linker, wherein the linker links the first strand and the second strand of the duplex and is at least 3 nucleotides in length; a P-domain; and a second duplex, wherein the second duplex is 3' of the P-domain and is adapted to bind to a site directed polypeptide; and modifying the target nucleic acid. In some embodiments, the method further comprises contacting with a site-directed polypeptide. In some embodiments, the contacting comprises contacting the spacer to the target nucleic acid. In some embodiments, the modifying comprises cleaving the target nucleic acid to produce a cleaved target nucleic acid. In some embodiments, the cleaving is performed by the site-directed polypeptide. In some embodiments, the method further comprises inserting a donor polynucleotide into the cleaved target nucleic acid. In some embodiments, the modifying comprises modifying transcription of the target nucleic acid.

In one aspect the disclosure provides for a vector comprising a polynucleotide sequence encoding a nucleic acid comprising: a spacer, wherein the spacer is between 12-30 nucleotides, inclusive, and wherein the spacer is adapted to hybridize to a sequence that is 5' to a PAM; a first duplex, wherein the first duplex is 3' to the spacer; a bulge, wherein the bulge comprises at least 3 unpaired nucleotides on a first strand of the first duplex and at least 1 unpaired nucleotide on a second strand of the first duplex; a linker, wherein the linker links the first strand and the second strand of the duplex and is at least 3 nucleotides in length; a P-domain; and a second duplex, wherein the second duplex is 3' of the P-domain and is adapted to bind to a site directed polypeptide.

In one aspect the disclosure provides for a kit comprising: a composition comprising: a nucleic acid comprising: a spacer, wherein the spacer is between 12-30 nucleotides, inclusive, and wherein the spacer is adapted to hybridize to a sequence that is 5' to a PAM; a first duplex, wherein the first duplex is 3' to the spacer; a bulge, wherein the bulge comprises at least 3 unpaired nucleotides on a first strand of the first duplex and at least 1 unpaired nucleotide on a second strand of the first duplex; a linker, wherein the linker links the first strand and the second strand of the duplex and is at least 3 nucleotides in length; a P-domain; and a second duplex, wherein the second duplex is 3' of the P-domain and is adapted to bind to a site directed polypeptide; and a buffer. In some embodiments, the kit further comprises a site-directed polypeptide. In some embodiments, the kit further comprises a donor polynucleotide. In some embodiments, the kit further comprises instructions for use.

In one aspect, the disclosure provides for a method of creating a synthetically designed nucleic acid-targeting nucleic acid comprising: designing a composition comprising: a nucleic acid comprising: a spacer, wherein the spacer is between 12-30 nucleotides, inclusive, and wherein the spacer is adapted to hybridize to a sequence that is 5' to a PAM; a first duplex, wherein the first duplex is 3' to the spacer; a bulge, wherein the bulge comprises at least 3 unpaired nucleotides on a first strand of the first duplex and at least 1 unpaired nucleotide on a second strand of the first duplex; a linker, wherein the linker links the first strand and the second strand of the duplex and is at least 3 nucleotides in length; a P-domain; and a second duplex, wherein the second duplex is 3' of the P-domain and is adapted to bind to a site directed polypeptide.

In one aspect, the disclosure provides for a pharmaceutical composition comprising an engineered nucleic acid-targeting nucleic acid selected from the group consisting of: an engineered nucleic acid-targeting nucleic acid comprising: a mutation in a P-domain of said nucleic acid-targeting nucleic acid; an engineered nucleic acid-targeting nucleic acid comprising: a mutation in a bulge region of a nucleic acid-targeting nucleic acid.

In one aspect the disclosure provides for a pharmaceutical composition comprising a composition selected from the group consisting of: A composition comprising: an engineered nucleic acid-targeting nucleic acid comprising a 3' hybridizing extension, and a donor polynucleotide, wherein said donor polynucleotide is hybridized to said 3' hybridizing extension; a composition comprising: an effector protein, and a nucleic acid, wherein said nucleic acid comprises: at least 50% sequence identity to a crRNA over 6 contiguous nucleotides, at least 50% sequence identity to a tracrRNA over 6 contiguous nucleotides, and a non-native sequence, wherein said nucleic acid is adapted to bind to said effector protein; a composition comprising: a multiplexed genetic targeting agent, wherein said multiplexed genetic targeting agent comprises one or more nucleic acid modules, wherein said nucleic acid module comprises a non-native sequence, and wherein said nucleic acid module is configured to bind to a polypeptide comprising at least 10% amino acid sequence identity to a nuclease domain of Cas9 and wherein said nucleic acid module is configured to hybridize to a target nucleic acid; a composition comprising: a modified site-directed polypeptide, wherein said polypeptide is modified such that it is adapted to target a second protospacer adjacent motif compared to a wild-type site-directed polypeptide; a composition comprising: a modified site-directed polypeptide, wherein said polypeptide is modified such that it is adapted to target a second nucleic acid-targeting nucleic acid compared to a wild-type site-directed polypeptide; a composition comprising: a modified site-directed polypeptide comprising a modification in a bridge helix as compared to SEQ ID: 8; a composition comprising: a modified site-directed polypeptide comprising a modification in a highly basic patch as compared to SEQ ID: 8; a composition comprising: a modified site-directed polypeptide comprising a modification in a polymerase-like domain as compared to SEQ ID: 8; a composition comprising: a modified site-directed polypeptide comprising a modification in a bridge helix, highly basic patch, nuclease domain, and polymerase domain as compared to SEQ ID: 8, or any combination thereof; a composition comprising: a modified site-directed polypeptide comprising a modified nuclease domain as compared to SEQ ID: 8; a composition comprising: a first complex comprising: a first site-directed polypeptide and a first nucleic acid-targeting nucleic acid, a second complex comprising: a second site-directed polypeptide and a second nucleic acid-targeting nucleic acid, wherein, said first and second nucleic acid-targeting nucleic acids are different; a composition comprising: a plurality of nucleic acid molecules, wherein each nucleic acid molecule comprises a nucleic acid-binding protein binding site, wherein at least one of said plurality of nucleic acid molecules encodes for a nucleic acid-targeting nucleic acid and one of said plurality of nucleic acid molecules encodes for a site-directed polypeptide, and a fusion polypeptide, wherein said fusion polypeptide comprises a plurality of said nucleic acid-binding proteins, wherein said plurality of nucleic acid-binding proteins are adapted to bind to their cognate nucleic acid-binding protein binding site; and a composition comprising: a nucleic acid comprising: a spacer, wherein said spacer is between 12-30 nucleotides, inclusive, and wherein said spacer is adapted to hybridize to a sequence that is 5' to a PAM, a first duplex, wherein said first duplex is 3' to said spacer, a bulge, wherein said bulge comprises at least 3 unpaired nucleotides on a first strand of said first duplex and at least 1 unpaired nucleotide on a second strand of said first duplex, a linker, wherein said linker links said first strand and said second strand of said duplex and is at least 3 nucleotides in length, a P-domain, and a second duplex, wherein said second duplex is 3' of said P-domain and is adapted to bind to a site directed polypeptide; or any combination thereof.

In one aspect, the disclosure provides for a pharmaceutical composition comprising a modified site-directed polypeptide comprising: a first nuclease domain, a second nuclease domain, and an inserted nuclease domain.

In one aspect the disclosure provides for a pharmaceutical composition comprising a donor polynucleotide comprising: a genetic element of interest, and a reporter element, wherein said reporter element comprises a polynucleotide sequence encoding a site-directed polypeptide, and one or more a nucleic acids, wherein said one or more nucleic acids comprises a sequence comprising at least 50% sequence identity to a crRNA over 6 contiguous nucleotides and a sequence comprising at least 50% sequence identity to a tracrRNA over 6 contiguous nucleotides.

In one aspect the disclosure provides for a pharmaceutical composition a vector selected from the group consisting of: a vector comprising a polynucleotide sequence encoding An engineered nucleic acid-targeting nucleic acid comprising: a mutation in a P-domain of said nucleic acid-targeting nucleic acid; a vector comprising a polynucleotide sequence encoding an engineered nucleic acid-targeting nucleic acid comprising: a mutation in a bulge region of a nucleic acid-targeting nucleic acid; and modifying the target nucleic acid; a vector comprising a polynucleotide sequence encoding a modified nucleic acid-targeting nucleic acid, wherein the modified nucleic acid-targeting nucleic acid comprises a non-native sequence; a vector comprising: a polynucleotide sequence encoding: a modified nucleic acid-targeting nucleic acid, wherein the modified nucleic acid-targeting nucleic acid comprises a sequence configured to bind to an effector protein, and a site-directed polypeptide; a vector comprising: a polynucleotide sequence encoding: a modified nucleic acid-targeting nucleic acid, wherein the modified nucleic acid-targeting nucleic acid comprises a non-native sequence, a site-directed polypeptide, and an effector protein; a vector comprising a polynucleotide sequence encoding a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 10% amino acid sequence identity to a nuclease domain of Cas9 and wherein the nucleic acid module is configured to hybridize to a target nucleic acid; a vector comprising a polynucleotide sequence encoding a modified site-directed polypeptide comprising a modification in a bridge helix, highly basic patch, nuclease domain, and polymerase domain as compared to SEQ ID: 8, or any combination thereof; a vector comprising a polynucleotide sequence encoding: two or more nucleic acid-targeting nucleic acids that differ by at least one nucleotide; and a site-directed polypeptide; a vector comprising: a polynucleotide sequence encoding a composition comprising: a plurality of nucleic acid molecules, wherein each nucleic acid molecule comprises a nucleic acid-binding protein binding site, wherein at least one of the plurality of nucleic acid molecules encodes for a nucleic acid-targeting nucleic acid and one of the plurality of nucleic acid molecules encodes for a site-directed polypeptide; and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site stoichiometrically delivering the composition to the subcellular location; an expression vector comprising a polynucleotide sequence encoding for a genetic element of interest; and a reporter element, wherein the reporter element comprises a polynucleotide sequence encoding a site-directed polypeptide, and one or more a nucleic acids, wherein the one or more nucleic acids comprises a sequence comprising at least 50% sequence identity to a crRNA over 6 contiguous nucleotides and a sequence comprising at least 50% sequence identity to a tracrRNA over 6 contiguous nucleotides; and a vector comprising a polynucleotide sequence encoding a nucleic acid comprising: a spacer, wherein the spacer is between 12-30 nucleotides, inclusive, and wherein the spacer is adapted to hybridize to a sequence that is 5' to a PAM; a first duplex, wherein the first duplex is 3' to the spacer; a bulge, wherein the bulge comprises at least 3 unpaired nucleotides on a first strand of the first duplex and at least 1 unpaired nucleotide on a second strand of the first duplex; a linker, wherein the linker links the first strand and the second strand of the duplex and is at least 3 nucleotides in length; a P-domain; and a second duplex, wherein the second duplex is 3' of the P-domain and is adapted to bind to a site directed polypeptide; or any combination thereof.

In one aspect the disclosure provides for a method of treating a disease comprising administering to a subject: an engineered nucleic acid-targeting comprising: a mutation in a P-domain of said nucleic acid-targeting nucleic acid; an engineered nucleic acid-targeting nucleic acid comprising: a mutation in a bulge region of a nucleic acid-targeting nucleic acid; a composition comprising: an engineered nucleic acid-targeting nucleic acid comprising a 3' hybridizing extension, and a donor polynucleotide, wherein said donor polynucleotide is hybridized to said 3' hybridizing extension; a composition comprising: an effector protein, and a nucleic acid, wherein said nucleic acid comprises: at least 50% sequence identity to a crRNA over 6 contiguous nucleotides, at least 50% sequence identity to a tracrRNA over 6 contiguous nucleotides, and a non-native sequence, wherein said nucleic acid is adapted to bind to said effector protein; a composition comprising: a multiplexed genetic targeting agent, wherein said multiplexed genetic targeting agent comprises one or more nucleic acid modules, wherein said nucleic acid module comprises a non-native sequence, and wherein said nucleic acid module is configured to bind to a polypeptide comprising at least 10% amino acid sequence identity to a nuclease domain of Cas9 and wherein said nucleic acid module is configured to hybridize to a target nucleic acid; a composition comprising: a modified site-directed polypeptide, wherein said polypeptide is modified such that it is adapted to target a second protospacer adjacent motif compared to a wild-type site-directed polypeptide; a composition comprising: a modified site-directed polypeptide, wherein said polypeptide is modified such that it is adapted to target a second nucleic acid-targeting nucleic acid compared to a wild-type site-directed polypeptide; a composition comprising: a modified site-directed polypeptide comprising a modification in a bridge helix as compared to SEQ ID: 8; a composition comprising: a modified site-directed polypeptide comprising a modification in a highly basic patch as compared to SEQ ID: 8; a composition comprising: a modified site-directed polypeptide comprising a modification in a polymerase-like domain as compared to SEQ ID: 8; a composition comprising: a modified site-directed polypeptide comprising a modification in a bridge helix, highly basic patch, nuclease domain, and polymerase domain as compared to SEQ ID: 8, or any combination thereof; a composition comprising: a modified site-directed polypeptide comprising a modified nuclease domain as compared to SEQ ID: 8; a composition comprising: a first complex comprising: a first site-directed polypeptide and a first nucleic acid-targeting nucleic acid, a second complex comprising: a second site-directed polypeptide and a second nucleic acid-targeting nucleic acid, wherein, said first and second nucleic acid-targeting nucleic acids are different; a composition comprising: a plurality of nucleic acid molecules, wherein each nucleic acid molecule comprises a nucleic acid-binding protein binding site, wherein at least one of said plurality of nucleic acid molecules encodes for a nucleic acid-targeting nucleic acid and one of said plurality of nucleic acid molecules encodes for a site-directed polypeptide, and a fusion polypeptide, wherein said fusion polypeptide comprises a plurality of said nucleic acid-binding proteins, wherein said plurality of nucleic acid-binding proteins are adapted to bind to their cognate nucleic acid-binding protein binding site; a composition comprising: a nucleic acid comprising: a spacer, wherein said spacer is between 12-30 nucleotides, inclusive, and wherein said spacer is adapted to hybridize to a sequence that is 5' to a PAM, a first duplex, wherein said first duplex is 3' to said spacer, a bulge, wherein said bulge comprises at least 3 unpaired nucleotides on a first strand of said first duplex and at least 1 unpaired nucleotide on a second strand of said first duplex, a linker, wherein said linker links said first strand and said second strand of said duplex and is at least 3 nucleotides in length, a P-domain, and a second duplex, wherein said second duplex is 3' of said P-domain and is adapted to bind to a site directed polypeptide; a modified site-directed polypeptide comprising: a first nuclease domain, a second nuclease domain, and an inserted nuclease domain; a donor polynucleotide comprising: a genetic element of interest, and a reporter element, wherein said reporter element comprises a polynucleotide sequence encoding a site-directed polypeptide, and one or more a nucleic acids, wherein said one or more nucleic acids comprises a sequence comprising at least 50% sequence identity to a crRNA over 6 contiguous nucleotides and a sequence comprising at least 50% sequence identity to a tracrRNA over 6 contiguous nucleotides; a vector comprising a polynucleotide sequence encoding An engineered nucleic acid-targeting nucleic acid comprising: a mutation in a P-domain of said nucleic acid-targeting nucleic acid; a vector comprising a polynucleotide sequence encoding an engineered nucleic acid-targeting nucleic acid comprising: a mutation in a bulge region of a nucleic acid-targeting nucleic acid; and modifying the target nucleic acid; a vector comprising a polynucleotide sequence encoding a modified nucleic acid-targeting nucleic acid, wherein the modified nucleic acid-targeting nucleic acid comprises a non-native sequence; a vector comprising: a polynucleotide sequence encoding: a modified nucleic acid-targeting nucleic acid, wherein the modified nucleic acid-targeting nucleic acid comprises a sequence configured to bind to an effector protein, and a site-directed polypeptide; a vector comprising: a polynucleotide sequence encoding: a modified nucleic acid-targeting nucleic acid, wherein the modified nucleic acid-targeting nucleic acid comprises a non-native sequence, a site-directed polypeptide, and an effector protein; a vector comprising a polynucleotide sequence encoding a multiplexed genetic targeting agent, wherein the multiplexed genetic targeting agent comprises one or more nucleic acid modules, wherein the nucleic acid module comprises a non-native sequence, and wherein the nucleic acid module is configured to bind to a polypeptide comprising at least 10% amino acid sequence identity to a nuclease domain of Cas9 and wherein the nucleic acid module is configured to hybridize to a target nucleic acid; a vector comprising a polynucleotide sequence encoding a modified site-directed polypeptide comprising a modification in a bridge helix, highly basic patch, nuclease domain, and polymerase domain as compared to SEQ ID: 8, or any combination thereof; a vector comprising a polynucleotide sequence encoding: two or more nucleic acid-targeting nucleic acids that differ by at least one nucleotide; and a site-directed polypeptide; a vector comprising: a polynucleotide sequence encoding a composition comprising: a plurality of nucleic acid molecules, wherein each nucleic acid molecule comprises a nucleic acid-binding protein binding site, wherein at least one of the plurality of nucleic acid molecules encodes for a nucleic acid-targeting nucleic acid and one of the plurality of nucleic acid molecules encodes for a site-directed polypeptide; and a fusion polypeptide, wherein the fusion polypeptide comprises a plurality of the nucleic acid-binding proteins, wherein the plurality of nucleic acid-binding proteins are adapted to bind to their cognate nucleic acid-binding protein binding site stoichiometrically delivering the composition to the subcellular location; an expression vector comprising a polynucleotide sequence encoding for a genetic element of interest; and a reporter element, wherein the reporter element comprises a polynucleotide sequence encoding a site-directed polypeptide, and one or more a nucleic acids, wherein the one or more nucleic acids comprises a sequence comprising at least 50% sequence identity to a crRNA over 6 contiguous nucleotides and a sequence comprising at least 50% sequence identity to a tracrRNA over 6 contiguous nucleotides; and a vector comprising a polynucleotide sequence encoding a nucleic acid comprising: a spacer, wherein the spacer is between 12-30 nucleotides, inclusive, and wherein the spacer is adapted to hybridize to a sequence that is 5' to a PAM; a first duplex, wherein the first duplex is 3' to the spacer; a bulge, wherein the bulge comprises at least 3 unpaired nucleotides on a first strand of the first duplex and at least 1 unpaired nucleotide on a second strand of the first duplex; a linker, wherein the linker links the first strand and the second strand of the duplex and is at least 3 nucleotides in length; a P-domain; and a second duplex, wherein the second duplex is 3' of the P-domain and is adapted to bind to a site directed polypeptide; or any combination thereof. In some embodiments, the administering comprises administering comprises administering by viral delivery. In some embodiments, the administering comprises administering comprises administering by electroporation. In some embodiments, the administering comprises administering comprises administering by nanoparticle delivery. In some embodiments, the administering comprises administering comprises administering by liposome delivery. In some embodiments, the administering comprises administering by a method selected from the group consisting of: intravenously, subcutaneously, intramuscularly, orally, rectally, by aerosol, parenterally, ophthalmicly, pulmonarily, transdermally, vaginally, otically, nasally, and by topical administration, or any combination thereof. In some embodiments, the methods of the disclosure are performed in a cell selected from the group consisting of: plant cell, microbe cell, and fungi cell, or any combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A depicts an exemplary embodiment of a single guide nucleic acid-targeting nucleic acid of the disclosure.

FIG. 20 depicts complementary portions of the nucleic acid sequences (SEQ ID NO: 569) of a pre-CRISPR nucleic acid and tracr nucleic acid sequences from *Streptococcus pyogenes* SF370.

FIG. 21 depicts an exemplary secondary structure of a synthetic single guide nucleic acid-targeting nucleic acid (SEQ ID NO: 1518).

FIGS. 22A and B shows exemplary single-guide nucleic acid-targeting nucleic acid backbone variants. Nucleotides in the boxes correspond to nucleotides that have been altered relative to CRISPR sequences labeled as FL-tracr-crRNA sequence. FIG. 22A discloses SEQ ID NOs: 1519, 1518, 1520, 1523, 1521, 1524, 1522, and 1525, respectively, in order of appearance.

FIG. 24 discloses SEQ ID NOs: 1519, 1534, 1538, 1535, 1539, 1536, 1540, 1537, and 1541, respectively, in order of appearance.

FIG. 25 discloses SEQ ID NOs: 1542, 1546, 1543, 1547, 1544, 1548, 1545, and 1549, respectively, in order of appearance.

FIG. 26A-B shows exemplary variants to the single guide nucleic acid-targeting nucleic acid structure within the region 3' to the complementary region/duplex. Nucleotides in the boxes correspond to nucleotides that have been altered relative to the naturally occurring *S. pyogenes* SF370 CRISPR nucleic acid and tracr nucleic acid sequence pairing. FIG. 26A discloses SEQ ID NOs: 1519, 1550, 1554, 1551, 1552, 1555, 1553, and 1556, respectively, in order of appearance. FIG. 26B discloses SEQ ID NOs: 1557, 1561, and 1558-1560, respectively, in order of appearance.

FIG. 27A-B shows exemplary variant nucleic acid-targeting nucleic acid structures comprising additional hairpin sequences derived from the CRISPR repeat in *Pseudomonas aeruginosa* (PA14). The sequences in the boxes can bind to the ribonuclease Csy4 from PA14. FIG. 27A discloses SEQ ID NOs: 1519, 1562, and 1563, respectively, in order of appearance. FIG. 27B discloses SEQ ID NOs: 1564 and 1565, respectively, in order of appearance.

FIG. 35 illustrates a sequence alignment of Cas9 orthologues (SEQ ID NOs: 1568-1579, respectively, in order of appearance). Amino acids with a "X" below them may be considered to be similar. Amino acids with a "Y" below them can be considered to be highly conserved or identical in all sequences. Amino acids residues without an "X" or a "Y" may not be conserved.

FIG. 36 shows the functionality of nucleic acid-targeting nucleic acid variants on target nucleic acid cleavage. The variants tested in FIG. 36 correspond to the variants depicted in FIG. 22A, FIG. 22B, FIG. 24, and FIG. 25.

FIG. 38 depicts exemplary amino acid sequences (SEQ ID NOs: 1580-1582, respectively, in order of appearance) of Csy4 from wild-type *P. aeruginosa*.

FIG. 39 depicts exemplary amino acid sequences (SEQ ID NOs: 1583-1584, respectively, in order of appearance) of an enzymatically inactive endoribonuclease (e.g., Csy4).

FIG. 40 depicts exemplary amino acid sequences (SEQ ID NOs: 1580-1582, respectively, in order of appearance) of Csy4 from *P. aeruginosa*.

FIG. 41A-J depicts exemplary Cas6 amino acid sequences (SEQ ID NOs: 1585-1603, respectively, in order of appearance).

FIG. 42A-C depicts exemplary Cas6 amino acid sequences (SEQ ID NOs: 1604-1608, respectively, in order of appearance).

DETAILED DESCRIPTION OF THE INVENTION

Definitions

Figure 1B:
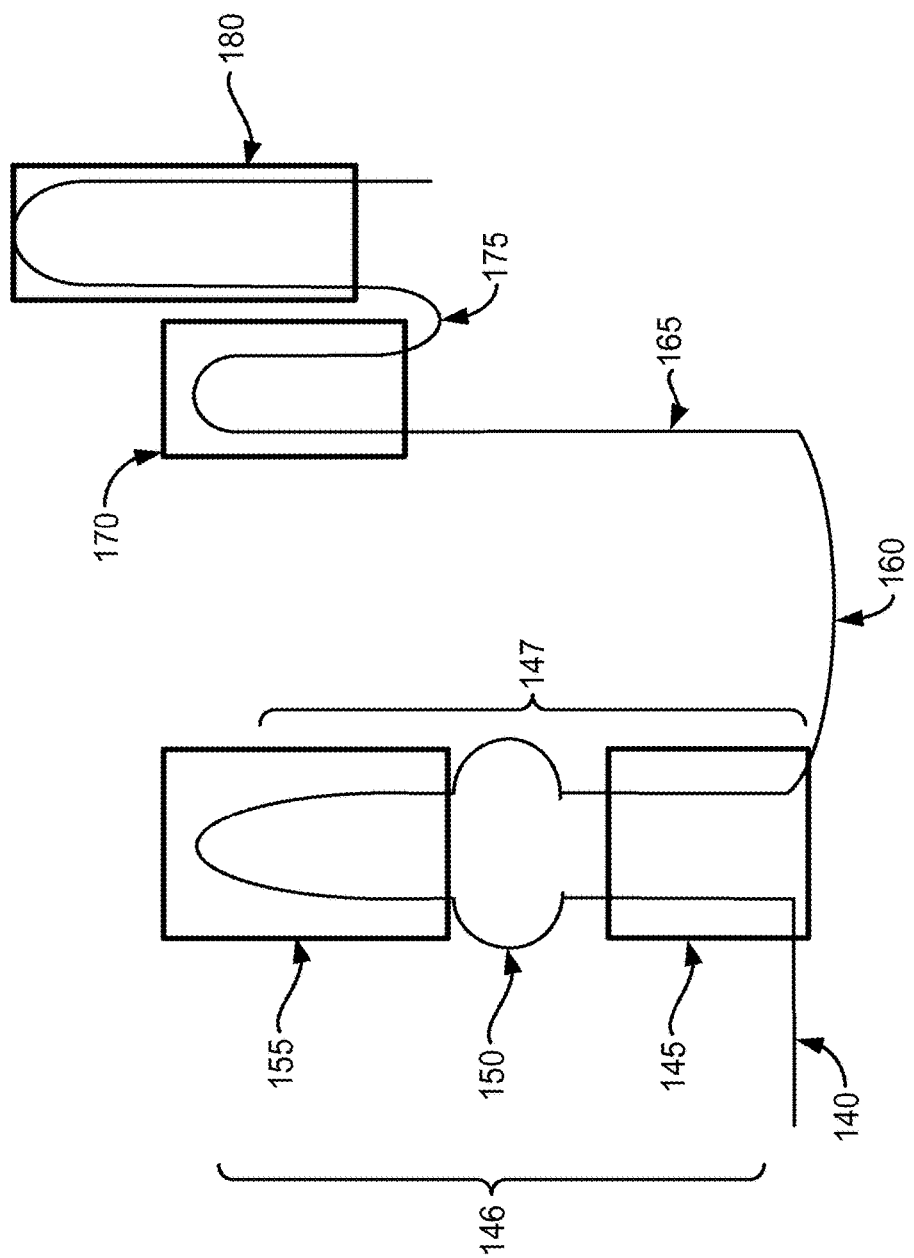
FIG. 1B depicts an exemplary embodiment of a single guide nucleic acid-targeting nucleic acid of the disclosure.

As used herein, "affinity tag" can refer to either a peptide affinity tag or a nucleic acid affinity tag. Affinity tag generally refer to a protein or nucleic acid sequence that can be bound to a molecule (e.g., bound by a small molecule, protein, covalent bond). An affinity tag can be a non-native sequence. A peptide affinity tag can comprise a peptide. A peptide affinity tag can be one that is able to be part of a split system (e.g., two inactive peptide fragments can combine together in trans to form an active affinity tag). A nucleic acid affinity tag can comprise a nucleic acid. A nucleic acid affinity tag can be a sequence that can selectively bind to a known nucleic acid sequence (e.g. through hybridization). A nucleic acid affinity tag can be a sequence that can selectively bind to a protein. An affinity tag can be fused to a native protein. An affinity tag can be fused to a nucleotide sequence. Sometimes, one, two, or a plurality of affinity tags can be fused to a native protein or nucleotide sequence. An affinity tag can be introduced into a nucleic acid-targeting nucleic acid using methods of in vitro or in vivo transcription. Nucleic acid affinity tags can include, for example, a chemical tag, an RNA-binding protein binding sequence, a DNA-binding protein binding sequence, a sequence hybridizable to an affinity-tagged polynucleotide, a synthetic RNA aptamer, or a synthetic DNA aptamer. Examples of chemical nucleic acid affinity tags can include, but are not limited to, ribo-nucleotriphosphates containing biotin, fluorescent dyes, and digoxeginin. Examples of protein-binding nucleic acid affinity tags can include, but are not limited to, the MS2 binding sequence, the U1A binding sequence, stem-loop binding protein sequences, the boxB sequence, the eIF4A sequence, or any sequence recognized by an RNA binding protein. Examples of nucleic acid affinity-tagged oligonucleotides can include, but are not limited to, biotinylated oligonucleotides, 2, 4-dinitrophenyl oligonucleotides, fluorescein oligonucleotides, and primary amine-conjugated oligonucleotides.

A nucleic acid affinity tag can be an RNA aptamer. Aptamers can include, aptamers that bind to theophylline, streptavidin, dextran B512, adenosine, guanosine, guanine/xanthine, 7-methyl-GTP, amino acid aptamers such as aptamers that bind to arginine, citrulline, valine, tryptophan, cyanocobalamine, N-methylmesoporphyrin IX, flavin, NAD, and antibiotic aptamers such as aptamers that bind to tobramycin, neomycin, lividomycin, kanamycin, streptomycin, viomycin, and chloramphenicol.

A nucleic acid affinity tag can comprise an RNA sequence that can be bound by a site-directed polypeptide. The site-directed polypeptide can be conditionally enzymatically inactive. The RNA sequence can comprise a sequence that can be bound by a member of Type I, Type II, and/or Type III CRISPR systems. The RNA sequence can be bound by a RAMP family member protein. The RNA sequence can be bound by a Cas6 family member protein (e.g., Csy4, Cas6). The RNA sequence can be bound by a Cas5 family member protein (e.g., Cas5). For example, Csy4 can bind to a specific RNA hairpin sequence with high affinity (Kd ~50 pM) and can cleave RNA at a site 3' to the hairpin. The Cas5 or Cas6 family member protein can bind an RNA sequence that comprises at least about or at most about 30%, 40%, 50%, 60%, 70%, 75%, 80%, 85%, 90%, 95%, or 100% sequence identity and/or sequence similarity to the following nucleotide sequences:

```
                                    (SEQ ID NO: 1347)
5'-GUUCACUGCCGUAUAGGCAGCUAAGAAA-3';

(SEQ ID NO: 1347)
5'-GUUCACUGCCGUAUAGGCAGCUAAGAAA-3';

(SEQ ID NO: 1348)
5'-GUUGCAAGGGAUUGAGCCCCGUAAGGGGAUUGCGAC-3';

(SEQ ID NO: 1349)
5'-GUUGCAAACCUCGUUAGCCUCGUAGAGGAUUGAAAC-3';

(SEQ ID NO: 1350)
5'-GGAUCGAUACCCACCCCGAAGAAAAGGGGACGAGAAC-3';

(SEQ ID NO: 1351)
5'-GUCGUCAGACCCAAAACCCCGAGAGGGGACGGAAAC-3';

(SEQ ID NO: 1352)
5'-GAUAUAAACCUAAUUACCUCGAGAGGGGACGGAAAC-3';

(SEQ ID NO: 1353)
5'-CCCCAGUCACCUCGGGAGGGGACGGAAAC-3';

(SEQ ID NO: 1354)
5'-GUUCCAAUUAAUCUUAAACCCUAUUAGGGAUUGAAAC-3';

(SEQ ID NO: 1348)
5'-GUUGCAAGGGAUUGAGCCCCGUAAGGGGAUUGCGAC-3';

(SEQ ID NO: 1349)
5'-GUUGCAAACCUCGUUAGCCUCGUAGAGGAUUGAAAC-3';

(SEQ ID NO: 1350)
5'-GGAUCGAUACCCACCCCGAAGAAAAGGGGACGAGAAC-3';

(SEQ ID NO: 1351)
5'-GUCGUCAGACCCAAAACCCCGAGAGGGGACGGAAAC-3';
```

```
                                            (SEQ ID NO: 1352)
5'-GAUAUAAACCUAAUUACCUCGAGAGGGGACGGAAAC-3';

(SEQ ID NO: 1353)
5'-CCCCAGUCACCUCGGGAGGGGACGGAAAC-3';

(SEQ ID NO: 1354)
5'-GUUCCAAUUAAUCUUAAACCCUAUUAGGGAUUGAAAC-3';

(SEQ ID NO: 1355)
5'-GUCGCCCCCACGCGGGGCGUGGAUUGAAAC-3';

(SEQ ID NO: 1356)
5'-CCAGCCGCCUUCGGGCGGCUGUGUGUUGAAAC-3';

(SEQ ID NO: 1357)
5'-GUCGCACUCUACAUGAGUGCGUGGAUUGAAAU-3';

(SEQ ID NO: 1358)
5'-UGUCGCACCUUAUAUAGGUGCGUGGAUUGAAAU-3';
and (SEQ ID NO: 1359)
5'-GUCGCGCCCCGCAUGGGGCGCGUGGAUUGAAA-3'.
```

A nucleic acid affinity tag can comprise a DNA sequence that can be bound by a site-directed polypeptide. The site-directed polypeptide can be conditionally enzymatically inactive. The DNA sequence can comprise a sequence that can be bound by a member of the Type I, Type II and/or Type III CRISPR system. The DNA sequence can be bound by an Argonaut protein. The DNA sequence can be bound by a protein containing a zinc finger domain, a TALE domain, or any other DNA-binding domain.

A nucleic acid affinity tag can comprise a ribozyme sequence. Suitable ribozymes can include peptidyl transferase 23S rRNA, RnaseP, Group I introns, Group II introns, GIR1 branching ribozyme, Leadzyme, hairpin ribozymes, hammerhead ribozymes, HDV ribozymes, CPEB3 ribozymes, VS ribozymes, glmS ribozyme, CoTC ribozyme, and synthetic ribozymes.

Peptide affinity tags can comprise tags that can be used for tracking or purification (e.g., a fluorescent protein, green fluorescent protein (GFP), YFP, RFP, CFP, mCherry, tdTomato, a his tag, (e.g., a 6×His tag), a hemagglutinin (HA) tag, a FLAG tag, a Myc tag, a GST tag, a MBP tag, and chitin binding protein tag, a calmodulin tag, a V5 tag, a streptavidin binding tag, and the like).

Both nucleic acid and peptide affinity tags can comprise small molecule tags such as biotin, or digitoxin, fluorescent label tags, such as for example, fluoroscein, rhodamin, Alexa fluor dyes, Cyanine3 dye, Cyanine5 dye.

Nucleic acid affinity tags can be located 5' to a nucleic acid (e.g., a nucleic acid-targeting nucleic acid). Nucleic acid affinity tags can be located 3' to a nucleic acid. Nucleic acid affinity tags can be located 5' and 3' to a nucleic acid. Nucleic acid affinity tags can be located within a nucleic acid. Peptide affinity tags can be located N-terminal to a polypeptide sequence. Peptide affinity tags can be located C-terminal to a polypeptide sequence. Peptide affinity tags can be located N-terminal and C-terminal to a polypeptide sequence. A plurality of affinity tags can be fused to a nucleic acid and/or a polypeptide sequence.

As used herein, "capture agent" can generally refer to an agent that can purify a polypeptide and/or a nucleic acid. A capture agent can be a biologically active molecule or material (e.g. any biological substance found in nature or synthetic, and includes but is not limited to cells, viruses, subcellular particles, proteins, including more specifically antibodies, immunoglobulins, antigens, lipoproteins, glycoproteins, peptides, polypeptides, protein complexes, (strept) avidin-biotin complexes, ligands, receptors, or small molecules, aptamers, nucleic acids, DNA, RNA, peptidic nucleic acids, oligosaccharides, polysaccharides, lipopolysccharides, cellular metabolites, haptens, pharmacologically active substances, alkaloids, steroids, vitamins, amino acids, and sugars). In some embodiments, the capture agent can comprise an affinity tag. In some embodiments, a capture agent can preferentially bind to a target polypeptide or nucleic acid of interest. Capture agents can be free floating in a mixture. Capture agents can be bound to a particle (e.g. a bead, a microbead, a nanoparticle). Capture agents can be bound to a solid or semisolid surface. In some instances, capture agents are irreversibly bound to a target. In other instances, capture agents are reversibly bound to a target (e.g. if a target can be eluted, or by use of a chemical such as imidizole).

As used herein, "Cas5" can generally refer to can refer to a polypeptide with at least about 5%, 10%, 20%, 30%, 40%, 50%, 60%, 70%, 80%, 90%, 100% sequence identity and/or sequence similarity to a wild type exemplary Cas5 polypeptide (e.g., Cas5 from D. vulgaris, and/or any sequences depicted in FIG. 42). Cas5 can generally refer to can refer to a polypeptide with at most about 5%, 10%, 20%, 30%, 40%, 50%, 60%, 70%, 80%, 90%, 100% sequence identity and/or sequence similarity to a wild type exemplary Cas5 polypeptide (e.g., a Cas5 from D. vulgaris). Cas5 can refer to the wild type or a modified form of the Cas5 protein that can comprise an amino acid change such as a deletion, insertion, substitution, variant, mutation, fusion, chimera, or any combination thereof.

As used herein, "Cas6" can generally refer to can refer to a polypeptide with at least about 5%, 10%, 20%, 30%, 40%, 50%, 60%, 70%, 80%, 90%, 100% sequence identity and/or sequence similarity to a wild type exemplary Cas6 polypeptide (e.g., a Cas6 from T. thermophilus, and/or sequences depicted in FIG. 41). Cas6 can generally refer to can refer to a polypeptide with at most about 5%, 10%, 20%, 30%, 40%, 50%, 60%, 70%, 80%, 90%, 100% sequence identity and/or sequence similarity to a wild type exemplary Cas6 polypeptide (e.g., from T. thermophilus). Cas6 can refer to the wild type or a modified form of the Cas6 protein that can comprise an amino acid change such as a deletion, insertion, substitution, variant, mutation, fusion, chimera, or any combination thereof.

As used herein, "Cas9" can generally refer to a polypeptide with at least about 5%, 10%, 20%, 30%, 40%, 50%, 60%, 70%, 80%, 90%, 100% sequence identity and/or sequence similarity to a wild type exemplary Cas9 polypeptide (e.g., Cas9 from S. pyogenes (SEQ ID NO: 8, SEQ ID NO: 1-256, SEQ ID NO: 795-1346). Cas9 can refer to can refer to a polypeptide with at most about 5%, 10%, 20%, 30%, 40%, 50%, 60%, 70%, 80%, 90%, 100% sequence identity and/or sequence similarity to a wild type exemplary Cas9 polypeptide (e.g., from S. pyogenes). Cas9 can refer to the wild type or a modified form of the Cas9 protein that can comprise an amino acid change such as a deletion, insertion, substitution, variant, mutation, fusion, chimera, or any combination thereof.

As used herein, a "cell" can generally refer to a biological cell. A cell can be the basic structural, functional and/or biological unit of a living organism. A cell can originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant (e.g. cells from plant crops, fruits, vegetables, grains, soy bean, corn, maize, wheat, seeds, tomatoes, rice, cassava, sugarcane, pumpkin, hay, potatoes, cotton, *cannabis*, tobacco, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens C. Agardh*, and the like), seaweeds (e.g. kelp) a fungal cell (e.g., a yeast cell, a cell from a mushroom), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), and etcetera. Sometimes a cell is not originating from a natural organism (e.g. a cell can be a synthetically made, sometimes termed an artificial cell).

A cell can be in vitro. A cell can be in vivo. A cell can be an isolated cell. A cell can be a cell inside of an organism. A cell can be an organism. A cell can be a cell in a cell culture. A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell.

A cell can be a stem cell or progenitor cell. Cells can include stem cells (e.g., adult stem cells, embryonic stem cells, iPS cells) and progenitor cells (e.g., cardiac progenitor cells, neural progenitor cells, etc.). Cells can include mammalian stem cells and progenitor cells, including rodent stem cells, rodent progenitor cells, human stem cells, human progenitor cells, etc. Clonal cells can comprise the progeny of a cell. A cell can comprise a target nucleic acid. A cell can be in a living organism. A cell can be a genetically modified cell. A cell can be a host cell.

A cell can be a totipotent stem cell, however, in some embodiments of this disclosure, the term "cell" may be used but may not refer to a totipotent stem cell. A cell can be a plant cell, but in some embodiments of this disclosure, the term "cell" may be used but may not refer to a plant cell. A cell can be a pluripotent cell. For example, a cell can be a pluripotent hematopoietic cell that can differentiate into other cells in the hematopoietic cell lineage but may not be able to differentiate into any other non-hematopoetic cell. A cell may be able to develop into a whole organism. A cell may or may not be able to develop into a whole organism. A cell may be a whole organism.

A cell can be a primary cell. For example, cultures of primary cells can be passaged 0 times, 1 time, 2 times, 4 times, 5 times, 10 times, 15 times or more. Cells can be unicellular organisms. Cells can be grown in culture.

A cell can be a diseased cell. A diseased cell can have altered metabolic, gene expression, and/or morphologic features. A diseased cell can be a cancer cell, a diabetic cell, and a apoptotic cell. A diseased cell can be a cell from a diseased subject. Exemplary diseases can include blood disorders, cancers, metabolic disorders, eye disorders, organ disorders, musculoskeletal disorders, cardiac disease, and the like.

If the cells are primary cells, they may be harvested from an individual by any method. For example, leukocytes may be harvested by apheresis, leukocytapheresis, density gradient separation, etc. Cells from tissues such as skin, muscle, bone marrow, spleen, liver, pancreas, lung, intestine, stomach, etc. can be harvested by biopsy. An appropriate solution may be used for dispersion or suspension of the harvested cells. Such solution can generally be a balanced salt solution, (e.g. normal saline, phosphate-buffered saline (PBS), Hank's balanced salt solution, etc.), conveniently supplemented with fetal calf serum or other naturally occurring factors, in conjunction with an acceptable buffer at low concentration. Buffers can include HEPES, phosphate buffers, lactate buffers, etc. Cells may be used immediately, or they may be stored (e.g., by freezing). Frozen cells can be thawed and can be capable of being reused. Cells can be frozen in a DMSO, serum, medium buffer (e.g., 10% DMSO, 50% serum, 40% buffered medium), and/or some other such common solution used to preserve cells at freezing temperatures.

As used herein, "conditionally enzymatically inactive site-directed polypeptide" can generally refer to a polypeptide that can bind to a nucleic acid sequence in a polynucleotide in a sequence-specific manner, but may not cleave a target polynucleotide except under one or more conditions that render the enzymatic domain active. A conditionally enzymatically inactive site-directed polypeptide can comprise an enzymatically inactive domain that can be conditionally activated. A conditionally enzymatically inactive site-directed polypeptide can be conditionally activated in the presence of imidazole. A conditionally enzymatically inactive site-directed polypeptide can comprise a mutated active site that fails to bind its cognate ligand, resulting in an enzymatically inactive site-directed polypeptide. The mutated active site can be designed to bind to ligand analogues, such that a ligand analogue can bind to the mutated active site and reactive the site-directed polypeptide. For example, ATP binding proteins can comprise a mutated active site that can inhibit activity of the protein, yet are designed to specifically bind to ATP analogues. Binding of an ATP analogue, but not ATP, can reactivate the protein. The conditionally enzymatically inactive site-directed polypeptide can comprise one or more non-native sequences (e.g., a fusion, an affinity tag).

As used herein, "crRNA" can generally refer to a nucleic acid with at least about 5%, 10%, 20%, 30%, 40%, 50%, 60%, 70%, 80%, 90%, 100% sequence identity and/or sequence similarity to a wild type exemplary crRNA (e.g., a crRNA from *S. pyogenes* (e.g., SEQ ID NO: 569, SEQ ID NO: 563-679). crRNA can generally refer to a nucleic acid with at most about 5%, 10%, 20%, 30%, 40%, 50%, 60%, 70%, 80%, 90%, 100% sequence identity and/or sequence similarity to a wild type exemplary crRNA (e.g., a crRNA from *S. pyogenes*). crRNA can refer to a modified form of a crRNA that can comprise an nucleotide change such as a deletion, insertion, or substitution, variant, mutation, or chimera. A crRNA can be a nucleic acid having at least about 60% identical to a wild type exemplary crRNA (e.g., a crRNA from *S. pyogenes*) sequence over a stretch of at least 6 contiguous nucleotides. For example, a crRNA sequence can be at least about 60% identical, at least about 65% identical, at least about 70% identical, at least about 75% identical, at least about 80% identical, at least about 85% identical, at least about 90% identical, at least about 95% identical, at least about 98% identical, at least about 99% identical, or 100% identical, to a wild type exemplary crRNA sequence (e.g., a crRNA from *S. pyogenes*) over a stretch of at least 6 contiguous nucleotides.

As used herein, "CRISPR repeat" or "CRISPR repeat sequence" can refer to a minimum CRISPR repeat sequence.

As used herein, "Csy4" can generally refer to a polypeptide with at most about 5%, 10%, 20%, 30%, 40%, 50%, 60%, 70%, 80%, 90%, 100% sequence identity and/or sequence similarity to a wild type exemplary Csy4 polypeptide (e.g., Csy4 from *P. aeruginosa*, see FIG. 40). Csy4 can generally refer to can refer to a polypeptide with at least about 5%, 10%, 20%, 30%, 40%, 50%, 60%, 70%, 80%, 90%, 100% sequence identity and/or sequence similarity to a wild type exemplary Csy4 polypeptide (e.g., Csy4 from *P. aeruginosa*). Csy4 can refer to the wild type or a modified form of the Csy4 protein that can comprise an amino acid change such as a deletion, insertion, substitution, variant, mutation, fusion, chimera, or any combination thereof.

As used herein, "endoribonuclease" can generally refer to a polypeptide that can cleave RNA. In some embodiments, an endoribonuclease can be a site-directed polypeptide. An endoribonuclease may be a member of a CRISPR system (e.g., Type I, Type II, Type III). Endoribonuclease can refer to a Repeat Associated Mysterious Protein (RAMP) superfamily of proteins (e.g., Cas6, Cas6, Cas5 families). Endoribonucleases can also include RNase A, RNase H, RNase I, RNase III family members (e.g., Drosha, Dicer, RNase N), RNase L, RNase P, RNase PhyM, RNase T1, RNase T2, RNase U2, RNase V1, RNase V. An endoribonuclease can refer to a conditionally enzymatically inactive endoribonuclease. An endoribonuclease can refer to a catalytically inactive endoribonuclease.

As used herein, "donor polynucleotide" can refer to a nucleic acid that can be integrated into a site during genome engineering or target nucleic acid engineering.

As used herein, "fixative" or "cross-linker" can generally refer to an agent that can fix or cross-link cells. Fixed or cross-linking cells can stabilize protein-nucleic acid complexes in the cell. Suitable fixatives and cross-linkers can include, formaldehyde, glutaraldehyde, ethanol-based fixatives, methanol-based fixatives, acetone, acetic acid, osmium tetraoxide, potassium dichromate, chromic acid, potassium permanganate, mercurials, picrates, formalin, paraformaldehyde, amine-reactive NETS-ester crosslinkers such as bis[sulfosuccinimidyl] suberate (BS3), 3,3'-dithiobis [sulfosuccinimidylpropionate] (DTSSP), ethylene glycol bis [sulfosuccinimidylsuccinate (sulfo-EGS), disuccinimidyl glutarate (DSG), dithiobis[succinimidyl propionate] (DSP), disuccinimidyl suberate (DSS), ethylene glycol bis[succinimidylsuccinate] (EGS), NHS-ester/diazirine crosslinkers such as NHS-diazirine, NHS-LC-diazirine, NHS-SS-diazirine, sulfo-NHS-diazirine, sulfo-NHS-LC-diazirine, and sulfo-NHS-SS-diazirine.

As used herein, "fusion" can refer to a protein and/or nucleic acid comprising one or more non-native sequences (e.g., moieties). A fusion can comprise one or more of the same non-native sequences. A fusion can comprise one or more different non-native sequences. A fusion can be a chimera. A fusion can comprise a nucleic acid affinity tag. A fusion can comprise a barcode. A fusion can comprise a peptide affinity tag. A fusion can provide for subcellular localization of the site-directed polypeptide (e.g., a nuclear localization signal (NLS) for targeting to the nucleus, a mitochondrial localization signal for targeting to the mitochondria, a chloroplast localization signal for targeting to a chloroplast, an endoplasmic reticulum (ER) retention signal, and the like). A fusion can provide a non-native sequence (e.g., affinity tag) that can be used to track or purify. A fusion can be a small molecule such as biotin or a dye such as alexa fluor dyes, Cyanine3 dye, Cyanine5 dye. The fusion can provide for increased or decreased stability.

In some embodiments, a fusion can comprise a detectable label, including a moiety that can provide a detectable signal. Suitable detectable labels and/or moieties that can provide a detectable signal can include, but are not limited to, an enzyme, a radioisotope, a member of a specific binding pair; a fluorophore; a fluorescent protein; a quantum dot; and the like.

A fusion can comprise a member of a FRET pair. FRET pairs (donor/acceptor) suitable for use can include, but are not limited to, EDANS/fluorescein, IAEDANS/fluorescein, fluorescein/tetramethylrhodamine, fluorescein/Cy 5, IEDANS/DABCYL, fluorescein/QSY-7, fluorescein/LC Red 640, fluorescein/Cy 5.5 and fluorescein/LC Red 705.

A fluorophore/quantum dot donor/acceptor pair can be used as a fusion. Suitable fluorophores ("fluorescent label") can include any molecule that may be detected via its inherent fluorescent properties, which can include fluorescence detectable upon excitation. Suitable fluorescent labels can include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705 and Oregon green.

A fusion can comprise an enzyme. Suitable enzymes can include, but are not limited to, horse radish peroxidase, luciferase, beta-galactosidase, and the like.

A fusion can comprise a fluorescent protein. Suitable fluorescent proteins can include, but are not limited to, a green fluorescent protein (GFP), (e.g., a GFP from *Aequoria victoria*, fluorescent proteins from *Anguilla japonica*, or a mutant or derivative thereof), a red fluorescent protein, a yellow fluorescent protein, any of a variety of fluorescent and colored proteins.

A fusion can comprise a nanoparticle. Suitable nanoparticles can include fluorescent or luminescent nanoparticles, and magnetic nanoparticles. Any optical or magnetic property or characteristic of the nanoparticle(s) can be detected.

A fusion can comprise quantum dots (QDs). QDs can be rendered water soluble by applying coating layers comprising a variety of different materials. For example, QDs can be solubilized using amphiphilic polymers. Exemplary polymers that have been employed can include octylamine-modified low molecular weight polyacrylic acid, polyethylene-glycol (PEG)-derivatized phospholipids, polyanhydrides, block copolymers, etc. QDs can be conjugated to a polypeptide via any of a number of different functional groups or linking agents that can be directly or indirectly linked to a coating layer. QDs with a wide variety of absorption and emission spectra are commercially available, e.g., from Quantum Dot Corp. (Hayward Calif.; now owned by Invitrogen) or from Evident Technologies (Troy, N.Y.). For example, QDs having peak emission wavelengths of approximately 525, 535, 545, 565, 585, 605, 655, 705, and 800 nm are available. Thus the QDs can have a range of different colors across the visible portion of the spectrum and in some cases even beyond.

Suitable radioisotopes can include, but are not limited to $^{14}C$, $^{3}H$, $^{32}P$, $^{33}P$, $^{35}S$, and $^{125}I$.

As used herein, "genetically modified cell" can generally refer to a cell that has been genetically modified. Some non-limiting examples of genetic modifications can include: insertions, deletions, inversions, translocations, gene fusions, or changing one or more nucleotides. A genetically modified cell can comprise a target nucleic acid with an introduced double strand break (e.g., DNA break). A genetically modified cell can comprise an exogenously introduced nucleic acid (e.g., a vector). A genetically modified cell can comprise an exogenously introduced polypeptide of the disclosure and/or nucleic acid of the disclosure. A genetically modified cell can comprise a donor polynucleotide. A genetically modified cell can comprise an exogenous nucleic acid integrated into the genome of the genetically modified cell. A genetically modified cell can comprise a deletion of DNA. A genetically modified cell can also refer to a cell with modified mitochondrial or chloroplast DNA.

As used herein, "genome engineering" can refer to a process of modifying a target nucleic acid. Genome engineering can refer to the integration of non-native nucleic acid into native nucleic acid. Genome engineering can refer to the targeting of a site-directed polypeptide and a nucleic acid-targeting nucleic acid to a target nucleic acid, without an integration or a deletion of the target nucleic acid. Genome engineering can refer to the cleavage of a target nucleic acid, and the rejoining of the target nucleic acid without an integration of an exogenous sequence in the target nucleic acid, or a deletion in the target nucleic acid. The native nucleic acid can comprise a gene. The non-native nucleic acid can comprise a donor polynucleotide. In the methods of the disclosure, site-directed polypeptides (e.g., Cas9) can introduce double-stranded breaks in nucleic acid, (e.g. genomic DNA). The double-stranded break can stimulate a cell's endogenous DNA-repair pathways (e.g. homologous recombination (HR) and/or non-homologous end joining (NHEJ), or A-NHEJ (alternative non-homologous end-joining)). Mutations, deletions, alterations, and integrations of foreign, exogenous, and/or alternative nucleic acid can be introduced into the site of the double-stranded DNA break.

As used herein, the term "isolated" can refer to a nucleic acid or polypeptide that, by the hand of a human, exists apart from its native environment and is therefore not a product of nature. Isolated can mean substantially pure. An isolated nucleic acid or polypeptide can exist in a purified form and/or can exist in a non-native environment such as, for example, in a transgenic cell.

As used herein, "non-native" can refer to a nucleic acid or polypeptide sequence that is not found in a native nucleic acid or protein. Non-native can refer to affinity tags. Non-native can refer to fusions. Non-native can refer to a naturally occurring nucleic acid or polypeptide sequence that comprises mutations, insertions and/or deletions. A non-native sequence may exhibit and/or encode for an activity (e.g., enzymatic activity, methyltransferase activity, acetyltransferase activity, kinase activity, ubiquitinating activity, etc.) that can also be exhibited by the nucleic acid and/or polypeptide sequence to which the non-native sequence is fused. A non-native nucleic acid or polypeptide sequence may be linked to a naturally-occurring nucleic acid or polypeptide sequence (or a variant thereof) by genetic engineering to generate a chimeric nucleic acid and/or polypeptide sequence encoding a chimeric nucleic acid and/or polypeptide. A non-native sequence can refer to a 3' hybridizing extension sequence.

As used herein, a "nucleic acid" can generally refer to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g. altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, florophores (e.g. rhodamine or flurescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine.

As used herein, a "nucleic acid sample" can generally refer to a sample from a biological entity. A nucleic acid sample can comprise nucleic acid. The nucleic acid from the nucleic acid sample can be purified and/or enriched. The nucleic acid sample may show the nature of the whole. Nucleic acid samples can come from various sources. Nucleic acid samples can come from one or more individuals. One or more nucleic acid samples can come from the same individual. One non limiting example would be if one sample came from an individual's blood and a second sample came from an individual's tumor biopsy. Examples of nucleic acid samples can include but are not limited to, blood, serum, plasma, nasal swab or nasopharyngeal wash, saliva, urine, gastric fluid, spinal fluid, tears, stool, mucus, sweat, earwax, oil, glandular secretion, cerebral spinal fluid, tissue, semen, vaginal fluid, interstitial fluids, including interstitial fluids derived from tumor tissue, ocular fluids, spinal fluid, throat swab, cheek swab, breath, hair, finger nails, skin, biopsy, placental fluid, amniotic fluid, cord blood, emphatic fluids, cavity fluids, sputum, pus, micropiota, meconium, breast milk, buccal samples, nasopharyngeal wash, other excretions, or any combination thereof. Nucleic acid samples can originate from tissues. Examples of tissue samples may include but are not limited to, connective tissue, muscle tissue, nervous tissue, epithelial tissue, cartilage, cancerous or tumor sample, bone marrow, or bone. The nucleic acid sample may be provided from a human or animal. The nucleic acid sample may be provided from a mammal, vertebrate, such as murines, simians, humans, farm animals, sport animals, or pets. The nucleic acid sample may be collected from a living or dead subject. The nucleic acid sample may be collected fresh from a subject or may have undergone some form of pre-processing, storage, or transport.

A nucleic acid sample can comprise a target nucleic acid. A nucleic acid sample can originate from cell lysate. The cell lysate can originate from a cell.

As used herein, "nucleic acid-targeting nucleic acid" can refer to a nucleic acid that can hybridize to another nucleic acid. A nucleic acid-targeting nucleic acid can be RNA. A nucleic acid-targeting nucleic acid can be DNA. The nucleic acid-targeting nucleic acid can be programmed to bind to a sequence of nucleic acid site-specifically. The nucleic acid to be targeted, or the target nucleic acid, can comprise nucleotides. The nucleic acid-targeting nucleic acid can comprise nucleotides. A portion of the target nucleic acid can be complementary to a portion of the nucleic acid-targeting nucleic acid. A nucleic acid-targeting nucleic acid can comprise a polynucleotide chain and can be called a "single guide nucleic acid" (i.e. a "single guide nucleic acid-targeting nucleic acid"). A nucleic acid-targeting nucleic acid can comprise two polynucleotide chains and can be called a "double guide nucleic acid" (i.e. a "double guide nucleic acid-targeting nucleic acid"). If not otherwise specified, the term "nucleic acid-targeting nucleic acid" can be inclusive, referring to both single guide nucleic acids and double guide nucleic acids.

A nucleic acid-targeting nucleic acid can comprise a segment that can be referred to as a "nucleic acid-targeting segment" or a "nucleic acid-targeting sequence," A nucleic acid-targeting nucleic acid can comprise a segment that can be referred to as a "protein binding segment" or "protein binding sequence."

A nucleic acid-targeting nucleic acid can comprise one or more modifications (e.g., a base modification, a backbone modification), to provide the nucleic acid with a new or enhanced feature (e.g., improved stability). A nucleic acid-targeting nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acid-targeting nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acid-targeting nucleic acids, the phosphate groups can commonly be referred to as forming the internucleoside backbone of the nucleic acid-targeting nucleic acid. The linkage or backbone of the nucleic acid-targeting nucleic acid can be a 3' to 5' phosphodiester linkage.

A nucleic acid-targeting nucleic acid can comprise a modified backbone and/or modified internucleoside linkages. Modified backbones can include those that retain a phosphorus atom in the backbone and those that do not have a phosphorus atom in the backbone.

Suitable modified nucleic acid-targeting nucleic acid backbones containing a phosphorus atom therein can include, for example, phosphorothioates, chiral phosphorothioates, phosphorodithioates, phosphotriesters, aminoalkylphosphotriesters, methyl and other alkyl phosphonates such as 3'-alkylene phosphonates, 5'-alkylene phosphonates, chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage. Suitable nucleic acid-targeting nucleic acids having inverted polarity can comprise a single 3' to 3' linkage at the 3'-most internucleotide linkage (i.e. a single inverted nucleoside residue in which the nucleobase is missing or has a hydroxyl group in place thereof). Various salts (e.g., potassium chloride or sodium chloride), mixed salts, and free acid forms can also be included.

A nucleic acid-targeting nucleic acid can comprise one or more phosphorothioate and/or heteroatom internucleoside linkages, in particular —CH$_2$—NH—O—CH$_2$—, —CH$_2$—N(CH$_3$)—O—CH$_2$— (i.e. a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—).

A nucleic acid-targeting nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid-targeting nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

A nucleic acid-targeting nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid-targeting nucleic acid can comprise linked morpholino units (i.e. morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acid-targeting nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—CH2-), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid-targeting nucleic acid can comprise one or more substituted sugar moieties. Suitable polynucleotides can comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)nO)$ $mCH_3$, $O(CH_2)_nOCH_3$, $O(CH_2)_nNH2$, $O(CH_2)_nCH_3$, $O(CH_2)_nONH_2$, and $O(CH_2)_nON((CH_2)_nCH_3)_2$, where n and m are from 1 to about 10. A sugar substituent group can be selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an nucleic acid-targeting nucleic acid, or a group for improving the pharmacodynamic properties of an nucleic acid-targeting nucleic acid, and other substituents having similar properties. A suitable modification can include 2'-methoxyethoxy (2'-O—$CH_2CH_2OCH_3$, also known as 2'-O-(2-methoxyethyl) or 2'-MOE i.e., an alkoxyalkoxy group). A further suitable modification can include 2'-dimethylaminooxyethoxy, (i.e., a $O(CH_2)_2ON(CH_3)_2$ group, also known as 2'-DMAOE), and 2'-dimethylaminoethoxyethoxy (also known as 2'-O-dimethyl-amino-ethoxy-ethyl or 2'-DMAEOE), i.e., 2'-O—CH2-O—$CH_2$—$N(CH_3)_2$.

Other suitable sugar substituent groups can include methoxy (—O—$CH_3$), aminopropoxy $CH_2CH_2CH_2NH_2$), allyl (—$CH_2$—CH═$CH_2$), —O-allyl (—O— $CH_2$—CH═$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked nucleotides and the 5' position of 5' terminal nucleotide. Oligomeric compounds may also have sugar mimetics such as cyclobutyl moieties in place of the pentofuranosyl sugar.

A nucleic acid-targeting nucleic acid may also include nucleobase (often referred to simply as "base") modifications or substitutions. As used herein, "unmodified" or "natural" nucleobases can include the purine bases, (e.g. adenine (A) and guanine (G)), and the pyrimidine bases, (e.g. thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine (1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4) benzoxazin-2(3H)-one), carbazole cytidine (2H-pyrimido(4, 5-b)indol-2-one), pyridoindole cytidine (Hpyrido(3',2':4,5) pyrrolo(2,3-d)pyrimidin-2-one).

Heterocyclic base moieties can include those in which the purine or pyrimidine base is replaced with other heterocycles, for example 7-deaza-adenine, 7-deazaguanosine, 2-aminopyridine and 2-pyridone. Nucleobases can be useful for increasing the binding affinity of a polynucleotide compound. These can include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions can increase nucleic acid duplex stability by 0.6-1.2° C. and can be suitable base substitutions (e.g., when combined with 2'-O-methoxyethyl sugar modifications).

A modification of a nucleic acid-targeting nucleic acid can comprise chemically linking to the nucleic acid-targeting nucleic acid one or more moieties or conjugates that can enhance the activity, cellular distribution or cellular uptake of the nucleic acid-targeting nucleic acid. These moieties or conjugates can include conjugate groups covalently bound to functional groups such as primary or secondary hydroxyl groups. Conjugate groups can include, but are not limited to, intercalators, reporter molecules, polyamines, polyamides, polyethylene glycols, polyethers, groups that enhance the pharmacodynamic properties of oligomers, and groups that can enhance the pharmacokinetic properties of oligomers. Conjugate groups can include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that can enhance the pharmacokinetic properties include groups that improve uptake, distribution, metabolism or excretion of a nucleic acid. Conjugate moieties can include but are not limited to lipid moieties such as a cholesterol moiety, cholic acid a thioether, (e.g., hexyl-S-tritylthiol), a thiocholesterol, an aliphatic chain (e.g., dodecandiol or undecyl residues), a phospholipid (e.g., di-hexadecyl-rac-glycerol or triethylammonium 1,2-di-O-hexadecyl-rac-glycero-3-H-phosphonate), a polyamine or a polyethylene glycol chain, or adamantane acetic acid, a palmityl moiety, or an octadecylamine or hexylamino-carbonyl-oxycholesterol moiety.

A modification may include a "Protein Transduction Domain" or PTD (i.e. a cell penetrating peptide (CPP)). The PTD can refer to a polypeptide, polynucleotide, carbohydrate, or organic or inorganic compound that facilitates traversing a lipid bilayer, micelle, cell membrane, organelle membrane, or vesicle membrane. A PTD can be attached to another molecule, which can range from a small polar molecule to a large macromolecule and/or a nanoparticle, and can facilitate the molecule traversing a membrane, for example going from extracellular space to intracellular space, or cytosol to within an organelle. A PTD can be covalently linked to the amino terminus of a polypeptide. A PTD can be covalently linked to the carboxyl terminus of a polypeptide. A PTD can be covalently linked to a nucleic acid. Exemplary PTDs can include, but are not limited to, a minimal peptide protein transduction domain; a polyarginine sequence comprising a number of arginines sufficient to direct entry into a cell (e.g., 3, 4, 5, 6, 7, 8, 9, 10, or 10-50 arginines), a VP22 domain, a *Drosophila* Antennapedia protein transduction domain, a truncated human calcitonin peptide, polylysine, and transportan, arginine homopolymer of from 3 arginine residues to 50 arginine residues. The PTD can be an activatable CPP (ACPP). ACPPs can comprise a polycationic CPP (e.g., Arg9 or "R9") connected via a cleavable linker to a matching polyanion (e.g., Glu9 or "E9"), which can reduce the net charge to nearly zero and thereby inhibits adhesion and uptake into cells. Upon cleavage of the linker, the polyanion can be released, locally unmasking the polyarginine and its inherent adhesiveness, thus "activating" the ACPP to traverse the membrane.

"Nucleotide" can generally refer to a base-sugar-phosphate combination. A nucleotide can comprise a synthetic nucleotide. A nucleotide can comprise a synthetic nucleotide analog. Nucleotides can be monomeric units of a nucleic acid sequence (e.g. deoxyribonucleic acid (DNA) and ribonucleic acid (RNA)). The term nucleotide can include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, dTTP, or derivatives thereof. Such derivatives can include, for example, [αS]dATP, 7-deaza-dGTP and 7-deaza-dATP, and nucleotide derivatives that confer nuclease resistance on the nucleic acid molecule containing them. The term nucleotide as used herein can refer to dideoxyribonucleoside triphosphates (ddNTPs) and their derivatives. Illustrative examples of dideoxyribonucleoside triphosphates can include, but are not limited to, ddATP, ddCTP, ddGTP, ddITP, and ddTTP. A nucleotide may be unlabeled or detectably labeled by well-known techniques. Labeling can also be carried out with quantum dots. Detectable labels can include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides can include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAMRA]ddGTP, [ROX]ddTTP, [dR6G]ddATP, [dR110]ddCTP, [dTAMRA]ddGTP, and [dROX]ddTTP available from Perkin Elmer, Foster City, Calif. FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides can also be labeled or marked by chemical modification. A chemically-modified single nucleotide can be biotin-dNTP. Some non-limiting examples of biotinylated dNTPs can include, biotin-dATP (e.g., bio-N6-ddATP, biotin-14-dATP), biotin-dCTP (e.g., biotin-11-dCTP, biotin-14-dCTP), and biotin-dUTP (e.g. biotin-11-dUTP, biotin-16-dUTP, biotin-20-dUTP).

As used herein, "P-domain" can refer to a region in a nucleic acid-targeting nucleic acid. The P-domain can interact with a protospacer adjacent motif (PAM), site-directed polypeptide, and/or nucleic acid-targeting nucleic acid. A P-domain can interact directly or indirectly with a protospacer adjacent motif (PAM), site-directed polypeptide, and/or nucleic acid-targeting nucleic acid nucleic acid. As used herein, the terms "PAM interacting region" "anti-repeat adjacent region" and "P-domain" can be used interchangeably.

As used here, "purified" can refer to a molecule (e.g., site-directed polypeptide, nucleic acid-targeting nucleic acid) that comprises at least 50, 60, 70, 80, 90, 95, 96, 97, 98, 99, or 100% of the composition. For example, a sample that comprises 10% of a site-directed polypeptide, but after a purification step comprises 60% of the site-directed polypeptide, then the sample can be said to be purified. A purified sample can refer to an enriched sample, or a sample that has undergone methods to remove particles other than the particle of interest.

As used herein, "reactivation agent" can generally refer to any agent that can convert an enzymatically inactive polypeptide into an enzymatically active polypeptide. Imidazole can be a reactivation agent. A ligand analogue can be a reactivation agent.

As used herein, "recombinant" can refer to sequence that originates from a source foreign to the particular host (e.g., cell) or, if from the same source, is modified from its original form. A recombinant nucleic acid in a cell can include a nucleic acid that is endogenous to the particular cell but has been modified through, for example, the use of site-directed mutagenesis. The term can include non-naturally occurring multiple copies of a naturally occurring DNA sequence. Thus, the term can refer to a nucleic acid that is foreign or heterologous to the cell, or homologous to the cell but in a position or form within the cell in which the nucleic acid is not ordinarily found. Similarly, when used in the context of a polypeptide or amino acid sequence, an exogenous polypeptide or amino acid sequence can be a polypeptide or amino acid sequence that originates from a source foreign to the particular cell or, if from the same source, is modified from its original form.

As used herein, "site-directed polypeptides" can generally refer to nucleases, site-directed nucleases, endoribonucleases, conditionally enzymatically inactive endoribonucleases, Argonauts, and nucleic acid-binding proteins. A site-directed polypeptide or protein can include nucleases such as homing endonucleases such as PI-TliII, H-DreI, I-DmoI and I-CreI, I-SceI, LAGLIDADG family nucleases, meganucleases, GIY-YIG family nucleases, His-Cys box family nucleases, Vsr-like nucleases, endoribonucleases, exoribonucleases, endonucleases, and exonucleases. A site-directed polypeptide can refer to a Cas gene member of the Type I, Type II, Type III, and/or Type U CRISPR/Cas systems. A site-directed polypeptide can refer to a member of the Repeat Associated Mysterious Protein (RAMP) superfamily (e.g., Cas5, Cas6 subfamilies). A site-directed polypeptide can refer to an Argonaute protein.

A site-directed polypeptide can be a type of protein. A site-directed polypeptide can refer to an nuclease. A site-directed polypeptide can refer to an endoribonuclease. A site-directed polypeptide can refer to any modified (e.g., shortened, mutated, lengthened) polypeptide sequence or homologue of the site-directed polypeptide. A site-directed polypeptide can be codon optimized. A site-directed polypeptide can be a codon-optimized homologue of a site-directed polypeptide. A site-directed polypeptide can be enzymatically inactive, partially active, constitutively active, fully active, inducible active and/or more active, (e.g. more than the wild type homologue of the protein or polypeptide.). A site-directed polypeptide can be Cas9. A site-directed polypeptide can be Csy4. A site-directed polypeptide can be Cas5 or a Cas5 family member. A site-directed polypeptide can be Cas6 or a Cas6 family member.

In some instances, the site-directed polypeptide (e.g., variant, mutated, enzymatically inactive and/or conditionally enzymatically inactive site-directed polypeptide) can target nucleic acid. The site-directed polypeptide (e.g., variant, mutated, enzymatically inactive and/or conditionally enzymatically inactive endoribonuclease) can target RNA. Endoribonucleases that can target RNA can include members of other CRISPR subfamilies such as Cas6 and Cas5.

As used herein, the term "specific" can refer to interaction of two molecules where one of the molecules through, for example chemical or physical means, specifically binds to the second molecule. Exemplary specific binding interactions can refer to antigen-antibody binding, avidin-biotin binding, carbohydrates and lectins, complementary nucleic acid sequences (e.g., hybridizing), complementary peptide sequences including those formed by recombinant methods, effector and receptor molecules, enzyme cofactors and enzymes, enzyme inhibitors and enzymes, and the like. "Non-specific" can refer to an interaction between two molecules that is not specific.

As used herein, "solid support" can generally refer to any insoluble, or partially soluble material. A solid support can refer to a test strip, a multi-well dish, and the like. The solid support can comprise a variety of substances (e.g., glass, polystyrene, polyvinyl chloride, polypropylene, polyethylene, polycarbonate, dextran, nylon, amylose, natural and modified celluloses, polyacrylamides, agaroses, and magnetite) and can be provided in a variety of forms, including agarose beads, polystyrene beads, latex beads, magnetic beads, colloid metal particles, glass and/or silicon chips and surfaces, nitrocellulose strips, nylon membranes, sheets, wells of reaction trays (e.g., multi-well plates), plastic tubes, etc. A solid support can be solid, semisolid, a bead, or a surface. The support can mobile in a solution or can be immobile. A solid support can be used to capture a polypeptide. A solid support can comprise a capture agent.

As used herein, "target nucleic acid" can generally refer to a nucleic acid to be used in the methods of the disclosure. A target nucleic acid can refer to a chromosomal sequence or an extrachromosomal sequence, (e.g. an episomal sequence, a minicircle sequence, a mitochondrial sequence, a chloroplast sequence, etc.). A target nucleic acid can be DNA. A target nucleic acid can be RNA. A target nucleic acid can herein be used interchangeably with "polynucleotide", "nucleotide sequence", and/or "target polynucleotide". A target nucleic acid can be a nucleic acid sequence that may not be related to any other sequence in a nucleic acid sample by a single nucleotide substitution. A target nucleic acid can be a nucleic acid sequence that may not be related to any other sequence in a nucleic acid sample by a 2, 3, 4, 5, 6, 7, 8, 9, or 10 nucleotide substitutions. In some embodiments, the substitution cannot occur within 5, 10, 15, 20, 25, 30, or 35 nucleotides of the 5' end of a target nucleic acid. In some embodiments, the substitution cannot occur within 5, 10, 15, 20, 25, 30, 35 nucleotides of the 3' end of a target nucleic acid.

As used herein, "tracrRNA" can generally refer to a nucleic acid with at least about 5%, 10%, 20%, 30%, 40%, 50%, 60%, 70%, 80%, 90%, 100% sequence identity and/or sequence similarity to a wild type exemplary tracrRNA sequence (e.g., a tracrRNA from S. pyogenes (SEQ ID 433), SEQ IDs 431-562). tracrRNA can refer to a nucleic acid with at most about 5%, 10%, 20%, 30%, 40%, 50%, 60%, 70%, 80%, 90%, 100% sequence identity and/or sequence similarity to a wild type exemplary tracrRNA sequence (e.g., a tracrRNA from S. pyogenes). tracrRNA can refer to a modified form of a tracrRNA that can comprise an nucleotide change such as a deletion, insertion, or substitution, variant, mutation, or chimera. A tracrRNA can refer to a nucleic acid that can be at least about 60% identical to a wild type exemplary tracrRNA (e.g., a tracrRNA from S. pyogenes) sequence over a stretch of at least 6 contiguous nucleotides. For example, a tracrRNA sequence can be at least about 60% identical, at least about 65% identical, at least about 70% identical, at least about 75% identical, at least about 80% identical, at least about 85% identical, at least about 90% identical, at least about 95% identical, at least about 98% identical, at least about 99% identical, or 100% identical, to a wild type exemplary tracrRNA (e.g., a tracrRNA from S. pyogenes) sequence over a stretch of at least 6 contiguous nucleotides. A tracrRNA can refer to a mid-tracrRNA. A tracrRNA can refer to a minimum tracrRNA sequence.

CRISPR Systems

A CRISPR (Clustered Regularly Interspaced Short Palindromic Repeats) can be a genomic locus found in the genomes of many prokaryotes (e.g., bacteria and archaea). CRISPR loci can provide resistance to foreign invaders (e.g., virus, phage) in prokaryotes. In this way, the CRISPR system can be thought to function as a type of immune system to help defend prokaryotes against foreign invaders. There can be three stages of CRISPR locus function: integration of new sequences into the locus, biogenesis of CRISPR RNA (crRNA), and silencing of foreign invader nucleic acid. There can be four types of CRISPR systems (e.g., Type I, Type II, Type III, Type U).

A CRISPR locus can include a number of short repeating sequences referred to as "repeats." Repeats can form hairpin structures and/or repeats can be unstructured single-stranded sequences. The repeats can occur in clusters. Repeats sequences can frequently diverge between species. Repeats can be regularly interspaced with unique intervening sequences referred to as "spacers," resulting in a repeat-spacer-repeat locus architecture. Spacers can be identical to or have high homology with known foreign invader sequences. A spacer-repeat unit can encode a crisprRNA (crRNA). A crRNA can refer to the mature form of the spacer-repeat unit. A crRNA can comprise a "seed" sequence that can be involved in targeting a target nucleic acid (e.g., possibly as a surveillance mechanism against foreign nucleic acid). A seed sequence can be located at the 5' or 3' end of the crRNA.

A CRISPR locus can comprise polynucleotide sequences encoding for Crispr Associated Genes (Cas) genes. Cas genes can be involved in the biogenesis and/or the interference stages of crRNA function. Cas genes can display extreme sequence (e.g., primary sequence) divergence between species and homologues. For example, Cas1 homologues can comprise less than 10% primary sequence identity between homologues. Some Cas genes can comprise homologous secondary and/or tertiary structures. For example, despite extreme sequence divergence, many members of the Cas6 family of CRISPR proteins comprise a N-terminal ferredoxin-like fold. Cas genes can be named according to the organism from which they are derived. For example, Cas genes in *Staphylococcus epidermidis* can be referred to as Csm-type, Cas genes in *Streptococcus thermophilus* can be referred to as Csn-type, and Cas genes in *Pyrococcus furiosus* can be referred to as Cmr-type.

Integration

The integration stage of CRISPR system can refer to the ability of the CRISPR locus to integrate new spacers into the crRNA array upon being infected by a foreign invader. Acquisition of the foreign invader spacers can help confer immunity to subsequent attacks by the same foreign invader. Integration can occur at the leader end of the CRISPR locus. Cas proteins (e.g., Cas1 and Cas2) can be involved in integration of new spacer sequences. Integration can proceed similarly for some types of CRISPR systems (e.g., Type I-III).

Biogenesis

Mature crRNAs can be processed from a longer polycistronic CRISPR locus transcript (i.e., pre-crRNA array). A pre-crRNA array can comprise a plurality of crRNAs. The repeats in the pre-crRNA array can be recognized by Cas genes. Cas genes can bind to the repeats and cleave the repeats. This action can liberate the plurality of crRNAs. crRNAs can be subjected to further events to produce the mature crRNA form such as trimming (e.g., with an exonuclese). A crRNA may comprise all, some, or none of the CRISPR repeat sequence.

Interference

Interference can refer to the stage in the CRISPR system that is functionally responsible for combating infection by a foreign invader. CRISPR interference can follow a similar mechanism to RNA interference (RNAi (e.g., wherein a target RNA is targeted (e.g., hybridized) by a short interfering RNA (siRNA)), which can result in target RNA degradation and/or destabilization. CRISPR systems can perform interference of a target nucleic acid by coupling crRNAs and Cas genes, thereby forming CRISPR ribonucleoproteins (crRNPs). crRNA of the crRNP can guide the crRNP to foreign invader nucleic acid, (e.g., by recognizing the foreign invader nucleic acid through hybridization). Hybridized target foreign invader nucleic acid-crRNA units can be subjected to cleavage by Cas proteins. Target nucleic acid interference may require a spacer adjacent motif (PAM) in a target nucleic acid.

Types of CRISPR Systems

There can be four types of CRISPR systems: Type I, Type II, Type III, and Type U. More than one CRISPR type system can be found in an organism. CRISPR systems can be complementary to each other, and/or can lend functional units in trans to facilitate CRISPR locus processing.

Type I CRISPR Systems crRNA biogenesis in Type I CRISPR systems can comprise endoribonuclease cleavage of repeats in the pre-crRNA array, which can result in a plurality of crRNAs. crRNAs of Type I systems may not be subjected to crRNA trimming. A crRNA can be processed from a pre-crRNA array by a multi-protein complex called Cascade (originating from CRISPR-associated complex for antiviral defense). Cascade can comprise protein subunits (e.g, CasA-CasE). Some of the subunits can be members of the Repeat Associated Mysterious Protein (RAMP) superfamily (e.g., Cas5 and Cas6 families). The Cascade-crRNA complex (i.e., interference complex) can recognize target nucleic acid through hybridization of the crRNA with the target nucleic acid. The Cascade interference complex can recruit the Cas3 helicase/nuclease which can act in trans to facilitate cleavage of target nucleic acid. The Cas3 nuclease can cleave target nucleic acid (e.g., with its HD nuclease domain). Target nucleic acid in a Type I CRISPR system can comprise a PAM. Target nucleic acid in a Type I CRISPR system can be DNA.

Type I systems can be further subdivided by their species of origin. Type I systems can comprise: Types IA (*Aeropyrum pernix* or CASS5); IB (*Thermotoga neapolitana*-*Haloarcula marismortui* or CASS7); IC (*Desulfovibrio vulgaris* or CASS1); ID; IE (*Escherichia coli* or CASS2); and IF (*Yersinia pestis* or CASS3) subfamilies.

Type II CRISPR Systems crRNA biogenesis in a Type II CRISPR system can comprise a trans-activating CRISPR RNA (tracrRNA). A tracrRNA can be modified by endogenous RNaseIII. The tracrRNA of the complex can hybridize to a crRNA repeat in the pre-crRNA array. Endogenous RnaseIII can be recruited to cleave the pre-crRNA. Cleaved crRNAs can be subjected to exoribonuclease trimming to produce the mature crRNA form (e.g., 5' trimming). The tracrRNA can remain hybridized to the crRNA. The tracrRNA and the crRNA can associate with a site-directed polypeptide (e.g., Cas9). The crRNA of the crRNA-tracrRNA-Cas9 complex can guide the complex to a target nucleic acid to which the crRNA can hybridize. Hybridization of the crRNA to the target nucleic acid can activate Cas9 for target nucleic acid cleavage. Target nucleic acid in a Type II CRISPR system can comprise a PAM. In some embodiments, a PAM is essential to facilitate binding of a site-directed polypeptide (e.g., Cas9) to a target nucleic acid. Type II systems can be further subdivided into II-A (Nmeni or CASS4) and II-B (Nmeni or CASS4).

Type III CRISPR Systems crRNA biogenesis in Type III CRISPR systems can comprise a step of endoribonuclease cleavage of repeats in the pre-crRNA array, which can result in a plurality of crRNAs. Repeats in the Type III CRISPR system can be unstructured single-stranded regions. Repeats can be recognized and cleaved by a member of the RAMP superfamily of endoribonucleases (e.g., Cas6). crRNAs of Type III (e.g., Type III-B) systems may be subjected to crRNA trimming (e.g., 3' trimming). Type III systems can comprise a polymerase-like protein (e.g., Cas10). Cas10 can comprise a domain homologous to a palm domain.

Type III systems can process pre-crRNA with a complex comprising a plurality of RAMP superfamily member proteins and one or more CRISPR polymerase-like proteins. Type III systems can be divided into III-A and III-B. An interference complex of the Type III-A system (i.e., Csm complex) can target plasmid nucleic acid. Cleavage of the plasmid nucleic acid can occur with the HD nuclease domain of a polymerase-like protein in the complex. An interference complex of the Type III-B system (i.e., Cmr complex) can target RNA.

Type U CRISPR Systems

Type U CRISPR systems may not comprise the signature genes of either of the Type I-III CRISPR systems (e.g., Cas3, Cas9, Cas6, Cas1, Cas2). Examples of Type U CRISPR Cas genes can include, but are not limited to, Csf1, Csf2, Csf3, Csf4. Type U Cas genes may be very distant homologues of Type I-III Cas genes. For example, Csf3 may be highly diverged but functionally similar to Cas5 family members. A Type U system may function complementarily in trans with a Type I-III system. In some instances, Type U systems may not be associated with processing CRISPR arrays. Type U systems may represent an alternative foreign invader defense system.

RAMP Superfamily

Repeat Associated Mysterious Proteins (RAMP proteins) can be characterized by a protein fold comprising a βαββαβ [beta-alpha-beta-beta-alpha-beta] motif of β-strands (β) and α-helices (α). A RAMP protein can comprise an RNA recognition motif (RRM) (which can comprise a ferredoxin or ferredoxin-like fold). RAMP proteins can comprise an N-terminal RRM. The C-terminal domain of RAMP proteins can vary, but can also comprise an RRM. RAMP family members can recognize structured and/or unstructured nucleic acid. RAMP family members can recognize single-stranded and/or double-stranded nucleic acid. RAMP proteins can be involved in the biogenesis and/or the interference stage of CRISPR Type I and Type III systems. RAMP superfamily members can comprise members of the Cas7, Cas6, and Cas5 families. RAMP superfamily members can be endoribonucleases.

RRM domains in the RAMP superfamily can be extremely divergent. RRM domains can comprise at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or 100% sequence or structural homology to a wild type exemplary RRM domain (e.g., an RRM domain from Cas7). RRM domains can comprise at most about 5%, at most about 10%, at most about 15%, at most about 20%, at most about 25%, at most about 30%, at most about 35%, at most about 40%, at most about 45%, at most about 50%, at most about 55%, at most about 60%, at most about 65%, at most about 70%, at most about 75%, at most about 80%, at most about 85%, at most about 90%, at most about 95%, or 100% sequence or structural homology to a wild type exemplary RRM domain (e.g., an RRM domain from Cas7).

Cas7 Family

Cas7 family members can be a subclass of RAMP family proteins. Cas7 family proteins can be categorized in Type I CRISPR systems. Cas7 family members may not comprise a glycine rich loop that is familiar to some RAMP family members. Cas7 family members can comprise one RRM domain. Cas7 family members can include, but are not limited to, Cas7 (COG1857), Cas7 (COG3649), Cas7 (CT1975), Csy3, Csm3, Cmr6, Csm5, Cmr4, Cmr1, Csf2, and Csc2.

Cas6 Family

The Cas6 family can be a RAMP subfamily. Cas6 family members can comprise two RNA recognition motif (RRM)-like domains. A Cas6 family member (e.g., Cas6f) can comprise a N-terminal RRM domain and a distinct C-terminal domain that may show weak sequence similarity or structural homology to an RRM domain. Cas6 family members can comprise a catalytic histidine that may be involved in endoribonuclease activity. A comparable motif can be found in Cas5 and Cas7 RAMP families. Cas6 family members can include, but are not limited to, Cas6, Cas6e, Cas6f (e.g., Csy4).

Cas5 Family

The Cas5 family can be a RAMP subfamily. The Cas5 family can be divided into two subgroups: one subgroup that can comprise two RRM domains, and one subgroup that can comprise one RRM domain. Cas5 family members can include, but are not limited to, Csm4, Csx10, Cmr3, Cas5, Cas5(BH0337), Csy2, Cscl, Csf3.

Cas Genes

Exemplary CRISPR Cas genes can include Cas1, Cas2, Cas3' (Cas3-prime), Cas3" (Cas3-double prime), Cas4, Cas5, Cash, Cas6e (formerly referred to as CasE, Cse3), Cas6f (i.e., Csy4), Cas7, Cas8a1, Cas8a2, Cas8b, Cas8c, Cas9, Cas10, Cas10d, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4. Table 1 provides an exemplary categorization of CRISPR Cas genes by CRISPR system type.

The CRISPR-Cas gene naming system has undergone extensive rewriting since the Cas genes were discovered. For the purposes of this application, Cas gene names used herein are based on the naming system outlined in Makarova et al. Evolution and classification of the CRISPR-Cas systems. Nature Reviews Microbiology. 2011 June; 9(6): 467-477. Doi:10.1038/nrmicro2577.

TABLE 1

Exemplary classification of CRISPR Cas genes by CRISPR Type

| System type or subtype | Gene Name |
|---|---|
| Type I | cas1, cas2, cas3' |
| Type II | cas1, cas2, cas9 |
| Type III | cas1, cas2, cas10 |
| Subtype I-A | cas3", cas4, cas5, cas6, cas7, cas8a1, cas8a2, csa5 |
| Subtype I-B | cas3", cas4, cas5, cas6, cas7, cas8b |
| Subtype I-C | cas4, cas5, cas7, cas8c |
| Subtype I-D | cas4, cas6, cas10d, csc1, csc2 |
| Subtype I-E | cas5, cas6e, cas7, cse1, cse2 |
| Subtype I-F | cas6f, csy1, csy2, csy3 |
| Subtype II-A | csn2 |
| Subtype II-B | cas4 |
| Subtype III-A | cas6, csm2, csm3, csm4, csm5, csm6 |
| Subtype III-B | cas6, cmr1, cmr3, cmr4, cmr5, cmr6 |
| Subtype I-U | csb1, csb2, csb3, csx17, csx14, csx10 |
| Subtype III-U | csx16, csaX, csx3, csx1 |
| Unknown | csx15 |
| Type U | csf1, csf2, csf3, csf4 |

Site-Directed Polypeptides

A site-directed polypeptide can be a polypeptide that can bind to a target nucleic acid. A site-directed polypeptide can be a nuclease.

A site-directed polypeptide can comprise a nucleic acid-binding domain. The nucleic acid-binding domain can comprise a region that contacts a nucleic acid. A nucleic acid-binding domain can comprise a nucleic acid. A nucleic acid-binding domain can comprise a proteinaceous material. A nucleic acid-binding domain can comprise nucleic acid and a proteinaceous material. A nucleic acid-binding domain can comprise RNA. There can be a single nucleic acid-binding domain. Examples of nucleic acid-binding domains can include, but are not limited to, a helix-turn-helix domain, a zinc finger domain, a leucine zipper (bZIP) domain, a winged helix domain, a winged helix turn helix domain, a helix-loop-helix domain, a HMG-box domain, a Wor3 domain, an immunoglobulin domain, a B3 domain, a TALE domain, a RNA-recognition motif domain, a double-stranded RNA-binding motif domain, a double-stranded nucleic acid binding domain, a single-stranded nucleic acid binding domains, a KH domain, a PUF domain, a RGG box domain, a DEAD/DEAH box domain, a PAZ domain, a Piwi domain, and a cold-shock domain.

A nucleic acid-binding domain can be a domain of an argonaute protein. An argonaute protein can be a eukaryotic argonaute or a prokaryotic argonaute. An argonaute protein can bind RNA, DNA, or both RNA and DNA. An argonaute protein can cleaved RNA, or DNA, or both RNA and DNA. In some instances, an argonaute protein binds a DNA and cleaves a target DNA.

In some instances, two or more nucleic acid-binding domains can be linked together. Linking a plurality of nucleic acid-binding domains together can provide increased polynucleotide targeting specificity. Two or more nucleic acid-binding domains can be linked via one or more linkers. The linker can be a flexible linker. Linkers can comprise 1, 2, 3, 4, 5, 6, 7, 8, 9, 10, 11, 12, 13, 14, 15, 16, 17, 18, 19, 20, 21, 22, 23, 24, 25, 30, 35, 40 or more amino acids in length. Linkers can comprise at least 5%, 10%, 15%, 20%, 25%, 30%, 35%, 40%, 45%, 50%, 55%, 60%, 65%, 70%, 75%, 80%, 85%, 90%, 95%, or 100% glycine content. Linkers can comprise at most 5%, 10%, 15%, 20%, 25%, 30%, 35%, 40%, 45%, 50%, 55%, 60%, 65%, 70%, 75%, 80%, 85%, 90%, 95%, or 100% glycine content. Linkers can comprise at least 5%, 10%, 15%, 20%, 25%, 30%, 35%, 40%, 45%, 50%, 55%, 60%, 65%, 70%, 75%, 80%, 85%, 90%, 95%, or 100% serine content. Linkers can comprise at most 5%, 10%, 15%, 20%, 25%, 30%, 35%, 40%, 45%, 50%, 55%, 60%, 65%, 70%, 75%, 80%, 85%, 90%, 95%, or 100% serine content.

Nucleic acid-binding domains can bind to nucleic acid sequences. Nucleic acid binding domains can bind to nucleic acids through hybridization. Nucleic acid-binding domains can be engineered (e.g. engineered to hybridize to a sequence in a genome). A nucleic acid-binding domain can be engineered by molecular cloning techniques (e.g., directed evolution, site-specific mutation, and rational mutagenesis).

A site-directed polypeptide can comprise a nucleic acid-cleaving domain. The nucleic acid-cleaving domain can be a nucleic acid-cleaving domain from any nucleic acid-cleaving protein. The nucleic acid-cleaving domain can originate from a nuclease. Suitable nucleic acid-cleaving domains include the nucleic acid-cleaving domain of endonucleases (e.g., AP endonuclease, RecBCD enonuclease, T7 endonuclease, T4 endonuclease IV, Bal 31 endonuclease, EndonucleaseI (endo I), Micrococcal nuclease, Endonuclease II (endo VI, exo III)), exonucleases, restriction nucleases, endoribonucleases, exoribonucleases, RNases (e.g., RNAse I, II, or III). In some instances, the nucleic acid-cleaving domain can originate from the FokI endonuclease. A site-directed polypeptide can comprise a plurality of nucleic acid-cleaving domains. Nucleic acid-cleaving domains can be linked together. Two or more nucleic acid-cleaving domains can be linked via a linker. In some embodiments, the linker can be a flexible linker. Linkers can comprise 1, 2, 3, 4, 5, 6, 7, 8, 9, 10, 11, 12, 13, 14, 15, 16, 17, 18, 19, 20, 21, 22, 23, 24, 25, 30, 35, 40 or more amino acids in length. In some embodiments, a site-directed polypeptide can comprise the plurality of nucleic acid-cleaving domains.

A site-directed polypeptide (e.g., Cas9, argonaute) can comprise two or more nuclease domains. Cas9 can comprise a HNH or HNH-like nuclease domain and/or a RuvC or RuvC-like nuclease domain. HNH or HNH-like domains can comprise a McrA-like fold. HNH or HNH-like domains can comprise two antiparallel β-strands and an α-helix. HNH or HNH-like domains can comprise a metal binding site (e.g., divalent cation binding site). HNH or HNH-like domains can cleave one strand of a target nucleic acid (e.g., complementary strand of the crRNA targeted strand). Proteins that comprise an HNH or HNH-like domain can include endonucleases, clicins, restriction endonucleases, transposases, and DNA packaging factors.

RuvC or RuvC-like domains can comprise an RNaseH or RNaseH-like fold. RuvC/RNaseH domains can be involved in a diverse set of nucleic acid-based functions including acting on both RNA and DNA. The RNaseH domain can comprise 5 β-strands surrounded by a plurality of α-helices. RuvC/RNaseH or RuvC/RNaseH-like domains can comprise a metal binding site (e.g., divalent cation binding site). RuvC/RNaseH or RuvC/RNaseH-like domains can cleave one strand of a target nucleic acid (e.g., non-complementary strand of the crRNA targeted strand). Proteins that comprise a RuvC, RuvC-like, or RNaseH-like domain can include RNaseH, RuvC, DNA transposases, retroviral integrases, and Argonaut proteins).

The site-directed polypeptide can be an endoribonuclease. The site-directed polypeptide can be an enzymatically inactive site-directed polypeptide. The site-directed polypeptide can be a conditionally enzymatically inactive site-directed polypeptide. Site-directed polypeptides can introduce double-stranded breaks or single-stranded breaks in nucleic acid, (e.g. genomic DNA). The double-stranded break can stimulate a cell's endogenous DNA-repair pathways (e.g. homologous recombination and non-homologous end joining (NHEJ) or alternative non-homologues end-joining (A-NHEJ)). NHEJ can repair cleaved target nucleic acid without the need for a homologous template. This can result in deletions of the target nucleic acid. Homologous recombination (HR) can occur with a homologous template. The homologous template can comprise sequences that are homologous to sequences flanking the target nucleic acid cleavage site. After a target nucleic acid is cleaved by a site-directed polypeptide the site of cleavage can be destroyed (e.g., the site may not be accessible for another round of cleavage with the original nucleic acid-targeting nucleic acid and site-directed polypeptide).

In some cases, homologous recombination can insert an exogenous polynucleotide sequence into the target nucleic acid cleavage site. An exogenous polynucleotide sequence can be called a donor polynucleotide. In some instances of the methods of the disclosure the donor polynucleotide, a portion of the donor polynucleotide, a copy of the donor polynucleotide, or a portion of a copy of the donor polynucleotide can be inserted into the target nucleic acid cleavage site. A donor polynucleotide can be an exogenous polynucleotide sequence. A donor polynucleotide can be a sequence that does not naturally occur at the target nucleic acid cleavage site. A vector can comprise a donor polynucleotide. The modifications of the target DNA due to NHEJ and/or HR can lead to, for example, mutations, deletions, alterations, integrations, gene correction, gene replacement, gene tagging, transgene insertion, nucleotide deletion, gene disruption, and/or gene mutation. The process of integrating non-native nucleic acid into genomic DNA can be referred to as genome engineering.

In some cases, the site-directed polypeptide can comprise an amino acid sequence having at most 10%, at most 15%, at most 20%, at most 30%, at most 40%, at most 50%, at most 60%, at most 70%, at most 75%, at most 80%, at most 85%, at most 90%, at most 95%, at most 99%, or 100%, amino acid sequence identity to a wild type exemplary site-directed polypeptide (e.g., Cas9 from *S. pyogenes*, SEQ ID NO: 8).

In some cases, the site-directed polypeptide can comprise an amino acid sequence having at least 10%, at least 15%, 20%, at least 30%, at least 40%, at least 50%, at least 60%, at least 70%, at least 75%, at least 80%, at least 85%, at least 90%, at least 95%, at least 99%, or 100%, amino acid sequence identity to a wild type exemplary site-directed polypeptide (e.g., Cas9 from S. pyogenes, SEQ ID NO: 8).

In some cases, the site-directed polypeptide can comprise an amino acid sequence having at most 10%, at most 15%, at most 20%, at most 30%, at most 40%, at most 50%, at most 60%, at most 70%, at most 75%, at most 80%, at most 85%, at most 90%, at most 95%, at most 99%, or 100%, amino acid sequence identity to the nuclease domain of a wild type exemplary site-directed polypeptide (e.g., Cas9 from S. pyogenes, SEQ ID NO: 8).

A site-directed polypeptide can comprise at least 70, 75, 80, 85, 90, 95, 97, 99, or 100% identity to wild-type site-directed polypeptide (e.g., Cas9 from S. pyogenes, SEQ ID NO: 8) over 10 contiguous amino acids. A site-directed polypeptide can comprise at most 70, 75, 80, 85, 90, 95, 97, 99, or 100% identity to wild-type site-directed polypeptide (e.g., Cas9 from S. pyogenes, SEQ ID NO: 8) over 10 contiguous amino acids. A site-directed polypeptide can comprise at least 70, 75, 80, 85, 90, 95, 97, 99, or 100% identity to a wild-type site-directed polypeptide (e.g., Cas9 from S. pyogenes, SEQ ID NO: 8) over 10 contiguous amino acids in a HNH nuclease domain of the site-directed polypeptide. A site-directed polypeptide can comprise at most 70, 75, 80, 85, 90, 95, 97, 99, or 100% identity to a wild-type site-directed polypeptide (e.g., Cas9 from S. pyogenes, SEQ ID NO: 8) over 10 contiguous amino acids in a HNH nuclease domain of the site-directed polypeptide. A site-directed polypeptide can comprise at least 70, 75, 80, 85, 90, 95, 97, 99, or 100% identity to a wild-type site-directed polypeptide (e.g., Cas9 from S. pyogenes, SEQ ID NO: 8) over 10 contiguous amino acids in a RuvC nuclease domain of the site-directed polypeptide. A site-directed polypeptide can comprise at most 70, 75, 80, 85, 90, 95, 97, 99, or 100% identity to a wild-type site-directed polypeptide (e.g., Cas9 from S. pyogenes, SEQ ID NO: 8) over 10 contiguous amino acids in a RuvC nuclease domain of the site-directed polypeptide.

In some cases, the site-directed polypeptide can comprise an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100%, amino acid sequence identity to the nuclease domain of a wild type exemplary site-directed polypeptide (e.g., Cas9 from S. pyogenes).

The site-directed polypeptide can comprise a modified form of a wild type exemplary site-directed polypeptide. The modified form of the wild type exemplary site-directed polypeptide can comprise an amino acid change (e.g., deletion, insertion, or substitution) that reduces the nucleic acid-cleaving activity of the site-directed polypeptide. For example, the modified form of the wild type exemplary site-directed polypeptide can have less than less than 90%, less than 80%, less than 70%, less than 60%, less than 50%, less than 40%, less than 30%, less than 20%, less than 10%, less than 5%, or less than 1% of the nucleic acid-cleaving activity of the wild-type exemplary site-directed polypeptide (e.g., Cas9 from S. pyogenes). The modified form of the site-directed polypeptide can have no substantial nucleic acid-cleaving activity. When a site-directed polypeptide is a modified form that has no substantial nucleic acid-cleaving activity, it can be referred to as "enzymatically inactive."

The modified form of the wild type exemplary site-directed polypeptide can have more than 90%, more than 80%, more than 70%, more than 60%, more than 50%, more than 40%, more than 30%, more than 20%, more than 10%, more than 5%, or more than 1% of the nucleic acid-cleaving activity of the wild-type exemplary site-directed polypeptide (e.g., Cas9 from S. pyogenes).

The modified form of the site-directed polypeptide can comprise a mutation. The modified form of the site-directed polypeptide can comprise a mutation such that it can induce a single-stranded break (SSB) on a target nucleic acid (e.g., by cutting only one of the sugar-phosphate backbones of the target nucleic acid). The mutation can result in less than 90%, less than 80%, less than 70%, less than 60%, less than 50%, less than 40%, less than 30%, less than 20%, less than 10%, less than 5%, or less than 1% of the nucleic acid-cleaving activity in one or more of the plurality of nucleic acid-cleaving domains of the wild-type site directed polypeptide (e.g., Cas9 from S. pyogenes). The mutation can result in one or more of the plurality of nucleic acid-cleaving domains retaining the ability to cleave the complementary strand of the target nucleic acid but reducing its ability to cleave the non-complementary strand of the target nucleic acid. The mutation can result in one or more of the plurality of nucleic acid-cleaving domains retaining the ability to cleave the non-complementary strand of the target nucleic acid but reducing its ability to cleave the complementary strand of the target nucleic acid. For example, residues in the wild type exemplary S. pyogenes Cas9 polypeptide such as Asp10, His840, Asn854 and Asn856 can be mutated to inactivate one or more of the plurality of nucleic acid-cleaving domains (e.g., nuclease domains). The residues to be mutated can correspond to residues Asp10, His840, Asn854 and Asn856 in the wild type exemplary S. pyogenes Cas9 polypeptide (e.g., as determined by sequence and/or structural alignment). Non-limiting examples of mutations can include D10A, H840A, N854A or N856A. One skilled in the art will recognize that mutations other than alanine substitutions are suitable.

A D10A mutation can be combined with one or more of H840A, N854A, or N856A mutations to produce a site-directed polypeptide substantially lacking DNA cleavage activity. A H840A mutation can be combined with one or more of D10A, N854A, or N856A mutations to produce a site-directed polypeptide substantially lacking DNA cleavage activity. A N854A mutation can be combined with one or more of H840A, D10A, or N856A mutations to produce a site-directed polypeptide substantially lacking DNA cleavage activity. A N856A mutation can be combined with one or more of H840A, N854A, or D10A mutations to produce a site-directed polypeptide substantially lacking DNA cleavage activity. Site-directed polypeptides that comprise one substantially inactive nuclease domain can be referred to as nickases.

Mutations of the disclosure can be produced by site-directed mutation. Mutations can include substitutions, additions, and deletions, or any combination thereof. In some instances, the mutation converts the mutated amino acid to alanine. In some instances, the mutation converts the mutated amino acid to another amino acid (e.g., glycine, serine, threonine, cysteine, valine, leucine, isoleucine, methionine, proline, phenylalanine, tyrosine, tryptophan, aspartic acid, glutamic acid, asparagines, glutamine, histidine, lysine, or arginine). The mutation can convert the mutated amino acid to a non-natural amino acid (e.g., selenomethionine). The mutation can convert the mutated amino acid to amino acid mimics (e.g., phosphomimics). The mutation can be a conservative mutation. For example, the mutation can convert the mutated amino acid to amino acids that resemble the size, shape, charge, polarity, conformation, and/or rotamers of the mutated amino acids (e.g., cysteine/serine mutation, lysine/asparagine mutation, histidine/phenylalanine mutation).

In some instances, the site-directed polypeptide (e.g., variant, mutated, enzymatically inactive and/or conditionally enzymatically inactive site-directed polypeptide) can target nucleic acid. The site-directed polypeptide (e.g., variant, mutated, enzymatically inactive and/or conditionally enzymatically inactive endoribonuclease) can target RNA. Site-directed polypeptides that can target RNA can include members of other CRISPR subfamilies such as Cas6 and Cas5.

The site-directed polypeptide can comprise one or more non-native sequences (e.g., a fusion).

A site-directed polypeptide can comprise an amino acid sequence comprising at least 15% amino acid identity to a Cas9 from a bacterium (e.g., *S. pyogenes*), a nucleic acid binding domain, and two nucleic acid cleaving domains (i.e., an HNH domain and a RuvC domain).

A site-directed polypeptide can comprise an amino acid sequence comprising at least 15% amino acid identity to a Cas9 from a bacterium (e.g., *S. pyogenes*), and two nucleic acid cleaving domains (i.e., an HNH domain and a RuvC domain).

A site-directed polypeptide can comprise an amino acid sequence comprising at least 15% amino acid identity to a Cas9 from a bacterium (e.g., *S. pyogenes*), and two nucleic acid cleaving domains, wherein one or both of the nucleic acid cleaving domains comprise at least 50% amino acid identity to a nuclease domain from Cas9 from a bacterium (e.g., *S. pyogenes*).

A site-directed polypeptide can comprise an amino acid sequence comprising at least 15% amino acid identity to a Cas9 from a bacterium (e.g., *S. pyogenes*), two nucleic acid cleaving domains (i.e., an HNH domain and a RuvC domain), and a linker linking the site-directed polypeptide to a non-native sequence.

A site-directed polypeptide can comprise an amino acid sequence comprising at least 15% amino acid identity to a Cas9 from a bacterium (e.g., *S. pyogenes*), two nucleic acid cleaving domains (i.e., an HNH domain and a RuvC domain), wherein the site-directed polypeptide comprises a mutation in one or both of the nucleic acid cleaving domains that reduces the cleaving activity of the nuclease domains by at least 50%.

A site-directed polypeptide can comprise an amino acid sequence comprising at least 15% amino acid identity to a Cas9 from a bacterium (e.g., *S. pyogenes*), and two nucleic acid cleaving domains (i.e., an HNH domain and a RuvC domain), wherein one of the nuclease domains comprises mutation of aspartic acid 10, and/or wherein one of the nuclease domains comprises mutation of histidine 840, and wherein the mutation reduce the cleaving activity of the nuclease domains by at least 50%.

Endoribonucleases

In some embodiments, a site-directed polypeptide can be an endoribonuclease.

In some cases, the endoribonuclease can comprise an amino acid sequence having at most about 20%, at most about 30%, at most about 40%, at most about 50%, at most about 60%, at most about 70%, at most about 75%, at most about 80%, at most about 85%, at most about 90%, at most about 95%, at most about 99%, or 100%, amino acid sequence identity and/or homology to a wild type reference endoribonuclease. The endoribonuclease can comprise an amino acid sequence having at least about 20%, at least about 30%, at least about 40%, at least about 50%, at least about 60%, at least about 70%, at least about 75%, at least about 80%, at least about 85%, at least about 90%, at least about 95%, at least about 99%, or 100%, amino acid sequence identity and/or homology to a wild type reference endoribonuclease (e.g., Csy4 from *P. aeruginosa*). The reference endoribonuclease can be a Cas6 family member (e.g., Csy4, Cas6). The reference endoribonuclease can be a Cas5 family member (e.g., Cas5 from *D. vulgaris*). The reference endoribonuclease can be a Type I CRISPR family member (e.g., Cas3). The reference endoribonucleases can be a Type II family member. The reference endoribonuclease can be a Type III family member (e.g., Cas6). A reference endoribonuclease can be a member of the Repeat Associated Mysterious Protein (RAMP) superfamily (e.g., Cas7).

The endoribonuclease can comprise amino acid modifications (e.g., substitutions, deletions, additions etc). The endoribonuclease can comprise one or more non-native sequences (e.g., a fusion, an affinity tag). The amino acid modifications may not substantially alter the activity of the endoribonuclease. An endoribonuclease comprising amino acid modifications and/or fusions can retain at least about 75%, at least about 80%, at least about 85%, at least about 90%, at least about 95%, at least about 97% or 100% activity of the wild-type endoribonuclease.

The modification can result in alteration of the enzymatic activity of the endoribonuclease. The modification can result in less than 90%, less than 80%, less than 70%, less than 60%, less than 50%, less than 40%, less than 30%, less than 20%, less than 10%, less than 5%, or less than 1% of the endoribonuclease. In some instances, the modification occurs in the nuclease domain of an endoribonuclease. Such modifications can result in less than 90%, less than 80%, less than 70%, less than 60%, less than 50%, less than 40%, less than 30%, less than 20%, less than 10%, less than 5%, or less than 1% of the nucleic acid-cleaving ability in one or more of the plurality of nucleic acid-cleaving domains of the wild-type endoribonuclease.

Conditionally Enzymatically Inactive Endoribonucleases

In some embodiments, an endoribonuclease can be conditionally enzymatically inactive. A conditionally enzymatically inactive endoribonuclease can bind to a polynucleotide in a sequence-specific manner. A conditionally enzymatically inactive endoribonuclease can bind a polynucleotide in a sequence-specific manner, but cannot cleave the target polyribonucleotide.

In some cases, the conditionally enzymatically inactive endoribonuclease can comprise an amino acid sequence having up to about 20%, up to about 30%, up to about 40%, up to about 50%, up to about 60%, up to about 70%, up to about 75%, up to about 80%, up to about 85%, up to about 90%, up to about 95%, up to about 99%, or 100%, amino acid sequence identity and/or homology to a reference conditionally enzymatically endoribonuclease (e.g., Csy4 from *P. aeruginosa*). In some cases, the conditionally enzymatically inactive endoribonuclease can comprise an amino acid sequence having at least about 20%, at least about 30%, at least about 40%, at least about 50%, at least about 60%, at least about 70%, at least about 75%, at least about 80%, at least about 85%, at least about 90%, at least about 95%, at least about 99%, or 100%, amino acid sequence identity and/or homology to a reference conditionally enzymatically endoribonuclease (e.g., Csy4 from *P. aeruginosa*).

The conditionally enzymatically inactive endoribonuclease can comprise a modified form of an endoribonuclease. The modified form of the endoribonuclease can comprise an amino acid change (e.g., deletion, insertion, or substitution) that reduces the nucleic acid-cleaving activity of the endoribonuclease. For example, the modified form of the conditionally enzymatically inactive endoribonuclease can have less than less than 90%, less than 80%, less than 70%, less than 60%, less than 50%, less than 40%, less than 30%, less than 20%, less than 10%, less than 5%, or less than 1% of the nucleic acid-cleaving activity of the reference (e.g., wild-type) conditionally enzymatically inactive endoribonuclease (e.g., Csy4 from *P. aeruginosa*). The modified form of the conditionally enzymatically inactive endoribonuclease can have no substantial nucleic acid-cleaving activity. When a conditionally enzymatically inactive endoribonuclease is a modified form that has no substantial nucleic acid-cleaving activity, it can be referred to as "enzymatically inactive."

The modified form of the conditionally enzymatically inactive endoribonuclease can comprise a mutation that can result in reduced nucleic acid-cleaving ability (i.e., such that the conditionally enzymatically inactive endoribonuclease can be enzymatically inactive in one or more of the nucleic acid-cleaving domains). The mutation can result in less than 90%, less than 80%, less than 70%, less than 60%, less than 50%, less than 40%, less than 30%, less than 20%, less than 10%, less than 5%, or less than 1% of the nucleic acid-cleaving ability in one or more of the plurality of nucleic acid-cleaving domains of the wild-type endoribonuclease (e.g., Csy4 from *P. aeruginosa*). The mutation can occur in the nuclease domain of the endoribonuclease. The mutation can occur in a ferredoxin-like fold. The mutation can comprise the mutation of a conserved aromatic amino acid. The mutation can comprise the mutation of a catalytic amino acid. The mutation can comprise the mutation of a histidine. For example, the mutation can comprise a H29A mutation in Csy4 (e.g., Csy4 from *P. aeruginosa*), or any corresponding residue to H29A as determined by sequence and/or structural alignment. Other residues can be mutated to achieve the same effect (i.e. inactivate one or more of the plurality of nuclease domains).

Mutations of the invention can be produced by site-directed mutation. Mutations can include substitutions, additions, and deletions, or any combination thereof. In some instances, the mutation converts the mutated amino acid to alanine. In some instances, the mutation converts the mutated amino acid to another amino acid (e.g., glycine, serine, threonine, cysteine, valine, leucine, isoleucine, methionine, proline, phenylalanine, tyrosine, tryptophan, aspartic acid, glutamic acid, asparagines, glutamine, histidine, lysine, or arginine). The mutation can convert the mutated amino acid to a non-natural amino acid (e.g., selenomethionine). The mutation can convert the mutated amino acid to amino acid mimics (e.g., phosphomimics). The mutation can be a conservative mutation. For example, the mutation can convert the mutated amino acid to amino acids that resemble the size, shape, charge, polarity, conformation, and/or rotamers of the mutated amino acids (e.g., cysteine/serine mutation, lysine/asparagine mutation, histidine/phenylalanine mutation).

A conditionally enzymatically inactive endoribonuclease can be enzymatically inactive in the absence of a reactivation agent (e.g., imidazole). A reactivation agent can be an agent that mimics a histidine residue (e.g., may have an imidazole ring). A conditionally enzymatically inactive endoribonuclease can be activated by contact with a reactivation agent. The reactivation agent can comprise imidazole. For example, the conditionally enzymatically inactive endoribonuclease can be enzymatically activated by contacting the conditionally enzymatically inactive endoribonuclease with imidazole at a concentration of from about 100 mM to about 500 mM. The imidazole can be at a concentration of about 100 mM, about 150 mM, about 200 mM, about 250 mM, about 300 mM, about 350 mM, about 400 mM, about 450 mM, about 500 mM, about 550 mM, or about 600 mM. The presence of imidazole (e.g., in a concentration range of from about 100 mM to about 500 mM) can reactivate the conditionally enzymatically inactive endoribonuclease such that the conditionally enzymatically inactive endoribonuclease becomes enzymatically active, e.g., the conditionally enzymatically inactive endoribonuclease exhibits at least about 50%, at least about 60%, at least about 70%, at least about 80%, at least about 90%, at least about 95%, or more than 95%, of the nucleic acid cleaving ability of a reference conditionally enzymatically inactive endoribonuclease (e.g., Csy4 from *P. aeruginosa* comprising H29A mutation).

A conditionally enzymatically inactive endoribonuclease can comprise at least 20% amino acid identity to Csy4 from *P. aeruginosa*, a mutation of histidine 29, wherein the mutation results in at least 50% reduction of nuclease activity of the endoribonuclease, and wherein at least 50% of the lost nuclease activity can be restored by incubation of the endoribonuclease with at least 100 mM imidazole.

Codon-Optimization

A polynucleotide encoding a site-directed polypeptide and/or an endoribonuclease can be codon-optimized. This type of optimization can entail the mutation of foreign-derived (e.g., recombinant) DNA to mimic the codon preferences of the intended host organism or cell while encoding the same protein. Thus, the codons can be changed, but the encoded protein remains unchanged. For example, if the intended target cell was a human cell, a human codon-optimized polynucleotide Cas9 could be used for producing a suitable site-directed polypeptide. As another non-limiting example, if the intended host cell were a mouse cell, then a mouse codon-optimized polynucleotide encoding Cas9 could be a suitable site-directed polypeptide. A polynucleotide encoding a site-directed polypeptide can be codon optimized for many host cells of interest. A host cell can be a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens C. Agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), etc. Codon optimization may not be required. In some instances, codon optimization can be preferable.

Nucleic Acid-Targeting Nucleic Acid

The present disclosure provides for a nucleic acid-targeting nucleic acid that can direct the activities of an associated polypeptide (e.g., a site-directed polypeptide) to a specific target sequence within a target nucleic acid. The nucleic acid-targeting nucleic acid can comprise nucleotides. The nucleic acid-targeting nucleic acid can be RNA. A nucleic acid-targeting nucleic acid can comprise a single guide nucleic acid-targeting nucleic acid. An exemplary single guide nucleic acid is depicted in FIG. 1A. The spacer extension 105 and the tracrRNA extension 135 can comprise elements that can contribute additional functionality (e.g., stability) to the nucleic acid-targeting nucleic acid. In some embodiments the spacer extension 105 and the tracrRNA extension 135 are optional. A spacer sequence 110 can comprise a sequence that can hybridize to a target nucleic acid sequence. The spacer sequence 110 can be a variable portion of the nucleic acid-targeting nucleic acid. The sequence of the spacer sequence 110 can be engineered to hybridize to the target nucleic acid sequence. The CRISPR repeat 115 (i.e. referred to in this exemplary embodiment as a minimum CRISPR repeat) can comprise nucleotides that can hybridize to a tracrRNA sequence 125 (i.e. referred to in this exemplary embodiment as a minimum tracrRNA sequence). The minimum CRISPR repeat 115 and the minimum tracrRNA sequence 125 can interact, the interacting molecules comprising a base-paired, double-stranded structure. Together, the minimum CRISPR repeat 115 and the minimum tracrRNA sequence 125 can facilitate binding to the site-directed polypeptide. The minimum CRISPR repeat 115 and the minimum tracrRNA sequence 125 can be linked together to form a hairpin structure through the single guide connector 120. The 3' tracrRNA sequence 130 can comprise a protospacer adjacent motif recognition sequence. The 3' tracrRNA sequence 130 can be identical or similar to part of a tracrRNA sequence. In some embodiments, the 3' tracrRNA sequence 130 can comprise one or more hairpins.

In some embodiments, a nucleic acid-targeting nucleic acid can comprise a single guide nucleic acid-targeting nucleic acid as depicted in FIG. 1B. A nucleic acid-targeting nucleic acid can comprise a spacer sequence 140. A spacer sequence 140 can comprise a sequence that can hybridize to the target nucleic acid sequence. The spacer sequence 140 can be a variable portion of the nucleic acid-targeting nucleic acid. The spacer sequence 140 can be 5' of a first duplex 145. The first duplex 145 comprises a region of hybridization between a minimum CRISPR repeat 146 and minimum tracrRNA sequence 147. The first duplex 145 can be interrupted by a bulge 150. The bulge 150 can comprise unpaired nucleotides. The bulge 150 can be facilitate the recruitment of a site-directed polypeptide to the nucleic acid-targeting nucleic acid. The bulge 150 can be followed by a first stem 155. The first stem 155 comprises a linker sequence linking the minimum CRISPR repeat 146 and the minimum tracrRNA sequence 147. The last paired nucleotide at the 3' end of the first duplex 145 can be connected to a second linker sequence 160. The second linker 160 can comprise a P-domain. The second linker 160 can link the first duplex 145 to a mid-tracrRNA 165. The mid-tracrRNA 165 can, in some embodiments, comprise one or more hairpin regions. For example the mid-tracrRNA 165 can comprise a second stem 170 and a third stem 180. A third linker 175 can link the second stem 170 and the third stem 180.

Figure 2:
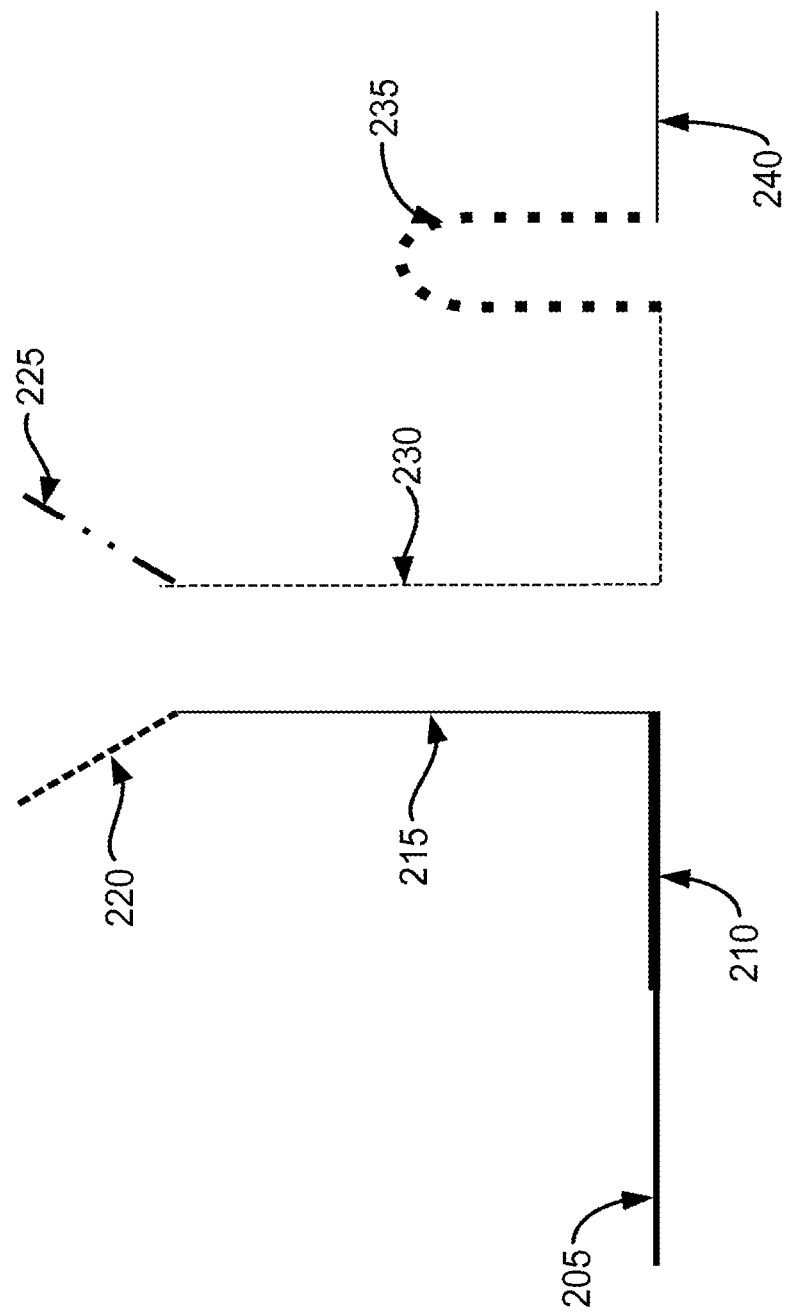
FIG. 2 depicts an exemplary embodiment of a double guide nucleic acid-targeting nucleic acid of the disclosure.

In some embodiments, the nucleic acid-targeting nucleic acid can comprise a double guide nucleic acid structure. FIG. 2 depicts an exemplary double guide nucleic acid-targeting nucleic acid structure. Similar to the single guide nucleic acid structure of FIG. 1, the double guide nucleic acid structure can comprise a spacer extension 205, a spacer 210, a minimum CRISPR repeat 215, a minimum tracrRNA sequence 230, a 3' tracrRNA sequence 235, and a tracrRNA extension 240. However, a double guide nucleic acid-targeting nucleic acid may not comprise the single guide connector 120. Instead the minimum CRISPR repeat sequence 215 can comprise a 3' CRISPR repeat sequence 220 which can be similar or identical to part of a CRISPR repeat. Similarly, the minimum tracrRNA sequence 230 can comprise a 5' tracrRNA sequence 225 which can be similar or identical to part of a tracrRNA. The double guide RNAs can hybridize together via the minimum CRISPR repeat 215 and the minimum tracrRNA sequence 230.

In some embodiments, the first segment (i.e., nucleic acid-targeting segment) can comprise the spacer extension (e.g., 105/205) and the spacer (e.g., 110/210). The nucleic acid-targeting nucleic acid can guide the bound polypeptide to a specific nucleotide sequence within target nucleic acid via the above mentioned nucleic acid-targeting segment.

In some embodiments, the second segment (i.e., protein binding segment) can comprise the minimum CRISPR repeat (e.g., 115/215), the minimum tracrRNA sequence (e.g., 125/230), the 3' tracrRNA sequence (e.g., 130/235), and/or the tracrRNA extension sequence (e.g., 135/240). The protein-binding segment of a nucleic acid-targeting nucleic acid can interact with a site-directed polypeptide. The protein-binding segment of a nucleic acid-targeting nucleic acid can comprise two stretches of nucleotides that that can hybridize to one another. The nucleotides of the protein-binding segment can hybridize to form a double-stranded nucleic acid duplex. The double-stranded nucleic acid duplex can be RNA. The double-stranded nucleic acid duplex can be DNA.

In some instances, a nucleic acid-targeting nucleic acid can comprise, in the order of 5' to 3', a spacer extension, a spacer, a minimum CRISPR repeat, a single guide connector, a minimum tracrRNA, a 3' tracrRNA sequence, and a tracrRNA extension. In some instances, a nucleic acid-targeting nucleic acid can comprise, a tracrRNA extension, a 3'tracrRNA sequence, a minimum tracrRNA, a single guide connector, a minimum CRISPR repeat, a spacer, and a spacer extension in any order.

A nucleic acid-targeting nucleic acid and a site-directed polypeptide can form a complex. The nucleic acid-targeting nucleic acid can provide target specificity to the complex by comprising a nucleotide sequence that can hybridize to a sequence of a target nucleic acid. In other words, the site-directed polypeptide can be guided to a nucleic acid sequence by virtue of its association with at least the protein-binding segment of the nucleic acid-targeting nucleic acid. The nucleic acid-targeting nucleic acid can direct the activity of a Cas9 protein. The nucleic acid-targeting nucleic acid can direct the activity of an enzymatically inactive Cas9 protein.

Methods of the disclosure can provide for a genetically modified cell. A genetically modified cell can comprise an exogenous nucleic acid-targeting nucleic acid and/or an exogenous nucleic acid comprising a nucleotide sequence encoding a nucleic acid-targeting nucleic acid.

Spacer Extension Sequence

A spacer extension sequence can provide stability and/or provide a location for modifications of a nucleic acid-targeting nucleic acid. A spacer extension sequence can have a length of from about 1 nucleotide to about 400 nucleotides. A spacer extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 40, 1000, 2000, 3000, 4000, 5000, 6000, or 7000 or more nucleotides. A spacer extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, 7000 or more nucleotides. A spacer extension sequence can be less than 10 nucleotides in length. A spacer extension sequence can be between 10 and 30 nucleotides in length. A spacer extension sequence can be between 30-70 nucleotides in length.

The spacer extension sequence can comprise a moiety (e.g., a stability control sequence, an endoribonuclease binding sequence, a ribozyme). A moiety can influence the stability of a nucleic acid targeting RNA. A moiety can be a transcriptional terminator segment (i.e., a transcription termination sequence). A moiety of a nucleic acid-targeting nucleic acid can have a total length of from about 10 nucleotides to about 100 nucleotides, from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, from about 15 nucleotides (nt) to about 80 nt, from about 15 nt to about 50 nt, from about 15 nt to about 40 nt, from about 15 nt to about 30 nt or from about 15 nt to about 25 nt. The moiety can be one that can function in a eukaryotic cell. In some cases, the moiety can be one that can function in a prokaryotic cell. The moiety can be one that can function in both a eukaryotic cell and a prokaryotic cell.

Non-limiting examples of suitable moieties can include: 5' cap (e.g., a 7-methylguanylate cap (m7 G)), a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like) a modification or sequence that provides for increased, decreased, and/or controllable stability, or any combination thereof. A spacer extension sequence can comprise a primer binding site, a molecular index (e.g., barcode sequence). The spacer extension sequence can comprise a nucleic acid affinity tag.

Spacer

The nucleic acid-targeting segment of a nucleic acid-targeting nucleic acid can comprise a nucleotide sequence (e.g., a spacer) that can hybridize to a sequence in a target nucleic acid. The spacer of a nucleic acid-targeting nucleic acid can interact with a target nucleic acid in a sequence-specific manner via hybridization (i.e., base pairing). As such, the nucleotide sequence of the spacer may vary and can determine the location within the target nucleic acid that the nucleic acid-targeting nucleic acid and the target nucleic acid can interact.

The spacer sequence can hybridize to a target nucleic acid that is located 5' of spacer adjacent motif (PAM). Different organisms may comprise different PAM sequences. For example, in S. pyogenes, the PAM can be a sequence in the target nucleic acid that comprises the sequence 5'-XRR-3', where R can be either A or G, where X is any nucleotide and X is immediately 3' of the target nucleic acid sequence targeted by the spacer sequence.

The target nucleic acid sequence can be 20 nucleotides. The target nucleic acid can be less than 20 nucleotides. The target nucleic acid can be at least 5, 10, 15, 16, 17, 18, 19, 20, 21, 22, 23, 24, 25, 30 or more nucleotides. The target nucleic acid can be at most 5, 10, 15, 16, 17, 18, 19, 20, 21, 22, 23, 24, 25, 30 or more nucleotides. The target nucleic acid sequence can be 20 bases immediately 5' of the first nucleotide of the PAM. For example, in a sequence comprising 5'-XRR-3' (SEQ ID NO: 1611) (X is any nucleotide (N) and X is immediately 3' of the target nucleic acid sequence targeted by the spacer sequence), the target nucleic acid can be the sequence that corresponds to the N's, wherein N is any nucleotide.

The nucleic acid-targeting sequence of the spacer that can hybridize to the target nucleic acid can have a length at least about 6 nt. For example, the spacer sequence that can hybridize the target nucleic acid can have a length at least about 6 nt, at least about 10 nt, at least about 15 nt, at least about 18 nt, at least about 19 nt, at least about 20 nt, at least about 25 nt, at least about 30 nt, at least about 35 nt or at least about 40 nt, from about 6 nt to about 80 nt, from about 6 nt to about 50 nt, from about 6 nt to about 45 nt, from about 6 nt to about 40 nt, from about 6 nt to about 35 nt, from about 6 nt to about 30 nt, from about 6 nt to about 25 nt, from about 6 nt to about 20 nt, from about 6 nt to about 19 nt, from about 10 nt to about 50 nt, from about 10 nt to about 45 nt, from about 10 nt to about 40 nt, from about 10 nt to about 35 nt, from about 10 nt to about 30 nt, from about 10 nt to about 25 nt, from about 10 nt to about 20 nt, from about 10 nt to about 19 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some cases, the spacer sequence that can hybridize the target nucleic acid can be 20 nucleotides in length. The spacer that can hybridize the target nucleic acid can be 19 nucleotides in length.

The percent complementarity between the spacer sequence the target nucleic acid can be at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. The percent complementarity between the spacer sequence the target nucleic acid can be at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%. In some cases, the percent complementarity between the spacer sequence and the target nucleic acid can be 100% over the six contiguous 5'-most nucleotides of the target sequence of the complementary strand of the target nucleic acid. In some cases, the percent complementarity between the spacer sequence and the target nucleic acid can be at least 60% over about 20 contiguous nucleotides. In some cases, the percent complementarity between the spacer sequence and the target nucleic acid can be 100% over the fourteen contiguous 5'-most nucleotides of the target sequence of the complementary strand of the target nucleic acid and as low as 0% over the remainder. In such a case, the spacer sequence can be considered to be 14 nucleotides in length. In some cases, the percent complementarity between the spacer sequence and the target nucleic acid can be 100% over the six contiguous 5'-most nucleotides of the target sequence of the complementary strand of the target nucleic acid and as low as 0% over the remainder. In such a case, the spacer sequence can be considered to be 6 nucleotides in length. The target nucleic acid can be more than about 50%, 60%, 70%, 80%, 90%, or 100% complementary to the seed region of the crRNA. The target nucleic acid can be less than about 50%, 60%, 70%, 80%, 90%, or 100% complementary to the seed region of the crRNA.

The spacer segment of a nucleic acid-targeting nucleic acid can be modified (e.g., by genetic engineering) to hybridize to any desired sequence within a target nucleic acid. For example, a spacer can be engineered (e.g., designed, programmed) to hybridize to a sequence in target nucleic acid that is involved in cancer, cell growth, DNA replication, DNA repair, HLA genes, cell surface proteins, T-cell receptors, immunoglobulin superfamily genes, tumor suppressor genes, microRNA genes, long non-coding RNA genes, transcription factors, globins, viral proteins, mitochondrial genes, and the like.

A spacer sequence can be identified using a computer program (e.g., machine readable code). The computer program can use variables such as predicted melting temperature, secondary structure formation, and predicted annealing temperature, sequence identity, genomic context, chromatin accessibility, % GC, frequency of genomic occurrence, methylation status, presence of SNPs, and the like.

Minimum CRISPR Repeat Sequence

A minimum CRISPR repeat sequence can be a sequence at least about 30%, 40%, 50%, 60%, 65%, 70%, 75%, 80%, 85%, 90%, 95%, or 100% sequence identity and/or sequence homology with a reference CRISPR repeat sequence (e.g., crRNA from *S. pyogenes*). A minimum CRISPR repeat sequence can be a sequence with at most about 30%, 40%, 50%, 60%, 65%, 70%, 75%, 80%, 85%, 90%, 95%, or 100% sequence identity and/or sequence homology with a reference CRISPR repeat sequence (e.g., crRNA from *S. pyogenes*). A minimum CRISPR repeat can comprise nucleotides that can hybridize to a minimum tracrRNA sequence. A minimum CRISPR repeat and a minimum tracrRNA sequence can form a base-paired, double-stranded structure. Together, the minimum CRISPR repeat and the minimum tracrRNA sequence can facilitate binding to the site-directed polypeptide. A part of the minimum CRISPR repeat sequence can hybridize to the minimum tracrRNA sequence. A part of the minimum CRISPR repeat sequence can be at least about 30%, 40%, 50%, 60%, 65%, 70%, 75%, 80%, 85%, 90%, 95%, or 100% complementary to the minimum tracrRNA sequence. A part of the minimum CRISPR repeat sequence can be at most about 30%, 40%, 50%, 60%, 65%, 70%, 75%, 80%, 85%, 90%, 95%, or 100% complementary to the minimum tracrRNA sequence.

The minimum CRISPR repeat sequence can have a length of from about 6 nucleotides to about 100 nucleotides. For example, the minimum CRISPR repeat sequence can have a length of from about 6 nucleotides (nt) to about 50 nt, from about 6 nt to about 40 nt, from about 6 nt to about 30 nt, from about 6 nt to about 25 nt, from about 6 nt to about 20 nt, from about 6 nt to about 15 nt, from about 8 nt to about 40 nt, from about 8 nt to about 30 nt, from about 8 nt to about 25 nt, from about 8 nt to about 20 nt or from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt. In some embodiments, the minimum CRISPR repeat sequence has a length of approximately 12 nucleotides.

The minimum CRISPR repeat sequence can be at least about 60% identical to a reference minimum CRISPR repeat sequence (e.g., wild type crRNA from *S. pyogenes*) over a stretch of at least 6, 7, or 8 contiguous nucleotides. The minimum CRISPR repeat sequence can be at least about 60% identical to a reference minimum CRISPR repeat sequence (e.g., wild type crRNA from *S. pyogenes*) over a stretch of at least 6, 7, or 8 contiguous nucleotides. For example, the minimum CRISPR repeat sequence can be at least about 65% identical, at least about 70% identical, at least about 75% identical, at least about 80% identical, at least about 85% identical, at least about 90% identical, at least about 95% identical, at least about 98% identical, at least about 99% identical or 100% identical to a reference minimum CRISPR repeat sequence over a stretch of at least 6, 7, or 8 contiguous nucleotides.

Minimum tracrRNA Sequence

A minimum tracrRNA sequence can be a sequence with at least about 30%, 40%, 50%, 60%, 65%, 70%, 75%, 80%, 85%, 90%, 95%, or 100% sequence identity and/or sequence homology to a reference tracrRNA sequence (e.g., wild type tracrRNA from *S. pyogenes*). A minimum tracrRNA sequence can be a sequence with at most about 30%, 40%, 50%, 60%, 65%, 70%, 75%, 80%, 85%, 90%, 95%, or 100% sequence identity and/or sequence homology to a reference tracrRNA sequence (e.g., wild type tracrRNA from *S. pyogenes*). A minimum tracrRNA sequence can comprise nucleotides that can hybridize to a minimum CRISPR repeat sequence. A minimum tracrRNA sequence and a minimum CRISPR repeat sequence can form a base-paired, double-stranded structure. Together, the minimum tracrRNA sequence and the minimum CRISPR repeat can facilitate binding to the site-directed polypeptide. A part of the minimum tracrRNA sequence can hybridize to the minimum CRISPR repeat sequence. A part of the minimum tracrRNA sequence can be 30%, 40%, 50%, 60%, 65%, 70%, 75%, 80%, 85%, 90%, 95%, or 100% complementary to the minimum CRISPR repeat sequence.

The minimum tracrRNA sequence can have a length of from about 6 nucleotides to about 100 nucleotides. For example, the minimum tracrRNA sequence can have a length of from about 6 nucleotides (nt) to about 50 nt, from about 6 nt to about 40 nt, from about 6 nt to about 30 nt, from about 6 nt to about 25 nt, from about 6 nt to about 20 nt, from about 6 nt to about 15 nt, from about 8 nt to about 40 nt, from about 8 nt to about 30 nt, from about 8 nt to about 25 nt, from about 8 nt to about 20 nt or from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt. In some embodiments, the minimum tracrRNA sequence has a length of approximately 14 nucleotides.

The minimum tracrRNA sequence can be at least about 60% identical to a reference minimum tracrRNA (e.g., wild type, tracrRNA from *S. pyogenes*) sequence over a stretch of at least 6, 7, or 8 contiguous nucleotides. The minimum tracrRNA sequence can be at least about 60% identical to a reference minimum tracrRNA (e.g., wild type, tracrRNA from *S. pyogenes*) sequence over a stretch of at least 6, 7, or 8 contiguous nucleotides. For example, the minimum tracrRNA sequence can be at least about 65% identical, at least about 70% identical, at least about 75% identical, at least about 80% identical, at least about 85% identical, at least about 90% identical, at least about 95% identical, at least about 98% identical, at least about 99% identical or 100% identical to a reference minimum tracrRNA sequence over a stretch of at least 6, 7, or 8 contiguous nucleotides.

The duplex (i.e., first duplex in FIG. 1B) between the minimum CRISPR RNA and the minimum tracrRNA can comprise a double helix. The first base of the first strand of the duplex (e.g., the minimum CRISPR repeat in FIG. 1B)

can be a guanine. The first base of the first strand of the duplex (e.g., the minimum CRISPR repeat in FIG. 1B) can be an adenine. The duplex (i.e., first duplex in FIG. 1B) between the minimum CRISPR RNA and the minimum tracrRNA can comprise at least about 1, 2, 3, 4, 5, 6, 7, 8, 9, or 10 or more nucleotides. The duplex (i.e., first duplex in FIG. 1B) between the minimum CRISPR RNA and the minimum tracrRNA can comprise at most about 1, 2, 3, 4, 5, 6, 7, 8, 9, or 10 or more nucleotides.

The duplex can comprise a mismatch. The duplex can comprise at least about 1, 2, 3, 4, or 5 mismatches. The duplex can comprise at most about 1, 2, 3, 4, or 5 mismatches. In some instances, the duplex comprises no more than 2 mismatches.

Bulge

A bulge can refer to an unpaired region of nucleotides within the duplex made up of the minimum CRISPR repeat and the minimum tracrRNA sequence. The bulge can be important in the binding to the site-directed polypeptide. A bulge can comprise, on one side of the duplex, an unpaired 5'-XXXY-3' where X is any purine and Y can be a nucleotide that can form a wobble pair with a nucleotide on the opposite strand, and an unpaired nucleotide region on the other side of the duplex.

For example, the bulge can comprise an unpaired purine (e.g., adenine) on the minimum CRISPR repeat strand of the bulge. In some embodiments, a bulge can comprise an unpaired 5'-AAGY-3' of the minimum tracrRNA sequence strand of the bulge, where Y can be a nucleotide that can form a wobble pairing with a nucleotide on the minimum CRISPR repeat strand.

A bulge on a first side of the duplex (e.g., the minimum CRISPR repeat side) can comprise at least 1, 2, 3, 4, or 5 or more unpaired nucleotides. A bulge on a first side of the duplex (e.g., the minimum CRISPR repeat side) can comprise at most 1, 2, 3, 4, or 5 or more unpaired nucleotides. A bulge on the first side of the duplex (e.g., the minimum CRISPR repeat side) can comprise 1 unpaired nucleotide.

A bulge on a second side of the duplex (e.g., the minimum tracrRNA sequence side of the duplex) can comprise at least 1, 2, 3, 4, 5, 6, 7, 8, 9, or 10 or more unpaired nucleotides. A bulge on a second side of the duplex (e.g., the minimum tracrRNA sequence side of the duplex) can comprise at most 1, 2, 3, 4, 5, 6, 7, 8, 9, or 10 or more unpaired nucleotides. A bulge on a second side of the duplex (e.g., the minimum tracrRNA sequence side of the duplex) can comprise 4 unpaired nucleotides.

Regions of different numbers of unpaired nucleotides on each strand of the duplex can be paired together. For example, a bulge can comprise 5 unpaired nucleotides from a first strand and 1 unpaired nucleotide from a second strand. A bulge can comprise 4 unpaired nucleotides from a first strand and 1 unpaired nucleotide from a second strand. A bulge can comprise 3 unpaired nucleotides from a first strand and 1 unpaired nucleotide from a second strand. A bulge can comprise 2 unpaired nucleotides from a first strand and 1 unpaired nucleotide from a second strand. A bulge can comprise 1 unpaired nucleotide from a first strand and 1 unpaired nucleotide from a second strand. A bulge can comprise 1 unpaired nucleotide from a first strand and 2 unpaired nucleotides from a second strand. A bulge can comprise 1 unpaired nucleotide from a first strand and 3 unpaired nucleotides from a second strand. A bulge can comprise 1 unpaired nucleotide from a first strand and 4 unpaired nucleotides from a second strand. A bulge can comprise 1 unpaired nucleotide from a first strand and 5 unpaired nucleotides from a second strand.

In some instances a bulge can comprise at least one wobble pairing. In some instances, a bulge can comprise at most one wobble pairing. A bulge sequence can comprise at least one purine nucleotide. A bulge sequence can comprise at least 3 purine nucleotides. A bulge sequence can comprise at least 5 purine nucleotides. A bulge sequence can comprise at least one guanine nucleotide. A bulge sequence can comprise at least one adenine nucleotide.

P-Domain (P-DOMAIN)

A P-domain can refer to a region of a nucleic acid-targeting nucleic acid that can recognize a protospacer adjacent motif (PAM) in a target nucleic acid. A P-domain can hybridize to a PAM in a target nucleic acid. As such, a P-domain can comprise a sequence that is complementary to a PAM. A P-domain can be located 3' to the minimum tracrRNA sequence. A P-domain can be located within a 3' tracrRNA sequence (i.e., a mid-tracrRNA sequence).

A P-domain starts at least about 1, 2, 3, 4, 5, 6, 7, 8, 9, 10, 15, or 20 or more nucleotides 3' of the last paired nucleotide in the minimum CRISPR repeat and minimum tracrRNA sequence duplex. A P-domain can start at most about 1, 2, 3, 4, 5, 6, 7, 8, 9 or 10 or more nucleotides 3' of the last paired nucleotide in the minimum CRISPR repeat and minimum tracrRNA sequence duplex.

A P-domain can comprise at least about 1, 2, 3, 4, 5, 6, 7, 8, 9, 10, 15, or 20 or more consecutive nucleotides. A P-domain can comprise at most about 1, 2, 3, 4, 5, 6, 7, 8, 9, 10, 15, or 20 or more consecutive nucleotides.

In some instances, a P-domain can comprise a CC dinucleotide (i.e., two consecutive cytosine nucleotides). The CC dinucleotide can interact with the GG dinucleotide of a PAM, wherein the PAM comprises a 5'-XGG-3' sequence.

A P-domain can be a nucleotide sequence located in the 3' tracrRNA sequence (i.e., mid-tracrRNA sequence). A P-domain can comprise duplexed nucleotides (e.g., nucleotides in a hairpin, hybridized together. For example, a P-domain can comprise a CC dinucleotide that is hybridized to a GG dinucleotide in a hairpin duplex of the 3' tracrRNA sequence (i.e., mid-tracrRNA sequence). The activity of the P-domain (e.g., the nucleic acid-targeting nucleic acid's ability to target a target nucleic acid) may be regulated by the hybridization state of the P-DOMAIN. For example, if the P-domain is hybridized, the nucleic acid-targeting nucleic acid may not recognize its target. If the P-domain is unhybridized the nucleic acid-targeting nucleic acid may recognize its target.

The P-domain can interact with P-domain interacting regions within the site-directed polypeptide. The P-domain can interact with an arginine-rich basic patch in the site-directed polypeptide. The P-domain interacting regions can interact with a PAM sequence. The P-domain can comprise a stem loop. The P-domain can comprise a bulge.

3' tracrRNA Sequence

A 3' tracrRNA sequence can be a sequence with at least about 30%, 40%, 50%, 60%, 65%, 70%, 75%, 80%, 85%, 90%, 95%, or 100% sequence identity and/or sequence homology with a reference tracrRNA sequence (e.g., a tracrRNA from *S. pyogenes*). A 3'tracr RNA sequence can be a sequence with at most about 30%, 40%, 50%, 60%, 65%, 70%, 75%, 80%, 85%, 90%, 95%, or 100% sequence identity and/or sequence homology with a reference tracr-RNA sequence (e.g., tracrRNA from *S. pyogenes*).

The 3' tracrRNA sequence can have a length of from about 6 nucleotides to about 100 nucleotides. For example, the 3' tracrRNA sequence can have a length of from about 6 nucleotides (nt) to about 50 nt, from about 6 nt to about 40 nt, from about 6 nt to about 30 nt, from about 6 nt to about 25 nt, from about 6 nt to about 20 nt, from about 6 nt to about 15 nt, from about 8 nt to about 40 nt, from about 8 nt to about 30 nt, from about 8 nt to about 25 nt, from about 8 nt to about 20 nt or from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt. In some embodiments, the 3' tracrRNA sequence has a length of approximately 14 nucleotides.

The 3' tracrRNA sequence can be at least about 60% identical to a reference 3' tracrRNA sequence (e.g., wild type 3' tracrRNA sequence from S. pyogenes) over a stretch of at least 6, 7, or 8 contiguous nucleotides. For example, the 3' tracrRNA sequence can be at least about 60% identical, at least about 65% identical, at least about 70% identical, at least about 75% identical, at least about 80% identical, at least about 85% identical, at least about 90% identical, at least about 95% identical, at least about 98% identical, at least about 99% identical, or 100% identical, to a reference 3' tracrRNA sequence (e.g., wild type 3' tracrRNA sequence from S. pyogenes) over a stretch of at least 6, 7, or 8 contiguous nucleotides.

A 3' tracrRNA sequence can comprise more than one duplexed region (e.g., hairpin, hybridized region). A 3' tracrRNA sequence can comprise two duplexed regions.

The 3' tracrRNA sequence can also be referred to as the mid-tracrRNA (See FIG. 1B). The mid-tracrRNA sequence can comprise a stem loop structure. In other words, the mid-tracrRNA sequence can comprise a hairpin that is different than a second or third stems, as depicted in FIG. 1B. A stem loop structure in the mid-tracrRNA (i.e., 3' tracrRNA) can comprise at least 1, 2, 3, 4, 5, 6, 7, 8, 9, 10, 15 or 20 or more nucleotides. A stem loop structure in the mid-tracrRNA (i.e., 3' tracrRNA) can comprise at most 1, 2, 3, 4, 5, 6, 7, 8, 9 or 10 or more nucleotides. The stem loop structure can comprise a functional moiety. For example, the stem loop structure can comprise an aptamer, a ribozyme, a protein-interacting hairpin, a CRISPR array, an intron, and an exon. The stem loop structure can comprise at least about 1, 2, 3, 4, or 5 or more functional moieties. The stem loop structure can comprise at most about 1, 2, 3, 4, or 5 or more functional moieties.

The hairpin in the mid-tracrRNA sequence can comprise a P-domain. The P-domain can comprise a double-stranded region in the hairpin.

tracrRNA Extension Sequence

A tracrRNA extension sequence can provide stability and/or provide a location for modifications of a nucleic acid-targeting nucleic acid. A tracrRNA extension sequence can have a length of from about 1 nucleotide to about 400 nucleotides. A tracrRNA extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400 or more nucleotides. A tracrRNA extension sequence can have a length from about 20 to about 5000 or more nucleotides. A tracrRNA extension sequence can have a length of more than 1000 nucleotides. A tracrRNA extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400 nucleotides. A tracrRNA extension sequence can have a length of less than 1000 nucleotides. A tracrRNA extension sequence can be less than 10 nucleotides in length. A tracrRNA extension sequence can be between 10 and 30 nucleotides in length. A tracrRNA extension sequence can be between 30-70 nucleotides in length.

The tracrRNA extension sequence can comprise a moiety (e.g., stability control sequence, ribozyme, endoribonuclease binding sequence). A moiety can influence the stability of a nucleic acid targeting RNA. A moiety can be a transcriptional terminator segment (i.e., a transcription termination sequence). A moiety of a nucleic acid-targeting nucleic acid can have a total length of from about 10 nucleotides to about 100 nucleotides, from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, from about 15 nucleotides (nt) to about 80 nt, from about 15 nt to about 50 nt, from about 15 nt to about 40 nt, from about 15 nt to about 30 nt or from about 15 nt to about 25 nt. The moiety can be one that can function in a eukaryotic cell. In some cases, the moiety can be one that can function in a prokaryotic cell. The moiety can be one that can function in both a eukaryotic cell and a prokaryotic cell.

Non-limiting examples of suitable tracrRNA extension moieties include: a 3' poly-adenylated tail, a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like) a modification or sequence that provides for increased, decreased, and/or controllable stability, or any combination thereof. A tracrRNA extension sequence can comprise a primer binding site, a molecular index (e.g., barcode sequence). In some embodiments of the disclosure, the tracrRNA extension sequence can comprise one or more affinity tags.

Single Guide Nucleic Acid

The nucleic acid-targeting nucleic acid can be a single guide nucleic acid. The single guide nucleic acid can be RNA. A single guide nucleic acid can comprise a linker (i.e. item 120 from FIG. 1A) between the minimum CRISPR repeat sequence and the minimum tracrRNA sequence that can be called a single guide connector sequence.

The single guide connector of a single guide nucleic acid can have a length of from about 3 nucleotides to about 100 nucleotides. For example, the linker can have a length of from about 3 nucleotides (nt) to about 90 nt, from about 3 nt to about 80 nt, from about 3 nt to about 70 nt, from about 3 nt to about 60 nt, from about 3 nt to about 50 nt, from about 3 nt to about 40 nt, from about 3 nt to about 30 nt, from about 3 nt to about 20 nt or from about 3 nt to about 10 nt. For example, the linker can have a length of from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. In some embodiments, the linker of a single guide nucleic acid is between 4 and 40 nucleotides. A linker can have a length at least about 100, 500, 1000, 1500, 2000, 2500, 3000, 3500, 4000, 4500, 5000, 5500, 6000, 6500, or 7000 or more nucleotides. A linker can have a length at most about 100, 500, 1000, 1500, 2000, 2500, 3000, 3500, 4000, 4500, 5000, 5500, 6000, 6500, or 7000 or more nucleotides.

The linker sequence can comprise a functional moiety. For example, the linker sequence can comprise an aptamer, a ribozyme, a protein-interacting hairpin, a CRISPR array, an intron, and an exon. The linker sequence can comprise at least about 1, 2, 3, 4, or 5 or more functional moieties. The linker sequence can comprise at most about 1, 2, 3, 4, or 5 or more functional moieties.

In some embodiments, the single guide connector can connect the 3' end of the minimum CRISPR repeat to the 5' end of the minimum tracrRNA sequence. Alternatively, the single guide connector can connect the 3' end of the tracrRNA sequence to the 5' end of the minimum CRISPR repeat. That is to say, a single guide nucleic acid can comprise a 5' DNA-binding segment linked to a 3' protein-binding segment. A single guide nucleic acid can comprise a 5' protein-binding segment linked to a 3' DNA-binding segment.

A nucleic acid-targeting nucleic acid can comprise a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., *S. pyogenes*) or phage over 6, 7, or 8 contiguous nucleotides and wherein the minimum CRISPR repeat has a length from 5-30 nucleotides; a minimum tracrRNA sequence comprising at least 60% identity to a tracrRNA from a bacterium (e.g., *S. pyogenes*) over 6, 7, or 8 contiguous nucleotides and wherein the minimum tracrRNA sequence has a length from 5-30 nucleotides; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., *S. pyogenes*) or phage over 6, 7, or 8 contiguous nucleotides and wherein the 3' tracrRNA comprises a length from 10-20 nucleotides, and comprises a duplexed region; and/or a tracrRNA extension comprising 10-5000 nucleotides in length, or any combination thereof. This nucleic acid-targeting nucleic acid can be referred to as a single guide nucleic acid-targeting nucleic acid.

A nucleic acid-targeting nucleic acid can comprise a spacer extension sequence from 10-5000 nucleotides in length; a spacer sequence of 12-30 nucleotides in length, wherein the spacer is at least 50% complementary to a target nucleic acid; a duplex comprising 1) a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides, 2) a minimum tracrRNA sequence comprising at least 60% identity to a tracrRNA from a bacterium (e.g., *S. pyogenes*) over 6 contiguous nucleotides and wherein the minimum tracrRNA sequence has a length from 5-30 nucleotides, and 3) a bulge wherein the bulge comprises at least 3 unpaired nucleotides on the minimum CRISPR repeat strand of the duplex and at least 1 unpaired nucleotide on the minimum tracrRNA sequence strand of the duplex; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., *S. pyogenes*) or phage over 6 contiguous nucleotides, wherein the 3' tracrRNA comprises a length from 10-20 nucleotides and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

Double Guide Nucleic Acid

A nucleic acid-targeting nucleic acid can be a double guide nucleic acid. The double guide nucleic acid can be RNA. The double guide nucleic acid can comprise two separate nucleic acid molecules (i.e. polynucleotides). Each of the two nucleic acid molecules of a double guide nucleic acid-targeting nucleic acid can comprise a stretch of nucleotides that can hybridize to one another such that the complementary nucleotides of the two nucleic acid molecules hybridize to form the double-stranded duplex of the protein-binding segment. If not otherwise specified, the term "nucleic acid-targeting nucleic acid" can be inclusive, referring to both single-molecule nucleic acid-targeting nucleic acids and double-molecule nucleic acid-targeting nucleic acids.

A double-guide nucleic acid-targeting nucleic acid can comprise 1) a first nucleic acid molecule comprising a spacer extension sequence from 10-5000 nucleotides in length; a spacer sequence of 12-30 nucleotides in length, wherein the spacer is at least 50% complementary to a target nucleic acid; and a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides; and 2) a second nucleic acid molecule of the double-guide nucleic acid-targeting nucleic acid can comprise a minimum tracrRNA sequence comprising at least 60% identity to a tracrRNA from a prokaryote (e.g., *S. pyogenes*) or phage over 6 contiguous nucleotides and wherein the minimum tracrRNA sequence has a length from 5-30 nucleotides; a 3' tracrRNA that comprises at least 60% identity to a tracrRNA from a bacterium (e.g., *S. pyogenes*) over 6 contiguous nucleotides and wherein the 3' tracrRNA comprises a length from 10-20 nucleotides, and comprises a duplexed region; and/or a tracrRNA extension comprising 10-5000 nucleotides in length, or any combination thereof.

In some instances, a double-guide nucleic acid-targeting nucleic acid can comprise 1) a first nucleic acid molecule comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides, and at least 3 unpaired nucleotides of a bulge; and 2) a second nucleic acid molecule of the double-guide nucleic acid-targeting nucleic acid can comprise a minimum tracrRNA sequence comprising at least 60% identity to a tracrRNA from a prokaryote (e.g., *S. pyogenes*) or phage over 6 contiguous nucleotides and wherein the minimum tracrRNA sequence has a length from 5-30 nucleotides and at least 1 unpaired nucleotide of a bulge, wherein the 1 unpaired nucleotide of the bulge is located in the same bulge as the 3 unpaired nucleotides of the minimum CRISPR repeat; a 3' tracrRNA that comprises at least 60% identity to a tracrRNA from a prokaryote (e.g., S. pyogenes) or phage over 6 contiguous nucleotides and wherein the 3' tracrRNA comprises a length from 10-20 nucleotides, and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

Complex of a Nucleic Acid-Targeting Nucleic Acid and a Site-Directed Polypeptide A nucleic acid-targeting nucleic acid can interact with a site-directed polypeptide (e.g., a nucleic acid-guided nucleases, Cas9), thereby forming a complex. The nucleic acid-targeting nucleic acid can guide the site-directed polypeptide to a target nucleic acid.

In some embodiments, a nucleic acid-targeting nucleic acid can be engineered such that the complex (e.g., comprising a site-directed polypeptide and a nucleic acid-targeting nucleic acid) can bind outside of the cleavage site of the site-directed polypeptide. In this case, the target nucleic acid may not interact with the complex and the target nucleic acid can be excised (e.g., free from the complex).

In some embodiments, a nucleic acid-targeting nucleic acid can be engineered such that the complex can bind inside of the cleavage site of the site-directed polypeptide. In this case, the target nucleic acid can interact with the complex and the target nucleic acid can be bound (e.g., bound to the complex).

In some instances, a complex can comprise a site-directed polypeptide, wherein the site-directed polypeptide can comprise an amino acid sequence comprising at least 15% amino acid identity to a Cas9 from S. pyogenes, and two nucleic acid cleaving domains (i.e., an HNH domain and a RuvC domain); and a double-guide nucleic acid-targeting nucleic acid comprising 1) a first nucleic acid molecule comprising a spacer extension sequence from 10-5000 nucleotides in length; a spacer sequence of 12-30 nucleotides in length, wherein the spacer is at least 50% complementary to a target nucleic acid; and a minimum CRISPR repeat comprising at least 60% identity to a crRNA from a prokaryote (e.g., S. pyogenes) or phage over 6 contiguous nucleotides and wherein the minimum CRISPR repeat has a length from 5-30 nucleotides; and 2) a second nucleic acid molecule of the double-guide nucleic acid-targeting nucleic acid can comprise a minimum tracrRNA sequence comprising at least 60% identity to a tracrRNA from a prokaryote (e.g., S. pyogenes) or phage over 6 contiguous nucleotides and wherein the minimum tracrRNA sequence has a length from 5-30 nucleotides; a 3' tracrRNA that comprises at least 60% identity to a tracrRNA from a bacterium (e.g., S. pyogenes) over 6 contiguous nucleotides and wherein the 3' tracrRNA comprises a length from 10-20 nucleotides, and comprises a duplexed region; and/or a tracrRNA extension comprising 10-5000 nucleotides in length, or any combination thereof.

In some instances, a complex can comprise a site-directed polypeptide, wherein the site-directed polypeptide can comprise an amino acid sequence comprising at least 15% amino acid identity to a Cas9 from S. pyogenes, and two nucleic acid cleaving domains (i.e., an HNH domain and a RuvC domain); and, a double-guide nucleic acid-targeting nucleic acid comprising 1) a first nucleic acid molecule comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., S. pyogenes) or phage over 6 contiguous nucleotides and wherein the minimum CRISPR repeat has a length from 5-30 nucleotides, and at least 3 unpaired nucleotides of a bulge; and 2) a second nucleic acid molecule of the double-guide nucleic acid-targeting nucleic acid can comprise a minimum tracrRNA sequence comprising at least 60% identity to a tracrRNA from a prokaryote (e.g., S. pyogenes) or phage over 6 contiguous nucleotides and wherein the minimum tracrRNA sequence has a length from 5-30 nucleotides and at least 1 unpaired nucleotide of a bulge, wherein the 1 unpaired nucleotide of the bulge is located in the same bulge as the 3 unpaired nucleotides of the minimum CRISPR repeat; a 3' tracrRNA that comprises at least 60% identity to a tracrRNA from a prokaryote (e.g., S. pyogenes) or phage over 6 contiguous nucleotides and wherein the 3' tracrRNA comprises a length from 10-20 nucleotides, and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

In some instances, a complex can comprise a site-directed polypeptide, wherein the site-directed polypeptide can comprise an amino acid sequence comprising at least 15% amino acid identity to a Cas9 from S. pyogenes and, two nucleic acid cleaving domains (i.e., an HNH domain and a RuvC domain); and, a nucleic acid-targeting nucleic acid comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., S. pyogenes) or phage over 6, 7, or 8 contiguous nucleotides and wherein the minimum CRISPR repeat has a length from 5-30 nucleotides; a minimum tracrRNA sequence comprising at least 60% identity to a tracrRNA from a bacterium (e.g., S. pyogenes) over 6, 7, or 8 contiguous nucleotides and wherein the minimum tracrRNA sequence has a length from 5-30 nucleotides; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., S. pyogenes) or phage over 6, 7, or 8 contiguous nucleotides and wherein the 3' tracrRNA comprises a length from 10-20 nucleotides, and comprises a duplexed region; and/or a tracrRNA extension comprising 10-5000 nucleotides in length, or any combination thereof. This nucleic acid-targeting nucleic acid can be referred to as a single guide nucleic acid-targeting nucleic acid.

In some instances, a complex can comprise a site-directed polypeptide, wherein the site-directed polypeptide can comprise an amino acid sequence comprising at least 15% amino acid identity to a Cas9 from S. pyogenes, and two nucleic acid cleaving domains (i.e., an HNH domain and a RuvC domain); and, a nucleic acid-targeting nucleic acid can comprising a spacer extension sequence from 10-5000 nucleotides in length; a spacer sequence of 12-30 nucleotides in length, wherein the spacer is at least 50% complementary to a target nucleic acid; a duplex comprising 1) a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides, 2) a minimum tracrRNA sequence comprising at least 60% identity to a tracrRNA from a bacterium (e.g., *S. pyogenes*) over 6 contiguous nucleotides and wherein the minimum tracrRNA sequence has a length from 5-30 nucleotides, and 3) a bulge wherein the bulge comprises at least 3 unpaired nucleotides on the minimum CRISPR repeat strand of the duplex and at least 1 unpaired nucleotide on the minimum tracrRNA sequence strand of the duplex; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., *S. pyogenes*) or phage over 6 contiguous nucleotides, wherein the 3' tracrRNA comprises a length from 10-20 nucleotides and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof. In some instances, a complex can comprise a site-directed polypeptide, wherein the site-directed polypeptide comprises an amino acid sequence comprising at least 15% amino acid identity to a Cas9 from *S. pyogenes*, two nucleic acid cleaving domains (i.e., an HNH domain and a RuvC domain), and a linker linking the site-directed polypeptide to a non-native sequence; and a double-guide nucleic acid-targeting nucleic acid comprising 1) a first nucleic acid molecule comprising a spacer extension sequence from 10-5000 nucleotides in length; a spacer sequence of 12-30 nucleotides in length, wherein the spacer is at least 50% complementary to a target nucleic acid; and a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides; and 2) a second nucleic acid molecule of the double-guide nucleic acid-targeting nucleic acid can comprise a minimum tracrRNA sequence comprising at least 60% identity to a tracrRNA from a prokaryote (e.g., *S. pyogenes*) or phage over 6 contiguous nucleotides and wherein the minimum tracrRNA sequence has a length from 5-30 nucleotides; a 3' tracrRNA that comprises at least 60% identity to a tracrRNA from a bacterium (e.g., *S. pyogenes*) over 6 contiguous nucleotides and wherein the 3' tracrRNA comprises a length from 10-20 nucleotides, and comprises a duplexed region; and/or a tracrRNA extension comprising 10-5000 nucleotides in length, or any combination thereof.

In some instances, a complex can comprise a site-directed polypeptide, wherein the site-directed polypeptide comprises an amino acid sequence comprising at least 15% amino acid identity to a Cas9 from *S. pyogenes*, two nucleic acid cleaving domains (i.e., an HNH domain and a RuvC domain), and a linker linking the site-directed polypeptide to a non-native sequence; and a double-guide nucleic acid-targeting nucleic acid comprising 1) a first nucleic acid molecule comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides, and at least 3 unpaired nucleotides of a bulge; and 2) a second nucleic acid molecule of the double-guide nucleic acid-targeting nucleic acid can comprise a minimum tracrRNA sequence comprising at least 60% identity to a tracrRNA from a prokaryote (e.g., *S. pyogenes*) or phage over 6 contiguous nucleotides and wherein the minimum tracrRNA sequence has a length from 5-30 nucleotides and at least 1 unpaired nucleotide of a bulge, wherein the 1 unpaired nucleotide of the bulge is located in the same bulge as the 3 unpaired nucleotides of the minimum CRISPR repeat; a 3' tracrRNA that comprises at least 60% identity to a tracrRNA from a prokaryote (e.g., *S. pyogenes*) or phage over 6 contiguous nucleotides and wherein the 3' tracrRNA comprises a length from 10-20 nucleotides, and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

In some instances, a complex can comprise a site-directed polypeptide, wherein the site-directed polypeptide comprises an amino acid sequence comprising at least 15% amino acid identity to a Cas9 from *S. pyogenes*, two nucleic acid cleaving domains (i.e., an HNH domain and a RuvC domain), and a linker linking the site-directed polypeptide to a non-native sequence; and a nucleic acid-targeting nucleic acid comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., *S. pyogenes*) or phage over 6, 7, or 8 contiguous nucleotides and wherein the minimum CRISPR repeat has a length from 5-30 nucleotides; a minimum tracrRNA sequence comprising at least 60% identity to a tracrRNA from a bacterium (e.g., *S. pyogenes*) over 6, 7, or 8 contiguous nucleotides and wherein the minimum tracrRNA sequence has a length from 5-30 nucleotides; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., *S. pyogenes*) or phage over 6, 7, or 8 contiguous nucleotides and wherein the 3' tracrRNA comprises a length from 10-20 nucleotides, and comprises a duplexed region; and/or a tracrRNA extension comprising 10-5000 nucleotides in length, or any combination thereof. This nucleic acid-targeting nucleic acid can be referred to as a single guide nucleic acid-targeting nucleic acid.

In some instances, a complex can comprise a site-directed polypeptide, wherein the site-directed polypeptide comprises an amino acid sequence comprising at least 15% amino acid identity to a Cas9 from *S. pyogenes*, two nucleic acid cleaving domains (i.e., an HNH domain and a RuvC domain), and a linker linking the site-directed polypeptide to a non-native sequence; and nucleic acid-targeting nucleic acid can comprising a spacer extension sequence from 10-5000 nucleotides in length; a spacer sequence of 12-30 nucleotides in length, wherein the spacer is at least 50% complementary to a target nucleic acid; a duplex comprising 1) a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides, 2) a minimum tracrRNA sequence comprising at least 60% identity to a tracrRNA from a bacterium (e.g., *S. pyogenes*) over 6 contiguous nucleotides and wherein the minimum tracrRNA sequence has a length from 5-30 nucleotides, and 3) a bulge wherein the bulge comprises at least 3 unpaired nucleotides on the minimum CRISPR repeat strand of the duplex and at least 1 unpaired nucleotide on the minimum tracrRNA sequence strand of the duplex; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., *S. pyogenes*) or phage over 6 contiguous nucleotides, wherein the 3' tracrRNA comprises a length from 10-20 nucleotides and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

In some instances, a complex can comprise a site-directed polypeptide, wherein the site-directed polypeptide comprises at least 15% amino acid identity to a Cas9 from *S. pyogenes*, two nucleic acid cleaving domains (i.e., an HNH domain and a RuvC domain), wherein the site-directed polypeptide comprises a mutation in one or both of the nucleic acid cleaving domains that reduces the cleaving activity of the nuclease domains by at least 50%; and a double-guide nucleic acid-targeting nucleic acid comprising 1) a first nucleic acid molecule comprising a spacer extension sequence from 10-5000 nucleotides in length; a spacer sequence of 12-30 nucleotides in length, wherein the spacer is at least 50% complementary to a target nucleic acid; and a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides; and 2) a second nucleic acid molecule of the double-guide nucleic acid-targeting nucleic acid can comprise a minimum tracrRNA sequence comprising at least 60% identity to a tracrRNA from a prokaryote (e.g., *S. pyogenes*) or phage over 6 contiguous nucleotides and wherein the minimum tracrRNA sequence has a length from 5-30 nucleotides; a 3' tracrRNA that comprises at least 60% identity to a tracrRNA from a bacterium (e.g., *S. pyogenes*) over 6 contiguous nucleotides and wherein the 3' tracrRNA comprises a length from 10-20 nucleotides, and comprises a duplexed region; and/or a tracrRNA extension comprising 10-5000 nucleotides in length, or any combination thereof.

In some instances, a complex can comprise a site-directed polypeptide, wherein the site-directed polypeptide comprises at least 15% amino acid identity to a Cas9 from *S. pyogenes*, two nucleic acid cleaving domains (i.e., an HNH domain and a RuvC domain), wherein the site-directed polypeptide comprises a mutation in one or both of the nucleic acid cleaving domains that reduces the cleaving activity of the nuclease domains by at least 50%; and a double-guide nucleic acid-targeting nucleic acid comprising 1) a first nucleic acid molecule comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides, and at least 3 unpaired nucleotides of a bulge; and 2) a second nucleic acid molecule of the double-guide nucleic acid-targeting nucleic acid can comprise a minimum tracrRNA sequence comprising at least 60% identity to a tracrRNA from a prokaryote (e.g., *S. pyogenes*) or phage over 6 contiguous nucleotides and wherein the minimum tracrRNA sequence has a length from 5-30 nucleotides and at least 1 unpaired nucleotide of a bulge, wherein the 1 unpaired nucleotide of the bulge is located in the same bulge as the 3 unpaired nucleotides of the minimum CRISPR repeat; a 3' tracrRNA that comprises at least 60% identity to a tracrRNA from a prokaryote (e.g., *S. pyogenes*) or phage over 6 contiguous nucleotides and wherein the 3' tracrRNA comprises a length from 10-20 nucleotides, and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

In some instances, a complex can comprise a site-directed polypeptide, wherein the site-directed polypeptide comprises at least 15% amino acid identity to a Cas9 from *S. pyogenes*, two nucleic acid cleaving domains (i.e., an HNH domain and a RuvC domain), wherein the site-directed polypeptide comprises a mutation in one or both of the nucleic acid cleaving domains that reduces the cleaving activity of the nuclease domains by at least 50%; and nucleic acid-targeting nucleic acid comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., *S. pyogenes*) or phage over 6, 7, or 8 contiguous nucleotides and wherein the minimum CRISPR repeat has a length from 5-30 nucleotides; a minimum tracrRNA sequence comprising at least 60% identity to a tracrRNA from a bacterium (e.g., *S. pyogenes*) over 6, 7, or 8 contiguous nucleotides and wherein the minimum tracrRNA sequence has a length from 5-30 nucleotides; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., *S. pyogenes*) or phage over 6, 7, or 8 contiguous nucleotides and wherein the 3' tracrRNA comprises a length from 10-20 nucleotides, and comprises a duplexed region; and/or a tracrRNA extension comprising 10-5000 nucleotides in length, or any combination thereof. This nucleic acid-targeting nucleic acid can be referred to as a single guide nucleic acid-targeting nucleic acid.

In some instances, a complex can comprise a site-directed polypeptide, wherein the site-directed polypeptide comprises at least 15% amino acid identity to a Cas9 from *S. pyogenes*, two nucleic acid cleaving domains (i.e., an HNH domain and a RuvC domain), wherein the site-directed polypeptide comprises a mutation in one or both of the nucleic acid cleaving domains that reduces the cleaving activity of the nuclease domains by at least 50%; and nucleic acid-targeting nucleic acid can comprising a spacer extension sequence from 10-5000 nucleotides in length; a spacer sequence of 12-30 nucleotides in length, wherein the spacer is at least 50% complementary to a target nucleic acid; a duplex comprising 1) a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides, 2) a minimum tracrRNA sequence comprising at least 60% identity to a tracrRNA from a bacterium (e.g., *S. pyogenes*) over 6 contiguous nucleotides and wherein the minimum tracrRNA sequence has a length from 5-30 nucleotides, and 3) a bulge wherein the bulge comprises at least 3 unpaired nucleotides on the minimum CRISPR repeat strand of the duplex and at least 1 unpaired nucleotide on the minimum tracrRNA sequence strand of the duplex; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., *S. pyogenes*) or phage over 6 contiguous nucleotides, wherein the 3' tracrRNA comprises a length from 10-20 nucleotides and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

In some instances, a complex can comprise a site-directed polypeptide, wherein the site-directed polypeptide comprises at least 15% amino acid identity to a Cas9 from *S. pyogenes*, two nucleic acid cleaving domains (i.e., an HNH domain and a RuvC domain), wherein the site-directed polypeptide comprises a mutation in one or both of the nucleic acid cleaving domains that reduces the cleaving activity of the nuclease domains by at least 50%; and a double-guide nucleic acid-targeting nucleic acid comprising 1) a first nucleic acid molecule comprising a spacer extension sequence from 10-5000 nucleotides in length; a spacer sequence of 12-30 nucleotides in length, wherein the spacer is at least 50% complementary to a target nucleic acid; and a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides; and 2) a second nucleic acid molecule of the double-guide nucleic acid-targeting nucleic acid can comprise a minimum tracrRNA sequence comprising at least 60% identity to a tracrRNA from a prokaryote (e.g., *S. pyogenes*) or phage over 6 contiguous nucleotides and wherein the minimum tracrRNA sequence has a length from 5-30 nucleotides; a 3' tracrRNA that comprises at least 60% identity to a tracrRNA from a bacterium (e.g., *S. pyogenes*) over 6 contiguous nucleotides and wherein the 3' tracrRNA comprises a length from 10-20 nucleotides, and comprises a duplexed region; and/or a tracrRNA extension comprising 10-5000 nucleotides in length, or any combination thereof.

In some instances, a complex can comprise a site-directed polypeptide, wherein the site-directed polypeptide comprises at least 15% amino acid identity to a Cas9 from *S. pyogenes*, two nucleic acid cleaving domains (i.e., an HNH domain and a RuvC domain), wherein the site-directed polypeptide comprises a mutation in one or both of the nucleic acid cleaving domains that reduces the cleaving activity of the nuclease domains by at least 50%; and a double-guide nucleic acid-targeting nucleic acid comprising 1) a first nucleic acid molecule comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides, and at least 3 unpaired nucleotides of a bulge; and 2) a second nucleic acid molecule of the double-guide nucleic acid-targeting nucleic acid can comprise a minimum tracrRNA sequence comprising at least 60% identity to a tracrRNA from a prokaryote (e.g., *S. pyogenes*) or phage over 6 contiguous nucleotides and wherein the minimum tracrRNA sequence has a length from 5-30 nucleotides and at least 1 unpaired nucleotide of a bulge, wherein the 1 unpaired nucleotide of the bulge is located in the same bulge as the 3 unpaired nucleotides of the minimum CRISPR repeat; a 3' tracrRNA that comprises at least 60% identity to a tracrRNA from a prokaryote (e.g., *S. pyogenes*) or phage over 6 contiguous nucleotides and wherein the 3' tracrRNA comprises a length from 10-20 nucleotides, and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

In some instances, a complex can comprise a site-directed polypeptide, wherein the site-directed polypeptide comprises at least 15% amino acid identity to a Cas9 from *S. pyogenes*, two nucleic acid cleaving domains (i.e., an HNH domain and a RuvC domain), wherein the site-directed polypeptide comprises a mutation in one or both of the nucleic acid cleaving domains that reduces the cleaving activity of the nuclease domains by at least 50%; and nucleic acid-targeting nucleic acid comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., *S. pyogenes*) or phage over 6, 7, or 8 contiguous nucleotides and wherein the minimum CRISPR repeat has a length from 5-30 nucleotides; a minimum tracrRNA sequence comprising at least 60% identity to a tracrRNA from a bacterium (e.g., *S. pyogenes*) over 6, 7, or 8 contiguous nucleotides and wherein the minimum tracrRNA sequence has a length from 5-30 nucleotides; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., *S. pyogenes*) or phage over 6, 7, or 8 contiguous nucleotides and wherein the 3' tracrRNA comprises a length from 10-20 nucleotides, and comprises a duplexed region; and/or a tracrRNA extension comprising 10-5000 nucleotides in length, or any combination thereof. This nucleic acid-targeting nucleic acid can be referred to as a single guide nucleic acid-targeting nucleic acid.

In some instances, a complex can comprise a site-directed polypeptide, wherein the site-directed polypeptide comprises at least 15% amino acid identity to a Cas9 from *S. pyogenes*, two nucleic acid cleaving domains (i.e., an HNH domain and a RuvC domain), wherein the site-directed polypeptide comprises a mutation in one or both of the nucleic acid cleaving domains that reduces the cleaving activity of the nuclease domains by at least 50%; and a nucleic acid-targeting nucleic acid can comprising a spacer extension sequence from 10-5000 nucleotides in length; a spacer sequence of 12-30 nucleotides in length, wherein the spacer is at least 50% complementary to a target nucleic acid; a duplex comprising 1) a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides, 2) a minimum tracrRNA sequence comprising at least 60% identity to a tracrRNA from a bacterium (e.g., *S. pyogenes*) over 6 contiguous nucleotides and wherein the minimum tracrRNA sequence has a length from 5-30 nucleotides, and 3) a bulge wherein the bulge comprises at least 3 unpaired nucleotides on the minimum CRISPR repeat strand of the duplex and at least 1 unpaired nucleotide on the minimum tracrRNA sequence strand of the duplex; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., *S. pyogenes*) or phage over 6 contiguous nucleotides, wherein the 3' tracrRNA comprises a length from 10-20 nucleotides and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

In some instances, a complex can comprise a site-directed polypeptide, wherein the site-directed polypeptide comprises at least 15% amino acid identity to a Cas9 from *S. pyogenes*, two nucleic acid cleaving domains (i.e., an HNH domain and a RuvC domain), wherein the site-directed polypeptide comprises a mutation in one or both of the nucleic acid cleaving domains that reduces the cleaving activity of the nuclease domains by at least 50%; and a double-guide nucleic acid-targeting nucleic acid comprising 1) a first nucleic acid molecule comprising a spacer extension sequence from 10-5000 nucleotides in length; a spacer sequence of 12-30 nucleotides in length, wherein the spacer is at least 50% complementary to a target nucleic acid; and a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides; and 2) a second nucleic acid molecule of the double-guide nucleic acid-targeting nucleic acid can comprise a minimum tracrRNA sequence comprising at least 60% identity to a tracrRNA from a prokaryote (e.g., *S. pyogenes*) or phage over 6 contiguous nucleotides and wherein the minimum tracrRNA sequence has a length from 5-30 nucleotides; a 3' tracrRNA that comprises at least 60% identity to a tracrRNA from a bacterium (e.g., *S. pyogenes*) over 6 contiguous nucleotides and wherein the 3' tracrRNA comprises a length from 10-20 nucleotides, and comprises a duplexed region; and/or a tracrRNA extension comprising 10-5000 nucleotides in length, or any combination thereof.

In some instances, a complex can comprise a site-directed polypeptide, wherein the site-directed polypeptide comprises at least 15% amino acid identity to a Cas9 from *S. pyogenes*, and two nucleic acid cleaving domains, wherein one or both of the nucleic acid cleaving domains comprise at least 50% amino acid identity to a nuclease domain from Cas9 from *S. pyogenes*; and a double-guide nucleic acid-targeting nucleic acid comprising 1) a first nucleic acid molecule comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides, and at least 3 unpaired nucleotides of a bulge; and 2) a second nucleic acid molecule of the double-guide nucleic acid-targeting nucleic acid can comprise a minimum tracrRNA sequence comprising at least 60% identity to a tracrRNA from a prokaryote (e.g., *S. pyogenes*) or phage over 6 contiguous nucleotides and wherein the minimum tracrRNA sequence has a length from 5-30 nucleotides and at least 1 unpaired nucleotide of a bulge, wherein the 1 unpaired nucleotide of the bulge is located in the same bulge as the 3 unpaired nucleotides of the minimum CRISPR repeat; a 3' tracrRNA that comprises at least 60% identity to a tracrRNA from a prokaryote (e.g., *S. pyogenes*) or phage over 6 contiguous nucleotides and wherein the 3' tracrRNA comprises a length from 10-20 nucleotides, and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

In some instances, a complex can comprise a site-directed polypeptide, wherein the site-directed polypeptide comprises at least 15% amino acid identity to a Cas9 from *S. pyogenes*, and two nucleic acid cleaving domains, wherein one or both of the nucleic acid cleaving domains comprise at least 50% amino acid identity to a nuclease domain from Cas9 from *S. pyogenes*; and nucleic acid-targeting nucleic acid comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., *S. pyogenes*) or phage over 6, 7, or 8 contiguous nucleotides and wherein the minimum CRISPR repeat has a length from 5-30 nucleotides; a minimum tracrRNA sequence comprising at least 60% identity to a tracrRNA from a bacterium (e.g., *S. pyogenes*) over 6, 7, or 8 contiguous nucleotides and wherein the minimum tracrRNA sequence has a length from 5-30 nucleotides; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., *S. pyogenes*) or phage over 6, 7, or 8 contiguous nucleotides and wherein the 3' tracrRNA comprises a length from 10-20 nucleotides, and comprises a duplexed region; and/or a tracrRNA extension comprising 10-5000 nucleotides in length, or any combination thereof. This nucleic acid-targeting nucleic acid can be referred to as a single guide nucleic acid-targeting nucleic acid.

In some instances, a complex can comprise a site-directed polypeptide, wherein the site-directed polypeptide comprises at least 15% amino acid identity to a Cas9 from *S. pyogenes*, and two nucleic acid cleaving domains, wherein one or both of the nucleic acid cleaving domains comprise at least 50% amino acid identity to a nuclease domain from Cas9 from *S. pyogenes*; and a nucleic acid-targeting nucleic acid can comprising a spacer extension sequence from 10-5000 nucleotides in length; a spacer sequence of 12-30 nucleotides in length, wherein the spacer is at least 50% complementary to a target nucleic acid; a duplex comprising 1) a minimum CRISPR repeat comprising at least 60% identity to a crRNA from a prokaryote (e.g., S. pyogenes) or phage over 6 contiguous nucleotides and wherein the minimum CRISPR repeat has a length from 5-30 nucleotides, 2) a minimum tracrRNA sequence comprising at least 60% identity to a tracrRNA from a bacterium (e.g., S. pyogenes) over 6 contiguous nucleotides and wherein the minimum tracrRNA sequence has a length from 5-30 nucleotides, and 3) a bulge wherein the bulge comprises at least 3 unpaired nucleotides on the minimum CRISPR repeat strand of the duplex and at least 1 unpaired nucleotide on the minimum tracrRNA sequence strand of the duplex; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., S. pyogenes) or phage over 6 contiguous nucleotides, wherein the 3' tracrRNA comprises a length from 10-20 nucleotides and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

Any nucleic acid-targeting nucleic acid of the disclosure, a site-directed polypeptide of the disclosure, an effector protein, a multiplexed genetic targeting agent, a donor polynucleotide, a tandem fusion protein, a reporter element, a genetic element of interest, a component of a split system and/or any nucleic acid or proteinaceous molecule necessary to carry out the embodiments of the methods of the disclosure may be recombinant, purified and/or isolated.

Nucleic Acids Encoding a Nucleic Acid-Targeting Nucleic Acid and/or a Site-Directed Polypeptide The present disclosure provides for a nucleic acid comprising a nucleotide sequence encoding a nucleic acid-targeting nucleic acid of the disclosure, a site-directed polypeptide of the disclosure, an effector protein, a multiplexed genetic targeting agent, a donor polynucleotide, a tandem fusion protein, a reporter element, a genetic element of interest, a component of a split system and/or any nucleic acid or proteinaceous molecule necessary to carry out the embodiments of the methods of the disclosure. In some embodiments, the nucleic acid encoding a nucleic acid-targeting nucleic acid of the disclosure, a site-directed polypeptide of the disclosure, an effector protein, a multiplexed genetic targeting agent, a donor polynucleotide, a tandem fusion protein, a reporter element, a genetic element of interest, a component of a split system and/or any nucleic acid or proteinaceous molecule necessary to carry out the embodiments of the methods of the disclosure can be a vector (e.g., a recombinant expression vector).

In some embodiments, the recombinant expression vector can be a viral construct, (e.g., a recombinant adeno-associated virus construct), a recombinant adenoviral construct, a recombinant lentiviral construct, a recombinant retroviral construct, etc.

Suitable expression vectors can include, but are not limited to, viral vectors (e.g. viral vectors based on vaccinia virus, poliovirus, adenovirus, adeno-associated virus, SV40, herpes simplex virus, human immunodeficiency virus, a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus), plant vectors (e.g., T-DNA vector), and the like. The following vectors can be provided by way of example, for eukaryotic host cells: pXT1, pSG5, pSVK3, pBPV, pMSG, and pSVLSV40 (Pharmacia). Other vectors may be used so long as they are compatible with the host cell.

In some instances, a vector can be a linearized vector. A linearized vector can comprise a site-directed polypeptide and/or a nucleic acid-targeting nucleic acid. A linearized vector may not be a circular plasmid. A linearized vector can comprise a double-stranded break. A linearized vector may comprise a sequence encoding a fluorescent protein (e.g., orange fluorescent protein (OFP)). A linearized vector may comprise a sequence encoding an antigen (e.g., CD4). A linearized vector can be linearized (e.g., cut) in a region of the vector encoding parts of the nucleic acid-targeting nucleic acid. For example a linearized vector can be linearized (e.g., cut) in a region of the nucleic acid-targeting nucleic acid 5' to the crRNA portion of the nucleic acid-targeting nucleic acid. A linearized vector can be linearized (e.g., cut) in a region of the nucleic acid-targeting nucleic acid 3' to the spacer extension sequence of the nucleic acid-targeting nucleic acid. A linearized vector can be linearized (e.g., cut) in a region of the nucleic acid-targeting nucleic acid encoding the crRNA sequence of the nucleic acid-targeting nucleic acid. In some instances, a linearized vector or a closed supercoiled vector comprises a sequence encoding a site-directed polypeptide (e.g., Cas9), a promoter driving expression of the sequence encoding the site-directed polypeptide (e.g., CMV promoter), a sequence encoding a linker (e.g., 2A), a sequence encoding a marker (e.g., CD4 or OFP), a sequence encoding portion of a nucleic acid-targeting nucleic acid, a promoter driving expression of the sequence encoding a portion of the nucleic acid-targeting nucleic acid, and a sequence encoding a selectable marker (e.g., ampicillin), or any combination thereof.

A vector can comprise a transcription and/or translation control element. Depending on the host/vector system utilized, any of a number of suitable transcription and translation control elements, including constitutive and inducible promoters, transcription enhancer elements, transcription terminators, etc. may be used in the expression vector.

In some embodiments, a nucleotide sequence encoding a nucleic acid-targeting nucleic acid of the disclosure, a site-directed polypeptide of the disclosure, an effector protein, a multiplexed genetic targeting agent, a donor polynucleotide, a tandem fusion protein, a reporter element, a genetic element of interest, a component of a split system and/or any nucleic acid or proteinaceous molecule necessary to carry out the embodiments of the methods of the disclosure can be operably linked to a control element (e.g., a transcriptional control element), such as a promoter. The transcriptional control element may be functional in a eukaryotic cell, (e.g., a mammalian cell), a prokaryotic cell (e.g., bacterial or archaeal cell). In some embodiments, a nucleotide sequence encoding a nucleic acid-targeting nucleic acid of the disclosure, a site-directed polypeptide of the disclosure, an effector protein, a multiplexed genetic targeting agent, a donor polynucleotide, a tandem fusion protein, a reporter element, a genetic element of interest, a component of a split system and/or any nucleic acid or proteinaceous molecule necessary to carry out the embodiments of the methods of the disclosure can be operably linked to multiple control elements.

Operable linkage to multiple control elements can allow expression of the nucleotide sequence encoding a nucleic acid-targeting nucleic acid of the disclosure, a site-directed polypeptide of the disclosure, an effector protein, a multiplexed genetic targeting agent, a donor polynucleotide, a tandem fusion protein, a reporter element, a genetic element of interest, a component of a split system and/or any nucleic acid or proteinaceous molecule necessary to carry out the embodiments of the methods of the disclosure in either prokaryotic or eukaryotic cells.

Non-limiting examples of suitable eukaryotic promoters (i.e. promoters functional in a eukaryotic cell) can include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-active promoter (CAG), murine stem cell virus promoter (MSCV), phosphoglycerate kinase-1 locus promoter (PGK) and mouse metallothionein-I. The promoter can be a fungi promoter. The promoter can be a plant promoter. A database of plant promoter can be found (e.g., PlantProm). The expression vector may also contain a ribosome binding site for translation initiation and a transcription terminator. The expression vector may also include appropriate sequences for amplifying expression. The expression vector may also include nucleotide sequences encoding non-native tags (e.g., 6×His tag, hemagglutinin tag, green fluorescent protein, etc.) that are fused to the site-directed polypeptide, thus resulting in a fusion protein.

In some embodiments, a nucleotide sequence or sequences encoding a nucleic acid-targeting nucleic acid of the disclosure, a site-directed polypeptide of the disclosure, an effector protein, a multiplexed genetic targeting agent, a donor polynucleotide, a tandem fusion protein, a reporter element, a genetic element of interest, a component of a split system and/or any nucleic acid or proteinaceous molecule necessary to carry out the embodiments of the methods of the disclosure can be operably linked to an inducible promoter (e.g., heat shock promoter, tetracycline-regulated promoter, steroid-regulated promoter, metal-regulated promoter, estrogen receptor-regulated promoter, etc.). In some embodiments, a nucleotide sequence encoding a nucleic acid-targeting nucleic acid of the disclosure, a site-directed polypeptide of the disclosure, an effector protein, a multiplexed genetic targeting agent, a donor polynucleotide, a tandem fusion protein, a reporter element, a genetic element of interest, a component of a split system and/or any nucleic acid or proteinaceous molecule necessary to carry out the embodiments of the methods of the disclosure can be operably linked to a constitutive promoter (e.g., CMV promoter, UBC promoter). In some embodiments, the nucleotide sequence can be operably linked to a spatially restricted and/or temporally restricted promoter (e.g., a tissue specific promoter, a cell type specific promoter, etc.).

A nucleotide sequence or sequences encoding a nucleic acid-targeting nucleic acid of the disclosure, a site-directed polypeptide of the disclosure, an effector protein, a multiplexed genetic targeting agent, a donor polynucleotide, a tandem fusion protein, a reporter element, a genetic element of interest, a component of a split system and/or any nucleic acid or proteinaceous molecule necessary to carry out the embodiments of the methods of the disclosure can be packaged into or on the surface of biological compartments for delivery to cells. Biological compartments can include, but are not limited to, viruses (lentivirus, adenovirus), nanospheres, liposomes, quantum dots, nanoparticles, polyethylene glycol particles, hydrogels, and micelles.

Introduction of the complexes, polypeptides, and nucleic acids of the disclosure into cells can occur by viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

Transgenic Cells and Organisms

The disclosure provides for transgenic cells and organisms. The nucleic acid of a genetically modified host cell and/or transgenic organism can be targeted for genome engineering.

Exemplary cells that can be used to generate transgenic cells according to the methods of the disclosure can include, but are not limited to, HeLa cell, Chinese Hamster Ovary cell, 293-T cell, a pheochromocytoma, a neuroblastomas fibroblast, a rhabdomyosarcoma, a dorsal root ganglion cell, a —NSO cell, Tobacco BY-2, CV-I (ATCC CCL 70), COS-I (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C 1271 (ATCC CRL 1616), BS-C-I (ATCC CCL 26), MRC-5 (ATCC CCL 171), L-cells, HEK-293 (ATCC CRL1 573) and PC 12 (ATCC CRL-1721), HEK293T (ATCC CRL-11268), RBL (ATCC CRL-1378), SH-SY5Y (ATCC CRL-2266), MUCK (ATCC CCL-34), SJ-RH30 (ATCC CRL-2061), HepG2 (ATCC HB-8065), ND7/23 (ECACC 92090903), CHO (ECACC 85050302), Vera (ATCC CCL 81), Caco-2 (ATCC HTB 37), K562 (ATCC CCL 243), Jurkat (ATCC TIB-152), Per.Có, Huvec (ATCC Human Primary PCS 100-010, Mouse CRL 2514, CRL 2515, CRL 2516), HuH-7D12 (ECACC 01042712), 293 (ATCC CRL 10852), A549 (ATCC CCL 185), IMR-90 (ATCC CCL 186), MCF-7 (ATC HTB-22), U-2 OS (ATCC HTB-96), and T84 (ATCC CCL 248), or any cell available at American Type Culture Collection (ATCC), or any combination thereof.

Organisms that can be transgenic can include bacteria, archaea, single-cell eukaryotes, plants, algae, fungi (e.g., yeast), invertebrates (e.g., fruit fly, cnidarian, echinoderm, nematode, etc), vertebrates (e.g., fish, amphibian, reptile, bird, mammal), mammals mammal (e.g., a pig, a cow, a goat, a sheep, a rodent, a rat, a mouse, a non-human primate, a human, etc.), etc.

Transgenic organisms can comprise genetically modified cells. Transgenic organisms and/or genetically modified cells can comprise organisms and/or cells that have been genetically modified with an exogenous nucleic acid comprising a nucleotide sequence encoding nucleic acid-targeting nucleic acid of the disclosure, an effector protein, and/or a site-directed polypeptide, or any combination thereof.

A genetically modified cell can comprise an exogenous site-directed polypeptide and/or an exogenous nucleic acid comprising a nucleotide sequence encoding a site-directed polypeptide. Expression of the site-directed polypeptide in the cell may take 0.1, 0.2, 0.5, 1, 2, 3, 4, 5, 6, or more days. Cells, introduced with the site-directed polypeptide, may be grown for 0.1, 0.2, 0.5, 1, 2, 3, 4, 5, 6, 7, 8, 9, 10 or even more days before the cells can be removed from cell culture and/or host organism.

Subjects

The disclosure provides for performing the methods of the disclosure in a subject. A subject can be a human. A subject can be a mammal (e.g., rat, mouse, cow, dog, pig, sheep, horse). A subject can be a vertebrate or an invertebrate. A subject can be a laboratory animal. A subject can be a patient. A subject can be suffering from a disease. A subject can display symptoms of a disease. A subject may not display symptoms of a disease, but still have a disease. A subject can be under medical care of a caregiver (e.g., the subject is hospitalized and is treated by a physician). A subject can be a plant or a crop.

Kits

The present disclosure provides kits for carrying out the methods of the disclosure. A kit can include one or more of: A nucleic acid-targeting nucleic acid of the disclosure, a polynucleotide encoding a nucleic acid-targeting nucleic acid, a site-directed polypeptide of the disclosure, a polynucleotide encoding a site-directed polypeptide, an effector protein, a polynucleotide encoding an effector protein, a multiplexed genetic targeting agent, a polynucleotide encoding a multiplexed genetic targeting agent, a donor polynucleotide, a tandem fusion protein, a polynucleotide encoding a tandem fusion protein, a reporter element, a genetic element of interest, a component of a split system and/or any nucleic acid or proteinaceous molecule necessary to carry out the embodiments of the methods of the disclosure, or any combination thereof.

A nucleic acid-targeting nucleic acid of the disclosure, a polynucleotide encoding a nucleic acid-targeting nucleic acid, a site-directed polypeptide of the disclosure, a polynucleotide encoding a site-directed polypeptide, an effector protein, a polynucleotide encoding an effector protein, a multiplexed genetic targeting agent, a polynucleotide encoding a multiplexed genetic targeting agent, a donor polynucleotide, a tandem fusion protein, a polynucleotide encoding a tandem fusion protein, a reporter element, a genetic element of interest, a component of a split system and/or any nucleic acid or proteinaceous molecule necessary to carry out the embodiments of the methods of the disclosure are described in detail above.

A kit can comprise: (1) a vector comprising a nucleotide sequence encoding a nucleic acid-targeting nucleic acid, (2) a vector comprising a nucleotide sequence encoding the site-directed polypeptide, and (3) a reagent for reconstitution and/or dilution of the vectors.

A kit can comprise: (1) a vector comprising (i) a nucleotide sequence encoding a nucleic acid-targeting nucleic acid, and (ii) a nucleotide sequence encoding the site-directed polypeptide, and (2) a reagent for reconstitution and/or dilution of the vector.

A kit can comprise: (1) a vector comprising a nucleotide sequence encoding a nucleic acid-targeting nucleic acid, (2) a vector comprising a nucleotide sequence encoding the site-directed polypeptide, (3) a vector comprising a nucleotide sequence encoding an effector protein, a multiplexed genetic targeting agent, a donor polynucleotide, a tandem fusion protein, a reporter element, a genetic element of interest, a component of a split system and/or any nucleic acid or proteinaceous molecule necessary to carry out the embodiments of the methods of the disclosure, and (4) a reagent for reconstitution and/or dilution of the vectors.

A kit can comprise: (1) a vector comprising (i) a nucleotide sequence encoding a nucleic acid-targeting nucleic acid, (ii) a nucleotide sequence encoding the site-directed polypeptide, (2) a vector comprising a nucleotide sequence encoding an effector protein, a multiplexed genetic targeting agent, a donor polynucleotide, a tandem fusion protein, a reporter element, a genetic element of interest, a component of a split system and/or any nucleic acid or proteinaceous molecule necessary to carry out the embodiments of the methods of the disclosure, and (3) a reagent for reconstitution and/or dilution of the recombinant expression vectors.

In some instances, a kit can comprise a site-directed polypeptide (and/or a nucleic acid encoding the same), wherein the site-directed polypeptide can comprise an amino acid sequence comprising at least 15% amino acid identity to a Cas9 from *S. pyogenes*, and two nucleic acid cleaving domains (i.e., an HNH domain and a RuvC domain); and a double-guide nucleic acid-targeting nucleic acid (and/or a nucleic acid encoding the same) comprising 1) a first nucleic acid molecule comprising a spacer extension sequence from 10-5000 nucleotides in length; a spacer sequence of 12-30 nucleotides in length, wherein the spacer is at least 50% complementary to a target nucleic acid; and a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides; and 2) a second nucleic acid molecule of the double-guide nucleic acid-targeting nucleic acid can comprise a minimum tracrRNA sequence comprising at least 60% identity to a tracrRNA from a prokaryote (e.g., *S. pyogenes*) or phage over 6 contiguous nucleotides and wherein the minimum tracrRNA sequence has a length from 5-30 nucleotides; a 3' tracrRNA that comprises at least 60% identity to a tracrRNA from a bacterium (e.g., *S. pyogenes*) over 6 contiguous nucleotides and wherein the 3' tracrRNA comprises a length from 10-20 nucleotides, and comprises a duplexed region; and/or a tracrRNA extension comprising 10-5000 nucleotides in length, or any combination thereof.

In some instances, a kit can comprise a site-directed polypeptide (and/or a nucleic acid encoding the same), wherein the site-directed polypeptide can comprise an amino acid sequence comprising at least 15% amino acid identity to a Cas9 from *S. pyogenes*, and two nucleic acid cleaving domains (i.e., an HNH domain and a RuvC domain); and, a double-guide nucleic acid-targeting nucleic acid (and/or a nucleic acid encoding the same) comprising 1) a first nucleic acid molecule comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides, and at least 3 unpaired nucleotides of a bulge; and 2) a second nucleic acid molecule of the double-guide nucleic acid-targeting nucleic acid can comprise a minimum tracrRNA sequence comprising at least 60% identity to a tracrRNA from a prokaryote (e.g., *S. pyogenes*) or phage over 6 contiguous nucleotides and wherein the minimum tracrRNA sequence has a length from 5-30 nucleotides and at least 1 unpaired nucleotide of a bulge, wherein the 1 unpaired nucleotide of the bulge is located in the same bulge as the 3 unpaired nucleotides of the minimum CRISPR repeat; a 3' tracrRNA that comprises at least 60% identity to a tracrRNA from a prokaryote (e.g., *S. pyogenes*) or phage over 6 contiguous nucleotides and wherein the 3' tracrRNA comprises a length from 10-20 nucleotides, and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

In some instances, a kit can comprise a site-directed polypeptide (and/or a nucleic acid encoding the same), wherein the site-directed polypeptide can comprise an amino acid sequence comprising at least 15% amino acid identity to a Cas9 from *S. pyogenes* and, two nucleic acid cleaving domains (i.e., an HNH domain and a RuvC domain); and, a nucleic acid-targeting nucleic acid (and/or a nucleic acid encoding the same) comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., *S. pyogenes*) or phage over 6, 7, or 8 contiguous nucleotides and wherein the minimum CRISPR repeat has a length from 5-30 nucleotides; a minimum tracrRNA sequence comprising at least 60% identity to a tracrRNA from a bacterium (e.g., *S. pyogenes*) over 6, 7, or 8 contiguous nucleotides and wherein the minimum tracrRNA sequence has a length from 5-30 nucleotides; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., *S. pyogenes*) or phage over 6, 7, or 8 contiguous nucleotides and wherein the 3' tracrRNA comprises a length from 10-20 nucleotides, and comprises a duplexed region; and/or a tracrRNA extension comprising 10-5000 nucleotides in length, or any combination thereof. This nucleic acid-targeting nucleic acid can be referred to as a single guide nucleic acid-targeting nucleic acid.

In some instances, a kit can comprise a site-directed polypeptide (and/or a nucleic acid encoding the same), wherein the site-directed polypeptide can comprise an amino acid sequence comprising at least 15% amino acid identity to a Cas9 from *S. pyogenes*, and two nucleic acid cleaving domains (i.e., an HNH domain and a RuvC domain); and, a nucleic acid-targeting nucleic acid (and/or a nucleic acid encoding the same) can comprising a spacer extension sequence from 10-5000 nucleotides in length; a spacer sequence of 12-30 nucleotides in length, wherein the spacer is at least 50% complementary to a target nucleic acid; a duplex comprising 1) a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides, 2) a minimum tracrRNA sequence comprising at least 60% identity to a tracrRNA from a bacterium (e.g., *S. pyogenes*) over 6 contiguous nucleotides and wherein the minimum tracrRNA sequence has a length from 5-30 nucleotides, and 3) a bulge wherein the bulge comprises at least 3 unpaired nucleotides on the minimum CRISPR repeat strand of the duplex and at least 1 unpaired nucleotide on the minimum tracrRNA sequence strand of the duplex; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., *S. pyogenes*) or phage over 6 contiguous nucleotides, wherein the 3' tracrRNA comprises a length from 10-20 nucleotides and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

In some instances, a kit can comprise a site-directed polypeptide (and/or a nucleic acid encoding the same), wherein the site-directed polypeptide comprises an amino acid sequence comprising at least 15% amino acid identity to a Cas9 from *S. pyogenes*, two nucleic acid cleaving domains (i.e., an HNH domain and a RuvC domain), and a linker linking the site-directed polypeptide to a non-native sequence; and a double-guide nucleic acid-targeting nucleic acid (and/or a nucleic acid encoding the same) comprising 1) a first nucleic acid molecule comprising a spacer extension sequence from 10-5000 nucleotides in length; a spacer sequence of 12-30 nucleotides in length, wherein the spacer is at least 50% complementary to a target nucleic acid; and a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides; and 2) a second nucleic acid molecule of the double-guide nucleic acid-targeting nucleic acid can comprise a minimum tracrRNA sequence comprising at least 60% identity to a tracrRNA from a prokaryote (e.g., *S. pyogenes*) or phage over 6 contiguous nucleotides and wherein the minimum tracrRNA sequence has a length from 5-30 nucleotides; a 3' tracrRNA that comprises at least 60% identity to a tracrRNA from a bacterium (e.g., *S. pyogenes*) over 6 contiguous nucleotides and wherein the 3' tracrRNA comprises a length from 10-20 nucleotides, and comprises a duplexed region; and/or a tracrRNA extension comprising 10-5000 nucleotides in length, or any combination thereof.

In some instances, a kit can comprise a site-directed polypeptide (and/or a nucleic acid encoding the same), wherein the site-directed polypeptide comprises an amino acid sequence comprising at least 15% amino acid identity to a Cas9 from *S. pyogenes*, two nucleic acid cleaving domains (i.e., an HNH domain and a RuvC domain), and a linker linking the site-directed polypeptide to a non-native sequence; and a double-guide nucleic acid-targeting nucleic acid (and/or a nucleic acid encoding the same) comprising 1) a first nucleic acid molecule comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides, and at least 3 unpaired nucleotides of a bulge; and 2) a second nucleic acid molecule of the double-guide nucleic acid-targeting nucleic acid can comprise a minimum tracrRNA sequence comprising at least 60% identity to a tracrRNA from a prokaryote (e.g., *S. pyogenes*) or phage over 6 contiguous nucleotides and wherein the minimum tracrRNA sequence has a length from 5-30 nucleotides and at least 1 unpaired nucleotide of a bulge, wherein the 1 unpaired nucleotide of the bulge is located in the same bulge as the 3 unpaired nucleotides of the minimum CRISPR repeat; a 3' tracrRNA that comprises at least 60% identity to a tracrRNA from a prokaryote (e.g., *S. pyogenes*) or phage over 6 contiguous nucleotides and wherein the 3' tracrRNA comprises a length from 10-20 nucleotides, and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

In some instances, a kit can comprise a site-directed polypeptide (and/or a nucleic acid encoding the same), wherein the site-directed polypeptide comprises an amino acid sequence comprising at least 15% amino acid identity to a Cas9 from *S. pyogenes*, two nucleic acid cleaving domains (i.e., an HNH domain and a RuvC domain), and a linker linking the site-directed polypeptide to a non-native sequence; and a nucleic acid-targeting nucleic acid (and/or a nucleic acid encoding the same) comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., *S. pyogenes*) or phage over 6, 7, or 8 contiguous nucleotides and wherein the minimum CRISPR repeat has a length from 5-30 nucleotides; a minimum tracrRNA sequence comprising at least 60% identity to a tracrRNA from a bacterium (e.g., *S. pyogenes*) over 6, 7, or 8 contiguous nucleotides and wherein the minimum tracrRNA sequence has a length from 5-30 nucleotides; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., *S. pyogenes*) or phage over 6, 7, or 8 contiguous nucleotides and wherein the 3' tracrRNA comprises a length from 10-20 nucleotides, and comprises a duplexed region; and/or a tracrRNA extension comprising 10-5000 nucleotides in length, or any combination thereof. This nucleic acid-targeting nucleic acid can be referred to as a single guide nucleic acid-targeting nucleic acid.

In some instances, a kit can comprise a site-directed polypeptide (and/or a nucleic acid encoding the same), wherein the site-directed polypeptide comprises an amino acid sequence comprising at least 15% amino acid identity to a Cas9 from *S. pyogenes*, two nucleic acid cleaving domains (i.e., an HNH domain and a RuvC domain), and a linker linking the site-directed polypeptide to a non-native sequence; and nucleic acid-targeting nucleic acid (and/or a nucleic acid encoding the same) comprising a spacer extension sequence from 10-5000 nucleotides in length; a spacer sequence of 12-30 nucleotides in length, wherein the spacer is at least 50% complementary to a target nucleic acid; a duplex comprising 1) a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides, 2) a minimum tracrRNA sequence comprising at least 60% identity to a tracrRNA from a bacterium (e.g., *S. pyogenes*) over 6 contiguous nucleotides and wherein the minimum tracrRNA sequence has a length from 5-30 nucleotides, and 3) a bulge wherein the bulge comprises at least 3 unpaired nucleotides on the minimum CRISPR repeat strand of the duplex and at least 1 unpaired nucleotide on the minimum tracrRNA sequence strand of the duplex; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., *S. pyogenes*) or phage over 6 contiguous nucleotides, wherein the 3' tracrRNA comprises a length from 10-20 nucleotides and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

In some instances, a kit can comprise a site-directed polypeptide (and/or a nucleic acid encoding the same), wherein the site-directed polypeptide comprises at least 15% amino acid identity to a Cas9 from *S. pyogenes*, two nucleic acid cleaving domains (i.e., an HNH domain and a RuvC domain), wherein the site-directed polypeptide comprises a mutation in one or both of the nucleic acid cleaving domains that reduces the cleaving activity of the nuclease domains by at least 50%; and a double-guide nucleic acid-targeting nucleic acid (and/or a nucleic acid encoding the same) comprising 1) a first nucleic acid molecule comprising a spacer extension sequence from 10-5000 nucleotides in length; a spacer sequence of 12-30 nucleotides in length, wherein the spacer is at least 50% complementary to a target nucleic acid; and a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides; and 2) a second nucleic acid molecule of the double-guide nucleic acid-targeting nucleic acid can comprise a minimum tracrRNA sequence comprising at least 60% identity to a tracrRNA from a prokaryote (e.g., *S. pyogenes*) or phage over 6 contiguous nucleotides and wherein the minimum tracrRNA sequence has a length from 5-30 nucleotides; a 3' tracrRNA that comprises at least 60% identity to a tracrRNA from a bacterium (e.g., *S. pyogenes*) over 6 contiguous nucleotides and wherein the 3' tracrRNA comprises a length from 10-20 nucleotides, and comprises a duplexed region; and/or a tracrRNA extension comprising 10-5000 nucleotides in length, or any combination thereof.

In some instances, a kit can comprise a site-directed polypeptide (and/or a nucleic acid encoding the same), wherein the site-directed polypeptide comprises at least 15% amino acid identity to a Cas9 from *S. pyogenes*, two nucleic acid cleaving domains (i.e., an HNH domain and a RuvC domain), wherein the site-directed polypeptide comprises a mutation in one or both of the nucleic acid cleaving domains that reduces the cleaving activity of the nuclease domains by at least 50%; and a double-guide nucleic acid-targeting nucleic acid (and/or a nucleic acid encoding the same) comprising 1) a first nucleic acid molecule comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides, and at least 3 unpaired nucleotides of a bulge; and 2) a second nucleic acid molecule of the double-guide nucleic acid-targeting nucleic acid can comprise a minimum tracrRNA sequence comprising at least 60% identity to a tracrRNA from a prokaryote (e.g., *S. pyogenes*) or phage over 6 contiguous nucleotides and wherein the minimum tracrRNA sequence has a length from 5-30 nucleotides and at least 1 unpaired nucleotide of a bulge, wherein the 1 unpaired nucleotide of the bulge is located in the same bulge as the 3 unpaired nucleotides of the minimum CRISPR repeat; a 3' tracrRNA that comprises at least 60% identity to a tracrRNA from a prokaryote (e.g., *S. pyogenes*) or phage over 6 contiguous nucleotides and wherein the 3' tracrRNA comprises a length from 10-20 nucleotides, and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

In some instances, a kit can comprise a site-directed polypeptide (and/or a nucleic acid encoding the same), wherein the site-directed polypeptide comprises at least 15% amino acid identity to a Cas9 from S. pyogenes, two nucleic acid cleaving domains (i.e., an HNH domain and a RuvC domain), wherein the site-directed polypeptide comprises a mutation in one or both of the nucleic acid cleaving domains that reduces the cleaving activity of the nuclease domains by at least 50%; and nucleic acid-targeting nucleic acid (and/or a nucleic acid encoding the same) comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., S. pyogenes) or phage over 6, 7, or 8 contiguous nucleotides and wherein the minimum CRISPR repeat has a length from 5-30 nucleotides; a minimum tracrRNA sequence comprising at least 60% identity to a tracrRNA from a bacterium (e.g., S. pyogenes) over 6, 7, or 8 contiguous nucleotides and wherein the minimum tracrRNA sequence has a length from 5-30 nucleotides; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., S. pyogenes) or phage over 6, 7, or 8 contiguous nucleotides and wherein the 3' tracrRNA comprises a length from 10-20 nucleotides, and comprises a duplexed region; and/or a tracrRNA extension comprising 10-5000 nucleotides in length, or any combination thereof. This nucleic acid-targeting nucleic acid can be referred to as a single guide nucleic acid-targeting nucleic acid.

In some instances, a kit can comprise a site-directed polypeptide (and/or a nucleic acid encoding the same), wherein the site-directed polypeptide comprises at least 15% amino acid identity to a Cas9 from S. pyogenes, two nucleic acid cleaving domains (i.e., an HNH domain and a RuvC domain), wherein the site-directed polypeptide comprises a mutation in one or both of the nucleic acid cleaving domains that reduces the cleaving activity of the nuclease domains by at least 50%; and nucleic acid-targeting nucleic acid (and/or a nucleic acid encoding the same) comprising a spacer extension sequence from 10-5000 nucleotides in length; a spacer sequence of 12-30 nucleotides in length, wherein the spacer is at least 50% complementary to a target nucleic acid; a duplex comprising 1) a minimum CRISPR repeat comprising at least 60% identity to a crRNA from a prokaryote (e.g., S. pyogenes) or phage over 6 contiguous nucleotides and wherein the minimum CRISPR repeat has a length from 5-30 nucleotides, 2) a minimum tracrRNA sequence comprising at least 60% identity to a tracrRNA from a bacterium (e.g., S. pyogenes) over 6 contiguous nucleotides and wherein the minimum tracrRNA sequence has a length from 5-30 nucleotides, and 3) a bulge wherein the bulge comprises at least 3 unpaired nucleotides on the minimum CRISPR repeat strand of the duplex and at least 1 unpaired nucleotide on the minimum tracrRNA sequence strand of the duplex; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., S. pyogenes) or phage over 6 contiguous nucleotides, wherein the 3' tracrRNA comprises a length from 10-20 nucleotides and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

In some instances, a kit can comprise a site-directed polypeptide (and/or a nucleic acid encoding the same), wherein the site-directed polypeptide comprises at least 15% amino acid identity to a Cas9 from S. pyogenes, two nucleic acid cleaving domains (i.e., an HNH domain and a RuvC domain), wherein the site-directed polypeptide comprises a mutation in one or both of the nucleic acid cleaving domains that reduces the cleaving activity of the nuclease domains by at least 50%; and a double-guide nucleic acid-targeting nucleic acid (and/or a nucleic acid encoding the same) comprising 1) a first nucleic acid molecule comprising a spacer extension sequence from 10-5000 nucleotides in length; a spacer sequence of 12-30 nucleotides in length, wherein the spacer is at least 50% complementary to a target nucleic acid; and a minimum CRISPR repeat comprising at least 60% identity to a crRNA from a prokaryote (e.g., S. pyogenes) or phage over 6 contiguous nucleotides and wherein the minimum CRISPR repeat has a length from 5-30 nucleotides; and 2) a second nucleic acid molecule of the double-guide nucleic acid-targeting nucleic acid can comprise a minimum tracrRNA sequence comprising at least 60% identity to a tracrRNA from a prokaryote (e.g., S. pyogenes) or phage over 6 contiguous nucleotides and wherein the minimum tracrRNA sequence has a length from 5-30 nucleotides; a 3' tracrRNA that comprises at least 60% identity to a tracrRNA from a bacterium (e.g., S. pyogenes) over 6 contiguous nucleotides and wherein the 3' tracrRNA comprises a length from 10-20 nucleotides, and comprises a duplexed region; and/or a tracrRNA extension comprising 10-5000 nucleotides in length, or any combination thereof.

In some instances, a kit can comprise a site-directed polypeptide (and/or a nucleic acid encoding the same), wherein the site-directed polypeptide comprises at least 15% amino acid identity to a Cas9 from S. pyogenes, two nucleic acid cleaving domains (i.e., an HNH domain and a RuvC domain), wherein the site-directed polypeptide comprises a mutation in one or both of the nucleic acid cleaving domains that reduces the cleaving activity of the nuclease domains by at least 50%; and a double-guide nucleic acid-targeting nucleic acid (and/or a nucleic acid encoding the same) comprising 1) a first nucleic acid molecule comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., S. pyogenes) or phage over 6 contiguous nucleotides and wherein the minimum CRISPR repeat has a length from 5-30 nucleotides, and at least 3 unpaired nucleotides of a bulge; and 2) a second nucleic acid molecule of the double-guide nucleic acid-targeting nucleic acid can comprise a minimum tracrRNA sequence comprising at least 60% identity to a tracrRNA from a prokaryote (e.g., S. pyogenes) or phage over 6 contiguous nucleotides and wherein the minimum tracrRNA sequence has a length from 5-30 nucleotides and at least 1 unpaired nucleotide of a bulge, wherein the 1 unpaired nucleotide of the bulge is located in the same bulge as the 3 unpaired nucleotides of the minimum CRISPR repeat; a 3' tracrRNA that comprises at least 60% identity to a tracrRNA from a prokaryote (e.g., *S. pyogenes*) or phage over 6 contiguous nucleotides and wherein the 3' tracrRNA comprises a length from 10-20 nucleotides, and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

In some instances, a kit can comprise a site-directed polypeptide (and/or a nucleic acid encoding the same), wherein the site-directed polypeptide comprises at least 15% amino acid identity to a Cas9 from *S. pyogenes*, two nucleic acid cleaving domains (i.e., an HNH domain and a RuvC domain), wherein the site-directed polypeptide comprises a mutation in one or both of the nucleic acid cleaving domains that reduces the cleaving activity of the nuclease domains by at least 50%; and nucleic acid-targeting nucleic acid (and/or a nucleic acid encoding the same) comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., *S. pyogenes*) or phage over 6, 7, or 8 contiguous nucleotides and wherein the minimum CRISPR repeat has a length from 5-30 nucleotides; a minimum tracrRNA sequence comprising at least 60% identity to a tracrRNA from a bacterium (e.g., *S. pyogenes*) over 6, 7, or 8 contiguous nucleotides and wherein the minimum tracrRNA sequence has a length from 5-30 nucleotides; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., *S. pyogenes*) or phage over 6, 7, or 8 contiguous nucleotides and wherein the 3' tracrRNA comprises a length from 10-20 nucleotides, and comprises a duplexed region; and/or a tracrRNA extension comprising 10-5000 nucleotides in length, or any combination thereof. This nucleic acid-targeting nucleic acid can be referred to as a single guide nucleic acid-targeting nucleic acid.

In some instances, a kit can comprise a site-directed polypeptide (and/or a nucleic acid encoding the same), wherein the site-directed polypeptide comprises at least 15% amino acid identity to a Cas9 from *S. pyogenes*, two nucleic acid cleaving domains (i.e., an HNH domain and a RuvC domain), wherein the site-directed polypeptide comprises a mutation in one or both of the nucleic acid cleaving domains that reduces the cleaving activity of the nuclease domains by at least 50%; and a nucleic acid-targeting nucleic acid (and/or a nucleic acid encoding the same) comprising a spacer extension sequence from 10-5000 nucleotides in length; a spacer sequence of 12-30 nucleotides in length, wherein the spacer is at least 50% complementary to a target nucleic acid; a duplex comprising 1) a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides, 2) a minimum tracrRNA sequence comprising at least 60% identity to a tracrRNA from a bacterium (e.g., *S. pyogenes*) over 6 contiguous nucleotides and wherein the minimum tracrRNA sequence has a length from 5-30 nucleotides, and 3) a bulge wherein the bulge comprises at least 3 unpaired nucleotides on the minimum CRISPR repeat strand of the duplex and at least 1 unpaired nucleotide on the minimum tracrRNA sequence strand of the duplex; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., *S. pyogenes*) or phage over 6 contiguous nucleotides, wherein the 3' tracrRNA comprises a length from 10-20 nucleotides and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

In some instances, a kit can comprise a site-directed polypeptide (and/or a nucleic acid encoding the same), wherein the site-directed polypeptide comprises at least 15% amino acid identity to a Cas9 from *S. pyogenes*, two nucleic acid cleaving domains (i.e., an HNH domain and a RuvC domain), wherein the site-directed polypeptide comprises a mutation in one or both of the nucleic acid cleaving domains that reduces the cleaving activity of the nuclease domains by at least 50%; and a double-guide nucleic acid-targeting nucleic acid (and/or a nucleic acid encoding the same) comprising 1) a first nucleic acid molecule comprising a spacer extension sequence from 10-5000 nucleotides in length; a spacer sequence of 12-30 nucleotides in length, wherein the spacer is at least 50% complementary to a target nucleic acid; and a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides; and 2) a second nucleic acid molecule of the double-guide nucleic acid-targeting nucleic acid can comprise a minimum tracrRNA sequence comprising at least 60% identity to a tracrRNA from a prokaryote (e.g., *S. pyogenes*) or phage over 6 contiguous nucleotides and wherein the minimum tracrRNA sequence has a length from 5-30 nucleotides; a 3' tracrRNA that comprises at least 60% identity to a tracrRNA from a bacterium (e.g., *S. pyogenes*) over 6 contiguous nucleotides and wherein the 3' tracrRNA comprises a length from 10-20 nucleotides, and comprises a duplexed region; and/or a tracrRNA extension comprising 10-5000 nucleotides in length, or any combination thereof.

In some instances, a kit can comprise a site-directed polypeptide (and/or a nucleic acid encoding the same), wherein the site-directed polypeptide comprises at least 15% amino acid identity to a Cas9 from *S. pyogenes*, and two nucleic acid cleaving domains, wherein one or both of the nucleic acid cleaving domains comprise at least 50% amino acid identity to a nuclease domain from Cas9 from *S. pyogenes*; and a double-guide nucleic acid-targeting nucleic acid (and/or a nucleic acid encoding the same) comprising: 1) a first nucleic acid molecule comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., *S. pyogenes*) or phage over 6 contiguous nucleotides and wherein the minimum CRISPR repeat has a length from 5-30 nucleotides, and at least 3 unpaired nucleotides of a bulge; and 2) a second nucleic acid molecule of the double-guide nucleic acid-targeting nucleic acid can comprise a minimum tracrRNA sequence comprising at least 60% identity to a tracrRNA from a prokaryote (e.g., S. pyogenes) or phage over 6 contiguous nucleotides and wherein the minimum tracrRNA sequence has a length from 5-30 nucleotides and at least 1 unpaired nucleotide of a bulge, wherein the 1 unpaired nucleotide of the bulge is located in the same bulge as the 3 unpaired nucleotides of the minimum CRISPR repeat; a 3' tracrRNA that comprises at least 60% identity to a tracrRNA from a prokaryote (e.g., S. pyogenes) or phage over 6 contiguous nucleotides and wherein the 3' tracrRNA comprises a length from 10-20 nucleotides, and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

In some instances, a kit can comprise a site-directed polypeptide (and/or a nucleic acid encoding the same), wherein the site-directed polypeptide comprises at least 15% amino acid identity to a Cas9 from S. pyogenes, and two nucleic acid cleaving domains, wherein one or both of the nucleic acid cleaving domains comprise at least 50% amino acid identity to a nuclease domain from Cas9 from S. pyogenes; and nucleic acid-targeting nucleic acid (and/or a nucleic acid encoding the same) comprising a spacer extension sequence from 10-5000 nucleotides in length; a spacer sequence of 12-30 nucleotides in length, wherein the spacer is at least 50% complementary to a target nucleic acid; a minimum CRISPR repeat comprising at least 60% identity to a crRNA from a prokaryote (e.g., S. pyogenes) or phage over 6, 7, or 8 contiguous nucleotides and wherein the minimum CRISPR repeat has a length from 5-30 nucleotides; a minimum tracrRNA sequence comprising at least 60% identity to a tracrRNA from a bacterium (e.g., S. pyogenes) over 6, 7, or 8 contiguous nucleotides and wherein the minimum tracrRNA sequence has a length from 5-30 nucleotides; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., S. pyogenes) or phage over 6, 7, or 8 contiguous nucleotides and wherein the 3' tracrRNA comprises a length from 10-20 nucleotides, and comprises a duplexed region; and/or a tracrRNA extension comprising 10-5000 nucleotides in length, or any combination thereof. This nucleic acid-targeting nucleic acid can be referred to as a single guide nucleic acid-targeting nucleic acid.

In some instances, a kit can comprise a site-directed polypeptide (and/or a nucleic acid encoding the same), wherein the site-directed polypeptide comprises at least 15% amino acid identity to a Cas9 from S. pyogenes, and two nucleic acid cleaving domains, wherein one or both of the nucleic acid cleaving domains comprise at least 50% amino acid identity to a nuclease domain from Cas9 from S. pyogenes; and a nucleic acid-targeting nucleic acid (and/or a nucleic acid encoding the same) comprising a spacer extension sequence from 10-5000 nucleotides in length; a spacer sequence of 12-30 nucleotides in length, wherein the spacer is at least 50% complementary to a target nucleic acid; a duplex comprising: 1) a minimum CRISPR repeat comprising at least 60% identity to a crRNA from a prokaryote (e.g., S. pyogenes) or phage over 6 contiguous nucleotides and wherein the minimum CRISPR repeat has a length from 5-30 nucleotides, 2) a minimum tracrRNA sequence comprising at least 60% identity to a tracrRNA from a bacterium (e.g., S. pyogenes) over 6 contiguous nucleotides and wherein the minimum tracrRNA sequence has a length from 5-30 nucleotides, and 3) a bulge wherein the bulge comprises at least 3 unpaired nucleotides on the minimum CRISPR repeat strand of the duplex and at least 1 unpaired nucleotide on the minimum tracrRNA sequence strand of the duplex; a linker sequence that links the minimum CRISPR repeat and the minimum tracrRNA and comprises a length from 3-5000 nucleotides; a 3' tracrRNA that comprises at least 60% identity to a tracrRNA from a prokaryote (e.g., S. pyogenes) or phage over 6 contiguous nucleotides, wherein the 3' tracrRNA comprises a length from 10-20 nucleotides and comprises a duplexed region; a P-domain that starts from 1-5 nucleotides downstream of the duplex comprising the minimum CRISPR repeat and the minimum tracrRNA, comprises 1-10 nucleotides, comprises a sequence that can hybridize to a protospacer adjacent motif in a target nucleic acid, can form a hairpin, and is located in the 3' tracrRNA region; and/or a tracrRNA extension comprising 10-5000 nucleotides in length, or any combination thereof.

In some embodiments of any of the above kits, the kit can comprise a single guide nucleic acid-targeting nucleic acid. In some embodiments of any of the above kits, the kit can comprise a double guide nucleic acid-targeting nucleic acid. In some embodiments of any of the above kits, the kit can comprise two or more double guide or single guide nucleic acid-targeting nucleic acids. In some embodiments, a vector may encode for a nucleic acid targeting nucleic acid.

In some embodiments of any of the above kits, the kit can further comprise a donor polynucleotide, or a polynucleotide sequence encoding the donor polynucleotide, to effect the desired genetic modification. Components of a kit can be in separate containers; or can be combined in a single container.

A kit described above further comprise one or more additional reagents, where such additional reagents can be selected from: a buffer, a buffer for introducing the a polypeptide or polynucleotide item of the kit into a cell, a wash buffer, a control reagent, a control vector, a control RNA polynucleotide, a reagent for in vitro production of the polypeptide from DNA, adaptors for sequencing and the like. A buffer can be a stabilization buffer, a reconstituting buffer, or a diluting buffer.

In some instances, a kit can comprise one or more additional reagents specific for plants and/or fungi. One or more additional reagents for plants and/or fungi can include, for example, soil, nutrients, plants, seeds, spores, *Agrobacterium*, T-DNA vector, and a pBINAR vector.

In addition to above-mentioned components, a kit can further include instructions for using the components of the kit to practice the methods. The instructions for practicing the methods are generally recorded on a suitable recording medium. For example, the instructions may be printed on a substrate, such as paper or plastic, etc. The instructions may be present in the kits as a package insert, in the labeling of the container of the kit or components thereof (i.e., associated with the packaging or subpackaging) etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g. via the Internet), can be provided. An example of this embodiment is a kit that includes a web address where the instructions can be viewed and/or from which the instructions can be downloaded. As with the instructions, this means for obtaining the instructions can be recorded on a suitable substrate.

In some embodiments, a kit can comprise a linearized vector. A linearized vector can comprise a plasmid comprising a site-directed polypeptide and/or a nucleic acid-targeting nucleic acid that is linearized (e.g., it is not circular). A linearized vector can be stored in a buffer comprising 10 mM Tris-HCl, pH 8.0 and 1 mM EDTA, pH 8.0. A kit can comprise about 20 microliters of the linearized CRISPR nuclease vector. In some embodiments, a kit can comprise one or more circular vectors.

In some embodiments a kit can comprise an oligonucleotide annealing buffer. An oligonucleotide annealing buffer can be a buffer used to anneal DNA oligos together to generate a double-stranded DNA that encode a nucleic acid-targeting nucleic acid. A oligonucleotide annealing buffer can be at least about, 1, 2, 3, 4, 5, 6, 7, 8, 9, or 10 or more concentrated than the concentration of use. An oligonucleotide annealing buffer can be 10 times more concentrated than the concentration when used. An oligonucleotide annealing buffer can comprise 100 mM Tris-HCl, pH 8.0, 10 mM EDTA, pH 8.0 and 1M NaCl. A kit can comprise 250 microliters of the oligonucleotide annealing buffer.

A kit can comprise DNase-free water. A kit can comprise RNAse-free water. A kit can comprise at least 1.5 milliliters of RNase-free and/or DNAse-free water.

A kit can comprise a ligation buffer. A ligation buffer can be used to ligate oligonucleotides to the linearized CRISPR nuclease vector. A ligation buffer can be at least about, 1, 2, 3, 4, 5, 6, 7, 8, 9, or 10 or more concentrated than the concentration of use. A ligation buffer can be 5 times as concentrated as the concentration of use. A 5× ligation buffer can comprise 250 mM Tris-HCl, pH 7.6, 50 mM MgCl$_2$, 5 mM ATP, 5 mM DTT, and 25% (w/v) polyethylene glycol-8000. A kit can comprise about 80 microliters of a ligation buffer.

A kit can comprise a DNA ligase. A DNA ligase can be used to ligate the oligonucleotides to the linearized CRISPR nuclease vector. A DNA ligase can comprise 10 mM Tris-HCl, pH 7.5, 50 mM KCl, 1 mM DTT, and 50% (v/v) glycerol. A kit can comprise 20 microliters of a DNA ligase.

A kit can comprise a sequencing primer. The sequencing primer can be used to sequence the vector once the oligonucleotides have been ligated into a linearized vector. A sequencing primer can be diluted in Tris-EDTA buffer pH 8.0. A kit can comprise 20 microliters of a sequencing primer.

A kit can comprise a control oligonucleotide. A control oligonucleotide can be an oligonucleotide to be ligated into a linearized vector but does not encode for a nucleic acid-targeting nucleic acid. A control oligonucleotide can be diluted in 1× concentration of the oligonucleotide annealing buffer. A kit can comprise 10 microliters of a control oligonucleotide.

In some instances, a kit can comprise a linearized vector comprising a site-directed polypeptide and a nucleic acid-targeting nucleic acid, an oligonucleotide annealing buffer, DNAse/RNAse free water, a ligation buffer, a ligase enzyme, a sequencing primer and a control oligonucleotide, or any combination thereof.

Pharmaceutical Compositions

Molecules, such as a nucleic acid-targeting nucleic acid of the disclosure as described herein, a polynucleotide encoding a nucleic acid-targeting nucleic acid, a site-directed polypeptide of the disclosure, a polynucleotide encoding a site-directed polypeptide, an effector protein, a polynucleotide encoding an effector protein, a multiplexed genetic targeting agent, a polynucleotide encoding a multiplexed genetic targeting agent, a donor polynucleotide, a tandem fusion protein, a polynucleotide encoding a tandem fusion protein, a reporter element, a genetic element of interest, a component of a split system and/or any nucleic acid or proteinaceous molecule necessary to carry out the embodiments of the methods of the disclosure, can be formulated in a pharmaceutical composition.

A pharmaceutical composition can comprise a combination of any molecules described herein with other chemical components, such as carriers, stabilizers, diluents, dispersing agents, suspending agents, thickening agents, and/or excipients. The pharmaceutical composition can facilitate administration of the molecule to an organism. Pharmaceutical compositions can be administered in therapeutically-effective amounts as pharmaceutical compositions by various forms and routes including, for example, intravenous, subcutaneous, intramuscular, oral, rectal, aerosol, parenteral, ophthalmic, pulmonary, transdermal, vaginal, otic, nasal, and topical administration.

A pharmaceutical composition can be administered in a local or systemic manner, for example, via injection of the molecule directly into an organ, optionally in a depot or sustained release formulation. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated readily by combining the molecules with pharmaceutically-acceptable carriers or excipients. Such carriers can be used to formulate tablets, powders, pills, dragees, capsules, liquids, gels, syrups, elixirs, slurries, suspensions and the like, for oral ingestion by a subject.

Pharmaceutical preparations for oral use can be obtained by mixing one or more solid excipient with one or more of the molecules described herein, optionally grinding the resulting mixture, and processing the mixture of granules, after adding suitable auxiliaries, if desired, to obtain tablets or dragee cores. Cores can be provided with suitable coatings. For this purpose, concentrated sugar solutions can be used, which can contain an excipient such as gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings, for example, for identification or to characterize different combinations of active compound doses.

Pharmaceutical preparations which can be used orally can include push-fit capsules made of gelatin, as well as soft, sealed capsules made of gelatin and a plasticizer, such as glycerol or sorbitol. In some embodiments, the capsule comprises a hard gelatin capsule comprising one or more of pharmaceutical, bovine, and plant gelatins. A gelatin can be alkaline-processed. The push-fit capsules can comprise the active ingredients in admixture with filler such as lactose, binders such as starches, and/or lubricants such as talc or magnesium stearate and, stabilizers. In soft capsules, the molecule can be dissolved or suspended in suitable liquids, such as fatty oils, liquid paraffin, or liquid polyethylene glycols. Stabilizers can be added. All formulations for oral administration are provided in dosages suitable for such administration.

For buccal or sublingual administration, the compositions can be tablets, lozenges, or gels.

Parental injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration can include aqueous solutions of the active compounds in water-soluble form.

Suspensions of molecules can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the molecules to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can comprise solubilizers, stabilizers, tonicity enhancing agents, buffers and preservatives.

Formulations suitable for transdermal administration of the molecules can employ transdermal delivery devices and transdermal delivery patches, and can be lipophilic emulsions or buffered aqueous solutions, dissolved and/or dispersed in a polymer or an adhesive. Such patches can be constructed for continuous, pulsatile, or on demand delivery of molecules. Transdermal delivery can be accomplished by means of iontophoretic patches and the like. Additionally, transdermal patches can provide controlled delivery. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices can be in the form of a bandage comprising a backing member, a reservoir containing compounds and carriers, a rate controlling barrier to deliver the compounds to the skin of the subject at a controlled and predetermined rate over a prolonged period of time, and adhesives to secure the device to the skin.

For administration by inhalation, the molecule can be in a form as an aerosol, a mist, or a powder. Pharmaceutical compositions can be delivered in the form of an aerosol spray presentation from pressurized packs or a nebuliser, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compounds and a suitable powder base such as lactose or starch.

The molecules can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone and PEG. In suppository forms of the compositions, a low-melting wax such as a mixture of fatty acid glycerides or cocoa butter can be used.

In practicing the methods of the disclosure, therapeutically-effective amounts of the compounds described herein can be administered in pharmaceutical compositions to a subject having a disease or condition to be treated. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the molecule into preparations that can be used pharmaceutically. Formulation can be modified depending upon the route of administration chosen. Pharmaceutical compositions comprising a molecule described herein can be manufactured, for example, by mixing, dissolving, granulating, dragee-making, levigating, emulsifying, encapsulating, entrapping, or compression processes.

The pharmaceutical compositions can include at least one pharmaceutically acceptable carrier, diluent, or excipient and molecule described herein as free-base or pharmaceutically-acceptable salt form. The methods and pharmaceutical compositions described herein include the use crystalline forms (also known as polymorphs), and active metabolites of these compounds having the same type of activity.

Methods for the preparation of compositions comprising the compounds described herein can include formulating the molecule with one or more inert, pharmaceutically-acceptable excipients or carriers to form a solid, semi-solid, or liquid composition. Solid compositions can include, for example, powders, tablets, dispersible granules, capsules, cachets, and suppositories. Liquid compositions can include, for example, solutions in which a compound is dissolved, emulsions comprising a compound, or a solution containing liposomes, micelles, or nanoparticles comprising a compound as disclosed herein. Semi-solid compositions can include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms can include feed, food, pellet, lozenge, liquid, elixir, aerosol, inhalant, spray, powder, tablet, pill, capsule, gel, geltab, nanosuspension, nanoparticle, microgel, suppository troches, aqueous or oily suspensions, ointment, patch, lotion, dentifrice, emulsion, creams, drops, dispersible powders or granules, emulsion in hard or soft gel capsules, syrups, phytoceuticals, and nutraceuticals, or any combination thereof.

Non-limiting examples of pharmaceutically-acceptable excipients can include granulating agents, binding agents, lubricating agents, disintegrating agents, sweetening agents, glidants, anti-adherents, anti-static agents, surfactants, antioxidants, gums, coating agents, coloring agents, flavouring agents, coating agents, plasticizers, preservatives, suspending agents, emulsifying agents, plant cellulosic material, and spheronization agents, or any combination thereof.

A composition can be, for example, an immediate release form or a controlled release formulation. An immediate release formulation can be formulated to allow the molecules to act rapidly. Non-limiting examples of immediate release formulations can include readily dissolvable formulations. A controlled release formulation can be a pharmaceutical formulation that has been adapted such that drug release rates and drug release profiles can be matched to physiological and chronotherapeutic requirements or, alternatively, has been formulated to effect release of a drug at a programmed rate. Non-limiting examples of controlled release formulations can include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, granular masses, and the like.

A controlled release formulation can be a delayed release form. A delayed release form can be formulated to delay a molecule's action for an extended period of time. A delayed release form can be formulated to delay the release of an effective dose of one or more molecules, for example, for about 4, about 8, about 12, about 16, or about 24 hours.

A controlled release formulation can be a sustained release form. A sustained release form can be formulated to sustain, for example, the molecule's action over an extended period of time. A sustained release form can be formulated to provide an effective dose of any molecule described herein (e.g., provide a physiologically-effective blood profile) over about 4, about 8, about 12, about 16 or about 24 hours.

Methods of Administration and Treatment Methods

Pharmaceutical compositions containing molecules described herein can be administered for prophylactic and/or therapeutic treatments. In therapeutic applications, the compositions can be administered to a subject already suffering from a disease or condition, in an amount sufficient to cure or at least partially arrest the symptoms of the disease or condition, or to cure, heal, improve, or ameliorate the condition. Amounts effective for this use can vary based on the severity and course of the disease or condition, previous therapy, the subject's health status, weight, and response to the drugs, and the judgment of the treating physician.

Multiple therapeutic agents can be administered in any order or simultaneously. If simultaneously, the multiple therapeutic agents can be provided in a single, unified form, or in multiple forms, for example, as multiple separate pills. The molecules can be packed together or separately, in a single package or in a plurality of packages. One or all of the therapeutic agents can be given in multiple doses. If not simultaneous, the timing between the multiple doses may vary to as much as about a month.

Molecules described herein can be administered before, during, or after the occurrence of a disease or condition, and the timing of administering the composition containing a compound can vary. For example, the pharmaceutical compositions can be used as a prophylactic and can be administered continuously to subjects with a propensity to conditions or diseases in order to prevent the occurrence of the disease or condition. The molecules and pharmaceutical compositions can be administered to a subject during or as soon as possible after the onset of the symptoms. The administration of the molecules can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A molecule can be administered as soon as is practicable after the onset of a disease or condition is detected or suspected, and for a length of time necessary for the treatment of the disease, such as, for example, from about 1 month to about 3 months. The length of treatment can vary for each subject.

A molecule can be packaged into a biological compartment. A biological compartment comprising the molecule can be administered to a subject. Biological compartments can include, but are not limited to, viruses (lentivirus, adenovirus), nanospheres, liposomes, quantum dots, nanoparticles, microparticles, nanocapsules, vesicles, polyethylene glycol particles, hydrogels, and micelles.

For example, a biological compartment can comprise a liposome. A liposome can be a self-assembling structure comprising one or more lipid bilayers, each of which can comprise two monolayers containing oppositely oriented amphipathic lipid molecules. Amphipathic lipids can comprise a polar (hydrophilic) headgroup covalently linked to one or two or more non-polar (hydrophobic) acyl or alkyl chains. Energetically unfavorable contacts between the hydrophobic acyl chains and a surrounding aqueous medium induce amphipathic lipid molecules to arrange themselves such that polar headgroups can be oriented towards the bilayer's surface and acyl chains are oriented towards the interior of the bilayer, effectively shielding the acyl chains from contact with the aqueous environment.

Examples of preferred amphipathic compounds used in liposomes can include phosphoglycerides and sphingolipids, representative examples of which include phosphatidylcholine, phosphatidylethanolamine, phosphatidylserine, phosphatidylinositol, phosphatidic acid, phoasphatidylglycerol, palmitoyloleoyl phosphatidylcholine, lysophosphatidylcholine, lysophosphatidylethanolamine, dimyristoylphosphatidylcholine (DMPC), dipalmitoylphosphatidylcholine (DPPC), dioleoylphosphatidylcholine, di stearoylphosphatidylcholine (DSPC), dilinoleoylphosphatidylcholine and egg sphingomyelin, or any combination thereof.

A biological compartment can comprise a nanoparticle. A nanoparticle can comprise a diameter of from about 40 nanometers to about 1.5 micrometers, from about 50 nanometers to about 1.2 micrometers, from about 60 nanometers to about 1 micrometer, from about 70 nanometers to about 800 nanometers, from about 80 nanometers to about 600 nanometers, from about 90 nanometers to about 400 nanometers, from about 100 nanometers to about 200 nanometers.

In some instances, as the size of the nanoparticle increases, the release rate can be slowed or prolonged and as the size of the nanoparticle decreases, the release rate can be increased.

The amount of albumin in the nanoparticles can range from about 5% to about 85% albumin (v/v), from about 10% to about 80%, from about 15% to about 80%, from about 20% to about 70% albumin (v/v), from about 25% to about 60%, from about 30% to about 50%, or from about 35% to about 40%. The pharmaceutical composition can comprise up to 30, 40, 50, 60, 70 or 80% or more of the nanoparticle. In some instances, the nucleic acid molecules of the disclosure can be bound to the surface of the nanoparticle.

A biological compartment can comprise a virus. The virus can be a delivery system for the pharmaceutical compositions of the disclosure. Exemplary viruses can include lentivirus, retrovirus, adenovirus, herpes simplex virus I or II, parvovirus, reticuloendotheliosis virus, and adeno-associated virus (AAV). Pharmaceutical compositions of the disclosure can be delivered to a cell using a virus. The virus can infect and transduce the cell in vivo, ex vivo, or in vitro. In ex vivo and in vitro delivery, the transduced cells can be administered to a subject in need of therapy.

Pharmaceutical compositions can be packaged into viral delivery systems. For example, the compositions can be packaged into virions by a HSV-1 helper virus-free packaging system.

Viral delivery systems (e.g., viruses comprising the pharmaceutical compositions of the disclosure) can be administered by direct injection, stereotaxic injection, intracerebroventricularly, by minipump infusion systems, by convection, catheters, intravenous, parenteral, intraperitoneal, and/or subcutaenous injection, to a cell, tissue, or organ of a subject in need. In some instances, cells can be transduced in vitro or ex vivo with viral delivery systems. The transduced cells can be administered to a subject having a disease.

For example, a stem cell can be transduced with a viral delivery system comprising a pharmaceutical composition and the stem cell can be implanted in the patient to treat a disease. In some instances, the dose of transduced cells given to a subject can be about $1 \times 10^5$ cells/kg, about $5 \times 10^5$ cells/kg, about $1 \times 10^6$ cells/kg, about $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, about $1 \times 10^7$ cells/kg, about $5 \times 10^7$ cells/kg, about $1 \times 10^8$ cells/kg, or more in one single dose.

Pharmaceutical compositions in biological compartments can be used to treat inflammatory diseases such as arthritis, cancers, such as, for example, bone cancer, breast cancer, skin cancer, prostate cancer, liver cancer, lung cancer, throat cancer and kidney cancer, bacterial infections, to treat nerve damage, lung, liver and kidney diseases, eye treatment, spinal cord injuries, heart disease, arterial disease.

Introduction of the biological compartments into cells can occur by viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

Dosage

Pharmaceutical compositions described herein can be in unit dosage forms suitable for single administration of precise dosages. In unit dosage form, the formulation can be divided into unit doses containing appropriate quantities of one or more compounds. The unit dosage can be in the form of a package containing discrete quantities of the formulation. Non-limiting examples can include packaged tablets or capsules, and powders in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A molecule described herein can be present in a composition in a range of from about 1 mg to about 2000 mg; from about 5 mg to about 1000 mg, from about 10 mg to about 25 mg to 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A molecule described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

A molecule (e.g., site-directed polypeptide, nucleic acid-targeting nucleic acid and/or complex of a site-directed polypeptide and a nucleic acid-targeting nucleic acid) described herein can be present in a composition that provides at least 0.1, 0.5, 1, 1.5, 2, 2.5 3, 3.5, 4, 4.5, 5, 5.5, 6, 6.5, 10 or more units of activity/mg molecule. In some embodiments, the total number of units of activity of the molecule delivered to a subject is at least 25,000, 30,000, 35,000, 40,000, 45,000, 50,000, 60,000, 70,000, 80,000, 90,000, 110,000, 120,000, 130,000, 140,000, 150,000, 160,000, 170,000, 180,000, 190,000, 200,000, 210,000, 220,000, 230,000, or 250,000 or more units. In some embodiments, the total number of units of activity of the molecule delivered to a subject is at most 25,000, 30,000, 35,000, 40,000, 45,000, 50,000, 60,000, 70,000, 80,000, 90,000, 110,000, 120,000, 130,000, 140,000, 150,000, 160,000, 170,000, 180,000, 190,000, 200,000, 210,000, 220,000, 230,000, or 250,000 or more units.

In some embodiments, at least about 10,000 units of activity is delivered to a subject, normalized per 50 kg body weight. In some embodiments, at least about 10,000, 15,000, 25,000, 30,000, 35,000, 40,000, 45,000, 50,000, 60,000, 70,000, 80,000, 90,000, 110,000, 120,000, 130,000, 140,000, 150,000, 160,000, 170,000, 180,000, 190,000, 200,000, 210,000, 220,000, 230,000, or 250,000 units or more of activity of the molecule is delivered to the subject, normalized per 50 kg body weight. In some embodiments, a therapeutically effective dose comprises at least $5 \times 10^5$, $1 \times 10^6$, $2 \times 10^6$, $3 \times 10^6$, 4, $10^6$, $5 \times 10^6$, $6 \times 10^6$, $7 \times 10^6$, $8 \times 10^6$, $9 \times 10^6$, $1 \times 10^7$, $1.1 \times 10^7$, $1.2 \times 10^7$, $1.5 \times 10^7$, $1.6 \times 10^7$, $1.7 \times 10^7$, $1.8 \times 10^7$, $1.9 \times 10^7$, $2 \times 10^7$, $2.1 \times 10^7$, or $3 \times 10^7$ or more units of activity of the molecule. In some embodiments, a therapeutically effective dose comprises at most $5 \times 10^5$, $1 \times 10^6$, $2 \times 10^6$, $3 \times 10^6$, 4, $10^6$, $5 \times 10^6$, $6 \times 10^6$, $7 \times 10^6$, $8 \times 10^6$, $9 \times 10^6$, $1 \times 10^7$, $1.1 \times 10^7$, $1.2 \times 10^7$, $1.5 \times 10^7$, $1.6 \times 10^7$, $1.7 \times 10^7$, $1.8 \times 10^7$, $1.9 \times 10^7$, $2 \times 10^7$, $2.1 \times 10^7$, or $3 \times 10^7$ or more units of activity of the molecule.

In some embodiments, a therapeutically effective dose is at least about 10,000, 15,000, 20,000, 22,000, 24,000, 25,000, 30,000, 40,000, 50,000, 60,000, 70,000, 80,000, 90,000, 100,000, 125,000, 150,000, 200,000, or 500,000 units/kg body weight. In some embodiments, a therapeutically effective dose is at most about 10,000, 15,000, 20,000, 22,000, 24,000, 25,000, 30,000, 40,000, 50,000, 60,000, 70,000, 80,000, 90,000, 100,000, 125,000, 150,000, 200,000, or 500,000 units/kg body weight.

In some embodiments, the activity of the molecule delivered to a subject is at least 10,000, 11,000, 12,000, 13,000, 14,000, 20,000, 21,000, 22,000, 23,000, 24,000, 25,000, 26,000, 27,000, 28,000, 30,000, 32,000, 34,000, 35,000, 36,000, 37,000, 40,000, 45,000, or 50,000 or more U/mg of molecule. In some embodiments, the activity of the molecule delivered to a subject is at most 10,000, 11,000, 12,000, 13,000, 14,000, 20,000, 21,000, 22,000, 23,000, 24,000, 25,000, 26,000, 27,000, 28,000, 30,000, 32,000, 34,000, 35,000, 36,000, 37,000, 40,000, 45,000, or 50,000 or more U/mg of molecule.

Pharmacokinetic and Pharmacodynamic Measurements

Pharmacokinetic and pharmacodynamic data can be obtained by various experimental techniques. Appropriate pharmacokinetic and pharmacodynamic profile components describing a particular composition can vary due to variations in drug metabolism in human subjects. Pharmacokinetic and pharmacodynamic profiles can be based on the determination of the mean parameters of a group of subjects. The group of subjects includes any reasonable number of subjects suitable for determining a representative mean, for example, 5 subjects, 10 subjects, 15 subjects, 20 subjects, 25 subjects, 30 subjects, 35 subjects, or more. The mean can be determined by calculating the average of all subject's measurements for each parameter measured. A dose can be modulated to achieve a desired pharmacokinetic or pharmacodynamics profile, such as a desired or effective blood profile, as described herein.

The pharmacokinetic parameters can be any parameters suitable for describing a molecule. For example, the $C_{max}$ can be, for example, not less than about 25 ng/mL; not less than about 50 ng/mL; not less than about 75 ng/mL; not less than about 100 ng/mL; not less than about 200 ng/mL; not less than about 300 ng/mL; not less than about 400 ng/mL; not less than about 500 ng/mL; not less than about 600 ng/mL; not less than about 700 ng/mL; not less than about 800 ng/mL; not less than about 900 ng/mL; not less than about 1000 ng/mL; not less than about 1250 ng/mL; not less than about 1500 ng/mL; not less than about 1750 ng/mL; not less than about 2000 ng/mL; or any other $C_{max}$ appropriate for describing a pharmacokinetic profile of a molecule described herein.

The $T_{max}$ of a molecule described herein can be, for example, not greater than about 0.5 hours, not greater than about 1 hours, not greater than about 1.5 hours, not greater than about 2 hours, not greater than about 2.5 hours, not greater than about 3 hours, not greater than about 3.5 hours, not greater than about 4 hours, not greater than about 4.5 hours, not greater than about 5 hours, or any other $T_{max}$ appropriate for describing a pharmacokinetic profile of a molecule described herein.

The $AUC_{(0-inf)}$ of a molecule described herein can be, for example, not less than about 50 ng·hr/mL, not less than about 100 ng/hr/mL, not less than about 150 ng/hr/mL, not less than about 200 ng·hr/mL, not less than about 250 ng/hr/mL, not less than about 300 ng/hr/mL, not less than about 350 ng/hr/mL, not less than about 400 ng/hr/mL, not less than about 450 ng/hr/mL, not less than about 500 ng/hr/mL, not less than about 600 ng/hr/mL, not less than about 700 ng/hr/mL, not less than about 800 ng/hr/mL, not less than about 900 ng/hr/mL, not less than about 1000 ng·hr/mL, not less than about 1250 ng/hr/mL, not less than about 1500 ng/hr/mL, not less than about 1750 ng/hr/mL, not less than about 2000 ng/hr/mL, not less than about 2500 ng/hr/mL, not less than about 3000 ng/hr/mL, not less than about 3500 ng/hr/mL, not less than about 4000 ng/hr/mL, not less than about 5000 ng/hr/mL, not less than about 6000 ng/hr/mL, not less than about 7000 ng/hr/mL, not less than about 8000 ng/hr/mL, not less than about 9000 ng/hr/mL, not less than about 10,000 ng/hr/mL, or any other $AUC_{(0-inf)}$ appropriate for describing a pharmacokinetic profile of a molecule described herein.

The plasma concentration of a molecule described herein about one hour after administration can be, for example, not less than about 25 ng/mL, not less than about 50 ng/mL, not less than about 75 ng/mL, not less than about 100 ng/mL, not less than about 150 ng/mL, not less than about 200 ng/mL, not less than about 300 ng/mL, not less than about 400 ng/mL, not less than about 500 ng/mL, not less than about 600 ng/mL, not less than about 700 ng/mL, not less than about 800 ng/mL, not less than about 900 ng/mL, not less than about 1000 ng/mL, not less than about 1200 ng/mL, or any other plasma concentration of a molecule described herein.

The pharmacodynamic parameters can be any parameters suitable for describing pharmaceutical compositions of the disclosure. For example, the pharmacodynamic profile can exhibit decreases in factors associated with inflammation after, for example, about 2 hours, about 4 hours, about 8 hours, about 12 hours, or about 24 hours.

Pharmaceutically-Acceptable Salts

The disclosure provides the use of pharmaceutically-acceptable salts of any molecule described herein. Pharmaceutically-acceptable salts can include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt, or any combination thereof.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine, or any combination thereof.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt, or any combination thereof.

Acid addition salts can arise from the addition of an acid to a molecule of the disclosure. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid, or any combination thereof.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate salt, an ethanesulfonate salt, a benzenesulfonate salt, a p-toluenesulfonate salt, a citrate salt, an oxalate salt, or a maleate salt, or any combination thereof.

Engineered Site-Directed Polypeptides

General Overview

The disclosure describes methods, compositions, systems, and/or kits for modifying site-directed polypeptides (e.g., Cas9, Csy4, Cas5, Cash, Argonaut, etc.) and/or related enzymes. Modifications may include any covalent or non-covalent modification to site-directed polypeptides. In some cases, this may include chemical modifications to one or more regions of the site-directed polypeptide. In some cases, modifications may include conservative or non-conservative amino acid substitutions of the site-directed polypeptide. In some cases, modifications may include the addition, deletion or substitution of any portion of the site-directed polypeptide with amino acids, peptides, or domains that are not found in the native site-directed polypeptide. In some cases, one or more non-native domains may be added, deleted or substituted in the site-directed polypeptide. In some cases the site-directed polypeptide may exist as a fusion protein.

In some cases, the present disclosure provides for the engineering of site-directed polypeptides to recognize a desired target nucleic acid sequence with desired enzyme specificity and/or activity. Modifications to a site-directed polypeptide can be performed through protein engineering. Protein engineering can include fusing functional domains to such engineered site-directed polypeptide which can be used to modify the functional state of the overall site-directed polypeptide or the actual target nucleic acid sequence of an endogenous cellular locus. The site-directed polypeptide of the disclosure can be used to regulate endogenous gene expression, both through activation and repression of endogenous gene transcription.

The site-directed polypeptide-fusions can also be linked to other regulatory or functional domains, for example nucleases, transposases or methylases, to modify endogenous chromosomal sequences. In some cases, the site-directed polypeptide may be linked to at least one or more regulatory domains, described herein. Non-limiting examples of regulatory or functional domains include transcription factor repressor or activator domains such as KRAB and VP16, co-repressor and co-activator domains, DNA methyl transferases, histone acetyltransferases, histone deacetylases, and DNA cleavage domains such as the cleavage domain from the endonuclease FokI.

In some instances, one or more specific domains, regions or structural elements of the site-directed polypeptide can be modified together. Modifications to the site-directed polypeptide may occur, but are not limited to site-directed polypeptide elements such as regions that recognize or bind to the spacer-adjacent motif (PAM), and/or regions that bind or recognize the nucleic acid-targeting nucleic acid. Such binding or recognition elements may include a conserved bridging helix, highly basic region, N-terminal region, C-terminal region, RuvC motifs (e.g., RuvC and/or RuvC-like nuclease domains) and one or more nuclease domains, such as HNH and/or HNH-like domains. Modifications may be made to additional domains, structural elements, sequence or amino acids within the site-directed polypeptide.

Modifications to one or more region of the site-directed polypeptide may be performed to alter various properties of the site-directed polypeptide. In some cases, modifications may alter binding recognition for certain nucleic acid target sequences. This may include but is not limited to increasing binding affinity and/or specificity to certain sequences or preferentially targeting of certain target nucleic acid sequences/recognition elements. In some cases, modifications may be used to alter native nuclease function. In some cases, modifications to the site-directed polypeptide may alter PAM specificity, tracrRNA specificity, crRNA specificity, or specificity for additional nucleic acid elements, such as a nucleic acid-targeting nucleic acid.

Described herein are also compositions and methods including fusion proteins comprising a site-directed polypeptide (e.g., Cas9) and one or more domains or regions engineered for genomic editing (e.g., cleaving of genes; alteration of genes, for example by cleavage followed by insertion (physical insertion or insertion via homology-directed repair) of an exogenous sequence and/or cleavage followed by NHEJ; partial or complete inactivation of one or more genes; generation of alleles with altered functional states of endogenous genes, insertion of regulatory elements; etc.) and alterations of the genome which are carried into the germline. Also disclosed are methods of making and using these compositions (i.e. reagents), for example to edit (i.e. alter) one or more genes in a target cell. Thus, the methods and compositions described herein provide highly efficient methods for targeted gene alteration (e.g., knock-in) and/or knockout (partial or complete) of one or more genes and/or for randomized mutation of the sequence of any target allele, and, therefore, allow for the generation of animal models of human diseases. One skilled in the art will recognize that although the term "genome engineering" or "genomic editing" is often used to describe the methods herein, the methods and compositions described herein can also be used to alter any target nucleic acid that may not be strictly speaking in the genome of a cell (e.g. can be used on a synthetic nucleic acid, a plasmid, a vector, a viral nucleic acid, a recombinant nucleic acid, etc.).

The methods and compositions described herein allow for novel therapeutic applications, (e.g., prevention and/or treatment of: genetic diseases, cancer, fungal, protozoal, bacterial, and viral infection, ischemia, vascular disease, arthritis, immunological disorders, etc.), novel diagnostics (e.g. prediction and/or diagnosis of a condition) as well as providing for research tools (e.g. kits, functional genomics assays, and generating engineered cell lines and animal models for research and drug screening), and means for developing plants with altered phenotypes, including but not limited to, increased disease resistance, and altering fruit ripening characteristics, sugar and oil composition, yield, and color. The methods and compositions described herein allow for novel epigenetic studies.

Protein Modifications and Engineering

Amino Acid Alterations

Site-directed polypeptides, as disclosed herein, can be modified. The modification can comprise modifications to an amino acid of the site-directed polypeptide. The modifications can alter the primary amino acid sequence and/or the secondary, tertiary, and quaternary amino acid structure. In some cases some amino acid sequences of site-directed polypeptide of the invention can be varied without a significant effect on the structure or function of the protein. The type of mutation may be completely unimportant if the alteration occurs in some regions (e.g. a non-critical) region of the protein. In some cases, depending upon the location of the replacement, the mutation may not have a major effect on the biological properties of the resulting variant. For example, properties and functions of the Cas9 variants can be of the same type as wild-type Cas9. In some cases, the mutation can critically impact the structure and/or function of the site-directed polypeptide.

The location of where to modify a site-directed polypeptide (e.g., a Cas9 variant) can be determined using sequence and/or structural alignment. Sequence alignment can identify regions of a polypeptide that similar and/or dissimilar (e.g., conserved, not conserved, hydrophobic, hydrophilic, etc). In some instances, a region in the sequence of interest that is similar to other sequences is suitable for modification. In some instances, a region in the sequence of interest that is dissimilar from other sequences is suitable for modification. For example, sequence alignment can be performed by database search, pairwise alignment, multiple sequence alignment, genomic analysis, motif finding, benchmarking, and/or programs such as BLAST, CS-BLAST, HHPRED, psi-BLAST, LALIGN, PyMOL, and SEQALN. Structural alignment can be performed by programs such as Dali, PHYRE, Chimera, COOT, O, and PyMOL. Alignment can be performed by database search, pairwise alignment, multiple sequence alignment, genomic analysis, motif finding, or bench marking, or any combination thereof.

A site-directed polypeptide can be modified to increase binding specificity to a nucleic acid-targeting nucleic acid and/or a target nucleic acid. A site-directed polypeptide can be modified to increase binding to specific regions of a nucleic acid-targeting nucleic acid (e.g., the spacer extension, the spacer, the minimum CRISPR repeat, the minimum tracrRNA sequence, the 3' tracrRNA sequence, the tracrRNA extension) and/or a target nucleic acid.

In some cases, the modification can comprise a conservative modification. A conservative amino acid change can involve substitution of one of a family of amino acids which are related in their side chains (e.g., cysteine/serine).

In some cases amino acid changes in the Cas9 protein disclosed herein are non-conservative amino acid changes, (i.e., substitutions of dissimilar charged or uncharged amino acids). A non-conservative amino acid change can involve substitution of one of a family of amino acids which may be unrelated in their side chains or a substitution that alters biological activity of the site-directed polypeptide.

The mutation of amino acids can also change the selectivity of binding to a target nucleic acid. The mutation may result in a change that may comprise a change in the dissociation constant (Kd) of binding between a mutated site-directed polypeptide and a target nucleic acid. The change in Kd of binding between a mutated site-directed polypeptide and a target nucleic acid may be more than 1000-fold, more than 500-fold, more than 100-fold, more than 50-fold, more than 25-fold, more than 10-fold, more than 5-fold, more than 4-fold, more than 3-fold, more than 2-fold higher or lower than the Kd of binding of binding between a non-mutated site-directed polypeptide and a target nucleic acid. The change in Kd of binding between a mutated site-directed polypeptide and a target nucleic acid may be less than 1000-fold, less than 500-fold, less than 100-fold, less than 50-fold, less than 25-fold, less than 10-fold, less than 5-fold, less than 4-fold, less than 3-fold, less than 2-fold higher or lower than the Kd of binding of binding between a non-mutated site-directed polypeptide and a target nucleic acid.

The mutation may result in a change that may comprise a change in $K_d$ of binding between a mutated site-directed polypeptide and a PAM motif. The change in $K_d$ of binding between a mutated site-directed polypeptide and a PAM motif may be more than 1000-fold, more than 500-fold, more than 100-fold, more than 50-fold, more than 25-fold, more than 10-fold, more than 5-fold, more than 4-fold, more than 3-fold, more than 2-fold higher or lower than the $K_d$ of binding between a non-mutated site-directed polypeptide and a PAM motif. The change in $K_d$ of binding between a mutated site-directed polypeptide and a PAM motif may be less than 1000-fold, less than 500-fold, less than 100-fold, less than 50-fold, less than 25-fold, less than 10-fold, less than 5-fold, less than 4-fold, less than 3-fold, less than 2-fold higher or lower than the $K_d$ of binding of binding between a non-mutated site-directed polypeptide and a PAM motif.

The mutation may result in a change that may comprise a change in $K_d$ of the binding between a mutated site-directed polypeptide and a nucleic acid-targeting nucleic acid. The change in $K_d$ of binding between a mutated site-directed polypeptide and a nucleic acid-targeting nucleic acid may be more than 1000-fold, more than 500-fold, more than 100-fold, more than 50-fold, more than 25-fold, more than 10-fold, more than 5-fold, more than 4-fold, more than 3-fold, more than 2-fold higher or lower than the $K_d$ of binding between a non-mutated site-directed polypeptide and a nucleic acid-targeting nucleic acid. The change in $K_d$ of binding between a mutated site-directed polypeptide and a nucleic acid-targeting nucleic acid may be less than 1000-fold, less than 500-fold, less than 100-fold, less than 50-fold, less than 25-fold, less than 10-fold, less than 5-fold, less than 4-fold, less than 3-fold, less than 2-fold higher or lower than the $K_d$ of binding between a non-mutated site-directed polypeptide and a nucleic acid-targeting nucleic acid.

The mutation of a site-directed polypeptide can also change the kinetics of the enzymatic action of the site-directed polypeptide. The mutation may result in a change that may comprise a change in the $K_m$ of the mutated site-directed polypeptide. The change in $K_m$ of the mutated site-directed polypeptide may be more than 1000-fold, more than 500-fold, more than 100-fold, more than 50-fold, more than 25-fold, more than 10-fold, more than 5-fold, more than 4-fold, more than 3-fold, more than 2-fold higher or lower than the $K_m$ of a non-mutated site-directed polypeptide. The change in $K_m$ of a mutated site-directed polypeptide may be less than 1000-fold, less than 500-fold, less than 100-fold, less than 50-fold, less than 25-fold, less than 10-fold, less than 5-fold, less than 4-fold, less than 3-fold, less than 2-fold higher or lower than the $K_m$ of a non-mutated site-directed polypeptide.

The mutation of a site-directed polypeptide may result in a change that may comprise a change in the turnover of the site-directed polypeptide. The change in the turnover of the mutated site-directed polypeptide may be more than 1000-fold, more than 500-fold, more than 100-fold, more than 50-fold, more than 25-fold, more than 10-fold, more than 5-fold, more than 4-fold, more than 3-fold, more than 2-fold higher or lower than the turnover of a non-mutated site-directed polypeptide. The change in the turnover of a mutated site-directed polypeptide may be less than 1000-fold, less than 500-fold, less than 100-fold, less than 50-fold, less than 25-fold, less than 10-fold, less than 5-fold, less than 4-fold, less than 3-fold, less than 2-fold higher or lower than the turnover of a non-mutated site-directed polypeptide.

The mutation may result in a change that may comprise a change in the ΔG of the enzymatic action of the site-directed polypeptide. The change in the ΔG of the mutated site-directed polypeptide may be more than 1000-fold, more than 500-fold, more than 100-fold, more than 50-fold, more than 25-fold, more than 10-fold, more than 5-fold, more than 4-fold, more than 3-fold, more than 2-fold higher or lower than the ΔG of a non-mutated site-directed polypeptide. The change in the turnover of a mutated site-directed polypeptide may be less than 1000-fold, less than 500-fold, less than 100-fold, less than 50-fold, less than 25-fold, less than 10-fold, less than 5-fold, less than 4-fold, less than 3-fold, less than 2-fold higher or lower than the ΔG of a non-mutated site-directed polypeptide.

The mutation may result in a change that may comprise a change in the $V_{max}$ of the enzymatic action of the site-directed polypeptide. The change in the $V_{max}$ of the mutated site-directed polypeptide may be more than 1000-fold, more than 500-fold, more than 100-fold, more than 50-fold, more than 25-fold, more than 10-fold, more than 5-fold, more than 4-fold, more than 3-fold, more than 2-fold higher or lower than the $V_{max}$ of a non-mutated site-directed polypeptide. The change in the turnover of a mutated site-directed polypeptide may be less than 1000-fold, less than 500-fold, less than 100-fold, less than 50-fold, less than 25-fold, less than 10-fold, less than 5-fold, less than 4-fold, less than 3-fold, less than 2-fold higher or lower than the $V_{max}$ of a non-mutated site-directed polypeptide.

The mutation may result in a change that may comprise a change in any kinetic parameter of the site-directed polypeptide. The mutation may result in in a change that may comprise a change in any thermodynamic parameter of the site-directed polypeptide. The mutation may result in in a change that may comprise a change in the surface charge, surface area buried, and/or folding kinetics of the site-directed polypeptide and/or enzymatic action of the site-directed polypeptide.

Amino acids in the site-directed polypeptide of the present invention that are essential for function can be identified by methods such as site-directed mutagenesis, alanine-scanning mutagenesis, protein structure analysis, nuclear magnetic resonance, photoaffinity labeling, and electron tomography, high-throughput screening, ELISAs, biochemical assays, binding assays, cleavage assays (e.g., Surveyor assay), reporter assays, and the like.

Other amino acid alterations may also include amino acids with glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue. In some cases mutated site-directed polypeptides may also include allelic variants and species variants.

Truncations of regions which do not affect functional activity of the Cas9 proteins may be engineered. Truncations of regions which do affect functional activity of the Cas9 protein may be engineered. A truncation may comprise a truncation of less than 5, less than 10, less than 15, less than 20, less than 25, less than 30, less than 35, less than 40, less than 45, less than 50, less than 60, less than 70, less than 80, less than 90, less than 100 or more amino acids. A truncation may comprise a truncation of more than 5, more than 10, more than 15, more than 20, more than 25, more than 30, more than 35, more than 40, more than 45, more than 50, more than 60, more than 70, more than 80, more than 90, more than 100 or more amino acids. A truncation may comprise truncation of about 5%, 10%, 15%, 20%, 25%, 30%, 35%, 40%, 45%, 50%, 55%, 60%, 65%, 70%, 75%, 80%, 85%, 90%, 95% or 100% of the site-directed polypeptide.

Deletions of regions which do not affect functional activity of the Cas9 proteins may be engineered. Deletions of regions which do affect functional activity of the Cas9 protein may be engineered. A deletion can comprise a deletion of less than 5, less than 10, less than 15, less than 20, less than 25, less than 30, less than 35, less than 40, less than 45, less than 50, less than 60, less than 70, less than 80, less than 90, less than 100 or more amino acids. A deletion may comprise a deletion of more than 5, more than 10, more than 15, more than 20, more than 25, more than 30, more than 35, more than 40, more than 45, more than 50, more than 60, more than 70, more than 80, more than 90, more than 100 or more amino acids. A deletion may comprise deletion of about 5%, 10%, 15%, 20%, 25%, 30%, 35%, 40%, 45%, 50%, 55%, 60%, 65%, 70%, 75%, 80%, 85%, 90%, 95% or 100% of the site-directed polypeptide. A deletion can occur at the N-terminus, the C-terminus, or at any region in the polypeptide chain.

Screens

The disclosure provides for methods for engineering a site-directed polypeptide. Screens can be used to engineering a site-directed polypeptide. For example, a screen can be set up to screen for the effect of mutations in a region of the site-directed polypeptide. For example, a screen can be set up to test modifications of the highly basic patch on the affinity for RNA structure (e.g., nucleic acid-targeting nucleic acid structure), or processing capability (e.g., target nucleic acid cleavage). Exemplary screening methods can include but are not limited to, cell sorting methods, mRNA display, phage display, and directed evolution.

Fusions

In some instances, the site-directed polypeptide is modified such that it comprises a non-native sequence (i.e. the polypeptide has a modification that alters it from the allele or sequence it was derived from) (e.g., the polypeptide can be referred to as a fusion). The non-native sequence can also include one or more additional proteins, protein domains, subdomains or polypeptides. For example, Cas9 may be fused with any suitable additional nonnative nucleic acid binding proteins and/or domains, including but not limited to transcription factor domains, nuclease domains, nucleic acid polymerizing domains. The non-native sequence can comprise a sequence of Cas9 and/or a Cas9 homologue.

The non-native sequence can confer new functions to the fusion protein. These functions can include for example, DNA cleavage, DNA methylation, DNA damage, DNA repair, modification of a target polypeptide associated with target DNA (e.g., a histone, a DNA-binding protein, etc.), leading to, for example, histone methylation, histone acetylation, histone ubiquitination, and the like. Other functions conferred by a fusion protein can include methyltransferase activity, demethylase activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, remodelling activity, protease activity, oxidoreductase activity, transferase activity, hydrolase activity, lyase activity, isomerase activity, synthase activity, synthetase activity, and demyristoylation activity, or any combination thereof.

Modifications to the Bridge Helix

In some cases, the bridge helix region of Cas9 may be modified (e.g., to alter PAM specificity). In some cases, the bridge helix may share homology with the bridge helix identified in the Cas9 protein of *S. pyogenes* (residues 551-566). In some cases, the bridge helix may share at least 5%, 10%, 15%, 20%, 25%, 30%, 35%, 40%, 45%, 50%, 55%, 60%, 65%, 70%, 75%, 80%, 85%, 90%, 95%, 98%, 99%, or 100% homology with residues 551-556 of *S. pyogenes* Cas9 bridge helix. In some cases, the bridge helix may share at most 5%, 10%, 15%, 20%, 25%, 30%, 35%, 40%, 45%, 50%, 55%, 60%, 65%, 70%, 75%, 80%, 85%, 90%, 95%, 98%, 99%, or 100% homology with residues 551-556 of *S. pyogenes* Cas9 bridge helix.

In some cases, modifications to the bridge helix may include but are not limited to individual amino acid modifications, as described herein. In some cases, modification to the bridge helix may include but are not limited to insertions, deletions or substitution of individual amino acids, or polypeptides, such as other protein elements (e.g domains, structural motifs, proteins).

Modifications may include modifications to at least 1, 2, 3, 4, 5, 6, 7, 8, 9, 10, 11, 12, 13, 14, 15, 16, 17, 18, 19, 20 or more amino acids of the bridge helix. Modifications may include modifications to at most 1, 2, 3, 4, 5, 6, 7, 8, 9, 10, 11, 12, 13, 14, 15, 16, 17, 18, 19, 20 or more amino acids of the bridge helix. Modifications may also include at least 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the bridge helix. Modifications may also include at most 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the bridge helix.

In some cases, modifications to site-directed polypeptide bridge helix sequences may include particular polypeptide structural motifs, including but not limited to alpha helix, beta strand, beta sheet, 310-helix, pi-helix, polyproline I motif, polyproline II motif, polyproline III motif, beta turn, alpha-turn-alpha, or helix kinks or hinges. For example, substitutions to the site-directed polypeptide bridge helix may include substitution or addition with one or more proline amino acid residues. Insertion of proline residues may introduce kinks in the bridge helix which may alter the binding specificity of the bridge helix for the PAM. In another example, substitution or addition may include one or more glycine amino acid residues. Insertion or substitution of glycine residues may introduce increased flexibility in the bridge helix, or "hinges" which may also alter the binding specificity of the bridge helix for the PAM. Altering binding specificity may or may not affect enzymatic activity of the Cas9 protein.

In some cases, modifications to site-directed polypeptide bridge helix sequences may include deletion of at least 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the bridge helix. In some cases, modifications to site-directed polypeptide bridge helix sequences may include deletion of at most 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the bridge helix.

In some cases, modifications to site-directed polypeptide bridge helix sequences may include addition or substitution of at least 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of a homologous site-directed polypeptide bridge helix. In some cases, modifications to site-directed polypeptide bridge helix sequences may include addition or substitution of at most 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of a homologous site-directed polypeptide bridge helix.

For example, nonnative Cas9 bridge helices may be derived from any suitable organism. In some cases, the Cas9 protein and bridge helix may be derived from prokaryotic organisms, including but not limited to archea, bacteria, protists (e.g., *E. coli, S. pyogenes, S. thermophilus, P. furiosus,* and etc.).

For example, the bridge helix of the *S. pyogenes* Cas9 enzyme may be substituted or inserted with the bridge helix, or fragment thereof, derived from another Cas9 enzyme from a different species.

In some instances, a site-directed polypeptide comprises an amino acid sequence comprising at least 15% amino acid identity to a Cas9 from *S. pyogenes*, two nucleic acid-cleaving domains (i.e., a HNH domain and RuvC domain), and a modified bridge helix.

Modifications to the Highly Basic Patch

PAM binding and specificity may also be affected by additional regions within the Cas9 protein. In some cases, a highly basic patch or region, comprising basic amino acid residues adjacent to the PAM binding site, may also be modified to alter PAM specificity. In some cases, the highly basic patch or region may share homology with the highly basic patch identified in the Cas9 of *S. pyogenes* contained within N-terminal region, or amino acid residues 1-270 of the *S. pyogenes* Cas9. In some cases, the highly basic patch may share at least 5%, 10%, 15%, 20%, 25%, 30%, 35%, 40%, 45%, 50%, 55%, 60%, 65%, 70%, 75%, 80%, 85%, 90%, 95%, 98%, 99%, or 100% homology with the *S. pyogenes* Cas9 highly basic patch. In some cases, the highly basic patch may share at most 5%, 10%, 15%, 20%, 25%, 30%, 35%, 40%, 45%, 50%, 55%, 60%, 65%, 70%, 75%, 80%, 85%, 90%, 95%, 98%, 99%, or 100% homology with the *S. pyogenes* Cas9 highly basic patch.

In some cases, modifications to the highly basic patch may include but are not limited to individual amino acid modifications, as described herein. In some cases, modification to the highly basic patch may include but are not limited to insertions, deletions or substitution of individual amino acids, or polypeptides, such as other protein elements (e.g domains, structural motifs, proteins).

Modifications may include modifications to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acids of the highly basic patch. Modifications may include modifications to at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acids of the highly basic patch. Modifications may also include at least 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the highly basic patch. Modifications may also include at most 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the highly basic patch.

In some cases, modifications to highly basic patch sequence of the site-directed polypeptide may include particular polypeptide structural motifs, including but not limited to alpha helix, beta strand, beta sheet, 310-helix, pi-helix, polyproline I motif, polyproline II motif, polyproline III motif, beta turn, alpha-turn-alpha, or helix kinks or hinges.

Substitutions to the highly basic patch of the site-directed polypeptide may include substitution or addition with one or more acidic amino acid residues. Insertion of acidic residues may decrease the overall basic charge of this area of the site-directed polypeptide and may alter the binding specificity of the highly basic patch for the PAM. In another example, substitution or addition may include one or more basic amino acid residues. Insertion or substitution of basic residues may increase the charge area or ionic strength of interaction between the polypeptide and the nucleic acid and may also alter the binding specificity of the highly basic patch for the PAM. Altering binding specificity may or may not affect enzymatic activity of the site-directed polypeptide.

In some cases, modifications to the site-directed polypeptide highly basic patch sequences may include deletion of at least 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the highly basic patch. In some cases, modifications to site-directed polypeptide highly basic patch sequences may include deletion of at most 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the highly basic patch.

In some cases, modifications to site-directed polypeptide highly basic patch sequences may include addition or substitution of at least 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of a homologous Cas9 highly basic patch. In some cases, modifications to the site-directed polypeptide highly basic patch sequences may include addition or substitution of at most 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of a homologous Cas9 highly basic patch.

Homologous Cas9 highly basic patch sequences may be derived from any suitable organism. In some cases, the Cas9 protein may be derived from prokaryotic organisms such as archea, bacteria, protists (e.g., *E. coli, S. pyogenes, S. thermophilus, P. furiosus*, and etc.). For example, the highly basic patch of the *S. pyogenes* Cas9 enzyme may be substituted or inserted with the highly basic patch, or fragment thereof, derived from a Cas9 of another species.

In some instances, a site-directed polypeptide comprises an amino acid sequence comprising at least 15% amino acid identity to a Cas9 from *S. pyogenes*, two nucleic acid-cleaving domains (i.e., a HNH domain and RuvC domain), and a modified highly basic patch.

Modifications to the HNH Domain

In some cases, the HNH domain in a site-directed polypeptide may be modified to alter PAM specificity. In some cases, the HNH domain may share homology with the HNH domain identified in the C terminal domain of the Cas9 protein of *S. pyogenes* (residues 860-1100). In some cases, the HNH domain may share at least 5%, 10%, 15%, 20%, 25%, 30%, 35%, 40%, 45%, 50%, 55%, 60%, 65%, 70%, 75%, 80%, 85%, 90%, 95%, 98%, 99%, or 100% homology with residues 551-556 of *S. pyogenes* Cas9 HNH domain. In some cases, the HNH domain may share at most 5%, 10%, 15%, 20%, 25%, 30%, 35%, 40%, 45%, 50%, 55%, 60%, 65%, 70%, 75%, 80%, 85%, 90%, 95%, 98%, 99%, or 100% homology with residues 860-1100 of *S. pyogenes* Cas9 HNH domain.

In some cases, modifications to the HNH domain may include but are not limited to individual amino acid modifications, as described herein. In some cases, modification to the HNH domain may include but are not limited to insertions, deletions or substitution of individual amino acids, or polypeptides, such as other protein elements (e.g domains, structural motifs, proteins).

Modifications may include modifications to at least 1, 2, 3, 4, 5, 6, 7, 8, 9, 10, 11, 12, 13, 14, 15, 16, 17, 18, 19, 20 or more amino acids of the HNH domain. Modifications may include modifications to at most 1, 2, 3, 4, 5, 6, 7, 8, 9, 10, 11, 12, 13, 14, 15, 16, 17, 18, 19, 20 or more amino acids of the HNH domain. Modifications may also include at least 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the HNH domain. Modifications may also include at most 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the HNH domain.

In some cases, modifications to site-directed polypeptide HNH domain sequences may include particular polypeptide structural motifs, including but not limited to alpha helix, beta strand, beta sheet, 310-helix, pi-helix, polyproline I motif, polyproline II motif, polyproline III motif, beta turn, alpha-turn-alpha, or helix kinks or hinges.

Substitutions to the HNH domain of the site-directed polypeptide may include substitution or addition with one or more amino acid residues. In some cases, the HNH domain may be replaced or fused with other suitable nucleic acid binding domains. A nucleic acid-binding domain can comprise RNA. There can be a single nucleic acid-binding domain. Examples of nucleic acid-binding domains can include, but are not limited to, a helix-turn-helix domain, a zinc finger domain, a leucine zipper (bZIP) domain, a winged helix domain, a winged helix turn helix domain, a helix-loop-helix domain, a HMG-box domain, a Wor3 domain, an immunoglobulin domain, a B3 domain, a TALE domain, a Zinc-finger domain, a RNA-recognition motif domain, a double-stranded RNA-binding motif domain, a double-stranded nucleic acid binding domain, a single-stranded nucleic acid binding domains, a KH domain, a PUF domain, a RGG box domain, a DEAD/DEAH box domain, a PAZ domain, a Piwi domain, and a cold-shock domain, a RNAseH domain, a HNH domain, a RuvC-like domain, a RAMP domain, a Cas5 domain, a Cas6 domain.

In some cases, modifications to site-directed polypeptide HNH domain sequences may include deletion of at least 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the HNH domain. In some cases, modifications to site-directed polypeptide HNH domain sequences may include deletion of at most 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the HNH domain.

In some cases, modifications to site-directed polypeptide HNH domain sequences may include addition or substitution of at least 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of a homologous Cas9 HNH domain. In some cases, modifications to site-directed polypeptide HNH domain sequences may include addition or substitution of at most 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of a homologous Cas9 HNH domain.

Homologous Cas9 HNH domains may be derived from any suitable organism. In some cases, the Cas9 protein may be derived from prokaryotic organisms such as archea, bacteria, protists (e.g., E. coli, S. pyogenes, S. thermophilus, P. furiosus, and etc.). For example, the HNH domain of the S. pyogenes Cas9 enzyme may be substituted or inserted with the HNH domain, or fragment thereof, derived from a Cas9 enzyme of another species. In some cases, at least one homologous Cas9 HNH domain may be inserted into the HNH domain. In some cases, the at least one homologous Cas9 HNH domain may form an HNH domain array, comprising at least two HNH domains. In some cases, an HNH domain array can comprise at least one Cas9 HNH domain and at least one second HNH domain.

In some instances, the modification to the HNH or HNH-like domain can comprise insertion of the same or similar HNH or HNH-like domain in tandem (e.g., adjacent) to the HNH domain of Cas9. The HNH or HNH-like domain can be inserted N-terminal and/or C-terminal of the HNH domain in Cas9. Insertion of one or more HNH or HNH-like domains in Cas9 can be useful in extending specificity in a target nucleic acid. Insertion of one or more HNH or HNH-like domains in Cas9 can be useful in duplicating specificity in a target nucleic acid. For example, insertion of one or more HNH or HNH-like domains can configure Cas9 to recognize a longer stretch of target nucleic acid, recognize a different RNA-DNA hybrid, and/or recognize a target nucleic acid with higher binding affinity.

In some instances, a site-directed polypeptide comprises an amino acid sequence comprising at least 15% amino acid identity to a Cas9 from S. pyogenes, two nucleic acid-cleaving domains (i.e., a HNH domain and RuvC domain), and a modified HNH domain.

Modifications to the RuvC or RuvC-Like Domains

In some cases, the RuvC or RuvC-like domain in the site-directed polypeptide may be modified to alter PAM specificity. In some cases, the RuvC or RuvC-like domain may share homology with the RuvC or RuvC-like domain identified in the Cas9 protein of S. pyogenes (residues 1-270). In some cases, the RuvC or RuvC-like domain may share at least 5%, 10%, 15%, 20%, 25%, 30%, 35%, 40%, 45%, 50%, 55%, 60%, 65%, 70%, 75%, 80%, 85%, 90%, 95%, 98%, 99%, or 100% homology with residues 551-556 of S. pyogenes Cas9 RuvC or RuvC-like domain. In some cases, the RuvC or RuvC-like domain may share at most 5%, 10%, 15%, 20%, 25%, 30%, 35%, 40%, 45%, 50%, 55%, 60%, 65%, 70%, 75%, 80%, 85%, 90%, 95%, 98%, 99%, or 100% homology with residues 1-270 of S. pyogenes Cas9 RuvC or RuvC-like domain.

In some cases, modifications to the RuvC or RuvC-like domain may include but are not limited to individual amino acid modifications, as described herein. In some cases, modification to the RuvC or RuvC-like domain may include but are not limited to insertions, deletions or substitution of individual amino acids, or polypeptides, such as other protein elements (e.g domains, structural motifs, proteins).

Modifications may include modifications to at least 1, 2, 3, 4, 5, 6, 7, 8, 9, 10, 11, 12, 13, 14, 15, 16, 17, 18, 19, 20 or more amino acids of the RuvC or RuvC-like domain. Modifications may include modifications to at most 1, 2, 3, 4, 5, 6, 7, 8, 9, 10, 11, 12, 13, 14, 15, 16, 17, 18, 19, 20 or more amino acids of the RuvC or RuvC-like domain. Modifications may also include at least 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the RuvC or RuvC-like domain. Modifications may also include at most 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the RuvC or RuvC-like domain.

In some cases, modifications to site-directed polypeptide RuvC or RuvC-like domain sequences may include particular polypeptide structural motifs, including but not limited to alpha helix, beta strand, beta sheet, 310-helix, pi-helix, polyproline I motif, polyproline II motif, polyproline III motif, beta turn, alpha-turn-alpha, or helix kinks or hinges.

Substitutions to the site-directed polypeptide RuvC or RuvC-like domain may include substitution or addition with one or more amino acid residues. In some cases, the RuvC or RuvC-like domain may be replaced or fused with other suitable nucleic acid binding domains. A nucleic acid-binding domain can comprise RNA. There can be a single nucleic acid-binding domain. Examples of nucleic acid-binding domains can include, but are not limited to, a helix-turn-helix domain, a zinc finger domain, a leucine zipper (bZIP) domain, a winged helix domain, a winged helix turn helix domain, a helix-loop-helix domain, a HMG-box domain, a Wor3 domain, an immunoglobulin domain, a B3 domain, a TALE domain, a Zinc-finger domain, a RNA-recognition motif domain, a double-stranded RNA-binding motif domain, a double-stranded nucleic acid binding domain, a single-stranded nucleic acid binding domains, a KH domain, a PUF domain, a RGG box domain, a DEAD/DEAH box domain, a PAZ domain, a Piwi domain, a cold-shock domain, a RNAseH domain, a HNH domain, a RuvC-like domain, a RAMP domain, a Cas5 domain, and a Cas6 domain.

In some cases, modifications to site-directed polypeptide RuvC or RuvC-like domain sequences may include deletion of at least 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the RuvC or RuvC-like domain. In some cases, modifications to site-directed polypeptide RuvC or RuvC-like domain sequences may include deletion of at most 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the RuvC or RuvC-like domain.

In some cases, modifications to site-directed polypeptide RuvC or RuvC-like domain sequences may include addition or substitution of at least 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of a homologous Cas9 RuvC or RuvC-like domain. In some cases, modifications to the site-directed polypeptide RuvC or RuvC-like domain sequences may include addition or substitution of at most 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of a homologous Cas9 RuvC or RuvC-like domain.

Homologous Cas9 RuvC or RuvC-like domains may be derived from any suitable organism. In some cases, the Cas9 protein may be derived from prokaryotic organisms such as archea, bacteria, protists (e.g., *E. coli, S. pyogenes, S. thermophilus, P. furiosus* and etc.). For example, the RuvC or RuvC-like domain of the *S. pyogenes* Cas9 enzyme may be substituted or inserted with the RuvC or RuvC-like domain, or fragment thereof, derived from another Cas9 enzyme, such as one from another species.

In some instances, the modification to the RuvC or RuvC-like domain can comprise insertion of the same or similar RuvC or RuvC-like domain in tandem (e.g., adjacent) to the RuvC or RuvC-like domain of Cas9. The RuvC or RuvC-like domain can be inserted N-terminal and/or C-terminal of the RuvC or RuvC-like domain in Cas9. Insertion of one or more RuvC or RuvC-like domains in Cas9 can be useful in extending specificity in a target nucleic acid. Insertion of one or more RuvC or RuvC-like domains in Cas9 can be useful in duplicating specificity in a target nucleic acid. For example, insertion of one or more RuvC or RuvC-like domains can configure Cas9 to recognize a longer stretch of target nucleic acid, recognize a different RNA-DNA hybrid, and/or recognize a target nucleic acid with higher binding affinity.

In some instances, a site-directed polypeptide comprises an amino acid sequence comprising at least 15% amino acid identity to a Cas9 from *S. pyogenes*, two nucleic acid-cleaving domains (i.e., a HNH domain and RuvC domain), and a modified RuvC domain.

Modifications to Cas9 Domains Containing RNA Polymerase Homologous Regions

In some cases, a site-directed polypeptide may be share homology with RNA polymerase. Both proteins may share similar functionally homologous domains that are involved in catalysis of binding and manipulation of nucleic acids. For example, RNA polymerase can comprise regions of polypeptide sequence that is involved in binding RNA-DNA duplexes. In some cases, these regions may aid in melting the duplex.

In some cases, a site-directed polypeptide may also comprise certain regions that affect the binding specificity of the enzyme for nucleic acids. In some cases, these regions may share either sequence or functional homology with domains or regions as found in RNA polymerase. In some cases, the basic region of the N-terminus of the site-directed polypeptide may be bind to the tracrRNA and crRNA or a single RNA (sgRNA). In *S. pyogenes*, this may correspond to a region of residues 50-100.

Generally, the present disclosure provides for any suitable modification to this region or adjacent regions. In some cases, the tracrRNA/crRNA binding region (e.g., the nucleic acid-targeting nucleic acid binding region) in the site-directed polypeptide may be modified to alter specificity for the nucleic acid. In some cases, the tracrRNA/crRNA binding region may share homology with the tracrRNA/crRNA binding region identified in the Cas9 protein of *S. pyogenes* (residues 50-100). In some cases, the tracrRNA/crRNA binding region may share at least 5%, 10%, 15%, 20%, 25%, 30%, 35%, 40%, 45%, 50%, 55%, 60%, 65%, 70%, 75%, 80%, 85%, 90%, 95%, 98%, 99%, or 100% homology with residues 50-100 of *S. pyogenes* Cas9 tracrRNA/crRNA binding region. In some cases, the tracrRNA/crRNA binding region may share at most 5%, 10%, 15%, 20%, 25%, 30%, 35%, 40%, 45%, 50%, 55%, 60%, 65%, 70%, 75%, 80%, 85%, 90%, 95%, 98%, 99%, or 100% homology with residues 50-100 of *S. pyogenes* Cas9 tracrRNA/crRNA binding region.

In some cases, modifications to the tracrRNA/crRNA binding region may include but are not limited to individual amino acid modifications, as described herein. In some cases, modification to the tracrRNA/crRNA binding region may include but are not limited to insertions, deletions or substitution of individual amino acids, or polypeptides, such as other protein elements (e.g domains, structural motifs, proteins).

Modifications may include modifications to at least 1, 2, 3, 4, 5, 6, 7, 8, 9, 10, 11, 12, 13, 14, 15, 16, 17, 18, 19, 20 or more amino acids of the tracrRNA/crRNA binding region. Modifications may include modifications to at most 1, 2, 3, 4, 5, 6, 7, 8, 9, 10, 11, 12, 13, 14, 15, 16, 17, 18, 19, 20 or more amino acids of the tracrRNA/crRNA binding region. Modifications may also include at least 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the tracrRNA/crRNA binding region. Modifications may also include at most 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the tracrRNA/crRNA binding region.

In some cases, modifications to the site-directed polypeptide tracrRNA/crRNA binding region sequences may include particular polypeptide structural motifs, including but not limited to alpha helix, beta strand, beta sheet, 310-helix, pi-helix, polyproline I motif, polyproline II motif, polyproline III motif, beta turn, alpha-turn-alpha, or helix kinks or hinges.

For example, substitutions to the site-directed polypeptide tracrRNA/crRNA binding region may include substitution or addition with one or more proteins or fragments thereof. For example, the tracrRNA/crRNA binding region could be substituted with the RNA-binding domain from any of the known RNA-binding Type I, Type II, or Type III CRISPR system member. The tracrRNA/crRNA binding region could be substituted with the RNA-binding domain from any of the known RNA-binding member of the RAMP superfamily. The tracrRNA/crRNA binding region could be substituted with the RNA-binding domain from any of the known RNA-binding member of the Cas7, Cash, Cas5 families. In one example, the tracr RNA requirement may be replaced with the requirement for a 5' hairpin sequence with the spacer sequence placed downstream of the hairpin for DNA recognition.

In some cases, modifications to site-directed polypeptide tracrRNA/crRNA binding region sequences may include deletion of at least 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the tracrRNA/crRNA binding region. In some cases, modifications to site-directed polypeptide tracrRNA/crRNA binding region sequences may include deletion of at most 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of the tracrRNA/crRNA binding region.

In some cases, modifications to site-directed polypeptide tracrRNA/crRNA binding region sequences may include addition or substitution of at least 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of a homologous Cas9 tracrRNA/crRNA binding region. In some cases, modifications to site-directed polypeptide tracrRNA/crRNA binding region sequences may include addition or substitution of at most 1%, 5%, 10%, 15%, 20%, 25%, 30%, 35%, 40%, 45%, 50%, 55%, 60%, 65%, 70%, 75%, 80%, 85%, 90%, 95%, 98%, 99%, or 100% of a homologous Cas9 tracrRNA/crRNA binding region.

Homologous site-directed polypeptide tracrRNA/crRNA binding regions may be derived from any suitable organism. In some cases, the tracrRNA/crRNA binding region may be derived from prokaryotic organisms, including but not limited to archea, bacteria, protists (e.g., *E. coli, S. pyogenes, S. thermophilus, P. furiosus* and etc.). For example, the tracrRNA/crRNA binding region of the *S. pyogenes* Cas9 may be substituted or inserted with the tracrRNA/crRNA binding region, or fragment thereof, derived from another Cas9, such as one derived from another species.

In some instances, a site-directed polypeptide comprises an amino acid sequence comprising at least 15% amino acid identity to a Cas9 from *S. pyogenes*, two nucleic acid-cleaving domains (i.e., a HNH domain and RuvC domain), and a modified polymerase-like domain.

Modifications to Alter PAM Specificity

In some instances, a site-directed polypeptide can recognize a protospacer adjacent motif (PAM). A PAM can be any sequence in a target nucleic acid that is recognized by a site-directed polypeptide and is immediately 3' of the target nucleic acid sequence targeted by the spacer of a nucleic acid-targeting nucleic acid. For example, a PAM can comprise 5'-NGG-3' or 5'-NGGNG-3', 5'-NNAAAAW-3', 5'-NNNNGATT-3', 5'-GNNNCNNA-3', 5'-NNNACA-3' where N is any nucleotide and N is immediately 3' of the target nucleic acid sequence targeted by the spacer sequence.

A site-directed polypeptide can be modified to alter PAM specificity. For example, a site-directed polypeptide can be modified such that prior to the modifying the polypeptide targets a first protospacer adjacent motif and after the modifying the site-directed polypeptide targets a second protospacer adjacent motif. In some instances, altered PAM specificity can comprise a change in binding specificity (e.g., increased binding, decreased binding), and/or a change in the binding constant (e.g., increase Kd, decrease Kd).

A site-directed polypeptide can be modified such that the site-directed polypeptide can recognize a new type of PAM different from the type the wild-type site-directed polypeptide recognizes. For example, a site-directed polypeptide that recognizes the 5'-NGG-3' PAM can be modified such that it can recognize the 5'-NGGNG-3' PAM, 5'-NNAAAAW-3', 5'-NNNNGATT-3', 5'-GNNNCNNA-3', or 5'-NNNACA-3'.

Any region of a site-directed polypeptide can be engineered (e.g., bridge helix, HNH and/or HNH-like domain, RuvC and/or RuvC-like domain, basic patch) to alter PAM specificity according to the methods of the disclosure.

Regions corresponding to residues 445-507, 446-497, 1096-1225, 1105-1138 of a wild-type site-directed polypeptide (e.g., Cas9 from *S. pyogenes*, SEQ ID NO: 8) can be engineered to modify PAM recognition. Engineering of these regions can comprise introducing mutations, replacing with corresponding regions from other Cas9 orthologues, deletions, insertions etc. Regions corresponding to residues 718-757, 22-49, 65-95, 445-507, 446-497, 1096-1225, 1105-1138 can be engineered to modify recognition of the nucleic-acid targeting nucleic acid. Regions corresponding to residues 445-507 and 1105-1138 can be engineered to modify P-domain recognition.

In some instances, a site-directed polypeptide comprises an amino acid sequence comprising at least 15% amino acid identity to a Cas9 from *S. pyogenes*, two nucleic acid-cleaving domains (i.e., a HNH domain and RuvC domain), and a modification, wherein prior to introduction of the modification the site-directed polypeptide is adapted to bind a first PAM and after introduction of the modification, the site-directed polypeptide is adapted to bind to a different PAM.

Modifications to Alter Nucleic Acid-Targeting Nucleic Acid Specificity

In some instances, a site-directed polypeptide can recognize a nucleic acid-targeting nucleic acid. A site-directed polypeptide can be modified to alter a nucleic acid-targeting nucleic acid specificity. For example, a site-directed polypeptide can be modified such that prior to the modifying the polypeptide targets a first a nucleic acid-targeting nucleic acid and after the modifying the site-directed polypeptide targets a second a nucleic acid-targeting nucleic acid. In some instances, altered nucleic acid-targeting nucleic acid specificity can comprise a change in binding specificity (e.g., increased binding, decreased binding), and/or a change in the binding constant (e.g., increase Kd, decrease Kd).

A site-directed polypeptide can be modified such that the site-directed polypeptide can recognize a new type of a nucleic acid-targeting nucleic acid different from the type the wild-type site-directed polypeptide recognizes. Any region of a site-directed polypeptide can be engineered (e.g., bridge helix, HNH and/or HNH-like domain, RuvC and/or RuvC-like domain, basic patch) to alter PAM specificity according to the methods of the disclosure.

In some instances, a site-directed polypeptide comprises an amino acid sequence comprising at least 15% amino acid identity to a Cas9 from *S. pyogenes*, two nucleic acid-cleaving domains (i.e., a HNH domain and RuvC domain), and a modification, wherein prior to introduction of the modification the site-directed polypeptide is adapted to bind a first a nucleic acid-targeting nucleic acid and after introduction of the modification, the site-directed polypeptide is adapted to bind to a different a nucleic acid-targeting nucleic acid.

Modifications to Alter Hybridization Requirements

Insertions

A site-directed polypeptide can be modified to increase binding specificity to a target nucleic acid. A sequence may be inserted into the site-directed polypeptide. In some instances, a HNH and/or HNH-like domain may be inserted in a site-directed polypeptide. The non-native sequence (e.g., HNH and/or HNH-like domain) may originate from any species. The insertion may take place at any location in the site-directed polypeptide. The insertion may occur in tandem (e.g., adjacent) to the native HNH and/or HNH-like domain of the site-directed polypeptide. The inserted HNH and/or HNH-like domain may comprise a mutation. The inserted HNH and/or HNH-like domain may comprise a mutation that reduces the nuclease activity of the domain. In some instances, a RuvC and/or RuvC-like domain may be inserted in a site-directed polypeptide. The insertion may take place at any location in the site-directed polypeptide. The insertion may occur in tandem (e.g., adjacent) to the native RuvC and/or RuvC-like domain of the site-directed polypeptide. The inserted RuvC and/or RuvC-like domain may comprise a mutation. The inserted RuvC and/or RuvC-like domain may comprise a mutation that reduces the nuclease activity of the domain.

A site-directed polypeptide can be modified to increase binding specificity to a nucleic acid-targeting nucleic acid. A sequence may be inserted into the site-directed polypeptide. A HNH and/or HNH-like domain may be inserted in a site-directed polypeptide. The non-native sequence (e.g., HNH and/or HNH-like domain) may originate from any species. The insertion may take place at any location in the site-directed polypeptide. The insertion may occur in tandem (e.g., adjacent) to the native HNH and/or HNH-like domain of the site-directed polypeptide. The inserted HNH and/or HNH-like domain may comprise a mutation. The inserted HNH and/or HNH-like domain may be comprise a mutation that reduces the nuclease activity of the domain. A RuvC and/or RuvC-like domain may be inserted in a site-directed polypeptide. The insertion may take place at any location in the site-directed polypeptide. The insertion may occur in tandem (e.g., adjacent) to the native RuvC and/or RuvC-like domain of the site-directed polypeptide. The inserted RuvC and/or RuvC-like domain may comprise a mutation. The inserted RuvC and/or RuvC-like domain may comprise a mutation that reduces the nuclease activity of the domain.

A site-directed polypeptide can be engineered to comprise a polypeptide domain that can bind to RNA-DNA hybrids (e.g., RNase domain, zinc finger domain). For example, a site-directed polypeptide can be engineered to comprise an RNaseH domain. The inserted RNaseH domain may comprise a mutation. The inserted RNaseH domain may be comprise a mutation that reduces the nuclease activity of the domain.

A site-directed polypeptide can be engineered to comprise a polypeptide domain that can bind to double-stranded DNA (e.g., domains comprising helix-turn-helix motifs, domains comprising leucine zipper motifs, domains comprising helix-loop-helix motifs, domains comprising zinc finger motifs). For example, a site-directed polypeptide can be engineered to comprise a helix-turn-helix motif. Non-limiting exemplary helix-turn-helix motifs include those from dnaB, TetR, MuB, P2R, CysB, BirA, the bacteriophage lambda repressor, Engrailed, Myb, LuxR, MarR, ETS, ZNF10a, Kox-1. The helix-loop-helix motif can be di-helical, tri-helical, tetrahelical, a winged helix-turn-helix, or other modified helix-loop-helix. The inserted domain may be comprise a mutation. The inserted domain may be comprise a mutation that reduces the nuclease activity of the domain.

Compensatory Mutations

A site-directed polypeptide can comprise a mutation and/or be engineered such that it may preferentially bind to a mutated and/or engineered nucleic acid-targeting nucleic acid. Such mutation of a site-directed polypeptide and nucleic acid-targeting nucleic acid pair can be referred to as a compensatory mutation. For example, a site-directed polypeptide can be engineered such that its nuclease domain (e.g., HNH and/or HNH-like, RuvC and/or RuvC-like) is replaced by a nucleic acid binding domain (e.g., Csy4, Cas5, Cas6 nucleic acid binding domain). A site-directed polypeptide can be engineered such that a nucleic acid binding domain (e.g., Csy4, Cas5, Cas6 nucleic acid binding domain) is inserted into the site-directed polypeptide. The resulting site-directed polypeptide can bind to a nucleic acid-targeting nucleic acid that is mutated and/or engineered to comprise a nucleic acid binding domain binding site (e.g., binding site for Csy4, Cas5, Cas6 nucleic acid binding domains). The nucleic acid-targeting nucleic acid can be mutated and/or engineered to comprise a nucleic acid-binding domain binding site in the minimum tracrRNA sequence. The nucleic acid-targeting nucleic acid can be mutated and/or engineered to comprise a nucleic acid binding domain binding site in the 3' tracrRNA sequence. The nucleic acid-targeting nucleic acid can be mutated and/or engineered to comprise a nucleic acid binding domain binding site in the tracrRNA extension.

In some instances, a site-directed polypeptide comprises an amino acid sequence comprising at least 15% amino acid identity to a Cas9 from *S. pyogenes*, two nucleic acid-cleaving domains (i.e., a HNH domain and RuvC domain), and a compensatory mutation, in which the site-directed polypeptide is such that it can bind to an engineered nucleic acid-targeting nucleic acid but not an unmodified nucleic acid-targeting nucleic acid.

Methods to Generate Sticky Ends and Blunt Cuts

In some instances, one or more nickases (i.e., a site-directed polypeptides comprising one substantially inactive nuclease domain) can be used to generate targeted double-stranded cuts in target nucleic acid. Each nickase of the one or more nickases can target one strand of the double-stranded target nucleic acid. In some instances, two nickases can be used to generate a targeted double-stranded cut.

The two nickases can cut the target nucleic acid generating a blunt end cut (wherein the cut sites of the target nucleic acid are the same location on each strand). The two nickases can cut the target nucleic acid at different locations within each strand such that some single-stranded nucleotides remain, thereby generating a sticky end.

Cleavage of target nucleic acid by two modified site-directed polypeptides having nickase activity may be used to incur deletions or insertions of nucleic acid material from a target nucleic acid by cleaving the target nucleic acid and allowing the cell to repair the sequence in the absence of an exogenously provided donor polynucleotide. In some instances, the methods of the disclosure can be used to knock out a gene. If a nucleic acid-targeting nucleic acid and two modified site-directed polypeptides having nickase activity are co-administered to cells with a donor polynucleotide sequence that includes at least a segment with homology to the target nucleic acid, new nucleic acid material may be inserted/copied into the site. Such methods may be used to add, i.e. insert or replace, nucleic acid material to a target nucleic acid (e.g., to "knock in" a nucleic acid that encodes a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, etc.), to modify a nucleic acid sequence (e.g., introduce a mutation), and the like.

Figure 32:
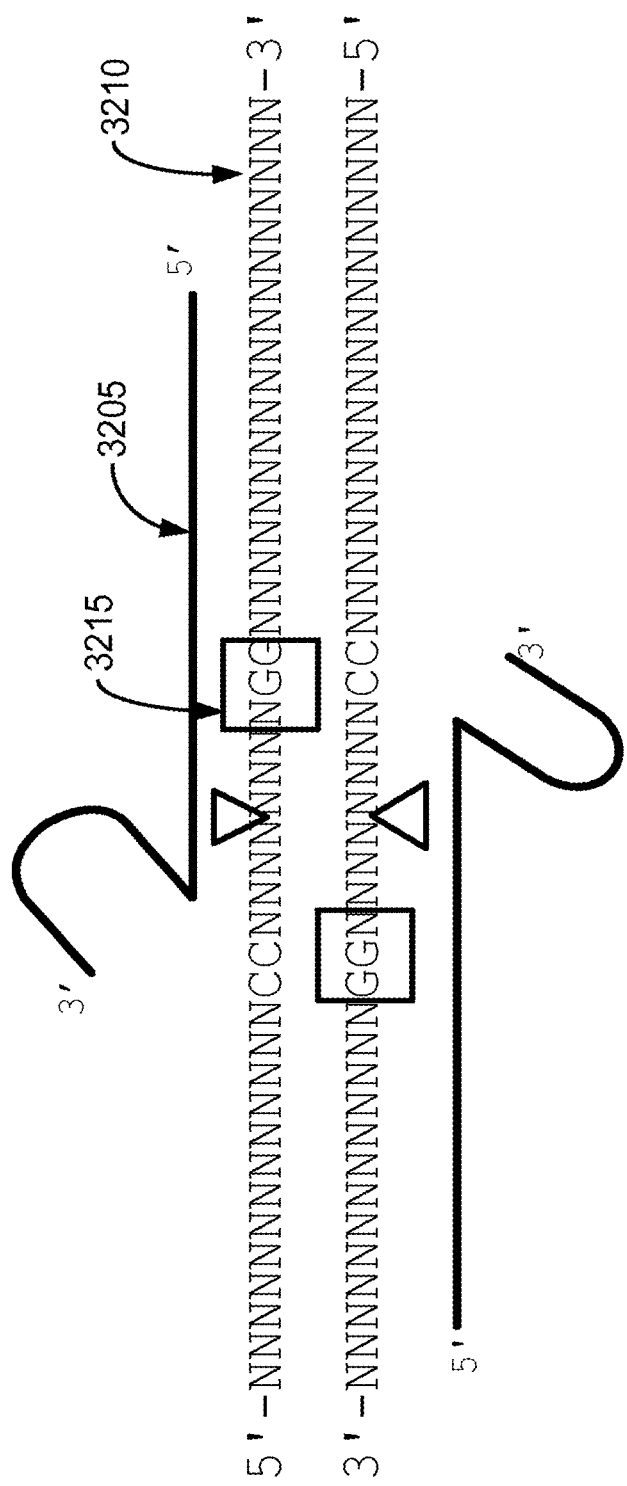
FIG. 32 depicts an exemplary embodiment of two nickases generating a blunt end cut in a target nucleic acid (SEQ ID NO: 1566). The site-directed modifying polypeptides complexed with nucleic acid-targeting nucleic acids are not shown.

FIG. 32 depicts a method for generating blunt ends by nickases. The target nucleic acid duplex 3210 can comprise a plurality of PAM sequences 3215 (boxed), wherein one PAM is on one strand of the target nucleic acid 3210 and one PAM is on the other strand of the target nucleic acid 3210. A nucleic acid-targeting nucleic acid 3205 as part of a complex with the nickase (nickase not shown) can hybridize to the spacer sequence adjacent to the PAM 3215 on each strand of the target nucleic acid 3210. The nickase can cleave one strand of the target nucleic acid 3210. Cleavage is indicated by the triangles. If the PAMs are appropriately spaced the nickases can cut the target nucleic acid in substantially the same place on each strand, thereby resulting in a blunt end. The PAM sequences may be separated by at least about 1, 2, 3, 4, 5, 6, 7, 8, 9, 10, 20, 30, 40, or 50 or more nucleotides. The PAM sequences may be separated by at most about 1, 2, 3, 4, 5, 6, 7, 8, 9, 10, 20, 30, 40, or 50 or more nucleotides. In some instances, the PAMs are spaced by 6 nucleotides (i.e., there are 6 nucleotides in between each PAM). In some instances, the nucleic acid-targeting nucleic acid cleaves about 3 nucleotides 5' of the PAM.

Figure 33:
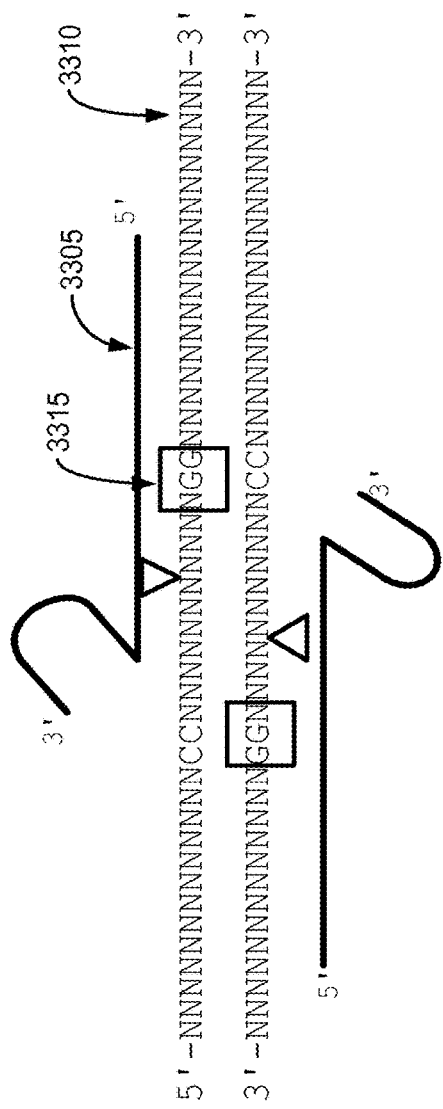
FIG. 33 depicts an exemplary embodiment of staggard cutting of a target nucleic acid (SEQ ID NO: 1566) using two nickases and generating sticky ends. The site-directed modifying polypeptides complexed with nucleic acid-targeting nucleic acids are not shown.
Figure 34:
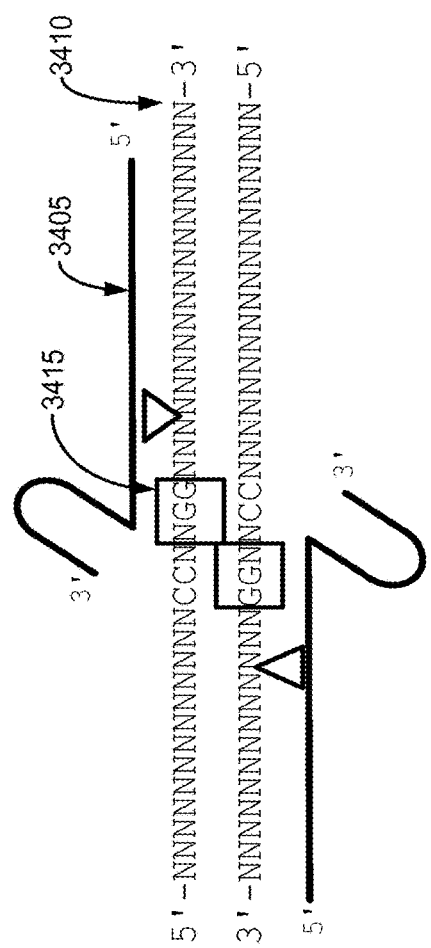
FIG. 34 depicts an exemplary embodiment of staggard cutting of a target nucleic acid (SEQ ID NO: 1567) using two nickases and generating medium-sized sticky ends. The site-directed modifying polypeptides complexed with nucleic acid-targeting nucleic acids are not shown.
Figure 37A:
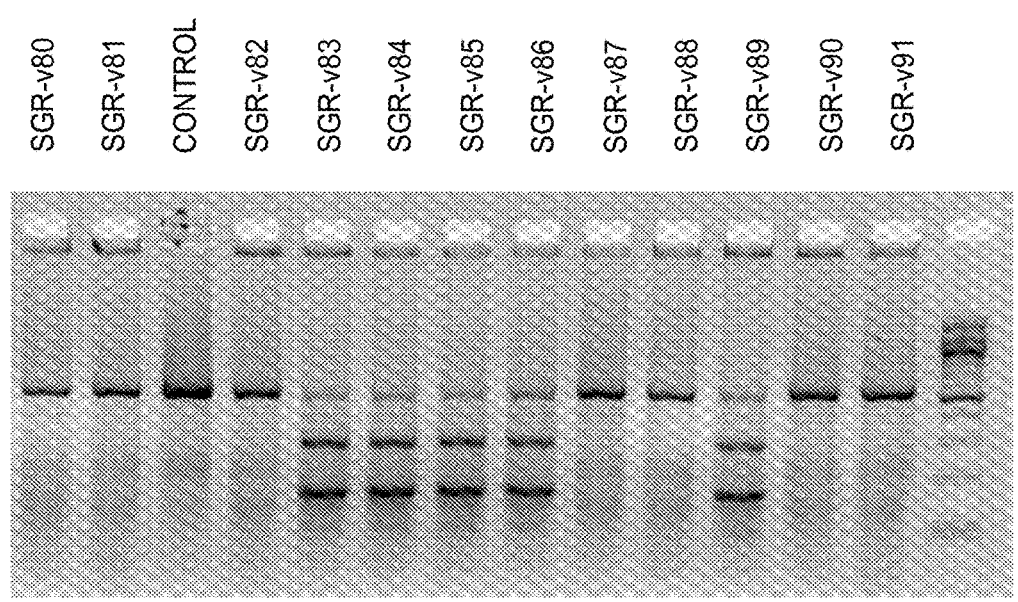
FIG. 37A-D shows in vitro cleavage assays using variant nucleic acid-targeting nucleic acids.
Figure 37B:
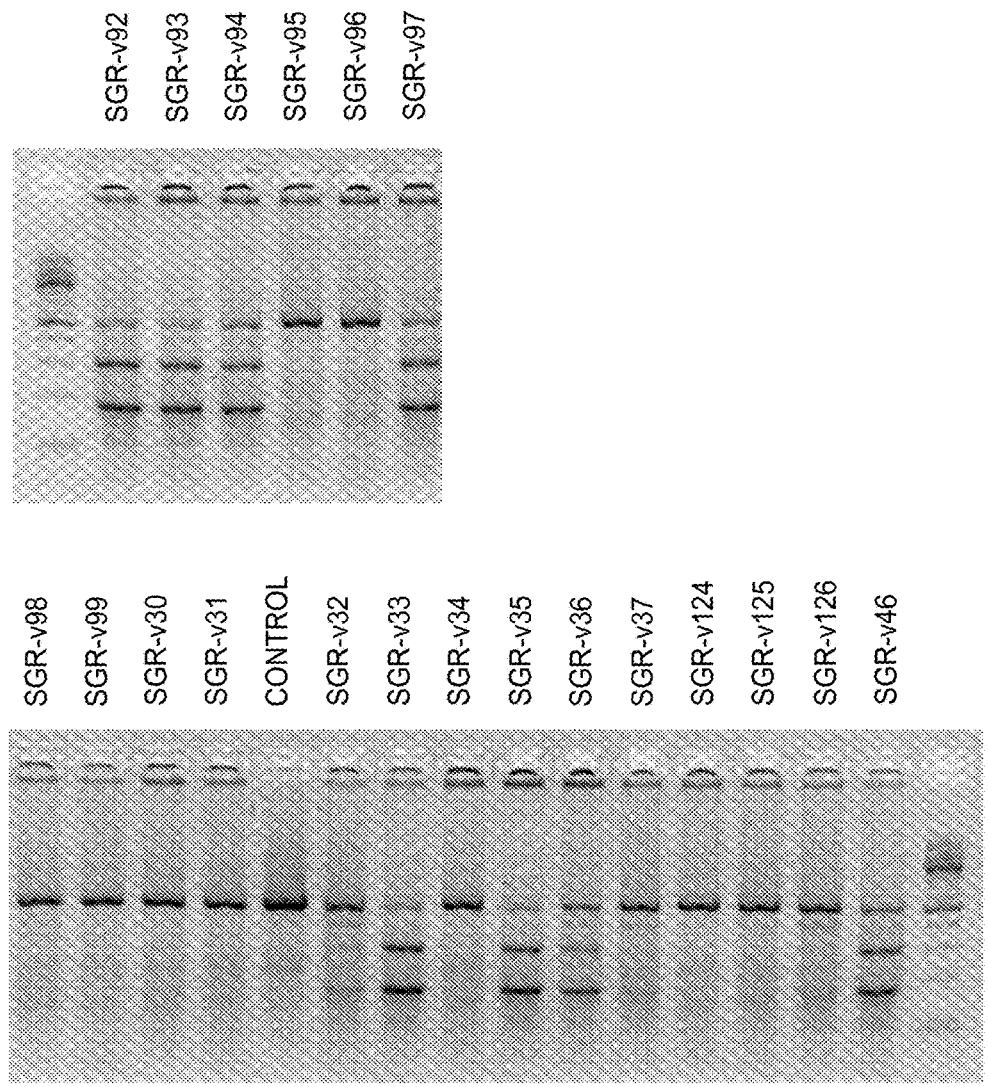
Figure 37C:
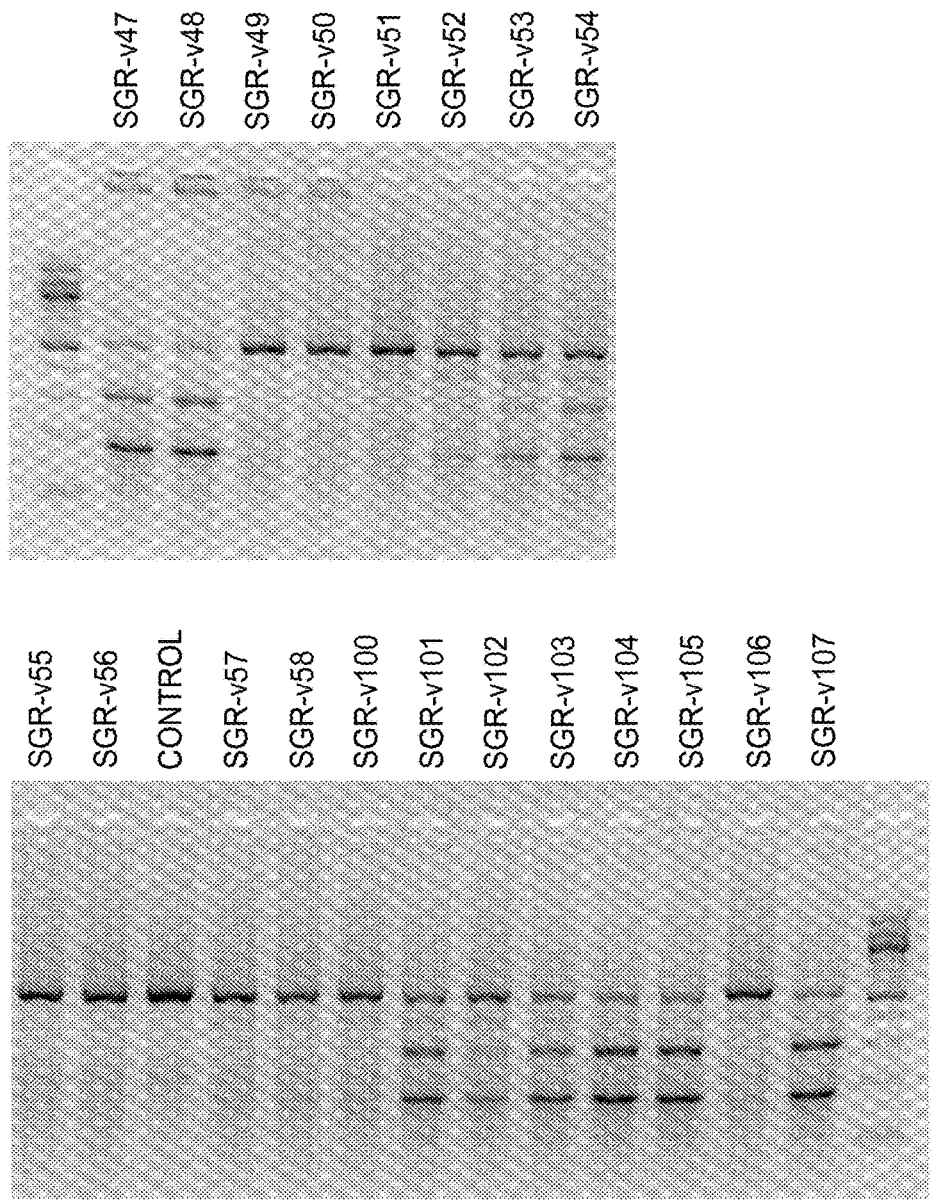
Figure 37D:
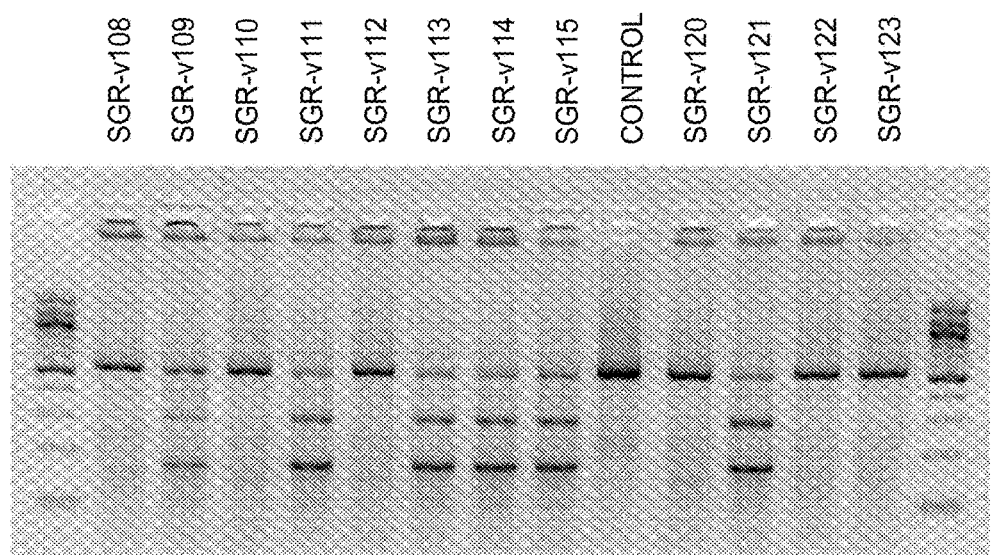

In some embodiments, two or more nickases can be employed to generate sticky ends. FIG. 33 illustrates how two nickases targeted to overlapping regions on a target nucleic acid can result in a staggered double-stranded break resulting in sticky ends. The target nucleic acid duplex 3310 can comprise a plurality of PAM sequences 3315 (boxed). A nucleic acid-targeting nucleic acid 3305 as part of a complex with the nickase (nickase not shown) can hybridize to the spacer sequence adjacent to the PAM 3315 on each strand of the target nucleic acid 3310. The nickase can cleave one strand of the target nucleic acid 3310. Cleavage is indicated by the triangles. If the PAMs are appropriately spaced the nickases can cut the target nucleic acid in staggered locations, thereby resulting in a sticky end. The PAM sequences may be separated by at least about 1, 2, 3, 4, 5, 6, 7, 8, 9, or 10 or more nucleotides. The PAM sequences may be separated by at most about 1, 2, 3, 4, 5, 6, 7, 8, 9, or 10 or more nucleotides. The distance of the PAM sequences can be related to the length of the sticky end generated. For example, the farther the PAMs are away from each other, the longer the sticky end will be.

A method for generating sticky ends using two or more nickases can involve PAM sequences substantially adjacent to one another (though on opposite strands). In some instances, the PAM sequences are separated by at least about 1, 2, 3, 4, 5, 6, 7, 8, 9, or 10 or more nucleotides. In some instances, the PAM sequences are separated by at most about 1, 2, 3, 4, 5, 6, 7, 8, 9, or 10 or more nucleotides. In some instances, the PAM sequences are separated by one nucleotide. In some instances, the PAM sequences are separated by no nucleotides.

Methods for Enrichment and Sequencing of Target Nucleic Acids

General Overview

Sequencing can be useful for diagnosing disease by identifying mutations and/or other sequence variants (e.g., polymorphisms). The methods of the disclosure provide for methods, kits, and compositions for enriching a target nucleic acid sequence without the use of amplification methodologies. A target nucleic acid can be enriched with the use of a site-directed polypeptide and a nucleic acid-targeting nucleic acid.

Figure 3:
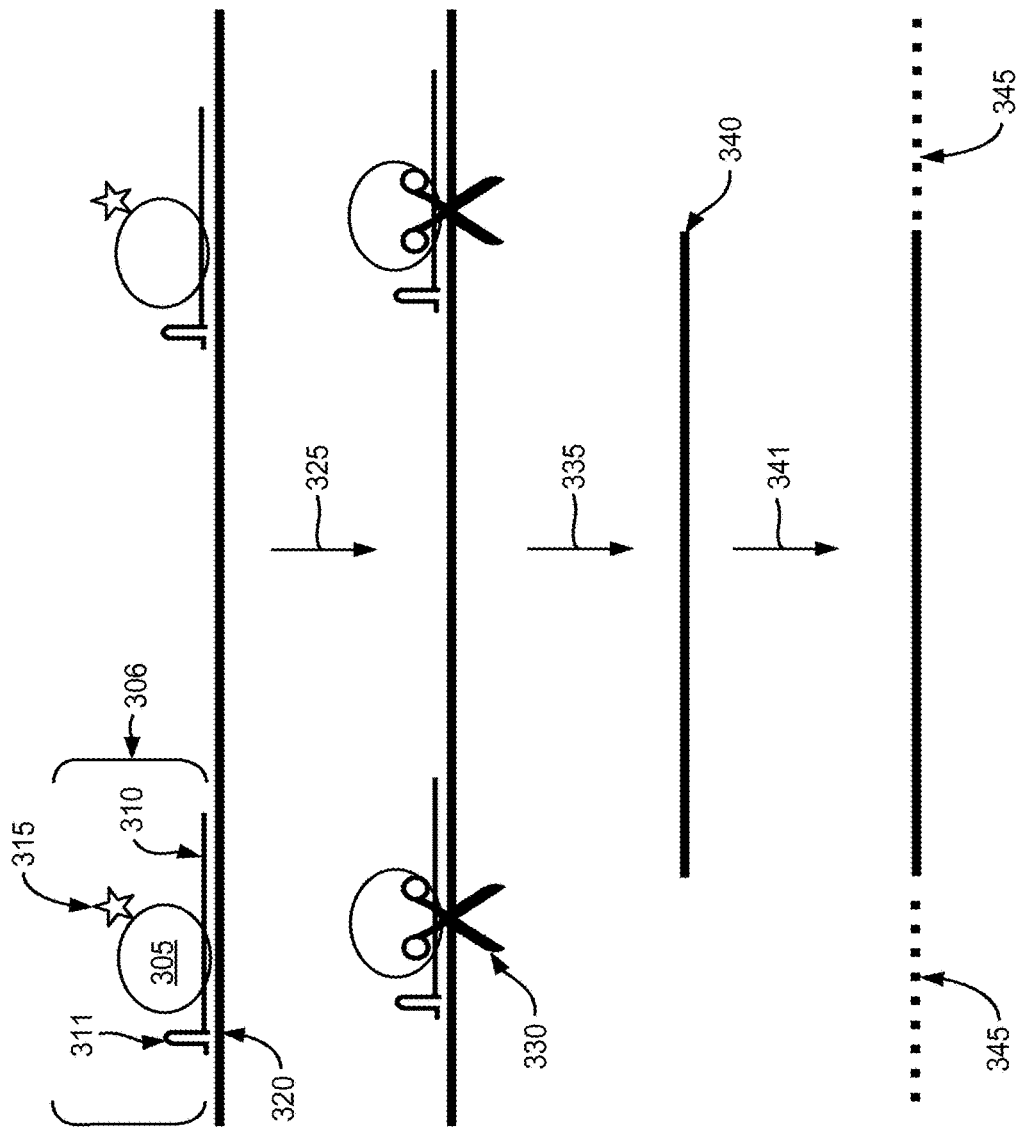
FIG. 3 depicts an exemplary embodiment of a sequence enrichment method of the disclosure utilizing target nucleic acid cleavage.

FIG. 3 depicts an exemplary embodiment of the methods of the disclosure. A site-directed polypeptide 305 can bind a nucleic acid-targeting nucleic acid 310, thereby forming a complex 306. The nucleic acid-targeting nucleic acid 310 can comprise a nucleic acid affinity tag 311. The site-directed polypeptide 305 can comprise a nuclease domain. The site-directed polypeptide 305 can be enzymatically active. The site-directed polypeptide 305 can comprise an affinity tag 315. The nucleic acid-targeting nucleic acid 310 can hybridize to a target nucleic acid 320. In some embodiments, a plurality of complexes 306 can hybridize to a plurality of locations within a target nucleic acid 320. In a cleavage step 325, the nuclease domain of a site-directed polypeptide 305 can cleave, or cut 330 the target nucleic acid 320. The excised target nucleic acid 340 can be purified in a purification step 335. Adaptors 345 can be ligated to the excised target nucleic acid. The adaptors can facilitate sequencing of the excised target nucleic acid.

Figure 4:
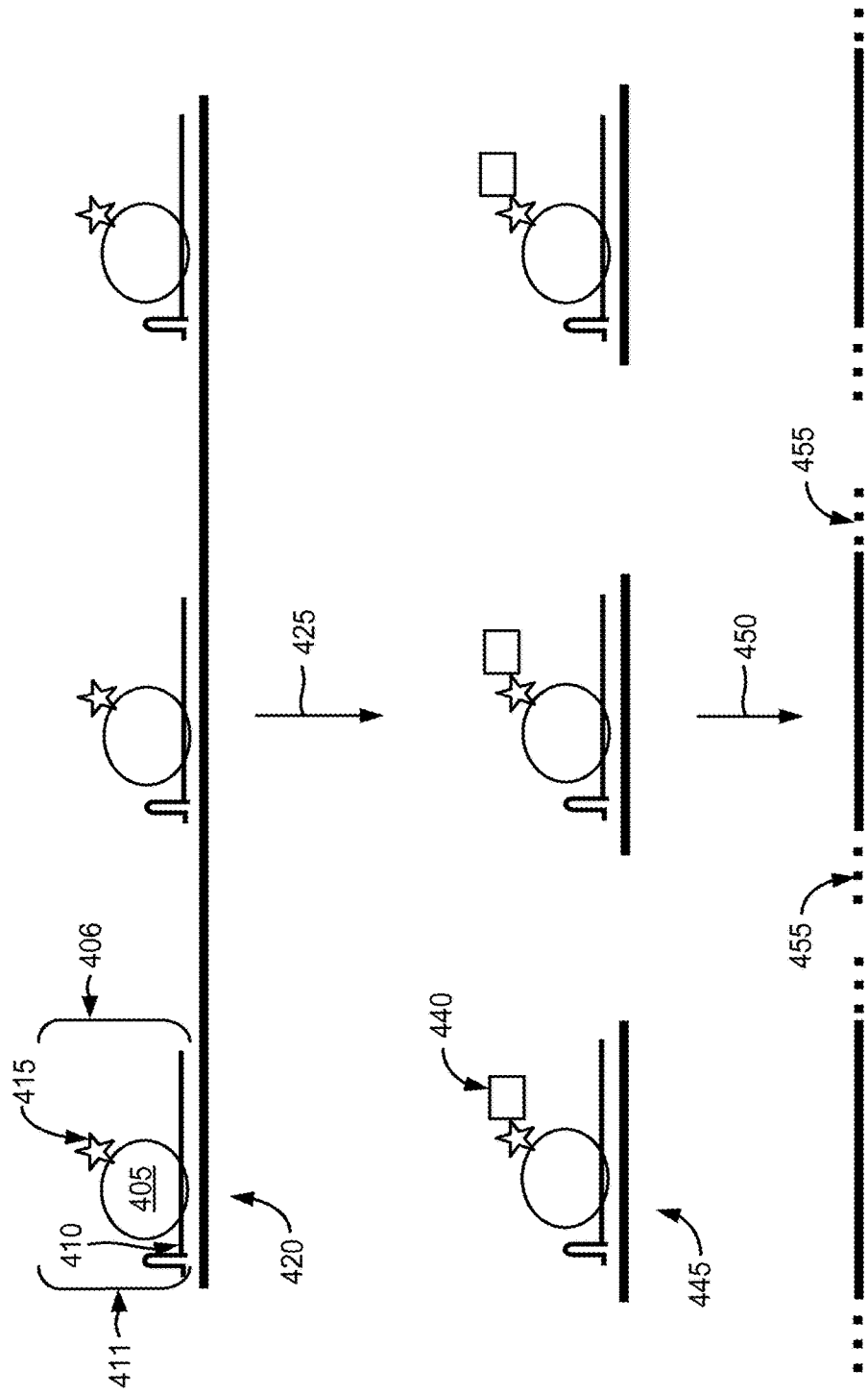
FIG. 4 depicts an exemplary embodiment of a sequence enrichment method of the disclosure utilizing target nucleic acid enrichment.

FIG. 4 depicts an exemplary embodiment of the methods of the disclosure. A site-directed polypeptide 405 can interact with a nucleic acid-targeting nucleic acid 410, thereby forming a complex 406. The site-directed polypeptide 405 can comprise a nuclease domain. In some embodiments, the nuclease domain of the site-directed polypeptide 405 can be enzymatically inactive. The site-directed polypeptide 405 can comprise an affinity tag 415. The nucleic acid-targeting nucleic acid 410 can hybridize to a target nucleic acid 420. The nucleic acid-targeting nucleic acid 410 can comprise a nucleic acid affinity tag 411. The affinity tag 411 of the nucleic acid-targeting nucleic acid can comprise a hairpin structure. A plurality of complexes 406 can hybridize to a plurality of locations within a target nucleic acid 420. In a fragmenting step 225, the target nucleic acid 420 can be fragmented into target nucleic acid fragment 445 (also herein referred to as a "target nucleic acid"). The site-directed polypeptide 405 can be purified by a capture agent 440 that can bind to the affinity tag 415 of the site-directed polypeptide 405. The fragmented target nucleic acid 445 can be eluted from the complex 406 in a purification step 450. In the same step, or optionally, in a different step, adaptors 455 can be ligated to the target nucleic acid. The adaptors can facilitate sequencing of the target nucleic acid.

Complex of a Nucleic Acid-Targeting Nucleic Acid and a Site-Directed Polypeptide A nucleic acid-targeting nucleic acid can interact with a site-directed polypeptide (e.g., a nucleic acid-guided nuclease, e.g. Cas9), thereby forming a complex. The nucleic acid-targeting nucleic acid can guide the site-directed polypeptide to a target nucleic acid.

In some embodiments, a nucleic acid-targeting nucleic acid can be engineered such that the complex (e.g., comprising a site-directed polypeptide and a nucleic acid-targeting nucleic acid) can bind outside of the cleavage site of the site-directed polypeptide. In this case, the target nucleic acid may not interact with the complex and the target nucleic acid can be excised (e.g., free from the complex).

In some embodiments, a nucleic acid-targeting nucleic acid can be engineered such that the complex can bind inside of the cleavage site of the site-directed polypeptide. In this case, the target nucleic acid can interact with the complex and the target nucleic acid can be bound (e.g., bound to the complex).

The nucleic acid-targeting nucleic acid can be engineered in such a way that the complex (e.g., comprising a site-directed polypeptide and/or a nucleic acid-targeting nucleic acid) can hybridize to a plurality of locations within a nucleic acid sample.

A plurality of complexes can be contacted to a nucleic acid sample. The plurality of complexes can comprise nucleic acid-targeting nucleic acids engineered to hybridize to the same sequence. The plurality of complexes can comprise nucleic acid-targeting nucleic acids engineered to hybridize to the different sequences.

The sequences can be at different locations within a target nucleic acid. The locations can comprise the same, or similar, target nucleic acid sequences. The locations can comprise different target nucleic acid sequences. The locations can be a defined distance from each other. The locations can be less than 10 kilobases (Kb) apart, less than 8 Kb apart, less than 6 Kb apart, less than 4 Kb apart, less than 2 Kb apart, less than 1 Kb apart, less than 900 nucleotides apart, less than 800 nucleotides apart, less than 700 nucleotides apart, less than 600 nucleotides apart, less than 500 nucleotides apart, less than 400 nucleotides apart, less than 300 nucleotides apart, less than 200 nucleotides apart, less than 100 nucleotides apart.

The complexes can cleave the target nucleic acid which can result in an excised target nucleic acid that can be less than 10 kilobases (Kb) long, less than 8 Kb long, less than 6 Kb long, less than 4 Kb long, less than 2 Kb long, less than 1 Kb long, less than 900 nucleotides long, less than 800 nucleotides long, less than 700 nucleotides long, less than 600 nucleotides long, less than 500 nucleotides long, less than 400 nucleotides long, less than 300 nucleotides long, less than 200 nucleotides long, less than 100 nucleotides long.

The complexes can be bound to a fragmented target nucleic acid that can be less than 10 kilobases (Kb) long, less than 8 Kb long, less than 6 Kb long, less than 4 Kb long, less than 2 Kb long, less than 1 Kb long, less than 900 nucleotides long, less than 800 nucleotides long, less than 700 nucleotides long, less than 600 nucleotides long, less than 500 nucleotides long, less than 400 nucleotides long, less than 300 nucleotides long, less than 200 nucleotides long, less than 100 nucleotides long.

Methods for Detecting Off-Target Binding Sites of Site-Directed Polypeptides

General Overview

This disclosure describes methods, compositions, systems, and/or kits for determining off target binding sites of site-directed polypeptides. In some embodiments of the disclosure a site-directed polypeptide can comprise a nucleic acid-targeting nucleic acid, thereby forming a complex. The complex can be contacted with a target nucleic acid. The target nucleic acid can be captured with capture agents that can bind to the affinity tags of the complex. The identity of the target nucleic acid can be determined through sequencing. Sequencing (e.g., high throughput sequencing, e.g., Illumina, Ion Torrent) can also identify the frequency of off-target binding sites of the site-directed polypeptide and/or complex, by counting the number of times a particular binding site is read. The methods, compositions, systems, and/or kits of the disclosure can facilitate the development of more accurately and specifically targeted site-directed polypeptides.

Figure 5:
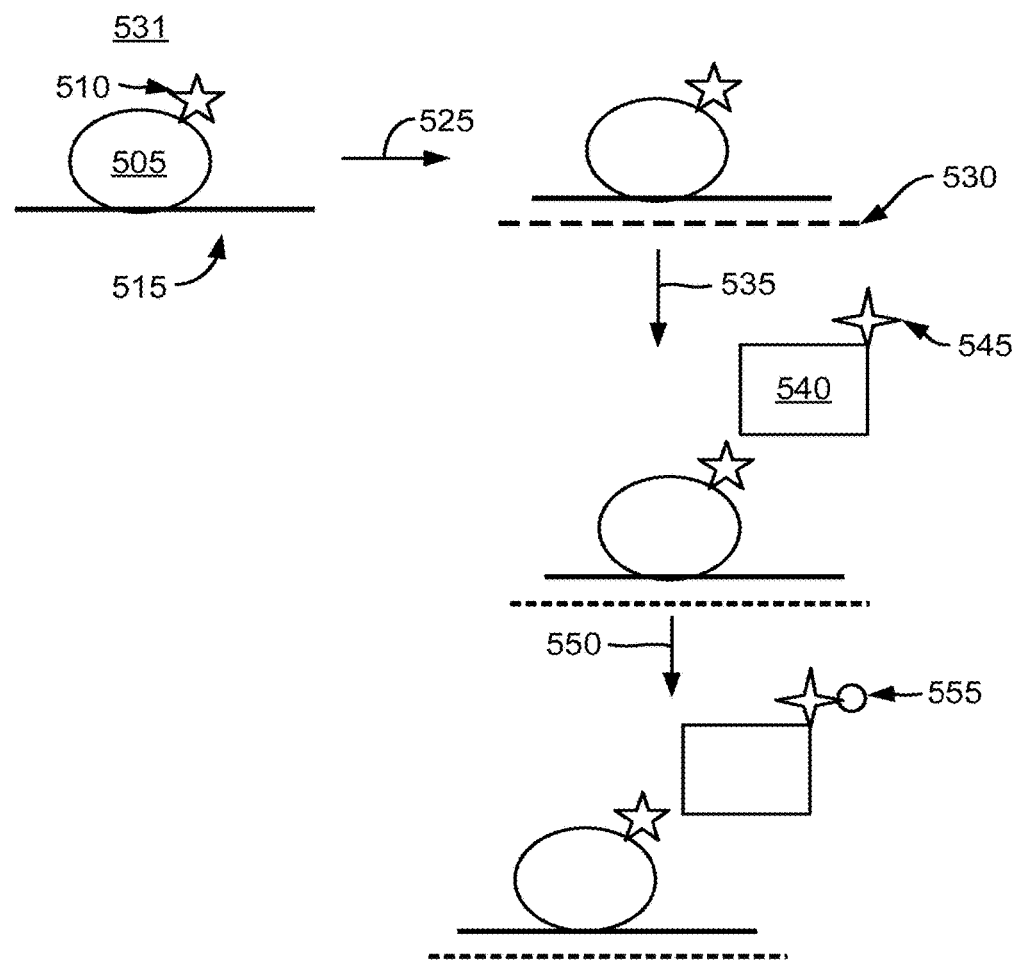
FIG. 5 depicts an exemplary embodiment of a method of the disclosure for determining off-target binding sites of a site-directed polypeptide utilizing purification of the site-directed polypeptide.

FIG. 5 depicts an exemplary embodiment of the methods of the disclosure. A site-directed polypeptide 505 can comprise an affinity tag 510. The site-directed polypeptide can comprise a nucleic acid-binding domain 515. The nucleic acid-binding domain 515 can be a nucleic acid. In some embodiments, the nucleic acid-binding domain 515, and the site-directed polypeptide 505 form a complex 531. The complex 531 can be contacted 525 with a target nucleic acid 530. In a preferred embodiment, the target nucleic acid 530 is DNA (e.g. genomic DNA or gDNA). The complex can be affinity purified 535 with a capture agent 540. The capture agent 540 can bind to the affinity tag 510 from the site-directed polypeptide 505. The capture agent 540 can comprise a second affinity tag 545. The capture agent 540 can be affinity purified 550 by binding to a solid support 555. In some embodiments, the solid support 555 is a bead coated with an affinity reagent that can bind to the affinity tag 545 of the capture agent. Optionally, the solid support 555 can bind to the affinity tag 510 of the site-directed polypeptide 505 to facilitate purification. In some embodiments, one or more rounds of purification can occur. Each round can comprise contacting a solid support 555 with the affinity tags of the site-directed polypeptide 510 and/or the capture agent 545. The affinity purified complex can be eluted from the target nucleic acid 530. The target nucleic acid can subsequently be prepared for further processing. Processing can include downstream analysis methods, e.g. sequencing.

Figure 6:
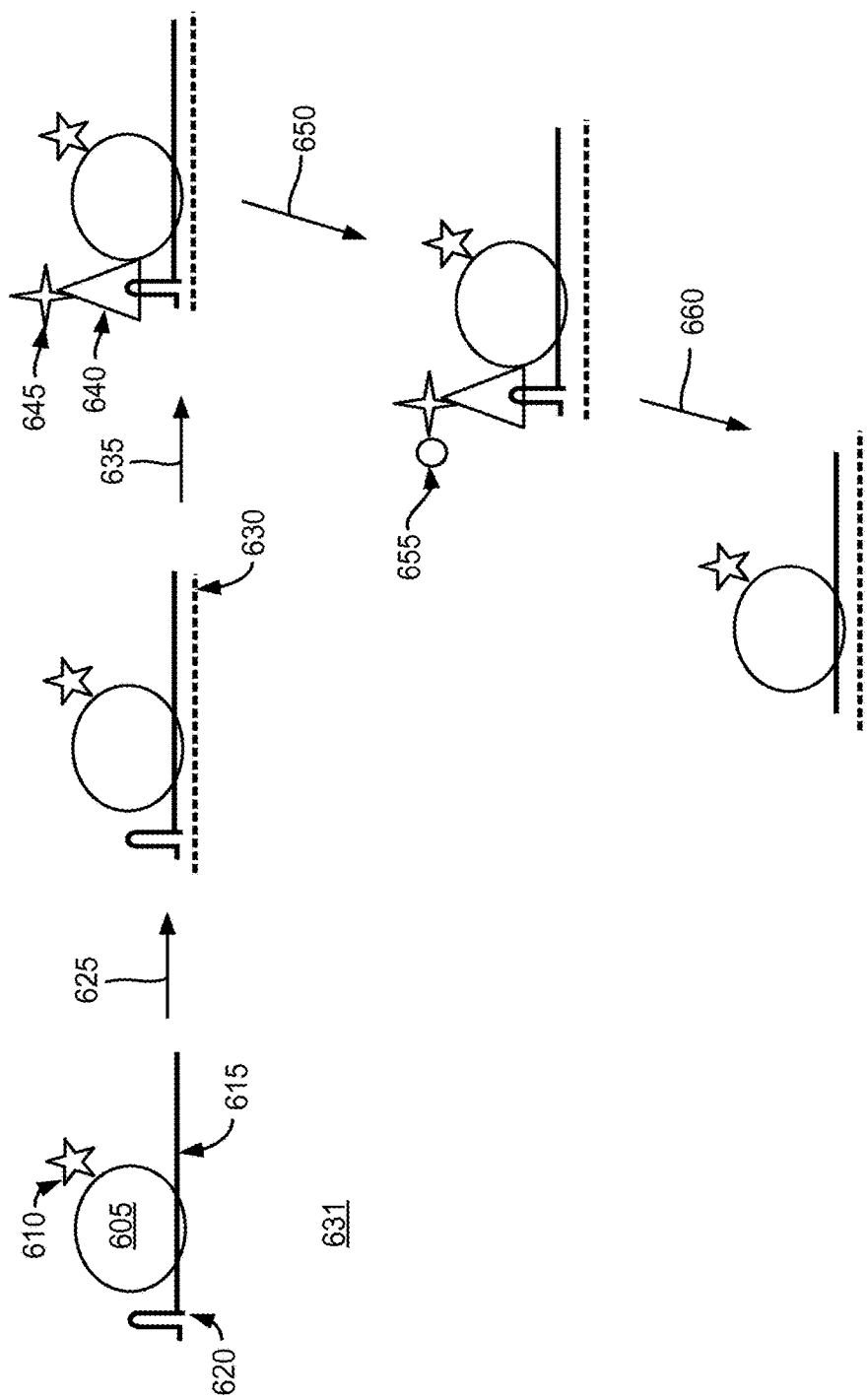
FIG. 6 depicts an exemplary embodiment of a method of the disclosure for determining off-target binding sites of a site-directed polypeptide utilizing purification of the nucleic acid-targeting nucleic acid.

FIG. 6 depicts an exemplary embodiment of the methods of the disclosure. A site-directed polypeptide 605 can comprise an affinity tag 610. The site-directed polypeptide 605 can comprise a nucleic acid-binding domain 615. The nucleic acid-binding domain 615 can be a nucleic acid. In some embodiments, the nucleic acid-binding domain 615 can comprise an affinity tag 620. In some embodiments, the nucleic acid-binding domain 615 and the site-specific polypeptide 605 can form a complex 631. The complex 631 may be contacted 625 with a target nucleic acid 630. In a preferred embodiment, the target nucleic acid 630 is DNA. The complex 631 can be affinity purified 635 with a capture agent 640. The capture agent 640 may be a conditionally enzymatically inactive site-directed polypeptide. The capture agent 640 can be a conditionally enzymatically inactive variant of Csy4. The capture agent 640 can bind to the affinity tag 620. The capture agent 640 can comprise an affinity tag 645. The capture agent 640 can be affinity purified 650 by binding to a solid support 655. In some embodiments, the solid support is a bead coated with an affinity reagent that can bind to the affinity tag 645 of the capture agent 640. Optionally, the solid support 655 can bind to the affinity tag 610 of the site-directed polypeptide 605 to facilitate purification. In some embodiments, two rounds of purification can occur, each comprising contacting a solid support 655 with the affinity tags of the site-directed polypeptide 610 and/or the capture agent 640. Cleavage of the affinity tag 620 can facilitate elution 660 of the target nucleic acid 630 from the solid support 655. The target nucleic acid 630 can subsequently be prepared for further downstream analysis methods such as sequencing.

Methods

The disclosure provides methods for nuclease immunoprecipitation and sequencing (NIP-Seq). In some embodiments, the method can comprise a) contacting a nucleic acid sample with a complex comprising an enzymatically inactive site-directed polypeptide, a site-directed polypeptide, and a nucleic acid-targeting nucleic acid. The complex can hybridize to a target nucleic acid. The complex can be captured with a capture agent, and the target nucleic acid bound to the complex can be sequenced. In some embodiments, the method can further comprise determining the identity of the off-target binding site. The method can be performed using any of the site-directed polypeptides, nucleic acid-targeting nucleic acids, and complexes of site-directed polypeptides and nucleic acid-targeting nucleic acids as described herein.

The methods can be performed outside of a cell. For example, a sample can comprise purified genomic DNA, cell lysate, homogenized tissue, plasma, and the like. The methods can be performed in cells.

The site-directed polypeptide-target nucleic acid complexes can be fixed or cross-linked to form complexes. The cells can be crosslinked before they are lysed. Fixed or cross-linking cells can stabilize protein-DNA complexes in the cell. Suitable fixatives and cross-linkers can include, formaldehyde, glutaraldehyde, ethanol-based fixatives, methanol-based fixatives, acetone, acetic acid, osmium tetraoxide, potassium dichromate, chromic acid, potassium permanganate, mercurials, picrates, formalin, paraformaldehyde, amine-reactive NETS-ester crosslinkers such as bis [sulfosuccinimidyl] suberate (BS3), 3,3"-dithiobis[sulfosuccinimidylpropionate] (DTSSP), ethylene glycol bis [sulfosuccinimidylsuccinate (sulfo-EGS), disuccinimidyl glutarate (DSG), dithiobis[succinimidyl propionate] (DSP), disuccinimidyl suberate (DSS), ethylene glycol bis[succinimidylsuccinate] (EGS), NHS-ester/diazirine crosslinkers such as NHS-diazirine, NHS-LC-diazirine, NHS-SS-diazirine, sulfo-NHS-diazirine, sulfo-NHS-LC-diazirine, and sulfo-NHS-SS-diazirine.

The nucleic acid (e.g., genomic DNA) can be treated to fragment the DNA before affinity purification. Fragmentation can be performed through physical, mechanical or enzymatic methods. Physical fragmentation can include exposing a target polynucleotide to heat or to ultraviolet (UV) light. Mechanical disruption may be used to mechanically shear a target polynucleotide into fragments of the desired range. Mechanical shearing may be accomplished through a number of methods known in the art, including repetitive pipetting of the target polynucleotide, sonication and nebulization. Target polynucleotides may also be fragmented using enzymatic methods. In some cases, enzymatic digestion may be performed using enzymes such as using restriction enzymes. Restriction enzymes may be used to perform specific or non-specific fragmentation of target polynucleotides. The methods may use one or more types of restriction enzymes, generally described as Type I enzymes, Type II enzymes, and/or Type III enzymes. Type II and Type III enzymes are generally commercially available and well known in the art. Type II and Type III enzymes recognize specific sequences of nucleotide nucleotides within a double-stranded polynucleotide sequence (a "recognition sequence" or "recognition site"). Upon binding and recognition of these sequences, Type II and Type III enzymes cleave the polynucleotide sequence. In some cases, cleavage will result in a polynucleotide fragment with a portion of overhanging single-stranded DNA, called a "sticky end." In other cases, cleavage will not result in a fragment with an overhang, creating a "blunt end." The methods may comprise use of restriction enzymes that generate either sticky ends or blunt ends. Fragments of nucleic acids can also be generated via amplification techniques (e.g. polymerase chain reaction, long range polymerase chain reaction, linear polymerase chain reaction, and etc.).

Once fragmented, the complexes comprising the site-directed polypeptide can be purified by incubation with a solid support. For example, if the site-directed polypeptide comprises a biotin tag, the solid support can be coated with avidin or streptavidin to bind to the biotin tag.

In some embodiments, once fragmented, the complexes comprising the site-directed polypeptide, the target nucleic acid, and/or the nucleic acid-targeting nucleic acid are purified by incubation with a capture agent. A capture agent can refer to any agent that can bind to an affinity tag fused to the site-directed polypeptide. Exemplary capture agents can include, biotin, streptavidin, and antibodies. For example, if the affinity tag fused to the site-directed polypeptide is a FLAG tag, then the capture agent will be an anti-FLAG-tag antibody. In some embodiments, the capture agent can comprise an affinity tag (e.g., biotin, streptavidin).

In some instances, the capture agent is an enzymatically inactive endoribonuclease. For example, a capture agent can be an enzymatically inactive site-directed polypeptide, an enzymatically inactive Csy4, Cas5, or Cash.

The capture agent can be purified with a solid support. For example, if the capture agent comprises a biotin tag, the bead can be coated with avidin or streptavidin to bind the biotinylated capture agent.

In some embodiments of the method, two or more rounds of purification can be performed. At least 1, 2, 3, 4, 5, 6, 7 or more rounds of purification can be performed. At most 1, 2, 3, 4, 5, 6, 7 or more rounds of purification can be performed. A first round of purification can comprise purification with a solid support that can bind to the affinity tag of the capture agent and a second round of purification can comprise purification with a solid support that can bind to the affinity tag of the site-directed polypeptide. A first round of purification can comprise purification with a solid support that can bind to the affinity tag of the site-directed polypeptide and a second round of purification can comprise purification with a solid support that will bind to the affinity tag of the capture agent. The method can be used to optimize the binding specificity of a site-directed polypeptide by performing the method more than once.

The captured complex can comprise site-directed polypeptide and a target nucleic acid. The target nucleic acid can be eluted from the site-directed polypeptide complex by methods such as high salt washing, ethanol precipitation, boiling, and gel purification.

The eluted DNA can be prepared for sequencing analysis (e.g., shearing, ligation of adaptors). Preparation for sequencing analysis can include the generation of sequencing libraries of the eluted target nucleic acid. Sequencing analysis can determine the identity and frequency of off-target binding sites of site-directed polypeptides. Sequence determination will also be performed using methods that determine many (typically thousands to billions) nucleic acid sequences in an intrinsically parallel manner, where many sequences are read out preferably in parallel using a high throughput serial process. Such methods include but are not limited to pyrosequencing (for example, as commercialized by 454 Life Sciences, Inc., Branford, Conn.); sequencing by ligation (for example, as commercialized in the SOLiD™ technology, Life Technology, Inc., Carlsbad, Calif.); sequencing by synthesis using modified nucleotides (such as commercialized in TruSeq™ and HiSeq™ technology by Illumina, Inc., San Diego, Calif., HeliScope™ by Helicos Biosciences Corporation, Cambridge, Mass., and PacBio RS by Pacific Biosciences of California, Inc., Menlo Park, Calif.), sequencing by ion detection technologies (Ion Torrent, Inc., South San Francisco, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and other known highly parallelized sequencing methods.

Figure 31:
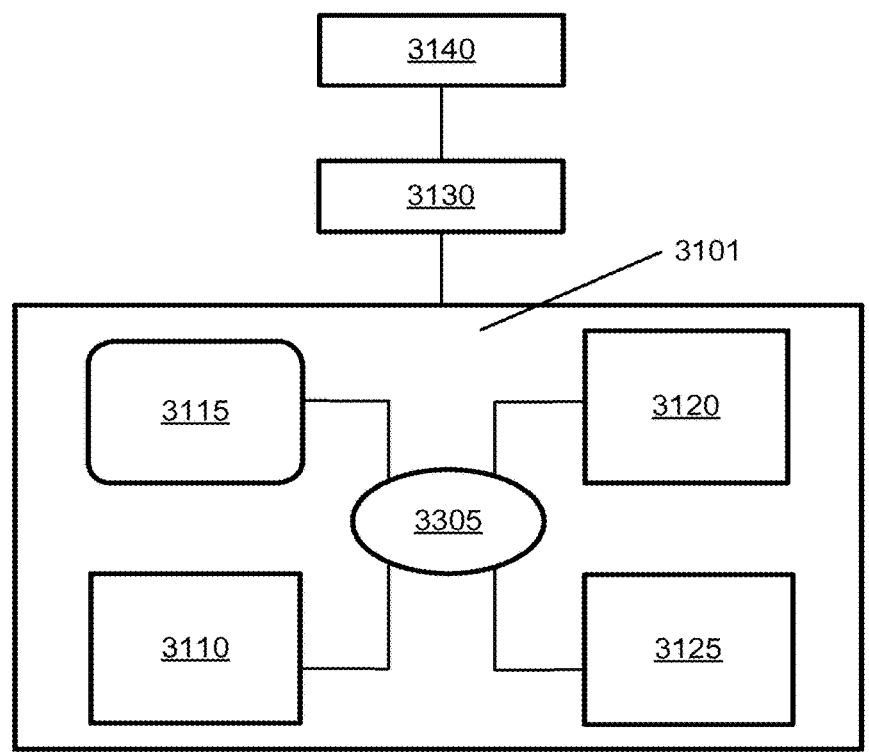
FIG. 31 depicts a system for storing and sharing electronic information.

In some embodiments, the method further comprises collecting data and storing data. The data can be machine readable and can be stored and/or collected on a computer server (e.g. FIG. 31 and Example 27).

Methods for Detecting Sequence Variants in Nucleic Acids

General Overview

Figure 7:
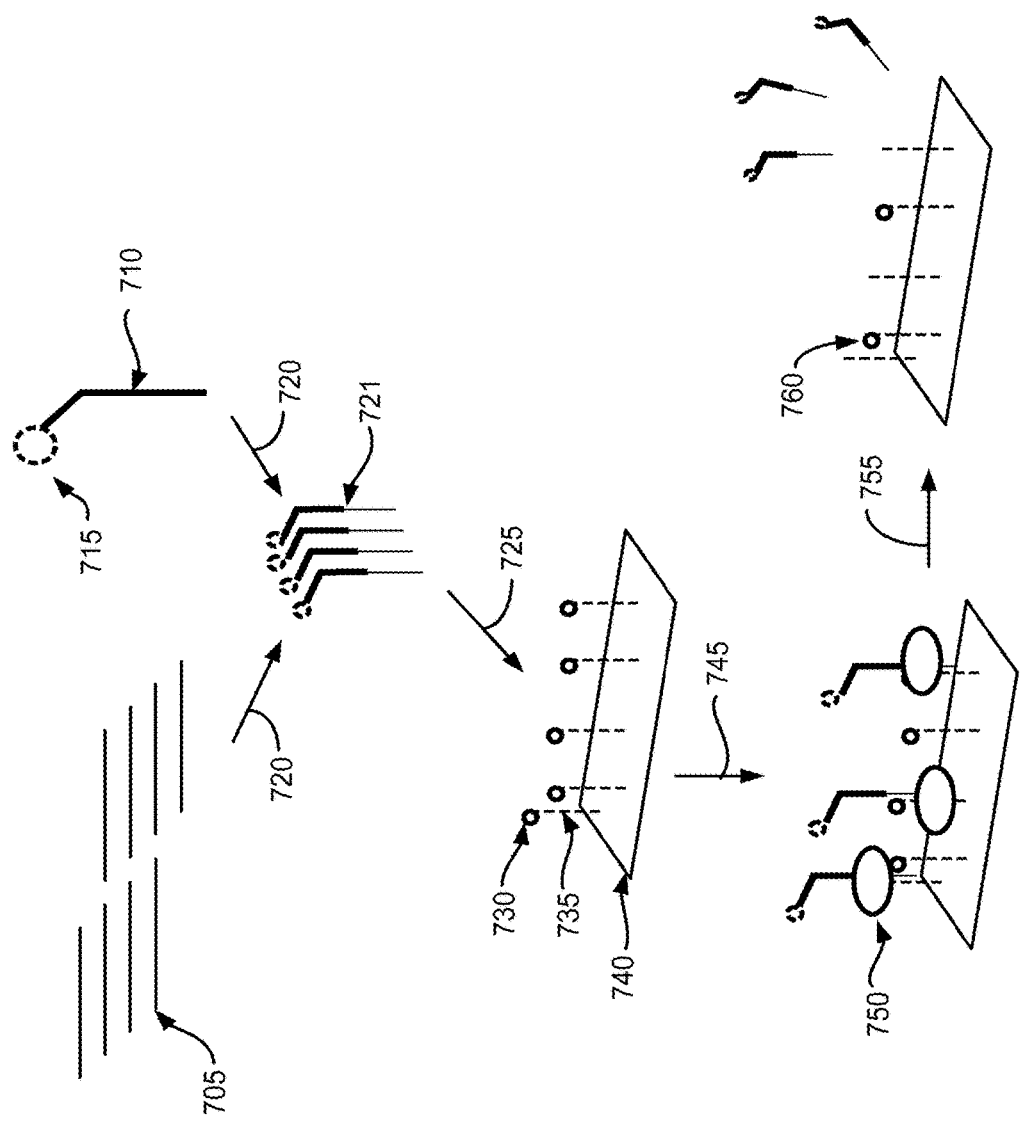
FIG. 7 illustrates an exemplary embodiment for an array-based sequencing method using a site-directed polypeptide of the disclosure.
Figure 8:
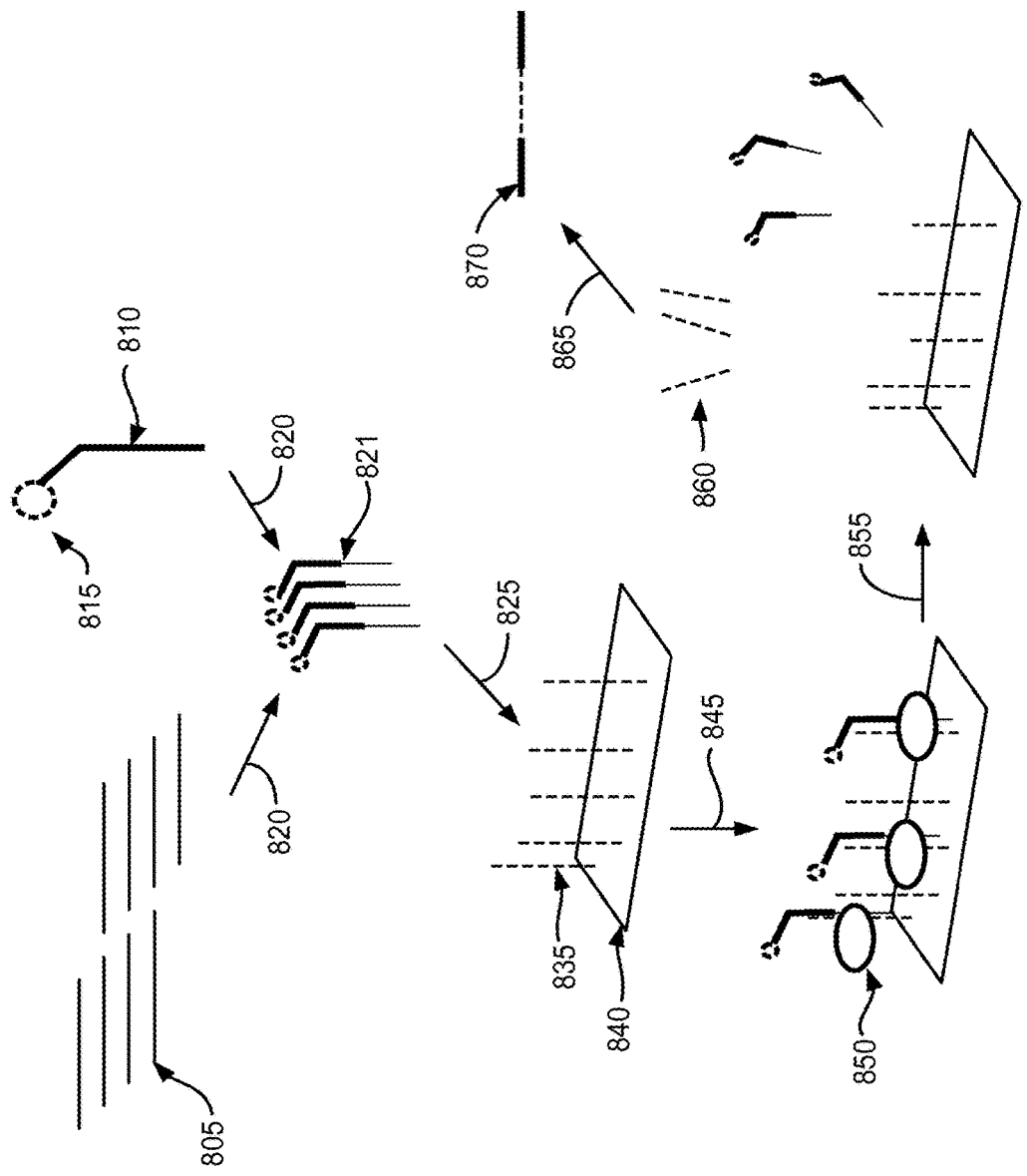
FIG. 8 illustrates an exemplary embodiment for an array-based sequencing method using a site-directed polypeptide of the disclosure, wherein cleaved products are sequenced.
Figure 9:
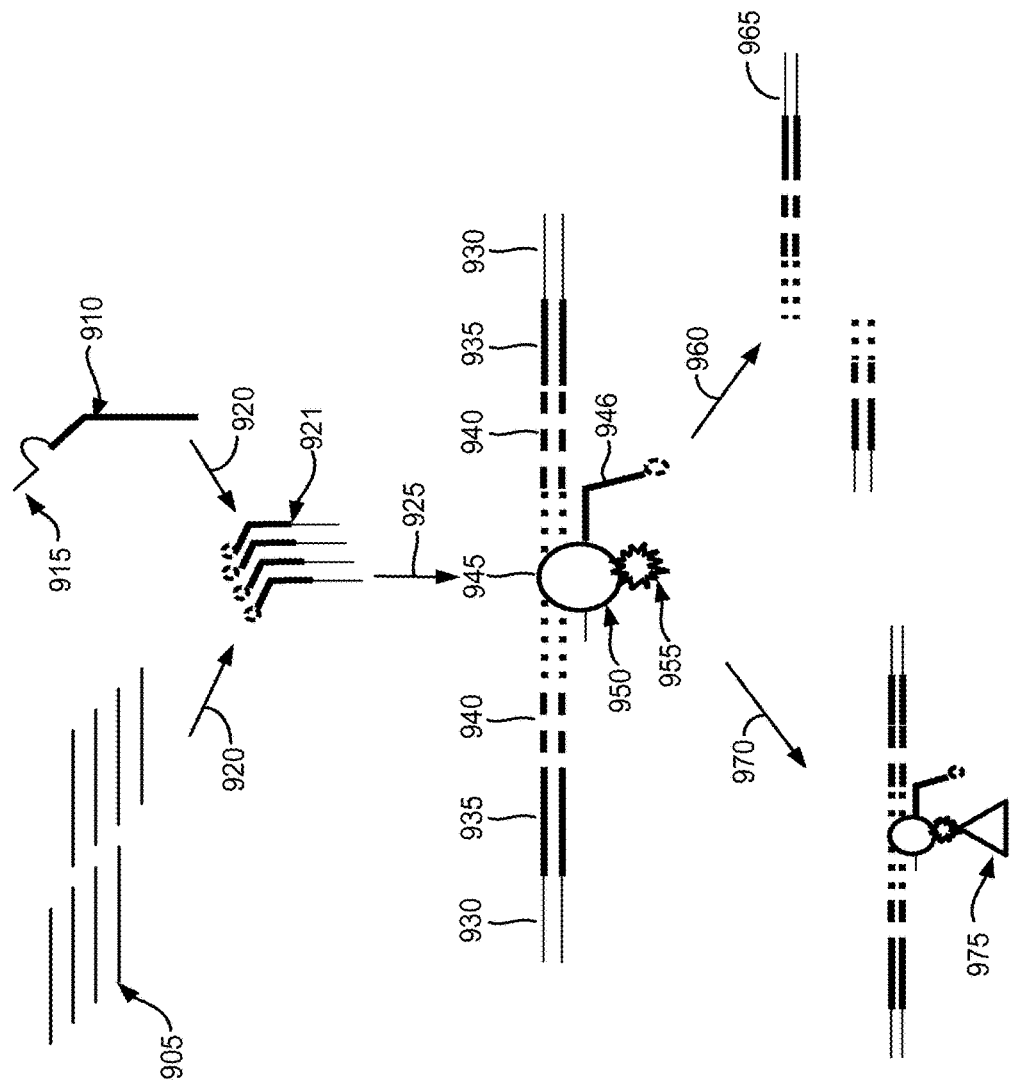
FIG. 9 illustrates an exemplary embodiment for a next-generation sequencing-based method using a site-directed polypeptide of the disclosure.

In some embodiments, the methods of the disclosure provide for detecting sequence variants in nucleic acids. The method can be performed using any of the site-directed polypeptides, nucleic acid-targeting nucleic acids, and complexes of site-directed polypeptides and nucleic acid-targeting nucleic acids as described herein. As depicted in FIG. 7, a nucleic acid sample 705 can be ligated 720 with a nucleic acid tag 710. The nucleic acid tag can be a single guide RNA. The nucleic acid tag can comprise a crRNA. The nucleic acid tag can comprise a detectable label 715. Together, the nucleic acid sample 705 ligated to the nuclei acid tag 710 can be referred to as a tagged test sample 721. The tagged test sample 721 can be contacted 725 to an array 740 comprising immobilized oligonucleotides 735. The immobilized oligonucleotides 735 can be referred to as a nucleic acid library. The oligonucleotides 735 can be double-stranded DNA. The oligonucleotides 735 can comprise a detectable label 730. The individual members of the tagged test sample 721 can hybridize 745 to the oligonucleotides 735 to which they share enough complementarity to facilitate hybridization. The amount of hybridization can be quantified by comparing the intensities of the two detectable labels 715 and 730. For example, hybridized oligonucleotides can display two detectable labels. Unhybridized oligonucleotides can display one detectable label 730. The hybridized sample can be contacted with a site-directed polypeptide 750. The site-directed polypeptide can cleave 755 the oligonucleotides 735 in the array 740 that have hybridized with members of the tagged test sample 721. Cleavage by the site-directed polypeptide can allow the hybridized members of the tagged test sample 721 to be removed. After cleavage by the site-directed polypeptide 750, only unhybridized oligonucleotide detectable labels 760 will remain on the array. The remaining detectable label 760 can be quantified. The quantification of the remaining detectable labels 760 can be correlated to which sequences were represented in the nucleic acid sample 705 and which were not. Oligonucleotides that do not display a remaining detectable label 760 correspond to sequences that were represented in the nucleic acid sample 705. Oligonucleotides that display a remaining detectable label 760 correspond to sequences that were not represented in the nucleic acid sample 705.

In some embodiments, a nucleic acid sample 805 can be ligated 820 with a nucleic acid tag 810. The nucleic acid tag can be a single guide RNA. The nucleic acid tag can comprise a crRNA. The nucleic acid tag can comprise a detectable label 815. Together, the nucleic acid sample ligated to the nuclei acid tag can be referred to as a tagged test sample 821. The tagged test sample 821 can be contacted 825 to an array 840 comprising immobilized oligonucleotides 835. The immobilized oligonucleotides can be referred to as a nucleic acid library. The oligonucleotides 835 can be double-stranded DNA. The individual members of the tagged test sample 821 can hybridize 845 to the oligonucleotides 835 to which they share enough complementarity to facilitate hybridization. The hybridized sample can be contacted with a site-directed polypeptide 850. The site-directed polypeptide can cleave 855 the oligonucleotides 835 in the array 840 that have hybridized with members of the tagged test sample 821. Cleavage by the site-directed polypeptide 850 can allow the hybridized members of the tagged test sample 821 to be removed. Cleavage by the site-directed polypeptide 850 can allow a portion of the immobilized olignucleotide to be cleaved and separated from the array 860. The separated cleaved oligonucleotides 860 can be ligated 865 to appropriate adaptors 870 for sequencing. Sequencing of the cleaved oligonucleotides 860 can determine the sequences represented in the nucleic acid sample 805.

In some embodiments, a nucleic acid library can be generated for sequencing analysis using commercially available high throughput sequencing platforms. The library can comprise nucleic acids that can comprise one or more sequencing tags 930 and a target sequence 945. The target sequence 945 can be a sequence that may be represented in a nucleic acid sample 905. A target sequence 945 can comprise a protospacer adjacent motif (PAM) sequence. Optionally, nucleic acids in a nucleic acid library can comprise one or more identifying polynucleotide sequences 935, and one or more extension sequences 940. In this embodiment, a nucleic acid sample 905 can be ligated 920 with a nucleic acid tag 910. The nucleic acid tag can be a single guide RNA. The nucleic acid tag can comprise a crRNA. Optionally, the nucleic acid tag can comprise an affinity tag 915. Together, the nucleic acid sample ligated to the nuclei acid tag can be referred to as a tagged test sample 921. The tagged test sample 921 can be contacted 925 to a nucleic acid library. The tagged test sample 921 can hybridize to a nucleic acid in the nucleic acid library, forming a complex 946. The hybridized tagged test sample and nucleic acid library can be contacted with a site-directed polypeptide 950. The site-directed polypeptide 950 can cleave the hybridized nucleic acid library members. The cleaved nucleic acid library members 965 can be separated from the uncleaved members. The uncleaved members can be subjected to sequencing analysis. Sequencing analysis can determine which sequences were represented in the nucleic acid sample 905. For example, the sequences of the uncleaved members can correspond to sequences that were not represented in the nucleic acid sample 905. These sequences can be removed from the known sequences in the nucleic acid library. The resulting sequences can be the sequences of the cleaved members 965 of the nucleic acid library which can correspond to sequences that were represented in the nucleic acid sample 905.

The site-directed polypeptide 950 can comprise an affinity tag 955. Optionally, the site-directed polypeptide 950 can be an enzymatically inactive variant of a site-directed polypeptide. In some embodiments, an enzymatically inactive site-directed polypeptide can be contacted to a hybridized nucleic acid library (e.g., complex 946). The site-directed polypeptide can bind but cannot cleave the hybridized nucleic acid library members. The site-directed polypeptide can be affinity purified 970 with a capture agent 975 that can bind to the affinity tag 955. Optionally, the complex 946 can be affinity purified with a capture agent that can bind to the affinity tag 915. The affinity purified nucleic acid library members can be subjected to sequencing analysis. In this embodiment, the sequenced nucleic acid library members can correspond to sequences that are represented in the nucleic acid sample 905.

Sequencing

Methods for detecting sequence variants can comprise sequencing the variants. Sequence determination can be performed using methods that determine many (typically thousands to billions) nucleic acid sequences in an intrinsically parallel manner, where many sequences are read out preferably in parallel using a high throughput serial process. Such methods can include but are not limited to pyrosequencing (for example, as commercialized by 454 Life Sciences, Inc., Branford, Conn.); sequencing by ligation (for example, as commercialized in the SOLiD™ technology, Life Technology, Inc., Carlsbad, Calif.); sequencing by synthesis using modified nucleotides (such as commercialized in TruSeq™ and HiSeq™ technology by Illumina, Inc., San Diego, Calif., HeliScope™ by Helicos Biosciences Corporation, Cambridge, Mass., and PacBio RS by Pacific Biosciences of California, Inc., Menlo Park, Calif.), sequencing by ion detection technologies (Ion Torrent, Inc., South San Francisco, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), capillary sequencing (e.g, such as commercialized in MegaBACE by Molecular Dynamics), electronic sequencing, single molecule sequencing (e.g., such as commercialized in SMRT™ technology by Pacific Biosciences, Menlo Park, Calif.), droplet microfluidic sequencing, sequencing by hybridization (such as commercialized by Affymetrix, Santa Clara, Calif.), bisulfate sequencing, and other known highly parallelized sequencing methods.

Real Time PCR

Methods for detecting sequence variants can comprise detecting the variants using real time PCR. Sequence determination can be performed by real time polymerase chain reaction (RT-PCR, also referred to as quantitative-PCR (QPCR)) can detect an amount of amplifiable nucleic acid present in a sample. QPCR is a technique based on the polymerase chain reaction, and can be used to amplify and simultaneously quantify a target nucleic acid. QPCR can allow for both detection and quantification of a specific sequence in a target nucleic acid sample. The procedure can follow the general principle of polymerase chain reaction, with the additional feature that the amplified target nucleic acid can be quantified as it accumulates in the reaction in real time after each amplification cycle. Two methods of quantification can be: (1) use of fluorescent dyes that intercalate with double-stranded target nucleic acid, and (2) modified DNA oligonucleotide probes that fluoresce when hybridized with a complementary target nucleic acid. In the first method, a target nucleic acid-binding dye can bind to all double-stranded (ds) nucleic acid in PCR, resulting in fluorescence of the dye. An increase in nucleic acid product during PCR therefore can lead to an increase in fluorescence intensity and can be measured at each cycle, thus allowing nucleic acid concentrations to be quantified. The reaction can be prepared similarly to a standard PCR reaction, with the addition of fluorescent (ds) nucleic acid dye. The reaction can be run in a thermocycler, and after each cycle, the levels of fluorescence can be measured with a detector; the dye can only fluoresce when bound to the (ds) nucleic acid (i.e., the PCR product). With reference to a standard dilution, the (ds) nucleic acid concentration in the PCR can be determined. The values obtained can not have absolute units associated with it. A comparison of a measured DNA/RNA sample to a standard dilution can give a fraction or ratio of the sample relative to the standard, allowing relative comparisons between different tissues or experimental conditions. To ensure accuracy in the quantification, the expression of a target gene can be normalized to a stably expressed gene. This can allow for correction of possible differences in nucleic acid quantity or quality across samples. The second method can use a sequence-specific RNA or DNA-based probe to quantify only the nucleic acid containing the probe sequence; therefore, use of the reporter probe can increase specificity, and can allow quantification even in the presence of some non-specific nucleic acid amplification. This can allow for multiplexing, (i.e., assaying for several genes in the same reaction by using specific probes with differently colored labels), provided that all genes are amplified with similar efficiency. This method can be carried out with a nucleic acid-based probe with a fluorescent reporter (e.g. 6-carboxyfluorescein) at one end and a quencher (e.g., 6-carboxy-tetramethylrhodamine) of fluorescence at the opposite end of the probe. The close proximity of the reporter to the quencher can prevent detection of its fluorescence. Breakdown of the probe by the 5' to 3' exonuclease activity of a polymerase (e.g., Taq polymerase) can break the reporter-quencher proximity and thus can allow unquenched emission of fluorescence, which can be detected. An increase in the product targeted by the reporter probe at each PCR cycle can result in a proportional increase in fluorescence due to breakdown of the probe and release of the reporter.

The reaction can be prepared similarly to a standard PCR reaction, and the reporter probe can be added. As the reaction commences, during the annealing stage of the PCR both probe and primers can anneal to the target nucleic acid. Polymerization of a new DNA strand can be initiated from the primers, and once the polymerase reaches the probe, its 5'-3'-exonuclease can degrade the probe, physically separating the fluorescent reporter from the quencher, resulting in an increase in fluorescence. Fluorescence can be detected and measured in a real-time PCR thermocycler, and geometric increase of fluorescence can correspond to exponential increase of the product is used to determine the threshold cycle in each reaction. Relative concentrations of DNA present during the exponential phase of the reaction can be determined by plotting fluorescence against cycle number on a logarithmic scale (so an exponentially increasing quantity can give a straight line). A threshold for detection of fluorescence above background can be determined. The cycle at which the fluorescence from a sample crosses the threshold can be called the cycle threshold, Ct. Since the quantity of DNA can double every cycle during the exponential phase, relative amounts of DNA can be calculated, (e.g. a sample with a Ct of 3 cycles earlier than another has $2^3=8$ times more template). Amounts of nucleic acid (e.g., RNA or DNA) can be determined by comparing the results to a standard curve produced by a real-time PCR of serial dilutions (e.g. undiluted, 1:4, 1:16, 1:64) of a known amount of nucleic acid. The QPCR reaction can involve a dual fluorophore approach that takes advantage of fluorescence resonance energy transfer (FRET), (e.g., LIGHTCYCLER hybridization probes, where two oligonucleotide probes can anneal to the amplicon). The oligonucleotides can be designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: SCORPIONS probes, Sunrise (or AMPLIFLOUR) primers, and LUX primers and MOLECULAR BEACONS probes. The QPCR reaction can use fluorescent Taqman methodology and an instrument capable of measuring fluorescence in real time (e.g., ABI Prism 7700 Sequence Detector). The Taqman reaction can use a hybridization probe labeled with two different fluorescent dyes. One dye can be a reporter dye (6-carboxyfluorescein), the other can be a quenching dye (6-carboxy-tetramethylrhodamine). When the probe is intact, fluorescent energy transfer can occur and the reporter dye fluorescent emission can be absorbed by the quenching dye. During the extension phase of the PCR cycle, the fluorescent hybridization probe can be cleaved by the 5'-3' nucleolytic activity of the DNA polymerase. On cleavage of the probe, the reporter dye emission can no longer transferred efficiently to the quenching dye, resulting in an increase of the reporter dye fluorescent emission spectra. Any nucleic acid quantification method, including real-time methods or single-point detection methods can be use to quantify the amount of nucleic acid in the sample. The detection can be performed several different methodologies (e.g., staining, hybridization with a labeled probe; incorporation of biotinylated primers followed by avidin-enzyme conjugate detection; incorporation of 32P-labeled deoxynucleotide triphosphates, such as dCTP or dATP, into the amplified segment. The quantification can or can not include an amplification step. The quantitation can not be experimental.

Microarray

Methods for detecting sequence variants can comprise sequencing and/or detecting the variants using a microarray. Microarrays can be used for determining the expression level of a plurality of genes in a nucleic acid sample. Microarrays can be used for determining sequence identity of a plurality of sequences in a nucleic acid sample.

A microarray can comprise a substrate. Substrates can include, but are not limited to, glass and modified or functionalized glass, plastics (including acrylics, polystyrene and copolymers of styrene and other materials, polypropylene, polyethylene, polybutylene, polyurethanes, Teflon™, and the like), polysaccharides, nylon or nitrocellulose, resins, silica or silica-based materials including silicon and modified silicon, carbon, metals, inorganic glasses, and plastics.

Microarrays can comprise a plurality of polynucleotide probes. A microarray can comprise about 1, 10, 100, 1000, 5000, 10000, 20000, 30000, 40000, 50000, 60000, 70000, 80000, 90000, 100000, 110000, 120000 or more probes.

Probes can be can be at least 10, 20, 30, 40, 50, 60, 70, 80, 90, 100, 110, 120, 130, 140 nucleotides or more in length.

In some embodiments, probes can comprise sequence information for a specific set of genes and/or species. A probe can be complementary to a nucleic acid sequence encoding a host protein. A probe can be complementary to a non-coding nucleic acid sequence. A probe can be complementary to a DNA sequence. A probe can be complementary to an RNA sequence.

Probes can be immobilized on a microarray. The immobilization of polynucleotides on a solid substrate can be achieved by direct synthesis (e.g., photolithographic synthesis) of polynucleotides on a solid substrate or by immobilization (spotting) of previously synthesized polynucleotides on predetermined regions of a solid substrate. Polynucleotides can be immobilized on a microarray substrate by activating a surface of a solid substrate with a nucleophilic functional group (e.g., an amino group), coupling biomolecules (e.g., polynucleotides) activated with a good leaving group to the surface-activated solid substrate, and removing unreacted reactants. Probes can be immobilized to a bead further conjugated through a covalent or ionic attachment to a solid support. Probes can be immobilized onto a substrate using a specific film having a low conductivity and a low melting temperature, namely a gold film. An applied electromagnetic radiation can melt and can ablate the film at the impingement site. The film can be in contact with a colloidal dispersion and upon melting can generate a convective flow at the reaction site, thereby leading to adhering of an insoluble particle in the dispersion to the specifically melted site.

A microarray can analyze a nucleic acid sample comprising nucleic acids of unknown identity (e.g., test sample) by comparing the nucleic acid sample of unknown identity with a reference sample. A nucleic acid sample can be prepared from DNA (e.g., isolated DNA, genomic DNA, extrachromasomal DNA). A nucleic acid sample can be prepared from RNA. RNA can be reverse transcribed into DNA with a gene-specific primer or a universal primer. The reverse transcribed DNA (e.g., cDNA), can be treated with Rnase or base (e.g., NaOH) to hydrolyze the RNA. The cDNA can be labelled with a dye (e.g, Cy3, Cy5) with N-hydroxysuccinimide chemistry or similar labeling chemistries. Suitable fluorescent dyes can include a variety of commercial dyes and dye derivatives such as those that are denoted Alexa, Fluorescein, Rhodamine, FAM, TAMRA, Joe, ROX, Texas Red, BODIPY, FITC, Oregon Green, Lissamine and others. The reference sample can be labeled with a different dye than the test sample.

The test sample and the reference sample can be applied to a microarray to contact multiple spots simultaneously. The test sample and the reference sample can be applied to the microarray under hybridizing conditions that can allow the nucleic acids in the nucleic acid sample to bind to a complement probe on the microarray. Various reaction steps can be performed with the bound molecules in the microarray, including exposure of bound reactant molecules to washing steps. The progress or outcome of the reaction can be monitored at each spot (e.g., probe) in the microarray in order to characterize the nucleic acid sample immobilized on the chip. Microarray analysis usually can require an incubation period that can range from minutes to hours. The duration of the incubation period can be assay dependent and can be determined by a variety of factors, such as the type of reactant, degree of mixing, sample volume, target copy number, and density of the array. During the incubation period, nucleic acids in the nucleic acid sample can be in intimate contact with the microarray probes.

Detection can be performed using a confocal scanning instrument with laser excitation and photomultiplier tube detection, such as the ScanArray 3000 provided by GSI Lumonics (Billerica, Mass.). Confocal and non-confocal fluorescent detection systems can be used to implement the method such as those provided by Axon Instruments (Foster City, Calif.), Genetic MicroSystems (Santa Clara, Calif.), Molecular Dynamics (Sunnyvale, Calif.) and Virtek (Woburn, Mass.). Alternative detection systems can include scanning systems that use gas, diode and solid state lasers as well as those that use a variety of other types of illumination sources such as xenon and halogen bulbs. In addition to photomultiplier tubes, detectors can include cameras that use charge coupled device (CCD) and complementary metal oxide silicon (CMOS) chips.

The ratio of the intensities of the two dyes from the test sample and the reference sample can be compared for each probe. The strength of the signal detected from a given microarray spot can be directly proportional to the degree of hybridization of a nucleic acid in the sample to the probe at a given spot (e.g., a spot comprises a probe). Analysis of the fluorescence intensities of hybridized microarrays can include spot segmentation, background determination (and possible subtraction), elimination of bad spots, followed by a method of normalization to correct for any remaining noise. Normalization techniques can include global normalization on all spots or a subset of the spots such as housekeeping genes, prelog shifting to obtain better baseline matches, or in the case of two (or more) channel hybridizations finding the best fit that helps to give an M vs. A plot that is centered about M=0 and/or that helps to give a log(Red) vs. log(Green) plot that is centered about the diagonal with the smallest spread. The M vs. A plot can also be referred to as the R vs. I plot, where R is a ratio, such as $R=\log_2(Red/Green)$ and I is an intensity, such as $I=\log \sqrt{Red*Green}$. Scaling, shifting, best fits through scatter plots, etc. can be techniques utilized to normalize microarray datasets and to give better footing for subsequent analysis. Most of these normalization methods can have some underlying hypothesis behind them (such as "most genes within the study do not vary much").

Tagged Nucleic Acids and Methods of Use
General Overview

Figure 10:
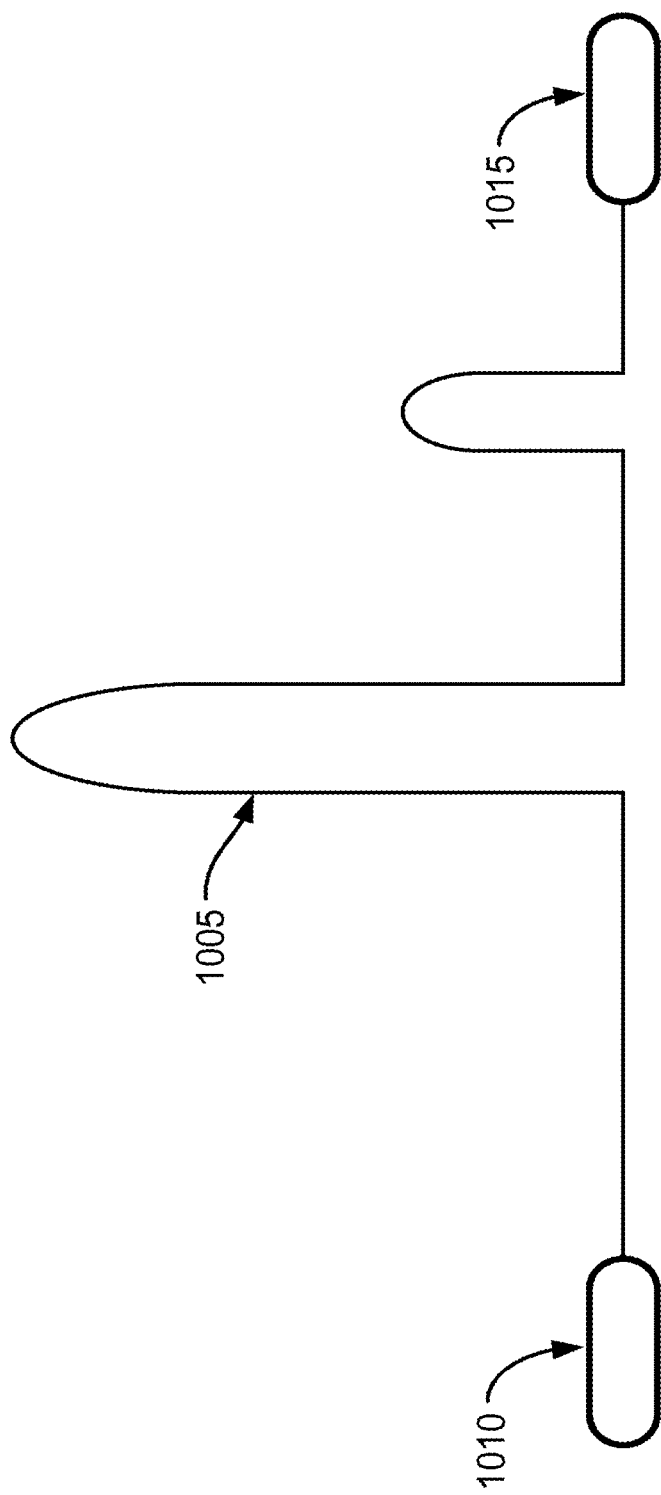
FIG. 10 depicts an exemplary tagged single guide nucleic acid-targeting nucleic acid.

The disclosure provides for kits, methods, and compositions for tagged nucleic acid-targeting nucleic acids, as described herein. FIG. 10 depicts an exemplary embodiment of nucleic acid-targeting nucleic acid 1005 of the disclosure. A nucleic acid-targeting nucleic acid can comprise one or more non-native sequences (e.g., tags) 1010/1015. A nucleic acid-targeting nucleic acid can comprise a non-native sequence 1010/1015 at either the 3' end, the 5' end, or both the 3' and 5' end of the nucleic acid-targeting nucleic acid.

In some instances, a nucleic acid-targeting nucleic acid can be nucleic acid-targeting nucleic acids as described herein, and comprise one or more non-native sequences, such as either at the 3' end, the 5' end or both the 3' and 5' ends of the nucleic acid-targeting nucleic acid.

Figure 11:
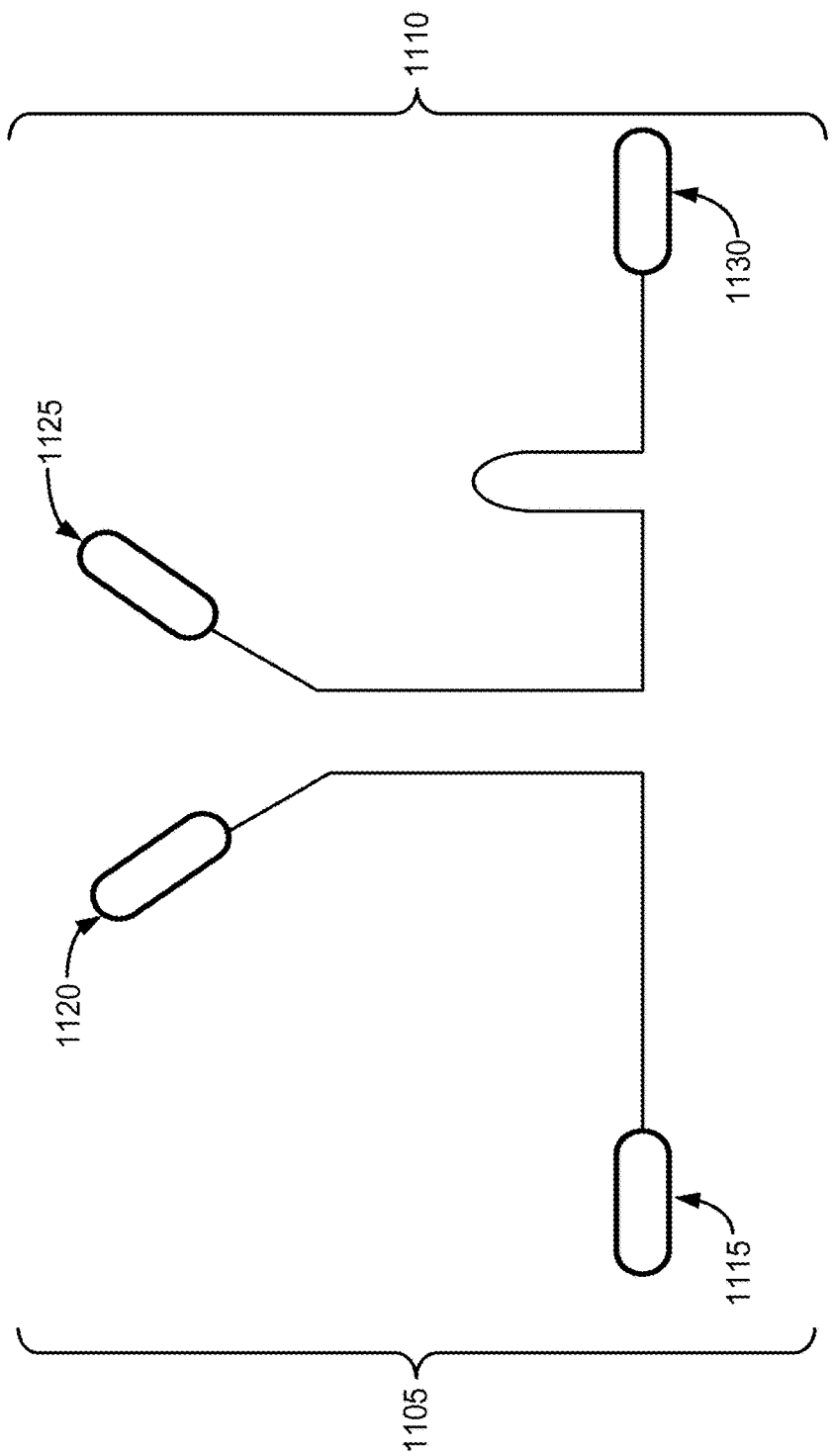
FIG. 11 depicts an exemplary tagged double guide nucleic acid-targeting nucleic acid.

In some instances, the nucleic acid-targeting nucleic acid is a double-guide nucleic acid-targeting nucleic acid as described herein, and as depicted in FIG. 11. A double-guide nucleic acid-targeting nucleic acid can comprise two nucleic acid molecules 1105/1110. A double-guide nucleic acid-targeting nucleic acid can comprise a plurality of non-native sequences 1115/1120/1125/1130. The non-native sequence can be located at the 3' end, 5' end or both 3' and 5' ends of each molecule of the nucleic acid-targeting nucleic acid. For example, the non-native sequence can be located at the 3' end, 5' end or both 3' and 5' ends of the first nucleic acid molecule 1105. The non-native sequence can be located at the 3' end, 5' end or both 3' and 5' ends of the second molecule 1110. A nucleic acid-targeting nucleic acid can comprise a one or more non-native sequences in any of the enumerated configurations in FIG. 11.

Figure 12:
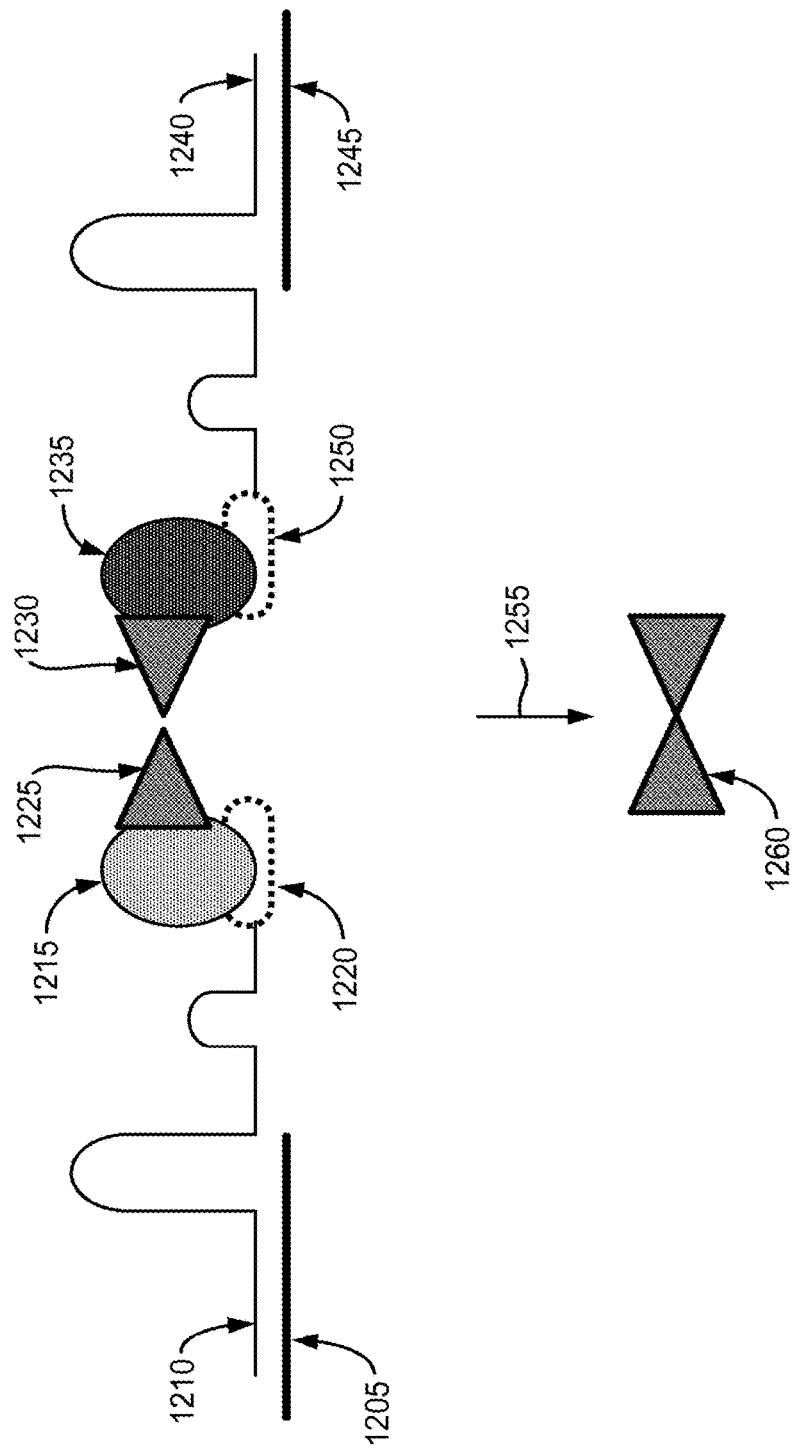
FIG. 12 illustrates an exemplary embodiment of a method of using tagged nucleic acid-targeting nucleic acid with a split system (e.g., split fluorescent system).

The disclosure provides for methods of use of tagged nucleic acid-targeting nucleic acids. The method can be performed using any of the site-directed polypeptides, nucleic acid-targeting nucleic acids, and complexes of site-directed polypeptides and nucleic acid-targeting nucleic acids as described herein. In some instances, a plurality of tagged nucleic acid-targeting nucleic acids can be contacted to a plurality of target nucleic acids. FIG. 12 depicts an exemplary method of use for tagged nucleic acid-targeting nucleic acids. A tagged nucleic acid-targeting nucleic acid can comprise a spacer 1210 that can hybridize with a target nucleic acid 1205. The nucleic acid-targeting nucleic acid can comprise a non-native sequence (e.g., tag) 1220. The non-native sequence 1220 can be an RNA-binding protein binding sequence. In some instances, the non-native sequence 1220 can be a CRISPR RNA-binding protein binding sequence. The non-native sequence 1220 can be bound by a RNA-binding protein 1215. The RNA-binding protein 1215 can comprise a non-native sequence 1225 (e.g., a fusion, i.e., the RNA-binding protein 1215 can be a fusion polypeptide). The non-native sequence (e.g., fusion) 1225 can alter the transcription of the target nucleic acid and/or an exogenous nucleic acid. The non-native sequence (e.g., fusion) 1225 can comprise a first portion of a split system.

In some embodiments, a second nucleic acid-targeting nucleic acid, comprising a second spacer 1240 that can hybridize to a second target nucleic acid 1245, can comprise a second non-native sequence (e.g., tag) 1250. The second non-native sequence (e.g., tag) 1250 can be an RNA-binding protein binding sequence. The second non-native sequence (e.g., tag) 1250 can be a CRISPR RNA-binding protein binding sequence. The second non-native sequence 1250 can be bound by a RNA-binding protein 1235. The RNA-binding protein can comprise a non-native sequence 1230 (e.g., fusion, i.e., the RNA-binding protein 1235 can be a fusion). The non-native sequence 1230 (e.g., fusion) can be a second portion of a split system.

In some instances, the first portion of the split system 1225 and the second portion of the split system 1230 can be close together in space, such that the first portion of the split system 1225 and the second portion of the split system 1230 interact 1255 to form an active split system 1260. An active split system 1260 can refer to an unsplit system, wherein the first portion and the second portion form a whole piece of the split system. Activation of the split system can indicate that two target nucleic acids 1205/1245 are close together in space.

Methods

The disclosure provides for methods for contacting a target nucleic acid with a complex comprising a site-directed polypeptide and a nucleic acid-targeting nucleic acid, and introducing one or more effector proteins, wherein the one or more effector proteins comprises a non-native sequence and can bind to the modified nucleic acid-targeting nucleic acid. An effector protein can refer to any protein with a functional effect. For example, an effector protein can comprise enzymatic activity, remodel biological molecules (e.g., folding chaperones), be a scaffolding protein, and/or bind a small molecule or metabolite. The effector protein can modify the target nucleic acid (e.g., cleavage, enzymatic modification, transcriptional modification). The methods of the disclosure provide for using the compositions of the disclosure as biosensors. For example, the complexes (e.g., comprising a modified nucleic acid-targeting nucleic acid, a site-directed polypeptide and/or an effector protein) can be used to monitor genetic mobility events, sense when sequences are close together in three-dimensional space, and conditionally alter transcription.

Genetic Mobility Event

The disclosure provides for methods for determining the occurrence of a genetic mobility event. The method can be performed using any of the site-directed polypeptides, nucleic acid-targeting nucleic acids, and complexes of site-directed polypeptides and nucleic acid-targeting nucleic acids as described herein. A genetic mobility event can comprise, for example, a translocation, a recombination, an integration, a transposition, a horizontal gene transfer event, a transformation, a transduction, a conjugation, a gene conversion event, a duplication, a translocation, an inversion, a deletion, a substitution, or any combination thereof.

A genetic mobility event can comprise a recombination between genes. The recombination can lead to deleterious gene products (e.g., the BCR-ABL recombination which can contribute to breast cancer). Recombination can include, for example, homologous recombination, non-homologous recombination (e.g., non-homologous end joining), and V(D)J recombination. Recombination can refer to chromosomal crossover. Recombination can occur during prophase I of meiosis (e.g., synapsis). Recombination can comprise double-stranded breakage of nucleic acid strands of DNA, followed by formation of a holliday junction by recombinases which can catalyze swapping of the DNA strands.

Genetic mobility events can cause disease. For example, chronic myelogenous leukemia can result from a genetic mobility event. Translocation between chromosome 9 and 22 can result in a fusion BCR-Abl1 gene, which can result in the lengthening of one chromosome (e.g., 9), and the shortening of another chromosome (e.g., 22, i.e., Philadelphia chromosome). The BCR-Abl1 translocation can lead to the production of a BCR-Abl fusion protein which can interact with receptors (e.g., interleukin-3 receptor) to promote cell division, leading to chronic myelogenous leukemia (CML). Other non-limiting exemplary genetic mobility events include BRD3-NUT, BRD4-NUT, KIAA1549-BRAF, FIG/GOPC-ROS1, ETV6-NTRK3, BCAS4-BCAS3, TBL1XR1-RGS17, ODZ4-NRG1, MALAT1-TFEB, APSCR1-TFE3, PRCC-TFE3, CLTC-TFE3, NONO-TFE3, SFPQ-TFE3, ETV6-NRTK3, EML4-ALK, EWSR1-ATF1, MN1-ETV6, CTNNB1-PLAG1, LIFR-PLAG1, TCEA1-PLAG1, FGFr1-PLAG1, CHCHD7-PLAG1, HMGA2-FHIT, HMGA-NFIB, CRTC1-MAM12, CRCT3-MAML2, EWSR1-POUF5F1, TMPRSS1-ERG, TMPRSS2-ETV4, TMPRSS2-ETV5, HNRNPA2B1-ETV1, HERV-K-ETV1, C15ORF21-ETV1, SLC45A3-ETV1, SLC45A3-ETV5, SLC45A3-ELK4, KLK2-ETV4, CANT1-ETV4, RET-PTC1/CCDC6, RET-PTC2/PRKAR1A, RET-PTC3,4/NCOA4, RET-PTC5/GOLGA5, RET-PTC6/TRIM24, RET-PTC7/TRIM33, RET-PTC8/KTN1, RET-PTC9/RFG9, RET-PTCM1, TFG-NTRK1, TPM3-NTRK1, TPR-NTRK1, RET-D10S170, ELKS-RET, HOOKS3-RET, RFP-RET, AKAP9-BRAF, and PAX8-PPARG.

Diseases that can be caused by genetic mobility events can include Charcot-Marie-Tooth disease type 1A (CMT1A), juvenile nephronophtisis (NPH), X-linked icthyosis, familial growth hormone deficiency type 1A, fascioscapulohumeral muscular dystrophy (FSHD), α-thalassemia, hemophilia A, Hunter syndrome (i.e., mucopolysaccharidosis II), Emery-Dreifuss musclar dystrophy, Hemoglobin Lepore, steroid 21-hydroxylase deficiency, glucocorticoid-suppressible hyperaldosteronism (GSH), colorblindness (e.g., visual dichromacy), autosomal recessive spinal muscular atrophy (SMA), cancer, T-cell acute lymphoblastic leukemia (T-ALL), aggressive midline carcinoma, Astrocytoma, Secretory breast carcinoma, Breast cancer, Kidney carcinoma, Mesoblastic nephroma, Lung adenocarcinoma, Melanoma, Meningioma, pleomorphic adenoma, mucoepidermoid cancer, Prostate carcinoma, Thyroid carcinoma, and acute promyelocytic leukemia.

The methods of the disclosure provide for determining the occurrence of a genetic mobility event in which a target nucleic acid can be contacted with two complexes, each complex comprising a site-directed polypeptide and a modified nucleic acid-targeting nucleic acid, and two or more effector proteins can be introduced, wherein the two or more effector proteins can bind to the modified nucleic acid-targeting nucleic acids, wherein one of the two or more effector proteins comprises a non-native sequence that is a first piece of a split system and one of the two or more effector proteins comprises a non-native sequence that is a second piece of the split system. A split system can refer to a protein complex composed of two or more protein fragments that individually are not fluorescent, but, when formed into a complex, result in a functional (that is, fluorescing) fluorescent protein complex. Individual protein fragments of a split system (e.g., split fluorescent protein) can be referred to as "complementing fragments" or "complementary fragments". Complementing fragments which can spontaneously assemble into a functional fluorescent protein complex are known as self-complementing, self-assembling, or spontaneously-associating complementing fragments. For example, a split system can comprise GFP. In a GFP split system, complementary fragments are derived from the three dimensional structure of GFP, which includes eleven anti-parallel outer beta strands and one inner alpha strand. A first fragment can comprise one of the eleven beta-strands of the GFP molecule (e.g., GFP S11), and a second fragment can comprise the remaining strands (e.g., GFP S1-10).

Prior to the genetic mobility event the target nucleic acid sequence targetable by one complex can be far apart from the target nucleic acid sequence targetable by another sequence. The distance between the two target nucleic acid sequences can comprise at least about 0.1, 0.5, 1, 2, 3, 4, 5, 6, 7, 8, 9, 10 or more Kb. The distance between the two target nucleic acid sequences can comprise at most about 0.1, 0.5, 1, 2, 3, 4, 5, 6, 7, 8, 9, 10 or more Kb. The two target nucleic acid sequences can be located on different chromosomes. The two target nucleic acid sequences can be located on the same chromosome.

Prior to the genetic mobility event the effector proteins that comprise pieces of the split system may not be able to interact with each other (e.g., the split system can be inactive). After the genetic mobility event, the target nucleic acid sequence targetable by one complex may be located in close proximity to the target nucleic acid sequence targetable by the other complex. After the genetic mobility event, the effector proteins that comprise pieces of the split system may be able to interact with each other, thereby activating the split system.

The activated split system can indicate the occurrence of the genetic mobility event. For example, if the activated split system is a fluorescent protein split system, then prior to the genetic mobility event fluorescence may not be detected in the sample. In some instances, the levels of fluorescence of the inactive split system (e.g., background levels) may be 0.01, 0.05, 0.1, 0.5, 1, 1.5, 2, 2.5, 3, 3.5 or more fold less fluorescent compared to a control sample (e.g., cell) that does not comprise the split system. In some instances, the levels of fluorescence of the inactive split system (e.g., background level) may be 0.01, 0.05, 0.1, 0.5, 1, 1.5, 2, 2.5, 3, 3.5 or more fold more fluorescent than a control sample (e.g., cell) that does not comprise the split system.

After the genetic mobility event, the two split pieces can unite to form an active fluorescent protein, and fluorescence can be detected in the sample. An active split system can result in at least about a 0.1, 0.5, 1, 2, 3, 4, 5, 6, 7, 8, 9, 10 or more fold increase in fluorescence. An active split system can result in at most about a 0.1, 0.5, 1, 2, 3, 4, 5, 6, 7, 8, 9, 10 or more fold increase in fluorescence.

Detection of a genetic mobility can be used to genotype a subject (e.g., a patient). A genotype can be indicative of a disease. The detection of a genetic mobility event can be used to diagnose a subject. The genetic and diagnostic information obtained from the methods described herein can be communicated to a subject. The genetic and diagnostic information obtained from the methods described herein can be used to develop a subject-specific treatment plan. For example, if the data obtained from the methods of the disclosure indicate that a patient has a genotype that makes them resistant to a particular therapeutic regimen, a new treatment plan can be made for the subject.

Altering Transcription

The methods of the disclosure can provide for altering the transcription of a nucleic acid. The method can be performed using any of the site-directed polypeptides, nucleic acid-targeting nucleic acids, and complexes of site-directed polypeptides and nucleic acid-targeting nucleic acids as described herein. The method provides for contacting a target nucleic acid with two complexes, each complex comprising a site-directed polypeptide and a modified nucleic acid-targeting nucleic acid, and introducing two or more effector proteins, wherein the two or more effector proteins can bind to the modified nucleic acid-targeting nucleic acids, wherein the one of the two or more effector proteins comprises a non-native sequence that is a first piece of a split transcription factor system and one of the two or more effector proteins comprises a non-native sequence that is a second piece of the split transcription factor system, and wherein an interaction between the first piece and the second piece of the split system forms a transcription factor that alters transcription of the nucleic acid.

The transcription factor can alter transcription levels of a nucleic acid and/or a target nucleic acid. Altered transcription can include increased transcription levels and/or decreased transcription levels. A transcription factor can alter transcription levels more than 2-fold, 3-fold, 5-fold, 10-fold, 50-fold, 100-fold, 1000-fold or more higher or lower than unaltered transcription levels. A transcription factor can alter transcription levels less than 2-fold, 3-fold, 5-fold, 10-fold, 50-fold, 100-fold, 1000-fold or more higher or lower than unaltered transcription levels.

The transcription factor can alter the transcription of a target nucleic acid and/or an exogenous nucleic acid. A target nucleic acid can be the nucleic acid that is contacted by the complex comprising the site-directed polypeptide and the nucleic acid-targeting nucleic acid. An exogenous nucleic acid can comprise a donor polynucleotide, a plasmid, and/or a target nucleic acid.

An exogenous nucleic acid can comprise a polynucleotide encoding genes involved in apoptosis. Suitable genes involved in apoptosis can include tumor necrosis factor (TNF), TNF-R1, TNF-R2, TNF receptor-associated death domain (TRADD), Fas receptor and Fas ligand, caspases (e.g., caspase-3, caspase-8, caspase-10), APAF-1, FADD, and apoptosis inducing factor (AIF). An exogenous nucleic acid can comprise a polynucleotide encoding genes that result in cell lysis. Suitable genes can include the Adenovirus death protein (ADP), defensins, membrane-permeabilizing lytic peptides derived from c-FLIP, procaspases, cell-penetrating peptides e.g. HIV TAT. An exogenous nucleic acid can comprise a polynucleotide encoding an antigen that can result in recruitment of immune cells to the cell location (e.g., MHC class peptides). An exogenous nucleic acid can comprise a polynucleotide encoding a nucleic-acid targeting nucleic acid that targets sequences that occur many times within the genome (e.g., microsatellites, tandem repeats), resulting in large scale genome fragmentation and cell-death.

Modification of Target Nucleic Acid

The disclosure provides for methods to modify a target nucleic acid using the nucleic acid-targeting nucleic acid of the disclosure. The method can be performed using any of the site-directed polypeptides, nucleic acid-targeting nucleic acids, and complexes of site-directed polypeptides and nucleic acid-targeting nucleic acids as described herein. For example, a target nucleic acid can be contacted with a complex comprising a site-directed polypeptide, a nucleic acid-targeting nucleic acid, and one or more effector proteins, wherein the one or more effector proteins comprises a non-native sequence and can bind to the modified nucleic acid-targeting nucleic acid. The non-native sequence can confer an enzymatic activity and/or transcriptional activity of the effector protein can modify the target nucleic acid. For example, if the effector protein comprises a non-native sequence corresponding to a methyltransferase, then the methyltransferase may be able to methylate the target nucleic acid. The modification of the target nucleic acid may occur at least 1, 2, 3, 4, 5, 6, 7, 8, 9, 10, 20, 30, 40, 50, 60, 70, 80, 90, 100 or more nucleotides away from the either the 5' or 3' end of the target nucleic acid. The modification of the target nucleic acid may occur at most 1, 2, 3, 4, 5, 6, 7, 8, 9, 10, 20, 30, 40, 50, 60, 70, 80, 90, 100 or more nucleotides away from the either the 5' or 3' end of the target nucleic acid. The modification can occur on a separate nucleic acid that does not comprise the target nucleic acid (e.g., another chromosome).

Exemplary modifications can comprise methylation, demethylation, acetylation, deacetylation, ubiquitination, deubiquitination, deamination, alkylation, depurination, oxidation, pyrimidine dimer formation, transposition, recombination, chain elongation, ligation, glycosylation. Phosphorylation, dephosphorylation, adenylation, deadenylation, SUMOylation, deSUMOylation, ribosylation, deribosylation, myristoylation, remodelling, cleavage, oxidoreduction, hydrolation, and isomerization.

Determining a Genotype and Treatment

The disclosure provides for methods for treating a disease using the nucleic acid-targeting nucleic acid of the disclosure. The method can be performed using any of the site-directed polypeptides, nucleic acid-targeting nucleic acids, and complexes of site-directed polypeptides and nucleic acid-targeting nucleic acids as described herein. For example, using the split system described herein, the presence of two or more target nucleic acids close together in space (e.g., in a genetic mobility event, in chromatin structure, or on a linear nucleic acid) can be indicative of a genotype (e.g., of a subject). A genotype can refer to the presence or absence of a particular sequence of nucleic acid, a nucleotide polymorphism (i.e., either a single nucleotide polymorphism, or a multi-nucleotide polymorphism), an allelic variant, or any other indication of the sequence of a nucleic acid. The genotype can indicate whether a patient suffers from a disease and/or is predisposed to contract a disease.

Determining a genotype can include, for example, determining if a subject comprises a mutant sequence (e.g., nucleic acid sequence comprising a mutation). In some instances, a first nucleic acid-targeting nucleic acid comprising the appropriate components as described herein to comprise a first part of a split system can be designed to target a region near a predicted mutant sequence. In some instances, a second nucleic acid-targeting nucleic acid comprising the appropriate components as described herein to comprise a second part of the split system can be designed to target a region comprising the predicted mutant sequence. If the mutant sequence does exist, the second nucleic acid-targeting nucleic acid can bind to it, and the two parts of the split system can interact. The interaction can generate a signal which can be indicative of the presence of a mutant sequence.

A genotype can be identified by a biomarker. A biomarker can be indicative of any physiological process. A biomarker can serve as a indicator of efficacy of a treatment (e.g., drug treatment). A biomarker can be a nucleic acid, a polypeptide, an analyte, a solute, a small molecule, an ion, an atom, a modification to a nucleic acid and/or polypeptide, and/or a degradation product. A biomarker can refer to relative expression levels of a nucleic acid and/or a polypeptide.

A subject-specific treatment plan may be identified from determining the genotype of the subject using the methods of the disclosure. For example, if a subject comprises a certain genotype known to be unresponsive to a particular therapy, then the subject can be treated with a different therapy. Determining of genotype can allow a subject to be selected or deselected for a clinical trial.

Determination of the genotype can be communicated from a caregiver to a subject (e.g., from a doctor to a patient, or from a person performing the genotype analysis to a customer). The communication can occur in person (e.g., in a doctor's office), over the phone, in writing, or electronically. The communication can further inform the subject of a subject-specific treatment regimen determined from the genotype of the subject.

The method can be performed more than once (e.g., iteratively) in a subject. For example, the genotype of a subject can be determined, a course of treatment can be prescribed for the subject, the genotype of the subject can be determined again. The two genotypes can be compared to determine the effectiveness of the course of treatment. The treatment plan can be altered based on the comparison of the genotypes.

Location of Sequences in Three-Dimensional Space

In some instances, the disclosure provide for a method for determining the location of sequences in three-dimensional space in a cell. The method can be performed using any of the site-directed polypeptides, nucleic acid-targeting nucleic acids, and complexes of site-directed polypeptides and nucleic acid-targeting nucleic acids as described herein. Determining the three-dimensional organization of chromatin and nucleic acid can be important for understanding gene regulation such as transcriptional activation and/or repression of genes. In some instances, the method comprises contacting a target nucleic acid with two complexes, wherein each complex binds to its cognate target nucleic acid. The complexes can comprise a site-directed polypeptide and a nucleic acid-target nucleic acid of the disclosure. Two or more effector proteins can be introduced, wherein the each of the two or more effector proteins binds to a complex. The effector proteins can be similar to the split system described above, wherein each effector protein can comprise an inactive fragment of a whole polypeptide. When the effector proteins are far apart in space, the effector proteins are inactive (e.g., no signal is detected). When the effector proteins are close enough in space to interact, they can form a detectable active polypeptide.

The effector proteins can be part of a split affinity tag system. In a split affinity tag system, the two inactive polypeptide fragments of the system can correspond to two inactive fragments of an affinity tag. When the two fragments bind together, the whole affinity tag is restored, such that the affinity tag can be detectable by a binding agent. A binding agent can refer to a molecule that can bind and purify the affinity tag. Examples of binding agents can include antibodies, antibody-conjugated beads, and small-molecule conjugated beads.

Introduction of the complexes and polypeptides of the disclosure can occur by viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery, and the like.

The cells can be cultured with the complexes for at least 1, 2, 3, 4, 5, 6, 7, 8, 9, 10 or more days. The cells can be cultured with the complexes for at most 1, 2, 3, 4, 5, 6, 7, 8, 9, 10 or more days. After an appropriate period of time (e.g., a period of time to allow the complexes to bind to their target nucleic acid), the cells can be lysed.

The cells can be crosslinked before they are lysed. Fixed or cross-linking cells can stabilize protein-DNA complexes in the cell. Suitable fixatives and cross-linkers can include, formaldehyde, glutaraldehyde, ethanol-based fixatives, methanol-based fixatives, acetone, acetic acid, osmium tetraoxide, potassium dichromate, chromic acid, potassium permanganate, mercurials, picrates, formalin, paraformaldehyde, amine-reactive NETS-ester crosslinkers such as bis[sulfosuccinimidyl] suberate (BS3), 3,3"-dithiobis[sulfosuccinimidylpropionate] (DTSSP), ethylene glycol bis[sulfosuccinimidylsuccinate (sulfo-EGS), disuccinimidyl glutarate (DSG), dithiobis[succinimidyl propionate] (DSP), disuccinimidyl suberate (DSS), ethylene glycol bis[succinimidylsuccinate] (EGS), NHS-ester/diazirine crosslinkers such as NHS-diazirine, NHS-LC-diazirine, NHS-SS-diazirine, sulfo-NHS-diazirine, sulfo-NHS-LC-diazirine, and sulfo-NHS—S S-diazirine.

Lysed cells can be contacted with a binding agent (e.g, an antibody) that is directed to bind to the affinity tag. The contacting can occur in a test-tube. The contacting can occur in a chromatographic setting (e.g., an affinity chromatography column). Contacting with the binding agent can occur for at least 1 minute, 5 minutes, 10 minutes, 15 minutes, 20 minutes, 25 minutes, 30 minutes, 1 hour, 2 hours, 3 hours, 4 hours, 5 hours, 6 hours, 7 hours, 8 hours, 9 hours, 10 hours, 15 hours, 20 hours, 25 hours, 30 hours, 35 hours, 40 hours, 45 or more hours. Contacting with the binding agent can occur for at most 1 minute, 5 minutes, 10 minutes, 15 minutes, 20 minutes, 25 minutes, 30 minutes, 1 hour, 2 hours, 3 hours, 4 hours, 5 hours, 6 hours, 7 hours, 8 hours, 9 hours, 10 hours, 15 hours, 20 hours, 25 hours, 30 hours, 35 hours, 40 hours, 45 or more hours. In some instances, contacting with a binding agent occurs prior to cell lysis.

The complexes can be purified with the binding agent. The purified complexes can be subjected to nucleic acid purification techniques to separate the target nucleic acid from the complexes. Nucleic acid purification techniques can include spin column separation, precipitation, and electrophoresis.

The nucleic acid (e.g., nucleic acid comprising the target nucleic acid) can be subjected to sequencing methodologies. The nucleic acid can be prepared for sequencing analysis by ligation of one or more adaptors. Sequenced nucleic acids can be analyzed to identify polymorphisms, diagnose a disease, determine a course of treatment for a disease, and/or determine the three-dimensional structure of the genome.

Tagged nucleic acid-targeting nucleic acids with linkers

Figure 13:
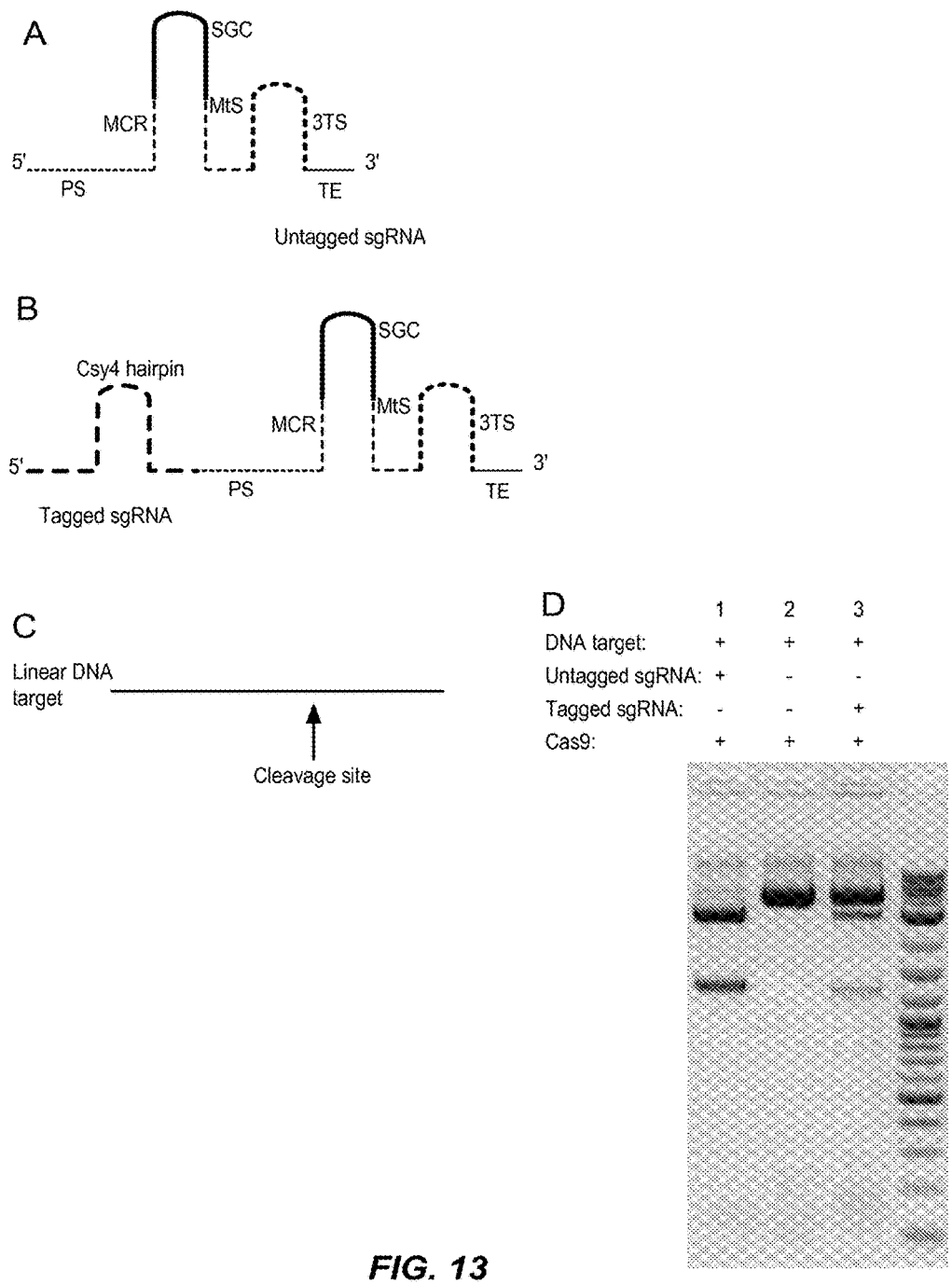
FIG. 13 depicts some exemplary data on the effect of a 5' tagged nucleic acid-targeting nucleic acid on target nucleic acid cleavage.

The disclosure provides for compositions and methods for generating and using tagged nucleic acid-targeting nucleic acids. FIG. 13A depicts an exemplary untagged nucleic acid-targeting nucleic acid. An untagged nucleic acid-targeting nucleic acid can comprise a protospacer (PS), a minimum CRISPR repeat (MCR), a single guide connector (SGC), a minimum tracrRNA sequence (MtS), a 3' tracrRNA sequence (3TS), and tracrRNA extension (TE). A tagged nucleic acid-targeting nucleic acid comprising a linker can refer to any of the nucleic acid-target nucleic acids described herein, and comprising a linker at either the 5' end, the 3' end, or both the 5' and 3' end of the nucleic acid-targeting nucleic acid.

A nucleic acid-targeting nucleic acid can comprise a non-native sequence as depicted in FIG. 13B. The non-native sequence can be referred to as a tag. The tag can be fused to either the 5' end, the 3' end or both the 5' and 3' end of the nucleic acid-targeting nucleic acid. The non-native sequence can comprise a binding sequence for an RNA-binding protein. The RNA-binding protein can be Csy4. The non-native sequence can be fused to the protospacer sequence of the nucleic acid-targeting nucleic acid.

Figure 14:
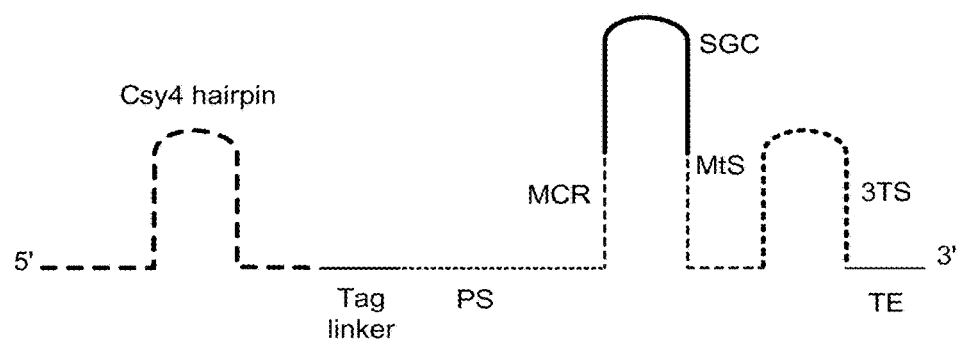
FIG. 14 illustrates an exemplary 5' tagged nucleic acid-targeting nucleic acid comprising a tag linker sequence between the nucleic acid-targeting nucleic acid and the tag.

The non-native fusion can be separated from the nucleic acid-targeting nucleic acid by a linker. FIG. 14 depicts an exemplary linker (e.g., Tag linker), separating the non-native sequence (e.g, Csy4 hairpin) from the protospacer of the nucleic acid-targeting nucleic acid. The linker sequence can be complementary to the target nucleic acid. The linker sequence can comprise at least 1, 2, 3, 4, 5, 6, 7, 8, 9, 10 or more mismatches with the target nucleic acid. The linker sequence can comprise at most 1, 2, 3, 4, 5, 6, 7, 8, 9, 10 or more mismatches with the target nucleic acid. In some instances, the fewer mismatches between the linker and target nucleic acid, the better cleavage efficiency of the Cas9:nucleic acid-targeting nucleic acid complex.

The linker sequence can be at least 1, 2, 3, 4, 5, 6, 7, 8, 9, 10, 11, 12, 13, 14, 15, 16, 17, 18, 19, 20, 25, 30, 35, 40, 45, 50, 55, 60 or more nucleotides in length. The linker sequence can be at most 1, 2, 3, 4, 5, 6, 7, 8, 9, 10, 11, 12, 13, 14, 15, 16, 17, 18, 19, 20, 25, 30, 35, 40, 45, 50, 55, 60 or more nucleotides in length.

Multiplexed Genetic Targeting Agents

General Overview

This disclosure describes methods, compositions, systems, and/or kits for muliplexed genome engineering. In some embodiments of the disclosure a site-directed polypeptide can comprise a nucleic acid-targeting nucleic acid, thereby forming a complex. The complex can be contacted with a target nucleic acid. The target nucleic acid can be cleaved, and/or modified by the complex. The methods, compositions, systems, and/or kits of the disclosure can be useful in modifying multiple target nucleic acids quickly, efficiently, and/or simultaneously. The method can be performed using any of the site-directed polypeptides, nucleic acid-targeting nucleic acids, and complexes of site-directed polypeptides and nucleic acid-targeting nucleic acids as described herein.

Figure 15:
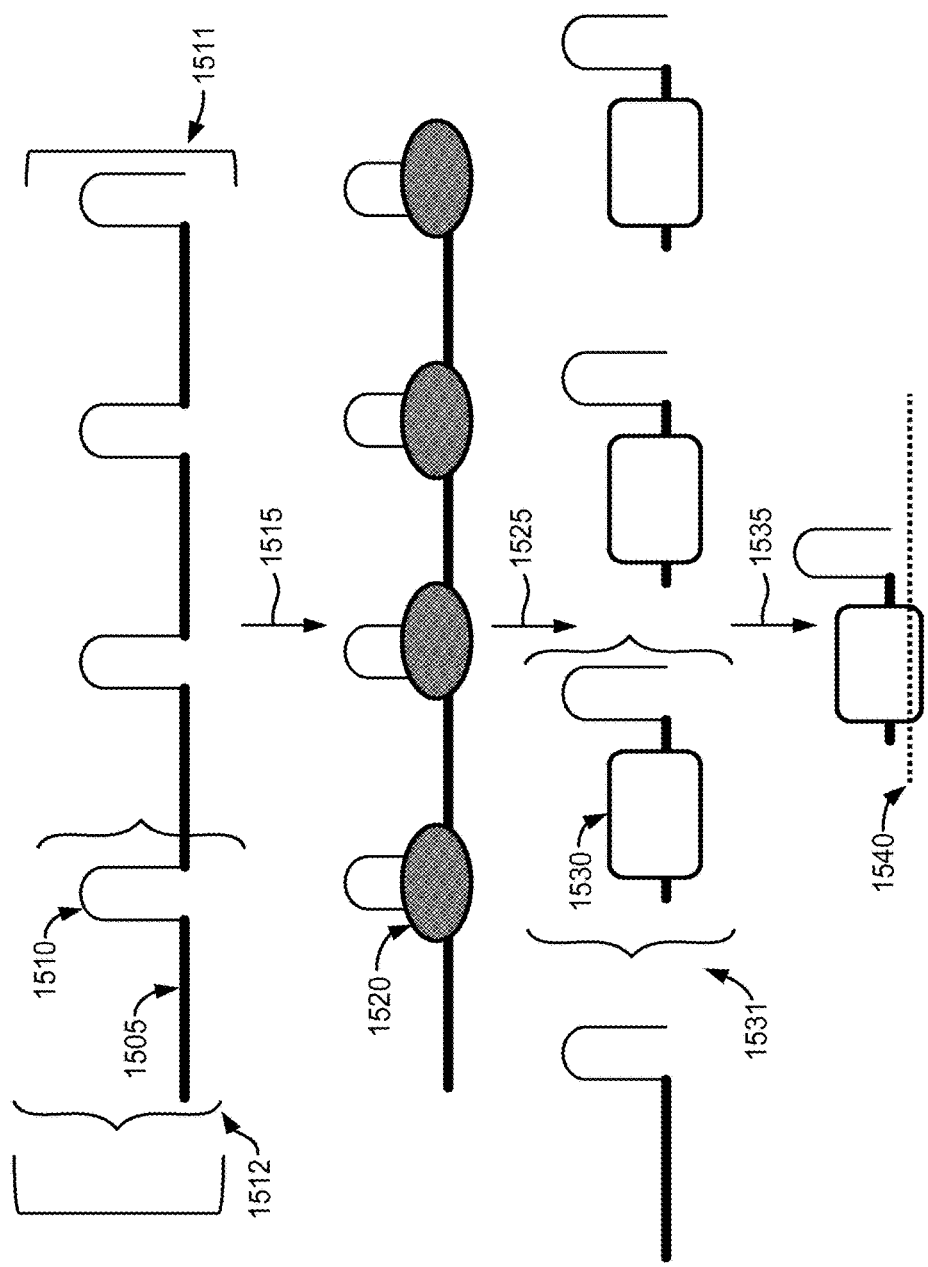
FIG. 15 depicts an exemplary embodiment of a method of multiplexed target nucleic acid cleavage.

FIG. 15 depicts an exemplary embodiment of the methods of the disclosure. A nucleic acid (e.g., a nucleic acid-targeting nucleic acid) 1505 can be fused to a non-native sequence (e.g., a moiety, an endoribonuclease binding sequence, ribozyme) 1510, thereby forming a nucleic acid module 1512. The nucleic acid module 1512 (e.g., comprising the nucleic acid fused to a non-native sequence) can be conjugated in tandem, thereby forming a multiplexed genetic targeting agent (e.g., polymodule, e.g., array) 1511. The multiplexed genetic targeting agent 1511 can comprise RNA. The multiplexed genetic targeting agent can be contacted 1515 with one or more endoribonucleases 1520. The endoribonucleases can bind to the non-native sequence 1510. The bound endoribonuclease can cleave a nucleic acid module 1512 of the multiplexed genetic targeting agent 1511 at a prescribed location defined by the non-native sequence 1510. The cleavage 1525 can process (e.g., liberate) individual nucleic acid modules 1512. In some embodiments, the processed nucleic acid modules 1512 can comprise all, some, or none, of the non-native sequence 1510. The processed nucleic acid modules 1512 can be bound by a site-directed polypeptide 1530, thereby forming a complex 1531. The complex 1531 can be targeted 1535 to a target nucleic acid 1540. The target nucleic acid 1540 can by cleaved and/or modified by the complex 1531.

Multiplexed Genetic Targeting Agents

A multiplexed genetic targeting agent can be used in modifying multiple target nucleic acids at the same time, and/or in stoichiometric amounts. A multiplexed genetic targeting agent can be any nucleic acid-targeting nucleic acid as described herein in tandem. A multiplexed genetic targeting agent can refer to a continuous nucleic acid molecule comprising one or more nucleic acid modules. A nucleic acid module can comprise a nucleic acid and a non-native sequence (e.g., a moiety, endoribonuclease binding sequence, ribozyme). The nucleic acid can be non-coding RNA such as microRNA (miRNA), short interfering RNA (siRNA), long non-coding RNA (lncRNA, or lincRNA), endogenous siRNA (endo-siRNA), piwi-interacting RNA (piRNA), trans-acting short interfering RNA (tasiRNA), repeat-associated small interfering RNA (rasiRNA), small nucleolar RNA (snoRNA), small nuclear RNA (snRNA), transfer RNA (tRNA), and ribosomal RNA (rRNA), or any combination thereof. The nucleic acid can be a coding RNA (e.g., a mRNA). The nucleic acid can be any type of RNA. In some embodiments, the nucleic acid can be a nucleic acid-targeting nucleic acid.

The non-native sequence can be located at the 3' end of the nucleic acid module. The non-native sequence can be located at the 5' end of the nucleic acid module. The non-native sequence can be located at both the 3' end and the 5' end of the nucleic acid module. The non-native sequence can comprise a sequence that can bind to a endoribonuclease (e.g., endoribonuclease binding sequence). The non-native sequence can be a sequence that is sequence-specifically recognized by an endoribonuclease (e.g., RNase T1 cleaves unpaired G bases, RNase T2 cleaves 3' end of As, RNase U2 cleaves 3' end of unpaired A bases). The non-native sequence can be a sequence that is structurally recognized by an endoribonuclease (e.g., hairpin structure, single-stranded-double-stranded junctions, e.g., Drosha recognizes a single-stranded-double-stranded junction within a hairpin). The non-native sequence can comprise a sequence that can bind to a CRISPR system endoribonuclease (e.g., Csy4, Cas5, and/or Cas6 protein). The non-native sequence can comprise a nucleotide sequence having at least or at most about 40%, 50%, 60%, 70%, 80%, 85%, 90%, 95%, 98%, 99%, or 100%, nucleotide sequence identity and/or sequence similarity to one of the following sequences:

```
                                          (SEQ ID NO: 1347)
5'-GUUCACUGCCGUAUAGGCAGCUAAGAAA-3';

(SEQ ID NO: 1348)
5'-GUUGCAAGGGAUUGAGCCCCGUAAGGGGAUUGCGAC-3';

(SEQ ID NO: 1349)
5'-GUUGCAAACCUCGUUAGCCUCGUAGAGGAUUGAAAC-3';

(SEQ ID NO: 1350)
5'-GGAUCGAUACCCACCCCGAAGAAAAGGGGACGAGAAC-3';

(SEQ ID NO: 1351)
5'-GUCGUCAGACCCAAAACCCCGAGAGGGGACGGAAAC-3';

(SEQ ID NO: 1352)
5'-GAUAUAAACCUAAUUACCUCGAGAGGGGACGGAAAC-3';

(SEQ ID NO: 1353)
5'-CCCCAGUCACCUCGGGAGGGGACGGAAAC-3';

(SEQ ID NO: 1354)
5'-GUUCCAAUUAAUCUUAAACCCUAUUAGGGAUUGAAAC-3';

(SEQ ID NO: 1348)
5'-GUUGCAAGGGAUUGAGCCCCGUAAGGGGAUUGCGAC-3';

(SEQ ID NO: 1349)
5'-GUUGCAAACCUCGUUAGCCUCGUAGAGGAUUGAAAC-3';

(SEQ ID NO: 1350)
5'-GGAUCGAUACCCACCCCGAAGAAAAGGGGACGAGAAC-3';

(SEQ ID NO: 1351)
5'-GUCGUCAGACCCAAAACCCCGAGAGGGGACGGAAAC-3';

(SEQ ID NO: 1352)
5'-GAUAUAAACCUAAUUACCUCGAGAGGGGACGGAAAC-3';

(SEQ ID NO: 1353)
5'-CCCCAGUCACCUCGGGAGGGGACGGAAAC-3';

(SEQ ID NO: 1354)
5'-GUUCCAAUUAAUCUUAAACCCUAUUAGGGAUUGAAAC-3';

(SEQ ID NO: 1355)
5'-GUCGCCCCCACGCGGGGCGUGGAUUGAAAC-3';
```

-continued

```
                                          (SEQ ID NO: 1356)
5'-CCAGCCGCCUUCGGGCGGCUGUGUGUUGAAAC-3';

(SEQ ID NO: 1357)
5'-GUCGCACUCUACAUGAGUGCGUGGAUUGAAAU-3';

(SEQ ID NO: 1358)
5'-UGUCGCACCUUAUAUAGGUGCGUGGAUUGAAAU-3';
and (SEQ ID NO: 1359)
5'-GUCGCGCCCCGCAUGGGGCGCGUGGAUUGAAA-3'.
```

In some embodiments, wherein the non-native sequence comprises an endoribonuclease binding sequence, the nucleic acid modules can be bound by the same endoribonuclease. The nucleic acid modules may not comprise the same endoribonuclease binding sequence. The nucleic acid modules may comprise different endoribonuclease binding sequences. The different endoribonuclease binding sequences can be bound by the same endoribonuclease. In some embodiments, the nucleic acid modules can be bound by different endoribonucleases.

The moiety can comprise a ribozyme. The ribozyme can cleave itself, thereby liberating each module of the multiplexed genetic targeting agent. Suitable ribozymes can include peptidyl transferase 23S rRNA, RnaseP, Group I introns, Group II introns, GIR1 branching ribozyme, Leadzyme, hairpin ribozymes, hammerhead ribozymes, HDV ribozymes, CPEB3 ribozymes, VS ribozymes, glmS ribozyme, CoTC ribozyme, an synthetic ribozymes.

The nucleic acids of the nucleic acid modules of the multiplexed genetic targeting agent can be identical. The nucleic acid modules can differ by 1, 2, 3, 4, 5, 6, 7, 8, 9, 10, 15, 20, 25, 30, 35, 40, 45, 50 or more nucleotides. For example, different nucleic acid modules can differ in the spacer region of the nucleic acid module, thereby targeting the nucleic acid module to a different target nucleic acid. In some instances, different nucleic acid modules can differ in the spacer region of the nucleic acid module, yet still target the same target nucleic acid. The nucleic acid modules can target the same target nucleic acid. The nucleic acid modules can target one or more target nucleic acids.

A nucleic acid module can comprise a regulatory sequence that can allow for appropriate translation or amplification of the nucleic acid module. For example, an nucleic acid module can comprise a promoter, a TATA box, an enhancer element, a transcription termination element, a ribosome-binding site, a 3' un-translated region, a 5' un-translated region, a 5' cap sequence, a 3' poly adenylation sequence, an RNA stability element, and the like.

Methods

The disclosure provides for methods for the modification of multiple target nucleic acids, simultaneously, through the use of a multiplexed genetic targeting agent. A site-directed polypeptide, an endoribonuclease, and a multiplexed genetic targeting agent can be introduced into a host cell. A vector of the disclosure (e.g., comprising a multiplexed genetic targeting agent, an endoribonuclease and/or a site-directed polypeptide) can be introduced into a host cell. In some instances, more than one endoribonuclease and/or multiplexed genetic targeting agent can be introduced into cells. If a multiplexed genetic targeting agent comprises different types of moieties, where the moieties are different endoribonuclease binding sequences, then one or more endoribonucleases corresponding to the types of binding sequences in the multiplexed genetic targeting agent may be introduced into cells.

Introduction can occur by any means to introduce a nucleic acid into a cell such viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery, and the like. The vector can be transiently expressed in the host cell. The vector can be stably expressed in the host cell (e.g., by stably integrating into the genome of the host cell).

In instances where a moiety comprises an endoribonuclease binding sequence, an endoribonuclease can be expressed and can bind to the endoribonuclease binding site on the multiplexed genetic targeting agent. The endoribonuclease can cleave the multiplexed genetic targeting agent into individual nucleic acid modules.

In instances where a moiety comprises a ribozyme, an endoribonuclease may not be required to be expressed in a host cell. The ribozyme can cleave itself, thereby resulting in cleavage of the multiplexed genetic targeting agent into individual nucleic acid modules.

Individual (e.g., cleaved) nucleic acid modules can comprise all, some, or none of the moiety (e.g., endoribonuclease binding sequence). For example, the liberated (e.g., processed) nucleic acid module can be subjected to exonuclease trimming and/or degradation that may result in removal of the 5' and/or 3' end of the nucleic acid module. In such instances, exonuclease trimming and/or degradation may result in the removal of all, part, or none of the moiety (e.g., endoribonuclease binding sequence).

The liberated (e.g., processed) nucleic acid module can bind to a site-directed polypeptide thereby forming a complex. The complex can be guided to a target nucleic acid by the nucleic acid-targeting nucleic acid which can hybridize with the target nucleic acid in a sequence-specific manner. Once hybridized, the site-directed polypeptide of the complex can modify the target nucleic acid (e.g., cleave the target nucleic acid). In some instances, the modification comprises introduction of a double-stranded break in the target nucleic acid. In some instances, the modification comprises introduction of a single-stranded break in the target nucleic acid.

In some embodiments, one or more donor polynucleotides and/or vectors encoding the same can introduced into the cell. One or more donor polynucleotides can be incorporated into the modified (e.g., cleaved) target nucleic acids, thereby resulting in an insertion. The same donor polynucleotide can be incorporated into multiple cleavage sites of target nucleic acids. One or more donor polynucleotides can be incorporated into one or more cleavage sites of target nucleic acids. This can be referred to as multiplex genome engineering. In some instances, no donor polynucleotide and/or vector encoding the same may be introduced into the cells. In these instances, the modified target nucleic acid can comprise a deletion.

Stoichiometric Delivery of Nucleic Acids

General Overview

Figure 16:
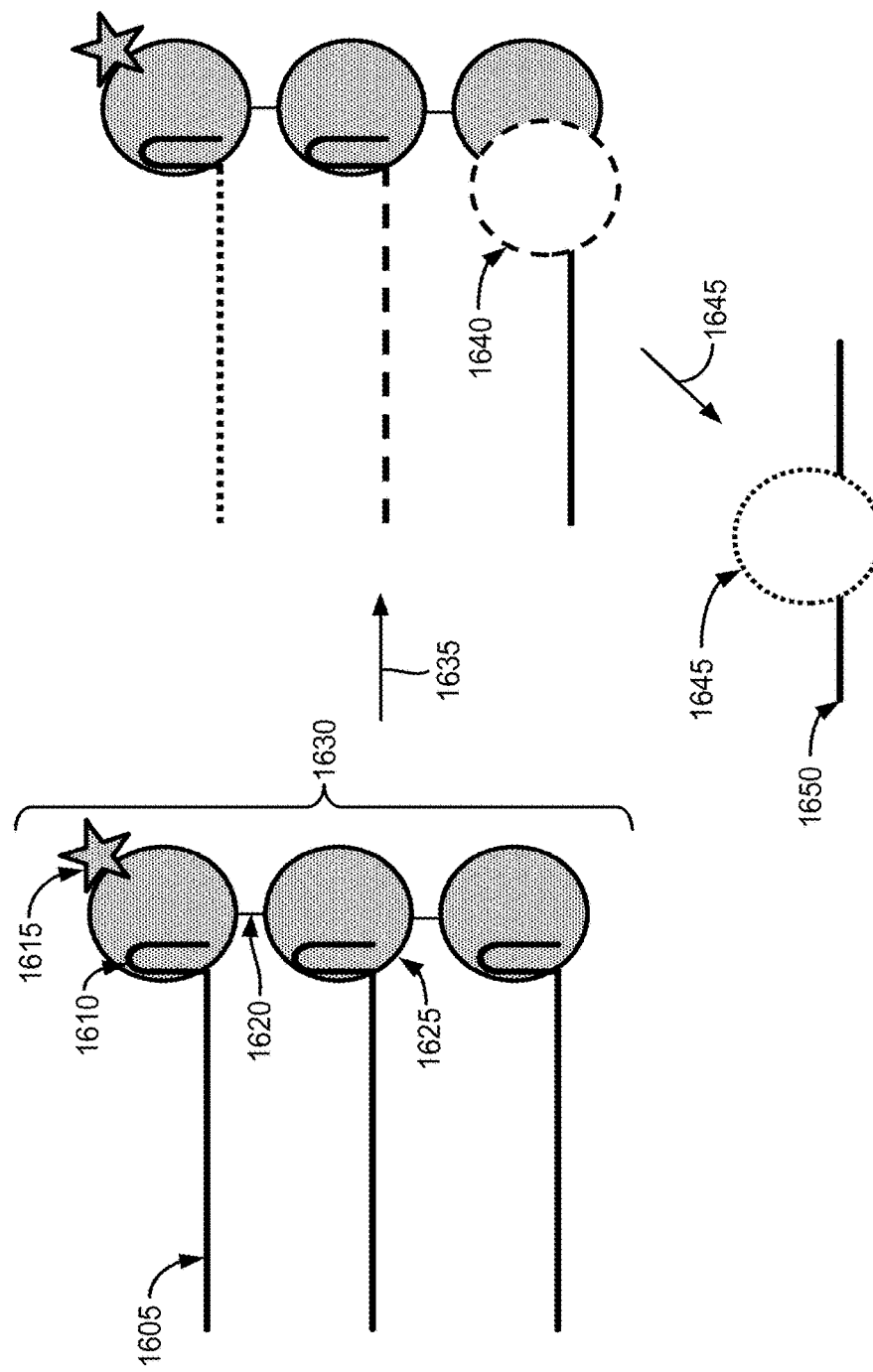
FIG. 16 depicts an exemplary embodiment of a method of stoichiometric delivery of RNA nucleic acids.

The disclosure provides for compositions, methods, and kits for stoichiometric delivery of a nucleic acid to a cell and/or subcellular localization. The stoichiometric delivery may be mediated by a complex. FIG. 16 depicts an exemplary complex for stoichiometric delivery of a plurality of nucleic acids to a cell and/or subcellular location. The complex can comprise a plurality of nucleic acids 1605. Each nucleic acid can comprise a nucleic acid-binding protein binding site 1610. The nucleic acid-binding protein binding sites 1610 can all be the same sequences, different sequences, or some can be same sequences and some can be different sequences. In some embodiments, the nucleic acid-binding protein binding sites can bind a Cash, Cas5, or Csy4 family member. The complex can comprise a tandem fusion polypeptide 1630. The tandem fusion polypeptide can comprise nucleic acid-binding proteins 1625 fused together in tandem. The nucleic acid-binding proteins can be separated by a linker 1620. The nucleic acid-binding proteins 1625 can be the same protein, can be different proteins, or some can be the same proteins and some can be different proteins. The nucleic acid-binding proteins 1625 can be Csy4 proteins. The nucleic acid-binding proteins 1625 can bind the nucleic acid-binding protein binding site 1610 on the nucleic acid 1605. The tandem fusion polypeptide 1630 can comprise a non-native sequence 1615. In some instances, the non-native sequence is a subcellular (e.g., nuclear) localization sequence. In some embodiments, the nucleic acid 1605 can encode a non-native sequence (e.g. a subcellular, (e.g., nuclear) localization sequence). The complex can be introduced 1635 into cells, wherein one or more of the nucleic acids 105 can be translated into polypeptides 1640. A translated polypeptide 1640 can bind and cleave the nucleic acid-binding protein binding site 1610 on the nucleic acid 1605. The cleavage 1645 can liberate the nucleic acid 1650 which can be a nucleic acid-targeting nucleic acid. The liberated nucleic acid 1650 can bind to a translated polypeptide 1645 (e.g., a site-directed polypeptide), thereby forming a unit. The translated polypeptide 1645 can comprise a nuclear localization signal. The unit can translocate to the nucleus, wherein the unit can be guided to a target nucleic acid hybridizable with the spacer of the liberated nucleic acid 1650. The unit can be hybridized to a target nucleic acid. The site-directed polypeptide of the unit can cleave the target nucleic acid. The cleavage of the target nucleic acid can be referred to as genome engineering. The method can be performed using any of the site-directed polypeptides, nucleic acid-targeting nucleic acids, and complexes of site-directed polypeptides and nucleic acid-targeting nucleic acids as described herein.

Figure 17:
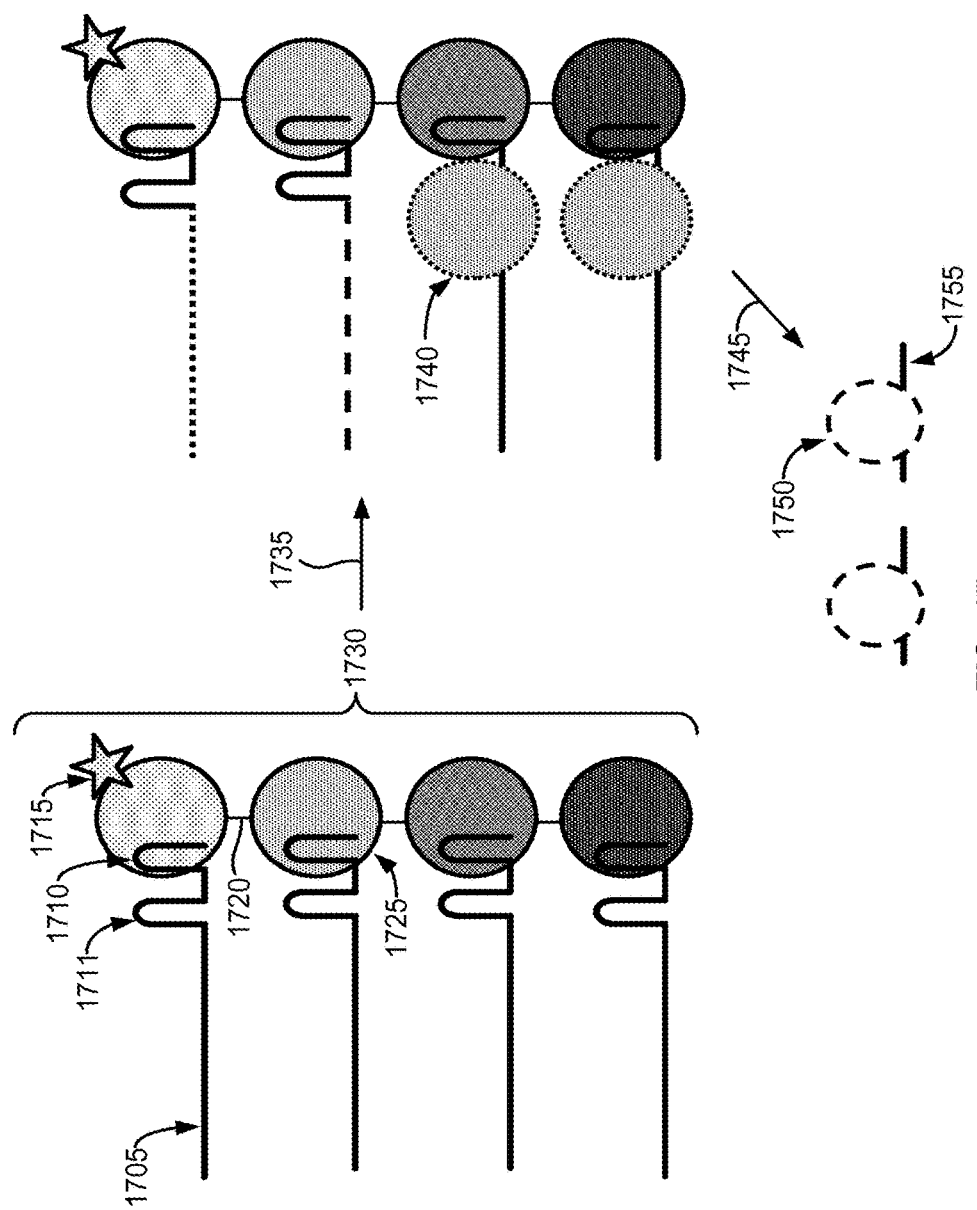
FIG. 17 depicts an exemplary embodiment of a method of stoichiometric delivery of nucleic acids.

In some embodiments, multiple nucleic acid-targeting nucleic acids can be stoichiometrically delivered to a cell and/or subcellular location. FIG. 17 depicts an exemplary complex for stoichiometric delivery of a plurality of nucleic acids. The complex can comprise a plurality of nucleic acids 1705. Each nucleic acid can comprise a plurality of nucleic acid-binding protein binding sites 1710/1711. The nucleic acid-binding protein binding sites 1710/1711 can all be the same sequences, different sequences, or some can be same sequences and some can be different sequences. In some embodiments, the nucleic acid-binding protein binding sites 1710/1711 can bind a Cas6, Cas5, or Csy4 family member. The complex can comprise a tandem fusion polypeptide 1730. The tandem fusion polypeptide can comprise nucleic acid-binding proteins 1725 fused together in tandem. The nucleic acid-binding proteins can be separated by a linker 1720. The nucleic acid-binding proteins 1725 can be the same protein, can be different proteins, or some can be the same proteins and some can be different proteins. The RNA-binding proteins 1725 can be a combination of Csy4, Cas5, and Cas6 polypeptides. The nucleic acid-binding proteins 1725 can bind the nucleic acid-binding protein binding site 1710 on the nucleic acid 1705. The tandem fusion polypeptide 1730 can comprise a non-native sequence 1715. In some instances, the non-native sequence is a subcellular (e.g., nuclear) localization sequence. In some embodiments, the nucleic acid 1705 can encode for a non-native sequence (e.g. a subcellular, (e.g., nuclear) localization sequence). The complex can be introduced into cells 1735, wherein one or more of the nucleic acids can be translated into polypeptides 1740/1750. A translated polypeptide 1740 can bind and cleave the nucleic acid-binding protein binding site 1711 on the nucleic acid 1705. The cleavage 1745 can liberate the nucleic acid 1755, which can be a nucleic acid-targeting nucleic acid and/or a donor polynucleotide. The liberated nucleic acid 1755 can bind to a translated polypeptide 1750 (e.g., a site-directed polypeptide), thereby forming a unit. In some instances, the translated polypeptide 1750 comprises a nuclear localization signal. The unit can translocate to the nucleus, wherein the unit can be guided to a target nucleic acid hybridizable with the spacer of the liberated RNA 1755. The unit can be hybridized to a target nucleic acid. The site-directed polypeptide of the unit can cleave the target nucleic acid.

Methods

The disclosure provides for methods for stoichiometric delivery of nucleic acids to a cell (e.g., stoichiometrically deliverable nucleic acids). The method can comprise binding a tandem fusion polypeptide to a plurality of stoichiometrically deliverable nucleic acids, thereby forming a complex. The complex can comprise stoichiometric amounts of the nucleic acids (e.g., the complex can comprise the plurality of nucleic acids in a prescribed ratio and/or amount). 1, 2, 3, 4, 5, 6, 7, 8, 9, 10 or more nucleic acids can be stoichiometrically delivered. In some instances, 3 stoichiometrically deliverable nucleic acids can be stoichiometrically delivered. In some instances, 4 stoichiometrically deliverable nucleic acids can be stoichiometrically delivered.

The stoichiometrically deliverable nucleic acid can encode for a polypeptide or a non-coding RNA. The polypeptide may be a CRISPR system polypeptide (e.g., a site-directed polypeptide, an endoribonuclease). The stoichiometrically deliverable nucleic acid can encode for more than one polypeptide. The stoichiometrically deliverable nucleic acid can comprise a plurality of stoichiometrically deliverable nucleic acids (e.g., in an array). The stoichiometrically deliverable nucleic acid can encode for a non-coding RNA. Examples of non-coding RNAs can include microRNA (miRNA), short interfering RNA (siRNA), long non-coding RNA (lncRNA, or lincRNA), endogenous siRNA (endo-siRNA), piwi-interacting RNA (piRNA), trans-acting short interfering RNA (tasiRNA), repeat-associated small interfering RNA (rasiRNA), small nucleolar RNA (snoRNA), small nuclear RNA (snRNA), transfer RNA (tRNA), and ribosomal RNA (rRNA). The stoichiometrically deliverable nucleic acid can be RNA.

The stoichiometrically deliverable nucleic acid can encode for a non-native sequence. In some instances, the stoichiometrically deliverable nucleic acid encodes for a non-native sequence such that when a polypeptide is translated from a stoichiometrically deliverable nucleic acid encoding a polypeptide, the polypeptide is fused to the non-native sequence (e.g., thereby generating a fusion protein). The non-native sequence can be a peptide affinity tag. The non-native sequence (e.g., peptide affinity tag) can be located at the N-terminus of the polypeptide, the C-terminus of the polypeptide, or any location within the polypeptide (e.g., a surface accessible loop). In some embodiments, the non-native sequence is a nuclear localization signal (NLS). A NLS can be monopartite or bipartite sequence. The NLS can be recognized by nuclear import machinery (e.g., importins). A NLS can be a small peptide (e.g., PKKKRKV (SEQ ID NO: 1363) of the SV40 large t-antigen). A NLS can be a polypeptide domain (e.g., acidic M9 domain of hnRNP A1).

The non-native sequence can be a nucleic acid affinity tag (e.g., nucleic acid localization signal). For example, a stoichiometrically deliverable nucleic acid encoding a DNA (e.g., a donor polynucleotide) can comprise a nucleic acid localization signal which can localize the DNA to the nucleus. Such nucleic acid localization signals can include, for example, peptide-nucleic acid (PNA) sequences.

The stoichiometrically deliverable nucleic acids can comprise regulatory sequences that can allow for appropriate translation or amplification of the nucleic acid. For example, an nucleic acid can comprise a promoter, a TATA box, an enhancer element, a transcription termination element, a DNA stability element, a ribosome-binding site, a 3' un-translated region, a 5' un-translated region, a 5' cap sequence, a 3' poly adenylation sequence, an RNA stability element, and the like.

The nucleic acid can comprise a nucleic acid-binding protein binding site. The nucleic acid-binding protein binding site can be bound by an nucleic acid-binding protein. The nucleic acid-binding protein binding site can be bound by a CRISPR polypeptide (e.g., a site-directed polypeptide, an endoribonuclease). The nucleic acid-binding protein binding site can be bound by a Cas5 or Cas6 family polypeptide. The nucleic acid-binding protein binding site can be bound by a Csy4, Cas5, or Cas6 polypeptide. Some examples of nucleic acid-binding protein binding sites can include, for example, sequences that can be bound by RNA-binding proteins such as the MS2 binding sequence, the U1A binding sequence, the boxB sequence, the eIF4A sequence, hairpins, sequences that can be bound by RNA recognition motif (RRM) domains (e.g., U1A), sequences that can be bound by double-stranded RNA binding domains (dsRBD) (e.g., Staufen), sequences that can be bound PAZ domains (e.g., PAZ, Argonaute), sequences that can be bound by PIWI domains (e.g., PIWI, MILI, MIWI, Argonaute), and the like. Some examples of nucleic acid-binding protein binding sites can include, for example, sequences that can be bound by DNA-binding proteins such as zinc fingers, a helix-turn-helix domain, a zinc finger domain, a leucine zipper (bZIP) domain, a winged helix domain, a winged helix turn helix domain, a helix-loop-helix domain, a HMG-box domain, a Wor3 domain, an immunoglobulin domain, a B3 domain, a TALE domain, and the like.

The nucleic acid can comprise one or more nucleic acid-binding protein binding sites. The nucleic acid can comprise 1, 2, 3, 4, 5, 6, 7, 8, 9, 10 or more nucleic acid-binding protein binding sites. The one or more nucleic acid-binding protein binding sites may be the same. The one or more nucleic acid-binding protein binding sites may be different. For example, the nucleic acid can comprise a Csy4 binding site and a MS2 binding site. The one or more nucleic acid-binding protein binding sites can be separated by 1, 2, 3, 4, 5, 6, 7, 8, 9, 10, 20, 30, 40, 50, 60, 70, 80, 90, 100, 110, 120, 130, 140, 150, 160, 170, 180, 190, 200, 250, 300, 350, 400, 450, 500 or more nucleotides. In some embodiments, the 3'-most nucleic acid-binding protein binding site can be bound by a tandem fusion polypeptide of the disclosure.

Tandem Fusion Polypeptide

In some embodiments, the method of the disclosure provides for binding a plurality of nucleic acids to a tandem fusion polypeptide. A tandem fusion polypeptide can comprise a plurality of nucleic acid binding proteins fused together in one polypeptide chain. A tandem fusion polypeptide can comprise 1, 2, 3, 4, 5, 6, 7, 8, 9, 10 or more nucleic acid-binding proteins. Nucleic acid-binding proteins of the tandem fusion polypeptide can bind to the nucleic acid-binding protein binding sites of the nucleic acids of the disclosure. Examples of nucleic acid-binding proteins can include MS2, U1A, boxB sequence binding proteins (e.g., zinc fingers), eIF4A, Staufen, PAZ, Argonaute, PIWI, MILI, MIWI, zinc fingers, a helix-turn-helix domain, a zinc finger domain, a leucine zipper (bZIP) domain, a winged helix domain, a winged helix turn helix domain, a helix-loop-helix domain, a HMG-box domain, a Wor3 domain, an immunoglobulin domain, a B3 domain, a TALE domain, and the like. In some embodiments, the nucleic acid-binding protein is an RNA-binding protein. The RNA-binding protein can be a member of a CRISPR system. In some embodiments, the RNA-binding protein can be a member of the Cas5 or Cas6 family of proteins. In some embodiments, the RNA-binding protein can be Csy4, Cas5, Cas6, or any combination thereof. In some embodiments, the nucleic acid-binding protein is a DNA-binding protein (e.g., a zinc finger).

In some instances, the nucleic acid-binding proteins are separated by a linker. A linker can comprise about 1, 2, 3, 4, 5, 6, 7, 8, 9, 10, 20, 30, 40, 50, 60, 70, 80, 90, 100 or more amino acids.

A tandem fusion polypeptide can comprise a non-native sequence (e.g., peptide affinity tag). The non-native sequence can comprise a nuclear localization signal (NLS) that can direct the tandem fusion polypeptide to a subcellular location (e.g., nucleus).

Each nucleic acid-binding protein of the tandem fusion polypeptide can comprise its own non-native sequence. The non-native sequence of each nucleic acid-binding protein can be the same. The non-native sequence of each nucleic acid-binding protein can be different. The non-native sequence of some of the nucleic acid-binding proteins of the tandem fusion polypeptide can be the same and the non-native sequence of some of the nucleic acid-binding proteins of the tandem fusion polypeptide can be different.

In some instances, the methods of the disclosure can provide for forming a complex comprising a tandem fusion polypeptide and a plurality of nucleic acids of the disclosure. Formation of the complex can comprise the nucleic acid-binding proteins of the tandem fusion polypeptide binding to their cognate nucleic acid-binding protein binding sequence in the nucleic acids of the disclosure. For example, a stoichiometrically deliverable nucleic acid comprising a Csy4 binding site, can bind to the Csy4 protein subunit in the tandem fusion protein. The complex can be formed outside of cells (e.g., in vitro). The complex can be formed in cells (e.g., in vivo). When a complex is formed in vitro it can be introduced into a cell by, for example, transfection, transformation, viral transduction, electroporation, injection, and the like.

The methods of the disclosure provide for therapeutic delivery of multiple nucleic acids both in vivo, in vitro, and ex vivo. The delivered nucleic acids can be used to treat a disease. For example, the delivered nucleic acids can be used in gene therapy and/or can integrate into the genome of the cell, thereby providing a therapeutic outcome. A therapeutic outcome can refer to increase or decrease in the levels of a protein, nucleic acid, or any biological molecule related to a disease such as a degradation product, small molecule, and/or ion. For example, a therapeutic outcome can comprise increasing the levels of an anti-inflammatory gene, or decreasing the levels of a protein in a pathway related to a disease. A therapeutic outcome can refer to a physiological effect. Physiological effects can include, morphological changes, metabolic changes, and/or structural changes in a cell. A therapeutic outcome can refer to changes in the modifications of a protein and/or nucleic acid, such as glycosylation, acetylation, methylation, demethylation, depurination, ubiquitinylation, and the like.

Table 2 can be a spacer that can be inserted into a nucleic acid-targeting nucleic acid. Exemplary spacers are companied by the name of the disorder and the gene involved in the disorder that is targeted by the spacers.

TABLE 2

Spacers of blood disorders.

| Gene | Spacer | Disease |
|---|---|---|
| Arylsulfatase A | AGGGTTTATTTTCTTACGCT (SEQ ID NO: 1364) | Metachromatic Leukodystrophy |
| Wiskott-Aldrich Syndrome protein | CCGAGGTCCCTAGTCCGGAA (SEQ ID NO: 1365) | Wiskott-Aldrich Syndrome |
| ATP-binding cassette D1 | CGGAGGTGGGCGGAGCCTCC (SEQ ID NO: 1366) | Adrenoleukodystrophy |
| C-C chemokine receptor type 5 | AGCTTTCTCGTCTGGGTATT (SEQ ID NO: 1367) | Human Immunodeficiency Virus |
| Hemoglobin beta subunit | GAAAATAAATGTTTTTTATT (SEQ ID NO: 1368) | Beta-thalassemia |
| Interleukin-2 recetor subunit gamma | ACAGAAACTTTATTTCTCAT (SEQ ID NO: 1369) | X-linked Severe Combined ID |
| Cystinosin | CTTTGGGAGGCCGAGGCGGG (SEQ ID NO: 1370) | MLSD cystinosis |
| Ribosomal protein S19 | TTTTAGAAACAGTATGAGAT (SEQ ID NO: 1371) | Diamon-Blackfan anemia |
| Fanconi anemia complimentation group B | ATGCACAAAATAAACAGCAG (SEQ ID NO: 1372) | Fanconi Anemia |
| Shwachman-Bodian-Diamond syndrome gene | GAGTTAGTTCACATCTACAG (SEQ ID NO: 1373) | Shwachman-Bodian-Diamond syndrome |

A therapeutic outcome can be measured by changes in the genetic makeup of the cell, the levels of biomolecules of interest in the cell, and/or the physiological changes in the cell. Measurements can be made using molecular biology techniques such as spectroscopy, spectrometry, sequencing, ELISA, microscopy, and/or x-ray crystallography. Measurements can be made using animal models, such as mouse, rats, dogs, and primates. For example, genetically modified cells of the disclosure can be introduced into mice and assessed for biological and physiological changes such as, for example, the ability to metastasize and/or differentiate.

Spacers for Blood Disorders

This disclosure provides for compositions, methods and kits, for genetic engineering of hematopoietic stem cells (HSCs).

Compositions

A HSC can comprise a site-directed polypeptide (e.g., Cas9).

A HSC can comprise a nucleic acid-targeting nucleic acid. The nucleic acid-targeting nucleic acid of the disclosure can target a gene involved in a genetic disorder. Table 3 lists exemplary genes that are involved in disorders. The genes listed in Table 3 can be genes that can be targeted by a nucleic acid-targeting nucleic acid. The nucleic acid-targeting nucleic acid of the disclosure can comprise a spacer that can target a gene listed in Table 3.

Table 2 depicts exemplary spacers of the nucleic acid-targeting nucleic acids of the disclosure. Each spacer of Methods The disclosure provides for methods for introducing a nucleic acid-targeting nucleic acid and site-directed polypeptide into an HSC. In some embodiments, the HSC is extracted from a patient prior to introduction. The extracted HSC can be purified (e.g., by apheresis). The site-directed polypeptide and/or the nucleic acid-targeting nucleic acid can be introduced into an HSC that has been purified. The site-directed polypeptide and/or the nucleic acid-targeting nucleic acid can be introduced into an HSC that has not been purified. The introduction can occur in an HSC in vitro (e.g., outside of the patient, extracted cell). In some instances, the introduction occurs in an HSC in vivo (e.g., inside of a patient, unextracted cell).

Introduction of the site-directed polypeptide and/or the nucleic acid-targeting nucleic acid of the disclosure can occur by for example, viral transduction, transfection, electroporation, optical transfection and/or chemical transfection.

Once introduced into a HSC, the nucleic acid-targeting nucleic acid of the disclosure and the site-directed polypeptide can form a complex. The complex can be guided to a target nucleic acid (e.g., the genes listed in Table 3) by the nucleic acid-targeting nucleic acid. The nucleic acid-targeting nucleic acid can hybridize with the target nucleic acid. The site-directed polypeptide can modify the target nucleic acid (e.g., by cleaving the target nucleic acid).

In some instances, the modified target nucleic acid comprises a deletion. In some instances, the modified target nucleic acid comprises an insertion of a donor polynucleotide. A donor polynucleotide, a portion of a donor polynucleotide, a portion of a donor polynucleotide or a portion of a copy of a donor polynucleotide can be inserted into a target nucleic acid. The method can be performed using any of the site-directed polypeptides, nucleic acid-targeting nucleic acids, and complexes of site-directed polypeptides and nucleic acid-targeting nucleic acids as described herein.

TABLE 3

List of Genes Involved in Diseases

| Name of Disease | Gene(s) |
| --- | --- |
| Metachromatic leukodystrophy (MLD) | Arylsulfatase A |
| Wiskott-Aldrich syndrome (WAS) | Wiskott-Aldrich Syndrome protein |
| Wiskott-Aldrich syndrome (WAS) | Leukosialin |
| Neutropenia | Wiskott-Aldrich Syndrome protein |
| Adrenoleukodystrophy | ATP-binding cassette D1 |
| Human Immunodeficiency Virus (HIV) | C-C chemokine receptor type 5 |
| Beta-thalassemia | hemoglobin subunit beta |
| Sickle-cell anemia | hemoglobin subunit beta |
| X-linked Severe Combined Immunodeficiency (X-SCID) | Interleukin-2 receptor subunit gamma |
| Multisystemic Lysosomal Storage Disorder cystinosis | Cystinosin |
| Diamond-Blackfan anemia | Ribosomal protein S19 |
| Fanconi Anemia | Fanconi anemia complementation groups A, B and C |
| Shwachman-Bodian-Diamond syndrome | SBDS gene |
| Gaucher's disease | Glucocerebrosidase |
| Hemophilia A | Anti-hemophiliac factor OR Factor VIII |
| Hemophilia B | Christmas factor, Serine protease, Factor IX |
| Adenosine deaminase deficiency (ADA-SCID) | Adenosine deaminase |
| GM1 gangliosidoses | beta-galactosidease |
| Glycogen storage disease type II, Pompe disease, acid maltase deficiency | acid alpha-glucosidase |
| Niemann-Pick disease, SMPD1-associated (Types A and B) | Sphingomyelin phosphodiesterase 1 OR acid sphingomyelinase |
| Krabbe disease, globoid cell leukodystrophy, galactosylceramide lipidosis | Galactosylceramidase OR galactercerebrosidease |
| Multiple Sclerosis (MS) | Human leukocyte angitens DR-15, DQ-6, DRB1 |

Computational Methods

The disclosure provides for computational methods to identify spacers for nucleic acid-targeting nucleic acids. The computational method can comprise scanning the nucleic acid sequence of a genome for a protospacer adjacent motif. Upon finding a protospacer adjacent motif, the program can automatically count between 10-30 nucleotides upstream of the protospacer adjacent motif. The 10-30 nucleotides upstream of the protospacer adjacent motif can constitute a putative spacer sequence. In other words, the 10-30 nucleotides upstream of the protospacer adjacent motif in the genome can correspond to a target nucleic acid, and a sequence complementary to the target nucleic acid can be referred to as a spacer.

The program can test every sequence iteration of the putative spacer sequence to ascertain how effective the sequence will be as a spacer in a nucleic acid-targeting nucleic acid. For example, the program can take each iteration of the putative spacer sequence and perform an in silico secondary structure prediction on the sequence. The secondary structure prediction can comprise appending the putative spacer sequences to a nucleic acid-targeting nucleic acid backbone (e.g., the nucleic acid-targeting nucleic acid without the spacer). The secondary structure prediction can perform a secondary structure prediction analysis of the docked putative spacer sequence in the nucleic acid-targeting nucleic acid backbone. Secondary structure prediction analysis can comprise, for example, predicting which nucleotides may form duplexes, hairpins, which nucleotides are unstructured, and/or which nucleotides may be unpaired.

The computational method can comprise implementing a folding test on each putative spacer sequence that has undergone secondary structure prediction analysis. The folding test can comprise in silico folding of the nucleic acid-targeting nucleic acid comprising the putative spacer sequence. The nucleic acid-targeting nucleic acid and putative spacer sequence can either pass or fail the folding test.

To pass the folding test, the secondary structure of the backbone nucleic acid-targeting nucleic acid may need to be conserved, less than 5, 4, 3, 2, or 1 nucleotide in the spacer hybridize with nucleotides outside of the spacer, and other second structure in the spacer is contained within the spacer.

Seamless Reporter Selection

General Overview

This disclosure describes methods, compositions, systems and kits for genetic modification of cells and selection of such genetically modified cells by seamless incorporation, detection and excision of a reporter element. In some embodiments of the disclosure, a donor polynucleotide can comprise a nucleic acid to be introduced to a cell genome (here called the genetic element of interest) as well as a nucleic acid sequence encoding a reporter element (e.g. GFP), a site-directed polypeptide and two nucleic acid-targeting nucleic acids. Either the site-directed polypeptide, the nucleic acid-targeting nucleic acids, and/or all three may be controlled by an inducible promoter. A site-directed polypeptide and a nucleic acid-targeting nucleic acid may form a complex which can target a site in the cell genome by hybridization of the nucleic acid targeting nucleic acid to a target nucleic acid in the genome. The site-directed polypeptide of the complex may cleave the target nucleic acid. The donor polynucleotide can be inserted into the cleaved target nucleic acid. After introduction of a double strand break (or single strand break) at the target site in the presence of the donor polynucleotide, the population of recipient cells may be screened for the presence of the reporter molecule as a proxy for the presence of the genetic element of interest. After isolation of reporter molecule-containing cells, the reporter element can be excised by induction of the site-directed polypeptide and/or nucleic acid-targeting nucleic acid expression. The nucleic acid-targeting nucleic acids can target the 5' and 3' ends of the reporter element and can result in the excision of the reporter element. The method can be performed using any of the site-directed polypeptides, nucleic acid-targeting nucleic acids, and complexes of site-directed polypeptides and nucleic acid-targeting nucleic acids as described herein.

Figure 18:
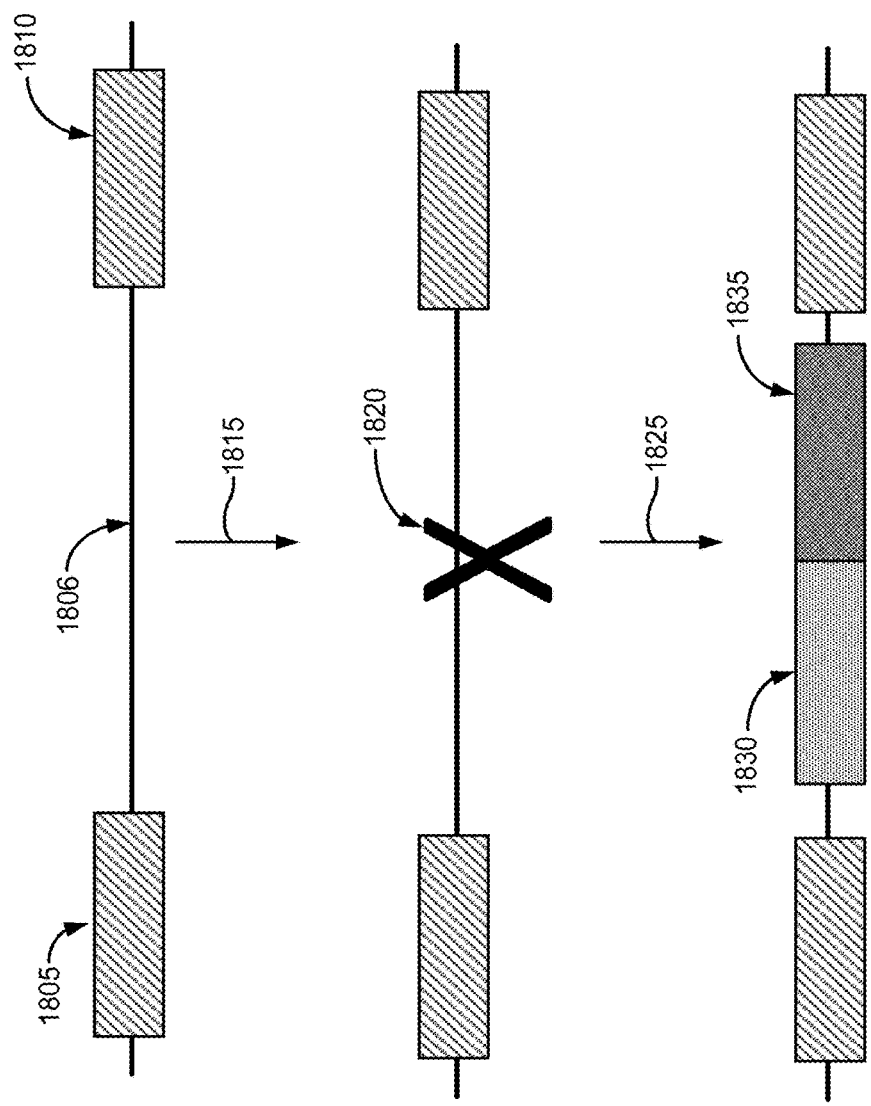
FIG. 18 depicts an exemplary embodiment of seamless insertion of a reporter element into a target nucleic acid using a site-directed polypeptide of the disclosure.

FIG. 18 depicts an exemplary embodiment of the methods of the disclosure. A nucleic acid can comprise a plurality of genetic elements 1805/1810. The genetic elements 1805 and 1810 can be, for example, genes, non-coding nucleic acids, introns, exons, DNA and/or RNA. The genetic elements 1805 and 1810 can be parts of the same gene. In between the genetic elements can be a target nucleic acid 1806 suitable for genetic engineering. A site-directed polypeptide and a nucleic acid-targeting nucleic acid of the disclosure can form a complex which can target 1815 the target nucleic acid

1806. The site-directed polypeptide of the complex can cleave 1820 the target nucleic acid 1806. A donor polynucleotide can be inserted 1825 into the cleaved target nucleic acid 1806. The donor polynucleotide can comprise a genetic element of interest 1830. The genetic element of interest 1830 can be a gene. The donor polynucleotide can also comprise a reporter element 1835. The donor polynucleotide can also comprise a polynucleotide sequence encoding a site-directed polypeptide and one or more nucleic acid-acid targeting nucleic acid. In some instances, the polynucleotide encoding the site-directed polypeptide and the one or more nucleic acid-targeting nucleic acids encodes two nucleic acid-targeting nucleic acids. The polynucleotide sequence encoding the site-directed polypeptide and the nucleic acid targeting nucleic acid can be operably linked to an inducible promoter. Insertion of the donor polynucleotide into the target nucleic acid 1806 can result in the expression of the reporter element 1835. The reporter element 1835 can be used as a way to select cells that comprise the donor polynucleotide.

Figure 19:
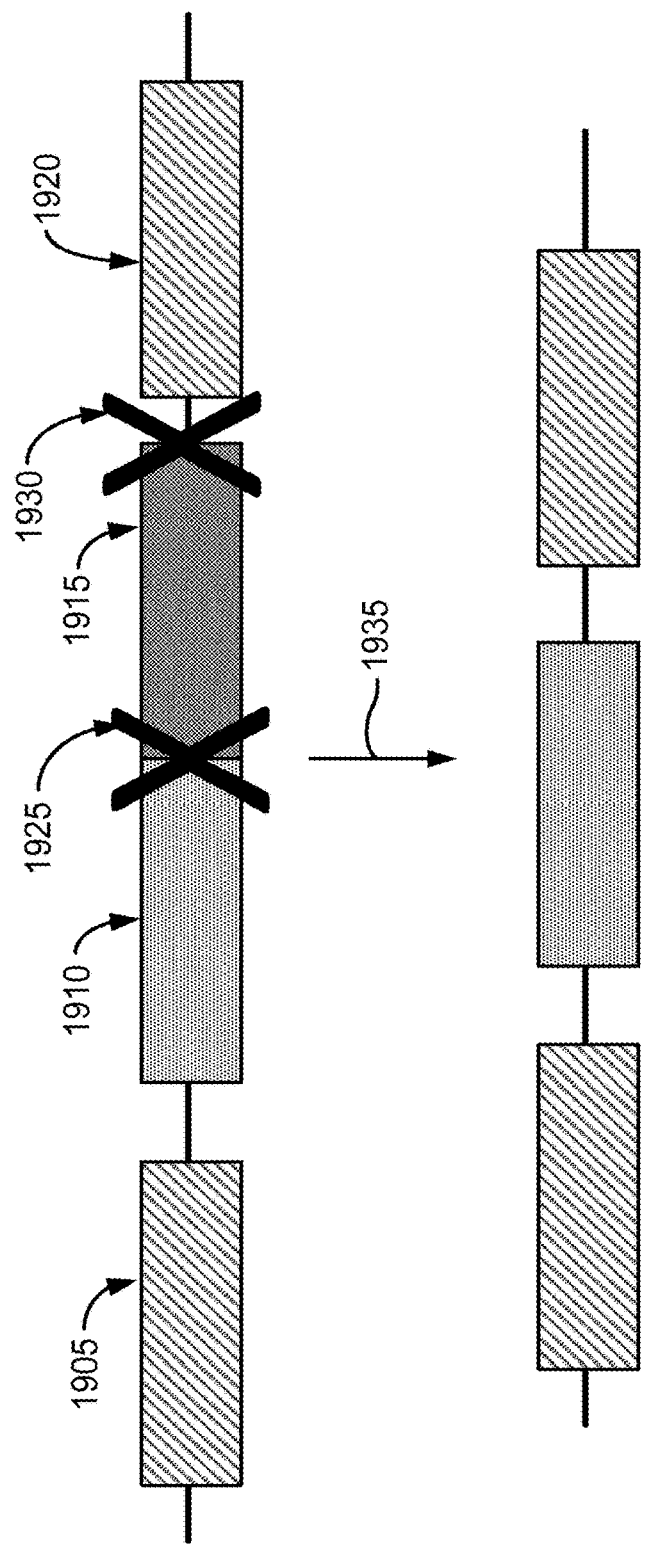
FIG. 19 depicts an exemplary embodiment for removing a reporter element from a target nucleic acid.

FIG. 19 depicts an exemplary embodiment for the removal of the reporter element 1915 from the target nucleic acid. A target nucleic acid can comprise a plurality of genetic elements 1905/1920. The reporter element 1915 can be fused to a genetic element of interest 1910. Expression of the reporter gene 1915 can be induced which can result in the production of a site-directed polypeptide and one or more nucleic acid-targeting nucleic acids. The site-directed polypeptide can form complexes with the nucleic acid-targeting nucleic acids. The complexes can be guided to the reporter element 1915 by the nucleic acid-targeting nucleic acid of the complex. One of the two nucleic acid-targeting nucleic acids can target 1925 the 5' end of the reporter element 1915. One of the two nucleic acid-targeting nucleic acids can target 1930 the 3' end of the reporter element 1915. The targeted ends of the reporter element 1915 can be cleaved by the site-directed polypeptide of the complex, thereby excising 1935 the reporter element 1915. The target nucleic acid can comprise the genetic element of interest 1910 portion of the donor polynucleotide. The nucleic acid-targeting nucleic acids can be designed such that the donor polynucleotide is excised (including the genetic element of interest).

Methods

The present disclosure provides for methods of selecting cells using a reporter element and excision of the reporter element. A site-directed polypeptide, an endoribonuclease, a nucleic acid targeting nucleic acid, a donor polynucleotide and/or a nucleic acid-targeting nucleic acid can be introduced into a cell. The donor polynucleotide may include one or more genetic elements of interest. The donor polynucleotide may include one or more reporter elements. The donor polynucleotide includes one or more genetic elements of interest and one or more reporter elements. More than one site-directed polypeptide, endoribonuclease, donor polynucleotide and and/or nucleic acid-targeting nucleic acid can be introduced into a cell. In some instances, the cell already expresses a site-directed polypeptide, and/or a nucleic acid-targeting nucleic acid. In some instances, the site-directed polypeptide, and/or nucleic acid targeting nucleic acid are encoded on a plasmid. In some instances, the site-directed polypeptide, and/or nucleic acid targeting nucleic acid is encoded on more than one plasmid. In some instances, more than one site-directed polypeptide or nucleic acid encoding a site-directed polypeptide is introduced into the cell. In some instances, the cell is a cell lysate.

Introduction can occur by any means to introduce a nucleic acid into a cell such as viral or bacteriophage infection, transfection, conjugation, protoplast fusion, lipofection, electroporation, calcium phosphate transfection, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery, and the like. The vector can be transiently expressed in the host cell. The vector can be stably expressed in the host cell (e.g., by stably integrating into the genome of the host cell).

A nucleic acid targeting nucleic acid can bind to a nucleic acid characterized by a particular target sequence and/or any sequence homologous to a particular sequence. The target sequence can be part or all of a gene, a 5' end of a gene, a 3' end of a gene, a regulatory element (e.g. promoter, enhancer), a pseudogene, non-coding DNA, a microsatellite, an intron, an exon, chromosomal DNA, mitrochondrial DNA, sense DNA, antisense DNA, nucleoid DNA, chloroplast DNA or RNA among other nucleic acid entities.

The site-directed polypeptide can cleave the target nucleic acid bound by a nucleic acid targeting nucleic acid. The site-directed polypeptide may not cleave the target nucleic acid. In some instances, an endoribonuclease cleaves the target nucleic acid. The endoribonuclease can be encoded by the vector. The endoribonuclease can be encoded by the donor polynucleotide. The endoribonuclease can be present in the cell. Expression of the endoribonuclease and/or site-directed polypeptide can be induced by a conditional promoter. A donor polynucleotide can be incorporated in the target nucleic acid at the site where it was cleaved.

Excision

The methods disclosed herein may further comprise excision of all, some or none of the reporter element. A first nucleic acid-targeting nucleic acids of the reporter element can target the 5' end of the reporter element. A second nucleic acid-targeting nucleic acids of the reporter element can target the 3' end of the reporter element. A nucleic acid-targeting nucleic acid can target both the 5' and 3' ends of the reporter element. A nucleic acid-targeting nucleic acid can target two sequences in the reporter element and/or donor polynucleotide. The two target sequences can be at least about 70, 75, 80, 85, 90, 91, 92, 93, 94, 95, 96, 97, 98, 99 or 100% identical. The two target sequences can be at most about 70, 75, 80, 85, 90, 91, 92, 93, 94, 95, 96, 97, 98, 99 or 100% identical. When the nucleic acid-targeting nucleic acids of the reporter element are expressed, they may form a complex with a site-directed polypeptide and target the 5' and 3' ends of the reporter element by hybridizing to a complementary region on the 5' and 3' ends of the reporter element. Hybridization of the complex with the reporter element can result in cleavage of all, some or none of the reporter element. The cleaved nucleic acid can be rejoined by, for example, non-homologous end-joining. The rejoined nucleic acid may not introduce a deletion or insertion. The rejoined nucleic acid may introduce a deletion or insertion. The cleaved nucleic acid can be rejoined by, for example, homologous recombination. Homologous recombination can be used to rejoin a cleaved nucleic acid when the target nucleic acid sites are substantially identical.

Screening

The methods disclosed herein may further comprise excising a reporter element from a selected cell, thereby forming a second cell; and screening the second cell. Screening may comprise screening for the absence of all or some of the reporter element. Screening can include fluorescence-activated cell-sorting (FACS), wherein cells expressing a fluorescent protein encoded for by the reporter element are separated from cells that do not express a fluorescent protein. Cells may be contacted with fluorescent protein, fluorescent probe or fluorochrome conjugated antibodies that bind proteins encoded for by the reporter element or genetic element and subsequently selected by FACS. Fluorochromes can include but are not limited to Cascade Blue, Pacific Blue, Pacific Orange, Lucifer yellow, NBD, R-Phycoerythrin (PE), PE-Cy5 conjugates, PE-Cy7 conjugates, Red 613, PerCP, TruRed, FluorX, Fluorescein, BODIPY-FL, TRITC, Texas Red, Allophycocyanin, APC-Cy7 conjugates (PharRed), various Alexa Fluor dyes, Cy2, Cy3, Cy3B, Cy3.5, Cy5, Cy5.5, Cy7, various DyLights, Y66H, Y66F, EBFP, EBFP2, Azurite, GFPuv, T-Sapphire, TagBFP, Cerulean, mCFP, ECFP, CyPet, Y66W, dKeima-Red, mKeima-Red, TagCFP, AmCyan1, mTFP1, S65A, Midoriishi-Cyan, GFP, Turbo GFP, TagGFP, TagGFP2, AcGFP1, S65L, Emerald, S65T, S65C, EGFP, Azami-Green, ZaGreenl, Dronpa-Green, TagYFP, EYFP, Topaz, Venus, mCitirine, YPet, Turbo YFP, PhiYFP, PhiYFPm, ZaYellowl, mBanana, Kusabira-Orange, mOrange, mOrane2, mKO, TurboRFP, tdTomato, DsRed-Express2, TagRFP, DsRed monomer, DsRed2, mStrawberry, Turbo FP602, AsRed2, mRFP1, J-Red, mCherry, HcRedl, mKate2, Katushka, mKate, TurboFP635, mPlum, mRaspberry, mNeptune, E2-Crimson.

Cells may be contacted with antibodies that bind peptide affinity tags encoded for by the reporter element or genetic element and subsequently can be selected by immunomagnetic beads which recognize the antibodies. Screening may comprise staining cells by adding X-gal when the reporter element or genetic element encodes b-galactosidase. Screening may comprise manual sorting (e.g. diluting cell suspensions) and microscopy (e.g. fluorescence microscopy). Screening may comprise high-content screening.

Reporter elements may encode drug resistance genes, thereby allowing for selection of cells containing the reporter element by the addition of drugs, the drugs killing the cells that do not express the reporter element. Such drug can include, but are not limited to erythromycin, clindamycin, chloramphenicol, gentamicin, kanamycin, streptomycin, tetracycline, the combination quinupristin-dalfopristin, enrofloxacin, vancomycin, oxacillin, penicillin, sulfonamide sulfisoxazole, trimethoprim, methoinine sulphoximine, methotrexate, puromycine, blasticidin, histidinol, hygromycin, zeocin, bleomycin and neomycin.

Libraries

The present disclosure provides for a library of expression vectors comprising donor polynucleotides. In some embodiments, the library can comprise expression vectors comprising polynucleotide sequences encoding for differing genetic elements of interest but the same reporter elements. In some embodiments, the library can comprise expression vectors comprising polynucleotide sequences encoding for differing genetic elements of interest and differing reporter elements. Reporter elements may differ in their nucleic acid targeting sequences (crRNA and tracrRNA). Reporter elements may differ in their reporter genes (e.g. genes encoding fluorescent proteins). The present disclosure provides for methods of using the library to generate a plurality of genetically modified cells. The present disclosure provides for methods of using the library for a high throughput genetic screen. These libraries can allow for analyzing large numbers of individual genes to infer gene function. Libraries can comprise from about 10 individual members to about $10^{12}$ individual members; e.g. a library can comprise from about 10 individual members to about $10^2$ individual members, from about $10^2$ individual members to about $10^3$ individual members, from about $10^3$ individual members to about $10^5$ individual members, from about $10^5$ individual members to about $10^7$ individual members, from about $10^7$ individual members to about $10^9$ individual members, or from about $10^9$ individual members to about $10^{12}$ individual members.

Modifying Cells (Transfection/Infection)

Methods of disclosure provide for selection of cells comprising the donor polynucleotide. In some embodiments, a method can involve contacting a target nucleic acid or introducing into a cell (or a population of cells) one or more nucleic acids comprising nucleotide sequences encoding a nucleic acid-targeting nucleic acid, a site-directed polypeptide, and/or donor polynucleotide of the disclosure. Methods for introducing a nucleic acid into a cell can include viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery, and the like. In some embodiments, contacting a target nucleic acid or introducing into a cell (or a population of cells) one or more nucleic acids may not comprise viral infection. In some embodiments, contacting a target nucleic acid or introducing into a cell (or a population of cells) one or more nucleic acids may not comprise bacteriophage infection. In some embodiments, contacting a target nucleic acid or introducing into a cell (or a population of cells) one or more nucleic acids may not comprise transfection.

Engineered Nucleic Acid-Targeting Nucleic Acids

Engineered P-Domains

A nucleic acid-targeting nucleic acid can be engineered (e.g., comprise modifications). An engineered nucleic acid-targeting nucleic acid can refer to any of the engineered nucleic acid-targeting nucleic acids as described herein. For example, an engineered nucleic acid-targeting nucleic acid can comprise a minimum CRISPR repeat, a minimum tracrRNA, and a 3' tracrRNA. A P-domain of a nucleic acid-targeting nucleic acid can interact with region of a site-directed polypeptide. A P-domain can interact with a plurality of regions of a site-directed polypeptide. A P-domain can interact with a plurality of regions of a site-directed polypeptide wherein at least one of the regions interacts with a PAM in a protospacer adjacent motif. Examples of these regions can include amino acids 1096-1225, and 1105-1138 of Cas9 in *S. pyogenes*.

A modification can be introduced into the P-domain. A P-domain can comprise at least about 1, 2, 3, 4, 5, 6, 7, 8, 9, 10, 15, 20, 25, or 30 or more adjacent nucleotides. A P-domain can comprise at most about 1, 2, 3, 4, 5, 6, 7, 8, 9, 10, 15, 20, 25, or 30 or more adjacent nucleotides. A P-domain can start one nucleotide 3' of the last paired nucleotide in the duplex comprising the minimum CRISPR repeat and the minimum tracrRNA sequence. A P-domain can start at least about 1, 2, 3, 4, 5, 6, 7, 8, 9, 10, 15, 20, 25, or 30 or more nucleotides 3' of the last paired nucleotide in the duplex comprising the minimum CRISPR repeat and the minimum tracrRNA sequence. A P-domain can start at most about 1, 2, 3, 4, 5, 6, 7, 8, 9, 10, 15, 20, 25, or 30 or more nucleotides 3' of the last paired nucleotide in the duplex comprising the minimum CRISPR repeat and the minimum tracrRNA sequence.

An engineered P-domain can comprise at least about 1, 2, 3, 4, 5, 6, 7, 8, 9, or 10 or more mutations. An engineered P-domain can comprise at most about 1, 2, 3, 4, 5, 6, 7, 8, 9, or 10 or more mutations. The mutations can be adjacent to one another (e.g., sequential). The mutations can be separated from one another. The mutations can be separated by at least about 1, 2, 3, 4, 5, 6, 7, 8, 9, or 10 or more nucleotides. The mutations can be separated by at least about 1, 2, 3, 4, 5, 6, 7, 8, 9, or 10 or more nucleotides. Mutations to a nucleic acid-targeting nucleic acid can comprise insertions, deletions, and substitutions of nucleotides in the nucleic acid-targeting nucleic acid.

In some instances, an engineered nucleic acid-targeting nucleic acid comprises at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30% or more nucleotide identity and/or similarity to a wild-type nucleic acid-targeting nucleic acid. In some instances, an engineered nucleic acid-targeting nucleic acid comprises at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30% or more nucleotide identity and/or similarity to a wild-type nucleic acid-targeting nucleic acid.

In some instances, a CRISPR nucleic acid portion of the engineered nucleic acid-targeting nucleic acid comprises at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30% or more nucleotide identity and/or similarity to a wild-type CRISPR nucleic acid. In some instances, a CRISPR nucleic acid portion of the engineered nucleic acid-targeting nucleic acid comprises at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30% or more nucleotide identity and/or similarity to a wild-type CRISPR nucleic acid.

A tracrRNA nucleic acid portion of the engineered nucleic acid-targeting nucleic acid can comprise at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30% or more nucleotide identity and/or similarity to a wild-type tracrRNA nucleic acid. A tracrRNA nucleic acid portion of the engineered nucleic acid-targeting nucleic acid can comprise at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30% or more nucleotide identity and/or similarity to a wild-type tracrRNA nucleic acid.

The modifications in the P-domain can be such that the engineered nucleic acid-targeting nucleic acid is newly configured to hybridize to a new PAM sequence in a target nucleic acid. The modification to the P-domain can be complementary to the PAM in the target nucleic acid. The modification to the P-domain can comprise the reverse complement of the PAM in the target nucleic acid. The new PAM can comprise at least about 1, 2, 3, 4, 5, 6, 7, 8, 9 or 10 or more nucleotides. The new PAM can comprise at most about 1, 2, 3, 4, 5, 6, 7, 8, 9 or 10 or more nucleotides. Modifications in the P domain can occur in concert with modifications to a P-domain binding and PAM-binding region of a site-directed polypeptide. These modifications can be compensatory, wherein a modified P-domain is specifically modified to bind to a modified site-directed polypeptide, wherein the modification enables the site-directed polypeptide to bind to the engineered P-domain with greater specificity.

An engineered P-domain can be engineered to bind to a new PAM (e.g., the engineered P-domain can hybridize to a new PAM). The new PAM (e.g., different PAM), can be bimodal (i.e., a bimodal PAM can comprise two separate regions of the PAM). The two separate regions of a bimodal PAM can be separated by at least about 1, 2, 3, 4, 5, 6, 7, 8, 9, or 10 or more nucleotides. The two separate regions of a bimodal PAM can be separated by at most about 1, 2, 3, 4, 5, 6, 7, 8, 9, or 10 or more nucleotides.

An engineered P-domain can be engineered to bind to a new PAM (e.g., different PAM), wherein the new PAM is trimodal. A trimodal PAM can comprise three separate regions of a PAM sequence (e.g., three separate regions that can be used in targeting a nucleic acid-targeting nucleic acid to a target nucleic acid). The three separate regions of a trimodal PAM can be separated by at least about 1, 2, 3, 4, 5, 6, 7, 8, 9, or 10 or more nucleotides. The three separate regions of a trimodal PAM can be separated by at most about 1, 2, 3, 4, 5, 6, 7, 8, 9, or 10 or more nucleotides.

An engineered nucleic acid-targeting nucleic acid can comprise at least two hairpins. A first hairpin can comprise a duplex between the minimum CRISPR repeat and the minimum tracrRNA sequence. The second hairpin can be downstream of the first hairpin. The second hairpin can start at least 1, 2, 3, 4, 5, 6, 7, 8, 9, or 10 or more nucleotides downstream of the last paired nucleotide of the first duplex. The second hairpin can start at most 1, 2, 3, 4, 5, 6, 7, 8, 9, or 10 or more nucleotides downstream of the last paired nucleotide of the first duplex. The second hairpin can comprise an engineered P-domain.

The engineered P-domain of the second hairpin can be located on one side of the duplex hairpin. The engineered P-domain of the second hairpin can be located on both sides of the duplex hairpin. The engineered P-domain of the second hairpin can comprise at least about 1, 2, 3, 4, 5, 10, or 20% of the nucleotides in the second hairpin. The engineered P-domain of the second hairpin can comprise at most about 1, 2, 3, 4, 5, 10, or 20% of the nucleotides in the second hairpin.

The second hairpin can comprise a tracrRNA (e.g., the mid-tracrRNA, or 3' tracrRNA of a nucleic acid-targeting nucleic acid). The second hairpin can comprise at least about 1, 5, 10, 15, 20, 25, 30, 35, 40, 45, or 50% or more identity to a tracrRNA. The second hairpin can comprise at most about 1, 5, 10, 15, 20, 25, 30, 35, 40, 45, or 50% or more identity to a tracrRNA.

The second hairpin comprising the engineered P-domain can be configured to de-duplex (e.g., melt, unwind). The second hairpin can de-duplex when in contact with a target nucleic acid. The second hairpin can de-duplex when in contact with a protospacer adjacent motif of a target nucleic acid.

In some instances, an engineered P-domain can be configured to hybridize to a region in a nucleic acid-targeting nucleic acid (e.g., the same nucleic acid-targeting nucleic acid comprising the engineered P-domain), and the engineered P-domain can be configured to hybridize to a target nucleic acid. In other words, the engineered P-domain can comprise a switchable sequence, in which in some instances, the P-domain is hybridized to the nucleic acid-targeting nucleic acid, thereby forming a hairpin, and in some instances the P-domain is hybridized to a PAM in a target nucleic acid.

An engineered nucleic acid-targeting nucleic acid comprising a modified P-domain can be engineered to bind to a PAM with a lower dissociation constant than a nucleic acid-targeting nucleic acid that does not comprise a modified P-domain (e.g., wild-type nucleic acid-targeting nucleic acid). An engineered nucleic acid-targeting nucleic acid comprising a modified P-domain can be engineered to bind to a PAM with a dissociation constant at least about 10, 50, 100, 150, 200, 250, 300, 350, 400, 450, 500, 550 or 600% or more lower or higher than a nucleic acid-targeting nucleic acid that does not comprise a modified P-domain.

An engineered nucleic acid-targeting nucleic acid comprising a modified P-domain can be engineered to bind to a PAM with a dissociation constant at most about 10, 50, 100, 150, 200, 250, 300, 350, 400, 450, 500, 550 or 600% or more lower or higher than a nucleic acid-targeting nucleic acid that does not comprise a modified P-domain. An engineered nucleic acid-targeting nucleic acid comprising a modified P-domain can be engineered to bind to a PAM with a dissociation constant at least about 1-fold, 2-fold, 3-fold, 4-fold, 5-fold, 10-fold, 20-fold, 30-fold, 40-fold, or 50-fold or more lower or higher than a nucleic acid-targeting nucleic acid that does not comprise a modified P-domain. An engineered nucleic acid-targeting nucleic acid comprising a modified P-domain can be engineered to bind to a PAM with a dissociation constant at most about 1-fold, 2-fold, 3-fold, 4-fold, 5-fold, 10-fold, 20-fold, 30-fold, 40-fold, or 50-fold or more lower or higher than a nucleic acid-targeting nucleic acid that does not comprise a modified P-domain.

An engineered nucleic acid-targeting nucleic acid comprising a modified P-domain can be engineered to bind to a PAM with greater specificity than a nucleic acid-targeting nucleic acid that does not comprise a modified P-domain (e.g., wild-type nucleic acid-targeting nucleic acid). Greater specificity can refer to a reduction in off-target binding (e.g., binding of the nucleic acid-targeting nucleic acid to an incorrect PAM or PAM-like sequence). For example, an engineered nucleic acid-targeting nucleic acid comprising a modified P-domain can be engineered to reduce non-specific binding by at least about 10, 50, 100, 150, 200, 250, 300, 350, 400, 450, 500, 550 or 600% or more than a nucleic acid-targeting nucleic acid that does not comprise a modified P-domain. An engineered nucleic acid-targeting nucleic acid comprising a modified P-domain can be engineered to reduce non-specific binding by at most about 10, 50, 100, 150, 200, 250, 300, 350, 400, 450, 500, 550 or 600% or more than a nucleic acid-targeting nucleic acid that does not comprise a modified P-domain. An engineered nucleic acid-targeting nucleic acid comprising a modified P-domain can be engineered to reduce non-specific binding by at least about 1-fold, 2-fold, 3-fold, 4-fold, 5-fold, 10-fold, 20-fold, 30-fold, 40-fold, or 50-fold or than a nucleic acid-targeting nucleic acid that does not comprise a modified P-domain. An engineered nucleic acid-targeting nucleic acid comprising a modified P-domain can be engineered to reduce non-specific binding by at most about 1-fold, 2-fold, 3-fold, 4-fold, 5-fold, 10-fold, 20-fold, 30-fold, 40-fold, or 50-fold or more than a nucleic acid-targeting nucleic acid that does not comprise a modified P-domain.

Engineered Bulges

An engineered nucleic acid-targeting nucleic acid can be engineered such that a modification can be introduced into the bulge region of the nucleic acid-targeting nucleic acid. A bulge is a typical nucleic acid feature that comprises unpaired nucleotides. A bulge can comprise unpaired nucleotides on each strand of the duplex that comprises the bulge. In other words, a bulge can comprise an unpaired nucleotide on the minimum CRISPR repeat strand of the duplex and an unpaired nucleotide on the minimum tracrRNA sequence strand of the duplex.

A bulge can comprise at least about 1, 2, 3, 4, 5, 6, 7, 8, 9 or 10 or more unpaired nucleotides on a first strand of a duplex in a nucleic acid-targeting nucleic acid (i.e., the minimum CRISPR repeat strand of the duplex comprising the minimum CRISPR repeat and minimum tracrRNA sequence). A bulge can comprise at most about 1, 2, 3, 4, 5, 6, 7, 8, 9 or 10 or more unpaired nucleotides on a first strand of a duplex in a nucleic acid-targeting nucleic acid (i.e., the minimum CRISPR repeat strand of the duplex comprising the minimum CRISPR repeat and minimum tracrRNA sequence). A bulge can comprise at least about 1, 2, 3, 4, 5, 6, 7, 8, 9 or 10 or more unpaired nucleotides on a second strand of a duplex in a nucleic acid-targeting nucleic acid (i.e., the minimum tracrRNA sequence strand of the duplex comprising the minimum CRISPR repeat and minimum tracrRNA sequence). A bulge can comprise at most about 1, 2, 3, 4, 5, 6, 7, 8, 9 or 10 or more unpaired nucleotides on a second strand of a duplex in a nucleic acid-targeting nucleic acid (i.e., the minimum tracrRNA sequence strand of the duplex comprising the minimum CRISPR repeat and minimum tracrRNA sequence). A bulge can comprise one unpaired nucleotide on the minimum CRISPR RNA sequence and 3 unpaired nucleotides on the minimum tracrRNA sequence strand.

The nucleotides adjacent to an unpaired nucleotide can be a nucleotide that forms a wobble base pairing interaction. Wobble base pairing interactions can include guanine-uracil, hypoanthine-uracil, hypoxanthine-adenine, and hypoxanthine-cytosine. At least 1, 2, 3, 4, or 5 or more nucleotides adjacent to an unpaired nucleotide can form a wobble pairing. At most 1, 2, 3, 4, or 5 or more nucleotides adjacent to an unpaired nucleotide can form a wobble pairing.

An engineered bulge can comprise at least about 1, 2, 3, 4, 5, 6, 7, 8, 9, or 10 or more mutations. An engineered bulge can comprise at most about 1, 2, 3, 4, 5, 6, 7, 8, 9, or 10 or more mutations. The mutations can be adjacent to one another (e.g., sequential). The mutations can be separated from one another. The mutations can be separated by at least about 1, 2, 3, 4, 5, 6, 7, 8, 9, or 10 or more nucleotides. The mutations can be separated by at least about 1, 2, 3, 4, 5, 6, 7, 8, 9, or 10 or more nucleotides. Mutations to a nucleic acid-targeting nucleic acid can comprise insertions, deletions, and substitutions of nucleotides in the nucleic acid-targeting nucleic acid.

A bulge of an engineered nucleic acid-targeting nucleic acid can comprise at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30% or more nucleotide identity and/or similarity to a wild-type nucleic acid-targeting nucleic acid. A bulge of an engineered nucleic acid-targeting nucleic acid can comprise at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30% or more nucleotide identity and/or similarity to a wild-type nucleic acid-targeting nucleic acid.

One strand of the bulge can be mutated and the other strand is not mutated. In other words, in some instances, the sequence of the bulge on the minimum CRISPR RNA strand is the same as a wild-type nucleic acid-targeting nucleic acid, and the sequence of the bulge on the minimum tracrRNA sequence is mutated. In other words, the sequence of the bulge on the minimum CRISPR RNA strand is mutated, and the sequence of the bulge on the minimum tracrRNA sequence is the same as a wild-type nucleic acid-targeting nucleic acid.

The modifications in the bulge can be such that the engineered nucleic acid-targeting nucleic acid is newly configured to bind to a new site-directed polypeptide. The new site-directed polypeptide can comprise at least about 5, 10, 15, 20, 25, 30, 35, 40, 45 or 50% or more amino acid sequence identity to a wild-type site-directed polypeptide. The new site-directed polypeptide can comprise at most about 5, 10, 15, 20, 25, 30, 35, 40, 45 or 50% or more amino acid sequence identity to a wild-type site-directed polypeptide. The new site-directed polypeptide can be a homologue of Cas9. The new site-directed polypeptide can be an orthologue of Cas9. The new site-directed polypeptide can be a chimera of two different site-directed polypeptides. The new site-directed polypeptide can comprise a mutation as disclosed herein.

An engineered nucleic acid-targeting nucleic acid comprising a modified bulge can be engineered to bind to a site-directed polypeptide with a lower or higher dissociation constant than a nucleic acid-targeting nucleic acid that does not comprise a modified bulge (e.g., wild-type nucleic acid-targeting nucleic acid). An engineered nucleic acid-targeting nucleic acid comprising a modified bulge can be engineered to bind to a site-directed polypeptide with a dissociation constant at least about 10, 50, 100, 150, 200, 250, 300, 350, 400, 450, 500, 550 or 600% or more lower or higher than a nucleic acid-targeting nucleic acid that does not comprise a modified bulge. An engineered nucleic acid-targeting nucleic acid comprising a modified bulge can be engineered to bind to a site-directed polypeptide with a dissociation constant at most about 10, 50, 100, 150, 200, 250, 300, 350, 400, 450, 500, 550 or 600% or more lower or higher than a nucleic acid-targeting nucleic acid that does not comprise a modified bulge. An engineered nucleic acid-targeting nucleic acid comprising a modified bulge can be engineered to bind to a site-directed polypeptide with a dissociation constant at least about 1-fold, 2-fold, 3-fold, 4-fold, 5-fold, 10-fold, 20-fold, 30-fold, 40-fold, or 50-fold or more lower or higher than a nucleic acid-targeting nucleic acid that does not comprise a modified bulge. An engineered nucleic acid-targeting nucleic acid comprising a modified bulge can be engineered to bind to a site-directed polypeptide with a dissociation constant at most about 1-fold, 2-fold, 3-fold, 4-fold, 5-fold, 10-fold, 20-fold, 30-fold, 40-fold, or 50-fold or more lower or higher than a nucleic acid-targeting nucleic acid that does not comprise a modified bulge.

Methods

The disclosure provides for methods for engineering nucleic acid-targeting nucleic acids. The methods can comprise modifying a nucleic acid-targeting nucleic acid. The modifying can comprise inserting, deleting, substituting, and mutating the nucleotides in the nucleic acid-targeting nucleic acid. The modifying can comprise modifying the nucleic acid-targeting nucleic acid such that the nucleic acid-targeting nucleic acid can bind to new protospacer adjacent motifs and/or new site-directed polypeptides as compared to a wild-type nucleic acid-targeting nucleic acid. The method can be performed using any of the site-directed polypeptides, nucleic acid-targeting nucleic acids, and complexes of site-directed polypeptides and nucleic acid-targeting nucleic acids as described herein.

An engineered nucleic acid-targeting nucleic acid can be used to cleave a target nucleic acid. An engineered nucleic acid-targeting nucleic acid can be introduced into cells with a site-directed polypeptide, thereby forming a complex. The complex can hybridize to a target nucleic acid, wherein the target nucleic acid comprises a protospacer adjacent motif. The site-directed polypeptide of the complex can cleave the target nucleic acid.

Complementary portions of the nucleic acid sequences of pre-CRISPR nucleic acid and tracr nucleic acid sequences from *Streptococcus pyogenes* SF370 are shown in FIG. 20.

FIG. 21 depicts exemplary structure of the duplex (e.g., hairpin) comprising the minimum CRISPR repeat and the minimum tracrRNA sequence and a portion of the 3' tracrRNA sequence. The duplex comprises a bulge region.

Table 4 contains the sequences of DNA templates used to synthesize the single guide nucleic acid-targeting nucleic acids of the disclosure.

TABLE 4

DNA templates of the guide nucleic acids of the disclosure

Duplex variants group 1

| | |
|---|---|
| TEMP3-FL | AGTAATAATACGACTCACTATAGGGGCCACTAGGGACAGGATGT<br>TTTAGAGCTATGCTGTTTTGGAAACAAAACAGCATAGCAAGTTAA<br>AATAAGGCTAGTCCGTTATCAACTTGAAAAAGTGGCACCGAGTCG<br>GTGCTTTTTTT (SEQ ID NO: 1374) |
| SGR-v2 | AGTAATAATACGACTCACTATAGGGGCCACTAGGGACAGGATGA<br>AAAAGAGCTAGAAATAGCAAGTTTTTTTAAGGCTAGTCCGTTATC<br>AACTTGAAAAAGTGGCACCGAGTCGGTGCTTTTTTT (SEQ ID NO: 1375) |
| SGR-v3 | AGTAATAATACGACTCACTATAGGGGCCACTAGGGACAGGATGA<br>TATAGCTAGAAATAGCAAGTTATATTAAGGCTAGTCCGTTATC<br>AACTTGAAAAAGTGGCACCGAGTCGGTGCTTTTTTT (SEQ ID NO: 1376) |
| SGR-v4 | AGTAATAATACGACTCACTATAGGGGCCACTAGGGACAGGATGT<br>TTTAGAGGATGAAAATCCAAGTTAAAATAAGGCTAGTCCGTTATC<br>AACTTGAAAAAGTGGCACCGAGTCGGTGCTTTTTTT (SEQ ID NO: 1377) |
| SGR-v5 | AGTAATAATACGACTCACTATAGGGGCCACTAGGGACAGGATGA<br>AAATGAGGATGAAAATCCAAGTATTTTTAAGGCTAGTCCGTTATC<br>AACTTGAAAAAGTGGCACCGAGTCGGTGCTTTTTTT (SEQ ID NO: 1378) |
| SGR-v6 | AGTAATAATACGACTCACTATAGGGGCCACTAGGGACAGGATGA<br>TTATGAGGATGAAAATCCAAGTATAATTAAGGCTAGTCCGTTATC<br>AACTTGAAAAAGTGGCACCGAGTCGGTGCTTTTTTT (SEQ ID NO: 1379) |
| SGR-v7 | AGTAATAATACGACTCACTATAGGGGCCACTAGGGACAGGATGT<br>AATTGAGGATGAAAATCCAAGTAATTATAAGGCTAGTCCGTTATC<br>AACTTGAAAAAGTGGCACCGAGTCGGTGCTTTTTTT (SEQ ID NO: 1380) |

TABLE 4-continued

DNA templates of the guide nucleic acids of the disclosure

SGR-v8    AGTAATAATACGACTCACTATAGGGGCCACTAGGGACAGGATGA
          AAATCAAGTGATGAAAATCGAGATTTTTAAGGCTAGTCCGTTATC
          AACTTGAAAAAGTGGCACCGAGTCGGTGCTTTTTTT (SEQ ID NO:
          1381)

SGR-v9    AGTAATAATACGACTCACTATAGGGGCCACTAGGGACAGGATGA
          AAATGAAGGATGAAAATCCAGTATTTTTAAGGCTAGTCCGTTATC
          AACTTGAAAAAGTGGCACCGAGTCGGTGCTTTTTTT (SEQ ID NO:
          1382)

SGR-v10   AGTAATAATACGACTCACTATAGGGGCCACTAGGGACAGGATGA
          TTTAGAGCTAGAAATAGCAAGTTAAATTAAGGCTAGTCCGTTATC
          AACTTGAAAAAGTGGCACCGAGTCGGTGCTTTTTTT (SEQ ID NO:
          1383)

SGR-v11   AGTAATAATACGACTCACTATAGGGGCCACTAGGGACAGGATGT
          CTCAGAGCTAGAAATAGCAAGTTGAGATAAGGCTAGTCCGTTATC
          AACTTGAAAAAGTGGCACCGAGTCGGTGCTTTTTTT (SEQ ID NO:
          1384)

SGR-v12   AGTAATAATACGACTCACTATAGGGGCCACTAGGGACAGGATGT
          CCCAGAGCTAGAAATAGCAAGTTGGGATAAGGCTAGTCCGTTATC
          AACTTGAAAAAGTGGCACCGAGTCGGTGCTTTTTTT (SEQ ID NO:
          1385)

SGR-v13   AGTAATAATACGACTCACTATAGGGGCCACTAGGGACAGGATGT
          TTTAGACTCAGAAATCAGAAGTTAAAATAAGGCTAGTCCGTTATC
          AACTTGAAAAAGTGGCACCGAGTCGGTGCTTTTTTT (SEQ ID NO:
          1386)

Duplex variants group 2

SGR-v14   AGTAATAATACGACTCACTATAGGGGCCACTAGGGACAGGATGT
          TTTAGAGCTAGAAATAGCTCTAAAATAAGGCTAGTCCGTTATCAA
          CTTGAAAAAGTGGCACCGAGTCGGTGCTTTTTTT (SEQ ID NO: 1387)

SGR-v15   AGTAATAATACGACTCACTATAGGGGCCACTAGGGACAGGATGT
          TTTAGAGGAAACTCTAAAATAAGGCTAGTCCGTTATCAACTTGAA
          AAAGTGGCACCGAGTCGGTGCTTTTTTT (SEQ ID NO: 1388)

SGR-v16   AGTAATAATACGACTCACTATAGGGGCCACTAGGGACAGGATGT
          TTTAGAAATAAAATAAGGCTAGTCCGTTATCAACTTGAAAAAGTG
          GCACCGAGTCGGTGCTTTTTTT (SEQ ID NO: 1389)

SGR-v17   AGTAATAATACGACTCACTATAGGGGCCACTAGGGACAGGATAT
          TTTAGAGCTAGAAATAGCAAGTTAAAATAAGGCTAGTCCGTTATC
          AACTTGAAAAAGTGGCACCGAGTCGGTGCTTTTTTT (SEQ ID NO:
          1390)

SGR-v18   AGTAATAATACGACTCACTATAGGGGCCACTAGGGACAGGATAT
          TTTAGAGCTAGAAATAGCAAGTTAAAACAAGGCTAGTCCGTTATC
          AACTTGAAAAAGTGGCACCGAGTCGGTGCTTTTTTT (SEQ ID NO:
          1391)

SGR-v19   AGTAATAATACGACTCACTATAGGGGCCACTAGGGACAGGATGA
          CGATAGAACGGAAACGTTGGACATCGTTAAGGCTAGTCCGTTATC
          AACTTGAAAAAGTGGCACCGAGTCGGTGCTTTTTTT (SEQ ID NO:
          1392)

SGR-v20   AGTAATAATACGACTCACTATAGGGGCCACTAGGGACAGGATGA
          CGATGAGACGGAAACGTCAAGTATCGTTAAGGCTAGTCCGTTATC
          AACTTGAAAAAGTGGCACCGAGTCGGTGCTTTTTTT (SEQ ID NO:
          1393)

SGR-v21   AGTAATAATACGACTCACTATAGGGGCCACTAGGGACAGGATGT
          TTTAAGACTAGAAATAGTGGACTAAAATAAGGCTAGTCCGTTATC
          AACTTGAAAAAGTGGCACCGAGTCGGTGCTTTTTTT (SEQ ID NO:
          1394)

SGR-v22   AGTAATAATACGACTCACTATAGGGGCCACTAGGGACAGGATCG
          TTTAGAGCTAGAAATAGCAAGTTAAAATAAGGCTAGTCCGTTATC
          AACTTGAAAAAGTGGCACCGAGTCGGTGCTTTTTTT (SEQ ID NO:
          1395)

TABLE 4-continued

DNA templates of the guide nucleic acids of the disclosure

SGR-v23  AGTAATAATACGACTCACTATAGGGGCCACTAGGGACAGGATGT
GGTAGAGCTAGAAATAGCAAGTTAAAATAAGGCTAGTCCGTTATC
AACTTGAAAAAGTGGCACCGAGTCGGTGCTTTTTTT (SEQ ID NO:
1396)

SGR-v24  AGTAATAATACGACTCACTATAGGGGCCACTAGGGACAGGATGT
TTGCGAGCTAGAAATAGCAAGTTAAAATAAGGCTAGTCCGTTATC
AACTTGAAAAAGTGGCACCGAGTCGGTGCTTTTTTT (SEQ ID NO:
1397)

SGR-v25  AGTAATAATACGACTCACTATAGGGGCCACTAGGGACAGGATGT
TTTAGAGTGAGAAATAGCAAGTTCACATAAGGCTAGTCCGTTATC
AACTTGAAAAAGTGGCACCGAGTCGGTGCTTTTTTT (SEQ ID NO:
1398)

SGR-v26  AGTAATAATACGACTCACTATAGGGGCCACTAGGGACAGGATGT
TTTAGAGCTAGAAATAGCAAGTTACACTAAGGCTAGTCCGTTATC
AACTTGAAAAAGTGGCACCGAGTCGGTGCTTTTTTT (SEQ ID NO:
1399)

SGR-v27  AGTAATAATACGACTCACTATAGGGGCCACTAGGGACAGGATGT
TTTAGAGCTAGAAATAGCAAGTTAACAGAAGGCTAGTCCGTTATC
AACTTGAAAAAGTGGCACCGAGTCGGTGCTTTTTTT (SEQ ID NO:
1400)

SGR-v28  AGTAATAATACGACTCACTATAGGGGCCACTAGGGACAGGATGT
TTTAGAGCTAGAAATAGCAAGTTAAAATAACTGGCTAGTCCGTTA
TCAACTTGAAAAAGTGGCACCGAGTCGGTGCTTTTTTT (SEQ ID
NO: 1401)

SGR-v29  AGTAATAATACGACTCACTATAGGGGCCACTAGGGACAGGATGT
TTTAGAGCTAGAAATAGCAAGTTAAAATGCTAGTCCGTTATCAACT
TGAAAAAGTGGCACCGAGTCGGTGCTTTTTTT (SEQ ID NO: 1402)

Tracr-Variant Group

SGR-v30  AGTAATAATACGACTCACTATAGGGGCCACTAGGGACAGGATGT
TTTAGAGCTAGAAATAGCAAGTTAAAATGGAACTAGTCCGTTATC
AACTTGAAAAAGTGGCACCGAGTCGGTGCTTTTTTT (SEQ ID NO:
1403)

SGR-v31  AGTAATAATACGACTCACTATAGGGGCCACTAGGGACAGGATGT
TTTAGAGCTAGAAATAGCAAGTTAAAATTTCGCTAGTCCGTTATCA
ACTTGAAAAAGTGGCACCGAGTCGGTGCTTTTTTT (SEQ ID NO:
1404)

SGR-v32  AGTAATAATACGACTCACTATAGGGGCCACTAGGGACAGGATGT
TTTAGAGCTAGAAATAGCAAGTTAAAATAAGCGAAGTCCGTTATC
AACTTGAAAAAGTGGCACCGAGTCGGTGCTTTTTTT (SEQ ID NO:
1405)

SGR-v33  AGTAATAATACGACTCACTATAGGGGCCACTAGGGACAGGATGT
TTTAGAGCTAGAAATAGCAAGTTAAAATAAGGCTTCACCGTTATC
AACTTGAAAAAGTGGCACCGAGTCGGTGCTTTTTTT (SEQ ID NO:
1406)

SGR-v34  AGTAATAATACGACTCACTATAGGGGCCACTAGGGACAGGATGT
TTTAGAGCTAGAAATAGCAAGTTAAAATAAGGCTAGTGGCTTATC
AACTTGAAAAAGTGGCACCGAGTCGGTGCTTTTTTT (SEQ ID NO:
1407)

SGR-v35  AGTAATAATACGACTCACTATAGGGGCCACTAGGGACAGGATGT
TTTAGAGCTAGAAATAGCAAGTTAAAATAAGGCTAGTCCGAATTC
AACTTGAAAAAGTGGCACCGAGTCGGTGCTTTTTTT  (SEQ ID NO:
1408)

SGR-v36  AGTAATAATACGACTCACTATAGGGGCCACTAGGGACAGGATGT
TTTAGAGCTAGAAATAGCAAGTTAAAATAAGGCTAGTCCGTTAAG
TACTTGAAAAAGTGGCACCGAGTCGGTGCTTTTTTT (SEQ ID NO:
1409)

SGR-v37  AGTAATAATACGACTCACTATAGGGGCCACTAGGGACAGGATGT
TTTAGAGCTAGAAATAGCAAGTTAAAATAAGGCTAGTCCGTTATC
ATGATGAAAAAGTGGCACCGAGTCGGTGCTTTTTTT (SEQ ID NO:
1410)

TABLE 4-continued

DNA templates of the guide nucleic acids of the disclosure

| | |
|---|---|
| SGR-v38-MMO | AGTAATAATACGACTCACTATAGGGGCCACTAGGGACAGGATGT TTTAGAGCTAGAAATAGCAAGTTAAAATAAGAATGATACATCACA AAAAAAAGGCTTTATGCCGTAACTACTACTTATTTTCAAAATAAGT AGTTTTTTTT (SEQ ID NO: 1411) |
| SGR-v39-ST2 | AGTAATAATACGACTCACTATAGGGGCCACTAGGGACAGGATGT TTTAGAGCTAGAAATAGCAAGTTAAAATAAGGCTTCATGCCGAAA TCAACACCCTGTCATTTTATGGCAGGGTGTTTTCGTTATTTTTT (SEQ ID NO: 1412) |
| SGR-v40-CJ | AGTAATAATACGACTCACTATAGGGGCCACTAGGGACAGGATGT TTTAGAGCTAGAAATAGCAAGTTAAAATAAAGAGTTTGCGGGACT CTGCGGGGTTACAATCCCCTAAAACCGCTTTTTTT (SEQ ID NO: 1413) |
| SGR-v41-NM | AGTAATAATACGACTCACTATAGGGGCCACTAGGGACAGGATGT TTTAGAGCTAGAAATAGCAAGTTAAAATAAGGCCGTCTGAAAAGA TGTGCCGCAACGCTCTGCCCCTTAAAGCTTCTGCTTTAAGGGGCAT TTTTT (SEQ ID NO: 1414) |
| Csy4-tag-group | |
| SGR-v42 | AGTAATAATACGACTCACTATAGGGGCCACTAGGGACAGGATGT TTTAGAGCTAGAAATAGCAAGTTAAAATAAGGCTAGTCCGTTATC AACTTATACTGCCGTATAGGCAGAGATTTTTT (SEQ ID NO: 1415) |
| SGR-v43 | AGTAATAATACGACTCACTATAGGGGCCACTAGGGACAGGATGT TTTAGAGCTAGAAATAGCAAGTTAAAATAAGGCTAGTCCGTTATC AACTTATACTGCCGTATAGGCAGAGAAATGGACTCGGAATACTGC CGTATAGGCAGAGATTTTTT (SEQ ID NO: 1416) |
| SGR-v44 | AGTAATAATACGACTCACTATAGGGGCCACTAGGGACAGGATGT TTTAGAGCTATCACTGCCGTATAGGCAGTGATAGCAAGTTAAAAT AAGGCTAGTCCGTTATCAACTTGAAAAAGTGGCACCGAGTCGGTG CTTTTTTT (SEQ ID NO: 1417) |
| SGR-v45 | AGTAATAATACGACTCACTATAGGGGCCACTAGGGACAGGATGT TTTAGAGCTATCACTGCCGTATAGGCAGTGATAGCAAGTTAAAAT AAGGCTAGTCCGTTATCAACTTGAAAAAGTGGCACCGAGTCGGTG CTAATGGACTCGATACTGCCGTATAGGCAGAGATTTTTT (SEQ ID NO: 1418) |

Table 4A shows the RNA sequences of the DNA templates in Table 4.

TABLE 4A

RNA sequences of single guide nucleic acid-targeting nucleic acids of the disclosure.
Single guide nucleic acid-targeting nucleic acid sequence Duplex variants group 1

| | |
|---|---|
| TEMP3-FL | GGGGCCACUAGGGACAGGAUGUUUUAGAGCUAUGCUGUUUUGGA AACAAAACAGCAUAGCAAGUUAAAAUAAGGCUAGUCCGUUAUCA ACUUGAAAAAGUGGCACCGAGUCGGUGCUUUUUUU (SEQ ID NO: 1419) |
| SGR-v2 | GGGGCCACUAGGGACAGGAUGAAAAAGAGCUAGAAAUAGCAAGU UUUUUUAAGGCUAGUCCGUUAUCAACUUGAAAAAGUGGCACCGA GUCGGUGCUUUUUUU (SEQ ID NO: 1420) |
| SGR-v3 | GGGGCCACUAGGGACAGGAUGAUAUAGAGCUAGAAAUAGCAAGU UAUAUUAAGGCUAGUCCGUUAUCAACUUGAAAAAGUGGCACCGA GUCGGUGCUUUUUUU (SEQ ID NO: 1421) |
| SGR-v4 | GGGGCCACUAGGGACAGGAUGUUUUAGAGGAUGAAAAUCCAAGU UAAAAUAAGGCUAGUCCGUUAUCAACUUGAAAAAGUGGCACCGA GUCGGUGCUUUUUUU (SEQ ID NO: 1422) |
| SGR-v5 | GGGGCCACUAGGGACAGGAUGAAAAUGAGGAUGAAAAUCCAAGU AUUUUUAAGGCUAGUCCGUUAUCAACUUGAAAAAGUGGCACCGA GUCGGUGCUUUUUUU (SEQ ID NO: 1423) |
| SGR-v6 | GGGGCCACUAGGGACAGGAUGAUUAUGAGGAUGAAAAUCCAAGU AUAAUUAAGGCUAGUCCGUUAUCAACUUGAAAAAGUGGCACCGA GUCGGUGCUUUUUUU (SEQ ID NO: 1424) |
| SGR-v7 | GGGGCCACUAGGGACAGGAUGUAAUUGAGGAUGAAAAUCCAAGU AAUUAUAAGGCUAGUCCGUUAUCAACUUGAAAAAGUGGCACCGA GUCGGUGCUUUUUUU (SEQ ID NO: 1425) |
| SGR-v8 | GGGGCCACUAGGGACAGGAUGAAAAUCAAGUGAUGAAAAUCGAG AUUUUUAAGGCUAGUCCGUUAUCAACUUGAAAAAGUGGCACCGA GUCGGUGCUUUUUUU (SEQ ID NO: 1426) |
| SGR-v9 | GGGGCCACUAGGGACAGGAUGAAAAUGAAGGAUGAAAAUCCAGU AUUUUUAAGGCUAGUCCGUUAUCAACUUGAAAAAGUGGCACCGA GUCGGUGCUUUUUUU (SEQ ID NO: 1427) |
| SGR-v10 | GGGGCCACUAGGGACAGGAUGAUUUAGAGCUAGAAAUAGCAAGU UAAAUUAAGGCUAGUCCGUUAUCAACUUGAAAAAGUGGCACCGA GUCGGUGCUUUUUUU (SEQ ID NO: 1428) |
| SGR-v11 | GGGGCCACUAGGGACAGGAUGUCUCAGAGCUAGAAAUAGCAAGU UGAGAUAAGGCUAGUCCGUUAUCAACUUGAAAAAGUGGCACCGA GUCGGUGCUUUUUUU (SEQ ID NO: 1429) |

TABLE 4A-continued

RNA sequences of single guide nucleic acid-targeting nucleic acids of the disclosure.
Single guide nucleic acid-targeting nucleic acid sequence

| | |
|---|---|
| SGR-v12 | GGGGCCACUAGGGACAGGAUGUCCCAGAGCUAGAAAUAGCAAGU UGGGAUAAGGCUAGUCCGUUAUCAACUUGAAAAAGUGGCACCGA GUCGGUGCUUUUUUU (SEQ ID NO: 1430) |
| SGR-v13 | GGGGCCACUAGGGACAGGAUGUUUUAGACUCAGAAAUCAGAAGU UAAAAUAAGGCUAGUCCGUUAUCAACUUGAAAAAGUGGCACCGA GUCGGUGCUUUUUUU (SEQ ID NO: 1431) |

Duplex variants group 2

| | |
|---|---|
| SGR-v14 | GGGGCCACUAGGGACAGGAUGUUUUAGAGCUAGAAAUAGCUCUA AAAUAAGGCUAGUCCGUUAUCAACUUGAAAAAGUGGCACCGAGU CGGUGCUUUUUUU (SEQ ID NO: 1432) |
| SGR-v15 | GGGGCCACUAGGGACAGGAUGUUUUAGAGGGAAACUCUAAAAUAA GGCUAGUCCGUUAUCAACUUGAAAAAGUGGCACCGAGUCGGUGC UUUUUUU (SEQ ID NO: 1433) |
| SGR-v16 | GGGGCCACUAGGGACAGGAUGUUUUAGAAAUAAAAUAAGGCUAG UCCGUUAUCAACUUGAAAAAGUGGCACCGAGUCGGUGCUUUUUU U (SEQ ID NO: 1434) |
| SGR-v17 | GGGGCCACUAGGGACAGGAUAUUUUAGAGCUAGAAAUAGCAAGU UAAAAUAAGGCUAGUCCGUUAUCAACUUGAAAAAGUGGCACCGA GUCGGUGCUUUUUUU (SEQ ID NO: 1435) |
| SGR-v18 | GGGGCCACUAGGGACAGGAUAUUUUAGAGCUAGAAAUAGCAAGU UAAAACAAGGCUAGUCCGUUAUCAACUUGAAAAAGUGGCACCGA GUCGGUGCUUUUUUU (SEQ ID NO: 1436) |
| SGR-v19 | GGGGCCACUAGGGACAGGAUGACGAUAGAACGGAAACGUUGGAC AUCGUUAAGGCUAGUCCGUUAUCAACUUGAAAAAGUGGCACCGA GUCGGUGCUUUUUUU (SEQ ID NO: 1437) |
| SGR-v20 | GGGGCCACUAGGGACAGGAUGACGAUGAGACGGAAACGUCAAGU AUCGUUAAGGCUAGUCCGUUAUCAACUUGAAAAAGUGGCACCGA GUCGGUGCUUUUUUU (SEQ ID NO: 1438) |
| SGR-v21 | GGGGCCACUAGGGACAGGAUGUUUUAGACUAGAAAUAGUGGAC UAAAAUAAGGCUAGUCCGUUAUCAACUUGAAAAAGUGGCACCGA GUCGGUGCUUUUUUU (SEQ ID NO: 1439) |
| SGR-v22 | GGGGCCACUAGGGACAGGAUCGUUUAGAGCUAGAAAUAGCAAGU UAAAAUAAGGCUAGUCCGUUAUCAACUUGAAAAAGUGGCACCGA GUCGGUGCUUUUUUU (SEQ ID NO: 1440) |
| SGR-v23 | GGGGCCACUAGGGACAGGAUGUGGUAGAGCUAGAAAUAGCAAGU UAAAAUAAGGCUAGUCCGUUAUCAACUUGAAAAAGUGGCACCGA GUCGGUGCUUUUUUU (SEQ ID NO: 1441) |
| SGR-v24 | GGGGCCACUAGGGACAGGAUGUUUGCGAGCUAGAAAUAGCAAGU UAAAAUAAGGCUAGUCCGUUAUCAACUUGAAAAAGUGGCACCGA GUCGGUGCUUUUUUU (SEQ ID NO: 1442) |
| SGR-v25 | GGGGCCACUAGGGACAGGAUGUUUUAGAGUGAGAAAUAGCAAGU UCACAUAAGGCUAGUCCGUUAUCAACUUGAAAAAGUGGCACCGA GUCGGUGCUUUUUUU (SEQ ID NO: 1443) |
| SGR-v26 | GGGGCCACUAGGGACAGGAUGUUUUAGAGCUAGAAAUAGCAAGU UACACUAAGGCUAGUCCGUUAUCAACUUGAAAAAGUGGCACCGA GUCGGUGCUUUUUUU (SEQ ID NO: 1444) |
| SGR-v27 | GGGGCCACUAGGGACAGGAUGUUUUAGAGCUAGAAAUAGCAAGU UAACAGAAGGCUAGUCCGUUAUCAACUUGAAAAAGUGGCACCGA GUCGGUGCUUUUUU (SEQ ID NO: 1445) |
| SGR-v28 | GGGGCCACUAGGGACAGGAUGUUUUAGAGCUAGAAAUAGCAAGU UAAAAUAACUGGCUAGUCCGUUAUCAACUUGAAAAAGUGGCACC GAGUCGGUGCUUUUUUU (SEQ ID NO: 1446) |
| SGR-v29 | GGGGCCACUAGGGACAGGAUGUUUUAGAGCUAGAAAUAGCAAGU UAAAAUGCUAGUCCGUUAUCAACUUGAAAAAGUGGCACCGAGUC GGUGCUUUUUUU (SEQ ID NO: 1447) |

TABLE 4A-continued

RNA sequences of single guide nucleic acid-targeting nucleic acids of the disclosure.
Single guide nucleic acid-targeting nucleic acid sequence Tracr-Variant Group

| | |
|---|---|
| SGR-v30 | GGGGCCACUAGGGACAGGAUGUUUUAGAGCUAGAAAUAGCAAGU UAAAAUGGAACUAGUCCGUUAUCAACUUGAAAAAGUGGCACCGA GUCGGUGCUUUUUUU (SEQ ID NO: 1448) |
| SGR-v31 | GGGGCCACUAGGGACAGGAUGUUUUAGAGCUAGAAAUAGCAAGU UAAAAUUUCGCUAGUCCGUUAUCAACUUGAAAAAGUGGCACCGA GUCGGUGCUUUUUUU (SEQ ID NO: 1449) |
| SGR-v32 | GGGGCCACUAGGGACAGGAUGUUUUAGAGCUAGAAAUAGCAAGU UAAAAUAAGCGAAGUCCGUUAUCAACUUGAAAAAGUGGCACCGA GUCGGUGCUUUUUUU (SEQ ID NO: 1450) |
| SGR-v33 | GGGGCCACUAGGGACAGGAUGUUUUAGAGCUAGAAAUAGCAAGU UAAAAUAAGGCUUCACCGUUAUCAACUUGAAAAAGUGGCACCGA GUCGGUGCUUUUUUU (SEQ ID NO: 1451) |
| SGR-v34 | GGGGCCACUAGGGACAGGAUGUUUUAGAGCUAGAAAUAGCAAGU UAAAAUAAGGCUAGUGGCUUAUCAACUUGAAAAAGUGGCACCGA GUCGGUGCUUUUUUU (SEQ ID NO: 1452) |
| SGR-v35 | GGGGCCACUAGGGACAGGAUGUUUUAGAGCUAGAAAUAGCAAGU UAAAAUAAGGCUAGUCCGAAUCAACUUGAAAAAGUGGCACCGA GUCGGUGCUUUUUUU (SEQ ID NO: 1453) |
| SGR-v36 | GGGGCCACUAGGGACAGGAUGUUUUAGAGCUAGAAAUAGCAAGU UAAAAUAAGGCUAGUCCGUUAAGUACUUGAAAAAGUGGCACCGA GUCGGUGCUUUUUUU (SEQ ID NO: 1454) |
| SGR-v37 | GGGGCCACUAGGGACAGGAUGUUUUAGAGCUAGAAAUAGCAAGU UAAAAUAAGGCUAGUCCGUUAUCAUGAUGAAAAGUGGCACCGA GUCGGUGCUUUUUUU (SEQ ID NO: 1455) |
| SGR-v38-MMO | GGGGCCACUAGGGACAGGAUGUUUUAGAGCUAGAAAUAGCAAGU UAAAAUAAGAAUGAUACAUCACAAAAAAAGGCUUUAUGCCGUA ACUACUACUUAUUUUCAAAAUAAGUAGUUUUUUUU (SEQ ID NO: 1456) |
| SGR-v39-ST2 | GGGGCCACUAGGGACAGGAUGUUUUAGAGCUAGAAAUAGCAAGU UAAAAUAAGGCUUCAUGCCGAAAUCAACACCCUGUCAUUUUAUG GCAGGGUGUUUUCGUUAUUUUUUU (SEQ ID NO: 1457) |
| SGR-v40-CJ | GGGGCCACUAGGGACAGGAUGUUUUAGAGCUAGAAAUAGCAAGU UAAAAUAAAGAGUUUGCGGGACUCUGCGGGGUUACAAUCCCCUA AAACCGCUUUUUUU (SEQ ID NO: 1458) |
| SGR-v41-NM | GGGGCCACUAGGGACAGGAUGUUUUAGAGCUAGAAAUAGCAAGU UAAAAUAAGGCCGUCUGAAAAGAUGUGCCGCAACGCUCUGCCCC UUUAAGCUUCUGCUUUAAGGGGCAUUUUUU (SEQ ID NO: 1459) |

Csy4-tag-group

| | |
|---|---|
| SGR-v42 | GGGGCCACUAGGGACAGGAUGUUUUAGAGCUAGAAAUAGCAAGU UAAAAUAAGGCUAGUCCGUUAUCAACUUUAUACUGCCGUAUAGGC AGAGAUUUUUU (SEQ ID NO: 1460) |
| SGR-v43 | GGGGCCACUAGGGACAGGAUGUUUUAGAGCUAGAAAUAGCAAGU UAAAAUAAGGCUAGUCCGUUAUCAACUUUAUACUGCCGUAUAGGC AGAGAAUGGACUCGGAAUACUGCCGUAUAGGCAGAGAUUUUUU (SEQ ID NO: 1461) |
| SGR-v44 | GGGGCCACUAGGGACAGGAUGUUUUAGAGCUAUCACUGCCGUAU AGGCAGUGAUAGCAAGUUAAAAUAAGGCUAGUCCGUUAUCAACU UGAAAAAGUGGCACCGAGUCGGUGCUUUUUUU (SEQ ID NO: 1462) |
| SGR-v45 | GGGGCCACUAGGGACAGGAUGUUUUAGAGCUAUCACUGCCGUAU AGGCAGUGAUAGCAAGUUAAAAUAAGGCUAGUCCGUUAUCAACU UGAAAAAGUGGCACCGAGUCGGUGCUAAUGGACUCGAUACUGCC GUAUAGGCAGAGAUUUUUU (SEQ ID NO: 1463) |

Table 5 indicates the activity and purpose of additional nucleic acid-targeting nucleic acid variants. + refers to active, − refers to inactive. The experimental data of these variants is shown in FIG. 37.

TABLE 5

Nucleic acid-targeting nucleic acid variants and their activity

| name | dCB ### | Activity | Purpose | Spacer | sgBackbone |
| --- | --- | --- | --- | --- | --- |
| SGR-v80 | | − | Linker length | GGGGCCACTAGGGACAGGAT (SEQ ID NO: 1464) | GTTTTAGAGCTAGAAATAGCAAGTTAAAATAACTCGGCTAGTCCGTTATCAACTTGAAAAGTGGCACCGAGTCGGTGCT (SEQ ID NO: 1465) |
| SGR-v81 | | − | Linker length | GGGGCCACTAGGGACAGGAT (SEQ ID NO: 1464) | GTTTTAGAGCTAGAAATAGCAAGTTAAAATAACTCTGGCTAGTCCGTTATCAACTTGAAAAAGTGGCACCCGAGTCGGTGCT (SEQ ID NO: 1466) |
| SGR-v82 | | − | Linker length | GGGGCCACTAGGGACAGGAT (SEQ ID NO: 1464) | GTTTTAGAGCTAGAAATAGCAAGTTAAAATAACTCTCTGGCTAGTCCGTTATCAACTTGAAAAAGTGGCACCGAGTCGGTGCT (SEQ ID NO: 1467) |
| SGR-v83 | | ++ | Control | GGGGCCACTAGGGACAGGAT (SEQ ID NO: 1464) | GTTTTAGAGCTAGAAATAGCAAGTTAAAATAAGGCTAGTCCGTTATCAACTTGAAAAAGTGGCACCGAGTCGGTGCT (SEQ ID NO: 1468) |
| SGR-v84 | | ++ | Minimal sgRNA | GGGGCCACTAGGGACAGGAT (SEQ ID NO: 1464) | GTTTTAGAGGAAACAAGTTAAAATAAGGCTAGTCCGTTATCAACTTGAAAAAGTGGCACCGAGTCGGTGCT (SEQ ID NO: 1469) |
| SGR-v85 | | ++ | Minimal sgRNA | GGGGCCACTAGGGACAGGAT (SEQ ID NO: 1464) | GTTTTAGAGACAAGTTAAAATAAGGCTAGTCCGTTATCAACTTGAAAAAGTGGCACCGAGTCGGTGCT (SEQ ID NO: 1470) |
| SGR-v86 | | ++ | Minimal sgRNA | GGGGCCACTAGGGACAGGAT (SEQ ID NO: 1464) | GTTTTAGGAGAAACTTTAAAATAAGGCTAGTCCGTTATCAACTTGAAAAAGTGGCACCGAGTCGGTGCT (SEQ ID NO: 1471) |
| SGR-v87 | | − | Minimal sgRNA | GGGGCCACTAGGGACAGGAT (SEQ ID NO: 1464) | GTTTTATCGAAATCTAAAATAAGGCTAGTCCGTTATCAACTTGAAAAAGTGGCACCGAGTCGGTGCT (SEQ ID NO: 1472) |
| SGR-v88 | | − | Minimal sgRNA | GGGGCCACTAGGGACAGGAT (SEQ ID NO: 1464) | GTTTTACTTCGGTAAAATAAGGCTAGTCCGTTATCAACTTGAAAAAGTGGCACCGAGTCGGTGCT (SEQ ID NO: 1473) |
| SGR-v89 | | ++ | Minimal sgRNA | GGGGCCACTAGGGACAGGAT (SEQ ID NO: 1464) | GTTTTAGATACTTAAAATAAGGCTAGTCCGTTATCAACTTGAAAAAGTGGCACCGAGTCGGTGCT (SEQ ID NO: 1474) |
| SGR-v90 | | − | Minimal sgRNA | GGGGCCACTAGGGACAGGAT (SEQ ID NO: 1464) | GTTTTATGAAACTAAAATAAGGCTAGTCCGTTATCAACTTGAAAAAGTGGCACCGAGTCGGTGCT (SEQ ID NO: 1475) |
| SGR-v91 | | − | Minimal sgRNA | GGGGCCACTAGGGACAGGAT (SEQ ID NO: 1464) | GTTTCTTCGGAAATAAGGCTAGTCCGTTATCAACTTGAAAAAGTGGCACCGAGTCGGTGCT (SEQ ID NO: 1476) |

TABLE 5-continued

Nucleic acid-targeting nucleic acid variants and their activity

| name | dCB ### | Activity | Purpose | Spacer | sgBackbone |
|---|---|---|---|---|---|
| SGR-v92 | | ++ | Change bulge angle | GGGGCCAC TAGGGACA GGAT (SEQ ID NO: 1464) | GTTTTAGGCTAGAAATAGC AAGTTAAAATAAGGCTAGT CCGTTATCAACTTGAAAAA GTGGCACCGAGTCGGTGCT (SEQ ID NO: 1477) |
| SGR-v93 | | ++ | Change bulge angle | GGGGCCAC TAGGGACA GGAT (SEQ ID NO: 1464) | GTTTTAGCTAGAAATAGCA AGTTAAAATAAGGCTAGTC CGTTATCAACTTGAAAAAG TGGCACCGAGTCGGTGCT (SEQ ID NO: 1478) |
| SGR-v94 | | ++ | Change bulge angle | GGGGCCAC TAGGGACA GGAT (SEQ ID NO: 1464) | GTTTTACTAGAAATAGCAA GTTAAAATAAGGCTAGTCC GTTATCAACTTGAAAAAGT GGCACCGAGTCGGTGCT (SEQ ID NO: 1479) |
| SGR-v95 | | − | Change bulge angle | GGGGCCAC TAGGGACA GGAT (SEQ ID NO: 1464) | GTTTTAGAGCTAGAAATAG CAGTTAAAATAAGGCTAGT CCGTTATCAACTTGAAAAA GTGGCACCGAGTCGGTGCT (SEQ ID NO: 1480) |
| SGR-v96 | | − | Change bulge angle | GGGGCCAC TAGGGACA GGAT (SEQ ID NO: 1464) | GTTTTAGAGCTAGAAATAG AGTTAAAATAAGGCTAGTC CGTTATCAACTTGAAAAAG TGGCACCGAGTCGGTGCT (SEQ ID NO: 1481) |
| SGR-v97 | | ++ | Change bulge angle | GGGGCCAC TAGGGACA GGAT (SEQ ID NO: 1464) | GTTTTAGAGCTAGAAATAA GTTAAAATAAGGCTAGTCC GTTATCAACTTGAAAAAGT GGCACCGAGTCGGTGCT (SEQ ID NO: 1482) |
| SGR-v98 | | − | Change bulge angle | GGGGCCAC TAGGGACA GGAT (SEQ ID NO: 1464) | GTTTTAGAGCTAGAAATAG TTAAAATAAGGCTAGTCCG TTATCAACTTGAAAAAGTG GCACCGAGTCGGTGCT (SEQ ID NO: 1483) |
| SGR-v99 | | − | Control | GGGGCCAC TAGGGACA GGAT (SEQ ID NO: 1464) | GTTTTAGAGCTAGAAATAG CAAGTTAAAATAAGGCTAG TCCGTTATCAACTTGAAAA AGTGGCACCGAGTCGGTGC T (SEQ ID NO: 1468) |
| SGR-v124 | dCB154 | − | nexus/hairpin variant | GGGGCCAC TAGGGACA GGAT (SEQ ID NO: 1464) | GTTTTAGAGCTAGAAATAG CAAGTTAAAATAACCCTAG TCCGTTATCAACTTGAAAA AGTGGCACCGAGTCGGTGC T (SEQ ID NO: 1484) |
| SGR-v125 | dCB 155 | +/− | nexus/hairpin variant | GGGGCCAC TAGGGACA GGAT (SEQ ID NO: 1464) | GTTTTAGAGCTAGAAATAG CAAGTTAAAATAACCCTAG TGGGTTATCAACTTGAAAA AGTGGCACCGAGTCGGTGC T (SEQ ID NO: 1485) |
| SGR-v126 | dCB156 | + | nexus/hairpin variant | GGGGCCAC TAGGGACA GGAT (SEQ ID NO: 1464) | GTTTTAGAGCTAGAAATAG CAAGTTAAAATAAGGCTAG TGGGTTATCAACTTGAAAA AGTGGCACCGAGTCGGTGC T (SEQ ID NO: 1486) |
| SGR-v46 | dCB157 | ++ | nexus/hairpin variant | GGGGCCAC TAGGGACA GGAT (SEQ ID NO: 1464) | GTTTTAGAGCTAGAAATAG CAAGTTAAAATAAGGCTAG TAAGTTATCAACTTGAAAA AGTGGCACCGAGTCGGTGC T (SEQ ID NO: 1487) |

TABLE 5-continued

Nucleic acid-targeting nucleic acid variants and their activity

| name | dCB ### | Activity | Purpose | Spacer | sgBackbone |
|---|---|---|---|---|---|
| SGR-v47 | dCB 158 | ++ | nexus/hairpin variant | GGGGCCACTAGGGACAGGAT (SEQ ID NO: 1464) | GTTTTAGAGCTAGAAATAGCAAGTTAAAATAAGGCTAGTTTGTTATCAACTTGAAAAAGTGGCACCGAGTCGGTGCT (SEQ ID NO: 1488) |
| SGR-v48 | dCB 159 | ++ | nexus/hairpin variant | GGGGCCACTAGGGACAGGAT (SEQ ID NO: 1464) | GTTTTAGAGCTAGAAATAGCAAGTTAAAATAAGACTAGTTCGTTATCAACTTGAAAAAGTGGCACCGAGTCGGTGCT (SEQ ID NO: 1489) |
| SGR-v49 | dCB160 | − | nexus/hairpin variant | GGGGCCACTAGGGACAGGAT (SEQ ID NO: 1464) | GTTTTAGAGCTAGAAATAGCAAGTTAAAATAAGGCTAGGAAACTAGCCTTCTCAA (SEQ ID NO: 1490) |
| SGR-v50 | dCB161 | − | nexus/hairpin variant | GGGGCCACTAGGGACAGGAT (SEQ ID NO: 1464) | GTTTTAGAGCTAGAAATAGCAAGTTAAAATAAGGCTAGGAAACTAGCCCTCAATA (SEQ ID NO: 1491) |
| SGR-v51 | dCB162 | +/− | nexus/hairpin variant | GGGGCCACTAGGGACAGGAT (SEQ ID NO: 1464) | GTTTTAGAGCTAGAAATAGCAAGTTAAAATAAGGCTAGTCCGTAGAAAATGCC (SEQ ID NO: 1492) |
| SGR-v52 | dCB163 | + | nexus/hairpin variant | GGGGCCACTAGGGACAGGAT (SEQ ID NO: 1464) | GTTTTAGAGCTAGAAATAGCAAGTTAAAATAAGGCTAGTCCGTAGAAATACGG (SEQ ID NO: 1493) |
| SGR-v53 | dCB164 | + | nexus/hairpin variant | GGGGCCACTAGGGACAGGAT (SEQ ID NO: 1464) | GTTTTAGAGCTAGAAATAGCAAGTTAAAATAAGGCTAGTCCGTAGAAATACTTAT (SEQ ID NO: 1494) |
| SGR-v54 | dCB165 | + | nexus/hairpin variant | GGGGCCACTAGGGACAGGAT (SEQ ID NO: 1464) | GTTTTAGAGCTAGAAATAGCAAGTTAAAATAAGGCTAGTCCGTTATTATTAGGGGGTTA (SEQ ID NO: 1495) |
| SGR-v55 | dCB166 | − | nexus truncation | GGGGCCACTAGGGACAGGAT (SEQ ID NO: 1464) | GTTTTAGAGCTAGAAATAGCAAGTTAAAATAAGG (SEQ ID NO: 1496) |
| SGR-v56 | dCB167 | − | nexus truncation | GGGGCCACTAGGGACAGGAT (SEQ ID NO: 1464) | GTTTTAGAGCTAGAAATAGCAAGTTAAAATAAGGCTAG (SEQ ID NO: 1497) |
| SGR-v57 | dCB168 | +/− | nexus truncation | GGGGCCACTAGGGACAGGAT (SEQ ID NO: 1464) | GTTTTAGAGCTAGAAATAGCAAGTTAAAATAAGGCTAGTCCG (SEQ ID NO: 1498) |
| SGR-v58 | dCB169 | +/− | nexus truncation | GGGGCCACTAGGGACAGGAT (SEQ ID NO: 1464) | GTTTTAGAGCTAGAAATAGCAAGTTAAAATAAGGCTAGTCCGTTAT (SEQ ID NO: 1499) |
| SGR-v100 | | +/− | nexus stem length | GGGGCCACTAGGGACAGGAT (SEQ ID NO: 1464) | GTTTTAGAGCTAGAAATAGCAAGTTAAAATAAGGGCTAGTCCCGTTATCAACTTGAAAAAGTGGCACCGAGTCGGTGCT (SEQ ID NO: 1500) |
| SGR-v101 | | ++ | nexus stem length | GGGGCCACTAGGGACAGGAT (SEQ ID NO: 1464) | GTTTTAGAGCTAGAAATAGCAAGTTAAAATAAGGGGCTAGTCCCCGTTATCAACTTGAAAAAGTGGCACCGAGTCGGTGCT (SEQ ID NO: 1501) |

TABLE 5-continued

Nucleic acid-targeting nucleic acid variants and their activity

| name | dCB ### | Activity | Purpose | Spacer | sgBackbone |
|---|---|---|---|---|---|
| SGR-v102 | | + | nexus stem length | GGGGCCAC TAGGGACA GGAT (SEQ ID NO: 1464) | GTTTTAGAGCTAGAAATAG CAAGTTAAAATAAGGGGGC TAGTCCCCCGTTATCAACTT GAAAAAGTGGCACCGAGTC GGTGCT (SEQ ID NO: 1502) |
| SGR-v103 | | ++ | nexus stem length | GGGGCCAC TAGGGACA GGAT (SEQ ID NO: 1464) | GTTTTAGAGCTAGAAATAG CAAGTTAAAATAAAACTAG TTTGTTATCAACTTGAAAA AGTGGCACCGAGTCGGTGC T (SEQ ID NO: 1503) |
| SGR-v104 | | ++ | nexus stem length | GGGGCCAC TAGGGACA GGAT (SEQ ID NO: 1464) | GTTTTAGAGCTAGAAATAG CAAGTTAAAATAAGGACTA GTTCCGTTATCAACTTGAA AAAGTGGCACCGAGTCGGT GCT (SEQ ID NO: 1504) |
| SGR-v105 | | ++ | Control | GGGGCCAC TAGGGACA GGAT (SEQ ID NO: 1464) | GTTTTAGAGCTAGAAATAG CAAGTTAAAATAAGGCTAG TCCGTTATCAACTTGAAAA AGTGGCACCGAGTCGGTGC T (SEQ ID NO: 1468) |
| SGR-v106 | | +/- | nexus stem length | GGGGCCAC TAGGGACA GGAT (SEQ ID NO: 1464) | GTTTTAGAGCTAGAAATAG CAAGTTAAAATAAGGCTAG TCCTGTTATCAACTTGAAA AAGTGGCACCGAGTCGGTG CT (SEQ ID NO: 1505) |
| SGR-v107 | | ++ | nexus stem length | GGGGCCAC TAGGGACA GGAT (SEQ ID NO: 1464) | GTTTTAGAGCTAGAAATAG CAAGTTAAAATAAAGCTAG TCTGTTATCAACTTGAAAA AGTGGCACCGAGTCGGTGC T (SEQ ID NO: 1506) |
| SGR-v108 | | - | nexus loop size | GGGGCCAC TAGGGACA GGAT (SEQ ID NO: 1464) | GTTTTAGAGCTAGAAATAG CAAGTTAAAATAAGGTCTA GTCCCGTTATCAACTTGAA AAAGTGGCACCGAGTCGGT GCT (SEQ ID NO: 1507) |
| SGR-v109 | | + | nexus loop size | GGGGCCAC TAGGGACA GGAT (SEQ ID NO: 1464) | GTTTTAGAGCTAGAAATAG CAAGTTAAAATAAGGTACT AGTCGCCGTTATCAACTTG AAAAAGTGGCACCGAGTCG GTGCT (SEQ ID NO: 1508) |
| SGR-v110 | | - | nexus loop size | GGGGCCAC TAGGGACA GGAT (SEQ ID NO: 1464) | GTTTTAGAGCTAGAAATAG CAAGTTAAAATAAGGTATC TAGTGCGCCGTTATCAACT TGAAAAAGTGGCACCGAGT CGGTGCT (SEQ ID NO: 1509) |
| SGR-v111 | | ++ | Control | GGGGCCAC TAGGGACA GGAT (SEQ ID NO: 1464) | GTTTTAGAGCTAGAAATAG CAAGTTAAAATAAGGCTAG TCCGTTATCAACTTGAAAA AGTGGCACCGAGTCGGTGC T (SEQ ID NO: 1468) |
| SGR-v112 | | - | Tracr hybrid - LRH | GGGGCCAC TAGGGACA GGAT (SEQ ID NO: 1464) | GTTTTAGAGCTAGAAATAG CAAGTTAAAATCAAACAAA GCTTCAGCTGAGTTTCAATT TCTGGCCCATGTTGGGCAC ATACATATGCCACCGAG (SEQ ID NO: 1510) |
| SGR-v113 | | ++ | Tracr hybrid - SM159 | GGGGCCAC TAGGGACA GGAT (SEQ ID NO: 1464) | GTTTTAGAGCTAGAAATAG CAAGTTAAAATAAGGCAGT GATTTTTAATCCAGTCCGTA CACAACTTGAAAAGTGCG CACCGATTCGGTGCTTTTTT (SEQ ID NO: 1511) |

TABLE 5-continued

Nucleic acid-targeting nucleic acid variants and their activity

| name | dCB ### | Activity | Purpose | Spacer | sgBackbone |
|------|---------|----------|---------|--------|------------|
| SGR-v114 | | ++ | Tracr hybrid - ST3 | GGGGCCAC TAGGGACA GGAT (SEQ ID NO: 1464) | GTTTTAGAGCTAGAAATAG CAAGTTAAAATAAGGCTTA GACCGTACTCAACTTGAAA AGGTGGCACCGATTCGGTG TTTTTTTT (SEQ ID NO: 1512) |
| SGR-v115 | | ++ | Tracr hybrid - LBU | GGGGCCAC TAGGGACA GGAT (SEQ ID NO: 1464) | GTTTTAGAGCTAGAAATAG CAAGTTAAAATCAAAGCGC TTTGCGCGGAGTTTCAACTT TT (SEQ ID NO: 1513) |
| SGR-v120 | | − | Major variant | GGGGCCAC TAGGGACA GGAT (SEQ ID NO: 1464) | GAGAATCTCCTAGAAATAG CTCTTATTCTTAAGGGATCA CCGAATACAACTTGAAAAA GTGGCACCGAGTCGGTGCT (SEQ ID NO: 1514) |
| SGR-v121 | | ++ | Major variant | GGGGCCAC TAGGGACA GGAT (SEQ ID NO: 1464) | GACGATGAGACGGAAACGT CAAGTATCGTTAAGGGATC ACCGAATACAACTTGAAAA AGTGGCACCGAGTCGGTGC T (SEQ ID NO: 1515) |
| SGR-v122 | | − | Major variant | GGGGCCAC TAGGGACA GGAT (SEQ ID NO: 1464) | AACGATGAGACGGAAACGT CAAGTATCGTCAAGGGATC ACCCAATACAACTTGAAAA AGTGGCACCGAGTCGGTGC T (SEQ ID NO: 1516) |
| SGR-v123 | | − | Major variant | GGGGCCAC TAGGGACA GGAT (SEQ ID NO: 1464) | AACGGTGAGGTGGAAACAC CAAGTACCGTCAAGGTAGC ACCCGACAAGTC (SEQ ID NO: 1517) |

Methods for the Generation of Tagged Cell Lines Using a Nucleic Acid-Targeting Nucleic Acid The methods of the disclosure provide for tagging a cell with a donor polynucleotide, wherein the donor polynucleotide can divide and/or differentiate, and the donor polynucleotide can be transmitted to each daughter cell during cell division. The method can be performed using any of the site-directed polypeptides, nucleic acid-targeting nucleic acids, and complexes of site-directed polypeptides and nucleic acid-targeting nucleic acids as described herein.

A tagged cell can be generated by contacting the cell with a donor polynucleotide, and a complex comprising a site-directed polypeptide and a nucleic acid-targeting nucleic acid. The donor polynucleotide can be inserted into the cleaved target nucleic acid, thereby generating a tagged cell. The tagged cell can be propagated such as in a cell line, or to produce a propagated population of cells.

A donor polynucleotide can be introduced into the cut site by use of a donor cassette for homologous recombination that comprises ends homologous to sequences on either side of the double-strand break. The donor polynucleotide can comprise an additional sequence between the two ends. The additional sequence can be a nucleic acid sequence. The additional sequence can encode for a gene. The additional sequence can encode for a non-coding nucleic acid element.

The donor polynucleotide (e.g., the additional sequence of a donor polynucleotide between two homologous ends) can comprise a marker. A marker can comprise a visualization marker (e.g., a fluorescent marker such as GFP). A marker can comprise a random polynucleotide sequence (e.g., such as a random hexamer sequence). A marker can be a barcode.

NHEJ can introduce unique sequence signature at each cut site. The repair mechanism can result in the introduction of insertions (e.g., insertion of a donor polynucleotide), deletions or mutations into a cut site. A cell that undergoes NHEJ to repair a double-strand break can comprise a unique sequence after repair has taken place (e.g., a unique sequence can be inserted into the double-strand break). If more than one site is cut within a cell, repair can introduce the donor polynucleotide at each site, thereby adding sequence diversity to that cell. The repaired site can provide a unique barcode sequence to the cell that can be preserved during cell division and passed on to all progeny of the modified cell. A donor polynucleotide can be inserted into at least about 1, 2, 3, 4, 5, 6, 7, 8, 9 or 10 or more sites (e.g, cleaved target nucleic acids). A donor polynucleotide can be inserted into at most about 1, 2, 3, 4, 5, 6, 7, 8, 9 or 10 or more sites (e.g, cleaved target nucleic acids).

Homologous recombination (HR) can be used to introduce barcode sequences into a cell and/or a cell population (e.g., a human cell, a mammalian cell, a yeast, a fungi, a protozoa, an archaea). A library of donor plasmids (e.g., comprising the donor polynucleotide) can be prepared with randomized sequences in the donor cassette. The library can be made from oligonucleotides, a piece of double-stranded DNA, a plasmid, and/or a minicircle.

Donor polynucleotide sequences can be introduced into the genomes of individual cells for the purpose of tracking cell lineage. Sites can be chosen for modification in silent or "safe-harbor" regions of the genome, distant from genes and regulatory elements, to minimize potentially deleterious effects on cellular function. Sites within functional genetic elements can also be used to track cell fate.

For example, donor polynucleotides can be introduced into stem cell and/or stem cell populations. The methods of the disclosure can be used for tracking cell lineage development in animal models. For example, cell fate development and/or differentiation in hematopoesis can be tracked using the methods of the disclosure. The methods of the disclosure can be used for therapeutic cell engineering-based therapies. For example, a cell can be tagged with a donor polynucleotide encoding a therapeutic protein. The cell can be propagated. The propagated cell can be introduced into a subject. As another example, a differentiated cell can be removed from a subject. The differentiated cell can be tagged with two markers: one expressed when the cell is differentiated, one expressed when the cell is de-differentiated. Identifying the markers can be useful in determining differentiation events. In another example, a differentiated cell can be obtained from a subject. The differentiated cell can be de-differentiated into a pluripotent cell. The pluripotent cell can be tagged with a donor polynucleotide encoding a therapeutic protein. The cell can be re-differentiated into a new cell type while expressing the therapeutic protein, thereby creating a patient-specific therapeutic cell. Tagged cells can divide and differentiate, and the modification(s) to their genome can be transmitted to each daughter cell during cell division.

In some instances, two cells can be tagged with two different donor polynucleotide markers. The two cells can be combined. The combined mixture can be assayed simultaneously. The donor polynucleotides can allow the multiplex analysis of the two cells because the donor polynucleotide can be used to distinguish the two cells.

A cell population can be chosen for introducing double-stranded breaks, or generating cellular signatures. Cells may be purified or selected. For example, a population of hematopoetic stem cells (CD45 positive) may be selected by FACS or magnetic bead purification. Bone marrow may be treated ex vivo with the nuclease. Cells may be targeted in vivo by the use of viruses with a particular tropism. Cells may be selected by using viruses engineered to target cells bearing a particular receptor.

Tagged cells can be analyzed by high-throughput sequencing either at the population level or at the single-cell level. At the population level, a collection of cells can be lysed. The genomic DNA can be extracted. PCR primers can be designed to amplify the genomic region that has been modified by the nuclease. Sequences can be enriched by hybridization. A sequence library can be prepared from the genomic DNA and enriched. The region of interest can be enriched, and a sequence library can be prepared. A sequence library can be prepared simultaneously during enrichment using primers comprising appropriate sequence tags to be used with nucleic acid sequencing technologies. If the double-stranded break is made within a region that can be transcribed, RNA can be used to prepare sequence libraries.

Once nucleic acid sequence data has been obtained, the sequences can be analyzed to determine the clonal structure. This can be carried out by gathering common sequences together and counting those sequences.

Cells can be sub-selected by sorting schemes based on cell surface markers using flow cytometry or affinity purification methods. Cell surface markers can be used to define cell states, and by comparing cell states with clonal structure, the fate of modified cell populations can be determined.

At the single-cell level, cells can be isolated. PCR products can be generated from each individual cell. This can be achieved in microwell arrays, microfluidic devices, and/or emulsions. Where more than one genomic modification is carried out per cell, PCR products can be coupled together, either physically, or chemically, to ensure their relationship to the parent cell.

Methods for Quantifying Genome-Editing Events

For RNA-dependent nucleases, such as Cas9, the nucleic acid recognition functionality and nuclease activities can be linked. In some instances, nucleic acid recognition functionality and nuclease activities may not be linked. The nuclease sites can be located within the specific sequence recognized by the nuclease.

Non-Homologous End-Joining can be an imperfect repair process that can result in the insertion of multiple bases at the site of the double-stranded break. NHEJ can result in the introduction of insertions, deletions and/or mutations into a cut site. NHEJ can significantly disrupt the original sequence. The disruption of the native sequence as a consequence of repair mechanisms can be used to assess the efficiency of genome editing approaches.

Homologous recombination can enable more complete repair of the target nucleic acid break by exchanging nucleotide sequences between similar or identical molecules of nucleic acid. An additional sequence can be introduced into the target nucleic acid at the cut site by use of a donor cassette (e.g., donor polynucleotide) that comprises ends homologous to sequences either side of the double-strand break and additional sequence between the two ends.

This disclosure describes an approach for assessing double-stranded break activity and NHEJ-mediated insertions/deletions introduced by nucleic acid-dependent nucleases, such as Cas9. The method takes advantage of the fact that the sites in a target nucleic acid recognized by Cas9 during the initial nuclease recognition and nucleic acid cleavage activity can be destroyed during the NHEJ process, either by the introduction of insertions or deletions.

In some instances, the method provides for the design of a nucleic acid-targeting nucleic acid to target a site of interest in a target nucleic acid (e.g., genome). A nucleic acid template encoding the nucleic acid-targeting nucleic acid can be designed with a promoter sequence appended at the 5' end of the nucleic acid-targeting nucleic acid to enable in vitro synthesis of the nucleic acid-targeting nucleic acid.

Primers can be designed at positions that flank the cleavage site. The cleavage site (and/or nucleic acid regions around the cleavage site) can be amplified (e.g., from genomic nucleic acid), thereby generating a product (e.g., amplified PCR product). The product (e.g., amplified PCR product) can be at least about 100, 200, 300, 400, 500, 600, 700, 800, 900, 1000, 1100, 1200 or more bases in length. The product (e.g., amplified PCR product) can be at most about 100, 200, 300, 400, 500, 600, 700, 800, 900, 1000, 1100, 1200 or more bases in length. The product (e.g., amplified PCR product) can be about 200-600 base pairs in length.

The products can be purified. The products can be incubated with an RNA-dependent nuclease (e.g. Cas9) and the nucleic acid-targeting nucleic acid. Those molecules that have been amplified from genomic nucleic acid that have not be modified by NHEJ can comprise the correct sequence that can be recognized and cleaved by Cas9. The molecules that have been amplified from genomic nucleic acid that has been modified by NHEJ may not comprise sites that can be recognized and/or cut by Cas9.

The digested products can then be analyzed by methods such as gel electrophoresis, capillary electrophoresis, high-throughput sequencing and/or quantitative PCR (e.g., qPCR). In the case of gel electrophoresis, a gel can be imaged. Once a gel has been imaged, the percentage of cells modified by NHEJ can be estimated by measuring the intensity of bands corresponding to digested products, and comparing to the intensity of bands corresponding to undigested products.

Methods for Delivering Donor Polynucleotide to a Double-Stranded Break for Insertion into the Double-Stranded Break This disclosure describes methods for bringing a donor polynucleotide into close proximity to a site-directed target nucleic acid break to enhance insertion (e.g., homologous recombination) of the donor polynucleotide into the site of the double-stranded break. The method can be performed using any of the site-directed polypeptides, nucleic acid-targeting nucleic acids, and complexes of site-directed polypeptides and nucleic acid-targeting nucleic acids as described herein.

In some instances, the methods of the disclosure provide for bringing a donor polynucleotide in close proximity to the site of a double-stranded break in a target nucleic acid, by binding it to the nuclease that generates the double-stranded break (e.g., Cas9).

Figure 30:
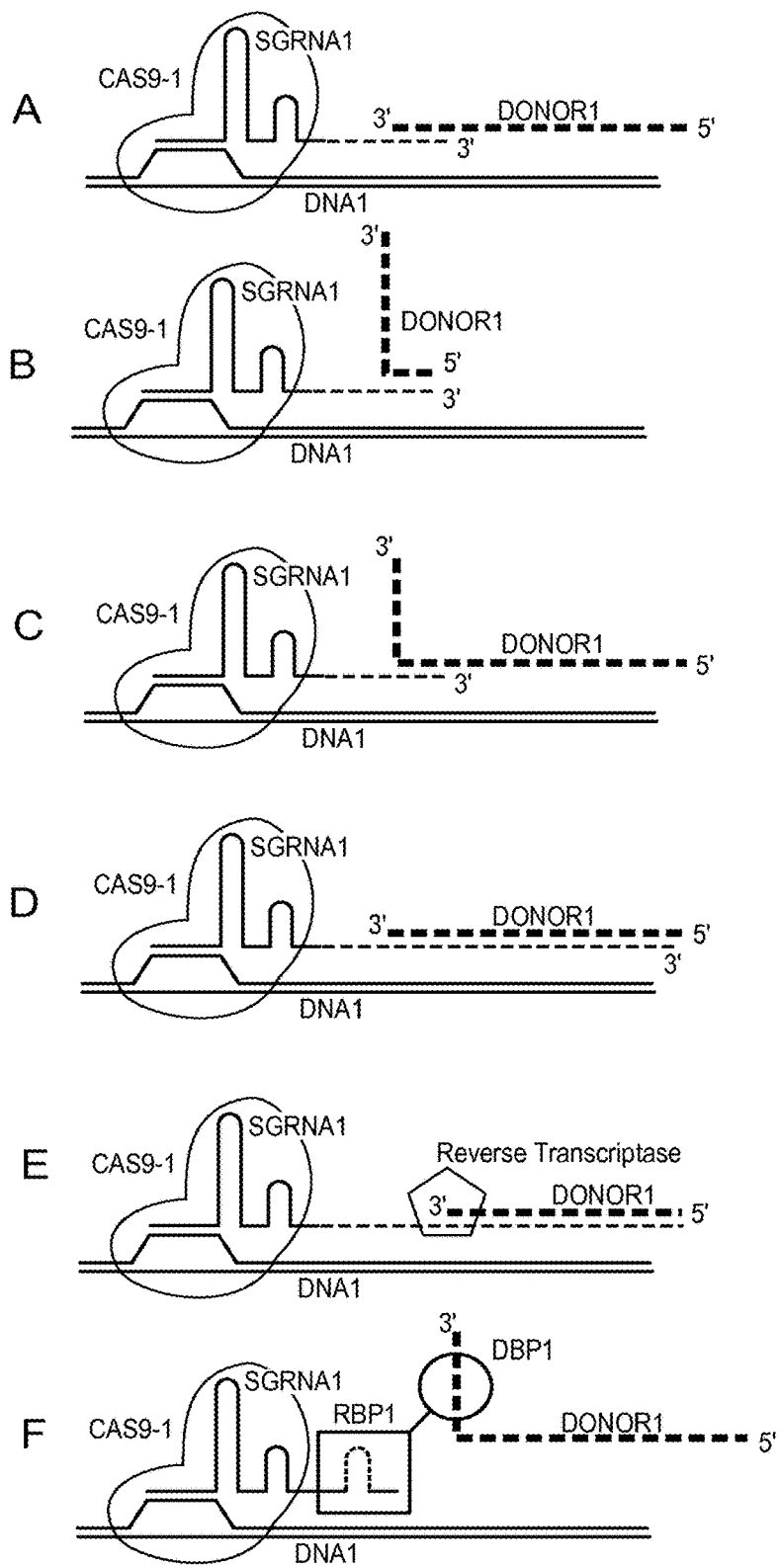
FIG. 30 depicts exemplary methods of the disclosure of bringing a donor polynucleotide to a modification site in a target nucleic acid.

A complex comprising a site-directed polypeptide, a nucleic acid-targeting nucleic acid, and a donor polynucleotide can be delivered to a target nucleic acid. FIG. 30 illustrates exemplary methods for bringing a donor polynucleotide into proximity to the site of a double-stranded break in a target nucleic acid. For example, a nucleic acid-targeting nucleic acid can comprise a 3' hybridizing extension sequence, which can be part of a tracrRNA extension sequence (shown in the light dotted line attached to the nucleic acid-targeting nucleic acid). A 3' hybridizing extension sequence can be a non-native sequence. FIG. 30A illustrates that the tracrRNA extension sequence at the 3' end of the nucleic acid-targeting nucleic acid can include a sequence that can hybridize to an end of the donor polynucleotide (e.g., the 3' end) (the donor polynucleotide is shown in bold thicker dashed line). The 3' hybridizing extension sequence can be at least about 1, 2, 3, 4, 5, 6, 7, 8, 9, or 10 or more nucleotides in length. The 3' hybridizing extension sequence can be at most about 1, 2, 3, 4, 5, 6, 7, 8, 9, or 10 or more nucleotides in length. The 3' hybridizing sequence can hybridize to at least about 1, 2, 3, 4, 5, 5, 6, 7, 8, 9, or 10 or more nucleotides of the donor polynucleotide. The 3' hybridizing sequence can hybridize to at most about 1, 2, 3, 4, 5, 5, 6, 7, 8, 9, or 10 or more nucleotides of the donor polynucleotide. The 3' hybridizing sequence can hybridize to the donor polynucleotide with at least 1, 2, 3, 4, 5, 6, 7, 8, 9, or 10 or more mismatches. The 3' hybridizing sequence can hybridize to the donor polynucleotide with at most 1, 2, 3, 4, 5, 6, 7, 8, 9, or 10 or more mismatches.

The 3' hybridizing extension can hybridize to the 3' end of the donor polynucleotide. The 3' hybridizing extension can hybridize to at least the 1, 2, 3, 4, 5, 6, 7, 8, 9, or 10 or more 3' most nucleotides of the donor polynucleotide. The 3' hybridizing extension can hybridize to at most the 1, 2, 3, 4, 5, 6, 7, 8, 9, or 10 or more 3' most nucleotides of the donor polynucleotide.

As depicted in FIG. 30B, the tracr nucleic acid extension at the 3' end of the nucleic acid-targeting nucleic acid can include a sequence that can hybridize to the 5' end of the donor DNA. The 3' hybridizing extension can hybridize to at least the 1, 2, 3, 4, 5, 6, 7, 8, 9, or 10 or more 5' most nucleotides of the donor polynucleotide. The 3' hybridizing extension can hybridize to at most the 1, 2, 3, 4, 5, 6, 7, 8, 9, or 10 or more 5' most nucleotides of the donor polynucleotide.

The tracr nucleic acid extension at the 3' end of the nucleic acid-targeting nucleic acid can include a sequence that can hybridize to a region between the 3' end and 5' end of the donor polynucleotide, as shown in FIG. 30C. The 3' hybridizing extension can hybridize to at least 1, 2, 3, 4, 5, 6, 7, 8, 9, or 10 or more nucleotides between the 3' and 5' end of the donor polynucleotide. The 3' hybridizing extension can hybridize to at most the 1, 2, 3, 4, 5, 6, 7, 8, 9, or 10 or more nucleotides between the 3' and 5' end of the donor polynucleotide.

The tracr nucleic acid extension at the 3' end of the nucleic acid-targeting nucleic acid can include a sequence that can hybridize along the full length of the donor polynucleotide, as shown in FIG. 30D. The nucleic acid-targeting nucleic acid can hybridize along at least about 20, 30, 40, 50, 60, 70, 80, 90, or 100% of the donor polynucleotide. The nucleic acid-targeting nucleic acid can hybridize along at most about 20, 30, 40, 50, 60, 70, 80, 90, or 100% of the donor polynucleotide. The 3' hybridizing extension sequence can hybridize along the full length of the donor polynucleotide with at least about 1, 2, 3, 4, 5, 6, 7, 8, 9 or 10 or more mismatches. The 3' hybridizing extension sequence can hybridize along the full length of the donor polynucleotide with at most about 1, 2, 3, 4, 5, 6, 7, 8, 9 or 10 or more mismatches.

The tracr nucleic acid extension at the 3' end of the nucleic acid-targeting nucleic acid (e.g., 3' hybridizing extension) can comprise a sequence that can be used as a template and converted by, for example, a reverse transcriptase to generate hybrid nucleic acid (e.g., the resulting nucleic acid is an RNA-DNA hybrid, wherein the newly transcribed nucleic acid can be DNA), as shown in FIG. 30E. Exemplary reverse transcriptases include SuperScript, ThermoScript, HIV reverse transcriptase, and MMLV reverse transcriptase. The reverse transcriptase can extend the donor polynucleotide sequence from the 3' hybridizing extension template.

The tracr nucleic acid extension at the 3' end of the nucleic acid-targeting nucleic acid can incorporate a nucleic acid sequence that can bind an RNA binding protein (RBP). The RNA-binding protein can be fused to a DNA binding protein (DBP), as shown in FIG. 30F. The DNA-binding protein can bind to the donor polynucleotide.

The sequences used to bring the donor polynucleotide into close proximity with a double-stranded break can be appended to the 5' end of the nucleic acid-targeting nucleic acid (e.g., the spacer extension). The sequences used to bring the donor polynucleotide into close proximity with a double-stranded break can be appended to both the 5' end and the 3' end of the nucleic acid-targeting nucleic acid.

The nuclease used in the methods of the disclosure (e.g., Cas9) can comprise nickase activity in which the nuclease can introduce single-stranded breaks in a target nucleic acid. Pairs of nucleases with nickase activity can be targeted to regions in close proximity to each other. A first nuclease can bind to a first nucleic acid-targeting nucleic acid that can interact with a first donor polynucleotide. A second nuclease can bind to a second nucleic acid-targeting nucleic acid that can interact with a second donor polynucleotide. The first and second donor polynucleotides can be designed to hybridize with each other to make a double-stranded donor polynucleotide. Two separate donor polynucleotides can be brought to the nuclease site.

In some embodiments, the donor polynucleotide can be single-stranded. In some embodiments, the donor polynucleotide can be double-stranded. In some embodiments, the donor DNA can be a minicircle. In some embodiments, the donor polynucleotide can be a plasmid. In some embodiments, the plasmid can be supercoiled. In some embodiments, the donor polynucleotide can be methylated. In some embodiments, the donor polynucleotide can be unmethylated. The donor polynucleotide can comprise a modification. Modifications can include those described here including, but not limited to, biotinylation, chemical conjugate, and synthetic nucleotides.

Methods for Cloning and Expressing a Vector Comprising a Site-Directed Polypeptide and a Nucleic Acid-Targeting Nucleic Acid The disclosure provides for methods for cloning an engineered nucleic acid-targeting nucleic acid into a vector (e.g., a linearized vector). The method can be performed using any of the site-directed polypeptides, nucleic acid-targeting nucleic acids, and complexes of site-directed polypeptides and nucleic acid-targeting nucleic acids as described herein.

A user (e.g., a scientist) can design single-stranded DNA oligonucleotides. The single-stranded DNA oliognucleotides can, when hybridized together encode a spacer sequence to target a target nucleic acid. The single-stranded DNA olignonucleotides can be at least about 5, 10, 15, 20, 25, 30 or more nucleotides in length. The single-stranded DNA oligonucleotides can be at most about 5, 10, 15, 20, 25, 30 or more nucleotides in length. The single-stranded DNA oligonucleotides can be 19-20 nucleotides in length.

A single-stranded DNA oligonucleotide can be designed such that it can hybridize to a target nucleic acid (e.g., a sequence adjacent to a protospacer adjacent motif, such as the 3' or 5' end of the protospacer adjacent motif). The DNA oligonucleotide can encode a sequence corresponding to the sense or antisense strand of the target nucleic acid sequence.

The single-stranded oligonucleotides can comprise a first portion that can hybridize and/or is complementary to a target nucleic acid. The single-stranded oligonucleotides can comprise a first portion that can hybridize and/or is complementary another single-stranded oligonucleotide. The single-stranded oligonuclotide can comprise a second portion that can hybridize to a sequence in the linearized vector. In other words, a pair of single-stranded oligonucleotides can comprise a first portion that hybridizes to each other and a second portion that comprise single-stranded overhangs, wherein the overhangs can hybridize to sticky ends in the linearized vector. In some instances, an overhang comprises 5'-GTTTT-3'. In some instances, an overhang comprises 5'-CGGTG-3'.

The single-stranded DNA nucleotides can be annealed together to generate a double-stranded oligonucleotide. The single-stranded DNA nucleotides can be annealed together in an oligonucleotide annealing buffer (e.g., comprising Tris-HCl, EDTA and NaCl). The double-stranded oligonucleotide can be diluted to a working concentration (e.g., a concentration suitable for ligation into a linearized plasmid). The diluted double-stranded oligonucleotide can be ligated into a linearized vector. Ligation can be performed in a ligation buffer (e.g., comprising Tris-HCl, $MgCl_2$, ATP) and with a ligase (e.g., T4 DNA ligase). The double-stranded oligonucleotide can be ligated into a linearized vector at a region within the sequence encoding the nucleic acid-targeting nucleic acid. In other words, the linearized vector can be linearized at a point within the region encoding the nucleic acid-targeting nucleic acid, wherein the linearization generates sticky ends that are complementary to the sticky ends of the double-stranded oligonucleotide. When the double-stranded oligonucleotide is ligated into the vector, it can generate a sequence encoding for an engineered nucleic acid-targeting nucleic acid comprising a spacer sequence corresponding to the double-stranded oligonucleotide sequence.

The ligated vector can be transformed into chemically competent cells (e.g., DH5-alpha, Top10) and selected for expression of the correctly ligated vector (e.g., by antibiotic screening). The selected transformants can be analyzed for the presence of an insert by sequencing. Sequencing can be performed using a sequencing primer that can hybridize to a portion of the vector.

Correctly ligated vector can be prepared (e.g., by large scale DNA preparation, maxiprep), and purified. The vector, comprising a site-directed polypeptide, a nucleic acid-targeting nucleic acid, wherein the nucleic acid-targeting nucleic acid comprise the double-stranded DNA oligonucleotides can be introduced (e.g., transfected) into a cell line of choice (e.g., mammalian cell line).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Examples

Example 1: Modification of a Site-Directed Polypeptide for Altered Pam Specificity In some embodiments, the disclosure provides for a modified site-directed polypeptide that is modified to alter PAM specificity. A nucleic acid encoding a modified site-directed polypeptide is introduced into cells by transfection. The modified site-directed polypeptide comprises an inserted HNH or RuvC nuclease domain. The modified site-directed polypeptide comprises a modified highly basic patch. A nucleic acid-targeting nucleic acid that comprises a spacer that can hybridize with the target nucleic acid is also introduced into cells by transfection. The modified site-directed polypeptide and the nucleic acid-targeting nucleic acid form a complex. The complex is guided to the target nucleic acid by the nucleic acid-targeting nucleic acid. Once hybridized with the nucleic acid-targeting nucleic acid, the target nucleic acid is cleaved by the nuclease domains of the site-directed polypeptide. In some embodiments, the modified site-directed polypeptide binds to the target nucleic acid with a lower Kd.

In some embodiments, a donor polynucleotide is also introduced into the cells. In some instances, the donor polynucleotide, a portion of the donor polynucleotide, a copy of the donor polynucleotide, or a portion of a copy of the donor polynucleotide is inserted into the cleaved target nucleic acid.

Example 2: Modification of a Site-Directed Polypeptide for Altered Target Nucleic Acid Specificity In some embodiments, the disclosure provides for a modified site-directed polypeptide that is modified to alter target nucleic acid specificity. A modified site-directed polypeptide is introduced into cells. The modified site-directed polypeptide comprises a modification in the highly basic patch and/or the HNH-like domain. A nucleic acid-targeting nucleic acid that comprises a spacer that can hybridize with the target nucleic acid is also introduced into cells. The modified site-directed polypeptide and the nucleic acid-targeting nucleic acid form a complex. The complex is guided to the target nucleic acid by the nucleic acid-targeting nucleic acid. Once hybridized with the nucleic acid-targeting nucleic acid, the target nucleic acid is cleaved by the site-directed polypeptide. In some embodiments, the modified site-directed polypeptide binds to the target nucleic acid with a lower Kd.

In some embodiments, a donor polynucleotide is also introduced into the cells. In some instances, the donor polynucleotide, a portion of the donor polynucleotide, a copy of the donor polynucleotide, or a portion of a copy of the donor polynucleotide is inserted into the cleaved target nucleic acid.

Example 3: Recombinant Expression of a Site-Directed Polypeptide

A recombinant DNA sequence can be assembled that encodes for a modified site-directed polypeptide, and enables the expression of the modified site-directed polypeptide in a host organism. The recombinant DNA sequence comprises a promoter sequence, and may additionally comprise an affinity tag for purification, or an epitope tag. In a non-limiting example, a plasmid comprises the recombinant DNA sequence for expression of the modified site-directed polypeptide.

Production of Recombinant Protein

A plasmid encoding the site directed modified polypeptide is introduced into bacterial cells (e.g., *E. coli*). The polypeptide is expressed in bacterial cells, and then purified from cell lysate using chromatography methods. The activity of the modified site-directed polypeptide is measured using assay methods designed to determine the specificity of the modified polypeptide, the PAM sequence, the specificity profile of the site-directed polypeptide and the nucleic acid preference (for example, DNA or RNA, or modified nucleic acids).

Software is designed to choose sites that can be cut using the modified site-directed polypeptide. Guide RNA sequences are designed to direct the activity of the site-directed polypeptide. Once designed, the site-directed polypeptide is used to cleave nucleic acids.

Introduction of the Modified Site-Directed Polypeptide into Cells

The modified peptide is introduced into cells to target nucleic acid sites. A polypeptide that retains nuclease activity is used to introduce single-stranded or double-stranded DNA breaks into target DNA. A polypeptide with DNA-binding but not DNA cutting activity, is used to bind double-stranded DNA to a cell. This can be used to effect transcriptional activation or repression.

Example 4: Selection of Sites for Modification within Cas9 Sequences

As described above Type II CRISPR systems containing Cas9 orthologues can be classified into three groups (Type II-A, Type II-B, and Type II-C) based on analysis of their CRISPR-Cas loci. Cas9 orthologues within these groups can be broadly defined by two clades comprising shorter (Cas9/Csn1-type) and longer (Cas9/Csx12-type) sequences. In addition to these larger groups, there can be two additional families of homologues that comprise HNH and RuvC domains arranged with similar topology to Cas9, but with significant differences in the length and sequence of insertions between conserved sequence elements. Secondary structure predictions and sequence alignments are used to define regions of the polypeptide for modification. Regions that fall between secondary structure elements or between regions of high sequence conservation are selected as candidates for insertions or deletions. Regions that have similarity to domains of known structure are analyzed to identify specific regions for inserting or deleting sequences.

Figure 35:
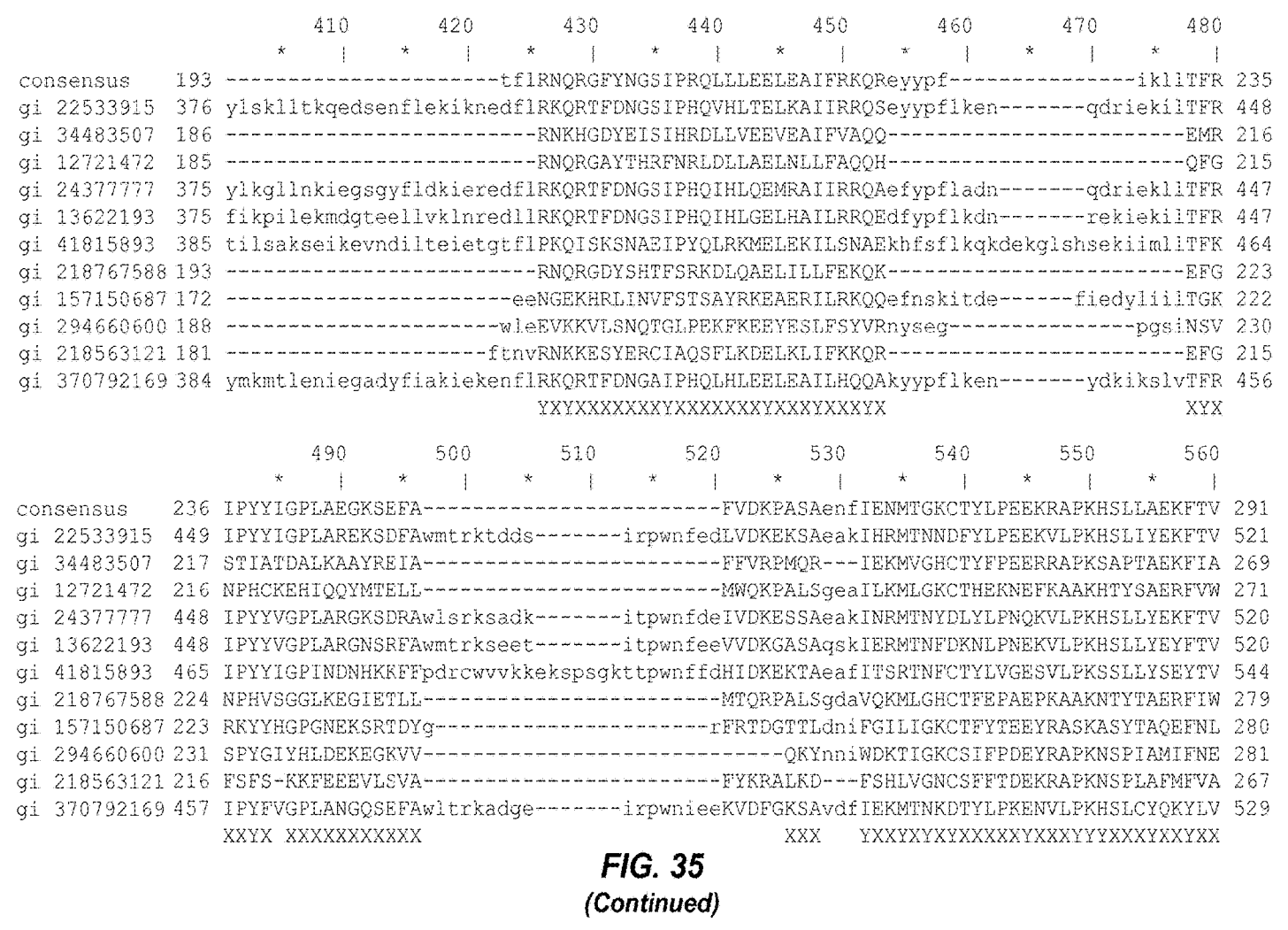
Figure 35:
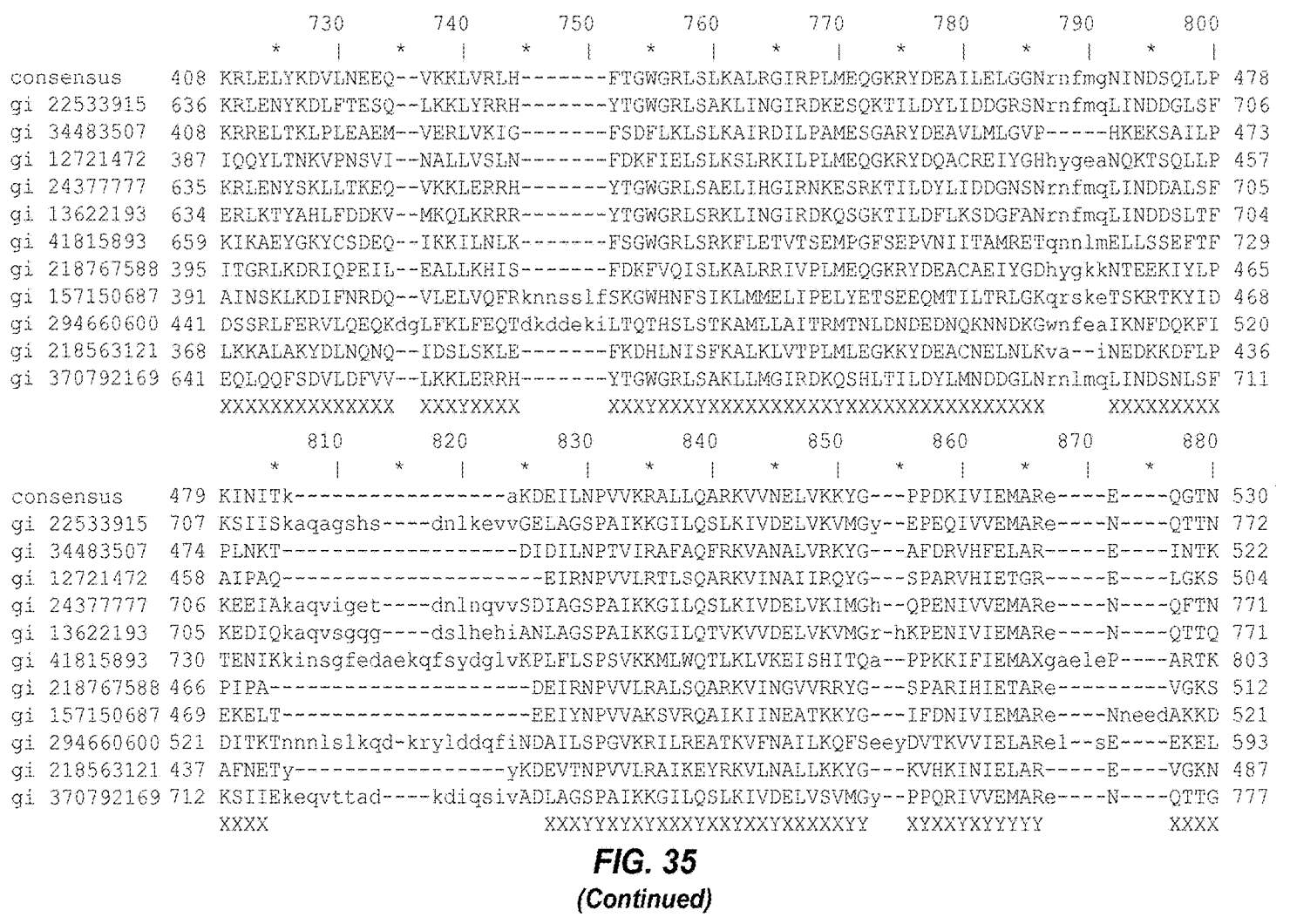
Figure 35:
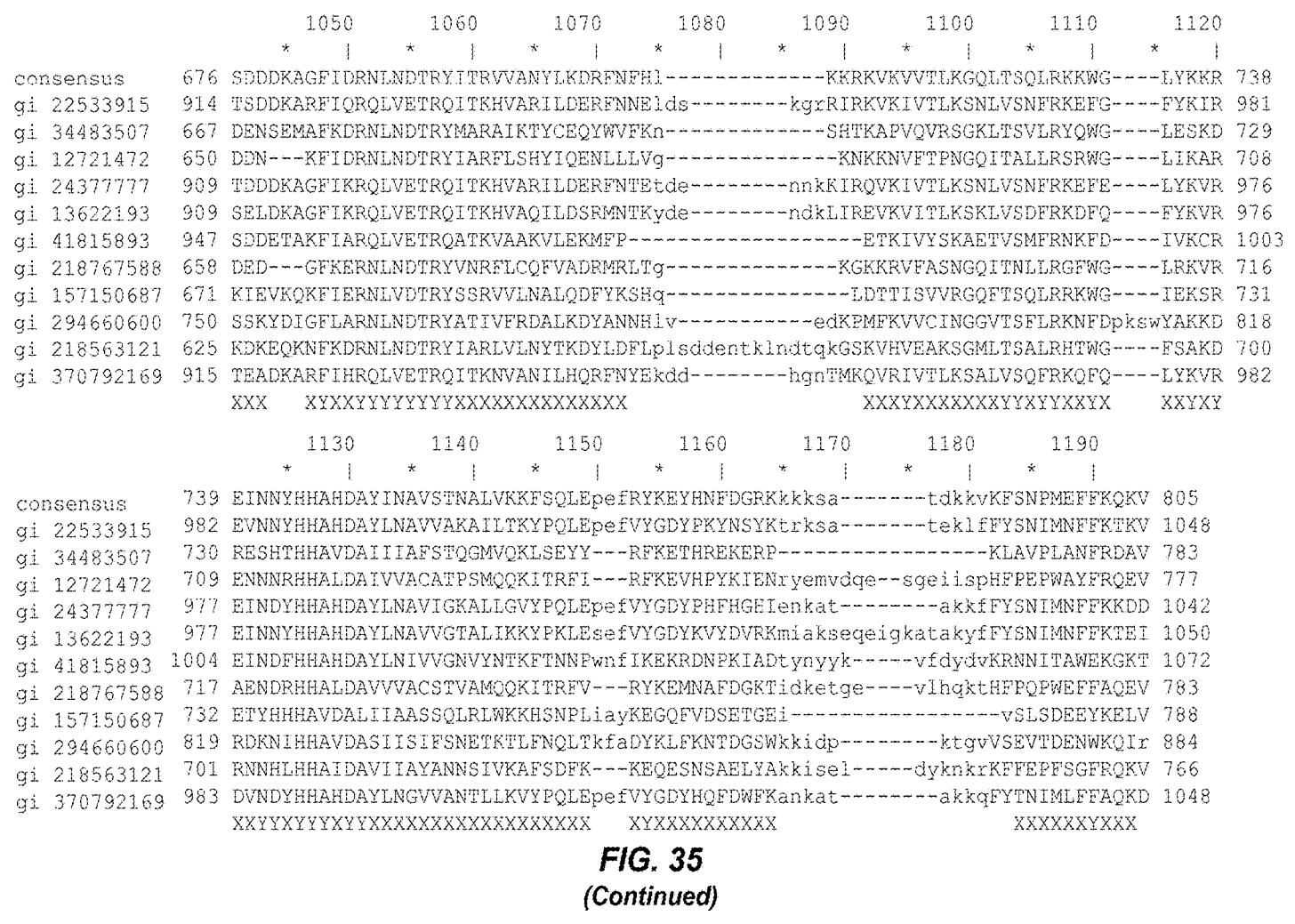

FIG. 35 shows the CDD sequence alignment TIGRO185 for a small number of diverse Cas9 orthologs. Amino acids with a "X" below them are considered to be similar. Amino acids with a "Y" below them can be considered to be highly conserved or identical in all sequences. Amino acids residues without an "X" or a "Y" are not conserved. This alignment does not include the C-terminal region (approximately corresponding to amino acid residues 1100-1350) of longer Cas9 orthologs. The sequences listed in FIG. 35 are listed in Table 6.

TABLE 6

Sequences listed in FIG. 35.

| Genbank | Accession | Species |
|---------|-----------|---------|
| gi | 22533915 | *Streptococcus agalactiae* 2603V/R |
| gi | 34483507 | *Wolinella succinogenes* |
| gi | 12721472 | *Pasteurella multocida* subsp. *multocida* str. Pm70 |
| gi | 24377777 | *Streptococcus mutans* UA159 |
| gi | 13622193 | *Streptococcus pyogenes* M1 GAS |
| gi | 41815893 | *Treponema denticola* ATCC 35405 |
| gi | 218767588 | *Neisseria meningitidis* Z2491 |
| gi | 157150687 | *Streptococcus gordonii* str. *Challis* substr. CH1 |
| gi | 294660600 | *Mycoplasma gallisepticum* str. R(low) |
| gi | 218563121 | *Campylobacter jejuni* subsp. *jejuni* NCTC 11168 = ATCC 700819 |
| gi | 370792169 | *Listeria innocua* ATCC 33091 |

Locations for insertion of new functional domains, regions for insertion of alternative sequences, or for deletion or reduction in region size that modify Cas9 activity can include, but are not limited to, the regions highlighted in Table 7. The numbers represent the amino-acid sequence numbers based on the Cas9 sequence from *Streptococcus pyogenes* M1 GAS.

TABLE 7

Exemplary locations for modifying Cas9

| gi\|13622193 Insertion/ Deletion site | *Streptococcus pyogenes* M1 GAS | | |
|---|---|---|---|
| | start | finish | Length |
| 1 | 22 | 42 | 20 |
| 2 | 97 | 134 | 37 |
| 3 | 170 | 312 | 142 |
| 4 | 350 | 400 | 50 |
| 5 | 426 | 444 | 18 |
| 6 | 455 | 492 | 37 |
| 7 | 528 | 541 | 13 |
| 8 | 578 | 589 | 11 |
| 9 | 600 | 612 | 12 |
| 10 | 628 | 634 | 6 |
| 11 | 654 | 658 | 4 |
| 12 | 684 | 692 | 8 |
| 13 | 710 | 727 | 17 |

TABLE 7-continued

Exemplary locations for modifying Cas9

| gi\|13622193 Insertion/ Deletion site | *Streptococcus pyogenes* M1 GAS | | |
|---|---|---|---|
| | start | finish | Length |
| 14 | 753 | 756 | 3 |
| 15 | 792 | 794 | 2 |
| 16 | 801 | 804 | 3 |
| 17 | 826 | 834 | 8 |
| 18 | 873 | 881 | 8 |
| 19 | 893 | 915 | 22 |
| 20 | 939 | 952 | 13 |
| 21 | 971 | 974 | 3 |
| 22 | 1005 | 1029 | 24 |
| 23 | 1096 | 1225 | 129 |
| 24 | 1105 | 1138 | 33 |

Once a region has been identified as a potential location for inserting a new polypeptide sequence into the protein, or deleting a region of the protein, the DNA sequence that codes for the protein is modified to incorporate the modification.

Example 5: Sequence Enrichment of Site-Directed Polypeptide-Bound Target Nucleic Acid The disclosure provides methods for sequence enrichment without amplification using site-directed polypeptides.

In some embodiments, the method will comprise a) contacting a target nucleic acid with a complex comprising a nucleic acid-targeting nucleic acid and a site-directed polypeptide, b) cleaving the target nucleic acid c) purifying the target nucleic acid, and d) sequencing the target nucleic acid, wherein said target nucleic acid is enriched.

In some embodiments, the site-directed polypeptide will be enzymatically inactive. Use of an enzymatically inactive site-directed polypeptide will facilitate binding of the target nucleic acid to the site-directed polypeptide complex. In some embodiments, the site-directed polypeptide will be enzymatically active.

In some embodiments, sequence enrichment will be performed outside of cells (e.g., cell-free sample). For example, a sample will comprise purified genomic DNA. In some embodiments, sequence enrichment will be performed on a cellular sample (e.g. cells, cell lysate).

In some instances, the site-directed polypeptide-target nucleic acid complexes will be fixed or cross-linked to form complexes. If the method is being performed on cells, cells will be lysed. Lysis conditions will be chosen to maintain intact protein-DNA complexes.

The nucleic acid sample will be treated to fragment the target nucleic acid before affinity purification. Fragmentation can be performed through physical, mechanical or enzymatic methods. Physical fragmentation will include exposing a target polynucleotide to heat or to ultraviolet (UV) light. Mechanical disruption will be used to mechanically shear a target polynucleotide into fragments of the desired range. Mechanical shearing will be accomplished through a number of methods, including repetitive pipetting of the target polynucleotide, sonication and nebulization. Target nucleic acids will also be fragmented using enzymatic methods. In some cases, enzymatic digestion will be performed using enzymes such as using restriction enzymes. Restriction enzymes will be used to perform specific or non-specific fragmentation of target polynucleotides. The methods will use one or more types of restriction enzymes, generally described as Type I enzymes, Type II enzymes, and/or Type III enzymes. Type II and Type III enzymes recognize specific sequences of nucleotides within a double-stranded polynucleotide sequence (a "recognition sequence" or "recognition site"). Upon binding and recognition of these sequences, Type II and Type III enzymes cleave the polynucleotide sequence. In some cases, cleavage will result in a polynucleotide fragment with a portion of overhanging single-stranded nucleic acid, called a "sticky end." In other cases, cleavage will not result in a fragment with an overhang, creating a "blunt end." The methods may comprise use of restriction enzymes that generate either sticky ends or blunt ends.

Once fragmented, the complexes comprising the site-directed polypeptide will be purified by incubation with a solid support. For example, if the site-directed polypeptide comprises a biotin tag, the solid support will be coated with avidin or streptavidin to bind to the biotin tag.

In an alternative embodiment, once fragmented, the complexes comprising the site-directed polypeptide, the target nucleic acid, and/or the nucleic acid-targeting nucleic acid, will be purified by incubation with a capture agent. The capture agent will bind to the affinity tag fused to the site-directed polypeptide. The capture agent will comprise an antibody. For example, if the affinity tag fused to the site-directed polypeptide is a FLAG tag, then the capture agent will be an anti-FLAG-tag antibody.

In some embodiments, the capture agent will be purified with a solid support. For example, if the capture agent comprises a biotin tag, the solid support will be coated with avidin or streptavidin to bind the biotinylated capture agent.

In some embodiments, the nucleic acid-targeting nucleic acid will comprise an affinity tag. The affinity tag will comprise a sequence that can bind to an endoribonuclease. In some instances, the affinity tag will comprise a sequence that can bind to a conditionally enzymatically inactive endoribonuclease. The conditionally enzymatically inactive endoribonuclease will bind, but not cleave, the affinity tag.

In some embodiments, the endoribonuclease and/or the conditionally enzymatically inactive endoribonuclease will comprise an affinity tag.

The conditionally enzymatically inactive endoribonuclease will be purified with a solid support. The solid support will bind to the affinity tag of the conditionally enzymatically inactive endoribonuclease. For example, if the conditionally enzymatically inactive endoribonuclease comprises a biotin tag, the solid support will be coated with avidin or streptavidin to bind the biotinylated capture agent.

In some embodiments, the conditionally enzymatically inactive endoribonuclease will be immobilized on any of a variety of insoluble support.

In some embodiments of the method, two rounds of purification will be performed. In some instances, a first round will comprise purification with a solid support that will bind to the affinity tag of the capture agent and a second round will comprise purification with a solid support that will bind to the affinity tag of the site-directed polypeptide. In some instances, a first round will comprise purification with a solid support that will bind to the affinity tag of the site-directed polypeptide and a second round will comprise purification with a solid support that will bind to the affinity tag of the capture agent.

In some embodiments, the methods of the disclosure will be used for multiplex sequence enrichment. In this embodiment, a plurality of nucleic acid-targeting nucleic acids can be contacted with a nucleic acid sample, wherein each nucleic acid-targeting nucleic acid is engineered to target a different target nucleic acid (e.g., sequence in a genome) within the nucleic acid sample.

The captured complexes will comprise a target nucleic acid. The target nucleic acid will be eluted from the site-directed polypeptide complex by standard methods including high salt washing, ethanol precipitation, boiling, gel purification, and the like.

The eluted DNA will be prepared for sequencing analysis by ligation of one or more adaptors.

The sequencing libraries will be sequenced as described herein. Sequenced libraries will be analyzed to identify polymorphisms, diagnose a disease, determine a course of treatment for a disease, and/or generate antibody libraries.

Example 6: Sequence Enrichment of Target Nucleic Acid not Bound to a Complex Comprising a Site-Directed Polypeptide In some embodiments, sequence enrichment will be performed with an enzymatically active site-directed polypeptide. In some instances, the site-directed polypeptide will be enzymatically active. In this instance, the target nucleic acid will not be bound to the site-directed polypeptide, but will be excised.

A target nucleic acid will be identified, and nucleic acid-targeting nucleic acids will be designed to direct the site-directed polypeptide to sequences that flank the target nucleic acid. The sample will be incubated with a complex comprising a designed nucleic acid-targeting nucleic acid and the site-directed polypeptide such that the site-directed polypeptide will cleave the DNA at both ends of the target nucleic acid. Upon cleavage of the target nucleic acid, the target nucleic acid will be cleaved from the parent nucleic acid. The cleaved target nucleic acid will be purified (e.g., by gel electrophoresis, size-selective elution from beads, or other carboxylate-derivatized beads, or by precipitation with appropriate concentrations of salt and PEG to preferentially precipitate larger or smaller DNA).

In some embodiments, sequence enrichment will be performed outside of cells (e.g., cell-free sample). For example, a sample will comprise purified genomic DNA. In some embodiments, sequence enrichment will be performed on a cellular sample (e.g. cells, cell lysate).

If the method is being performed on cells, cells will be lysed. Lysis conditions will be chosen to maintain intact protein-DNA complexes.

In some embodiments, the target nucleic acid to be sequenced will not be bound to a nucleic acid-targeting nucleic acid and/or a site-directed polypeptide. In this embodiment, the nucleic acid bound to the site-directed polypeptide and/or the nucleic acid-targeting nucleic acid will be purified away. The purification of the site-directed polypeptide will proceed as previously described herein. Briefly, the complexes comprising the site-directed polypeptide will be purified by incubation with a solid support. For example, if the site-directed polypeptide comprises a biotin tag, the solid support will be coated with avidin or streptavidin to bind to the biotin tag.

In an alternative embodiment, once fragmented, the complexes comprising the site-directed polypeptide, the nucleic acid-targeting nucleic acid, and non-target nucleic acid, will be purified by incubation with a capture agent. The capture agent will bind to the affinity tag fused to the site-directed polypeptide. The capture agent will comprise an antibody. For example, if the affinity tag fused to the site-directed polypeptide is a FLAG tag, then the capture agent will be an anti-FLAG-tag antibody.

The capture agent will be purified with a solid support. For example, if the capture agent comprises a biotin tag, the solid support will be coated with avidin or streptavidin to bind the biotinylated capture agent.

In some embodiments, the methods of the disclosure will be used for multiplex sequence enrichment. In this embodiment, a plurality of nucleic acid-targeting nucleic acids can be introduced into a cell, wherein each nucleic acid-targeting nucleic acid is engineered to target a different target nucleic acid (e.g., sequence in a genome).

The captured complex will not comprise a target nucleic acid.

The target nucleic acid will comprise the nucleic acid that is not bound to the complexes comprising the site-directed polypeptide. The target nucleic acid can be collected by standard nucleic acid purification methods (e.g., a commercially available PCR purification kit, an agarose gel).

The collected target nucleic acid will be prepared for sequencing analysis (e.g., deep sequencing) by ligation of one or more adapters as described herein.

Sequenced target nucleic acid will be analyzed to identify polymorphisms, diagnose a disease, determine a course of treatment for a disease, and/or generate antibody libraries.

Example 7: Sequencing

The eluted target nucleic acids will be prepared for sequencing analysis. Preparation for sequencing analysis will include the generation of sequencing libraries of the eluted target nucleic acid. Sequencing analysis will determine the identity and frequency of off-target binding sites of site-directed polypeptides.

Sequence determination will be performed using methods that determine many (typically thousands to billions) nucleic acid sequences in an intrinsically parallel manner, where many sequences are read out preferably in parallel using a high throughput serial process. Such methods can include but are not limited to pyrosequencing (for example, as commercialized by 454 Life Sciences, Inc., Branford, Conn.); sequencing by ligation (for example, as commercialized in the SOLiD™ technology, Life Technology, Inc., Carlsbad, Calif.); sequencing by synthesis using modified nucleotides (such as commercialized in TruSeq™ and HiSeq™ technology by Illumina, Inc., San Diego, Calif., HeliScope™ by Helicos Biosciences Corporation, Cambridge, Mass., and PacBio RS by Pacific Biosciences of California, Inc., Menlo Park, Calif.), sequencing by ion detection technologies (Ion Torrent, Inc., South San Francisco, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), capillary sequencing (e.g, such as commercialized in MegaBACE by Molecular Dynamics), electronic sequencing, single molecule sequencing (e.g., such as commercialized in SMRT™ technology by Pacific Biosciences, Menlo Park, Calif.), droplet microfluidic sequencing, sequencing by hybridization (such as commercialized by Affymetrix, Santa Clara, Calif.), bisulfate sequencing, and other known highly parallelized sequencing methods.

In some embodiments, sequencing will be performed by microarray analysis.

Example 8: Generation of Antibody Libraries

The methods disclosed herein will be used to generate protein libraries (e.g., antibody libraries). Protein libraries will be useful for preparing expression libraries, which will be used for screening proteins (e.g. antibodies) for use in therapeutics, reagents, and/or diagnostics. Protein libraries will also be useful for synthesizing and/or cloning additional antibodies.

Protein libraries will be generated by engineering a nucleic acid-targeting nucleic acid to hybridize to target nucleic acid sequences encoding immunoglobulins. The complexes comprising a site-directed polypeptide and the nucleic acid-targeting nucleic acid will be purified using methods described herein. In some embodiments, the nucleic acid hybridizing to the nucleic acid-targeting nucleic acid will be the target nucleic acid and will be eluted and sequenced, using methods described herein. In some embodiments, the nucleic acid hybridizing to the nucleic-acid targeting nucleic acid will not be the target nucleic acid. The target nucleic acid will be the nucleic acid that is excised between the cleavage sites of a plurality of complexes (e.g., complexes comprising a site-directed polypeptide and nucleic acid-targeting nucleic acid). The excised target nucleic acid will be purified and sequenced, using methods described herein.

Example 9: Genotyping

The methods disclosed herein will be used to perform Human Leukocyte Antigen (HLA) typing. HLA genes are some of the most polymorphic genes in humans. Understanding the genotypes of these regions will be important for obtaining a good match for tissue and organ transplants.

To perform HLA typing, a nucleic acid-targeting nucleic acid will be engineered to hybridize to target nucleic acid sequences in HLA genes. The complexes comprising a site-directed polypeptide and the nucleic acid-targeting nucleic acid will be purified using methods described herein. In some embodiments, the nucleic acid hybridizing to the nucleic acid-targeting nucleic acid will be the target nucleic acid and will be eluted and sequenced, using methods described herein. In some embodiments, the nucleic acid hybridizing to the nucleic-acid targeting nucleic acid will not be the target nucleic acid. The target nucleic acid will be the nucleic acid that is excised between the cleavage sites of a plurality of complexes (e.g., complexes comprising a site-directed polypeptide and nucleic acid-targeting nucleic acid). The excised target nucleic acid will be purified and sequenced, using methods described herein.

Example 10: Site-Directed Polypeptide Immunoprecipitation

The disclosure provides methods for nuclease immunoprecipitation and sequencing (NIP-Seq). In some embodiments, the method will comprise a) contacting a nucleic acid sample with an enzymatically inactive site-directed polypeptide, wherein the enzymatically inactive site-directed polypeptide binds a target nucleic acid, thereby forming a complex, b) capturing the complex with a capture agent, and c) sequencing the target nucleic acid. In some embodiments, the method will further comprise d) determining the identity of the off-target binding site.

In some embodiments, the methods of the disclosure will be performed outside of cells. For example, a sample will comprise purified genomic DNA.

The site-directed polypeptide-target nucleic acid complexes will be fixed or cross-linked to form complexes.

The nucleic acid (e.g., genomic DNA) will be treated to fragment the DNA before affinity purification. Fragmentation can be performed through physical, mechanical or enzymatic methods. Physical fragmentation can include exposing a target polynucleotide to heat or to ultraviolet (UV) light. Mechanical disruption may be used to mechanically shear a target polynucleotide into fragments of the desired range. Mechanical shearing may be accomplished through a number of methods known in the art, including repetitive pipetting of the target polynucleotide, sonication and nebulization. Target polynucleotides may also be fragmented using enzymatic methods. In some cases, enzymatic digestion may be performed using enzymes such as using restriction enzymes. Restriction enzymes may be used to perform specific or non-specific fragmentation of target polynucleotides. The methods may use one or more types of restriction enzymes, generally described as Type I enzymes, Type II enzymes, and/or Type III enzymes. Type II and Type III enzymes are generally commercially available and well known in the art. Type II and Type III enzymes recognize specific sequences of nucleotide nucleotides within a double-stranded polynucleotide sequence (a "recognition sequence" or "recognition site"). Upon binding and recognition of these sequences, Type II and Type III enzymes cleave the polynucleotide sequence. In some cases, cleavage will result in a polynucleotide fragment with a portion of overhanging single-stranded DNA, called a "sticky end." In other cases, cleavage will not result in a fragment with an overhang, creating a "blunt end." The methods may comprise use of restriction enzymes that generate either sticky ends or blunt ends.

Once fragmented, the complexes comprising the site-directed polypeptide will be purified by incubation with a solid support For example, if the site-directed polypeptide comprises a biotin tag, the solid support will be coated with avidin or streptavidin to bind to the biotin tag.

In an alternative embodiment, once fragmented, the complexes comprising the site-directed polypeptide, the target nucleic acid, and/or the nucleic acid-targeting nucleic acid, will be purified by incubation with a capture agent. The capture agent will bind to the affinity tag fused to the site-directed polypeptide. The capture agent will comprise an antibody. For example, if the affinity tag fused to the site-directed polypeptide is a FLAG tag, then the capture agent will be an anti-FLAG-tag antibody.

The capture agent will be purified with a solid support. For example, if the capture agent comprises a biotin tag, the bead will be coated with avidin or streptavidin to bind the biotinylated capture agent.

In some embodiments of the method, two or more rounds of purification will be performed. A first round will comprise purification with a solid support that can bind to the affinity tag of the capture agent and a second round will comprise purification with a solid support that can bind to the affinity tag of the site-directed polypeptide. A first round will comprise purification with a solid support that will bind to the affinity tag of the site-directed polypeptide and a second round will comprise purification with a solid support that will bind to the affinity tag of the capture agent.

In some embodiments, the method will be used to optimize the binding specificity of a site-directed polypeptide by performing the method more than once.

The captured complex will comprise site-directed polypeptide and a target nucleic acid. The target nucleic acid will be eluted from the site-directed polypeptide complex by standard methods including high salt washing, ethanol precipitation, boiling, gel purification, and the like.

The eluted DNA will be prepared for sequencing analysis using standard methods. The sequencing libraries will be sequenced and analyzed to identify the sequence, and frequency of nuclease-binding sites.

In some embodiments, the method will be performed a plurality of times. In some embodiments, the method further comprises collecting data and storing data. The data can be stored collected and stored on a computer server.

Example 11: In Vivo Site-Directed Polypeptide Immunoprecipitation

In some embodiments, the method will comprise: a) introducing an enzymatically inactive site-directed polypeptide into a cell, wherein the enzymatically inactive site-directed polypeptide binds a target nucleic acid, thereby forming a complex, b) capturing the complex with a capture agent, and c) sequencing the target nucleic acid. In some embodiments, the method will further comprise d) determining the identity of the off-target binding site.

In some instances, the site-directed polypeptide will comprise an affinity tag. Polypeptides comprising an affinity tag have been described herein.

Cells will be fixed or cross-linked. Fixed and/or cross-linked cells will be lysed. Lysis conditions will be chosen to maintain intact protein-DNA complexes. The lysate will be treated to fragment the DNA before affinity purification. Suitable fragmentation techniques are described herein.

Once fragmented, the complexes comprising the site-directed polypeptide, the target nucleic acid and/or the nucleic acid-targeting nucleic acid, will be purified from the lysate by incubation with a solid support. For example, if the site-directed polypeptide comprises a biotin tag, the solid support will be coated with avidin or streptavidin to bind to the biotin tag.

In an alternative embodiment, once fragmented, the complexes comprising the site-directed polypeptide, will be purified from the lysate by incubation with a capture agent. The capture agent will bind to the affinity tag fused to the site-directed polypeptide. The capture agent will comprise an antibody. For example, if the affinity tag fused to the site-directed polypeptide is a FLAG tag, then the capture agent will be a FLAG-tag antibody.

In some embodiments, the capture agent will comprise an affinity tag. The capture agent will be purified with a solid support. The solid support will bind to the affinity tag of the capture agent. For example, if the capture agent comprises a biotin tag, the bead will be coated with avidin or streptavidin to bind the biotinylated capture agent.

In some embodiments of the method, two rounds of purification will be performed. In some instances, a first round will comprise purification with a solid support that will bind to the affinity tag of the capture agent and a second round will comprise purification with a solid support that will bind to the affinity tag of the site-directed polypeptide. In some instances, a first round will comprise purification with a solid support that will bind to the affinity tag of the site-directed polypeptide, and a second round will comprise purification with a solid support that will bind to the affinity tag of the capture agent.

In some embodiments, the method will be used to optimize the binding specificity of a site-directed polypeptide by performing the method more than once.

The captured complex will comprise site-directed polypeptide and a target nucleic acid. The target nucleic acid will be eluted from the site-directed polypeptide complex by standard methods including high salt washing, ethanol precipitation, boiling, gel purification, and the like.

The eluted DNA will be prepared for sequencing analysis. Sequencing libraries will be made from the eluted target nucleic acid. The sequencing libraries will be sequenced and analyzed to identify the sequence, and frequency of nuclease-binding sites.

Example 12: Immunoprecipitation with an Enzymatically Inactive Endoribonuclease Capture Agent A method for determining the identity of an off-target binding site of a nuclease will comprise: a) contacting a nucleic acid sample with a enzymatically inactive site-directed polypeptide and a nucleic acid-targeting nucleic acid, wherein the enzymatically inactive site-directed polypeptide and nucleic acid-targeting nucleic acid binds a target nucleic acid, thereby forming a complex, b) capturing the complex with a capture agent, wherein the capture agent comprises a conditionally enzymatically inactive site-directed polypeptide, c) sequencing the target nucleic acid, and d) determining the identity of the off-target binding site. This method is designed to be performed on a cell-free nucleic acid sample, and/or a nucleic acid sample originating from a cell.

The site-directed polypeptide-target nucleic acid complexes will be fixed or cross-linked to form complexes.

If the nucleic acid sample originates from cells, the fixed and/or cross-linked complexes will be lysed. Lysis conditions can be chosen to maintain intact protein-DNA complexes. The lysate will be treated to fragment the DNA before affinity purification. If the nucleic acid sample originates from a cell-free sample, the cell-free nucleic acid will be treated to fragment the DNA. Suitable fragmentation techniques are described herein.

In some embodiments, the nucleic acid-targeting nucleic acid will comprise an affinity tag. The affinity tag will comprise a sequence that can bind to a conditionally enzymatically inactive site-directed polypeptide. In some instances, the affinity tag will comprise a sequence that can bind to a conditionally enzymatically inactive endoribonuclease. In some instances, the affinity tag will comprise a sequence that can bind to a conditionally enzymatically inactive Csy4 protein. The conditionally enzymatically inactive site-directed polypeptide will bind, but not cleave, the affinity tag. The affinity tag will comprise the nucleotide sequence 5'-GUUCACUGCCGUAUAGGCAGC-UAAGAAA-3' (SEQ ID NO: 1347). The affinity tag will be introduced into a nucleic acid using standard recombinant methods.

Once fragmented, the complexes comprising the site-directed polypeptide, the target nucleic acid, and/or the nucleic acid-targeting nucleic acid will be purified by incubation with a conditionally enzymatically inactive site-directed polypeptide (e.g., variant Csy4).

In some embodiments, the conditionally enzymatically inactive site-directed polypeptide will comprise an affinity tag.

The conditionally enzymatically inactive site-directed polypeptide will be purified with a solid support. The solid support will bind to the affinity tag of the conditionally enzymatically inactive site-directed polypeptide. For example, if the conditionally enzymatically inactive site-directed polypeptide comprises a biotin tag, the bead will be coated with avidin or streptavidin to bind the biotinylated capture agent.

In some embodiments, the enzymatically inactive site-directed polypeptide will be immobilized on any of a variety of insoluble support.

In some embodiments of the method, two rounds of purification will be performed. In some instances, a first round will comprise purification with a solid support that will bind to the affinity tag of the conditionally enzymatically inactive site-directed polypeptide (e.g., variant Csy4) and a second round will comprise purification with a solid support that will bind to the affinity tag of the site-directed polypeptide. In some instances, a first round will comprise purification with a solid support that will bind to the affinity tag of the site-directed polypeptide and a second round will comprise purification with a solid support that will bind to the affinity tag of the conditionally enzymatically inactive site-directed polypeptide (e.g., variant Csy4).

In some embodiments, the method will be used to optimize the binding specificity of a site-directed polypeptide by performing the method more than once.

The captured complex will comprise a site-directed polypeptide and a target nucleic acid. The target nucleic acid will be eluted from the site-directed polypeptide complex by standard methods including high salt washing, ethanol precipitation, boiling, gel purification, and the like.

The eluted DNA will be prepared for sequencing analysis. The sequencing libraries will be sequenced and analyzed to identify the sequence, and frequency of nuclease-binding sites.

Example 13: Sequencing

The eluted target nucleic acids will be prepared for sequencing analysis. Preparation for sequencing analysis will include the generation of sequencing libraries of the eluted target nucleic acid. Sequencing analysis will determine the identity and frequency of off-target binding sites of site-directed polypeptides.

Sequence determination will also be performed using methods that determine many (typically thousands to billions) nucleic acid sequences in an intrinsically parallel manner, where many sequences are read out preferably in parallel using a high throughput serial process. Such methods include but are not limited to pyrosequencing (for example, as commercialized by 454 Life Sciences, Inc., Branford, Conn.); sequencing by ligation (for example, as commercialized in the SOLiD™ technology, Life Technology, Inc., Carlsbad, Calif.); sequencing by synthesis using modified nucleotides (such as commercialized in TruSeq™ and HiSeq™ technology by Illumina, Inc., San Diego, Calif., HeliScope™ by Helicos Biosciences Corporation, Cambridge, Mass., and PacBio RS by Pacific Biosciences of California, Inc., Menlo Park, Calif.), sequencing by ion detection technologies (Ion Torrent, Inc., South San Francisco, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and other known highly parallelized sequencing methods.

Example 14: Modification of a Target Nucleic Acid with an Effector Protein

A vector comprising a site-directed polypeptide, a nucleic acid-targeting nucleic acid, and/or an effector protein is introduced into a cell. Once inside the cell a complex is formed comprising the elements encoded in the vector. The nucleic acid-targeting nucleic acid is modified with a Csy4 protein binding sequence. The effector protein, Csy4, binds to the modified nucleic acid-targeting nucleic acid. Csy4 comprises a non-native sequence (e.g., a fusion), that modifies a target nucleic acid. The non-native sequence is a sequence that modifies the transcription of the target nucleic acid. The non-native sequence is a transcription factor. The transcription factor increases the level of transcription of the target nucleic acid. In some cases, the non-native sequence is a methylase. The methylase results in increases in methylation of the target nucleic acid. In some cases the non-native sequence is a demethylase. The demethylase results in decreases in methylation of the target nucleic acid. In some cases, the non-native sequence is a Rad51-recruiting peptide. The Rad51-recruiting peptide increases the level of homologous recombination at the target site. In some cases, the non-native sequence is a BCRA-2 recruiting peptide. The BRCA-2-recruiting peptide increases the level of homologous recombination at the target site.

Example 15: Use of a Site-Directed Polypeptide as a Biosensor for a Genetic Mobility Event A vector(s) comprising a site-directed polypeptide, a nucleic acid-targeting nucleic acid, and/or an effector protein is introduced into a cell. The site-directed polypeptide and effector proteins are fused to cellular localization sequences (e.g. a nuclear localization signal). Once inside the cell a complex is formed comprising the elements encoded in the vector(s). In some instances, two vectors are introduced into the cell. The vector(s) encodes for a first effector protein (Csy4) that comprises a first inactive portion of a split green fluorescent protein (GFP) and binds to a first nucleic acid-targeting nucleic acid and a second effector protein (Csy4, Cas5, or Cas6) that comprises a second inactive portion of the split GFP and binds to a second nucleic acid-targeting nucleic acid. The first nucleic acid-targeting nucleic acid is modified with a first Csy4, Cas5 or Cas6 protein binding sequence that can be bound by a first Csy4, Cas5 or Cas6 protein. The second nucleic acid-targeting nucleic acid is modified with a second Csy4, Cas5 or Cas6 protein binding sequence that can be bound by a second Csy4, Cas5 or Cas6 protein. In some embodiments, the first Csy4, Cas5 or Cas6 protein interacts with the first Csy4, Cas5 or Cas6 protein binding sequence, and the second Csy4, Cas5 or Cas6 protein interacts with the second Csy4, Cas5 or Cas6 protein binding sequence. When the first and second nucleic acid-targeting nucleic acids direct the site-directed polypeptide to bind to two sequences that are in close proximity, the first effector protein and the second effector protein will bring the first inactive portion of the split GFP into contact with the second inactive portion of the split GFP, to generate an active GFP. The nucleic acid-targeting nucleic acids of the complex are designed such that one nucleic acid-targeting nucleic acid guides the complex to, for example, a region at or near the Bcr gene, and another nucleic acid-targeting nucleic acid guides the complex to, for example, a region at or near the Abl gene. If a translocation event has not occurred the Bcr gene is on chromosome 22 and the Abl gene is on chromosome 9, and the target nucleic acid sequences are sufficiently far enough apart such that the two inactive portions of the split GFP system are unable to interact, thereby not generating a signal. If a translocation event has occurred, the Bcr gene and the Abl gene are translocated such that the genes are close together. In this instance, the target nucleic acid sequences are sufficiently close enough together such that the two inactive portions of the split GFP system come together to form an active GFP.

A GFP signal can be detected by a fluorometer. The signal is indicative of a particular genotype resulting from the genetic mobility event.

Example 16: Use of a Site-Directed Polypeptide as a Biosensor for a Genetic Mutation The system described in Example 15 can also be used to detect the presence of specific mutation within a cell. In this example, a first nucleic-acid targeting nucleic acid is chosen to direct the site directed polynucleotide to a native sequence located near a mutation site. The second nucleic-acid targeting nucleic acid is chosen to recognize a mutant sequence (e.g., the mutant sequence having been identified by DNA sequencing). The nucleic-acid targeting nucleic acid is chosen such that the mutant sequence occurs within the first 12 nucleic acids immediately 5' to the PAM sequence in the site. In this instance, the target nucleic acid sequences are sufficiently close enough together such that the two inactive portions of the split GFP system come together to form an active GFP. A GFP signal can be detected by a fluorometer. The signal is indicative of a particular genotype.

Example 17: Use of a Site-Directed Polypeptide as a Therapeutic for Diseases that Comprise a Genetic Mobility Event A vector(s) comprising a site-directed polypeptide, a nucleic acid-targeting nucleic acid, and/or an effector protein, a nucleic acid comprising a cell-lysis inducing peptide (e.g. Adenovirus death protein) operably linked to a first promoter will also be introduced into the cell. Once inside the cell a complex is formed comprising the elements encoded in the vector(s). In some instances, two vectors are introduced into the cell. The vector(s) encodes for a first effector protein (comprising a first Csy4, Cas5 or Cas6 protein sequence) that binds to a first nucleic acid-targeting nucleic acid and comprises an activator domain for a first transcription factor that binds to the first promoter and a second effector protein (comprising a second Csy4, Cas5 or Cas6 protein sequence) that binds to a second nucleic acid-targeting nucleic acid and comprises the DNA binding domain for the first transcription factor. The first nucleic acid-targeting nucleic acid is modified with a first Csy4, Cas5 or Cas6 protein binding sequence that can be bound by a first Csy4, Cas5 or Cas6 protein sequence. The second nucleic acid-targeting nucleic acid is modified with a second Csy4, Cas5 or Cas6 protein binding sequence that can be bound by a second Csy4, Cas5 or Cas6 protein. In some embodiments, the first Csy4, Cas5 or Cas6 protein interacts preferentially with the first Csy4, Cas5 or Cas6 protein binding sequence, and the second Csy4, Cas5 or Cas6 protein interacts preferentially with the second Csy4, Cas5 or Cas6 protein binding sequence. If a diseased cell comprises a genome containing a genetic mobility event, when the first and second nucleic acid-targeting nucleic acids direct the site-directed polypeptide to bind to two sequences that are in close proximity, the first effector protein and the second effector protein will bring the activator domain and the DNA-binding domain of the first transcription factor into close proximity. The DNA-binding domain of the first transcription factor can bind to the first promoter operably linked to the cell-lysis inducing peptide, and the proximal activator domain will induce transcription of RNA encoding the cell-lysis inducing peptide. In a non-diseased cell, that does not comprise the genetic mobility event, the DNA-binding domain and the activator domains of the first transcription factor will not be brought into close proximity, and there will be no transcription of the cell-lysis inducing peptide.

The nucleic acid-targeting nucleic acids of the complex are designed such that one nucleic acid-targeting nucleic acid guides the complex to, for example, a region at or near the Bcr gene, and another nucleic acid-targeting nucleic acid guides the complex to, for example, a region at or near the Abl gene. In a non-diseased cell, a translocation event has not occurred, the Bcr gene is on chromosome 22 and the Abl gene is on chromosome 9, and the target nucleic acid sequences are sufficiently far enough apart such that the two inactive portions of the transcription factor system are unable to interact, and cannot induce transcription of the cell-lysis inducing peptide. In a diseased cell, in which a translocation event has occurred, the Bcr gene and the Abl gene are translocated such that the genes are close together. In this instance, the target nucleic acid sequences are sufficiently close enough together such that the two inactive portions of the transcription factor system come together to induce transcription of the cell-death inducing peptide. Cell-lysis will be dependent upon a particular genotype resulting from the genetic mobility event.

Example 18: Use of a Site-Directed Polypeptide as a Therapeutic for Diseases that Comprise a Genetic Mutation The system described in Example 17 can also be used to detect the presence of specific mutation within a cell. In this example, the first nucleic-acid targeting nucleic acid is chosen to direct the site directed polynucleotide to a native sequence located near a mutation site. The second nucleic-acid targeting nucleic acid is chosen to recognize a mutant sequence (e.g., the mutant sequence having been identified by DNA sequencing). The nucleic-acid targeting nucleic acid is chosen such that the mutant sequence occurs within the first 12 nucleic acids immediately 5' to the PAM sequence in the site. In this instance, the target nucleic acid sequences are sufficiently close enough together such that the two inactive portions of the transcription factor come together to enable transcription of a cell-lysis inducing peptide.

Example 19: Recruiting the Immune System to Attack Diseased Tissue Containing a Genetic Mobility Event or a Genetic Mutation The system described in Example 17 and/or 18 can also be used to direct transcription by the split transcription factor system that will result in the display of an antigen on the cell surface. In some instances, the antigen is a peptide displayed by an MEW class II molecules. In some instances, the antigen is a cell-surface protein that recruits immune effector cells to the site.

Example 20: Detecting Three-Dimensional Position of Nucleic Acids

A vector(s) comprising a site-directed polypeptide, a nucleic acid-targeting nucleic acid, and/or an effector protein is introduced into a cell. Once inside the cell a complex is formed comprising the elements encoded in the vector(s). Two vectors are introduced into the cell. One vector encodes for an effector protein (Csy4) that comprises a first inactive portion of a split affinity tag system. A second vector encodes for an effector protein (Csy4, Cas5, or Cas6) that comprises a second inactive portion of the split affinity tag. The nucleic acid-targeting nucleic acid of the complexes is modified with a Csy4, Cas5 or Cas6 protein binding sequence. The effector proteins bind to the modified nucleic acid-targeting nucleic acid. The nucleic acid-targeting nucleic acids are designed to guide the complexes to regions of interest in a three-dimensional nucleic acid structure (e.g., chromatin). If the target sequences are not close together in space, the two inactive portions of the split affinity tag are unable to interact. If the target sequences are close together in space, then the two inactive portions of the split affinity tag can come together to form the whole affinity tag.

The cells are lysed and the cell lysis is incubated with an antibody that binds to the affinity tag. The antibody is purified, thereby purifying the affinity tag and the nucleic acid to which the complexes are bound. The purified nucleic acid is dissociated from the complexes using high salt wash. The dissociated purified nucleic acid is prepared for sequencing analysis, and sequenced. The sequencing results correspond to regions of chromatin that are close together in three-dimensional space. The sequencing results can be used to further understand gene expression and treat disease.

Example 21: Multiplex Genome Engineering

A vector comprising a multiplexed genetic targeting agent comprising nucleic acid modules which comprise a nucleic acid-targeting nucleic acid and an endoribonuclease binding sequence is introduced into a cell. In some embodiments, the cell already comprises a site-directed polypeptide and an endoribonuclease. In some instances, the cell is contacted with a vector comprising a polynucleotide sequence encoding a site-directed polypeptide and a vector comprising a polynucleotide sequence encoding an endoribonuclease. In some instances, the cell is contacted with a vector comprising a polynucleotide sequence encoding both the site-directed polypeptide and the endoribonuclease. In some embodiments, the vector comprises a polynucleotide sequence encoding one or more endoribonucleases. In some embodiments, the vector comprises a polynucleotide sequence encoding a multiplexed genetic targeting agent, a site-directed polypeptide, and one or more endoribonucleases. The array is transcribed into RNA. The one or more endoribonucleases binds to the one or more endoribonuclease binding sequences in the multiplexed genetic targeting agent. The one or more endoribonucleases cleaves the one or more endoribonuclease binding sequences in the multiplexed genetic targeting agent, thus liberating the individual nucleic acid modules. In some embodiments, the nucleic acid modules comprise all, some, or none, of the endoribonuclease binding sequence.

The liberated nucleic acid modules bind to site-directed polypeptides, thereby forming complexes. The complexes are targeted to one or more target nucleic acids. The one or more nucleic acid modules hybridizes to the one or more target nucleic acids. The one or more site-directed polypeptides cleaves the one or more target nucleic acids at a cleavage site defined by the nucleic acid module, thus resulting in one or more modified target nucleic acids.

In some embodiments, one or more donor polynucleotides and/or a vectors encoding the same are introduced into the cell. One or more donor polynucleotides are incorporated into the one or more cleaved target nucleic acids, thereby resulting in one or more modified target nucleic acids (e.g., addition). In some instances, the same donor polynucleotide is incorporated into multiple cleavage sites. In some instances, one or more donor polynucleotides are incorporated into multiple cleavage sites. In some instances, no donor polynucleotide and/or vector encoding the same are introduced into the cells. In these instances, the modified target nucleic acid can comprise a deletion.

Example 22: Method of Stoichiometric Delivery of RNA to a Cell

In some embodiments, the disclosure provides for a method for stoichiometric delivery of nucleic acids to the nucleus of a cell. In some embodiments, three stoichiometrically deliverable nucleic acid are used: one encoding for Cas9, one encoding for a nucleic-acid targeting nucleic acid, and one encoding Csy4. Each of the three nucleic acids comprises a Csy4-binding site.

In some embodiments, the method provides for a tandem fusion polypeptide. The fusion polypeptide comprises three Csy4 polypeptides. The three Csy4 polypeptides are separated by a linker. The three Csy4 polypeptides bind to the Csy4-binding sites on each of the three nucleic acid molecules, thereby forming a complex.

In some embodiments, the complex is formed outside of a cell and introduced into the cell. The complex is formed by mixing the three stoichiometrically deliverable nucleic acids and the fusion protein and letting the reaction occur to allow binding between the tandem fusion polypeptide and three Csy4-binding sites. The complex is introduced by injection, electroporation, transfection, transformation, viral transduction, and the like. Inside the cell, some of the nucleic acids of the complex are translated. In some embodiments, the resulting translation products are Csy4 and NLS-Cas9 (e.g., Cas9 comprising an NLS. The NLS may not have to be at the N-terminus). The Csy4 cleaves the Csy4-binding site on the nucleic acid encoding the nucleic acid-targeting nucleic acid, thereby liberating the nucleic acid-targeting nucleic acid from the tandem fusion polypeptide. NLS-Cas9 binds the liberated nucleic acid-targeting nucleic acid, thereby forming a unit. This unit translocates to the nucleus. Inside the nucleus, the unit is guided to a target nucleic acid that hybridizes with the spacer of the nucleic acid-targeting nucleic acid. The Cas9 of the unit cleaves the target nucleic acid. The cleavage of the target nucleic acid by Cas9 is referred to as genome engineering.

In some embodiments, the complex is formed inside of a cell. A vector encoding the three stoichiometrically deliverable nucleic acids is introduced into the cell. Three different vectors encoding one of each of the three stoichiometrically deliverable nucleic acids is introduced the cell. Two vectors are introduced into the cell, wherein one of the two vectors encodes for two stoichiometrically deliverable nucleic acids and one of the two vectors encodes for one stoichiometrically deliverable nucleic acid. Any of the vectors can encode the tandem fusion polypeptide.

Inside the cell, vector nucleic acid encoding RNA or a polypeptide is transcribed into RNA. A complex comprising the three nucleic acids and the tandem fusion polypeptide is formed, whereby each of the Csy4-binding proteins binds to the Csy4-binding site on each of the three nucleic acids. The nucleic acids of the complex are translated. In some embodiments, the resulting translation products are Csy4 and NLS-Cas9 (e.g., Cas9 comprising an NLS. The NLS may not have to be at the N-terminus). The Csy4 cleaves the Csy4-binding site on the nucleic acid encoding the nucleic acid-targeting nucleic acid, thereby liberating the nucleic acid-targeting nucleic acid from the tandem fusion polypeptide. NLS-Cas9 binds the liberated nucleic acid-targeting nucleic acid, thereby forming a unit. This unit translocates to the nucleus.

Inside the nucleus, the unit is guided to a target nucleic acid that hybridizes with the spacer of the nucleic acid-targeting nucleic acid. The Cas9 of the unit cleaves the target nucleic acid.

Example 23: Method of Stoichiometric Delivery of Multiple Nucleic Acid-Targeting Nucleic Acids to a Cell In some embodiments, the disclosure provides for a method for stoichiometric delivery of a plurality of nucleic acids to a cell, wherein some of the plurality of nucleic acids are nucleic acid-targeting nucleic acids. In some embodiments, the plurality of nucleic acids comprises four nucleic acids: one encoding for Cas9, two encoding for nucleic-acid targeting nucleic acids, and one encoding for Csy4.

The nucleic acids comprise two or more nucleic acid-binding protein binding sites. In some instances, the first nucleic acid-binding protein binding site (e.g., the more 5' site) comprises a Csy4 binding site. In some instances, the second nucleic acid-binding protein binding site (e.g., the more 3' site) comprises a different nucleic acid-binding protein binding site (e.g., MS2 binding site). In some instances, the second nucleic acid-binding protein binding site from each of the stoichiometrically deliverable nucleic acids is different. For example, the second nucleic acid-binding protein binding site can be a site that binds one of a CRISPR polypeptide (e.g., Cas5, Cas6) In some instances, the nucleic acid encoding Cas9 also comprises a nuclear localization signal (NLS).

In some embodiments, the tandem fusion polypeptide comprises three nucleic acid-binding proteins. The three nucleic acid-binding proteins are Csy4, Cas5, Cas6. The tandem fusion polypeptide comprises a nuclear localization signal. The tandem fusion polypeptides comprises more than one copy of a nucleic acid-binding protein (e.g., 2 copies of Csy4, one copy of Cas5, one copy of Cas6).

In some embodiments, a complex comprising the tandem fusion protein and the four nucleic acids is formed outside of a cell. The complex is formed by mixing the four nucleic acids and the tandem fusion protein and letting the reaction occur to allow binding between the tandem fusion polypeptide and four nucleic acid-binding protein binding sites. The complex is introduced into the cell. Introduction occurs by either transformation, transfection, viral transduction, microinjection, or electroporation, or any technique capable of introducing biomolecules across a cell membrane. The complex is formed inside the cell (e.g., after introduction of vectors comprising nucleic acid sequences encoding the nucleic acids and tandem fusion protein).

Inside the cell, the nucleic acids encoding Csy4 and Cas9 are translated, resulting in Csy4 and NLS-Cas9 (e.g., Cas9 comprising an NLS. The NLS may not have to be at the N-terminus). Csy4 cleaves the Csy4-binding site on the nucleic acids encoding the nucleic acid-targeting nucleic acids, thereby liberating them from the tandem fusion polypeptide.

NLS-Cas9 binds the liberated nucleic acid-targeting nucleic acids, thereby forming a plurality units. The units translocate to the nucleus. Inside the nucleus, the units are guided to a target nucleic acid that hybridizes with the spacer of the nucleic acid-targeting nucleic acid of the unit. The Cas9 of the unit cleaves the target nucleic acid.

Example 24: Method of Stoichiometric Delivery of RNA and a Donor Polynucleotide

The disclosure provides for a method of stoichiometric delivery of RNA components that can be used in genome engineering. The method can also comprise delivery of a donor polynucleotide that can be inserted into a site of genome engineering.

The disclosure provides for a method for stoichiometric delivery of a plurality of RNAs and a donor polynucleotide to a cell. In some embodiments, the plurality of RNAs comprises three RNAs and a DNA. In some instances, the three RNAs are: one encoding for Cas9, one encoding for Csy4, and one encoding for a nucleic acid-targeting nucleic acid. The DNA is a DNA encoding a donor polynucleotide.

In some instances, the RNAs comprise a plurality of nucleic acid-binding protein binding sites (e.g., two nucleic acid-binding protein binding sites). The first nucleic acid-binding protein binding site (e.g., the more 5' site) comprises a Csy4 binding site. The second nucleic acid-binding protein binding site (e.g., the more 3' site comprises a different nucleic acid-binding protein binding site). The second nucleic acid-binding protein binding site in each of the nucleic acids of the disclosure is different. For example, the second nucleic acid-binding protein binding site binds a CRISPR polypeptide (e.g., Cas5, Cas6) and/or a DNA binding protein (e.g., a zinc finger protein). The nucleic acids of the method also comprise a sequence encoding for a nuclear localization signal (e.g., the RNA encoding Cas9, and the DNA encoding a donor polynucleotide).

In some embodiments, the tandem fusion polypeptide comprises four nucleic acid-binding proteins (e.g., RNA-binding proteins and DNA-binding proteins). In some instances, three nucleic acid-binding proteins are Csy4, Cas5, Cas6, and the fourth nucleic acid-binding protein is a DNA-binding protein (e.g., zinc finger protein). In some instances, the tandem fusion polypeptide comprises a nuclear localization signal.

In some embodiments, a complex comprising the tandem fusion protein and the nucleic acids (e.g., three RNAs and one DNA) is formed outside of a cell. The complex is formed by mixing the nucleic acids (e.g., three RNAs and one DNA) and the tandem fusion protein and letting the reaction occur to allow binding between the tandem fusion polypeptide and four RNA-binding protein binding sites. The complex can be introduced into the cell. The complex is formed inside the cell (e.g., after introduction of vectors comprising nucleic acid sequences encoding the nucleic acids and tandem fusion protein).

Inside the cell, the RNAs encoding Csy4 and Cas9 are translated, resulting in Csy4 and NLS-Cas9 (e.g., Cas9 comprising an NLS. The NLS may not have to be at the N-terminus as written here). Csy4 can cleave the Csy4-binding site on the RNAs encoding the nucleic acid-targeting nucleic acid and the DNA, thereby liberating them from the tandem fusion polypeptide. In some instances, the liberated donor polynucleotide translocates to the nucleus by its nuclear localization signal.

NLS-Cas9 binds the liberated nucleic acid-targeting nucleic acid, thereby forming a unit. The unit translocates to the nucleus. Inside the nucleus, the unit is guided to a target nucleic acid that hybridizes with the spacer of the nucleic acid-targeting nucleic acid of the unit. The Cas9 of the unit cleaves the target nucleic acid. The donor polynucleotide, a portion of the donor polynucleotide, a copy of the donor polynucleotide, or a portion of a copy of the donor polynucleotide can be inserted into the cleaved target nucleic acid.

Example 25: Seamless Selection of Genetically Modified Cells

A plurality of cells is contacted with a vector comprising sequences encoding a polypeptide homologous to Cas9, a nucleic acid-targeting nucleic acid and a donor polynucleotide. In some cases, one or more of the sequences encoding the polypeptide homologous to Cas9, the nucleic acid-targeting nucleic acid and the donor polynucleotide are located on different vectors. e cells are transfected with the vector. In some instances, the cells are infected with a virus carrying the vector. In some instances, the cell already comprises a protein homologous to Cas9 and the vector does not encode this polypeptide. In some instances, the cell already comprises a CRISPR system (e.g. Cas proteins, crRNA and tracrRNA) and the vector only encodes the donor polynucleotide. The donor polynucleotide comprises sequences encoding a genetic element of interest and a reporter element. The reporter element comprises nucleic acid-targeting nucleic acid sequences, a protein homologous to Cas 9 and a fluorescent protein. The nucleic acid-targeting nucleic acid guide Cas9 to a target nucleic acid (e.g. a site in the host cell genome), resulting in a double-stranded DNA break of the target nucleic acid and insertion of the donor polynucleotide. Insertion of the donor polynucleotide is screened for by screening for the reporter. In some cases, screening comprises fluorescence-activated cell sorting. Screening comprises multiple selection methods. Cas9 and/or the nucleic acid-targeting nucleic acids are controlled by an inducible promoter. After selecting a population of cells that comprise the reporter signal, the reporter element is removed by activating the inducible promoter, which transcribes the nucleic acid-targeting nucleic acids and the site-directed polypeptide of the donor polynucleotide. The transcribed nucleic acid-targeting nucleic acids and the transcribed site-directed polypeptide can form complexes. One complex can be targeted to the 3' end of the reporter element of the donor polynucleotide. One complex can be targeted to the 5' end of the reporter element of the donor polynucleotide. The 3' and 5' ends of the reporter element can be cleaved. The cleaved target nucleic acid can be rejoined by cellular mechanisms, thereby resulting in an in-frame nucleic acid sequence encoding the same nucleic acid sequence as prior to insertion of the donor polynucleotide. In this way, the reporter element is seamlessly inserted and removed from cells.

Example 26: Method for Cas9 Cleavage Using Engineered Nucleic Acid-Targeting Nucleic Acids Reagents
pCB002 plasmid containing temp3 target DNA sequence was digested with 1 U of AscI per 1 ug of DNA to linearize the vector. The reaction was stopped by incubating reaction mix at 80° C. for 20 min. Reaction was then purified using Qiagen PCR clean up kit.

Single guide nucleic acid were generated using T7 High Yield RNA Synthesis Kit (Cat No. E2040S), using half the volume of reagents recommended by the manufactures for RNA of >300 nucleotides. Generally between 200-350 ng of template were used in a 20 uL reaction that incubates for 16 hours. Samples were treated with DNase, and purified using Thermo GeneJet RNA purification Kit (Cat No. K0732), and eluted in 20 uL. Typical yields range from 1.4-2 ug/uL.

At the start of cleavage assay set-up, all sgRNA were diluted to 3500 nM concentration and heat shocked at 80° C. for 15 minutes. Samples were removed from heating element and allowed to equilibrate to room temperature. An aliquot of 4 uL of single guide nucleic acid-targeting nucleic acid can be run out on an agarose gel to confirm RNA integrity.

Aliquots of Cas9 at 2-2.5 mg/mL were removed from freezer and thawed as quickly as possible and then diluted in 1× cleavage buffer to appropriate stock concentration.

Cleavage Assay
A master mix of water, 5× cleavage buffer of (100 mM HEPES, 500 mM KCl, 25 mM MgCl2, 5 mM DTT, and 25% glycerol at pH 7.4), and Cas9 to 250 nM was aliquoted into thin wall PCR tubes. sgRNA was added to appropriate tubes at a final concentration of 250 nM.

Figure 22A:
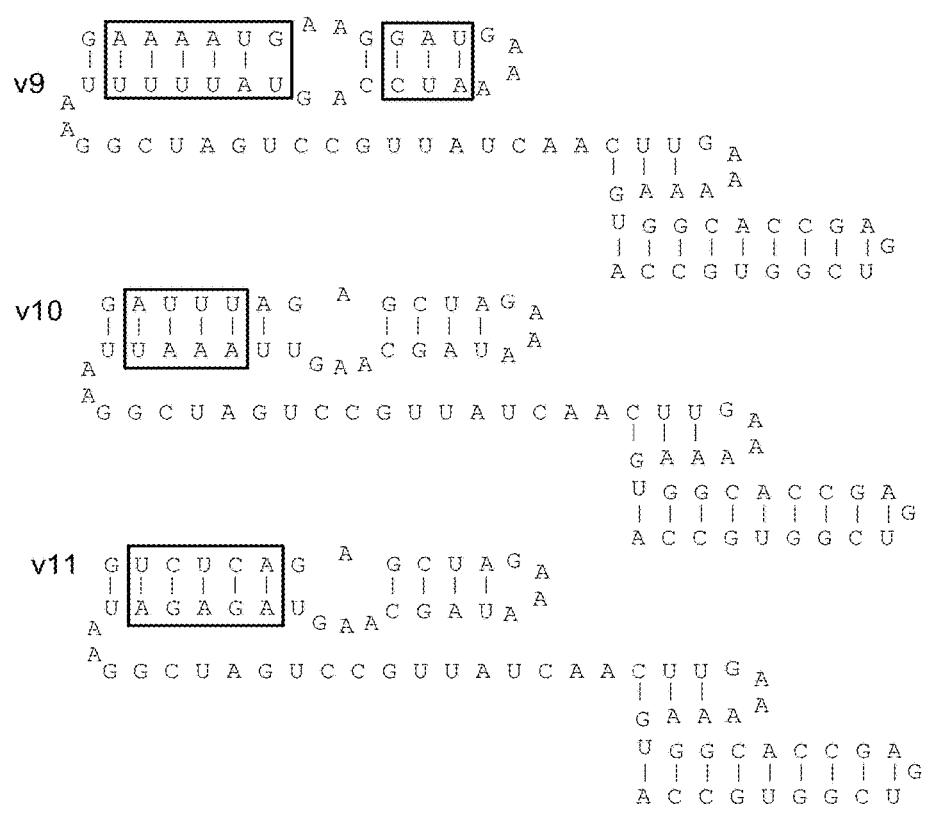
Figure 22B:
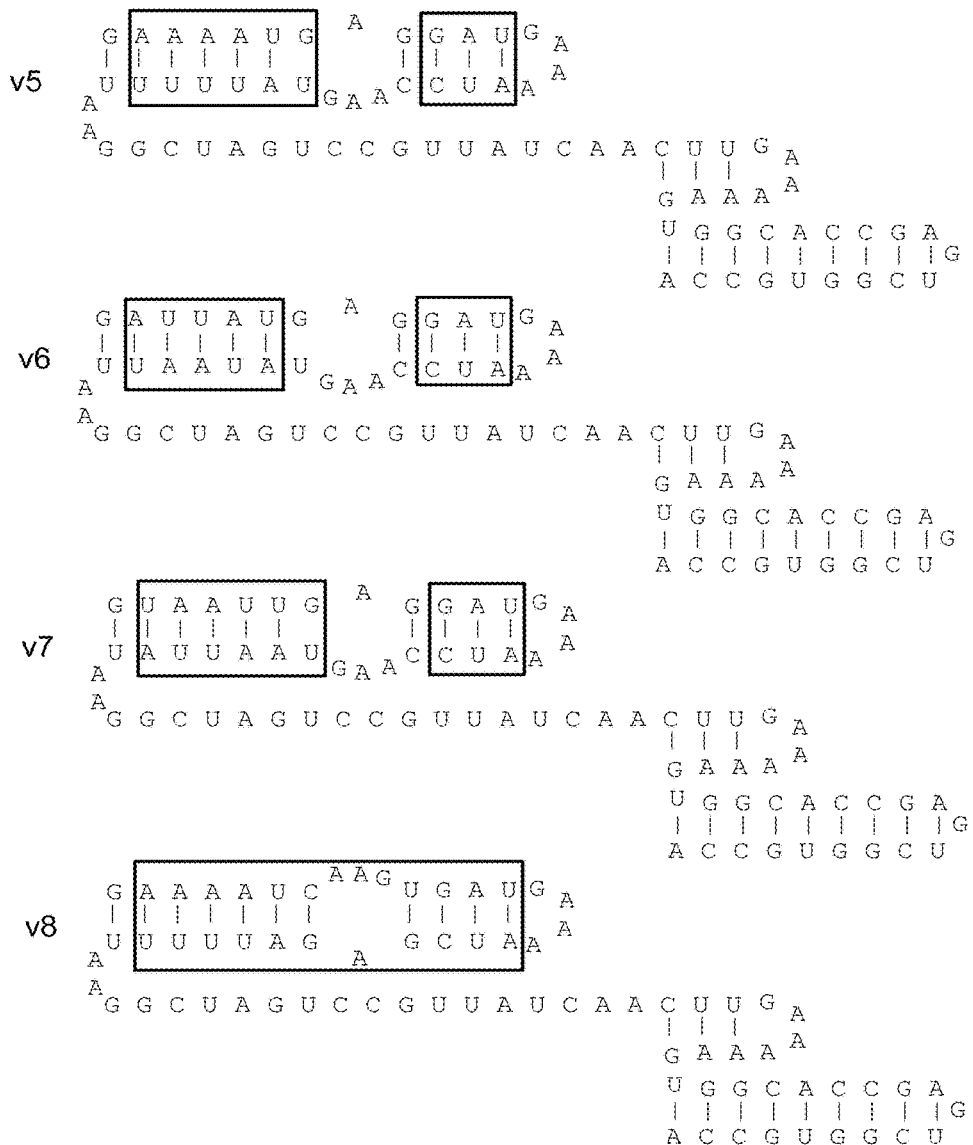
FIG. 22B discloses 1526, 1530, 1527, 1531, 1528, 1532, 1529, and 1533, respectively, in order of appearance.
Figure 23A:
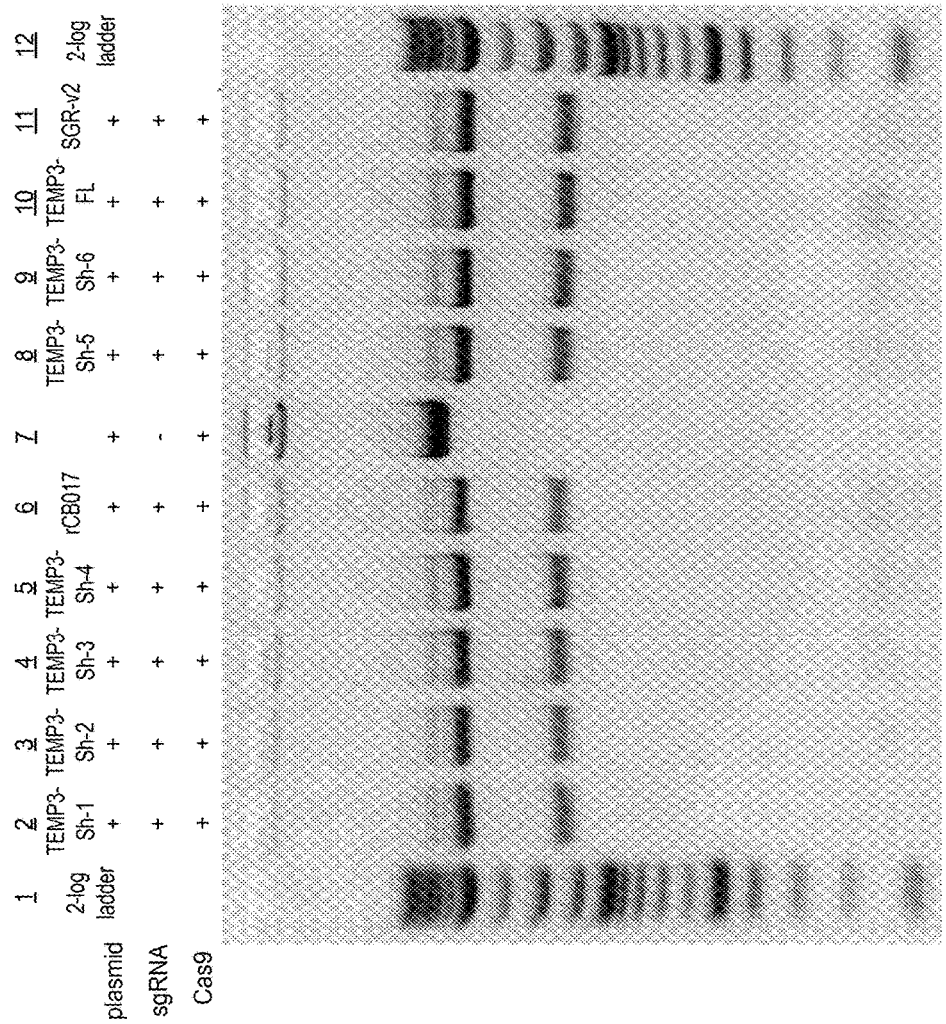
FIG. 23A-C shows exemplary data from an in vitro cleavage assay. The results demonstrate that more than one synthetic nucleic acid-targeting nucleic acid backbone sequences can support cleavage by a site-directed polypeptide (e.g., Cas9).
Figure 23B:
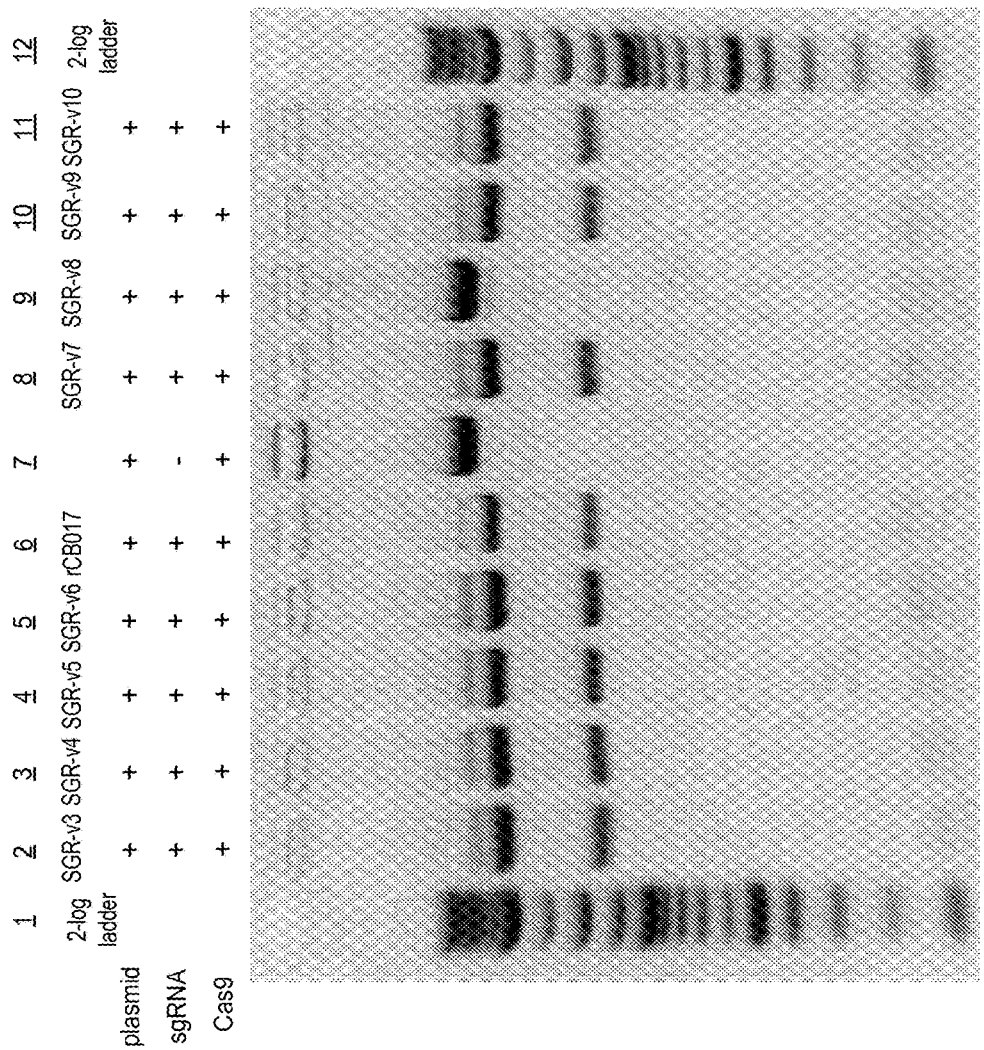
Figure 23C:
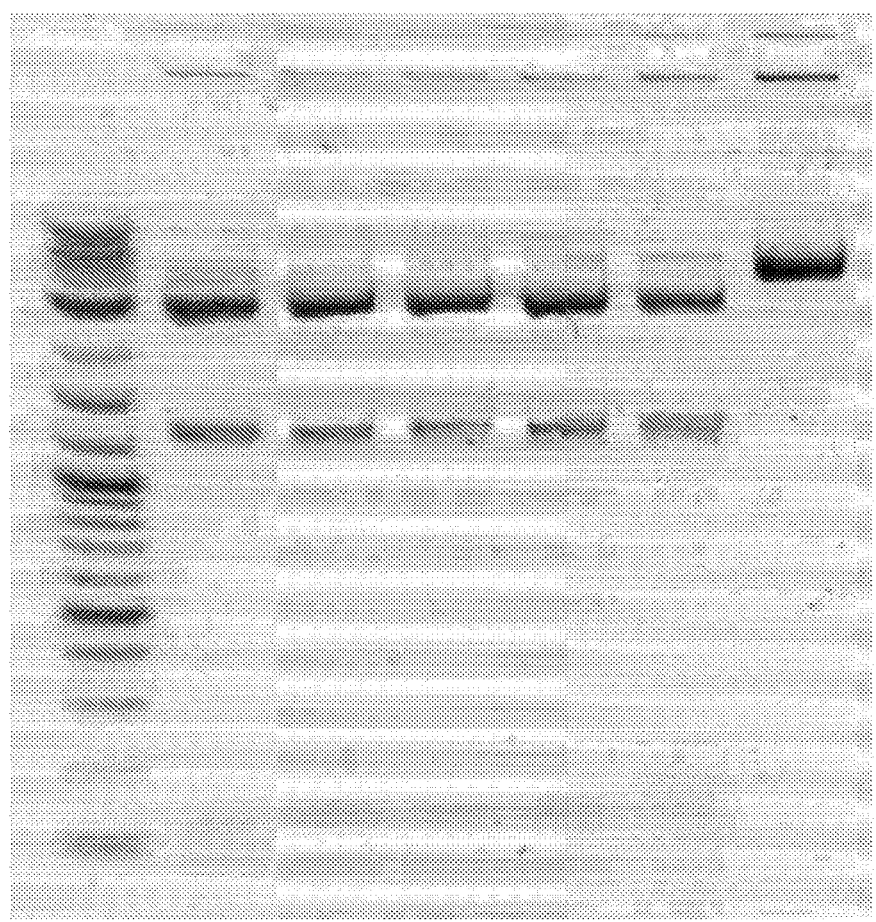

The reaction was incubated at 37° C. for 10 minutes, 10 nM linearized plasmid was added and reactions (final reaction volume 20 uL) were incubated at 37° C. for and hour. The reaction was terminated by heating reaction to 60° C. for 20 minutes. 10 uL aliquots were mixed with 2 uL 6×DNA loading dye and analyzed by electrophoresis on a 1.5% agarose gel stained with SYBR safe. The appearance of a ~2800 bp and ~1300 bp fragments was indicative of Cas9 mediated cleavage. The results of the experiments are shown in FIG. 23A, FIG. 23B, and FIG. 23C. All synthetic guide RNA sequences designed and shown in FIG. 22A and FIG. 22B supported sgRNA cleavage, except for SGRv8, in which the entire complementary region was inverted. These results indicate that different regions of the sgRNA can be amenable to engineering and still retain function.

Engineered nucleic acid-targeting nucleic acids were tested in the assay described above. FIGS. 22A and 22B shows the designs of an initial set of duplex variants in single-guide nucleic acid-targeting nucleic acid backbone variants used to test targeting and cleavage activity.

Figure 24:
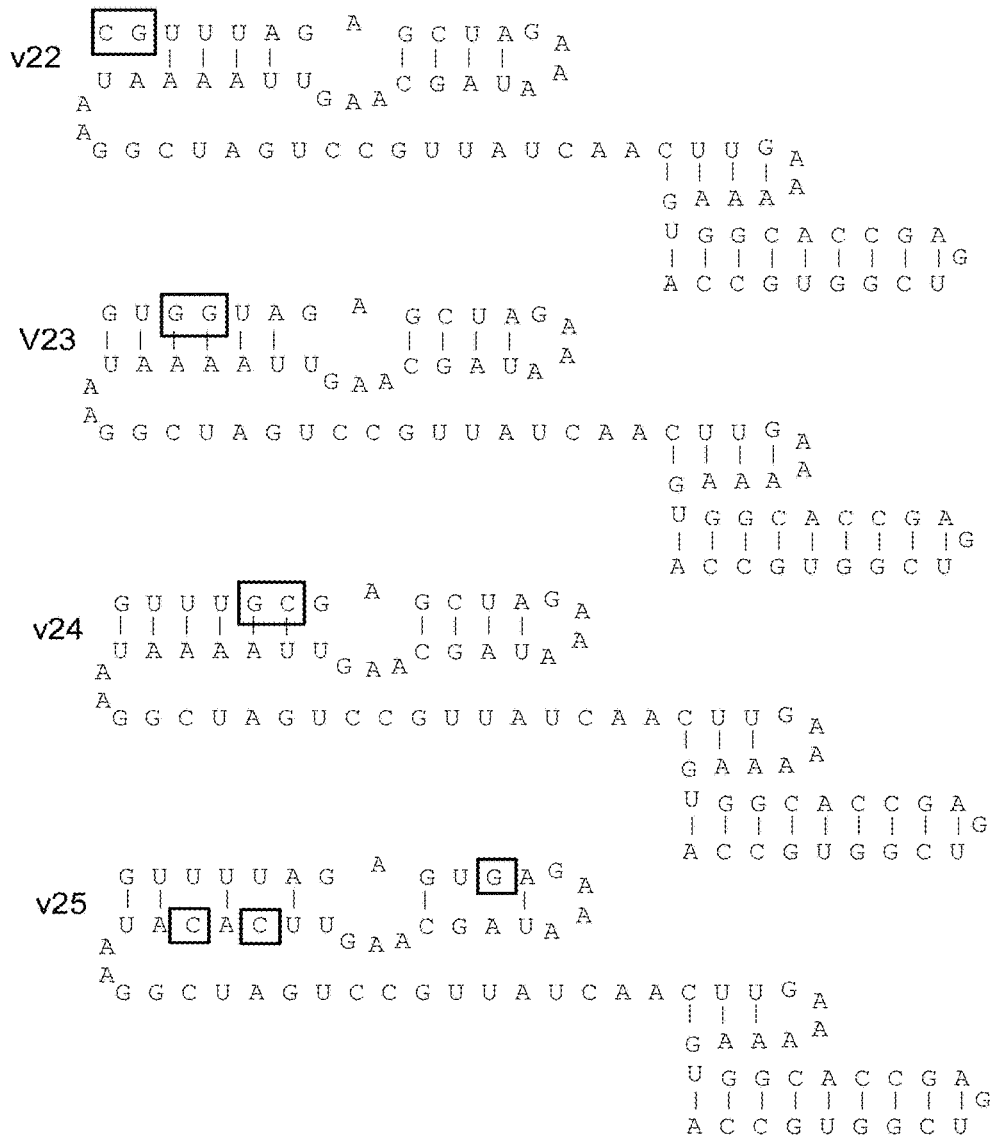
FIG. 24 shows exemplary synthetic single-guide nucleic acid-targeting nucleic acid sequences containing variants in the complementary region/duplex. Nucleotides in the boxes correspond to nucleotides that have been altered relative to the CRISPR sequences labeled as FL-tracr-crRNA sequence.
Figure 25:
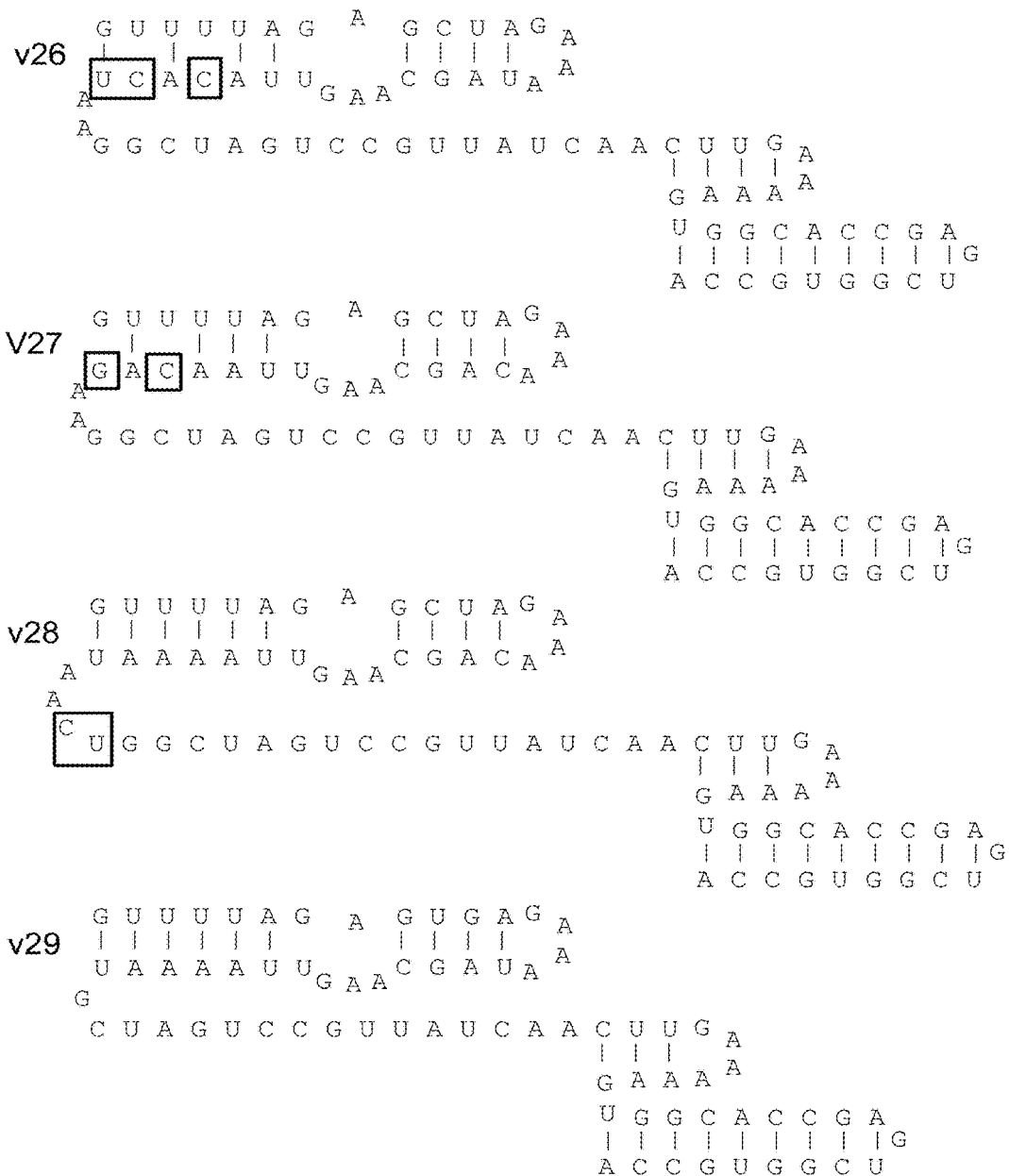
FIG. 25 shows exemplary variants to the single guide nucleic acid-targeting nucleic acid structure within the region 3' to the complementary region/duplex. Nucleotides in the boxes correspond to nucleotides that have been altered relative to the naturally occurring *S. pyogenes* SF370 CRISPR nucleic acid and tracr nucleic acid sequence pairing.

FIG. 24 and FIG. 25 illustrate a second set of duplex variants with smaller modifications in the duplex. V28 comprises a 2 base insertion 3' to the complementary region; V29 comprises a 3 base deletion 3' to the complementary region.

Figure 26A:
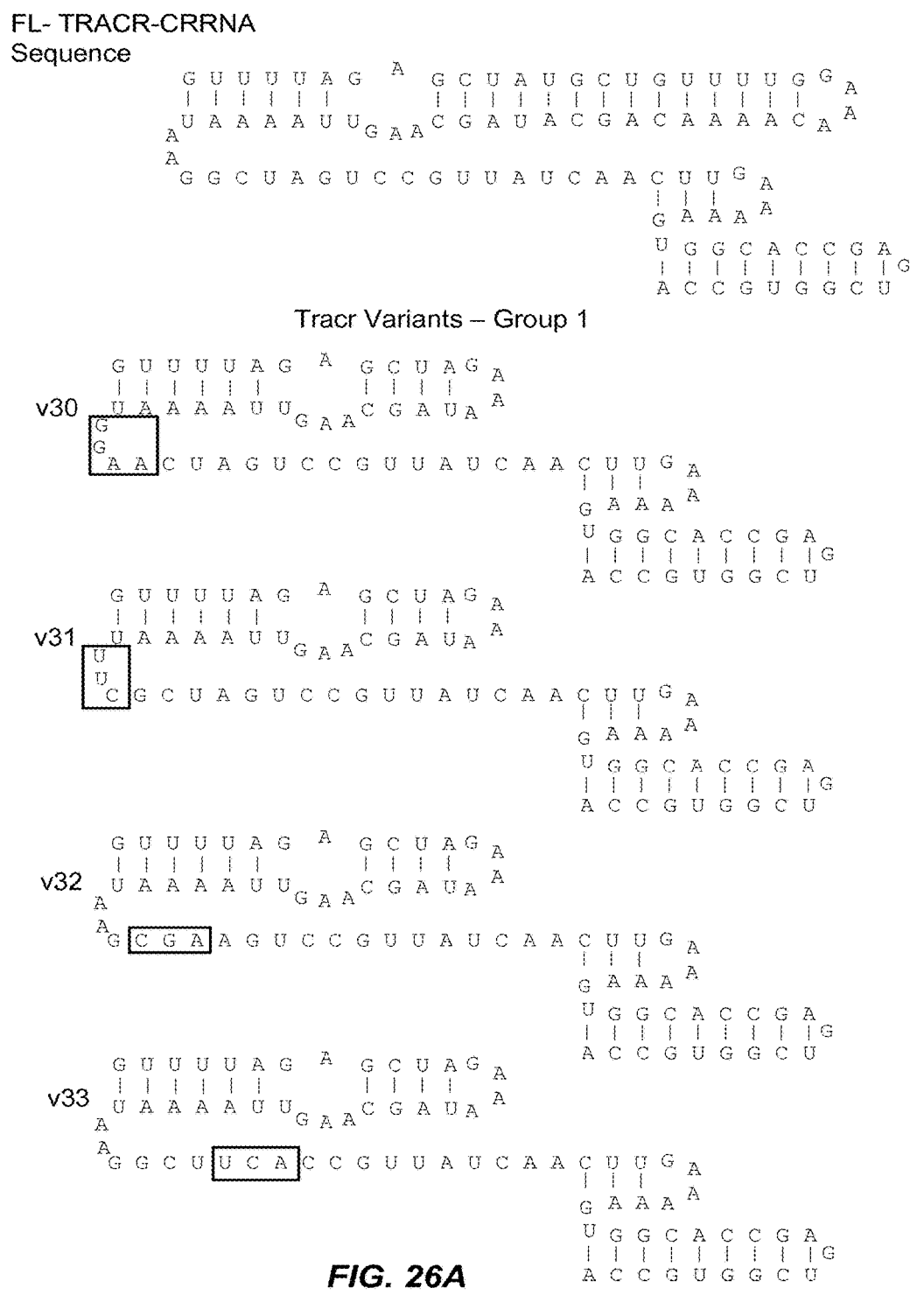
Figure 26A:
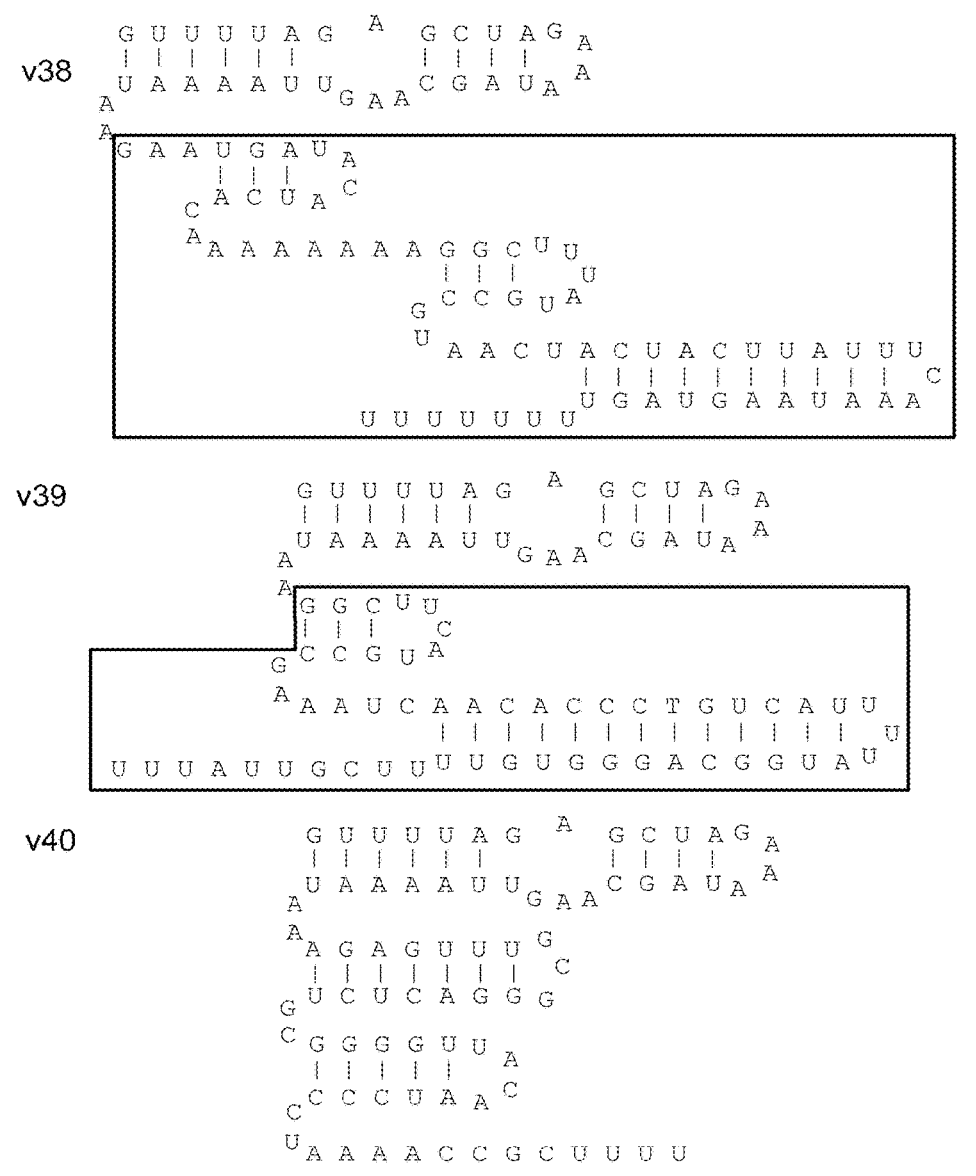
Figure 26B:
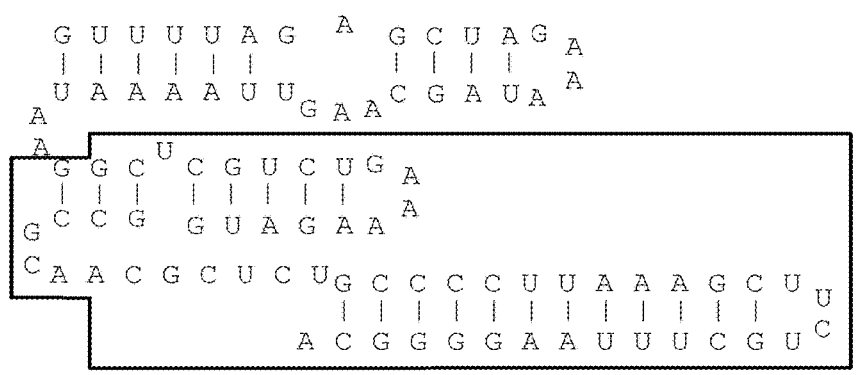

FIG. 26A and FIG. 26B illustrate tracr variants which comprise mutations in the tracrRNA portion of the nucleic acid-targeting nucleic acid (i.e., minimum tracrRNA sequence and 3' tracrRNA sequence). V38-V41 comprise fusions between the complementary region/duplex and the 3' ends of the tracr nucleic acid sequences from M mobile 163K (v38), S. thermophilus LMD-9 (V39), C. jejuni (V40), and N. meningitides.

Figure 27A:
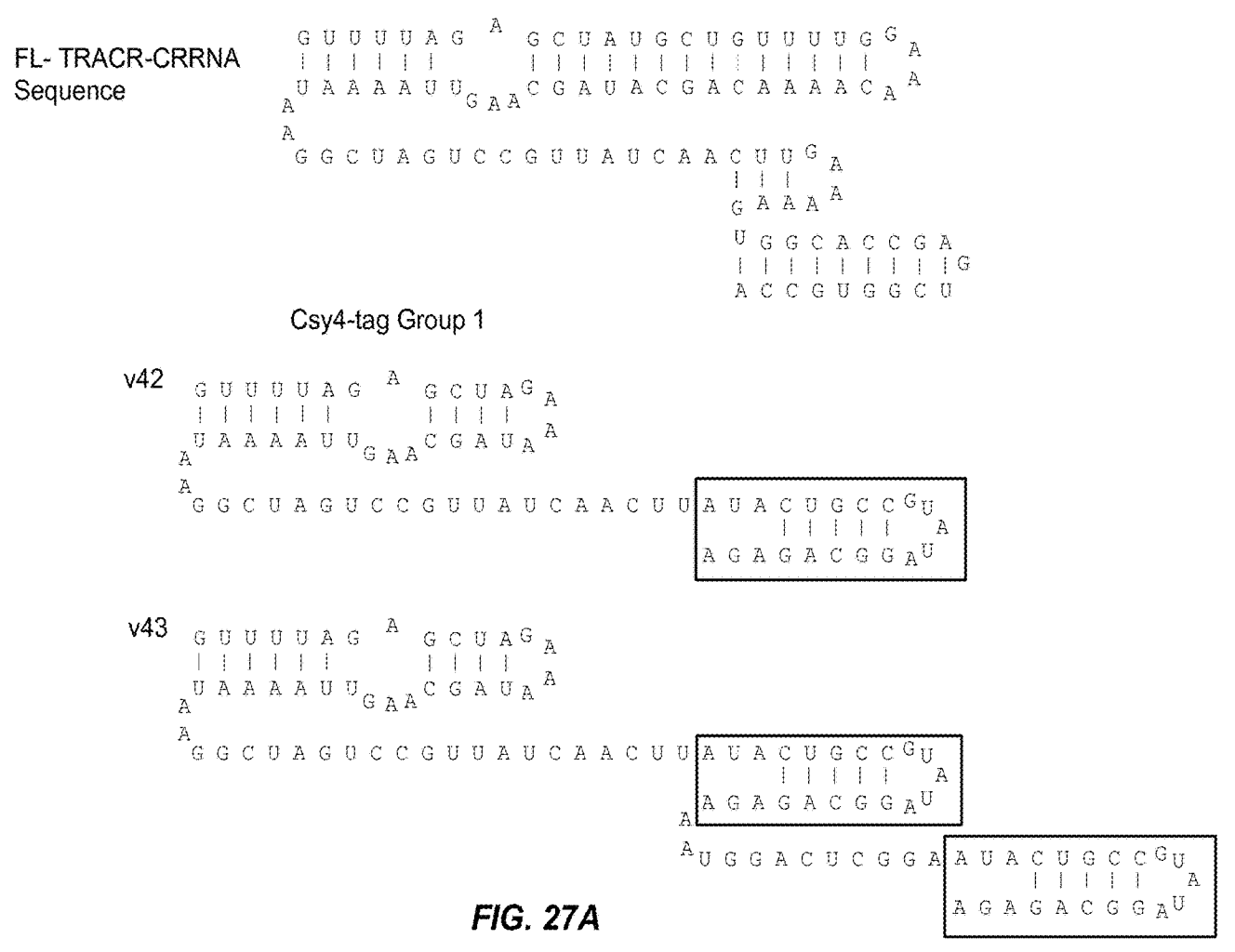
Figure 27B:
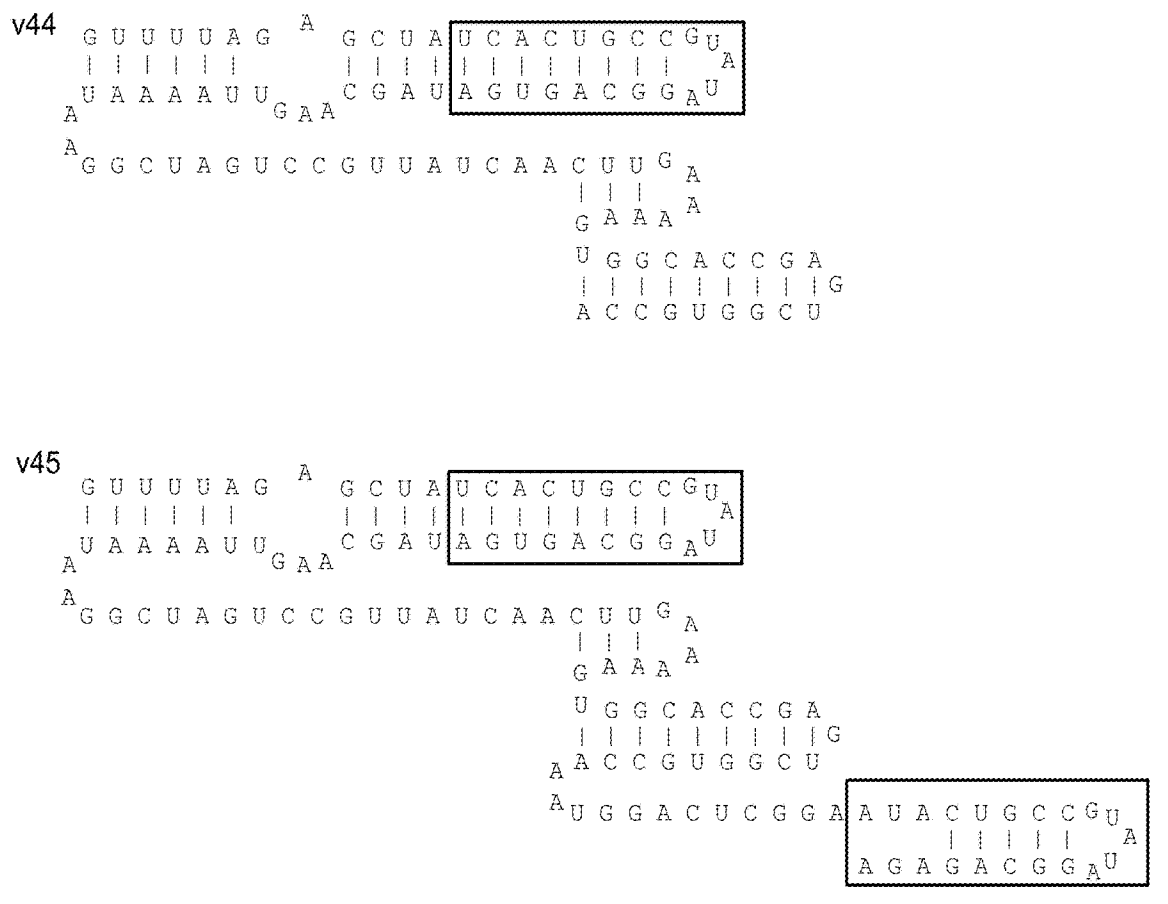

FIG. 27A and FIG. 27B depict variants comprising modifications to enable Csy4 binding to the nucleic acid-targeting nucleic acid. The additional hairpin sequences are derived from the CRISPR repeat in Pseudomonas aeruginosa PA14.

FIG. 23A, FIG. 23B, and FIG. 23C show data from the in vitro cleavage assay demonstrating the activity of the nucleic acid-targeting nucleic acid variants on Cas9 cleavage. Variant SGRv8 failed to support target nucleic acid cleavage (FIG. 23B lane 9).

Figure 28:
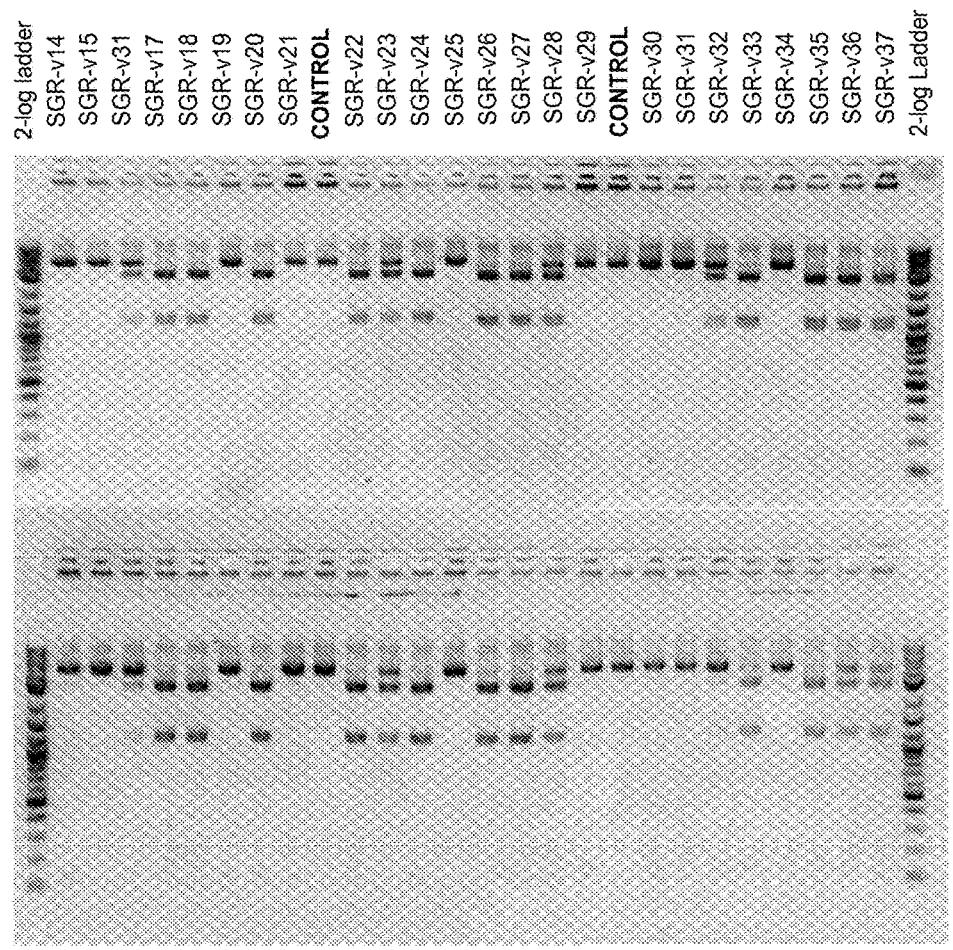
FIG. 28 shows exemplary data from an in vitro cleavage assay demonstrating that multiple synthetic nucleic acid-targeting nucleic acid backbone sequences support Cas9 cleavage. The top and bottom gel images represent two independent repeats of the assay.
Figure 29:
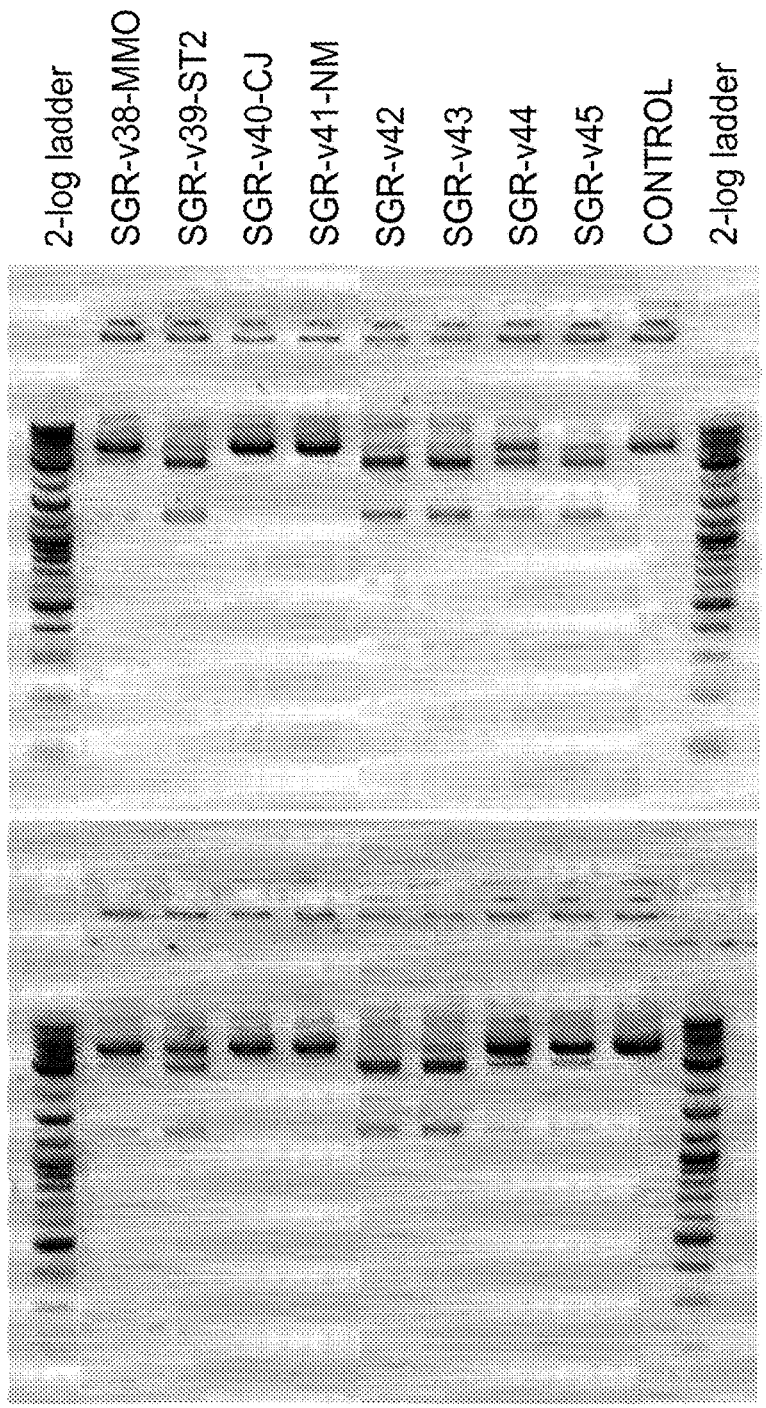
FIG. 29 shows exemplary data from an in vitro cleavage assay demonstrating that multiple synthetic nucleic acid-targeting nucleic acid backbone sequences support Cas9 cleavage. The top and bottom gel images represent two independent repeats of the assay.

FIG. 28 and FIG. 29 show two independent repeats of the Cas9 cleavage assay testing the variants depicted in FIGS. 24, 25, 26A, 26B, 27A, and 27B.

Additional engineered nucleic acid-targeting nucleic acids were made as listed in Table 5, and tested in the same assay. The results of the assay are shown in FIGS. 37A, 37B, 37C, and 37D and listed in the activity column of Table 5.

The results of these experiments indicate the importance of the bulge and P-domain regions in effecting target nucleic acid cleavage. The functionality of variants 42-45 indicates that the addition of a Csy4 binding sequence to a nucleic acid-targeting nucleic acid does not disrupt target nucleic acid cleavage.

Example 27: Sequencing Analysis Systems

FIG. 30 depicts a system that is configured to implement the methods of the disclosure. The system can include a computer server ("server") that is programmed to implement the methods described herein. FIG. 30 depicts a system 3000 adapted to enable a user to detect, analyze, and communicate sequencing results of, for example, nuclease-targeted enriched nucleic acids, sequenced target nucleic acids, data concerning the methods of the disclosure, diagnose a disease, genotype a patient, make a patient-specific treatment decision, or any combination thereof. The system 3000 includes a central computer server 3001 that is programmed to implement exemplary methods described herein. The server 3001 includes a central processing unit (CPU, also "processor") 3005 which can be a single core processor, a multi core processor, or plurality of processors for parallel processing. The server 3001 also includes memory 3010 (e.g. random access memory, read-only memory, flash memory); electronic storage unit 3015 (e.g. hard disk); communications interface 3020 (e.g. network adaptor) for communicating with one or more other systems; and peripheral devices 3025 which may include cache, other memory, data storage, and/or electronic display adaptors. The memory 3010, storage unit 3015, interface 3020, and peripheral devices 3025 are in communication with the processor 3005 through a communications bus (solid lines), such as a motherboard. The storage unit 3015 can be a data storage unit for storing data. The server 3001 is operatively coupled to a computer network ("network") 3030 with the aid of the communications interface 3020. The network 3030 can be the Internet, an intranet and/or an extranet, an intranet and/or extranet that is in communication with the Internet, a telecommunication or data network. The network 3030 in some cases, with the aid of the server 3001, can implement a peer-to-peer network, which may enable devices coupled to the server 3001 to behave as a client or a server. The microscope and micromanipulator can be peripheral devices 3025 or remote computer systems 3040.

The storage unit 3015 can store files, such as sequencing results, target binding sites, personalized genetic data, genotypes, images, data analysis of images and/or sequencing results, or any aspect of data associated with the disclosure.

The server can communicate with one or more remote computer systems through the network 3030. The one or more remote computer systems may be, for example, personal computers, laptops, tablets, telephones, Smart phones, or personal digital assistants.

In some situations the system 3000 includes a single server 3001. In other situations, the system includes multiple servers in communication with one another through an intranet, extranet and/or the Internet.

The server 3001 can be adapted to store sequencing results, target binding sites, personalized genetic data, and/or other information of potential relevance. Such information can be stored on the storage unit 3015 or the server 3001 and such data can be transmitted through a network.

Methods as described herein can be implemented by way of machine (or computer processor) executable code (or software) stored on an electronic storage location of the server 3001, such as, for example, on the memory 3010, or electronic storage unit 3015. During use, the code can be executed by the processor 3005. In some cases, the code can be retrieved from the storage unit 3015 and stored on the memory 3010 for ready access by the processor 3005. In some situations, the electronic storage unit 3015 can be precluded, and machine-executable instructions are stored on memory 3010. Alternatively, the code can be executed on a second computer system 3040.

Aspects of the systems and methods provided herein, such as the server 3001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless likes, optical links, or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, tangible storage medium, a carrier wave medium, or physical transmission medium. Non-volatile storage media can include, for example, optical or magnetic disks, such as any of the storage devices in any computer(s) or the like, such may be used to implement the system. Tangible transmission media can include: coaxial cables, copper wires, and fiber optics (including the wires that comprise a bus within a computer system). Carrier-wave transmission media may take the form of electric or electromagnetic signals, or acoustic or light waves such as those generated during radio frequency (RF) and infrared (IR) data communications. Common forms of computer-readable media therefore include, for example: a floppy disk, a flexible disk, hard disk, magnetic tape, any other magnetic medium, a CD-ROM, DVD, DVD-ROM, any other optical medium, punch cards, paper tame, any other physical storage medium with patterns of holes, a RAM, a ROM, a PROM and EPROM, a FLASH-EPROM, any other memory chip or cartridge, a carrier wave transporting data or instructions, cables, or links transporting such carrier wave, or any other medium from which a computer may read programming code and/or data. Many of these forms of computer readable media may be involved in carrying one or more sequences of one or more instructions to a processor for execution.

Example 28: Array-Based Sequencing Using a Site-Directed Polypeptide

A nucleic acid sample is ligated with a nucleic acid tag comprising a single guide RNA and a detectable label. Together, the nucleic acid sample ligated to the nuclei acid tag is referred to as a tagged test sample. The tagged test sample is contacted to a microarray comprising immobilized oligonucleotides. The immobilized oligonucleotides are a double-stranded nucleic acid library. The oligonucleotides comprise a detectable label (e.g., fluorescent label. The individual members of the tagged test sample hybridize to the oligonucleotides to which they share enough complementarity to facilitate hybridization. The amount of hybridization can be quantified by comparing the intensities of the two detectable labels from the sample library and the immobilized oligonucleotides. For example, hybridized oligonucleotides can display two detectable labels (that from the sample library and the oligonucleotide). Unhybridized oligonucleotides can display one detectable label (that from the oligonucleotide). The hybridized probes are contacted with Cas9. Cas9 cleaves the oligonucleotides in the microarray that have hybridized with members of the tagged test sample. Cleavage by the site-directed polypeptide allows the hybridized members of the tagged test sample to be removed. After cleavage by the site-directed polypeptide, only unhybridized oligonucleotide detectable labels remain on the microarray. The remaining detectable label is quantified. The quantification of the remaining detectable labels is correlated to which sequences were represented in the nucleic acid sample and which were not (e.g., by position mapping). Oligonucleotides that do not display a remaining detectable label correspond to sequences that were represented in the nucleic acid sample. Oligonucleotides that display a remaining detectable label correspond to sequences that were not represented in the nucleic acid sample.

Example 29: Cleavage of a Target Nucleic Acid with a Tagged Nucleic Acid-Targeting Nucleic Acid This example describes the results of target nucleic acid cleavage with a nucleic acid-targeting nucleic acid comprising a Csy4 binding sequence on the 5' end of the nucleic acid-targeting nucleic acid. Cas9 was incubated with or without a guide RNA targeting a single site in a linear double-stranded DNA sequence. After 1 hour, cleavage products were separated and visualized on an agarose gel. FIG. 13D illustrates that Cas9 cleavage mediated by a tagged nucleic acid-targeting nucleic acid (lane 3) was less efficient than Cas9 cleavage mediated by an untagged nucleic acid-targeting nucleic acid (lane 1). After 1 hour, ~100% of the target was cleaved by Cas9 guided by the untagged nucleic acid-targeting nucleic acid, where as only a small fraction of the target was cleaved in the same time by Cas9 guided by the tagged nucleic acid-targeting nucleic acid. These experiments indicate the location of the non-native sequence can be used to tune cleavage effectiveness of cleavage of the Cas9: nucleic acid-targeting nucleic acid complex. For example, FIG. 27A, FIG. 27B, and FIG. 29 show the functionality of the addition of a Csy4 binding sequence to various locations in the nucleic acid-targeting nucleic acid that retain activity.

Example 30: Genome Engineering Genes in Blood Disorders

A nucleic acid-targeting nucleic acid comprising a spacer sequence described in Table 2 is introduced into a cell with a site-directed polypeptide, thereby forming a complex. The complex targets the gene involved in a blood disorder that has substantial complementarity to the spacer sequence of the nucleic acid-targeting nucleic acid. Once the nucleic acid-targeting nucleic acid is hybridized to the target nucleic acid the site-directed polypeptide cleaves the target nucleic acid. The cleaved target nucleic acid is can be engineered with a donor polynucleotide.

Example 31: Protocol to Determine Target Nucleic Acid Cleavage and Modification This protocol can be used to determine if a target nucleic acid has been cleaved or if the target nucleic acid has been modified such as with an insertion or deletion. Primers surrounding the target site are used to PCR amplify, in a 25 µL reaction, a 500-600 nt product from gDNA. The primers comprise at least 100 nt on either side of the cut site. The resulting products from the cleavage assay are about greater than 100 nt.

About 5 µL of PCR product is run on an agarose gel to determine if amplification is clean. With the remaining PCR product the melt and annealing protocol is as follows:

| | |
|---|---|
| 95° C. | 10 min |
| 95° C. to 85° C. | (−2.0° C./s) |
| 85° C. | 1 min |
| 85° C. to 75° C. | (−0.3° C./s) |
| 75° C. | 1 min |
| 75° C. to 65° C. | (−0.3° C./s) |
| 65° C. | 1 min |
| 65° C. to 55° C. | (−0.3° C./s) |
| 55° C. | 1 min |
| 55° C. to 45° C. | (−0.3° C./s) |
| 45° C. | 1 min |
| 45° C. to 35° C. | (−0.3° C./s) |
| 35° C. | 1 min |
| 35° C. to 25° C. | (−0.3° C./s) |
| 25° C. | 1 min |
| 4° C. | Hold |

A T7E1 Master Mix of water, NEB2 buffer, and T7E1 enzyme is prepared. Multiply for each reaction, plus extra. Table 8 shows the components of the T7E1 master mix.

TABLE 8

Reaction components for T7E1 Master Mix.

| | 1X reaction |
|---|---|
| Water | 7.5 µL |
| NEB 2 buffer | 2 µL |
| T7E1 enzyme | 0.5 µL |
| PCR product | 10 µL |
| Total | 20 µL |

To each reaction, in a 200 µL strip cap tube, the following reagents are added: T7E1 master mix (10 µL), and PCR sample (10 µL). The reaction is incubated at 37° C. for 25 minutes.

Loading buffer is added to the sample and the entire sample is run on a 3% gel at 120 V for 20 minutes. The gel may be run longer if more resolution is required. Image and save the gel image.

The image is quantified to determine the amount of cleavage of the target nucleic acid.

Example 32: Cellular Testing of Nucleic Acid-Targeting Nucleic Acid Variants This example shows that nucleic acid-targeting nucleic acid variants depicted in FIGS. 22A, 22B, 24, 25, and Example 26 were tested in a cell-based assay to determine if the in vitro functionality determined in Example 26 matched in vivo functionality. HEK293 cells were grown to 60-70% confluence in 10 cm dishes. Cells were removed by trypsinization, counted using a hemocytometer and then separated in to aliquots of 7×10⁴ cells for each well to be transfected. For each well, 250 ng pCB045 plasmid expressing mammalian codon-optimized Cas9 was mixed with 30 ng guide RNA and 40 ng copGFP DNA and 0.5 ul Lipofectamine 2000 in a final volume of 50 ul DMEM. DNA and lipid were incubated for 15 minutes prior to transfection. Transfections were carried out at the time of plating, by adding the lipid:DNA mix to 450 ul DMEM+10% Fetal Bovine Serum containing 7×10⁴ cells. The transfection/cell mix was added to 96 well tissue culture plates coated with Rat Tail Collagen I. Cells were incubated at 37° C. in an incubator with 5% $CO_2$ for 40 hours.

Media was removed from each of the wells and cells were lysed using Quickextract solution (Epicentre) according to manufacturer's instructions. DNA harvested from QuickExtract lysis was diluted 1:10 and used as a template in PCR reactions for T7E1 assays as described in Example 30.

FIG. 36 indicates that all variants except v8 and v9 were able to cleave target nucleic acid. Nucleic acid-targeting nucleic acid variant v8 was also substantially inactive in in vitro assays as depicted in FIG. 23B. Nucleic acid-targeting nucleic acid variant v9 was very weakly active in the in vitro assay depicted in FIG. 23B.

Example 33: Determining a Cell Fate with a Tagged Cell

This example describes how to track a cell developing from a cell lineage. A hematopoietic stem cell (e.g., a hemocytoblast) is contacted with a site-directed polypeptide, a nucleic acid-targeting nucleic acid, and a donor polynucleotide. The site-directed polypeptide and nucleic acid-targeting nucleic acid form a complex and target a region of the hematopoietic genome for cleavage. Once cleaved, the donor polynucleotide is inserted into the cleaved site in the hepatopoietic cell's genome. The hematopoietic stem cell is induced to differentiate through normal differentiation processes. At different stages of differentiation the sample comprising the differentiated hematopoietic cells can be assayed for the presence of the donor polynucleotide. In this way, the differentiation process of a cell can be tracked.

Example 34: Clone Double-Stranded Oligonucleotide Encoding a Nucleic Acid-Targeting Nucleic Acid into a Linearized Vector This example describes how to generate a double-stranded oligonucleotide encoding a portion of nucleic acid-targeting nucleic acid (e.g., a spacer) and insert it into a linearized vector. The linearized vector or a closed supercoiled vector comprises a sequence encoding a site-directed polypeptide (e.g., Cas9), a promoter driving expression of the sequence encoding the site-directed polypeptide (e.g., CMV promoter), a sequence encoding a linker (e.g., 2A), a sequence encoding a marker (e.g., CD4 or OFP), a sequence encoding portion of a nucleic acid-targeting nucleic acid, a promoter driving expression of the sequence encoding a portion of the nucleic acid-targeting nucleic acid, and a sequence encoding a selectable marker (e.g., ampicillin), or any combination thereof.

Equal amounts of two single-stranded oligonucleotides are annealed together (e.g., 50 micromolar). The two single-stranded oligonucleotides can hybridize together. At least one of the two single-stranded oligonucleotides is complementary to a target nucleic acid (e.g., a 10-30 nucleotide region adjacent to a protospacer adjacent motif in a target). At least one of the two single-stranded nucleotides comprises a 3' overhang sequence comprising the sequence 5'-GTTT-3'. At least one of the two single-stranded oligonucleotides comprises a 3' overhang comprising the sequence 5'-CGGTG-3'. In some instances, one of the two single-stranded oligonucleotides comprises a 5'-GTTT-3' overhang and the other of the two single-stranded oligonucleotides comprises a 5'-CGGTG-3'. Annealing is performed in an annealing buffer comprising at least 10 mM tris HCl pH 8.0, 1 mM EDTA, pH 8.0, and 100 mM NaCl. Annealing is performed by heating the oligonucleotide mixture at 95° C. for 3-5 minutes, removing the oligonucleotide mixture from the heating source, and allowing the mixture to cool to room temperature for 5-10 minutes. The double-stranded oligonucleotide mixture is centrifuged gently. After annealing the mixture may be stored at 4° C. or −20° C. The mixture, now of double-stranded oligonucleotides, is diluted to prepare two stock solutions of 500 nanomolar and 5 nanomolar. The stock solutions are prepared by diluting the oligonucleotide mixture in water.

The double-stranded oligonucleotide (dsOligonucleotide) is ligated into a linearized vector. The linearized vector comprises a sequence encoding a site-directed polypeptide (e.g., Cas9), a marker protein (e.g., orange fluorescent protein), and/or a sequence encoding a nucleic acid-targeting nucleic acid, wherein the linearized vector is linearized at a region of the sequence encoding the nucleic acid-targeting nucleic acid, such that the sticky ends generated match the overhang ends of the dsOligonucleotide. The ligation reaction can comprise 1× ligation buffer (e.g., 50 mM Tris-HCl pH 7.6, 5 mM $MgCl_2$, 1 mM ATP, 1 mM DTT, and/or 5% PEG 8000), 30 nanogram linearized vector, 5 nM dsOligonucleotide, and DNA ligase (e.g., 4 microliters 5× ligation buffer, 2 microliters linearized vector at 15 nanogram/microliter, 2 microliters 5 nanomolar dsOligonucleotide, 11 microliters water, 1 microliter T4 DNA ligase). The reaction is mixed. The reaction is incubated at room temperature for 10 minutes-2 hours. The reaction is placed on ice and transformed into competent cells.

Transformation into competent cells comprises transforming into chemically competent TOP10 *E. coli* cells. Competent cells are thawed on ice. 3 microliters of the reaction mixture is added to the competent cells and mixed gently. The cells are incubated on ice for 10-30 minutes. The cells are heat-shocked for 30 seconds at 42° C. The cells are transferred to ice for 2 minutes. 250 microliters of medium (SOC or LB) is added to the cells. The cells are shaked at 200 rpm for 1 hour at 37° C. The cells are then spread on an agar plate comprising 100 micrograms/milliliter ampicillin and stored overnight at 37° C.

The transformants are analyzed. For example, the transformants are analyzed to determine the identity of the dsOligonucleotide ligated into the vector, and/or confirm the ligation is not a false positive. To analyze transformants, colonies are picked and cultured overnight in LB medium comprising 100 micrograms/milliliter ampicillin at 37° C. The plasmid comprising the site-directed polypeptide and dsOligonucleotide is isolated (e.g., by miniprep kit). A sequencing reaction is performed on the isolated plasmid. The sequencing reaction utilizes a sequencing primer that is designed to sequence the dsOligonucleotide (e.g., the sequencing primer is a U6 sequencing primer that binds to the U6 promoter which is located just upstream of the sequence encoding the dsOligonucleotide.

Once a desired dsOligonucleotide insertion is identified, the plasmid can be stored at −20° C. or in a glycerol stock at −80° C. To make a glycerol stock, the original colony comprising the desired plasmid is streaked on an agar plate comprising 100 micrograms/milliliter ampicillin and incubated overnight at 37° C. A single colony is isolated grown in LB comprising 100 micrograms/milliliter ampicillin until the culture reaches stationary phase. The culture is mixed with glycerol and flash frozen in liquid nitrogen (e.g., 0.85 mL culture is mixed with 0.15 mL glycerol).

The purified plasmid comprising the desired dsOligonucleotide is inserted into a cell line (e.g., mammalian cell line, HeLa) by transfection. To transfect the plasmid, the plasmid is purified at high concentrations using for example, a maxi prep kit. The plasmid is transfected with lipid-based buffer (e.g., Lipofectamine 2000) into cells which are plated at 70% confluency. 3 micrograms of the vector is transfected into the cells.

Example 35: Nanoparticle Delivery of an Engineered Nucleic Acid-Targeting Nucleic Acid A nanoparticle encapsulating a nucleic acid encoding an engineered nucleic acid-targeting nucleic acid and a site-directed polypeptide will be prepared. Nanoparticles will be prepared by mixing DOPE, Chol, DSPE-PEG and $C_{16}$mPEG-Ceramide at a molar ratio of 18:60:20:1:1 in 10 mL of 90% ethanol (total lipid 30 µmole). The nucleic acid will be dissolved in 10 mL of 20 mM Tris buffer (pH 7.4-7.6). After being heated to 37° C., the two solutions will be mixed together through a duel syringe pump and the mixed solution will be subsequently diluted with 20 mL of 20 mM Tris buffer (300 mM NaCl, pH 7.4-7.6). The mixture will be incubated at 37° C. for 30 minutes and dialyzed in 10 mM PBS buffer (138 mM NaCl, 2.7 mM KCl, pH 7.4). Stable particles will be obtained after the removal of ethanol from the mixture by dialysis. The nanoparticle solution will be concentrated by centrifugation at 3,000 rpm and a temperature of 4° C. The concentrated suspension will be collected after a given time and will be sterilized by filtration through a 0.22 µm syringe filter (Millex-GV, Millipore, USA). A homogeneous suspension of the nanoparticles comprising the nucleic acid encoding the engineered nucleic acid-targeting nucleic acid and the site-directed polypeptide will be obtained.

The nanoparticles will be contacted to a cell. The nanoparticle will enter the cell. Inside the cell, the nanoparticle will release the nucleic acid encoding the engineered nucleic acid-targeting nucleic acid and the site-directed polypeptide. The nucleic acid will be transcribed and/or translated to produce an engineered nucleic acid-targeting nucleic acid that binds to a site-directed polypeptide protein, thereby forming a complex. The complex will target a target nucleic acid that hybridizes with the engineered nucleic acid-targeting nucleic acid. The complex will cleave the target nucleic acid.

In some instances, the nanoparticle will further comprise a nucleic acid encoding a donor polynucleotide. When the target nucleic acid is cleaved by the site-directed polypeptide, the donor polynucleotide will be inserted into the site of the cleaved target nucleic acid.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10125361B2). An electronic copy of the "Sequence Listing" will also be available from the USPTO upon request and payment of the fee set forth in 37 CFR 1.19(b)(3).

What is claimed is:

1. An engineered CRISPR Cas9 protein comprising:
   a modification in a region of a CRISPR Cas9 protein corresponding to a region of amino acid residues 170-312 of a *S. pyogenes*-Cas9 protein (SEQ ID NO:8), wherein the modification comprises an insertion, deletion, or combination thereof.

2. The engineered CRISPR Cas9 protein of claim 1, wherein the modification is made in identified regions of sequence similarity between the Cas9 protein and the *S. pyogenes*-Cas9 protein (SEQ ID NO:8).

3. The engineered CRISPR Cas9 protein of claim 1, wherein the modification comprises a deletion.

4. The engineered CRISPR Cas9 protein of claim 1, wherein the modification comprises a deletion of more than 5 amino acid residues.

5. The engineered CRISPR Cas9 protein of claim 1, wherein the modification comprises a deletion of more than 100 amino acid residues.

6. The engineered CRISPR Cas9 protein of claim 1, wherein the modification comprises a deletion and an insertion of a non-native amino acid sequence.

7. The engineered CRISPR Cas9 protein of claim 1, wherein the modification comprises an insertion of a non-native amino acid sequence to form a fusion protein.

8. The engineered CRISPR Cas9 protein of claim 7, wherein the non-native amino acid sequence comprises a functional domain.

9. The engineered CRISPR Cas9 protein of claim 1, wherein the engineered CRISPR Cas9 protein is a fusion.

10. The engineered CRISPR Cas9 protein of claim 9, wherein the engineered CRISPR Cas9 fusion comprises a detectable label.

11. The engineered CRISPR Cas9 protein of claim 9, wherein the engineered CRISPR Cas9 fusion comprises the engineered CRISPR Cas9 protein and an endonuclease.

12. The engineered CRISPR Cas9 protein of claim 11, wherein the endonuclease is FokI.

13. The engineered CRISPR Cas9 protein of claim 1, wherein the engineered CRISPR Cas9 protein is enzymatically inactive.

14. The engineered CRISPR Cas9 protein of claim 1, wherein the engineered CRISPR Cas9 protein is codon optimized for a host cell of interest.

15. The engineered CRISPR Cas9 protein of claim 14, wherein the host cell of interest is a bacterial cell, an archaeal cell, a cell of a single-cell eukaryotic organism, a plant cell, an algal cell, a fungal cell, an animal cell, a cell from an invertebrate animal, a cell from a vertebrate animal, or a cell from a mammal.

16. The engineered CRISPR Cas9 protein of claim 15, wherein the host cell is a human cell.

17. A polynucleotide encoding the engineered CRISPR Cas9 protein of claim 1.

18. The polynucleotide of claim 17, wherein the modification of the engineered CRISPR Cas9 protein is a deletion of more than 5 amino acid residues.

19. The polynucleotide of claim 17, wherein the modification of the engineered CRISPR Cas9 protein is a deletion of more than 100 amino acid residues.

20. A kit comprising:
the engineered CRISPR Cas9 protein of claim 1 or a polynucleotide encoding the engineered CRISPR Cas9 protein; and
a reagent.

* * * * *